United States Patent
McDonald et al.

(10) Patent No.: US 10,301,284 B2
(45) Date of Patent: May 28, 2019

(54) THERAPEUTIC INHIBITORY COMPOUNDS

(71) Applicant: LifeSci Pharmaceuticals, Inc., St. Michael (BB)

(72) Inventors: Andrew McDonald, New York, NY (US); Shawn Qian, New York, NY (US)

(73) Assignee: LIFESCI PHARMACEUTICALS, INC., St. Michael (BB)

( * ) Notice: Subject to any disclaimer, the term of this patent is extended or adjusted under 35 U.S.C. 154(b) by 0 days.

(21) Appl. No.: 16/016,167

(22) Filed: Jun. 22, 2018

(65) Prior Publication Data
US 2018/0297984 A1  Oct. 18, 2018

Related U.S. Application Data

(63) Continuation of application No. PCT/IB2017/000984, filed on Jul. 11, 2017.

(60) Provisional application No. 62/360,902, filed on Jul. 11, 2016.

(51) Int. Cl.
*C07D 401/14* (2006.01)
*C07D 413/14* (2006.01)
*C07D 471/04* (2006.01)
*C07D 487/04* (2006.01)

(52) U.S. Cl.
CPC ......... *C07D 401/14* (2013.01); *C07D 413/14* (2013.01); *C07D 471/04* (2013.01); *C07D 487/04* (2013.01)

(58) Field of Classification Search
CPC .. C07D 401/14; C07D 413/14; C07D 471/04; C07D 487/04; A61K 31/421
USPC .......................................... 546/152; 514/314
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 9,533,987 B2 | 1/2017 | Davie et al. |
| 9,611,252 B2 | 4/2017 | McDonald et al. |
| 10,023,557 B2 | 7/2018 | McDonald et al. |
| 2007/0254894 A1 | 11/2007 | Kane et al. |
| 2009/0099184 A1 | 4/2009 | Delombaert et al. |
| 2009/0270407 A1 | 10/2009 | Tseng et al. |
| 2011/0118236 A1 | 5/2011 | Mochizuki et al. |
| 2011/0124626 A1 | 5/2011 | Pooni et al. |
| 2012/0035168 A1 | 2/2012 | Brandl et al. |
| 2014/0350034 A1 | 11/2014 | Brandl et al. |
| 2014/0378474 A1 | 12/2014 | Flohr et al. |
| 2016/0108036 A1 | 4/2016 | Davie et al. |
| 2016/0168123 A1 | 6/2016 | Edwards et al. |
| 2017/0260163 A1 | 9/2017 | McDonald et al. |
| 2018/0170906 A1 | 6/2018 | McDonald et al. |

FOREIGN PATENT DOCUMENTS

| | | |
|---|---|---|
| EP | 2269990 A1 | 1/2011 |
| WO | WO-2005079800 A1 | 9/2005 |
| WO | WO-2008071451 A1 | 6/2008 |
| WO | WO-2009083553 A1 | 7/2009 |
| WO | WO-2009119088 A1 | 10/2009 |
| WO | WO-2010051188 A1 | 5/2010 |
| WO | WO-2010108733 A1 | 9/2010 |
| WO | WO-2013017020 A1 | 2/2013 |
| WO | WO-2013040436 A2 | 3/2013 |
| WO | WO-2013111108 A1 | 8/2013 |
| WO | WO-2014086805 A1 | 6/2014 |
| WO | WO-2014188211 A1 | 11/2014 |
| WO | WO-2015022546 A1 | 2/2015 |
| WO | WO-2015103317 A1 | 7/2015 |
| WO | WO-2016011209 A1 | 1/2016 |
| WO | WO-2016083816 A1 | 6/2016 |
| WO | WO-2017001924 A1 | 1/2017 |
| WO | WO-2018011628 A1 | 1/2018 |

OTHER PUBLICATIONS

Berge et al. Pharmaceutical Salts. Journal of Pharmaceutical Sciences 66(1):1-19 (Jan. 1977).
Bork et al. Treatment of 193 episodes of laryngeal edema with C1 inhibitor concentrate in patients with hereditary angioedema. Arch. Intern. Med. 161:714-718 (2001).
Bork et al. Treatment with C1 inhibitor concentrate in abdominal pain attacks of patients with hereditary angioedema. Transfusion 45:1774-1784 (2005).
Bundgaard et al. Design of Prodrugs pp. 7-9, 21-24 (1985).
Chemical Abstracts Search (15 pgs) (Jul. 7, 2015).
Colman et al. Effect of cleavage of the heavy chain of human plasma kallikrein on its functional properties. Blood 65:311-318 (1985).
Cool. Characterization of the human blood coagulation factor XII gene. Intron/exon gene organization and analysis of the 5'-flanking region. The Journal of Biological Chemistry 262(28):13662-13673 (1987).
Co-pending U.S. Appl. No. 16/009,093, filed Jun. 14, 2018.
Cugno et al. C1-inhibitor deficiency and angioedema: molecular mechanisms and clinical progress. Trends Mol. Med. 15(2):69-78 (2009).
Cugno et al. Generation of plasmin during acute attacks of hereditary angioedema. The Journal of Laboratory and Clinical Medicine 121(1):38-43 (1993).
Evans. Synthesis of radiolabeled compounds. J Radioanal Chem 64(1-2):9-32 (1981).
Gao et al. Extracellular carbonic anhydrase mediates hemorrhagic retinal and cerebral vascular permeability through prekallikrein activation. Nat Med 13(2):181-188 (2007).
Higuchi et al. Pro-drugs as Novel Delivery Systems. A.C.S. Symposium Series vol. 14 (1975).

(Continued)

*Primary Examiner* — Deepak R Rao
(74) *Attorney, Agent, or Firm* — Wilson Sonsini Goodrich & Rosati

(57) ABSTRACT

Provided herein are heterocyclic derivative compounds and pharmaceutical compositions comprising said compounds that are useful for inhibiting plasma kallikrein. Furthermore, the subject compounds and compositions are useful for the treatment of diseases wherein the inhibition of plasma kallikrein inhibition has been implicated, such as angioedema and the like.

11 Claims, No Drawings

(56) References Cited

OTHER PUBLICATIONS

Kabalka et al. The Synthesis of Radiolabeled Compounds via Organometallic Intermediates. Tetrahedron 45(21):6601-6621 (1989).
Kaplan et al. Angioedema. J. Am. Acad. Dermatol. 53(3):373-388 (2005).
Kaplan et al. The intrinsic coagulation/kinin-forming cascade: assembly in plasma and cell surfaces in inflammation. Advances in Immunology 66:225-272 (1997).
Liu et al. Author response: retinal microglia. Invest. Ophthalmol. Vis. Sci. 54(2):pii (2013).
Liu et al. Hyperoxia causes regression of vitreous neovascularization by downregulating VEGF/VEGFR2 pathway. Invest. Ophthalmol. Vis. Sci. 54(2):918-931 (2013).
Liu et al. Intraocular hemorrhage causes retinal vascular dysfunction via plasma kallikrein. Invest. Ophthalmol. Vis. Sci. 54(2):1086-1094 (2013).
Liu et al. Plasma kallikrein-kinin system and diabetic retinopathy. Biol Chem 394(3):319-328 (2013).
Liu et al. TGFβ signaling induces expression of Gadd45b in retinal ganglion cells. Invest. Ophthalmol. Vis. Sci. 54(2):1061-1069 (2013).
Mehta et al. Signaling mechanisms regulating endothelial permeability. Physiol. Rev. 86(1):279-367 (2006).
Mochizuki et al. Preparation of indazole derivatives as AMPA receptor function enhancing agent. Document No. 151:425739. CAPLUS Accession No. 2009:1204289 (© 2015) (15 pgs).
Muller et al. Novel roles for factor XII-driven plasma contact activation system. Curr. Opin. Hematol. 15:516-521 (2008).
Ny et al. The structure of the human tissue-type plasminogen activator gene: correlation of intron and exon structures to functional and structural domains. PNAS USA 81(17):5355-5359 (1984).
PCT/IB2016/001048 International Preliminary Report on Patentability dated Jan. 11, 2018.
PCT/IB2016/01048 International Search Report and Written Opinion dated Nov. 15, 2016.
PCT/IB2017/000984 International Search Report and Written Opinion dated Dec. 26, 2017.
PCT/US2014/072851 International Preliminary Report on Patentability dated Jul. 14, 2016.
PCT/US2014/072851 International Search Report and Written Opinion dated May 15, 2015.
PCT/US2015/040659 International Preliminary Report on Patentability dated Jan. 26, 2017.
PCT/US2015/040659 International Search Report and Written Opinion dated Oct. 16, 2015.
Phipps et al. Plasma kallikrein mediates angiotensin II type 1 receptor-stimulated retinal vascular permeability. Hypertension 53:175-181 (2009).
Pixley et al. The regulation of human factor XIIa by plasma proteinase inhibitors. The Journal of Biological Chemistry 260(3):1723-1729 (1985).
PubChem-CID-117776872, Create Date: Feb. 23, 2016 (10 pgs).
PubChem-CID-89715158, Create Date: Feb. 13, 2015 (11 pgs).
Sandoval et al. Ca(2+) signalling and PKCalpha activate increased endothelial permeability by disassembly of VE-cadherin junctions. J. Physiol. 533(pt 2):433-445 (2001).
Schapira et al. Protection of human plasma kallikrein from inactivation by C1 inhibitor and other protease inhibitors. The role of high molecular weight kininogen. Biochemistry 20:2738-2743 (1981).
Stahl et al. Handbook of Pharmaceutical Salts. Verlag Helvetica Chimica Acta, Zurich, 2002.
Stavrou. Factor XII: what does it contribute to our understanding of the physiology and pathophysiology of hemostasis & thrombosis. Thrombosis Research 125(3):210-215 (2010).
Storini et al. Selective Inhibition of Plasma Kallikrein Protects brain from Reperfusion Injury. JPET 381:849-954 (2006).
Ulven et al. 6-Acylamino-2-amino-4-methylquinolines as potent melanin-concentrating hormone 1 receptor antagonists: structure-activity exploration of eastern and western parts. Bioorg Med Chem Lett 16(4):1070-1075 (2006).
U.S. Appl. No. 14/800,631 1st Action Interview dated May 30, 2018.
U.S. Appl. No. 15/042,102 1st Action Interview dated Apr. 27, 2016.
U.S. Appl. No. 15/042,102 Office Action dated Oct. 13, 2016.
U.S. Appl. No. 15/199,785 Office Action dated Apr. 10, 2017.
U.S. Appl. No. 15/199,785 Office Action dated Nov. 24, 2017.
U.S. Appl. No. 15/470,736 Office Action dated Apr. 26, 2018.
File History for co-pending U.S. Appl. No. 14/800,631, filed Jul. 15, 2015.
File History for co-pending U.S. Appl. No. 15/470,736, filed Mar. 27, 2017.
File History for co-pending U.S. Appl. No. 16/009,093, filed Jun. 14, 2018.
File History for U.S. Pat. No. 10,023,557, Issued Jul. 17, 2018 (U.S. Appl. No. 15/199,785, filed Jun. 30, 2016).
File History for U.S. Pat. No. 9,611,252, Issued Apr. 4, 2017 (U.S. Appl. No. 15/042,102, filed Feb. 11, 2016).

THERAPEUTIC INHIBITORY COMPOUNDS

CROSS REFERENCE

This application is a continuation application of International Application No. PCT/IB2017/000984, filed Jul. 11, 2017, and claims the benefit of U.S. Provisional Application No. 62/360,902, filed Jul. 11, 2016, all of which are incorporated by reference herein in their entirety.

BACKGROUND

A need exists in the medicinal arts for the effective treatment of diseases and disorders related to the vascular system. Such diseases and disorders include, but are not limited to, angioedema, macular edema and brain edema.

BRIEF SUMMARY OF THE INVENTION

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

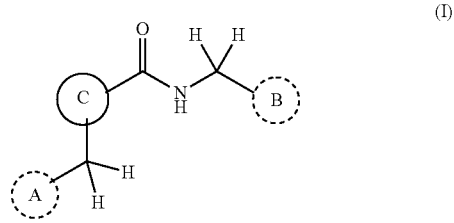

(I)

wherein,

Ring A is an optionally substituted bicyclic heteroaryl ring;

Ring B is an optionally substituted monocyclic heteroaryl ring or optionally substituted bicyclic heteroaryl ring; and Ring C is an optionally substituted five-membered monocyclic heteroaryl ring or optionally substituted bicyclic heteroaryl ring.

One embodiment provides a pharmaceutical composition comprising a compound of Formula (I), or a pharmaceutically acceptable salt thereof, and a pharmaceutically acceptable excipient.

One embodiment provides a method of inhibiting kallikrein enzyme comprising contacting the kallikrein enzyme with a compound of Formula (I).

One embodiment provides a method for treating angioedema in a patient in need thereof comprising administering to the patient a composition comprising a compound of Formula (I), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC (O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hickel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

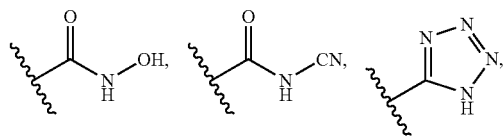

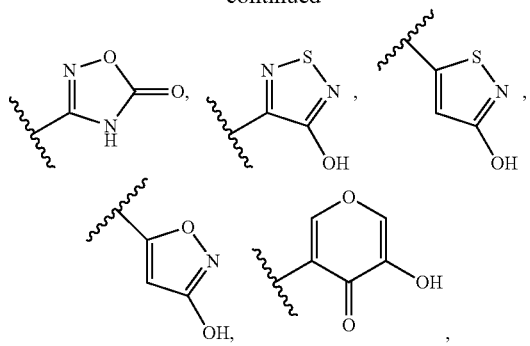

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N(R^a)_2$, —$R^b$—N(R^a)_2$, —$R^b$—C(O)R^a$, —$R^b$—C(O)OR^a$, —$R^b$—C(O)N(R^a)_2$, —$R^b$—O—$R^c$—C(O)N(R^a)_2$, —$R^b$—N(R^a)C(O)OR^a$, —$R^b$—N(R^a)C(O)R^a$, —$R^b$—N(R^a)S(O)_tR^a$ (where t is 1 or 2), —$R^b$—S(O)_tR^a$ (where t is 1 or 2), —$R^b$—S(O)_tOR^a$ (where t is 1 or 2) and —$R^b$—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

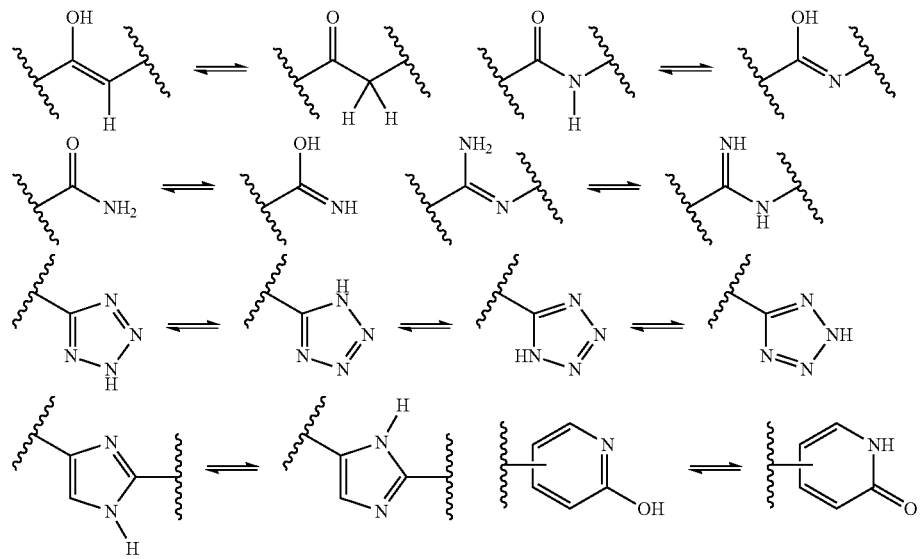

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

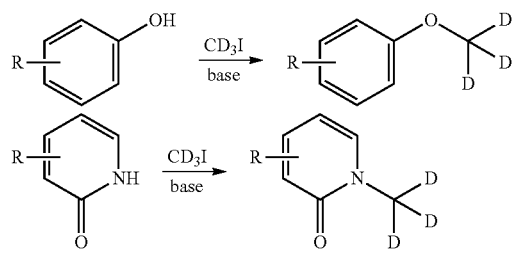

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

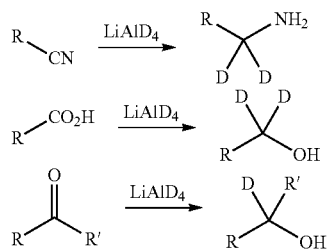

Deuterium gas and palladium catalyst are employed to reduce unsaturated carbon-carbon linkages and to perform a reductive substitution of aryl carbon-halogen bonds as illustrated, by way of example only, in the reaction schemes below.

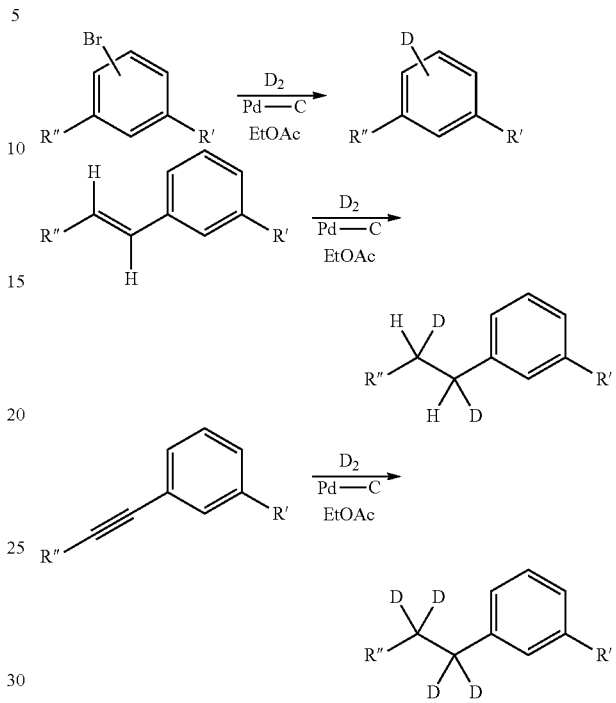

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the kallikrein inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Kallikrein Inhibitory Compounds

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

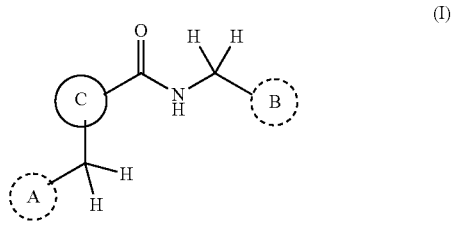

wherein,

Ring A is an optionally substituted bicyclic heteroaryl ring;

Ring B is an optionally substituted monocyclic heteroaryl ring or optionally substituted bicyclic heteroaryl ring; and Ring C is an optionally substituted five-membered monocyclic heteroaryl ring or optionally substituted bicyclic heteroaryl ring.

Another embodiment provides the compound of Formula (I), or a pharmaceutically acceptable salt thereof, wherein Ring A is selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl.

Another embodiment provides the compound of Formula (I), or a pharmaceutically acceptable salt thereof, wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl.

Another embodiment provides the compound of Formula (I), or a pharmaceutically acceptable salt thereof, wherein Ring A is an optionally substituted quinolin-6-yl or an optionally substituted quinolin-3-yl.

Another embodiment provides the compound of Formula (I), or a pharmaceutically acceptable salt thereof, wherein the optionally substituted quinolin-6-yl or optionally substituted quinolin-3-yl is substituted with at least one substituent selected from optionally substituted C1-C3 alkyl, C3-C7 cycloalkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or —OMe.

Another embodiment provides the compound of Formula (I), or a pharmaceutically acceptable salt thereof, wherein the optionally substituted quinolin-6-yl is substituted at least at the 3-position.

Another embodiment provides the compound of Formula (I), or a pharmaceutically acceptable salt thereof, wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

Another embodiment provides the compound of Formula (I), or a pharmaceutically acceptable salt thereof, wherein the optionally substituted quinolin-3-yl is substituted at least at the 6-position or the 7-position.

Another embodiment provides the compound of Formula (I), or a pharmaceutically acceptable salt thereof, wherein Ring B is selected from an optionally substituted monocyclic heteroaryl ring.

Another embodiment provides the compound of Formula (I), or a pharmaceutically acceptable salt thereof, wherein the optionally substituted monocyclic heteroaryl ring is selected from optionally substituted imidazolyl, optionally substituted pyrazolyl, optionally substituted pyridinyl, optionally substituted pyridazinyl, optionally substituted pyrimidinyl, or optionally substituted pyrazinyl.

Another embodiment provides the compound of Formula (I), or a pharmaceutically acceptable salt thereof, wherein the optionally substituted monocyclic heteroaryl ring is an optionally substituted pyridinyl.

Another embodiment provides the compound of Formula (I), or a pharmaceutically acceptable salt thereof, wherein the optionally substituted pyridinyl is an optionally substituted aminopyridinyl.

Another embodiment provides the compound of Formula (I), or a pharmaceutically acceptable salt thereof, wherein the optionally substituted aminopyridinyl is an optionally substituted 6-aminopyridin-3-yl.

Another embodiment provides the compound of Formula (I), or a pharmaceutically acceptable salt thereof, wherein Ring B is selected from an optionally substituted bicyclic heteroaryl ring.

Another embodiment provides the compound of Formula (I), or a pharmaceutically acceptable salt thereof, wherein the optionally substituted bicyclic heteroaryl ring is selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl.

Another embodiment provides the compound of Formula (I), or a pharmaceutically acceptable salt thereof, wherein the optionally substituted bicyclic heteroaryl ring is an optionally substituted indolyl or an optionally substituted indazolyl.

Another embodiment provides the compound of Formula (I), or a pharmaceutically acceptable salt thereof, wherein the optionally substituted indolyl is an optionally substituted indol-5-yl or an optionally substituted indazol-5-yl.

Another embodiment provides the compound of Formula (I), or a pharmaceutically acceptable salt thereof, wherein the optionally substituted bicyclic heteroaryl ring is an optionally substituted 1H-pyrrolo[2,3-b]pyridinyl.

Another embodiment provides the compound of Formula (I), or a pharmaceutically acceptable salt thereof, wherein Ring A is an optionally substituted quinolyl; and Ring B is selected from an optionally substituted indolyl, an optionally substituted indazolyl, or an optionally substituted 1H-pyrrolo[2,3-b]pyridinyl.

Another embodiment provides the compound of Formula (I), or a pharmaceutically acceptable salt thereof, wherein Ring A is an optionally substituted quinolyl; and Ring B is an optionally substituted 6-aminopyridin-3-yl.

Another embodiment provides the compound of Formula (I), or a pharmaceutically acceptable salt thereof, wherein Ring C is a 1,3-substituted heteroaryl ring system chosen from:
(a) pyrazole, imidazole, triazole, oxadiazole, thiadiazole, thiophene, thiazole, isothiazole, oxazole, isoxazole, furan or pyrrole;
(b) indole, indazole, pyrrolopyridine, or imidazopyridine wherein the 1,3-substitution occurs on the five-membered ring of the ring;
(c) naphthyridine or quinoline wherein the 1,3-substitution occurs at the 2- and 4-position of the ring;
(d) 1,4-dihydro-5H-pyrrolo[3,2-b]pyridin-5-one, 1,4-dihydro-5H-pyrazolo[4,3-b]pyridin-5-one, 1,5-dihydro-4H-pyrrolo[3,2-c]pyridin-4-one, 1,5-dihydro-4H-pyrazolo[4,3-c]pyridin-4-one, 1,6-dihydro-5H-pyrrolo[2,3-c]pyridin-5-one, or
(e) 1,6-dihydro-5H-pyrazolo[3,4-c]pyridin-5-one; or pyrrolopyridine, imidazopyridine, furopyridine, or thienopyridine wherein the 1,3-substitution occurs on the pyridine ring of the ring.

Another embodiment provides the compound of Formula (I), or a pharmaceutically acceptable salt thereof, wherein Ring C is chosen from pyrazole, imidazole, triazole, oxadiazole, thiadiazole, thiophene, thiazole, isothiazole, oxazole, isoxazole, furan or pyrrole.

Another embodiment provides the compound of Formula (I), or a pharmaceutically acceptable salt thereof, wherein Ring C is chosen from:

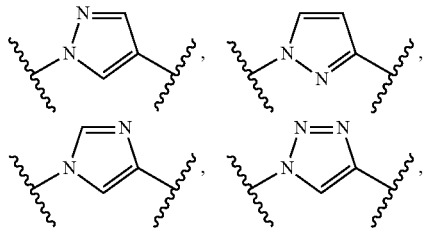

-continued

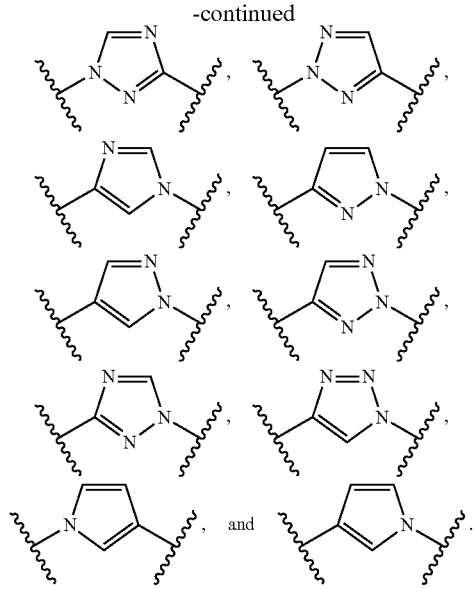

Another embodiment provides the compound of Formula (I), or a pharmaceutically acceptable salt thereof, wherein Ring C is chosen from:

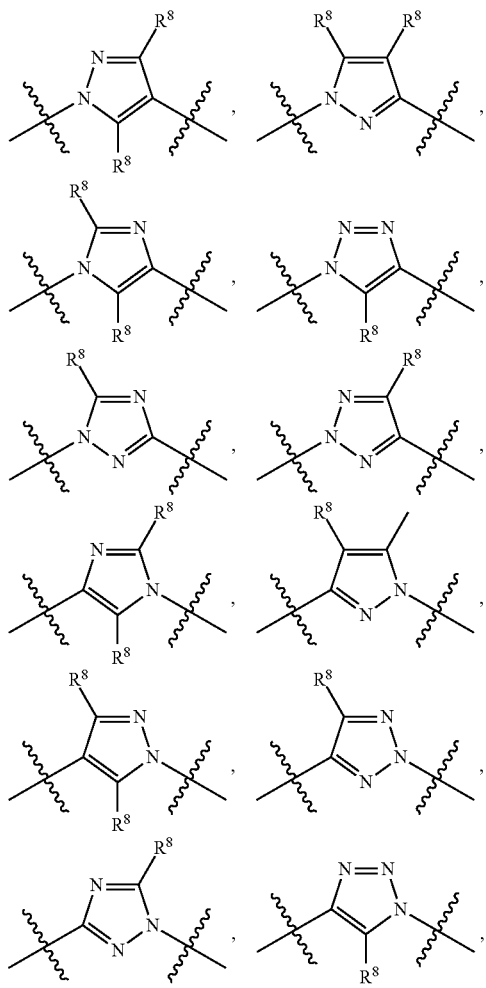

-continued

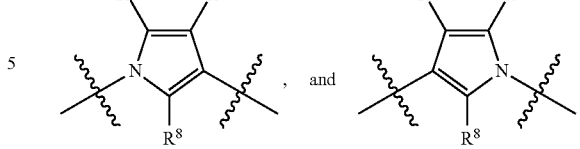

wherein each $R^8$ is independently hydrogen, —$NH_2$, —$NO_2$, —$NHCOCH_3$, —CN, —$CF_3$, —$CONH_2$, or optionally substituted C1-C4 alkyl, or optionally substituted C1-C4 alkoxy.

Another embodiment provides the compound of Formula (I), or a pharmaceutically acceptable salt thereof, wherein Ring C is chosen from:

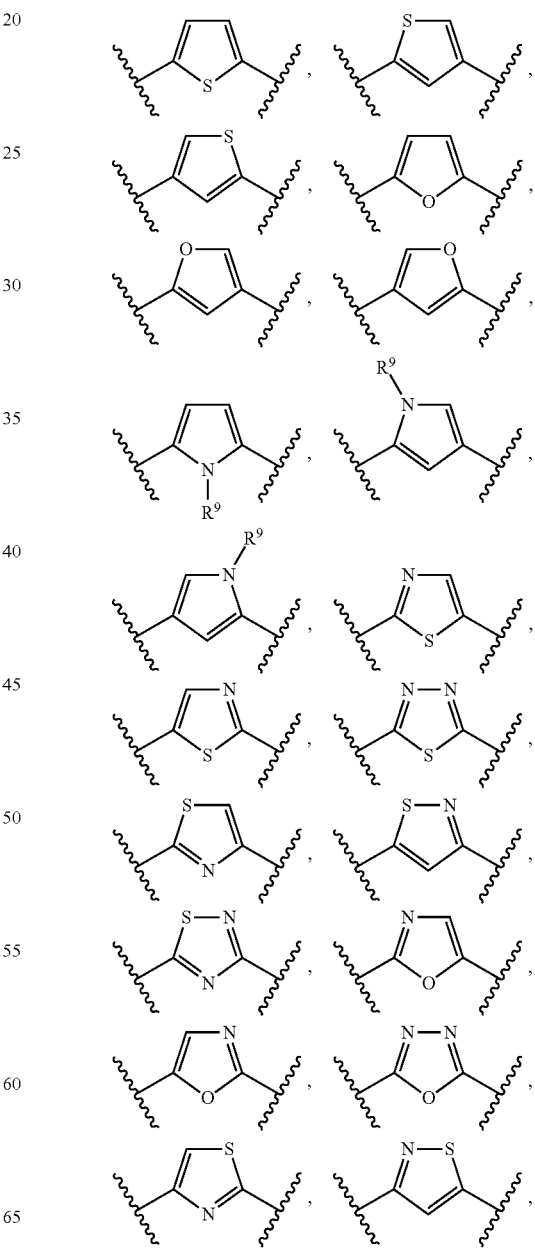

-continued

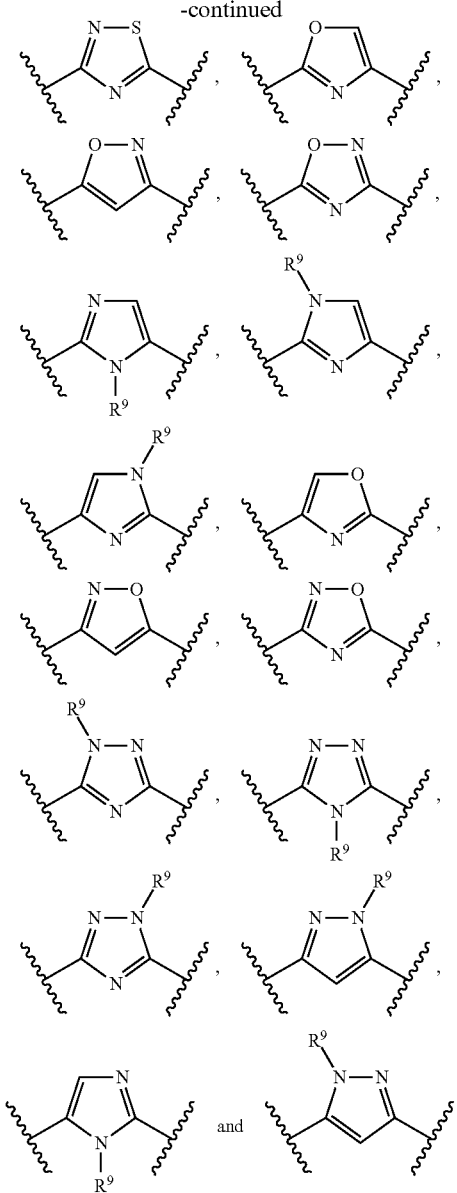

wherein R⁹ is hydrogen or alkyl.

Another embodiment provides the compound of Formula (I), or a pharmaceutically acceptable salt thereof, wherein Ring C is chosen from:

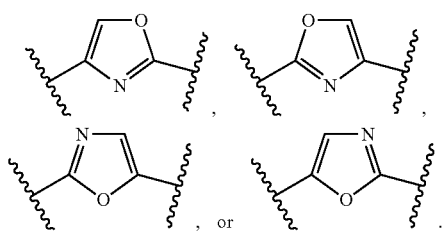

Another embodiment provides the compound of Formula (I), or a pharmaceutically acceptable salt thereof, wherein Ring C is:

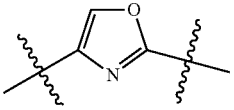

Another embodiment provides the compound of Formula (I), or a pharmaceutically acceptable salt thereof, wherein Ring C is:

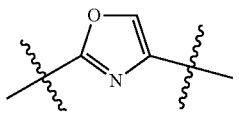

Another embodiment provides the compound of Formula (I), or a pharmaceutically acceptable salt thereof, wherein Ring C is:

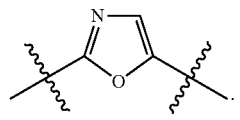 [SMILES: *c1cnc(*)o1]

Another embodiment provides the compound of Formula (I), or a pharmaceutically acceptable salt thereof, wherein Ring C is:

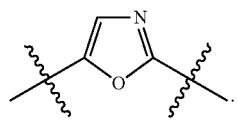 [SMILES: *c1cnc(*)o1]

Another embodiment provides the compound of Formula (I), or a pharmaceutically acceptable salt thereof, wherein Ring C is:

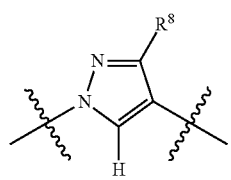

and R⁸ is selected from —NH₂, —NO₂, —NHCOCH₃, —CN, —CF₃, —CONH₂, or optionally substituted C1-C4 alkyl, or optionally substituted C1-C4 alkoxy.

Another embodiment provides the compound of Formula (I), or a pharmaceutically acceptable salt thereof, wherein Ring C is:

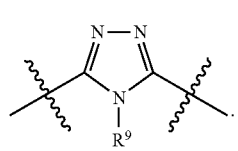

Another embodiment provides the compound of Formula (I), or a pharmaceutically acceptable salt thereof, wherein $R^9$ is hydrogen.

Another embodiment provides the compound of Formula (I), or a pharmaceutically acceptable salt thereof, wherein Ring C is:

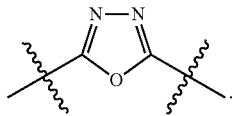 [SMILES: *c1nnc(*)o1]

Another embodiment provides the compound of Formula (I), or a pharmaceutically acceptable salt thereof, wherein Ring C is:

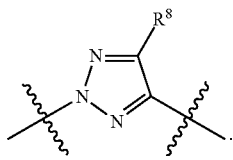

Another embodiment provides the compound of Formula (I), or a pharmaceutically acceptable salt thereof, wherein $R^8$ is hydrogen.

Another embodiment provides the compound of Formula (I), or a pharmaceutically acceptable salt thereof, wherein Ring C is chosen from indole, indazole, pyrrolopyridine, or imidazopyridine wherein the 1,3-substitution occurs on the five-membered ring of the ring.

Another embodiment provides the compound of Formula (I), or a pharmaceutically acceptable salt thereof, wherein Ring C is chosen from:

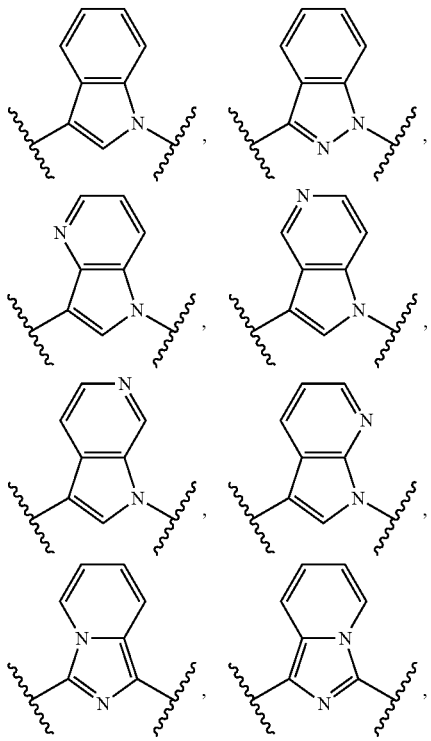

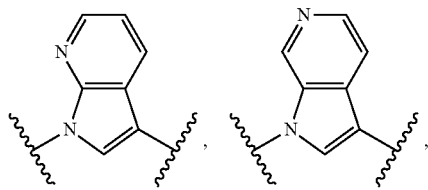

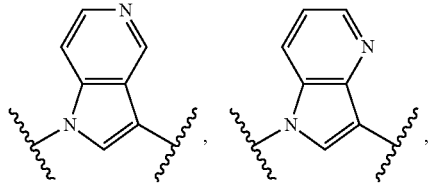

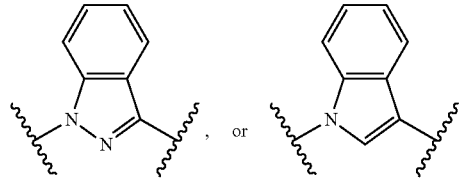

Another embodiment provides the compound of Formula (I), or a pharmaceutically acceptable salt thereof, wherein Ring C is chosen from:

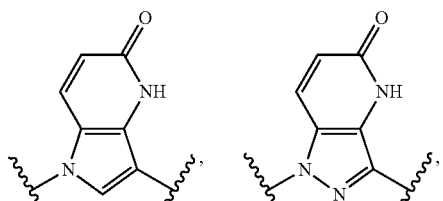

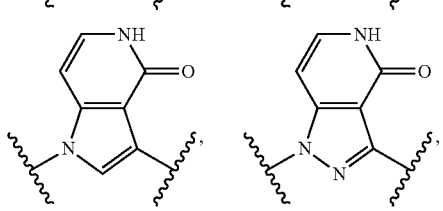

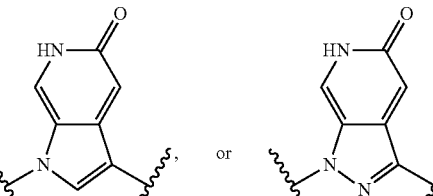

Another embodiment provides the compound of Formula (I), or a pharmaceutically acceptable salt thereof, wherein Ring C is chosen from naphthyridine or quinoline wherein the 1,3-substitution occurs at the 2- and 4-position of the ring.

Another embodiment provides the compound of Formula (I), or a pharmaceutically acceptable salt thereof, wherein Ring C is chosen from:

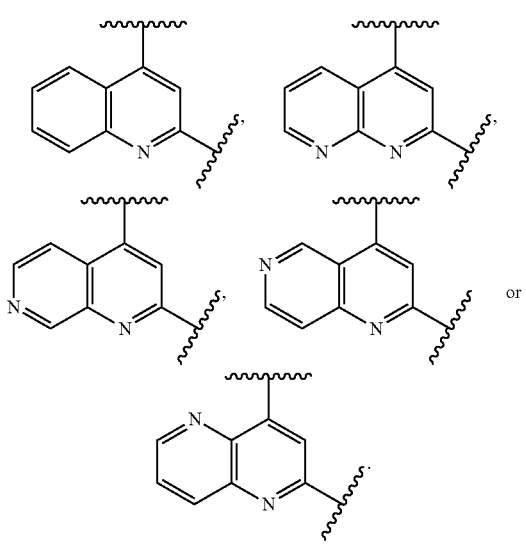

Another embodiment provides the compound of Formula (I), or a pharmaceutically acceptable salt thereof, wherein Ring C is chosen from pyrrolopyridine, imidazopyridine, furopyridine, or thienopyridine wherein the 1,3-substitution occurs on the pyridine ring of the ring.

Another embodiment provides the compound of Formula (I), or a pharmaceutically acceptable salt thereof, wherein Ring C is chosen from:

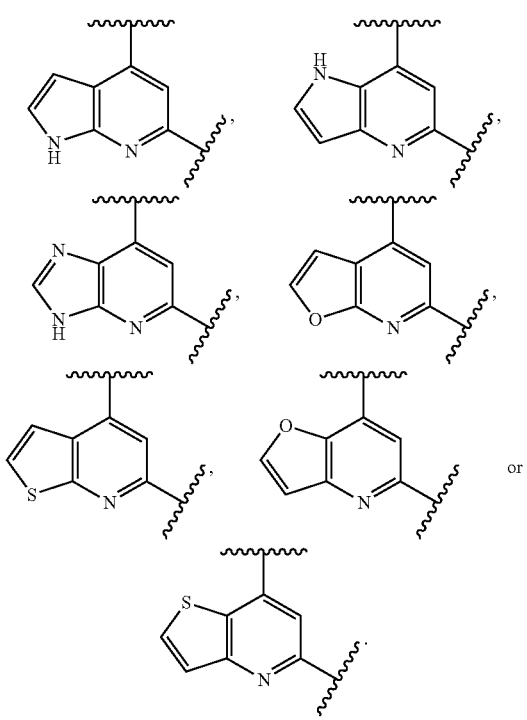

Another embodiment provides the compound of Formula (I), or a pharmaceutically acceptable salt thereof, selected from:

N-((6-amino-2,4-dimethylpyridin-3-yl)methyl)-1-((3-chloroquinolin-6-yl)methyl)-1H-pyrazole-3-carboxamide,
N-((6-amino-2,4-dimethylpyridin-3-yl)methyl)-1-((3-chloroquinolin-6-yl)methyl)-1H-imidazole-4-carboxamide,
N-((6-amino-2,4-dimethylpyridin-3-yl)methyl)-1-((3-chloroquinolin-6-yl)methyl)-1H-1,2,4-triazole-3-carboxamide,
N-((6-amino-2,4-dimethylpyridin-3-yl)methyl)-2-((3-chloroquinolin-6-yl)methyl)-1H-imidazole-5-carboxamide,
N-((6-amino-2,4-dimethylpyridin-3-yl)methyl)-3-((3-chloroquinolin-6-yl)methyl)-1,2,4-oxadiazole-5-carboxamide,
N-((6-amino-2,4-dimethylpyridin-3-yl)methyl)-5-((3-chloroquinolin-6-yl)methyl)-1,2,4-oxadiazole-3-carboxamide,
N-((6-amino-2,4-dimethylpyridin-3-yl)methyl)-1-((3-chloroquinolin-6-yl)methyl)-1H-pyrrolo[3,2-b]pyridine-3-carboxamide,
N-((6-amino-2,4-dimethylpyridin-3-yl)methyl)-3-((3-chloroquinolin-6-yl)methyl)imidazo[1,5-a]pyridine-1-carboxamide,
N-((6-amino-2,4-dimethylpyridin-3-yl)methyl)-1-((3-chloroquinolin-6-yl)methyl)-1H-1,2,3-triazole-4-carboxamide,
N-((6-amino-2,4-dimethylpyridin-3-yl)methyl)-1-((3-chloroquinolin-6-yl)methyl)-1H-indole-3-carboxamide
N-((6-amino-2,4-dimethylpyridin-3-yl)methyl)-1-((3-chloroquinolin-6-yl)methyl)-1H-pyrrolo[2,3-b]pyridine-3-carboxamide,
N-((6-amino-2,4-dimethylpyridin-3-yl)methyl)-1-((3-chloroquinolin-6-yl)methyl)-1H-indazole-3-carboxamide,
N-((6-amino-2,4-dimethylpyridin-3-yl)methyl)-2-((3-chloroquinolin-6-yl)methyl)-2H-indazole-3-carboxamide,
N-((6-amino-2,4-dimethylpyridin-3-yl)methyl)-1-((3-chloroquinolin-6-yl)methyl)-3-(trifluoromethyl)-1H-pyrazole-4-carboxamide,
N-((6-amino-2,4-dimethylpyridin-3-yl)methyl)-1-((3-chloroquinolin-6-yl)methyl)-1H-pyrrolo[2,3-c]pyridine-3-carboxamide,
3-amino-N-((6-amino-2,4-dimethylpyridin-3-yl)methyl)-1-((3-chloroquinolin-6-yl)methyl)-1H-pyrazole-4-carboxamide,
N-((6-amino-2,4-dimethylpyridin-3-yl)methyl)-1-((3-chloroquinolin-6-yl)methyl)-4-nitro-1H-pyrazole-3-carboxamide,
4-acetamido-N-((6-amino-2,4-dimethylpyridin-3-yl)methyl)-1-((3-chloroquinolin-6-yl)methyl)-1H-pyrazole-3-carboxamide,
5-amino-N-((6-amino-2,4-dimethylpyridin-3-yl)methyl)-1-((3-chloroquinolin-6-yl)methyl)-1H-1,2,4-triazole-3-carboxamide,
N-((6-amino-2,4-dimethylpyridin-3-yl)methyl)-2-((3-chloroquinolin-6-yl)methyl)-2H-1,2,3-triazole-4-carboxamide,
N-((6-amino-2,4-dimethylpyridin-3-yl)methyl)-1-((3-chloroquinolin-6-yl)methyl)-4-(trifluoromethyl)-1H-pyrazole-3-carboxamide,
N-((6-amino-2,4-dimethylpyridin-3-yl)methyl)-1-((3-chloroquinolin-6-yl)methyl)imidazo[1,5-a]pyridine-3-carboxamide,
4-amino-N-((6-amino-2,4-dimethylpyridin-3-yl)methyl)-1-((3-chloroquinolin-6-yl)methyl)-1H-pyrazole-3-carboxamide,
N-((6-amino-2,4-dimethylpyridin-3-yl)methyl)-1-((3-chloroquinolin-6-yl)methyl)-3-cyano-1H-pyrazole-4-carboxamide,
N4-((6-amino-2,4-dimethylpyridin-3-yl)methyl)-1-((3-chloroquinolin-6-yl)methyl)-1H-pyrazole-3,4-dicarboxamide, N-((6-amino-2,4-dimethylpyridin-3-yl)methyl)-3-(aminomethyl)-1-((3-chloroquinolin-6-yl)methyl)-1H-pyrazole-4-carboxamide, 2-amino-N-((6-amino-2,4-dimethylpyridin-3-yl)methyl)-1-((3-chloroquinolin-6-yl)methyl)-1H-imidazole-4-carboxamide, N-((6-amino-2,4-dimethylpyridin-3-yl)methyl)-2-((3-chloroquinolin-6-yl)methyl)oxazole-4-carboxamide, N-((6-amino-2,4-dimethylpyridin-3-yl)methyl)-5-((3-chloroquinolin-6-yl)methyl)-1,3,4-oxadiazole-2-carboxamide, N-((6-amino-2,4-dimethylpyridin-3-yl)methyl)-5-((3-chloroquinolin-6-yl)methyl)oxazole-2-carboxamide, N-((6-amino-2,4-dimethylpyridin-3-yl)methyl)-7-((3-chloroquinolin-6-yl)methyl)-7H-pyrrolo[2,3-d]pyrimidine-5-carboxamide, 4-amino-N-((6-amino-2,4-dimethylpyridin-3-yl)methyl)-1-((3-chloroquinolin-6-yl)methyl)-1H-indazole-3-carboxamide, 4-amino-N-((6-amino-2,4-dimethylpyridin-3-yl)methyl)-7-((3-chloroquinolin-6-yl)methyl)-7H-pyrrolo[2,3-d]pyrimidine-5-carboxamide, N-((6-amino-2,4-dimethylpyridin-3-yl)methyl)-1-((3-chloroquinolin-6-yl)methyl)-1H-pyrrolo[3,2-c]pyridine-3-carboxamide, N-((6-amino-2,4-dimethylpyridin-3-yl)methyl)-1-((3-chloroquinolin-6-yl)methyl)-4-cyano-1H-pyrazole-3-carboxamide, N-((6-amino-2,4-dimethylpyridin-3-yl)methyl)-2-((3-chloroquinolin-6-yl)methyl)-4-(trifluoromethyl)oxazole-5-carboxamide, N-((6-amino-2,4-dimethylpyridin-3-yl)methyl)-1-((3-chloroquinolin-6-yl)methyl)-3-methyl-1H-pyrazole-4-carboxamide, N-((6-amino-2,4-dimethylpyridin-3-yl)methyl)-1-((3-chloroquinolin-6-yl)methyl)-3-methoxy-1H-pyrazole-4-carboxamide, N-((6-amino-2,4-dimethylpyridin-3-yl)methyl)-1-((3-chloroquinolin-6-yl)methyl)-5-cyano-1H-pyrazole-4-carboxamide, N-((6-amino-2,4-dimethylpyridin-3-yl)methyl)-5-((3-chloroquinolin-6-yl)methyl)-1H-imidazole-2-carboxamide, N-((5-chloro-1H-indazol-3-yl)methyl)-5-((3-chloroquinolin-6-yl)methyl)-1,3,4-oxadiazole-2-carboxamide, N-((3-chloro-4-fluoro-1H-indol-5-yl)methyl)-5-((3-chloroquinolin-6-yl)methyl)-1,3,4-oxadiazole-2-carboxamide, N-((3-chloro-6-fluoro-1H-indol-5-yl)methyl)-5-((3-chloroquinolin-6-yl)methyl)-1,3,4-oxadiazole-2-carboxamide, N-((3-chloro-1H-pyrrolo[2,3-b]pyridin-5-yl)methyl)-5-((3-chloroquinolin-6-yl)methyl)-1,3,4-oxadiazole-2-carboxamide, N-((1-aminoisoquinolin-6-yl)methyl)-5-((3-chloroquinolin-6-yl)methyl)-1,3,4-oxadiazole-2-carboxamide, N-((3-chloro-4-fluoro-1H-indol-5-yl)methyl)-1-((3-chloroquinolin-6-yl)methyl)-3-cyano-1H-pyrazole-4-carboxamide, N-((5-chloro-1H-indazol-3-yl)methyl)-1-((3-chloroquinolin-6-yl)methyl)-3-cyano-1H-pyrazole-4-carboxamide, N-((1-aminoisoquinolin-6-yl)methyl)-1-((3-chloroquinolin-6-yl)methyl)-3-cyano-1H-pyrazole-4-carboxamide, N-((3-chloro-1H-pyrrolo[2,3-b]pyridin-5-yl)methyl)-1-((3-chloroquinolin-6-yl)methyl)-3-cyano-1H-pyrazole-4-carboxamide, N-((3-chloro-6-fluoro-1H-indol-5-yl)methyl)-1-((3-chloroquinolin-6-yl)methyl)-3-cyano-1H-pyrazole-4-carboxamide, N-((6-amino-2,4-dimethylpyridin-3-yl)methyl)-1-((3-chloro-8-fluoroquinolin-6-yl)methyl)-3-cyano-1H-pyrazole-4-carboxamide, N-((3-chloro-6-fluoro-1H-indol-5-yl)methyl)-1-((3-chloro-8-fluoroquinolin-6-yl)methyl)-3-cyano-1H-pyrazole-4-carboxamide, N-((1-aminoisoquinolin-6-yl)methyl)-1-((3-chloro-8-fluoroquinolin-6-yl)methyl)-3-cyano-1H-pyrazole-4-carboxamide, N-((5-chloro-1H-indazol-3-yl)methyl)-1-((3-chloro-8-fluoroquinolin-6-yl)methyl)-3-cyano-1H-pyrazole-4-carboxamide, N-((3-chloro-H-pyrrolo[2,3-b]pyridin-5-yl)methyl)-1-((3-chloro-8-fluoroquinolin-6-yl)methyl)-3-cyano-1H-pyrazole-4-carboxamide, N-((3-chloro-4-fluoro-1H-indol-5-yl)methyl)-1-((3-chloro-8-fluoroquinolin-6-yl)methyl)-3-cyano-1H-pyrazole-4-carboxamide, N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide, N-((1-aminoisoquinolin-6-yl)methyl)-1-((3-chloro-8-(2-hydroxypropan-2-yl)quinolin-6-yl)methyl)-3-cyano-1H-pyrazole-4-carboxamide, N-((6-amino-2,4-dimethylpyridin-3-yl)methyl)-1-((3-chloro-8-sulfamoylquinolin-6-yl)methyl)-3-cyano-1H-pyrazole-4-carboxamide, N-((6-amino-2,4-dimethylpyridin-3-yl)methyl)-3-cyano-1-((3-methyl-8-(methylsulfonyl)quinolin-6-yl)methyl)-1H-pyrazole-4-carboxamide, N-((6-amino-2,4-dimethylpyridin-3-yl)methyl)-3-cyano-1-((8-cyano-3-methylquinolin-6-yl)methyl)-1H-pyrazole-4-carboxamide, N4-((6-amino-2,4-dimethylpyridin-3-yl)methyl)-1-((8-cyano-3-methylquinolin-6-yl)methyl)-1H-pyrazole-3,4-dicarboxamide, N-((6-amino-2,4-dimethylpyridin-3-yl)methyl)-1-((3-chloroquinolin-6-yl)methyl)-4-cyano-1H-pyrazole-5-carboxamide, N-((6-amino-2,4-dimethylpyridin-3-yl)methyl)-3-cyano-1-((3-cyclopropylquinolin-6-yl)methyl)-1H-pyrazole-4-carboxamide, N-((6-amino-2-methylpyridin-3-yl)methyl)-3-cyano-1-((3-cyclopropylquinolin-6-yl)methyl)-1H-pyrazole-4-carboxamide, N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide, N-((6-amino-2,4-dimethylpyridin-3-yl)methyl)-1-((3-chloro-8-(methylsulfonyl)quinolin-6-yl)methyl)-3-cyano-1H-pyrazole-4-carboxamide, N-((6-amino-2,4-dimethylpyridin-3-yl)methyl)-1-((3-chloro-8-cyanoquinolin-6-yl)methyl)-3-cyano-1H-pyrazole-4-carboxamide, N-((6-amino-2,4-dimethylpyridin-3-yl)methyl)-1-((3-chloro-8-fluoroquinolin-6-yl)methyl)-5-cyano-1H-pyrazole-4-carboxamide, N4-((6-amino-2,4-dimethylpyridin-3-yl)methyl)-1-((3-chloro-8-fluoroquinolin-6-yl)methyl)-1H-pyrazole-4,5-dicarboxamide, 6-((4-((((6-amino-2,4-dimethylpyridin-3-yl)methyl)carbamoyl)-3-cyano-1H-pyrazol-1-yl)methyl)-3-chloroquinoline-8-carboxamide, N-((6-amino-2,4-dimethylpyridin-3-yl)methyl)-3-cyano-1-((3-(trifluoromethyl)quinolin-6-yl)methyl)-1H-pyrazole-4-carboxamide, N-((6-amino-2-methylpyridin-3-yl)methyl)-3-cyano-1-((3-(trifluoromethyl)quinolin-6-yl)methyl)-1H-pyrazole-4-carboxamide, N-((6-amino-2,4-dimethylpyridin-3-yl)methyl)-5-((3-chloro-8-fluoroquinolin-6-yl)methyl)-1,3,4-oxadiazole-2-carboxamide, N-((6-amino-2,4-dimethylpyridin-3-yl)methyl)-1-((3-chloroquinolin-6-yl)methyl)-4-cyano-1H-pyrazolo[4,3-c]pyridine-3-carboxamide, N-((6-amino-2-methylpyridin-3-yl)methyl)-1-((3-chloroquinolin-6-yl)methyl)-3-cyano-H-pyrazole-4-carboxamide, 6-((4-((((6-amino-2,4-dimethylpyridin-3-yl)methyl)carbamoyl)-3-cyano-1H-pyrazol-1-yl)methyl)-3-methylquinoline-8-carboxamide, N-((6-amino-2-methylpyridin-3-yl)methyl)-5-((3-chloroquinolin-6-yl)methyl)-1,3,4-oxadiazole-2-carboxamide, N-((6-amino-2,4-dimethylpyridin-3-yl)methyl)-2-(3-chloroquinoline-6-carbonyl)oxazole-5-carboxamide, N-((6-amino-2,4-dimethylpyridin-3-yl)methyl)-3-cyano-1-((3-methylquinolin-6-yl)methyl)-1H-pyrazole-4-carboxamide, N-((6-amino-2-methylpyridin-3-yl)methyl)-3-cyano-1-((3-methylquinolin-6-yl)methyl)-1H-pyrazole-4-carboxamide, N-((6-amino-2-methylpyridin-3-yl)methyl)-2-((3-chloroquinolin-6-yl)methyl)oxazole-4-carboxamide, N-((6-amino-2-methylpyridin-3-yl)methyl)-5-((3-chloroquinolin-6-yl)methyl)oxazole-2-carboxamide, N-((6-amino-2-methylpyridin-3-yl)methyl)-1-((3-chloroquinolin-6-yl)methyl)-3-methyl-H-pyrazole-4-carboxamide, N-((6-amino-2,4-dimethylpyridin-3-yl)methyl)-5-((3-chloro-8-(2-hydroxypropan-2-yl)quinolin-6-yl)methyl)-1,3,4-oxadiazole-2-carboxamide, N-((6-amino-2,4-dimethylpyridin-3-yl)methyl)-2-((3-chloroquinolin-6-yl)methyl)-4-cyanooxazole-5-carboxamide, N-((6-amino-2-methylpyridin-3-yl)methyl)-2-((3-chloroquinolin-6-yl)methyl)-4-cyanooxazole-5-carboxamide, N-((6-amino-2,4-dimethylpyridin-3-yl)methyl)-2-((3-chloroquinolin-6-yl)methyl)oxazole-5-carboxamide, N-((6-amino-2-methylpyridin-3-yl)methyl)-2-((3-chloroquinolin-6-yl)methyl)oxazole-5-carboxamide, N-((6-amino-2,4-dimethylpyridin-3-yl)methyl)-1-((3-chloroquinolin-6-yl)methyl)-3-(difluoromethyl)-1H-pyrazole-4-carboxamide, N-((6-amino-2,4-dimethylpyridin-3-yl)methyl)-1-((3-chloroquinolin-6-yl)methyl)-3-(hydroxymethyl)-1H-pyrazole-4-carboxamide, N-((6-amino-2,4-dimethylpyridin-3-yl)methyl)-1-((3-chloroquinolin-6-yl)methyl)-3-(fluoromethyl)-1H-pyrazole-4-carboxamide, N-((6-amino-2,4-dimethylpyridin-3-yl)methyl)-1-((3-chloroquinolin-6-yl)methyl)-3-(1-hydroxyethyl)-1H-pyrazole-4-carboxamide, N-((6-amino-2,4-dimethylpyridin-3-yl)methyl)-2-((3-chloroquinolin-6-yl)methyl)-5-cyano-2H-1,2,3-triazole-4-carboxamide,N-((6-amino-2,4-dimethylpyridin-3-yl)methyl)-5-((3-chloroquinolin-6-yl)methyl)-4H-1,2,4-triazole-3-carboxamide, N-((6-amino-2-methylpyridin-3-yl)methyl)-5-((3-chloroquinolin-6-yl)methyl)-4H-1,2,4-triazole-3-carboxamide, N-((6-amino-2,4-dimethylpyridin-3-yl)methyl)-5-((3-chloroquinolin-6-yl)methyl)-4-methyl-4H-1,2,4-triazole-3-carboxamide, N-((6-amino-2,4-dimethylpyridin-3-yl)methyl)-3-((3-chloroquinolin-6-yl)methyl)-1-methyl-1H-1,2,4-triazole-5-carboxamide, N-((6-amino-2,4-dimethylpyridin-3-yl)methyl)-5-bromo-1-((3-chloroquinolin-6-yl)methyl)-1H-1,2,4-triazole-3-carboxamide, N-((6-amino-2,4-dimethylpyridin-3-yl)methyl)-1-((3-chloroquinolin-6-yl)methyl)-5-cyano-1H-1,2,4-triazole-3-carboxamide, methyl 3-((((6-amino-2,4-dimethylpyridin-3-yl)methyl)carbamoyl)-1-((3-chloroquinolin-6-yl)methyl)-1H-1,2,4-triazole-5-carboxylate, N-((6-amino-2,4-dimethylpyridin-3-yl)methyl)-2-((3-chloroquinolin-6-yl)methyl)-1H-imidazole-4-carboxamide, N-((6-amino-2,4-dimethylpyridin-3-yl)methyl)-2-((3-chloroquinolin-6-yl)methyl)-1-methyl-1H-imidazole-4-carboxamide, N-((6-amino-2,4-dimethylpyridin-3-yl)methyl)-2-((3-chloroquinolin-6-yl)methyl)-1-methyl-1H-imidazole-5-carboxamide, N-((6-amino-2,4-dimethylpyridin-3-yl)methyl)-4-bromo-2-((3-chloroquinolin-6-yl)methyl)-1H-imidazole-5-carboxamide, N-((6-amino-2,4-dimethylpyridin-3-yl)methyl)-1-((3-chloroquinolin-6-yl)methyl)-5-cyano-1H-1,2,4-triazole-3-carboxamide, N-((6-amino-2,4-dimethylpyridin-3-yl)methyl)-1-((3-chloroquinolin-6-yl)methyl)-5-cyano-1H-pyrazole-3-carboxamide, N-((6-amino-2,4-dimethylpyridin-3-yl)methyl)-1-((3-chloroquinolin-6-yl)methyl)-3-cyano-1H-pyrazole-5-carboxamide, N-((6-amino-2,4-dimethylpyridin-3-yl)methyl)-1-((3-chloroquinolin-6-yl)methyl)-2-(hydroxymethyl)-1H-imidazole-4-carboxamide, N4-((6-amino-2,4-dimethylpyridin-3-yl)methyl)-1-((3-chloroquinolin-6-yl)methyl)-1H-imidazole-2,4-dicarboxamide, N-((6-amino-2,4-dimethylpyridin-3-yl)methyl)-2-(aminomethyl)-1-((3-chloroquinolin-6-yl)methyl)-1H-imidazole-4-carboxamide, N-((6-amino-2,4-dimethylpyridin-3-yl)methyl)-1-((3-chloroquinolin-6-yl)methyl)-2-cyano-1H-imidazole-4-carboxamide, N-((6-amino-2,4-dimethylpyridin-3-yl)methyl)-2-((3-chloroquinolin-6-yl)methyl)oxazole-5-carboxamide, N-((6-amino-2,4-dimethylpyridin-3-yl)methyl)-2-((3-chloroquinolin-6-yl)methyl)-5-(trifluoromethyl)-2H-1,2,3-triazole-4-carboxamide, N-((6-amino-2,4-dimethylpyridin-3-yl)methyl)-1-((3-chloroquinolin-6-yl)methyl)-5-(trifluoromethyl)-1H-pyrazole-3-carboxamide, N-((6-amino-2,4-dimethylpyridin-3-yl)methyl)-5-chloro-1-((3-chloroquinolin-6-yl)methyl)-1H-pyrrolo[2,3-c]pyridine-3-carboxamide, N-((6-amino-2,4-dimethylpyridin-3-yl)methyl)-1-((3-chloroquinolin-6-yl)methyl)-4-oxo-4,5-dihydro-1H-pyrrolo[3,2-c]pyridine-3-carboxamide, N-((6-amino-2,4-dimethylpyridin-3-yl)methyl)-4-chloro-1-((3-chloroquinolin-6-yl)methyl)-1H-pyrazolo[4,3-c]pyridine-3-carboxamide N-((6-amino-2,4-dimethylpyridin-3-yl)methyl)-1-((3-chloroquinolin-6-yl)methyl)-4-oxo-4,5-dihydro-1H-pyrazolo[4,3-c]pyridine-3-carboxamide, N-((6-amino-2,4-dimethylpyridin-3-yl)methyl)-1-((3-chloroquinolin-6-yl)methyl)-5-methoxy-1H-pyrrolo[2,3-c]pyridine-3-carboxamide N-((6-amino-2,4-dimethylpyridin-3-yl)methyl)-1-((3-chloroquinolin-6-yl)methyl)-5-methoxy-1H-pyrazolo[3,4-c]pyridine-3-carboxamide N-((6-amino-2,4-dimethylpyridin-3-yl)methyl)-1-((3-chloroquinolin-6-yl)methyl)-4-cyano-1H-pyrrolo[2,3-c]pyridine-3-carboxamide, N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide, N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide N-((6-amino-2,4-dimethylpyridin-3-yl)methyl)-1-((3-chloroquinolin-6-yl)methyl)-5-oxo-4,5-dihydro-1H-pyrrolo[3,2-b]pyridine-3-carboxamide, N-((6-amino-2,4-dimethylpyridin-3-yl)methyl)-1-((3-chloroquinolin-6-yl)methyl)-4-cyano-1H-pyrrolo[2,3-b]pyridine-3-carboxamide, N-((6-amino-2,4-dimethylpyridin-3-yl)methyl)-1-((3-chloroquinolin-6-yl)methyl)-5-methoxy-1H-pyrrolo[3,2-b]pyridine-3-carboxamide, N-((6-amino-2,4-dimethylpyridin-3-yl)methyl)-1-((3-chloroquinolin-6-yl)methyl)-4-cyano-1H-pyrazolo[3,4-c]pyridine-3-carboxamide, N-((6-amino-2,4-dimethylpyridin-3-yl)methyl)-1-((3-chloroquinolin-6-yl)methyl)-5-cyano-1H-pyrazolo[3,4-c]pyridine-3-carboxamide, N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide, N-((6-amino-2,4-dimethylpyridin-3-yl)methyl)-1-((3-chloroquinolin-6-yl)methyl)-4-cyano-1H-pyrrolo[3,2-c]pyridine-3-carboxamide, N-((6-amino-2,4-dimethylpyridin-3-yl)methyl)-1-((3-chloroquinolin-6-yl)methyl)-5-cyano-1H-pyrrolo[2,3-c]pyridine-3-carboxamide, N-((6-amino-2,4-dimethylpyridin-3-yl)methyl)-1-((3-chloroquinolin-6-yl)methyl)-5-cyano-1H-pyrrolo[2,3-b]pyridine-3-carboxamide N-((6-amino-2,4-dimethylpyridin-3-yl)methyl)-7-((3-chloroquinolin-6-yl)methyl)-4-cyano-7H-pyrrolo[2,3-d]pyrimidine-5-carboxamide N-((6-amino-2,4-dimethylpyridin-3-yl)methyl)-1-((3-chloroquinolin-6-yl)methyl)-5-methoxy-1H-pyrazolo[4,3-b]pyridine-3-carboxamide, N-((6-amino-2,4-dimethylpyridin-3-yl)methyl)-1-((3-chloroquinolin-6-yl)methyl)-5-oxo-4,5-dihydro-1H-pyrazolo[4,3-b]pyridine-3-carboxamide, N-((6-amino-2-methylpyridin-3-yl)methyl)-1-((3-chloroquinolin-6-yl)methyl)-5-oxo-4,5-dihydro-1H-pyrazolo[4,3-b]pyridine-3-carboxamide, 4-amino-N-((6-amino-2,4-dimethylpyridin-3-yl)methyl)-2-((3-chloroquinolin-6-yl)methyl)-2H-indazole-3-carboxamide, N-((6-amino-2,4-dimethylpyridin-3-yl)methyl)-1-((3-chloroquinolin-6-yl)methyl)-4-(trifluoromethyl)-1H-1,2,3-triazole-5-carboxamide, or ethyl 3-(((6-amino-2,4-dimethylpyridin-3-yl)methyl)carbamoyl)-1-((3-chloroquinolin-6-yl)methyl)-1H-1,2,4-triazole-5-carboxylate.

One embodiment provides a compound, or a pharmaceutically acceptable salt thereof, having the structure of Formula (Ia):

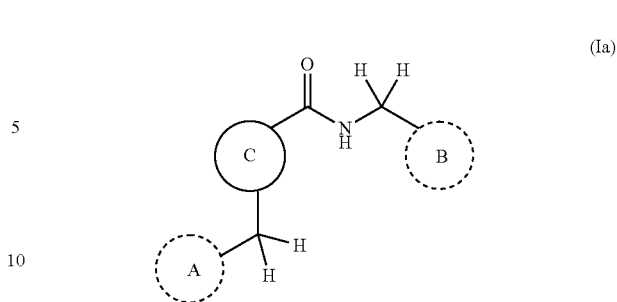

wherein,

Ring A is an optionally substituted bicyclic heteroaryl ring;

Ring B is an optionally substituted monocyclic heteroaryl ring or optionally substituted bicyclic heteroaryl ring; and Ring C is a 1,3-substituted heteroaryl ring system chosen from:

(a) pyrazole, imidazole, triazole, oxadiazole, thiadiazole, thiophene, thiazole, isothiazole, oxazole, isoxazole, furan or pyrrole;

(b) indole, indazole, pyrrolopyridine, or imidazopyridine wherein the 1,3-substitution occurs on the five-membered ring of the ring;

(c) naphthyridine or quinoline wherein the 1,3-substitution occurs at the 2- and 4-position of the ring; or (d) pyrrolopyridine, imidazopyridine, furopyridine, or thienopyridine wherein the 1,3-substitution occurs on the pyridine ring of the ring.

Another embodiment provides the compound of Formula (Ia), or a pharmaceutically acceptable salt thereof, wherein Ring A is selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl.

Another embodiment provides the compound of Formula (Ia), or a pharmaceutically acceptable salt thereof, wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl.

Another embodiment provides the compound of Formula (Ia), or a pharmaceutically acceptable salt thereof, wherein Ring A is an optionally substituted quinolin-6-yl or an optionally substituted quinolin-3-yl. Another embodiment provides the compound of Formula (Ia), or a pharmaceutically acceptable salt thereof, wherein the optionally substituted quinolin-6-yl or optionally substituted quinolin-3-yl is substituted with at least one substituent selected from optionally substituted C1-C3 alkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or —OMe. Another embodiment provides the compound of Formula (Ia), or a pharmaceutically acceptable salt thereof, wherein the optionally substituted quinolin-6-yl is substituted at least at the 3-position. Another embodiment provides the compound of Formula (Ia), or a pharmaceutically acceptable salt thereof, wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl. Another embodiment provides the compound of Formula (Ia), or a pharmaceutically acceptable salt thereof, wherein the optionally substituted quinolin-3-yl is substituted at least at the 6-position or the 7-position.

Another embodiment provides the compound of Formula (Ia), or a pharmaceutically acceptable salt thereof, wherein Ring B is selected from an optionally substituted monocyclic heteroaryl ring. Another embodiment provides the compound of Formula (Ia), or a pharmaceutically acceptable salt thereof, wherein the optionally substituted monocyclic heteroaryl ring is selected from optionally substituted imidazolyl, optionally substituted pyrazolyl, optionally substituted pyridinyl, optionally substituted pyridazinyl, optionally substituted pyrimidinyl, or optionally substituted pyrazinyl. Another embodiment provides the compound of Formula (Ia), or a pharmaceutically acceptable salt thereof, wherein the optionally substituted monocyclic heteroaryl ring is an optionally substituted pyridinyl. Another embodiment provides the compound of Formula (Ia), or a pharmaceutically acceptable salt thereof, wherein the optionally substituted pyridinyl is an optionally substituted aminopyridinyl. Another embodiment provides the compound of Formula (Ia), or a pharmaceutically acceptable salt thereof, wherein the optionally substituted aminopyridinyl is an optionally substituted 6-aminopyridin-3-yl.

Another embodiment provides the compound of Formula (Ia), or a pharmaceutically acceptable salt thereof, wherein Ring B is selected from an optionally substituted bicyclic heteroaryl ring. Another embodiment provides the compound of Formula (Ia), or a pharmaceutically acceptable salt thereof, wherein the optionally substituted bicyclic heteroaryl ring is selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl. Another embodiment provides the compound of Formula (Ia), or a pharmaceutically acceptable salt thereof, wherein the optionally substituted bicyclic heteroaryl ring is an optionally substituted indolyl or an optionally substituted indazolyl. Another embodiment provides the compound of Formula (Ia), or a pharmaceutically acceptable salt thereof, wherein the optionally substituted indolyl is an optionally substituted indol-5-yl or an optionally substituted indazol-5-yl. Another embodiment provides the compound of Formula (Ia), or a pharmaceutically acceptable salt thereof, wherein the optionally substituted bicyclic heteroaryl ring is an optionally substituted 1H-pyrrolo[2,3-b]pyridinyl.

Another embodiment provides the compound of Formula (Ia), or a pharmaceutically acceptable salt thereof, wherein Ring A is an optionally substituted quinolyl; and Ring B is selected from an optionally substituted indolyl, an optionally substituted indazolyl, or an optionally substituted 1H-pyrrolo[2,3-b]pyridinyl.

Another embodiment provides the compound of Formula (Ia), or a pharmaceutically acceptable salt thereof, wherein Ring A is an optionally substituted quinolyl; and Ring B is an optionally substituted 6-aminopyridin-3-yl.

Another embodiment provides the compound of Formula (Ia), or a pharmaceutically acceptable salt thereof, wherein Ring C is chosen from pyrazole, imidazole, triazole, oxadiazole, thiadiazole, thiophene, thiazole, isothiazole, oxazole, isoxazole, furan or pyrrole. Another embodiment provides the compound of Formula (Ia), or a pharmaceutically acceptable salt thereof, wherein Ring C is chosen from:

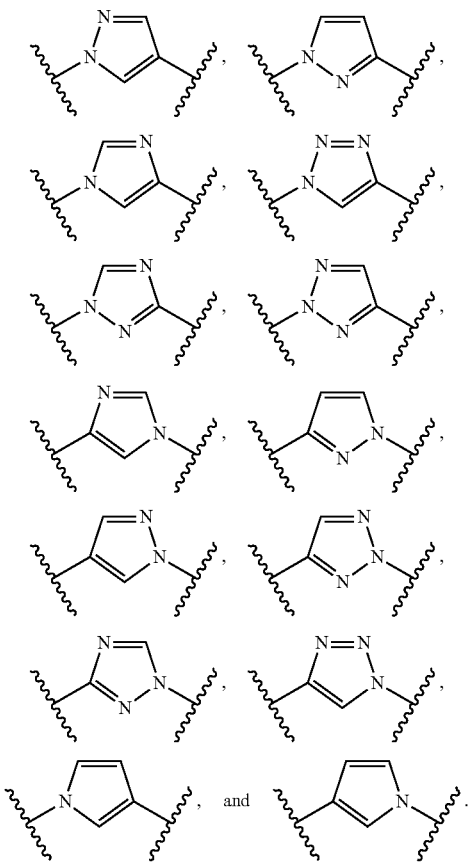

Another embodiment provides the compound of Formula (Ia), or a pharmaceutically acceptable salt thereof, wherein Ring C is chosen from:

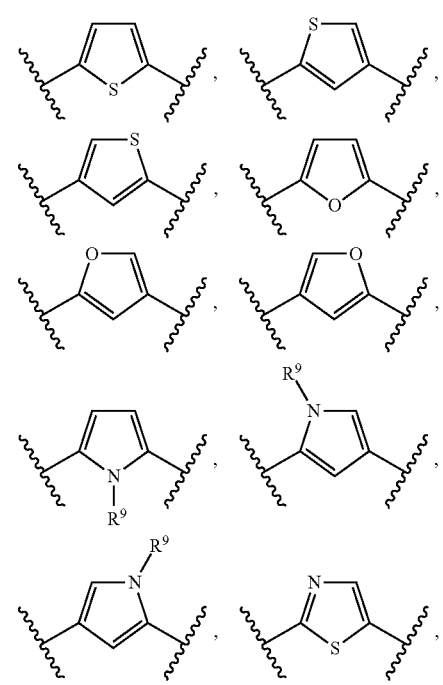

-continued

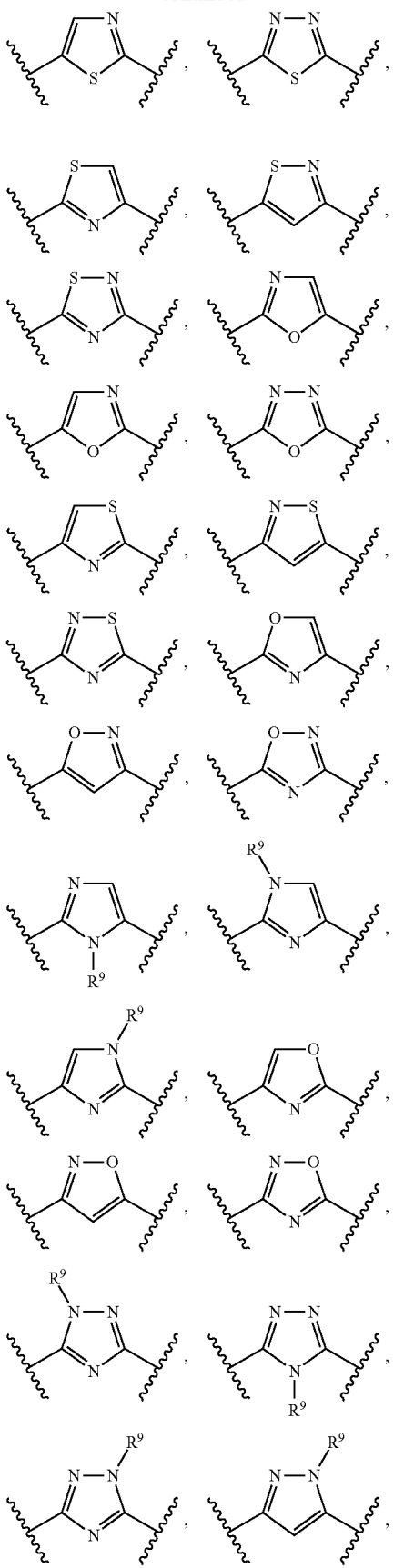

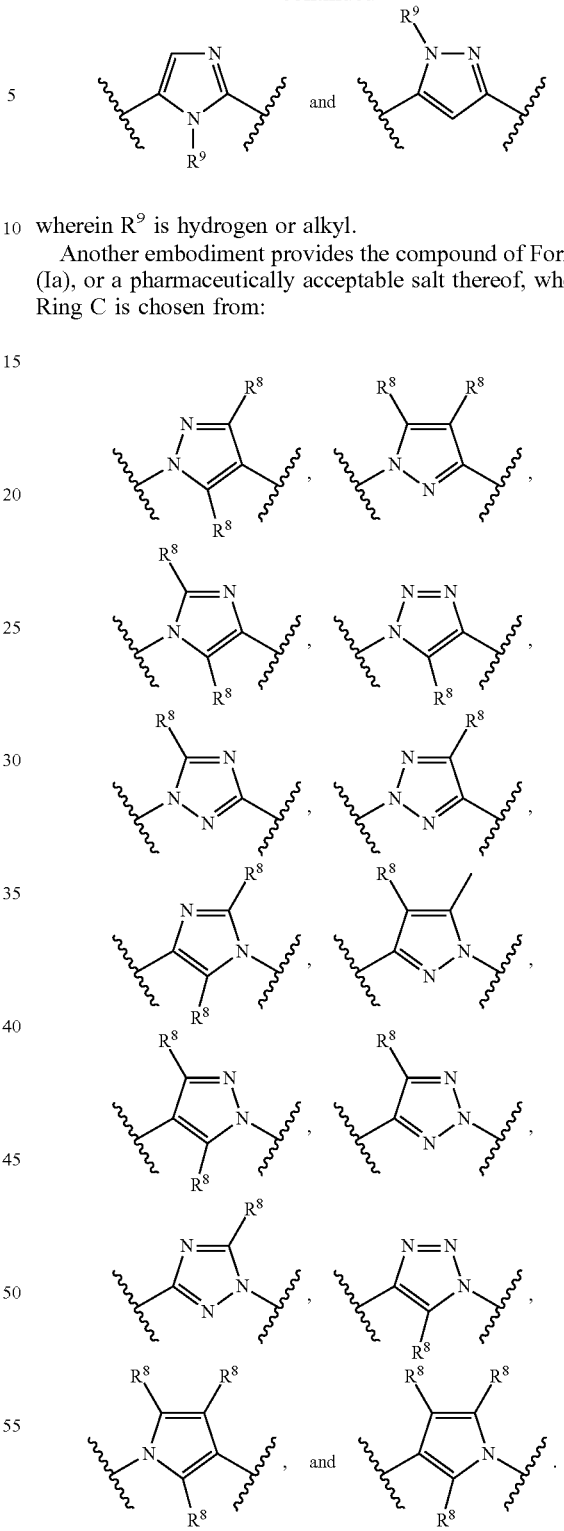

wherein $R^9$ is hydrogen or alkyl.

Another embodiment provides the compound of Formula (Ia), or a pharmaceutically acceptable salt thereof, wherein Ring C is chosen from:

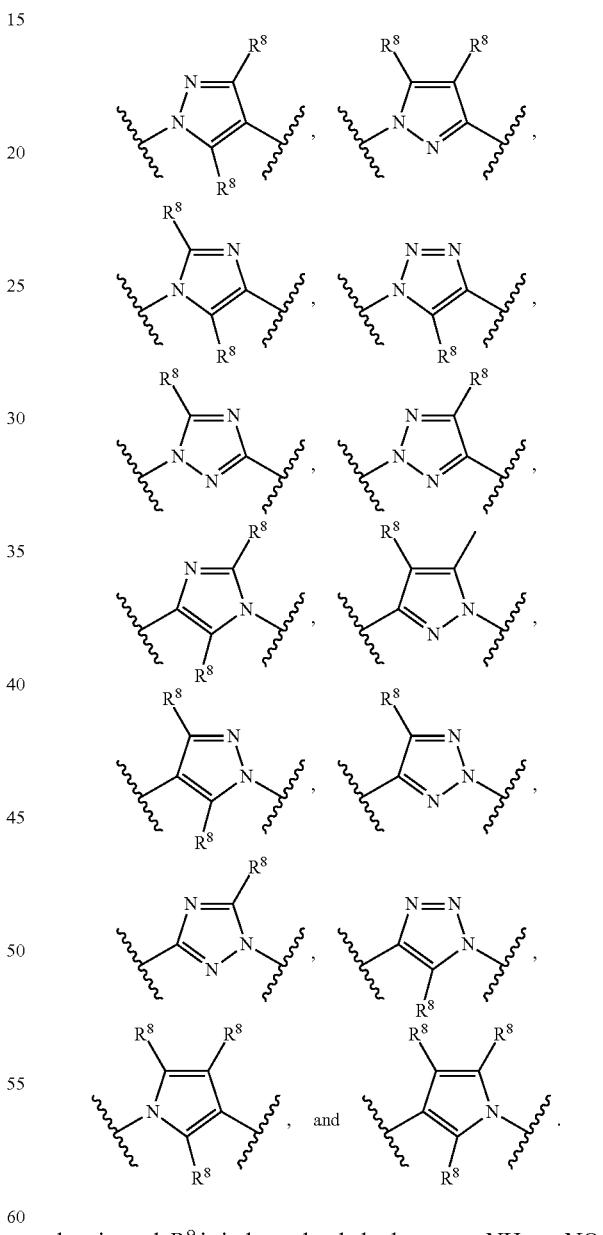

wherein each $R^9$ is independently hydrogen, $-NH_2$, $-NO_2$, $-NHCOCH_3$, $-CN$, $-CF_3$, or optionally substituted C1-C4 alkyl.

Another embodiment provides the compound of Formula (Ia), or a pharmaceutically acceptable salt thereof, wherein Ring C is chosen from indole, indazole, pyrrolopyridine, or imidazopyridine wherein the 1,3-substitution occurs on the five-membered ring of the ring. Another embodiment provides the compound of Formula (Ia), or a pharmaceutically acceptable salt thereof, wherein Ring C is chosen from:

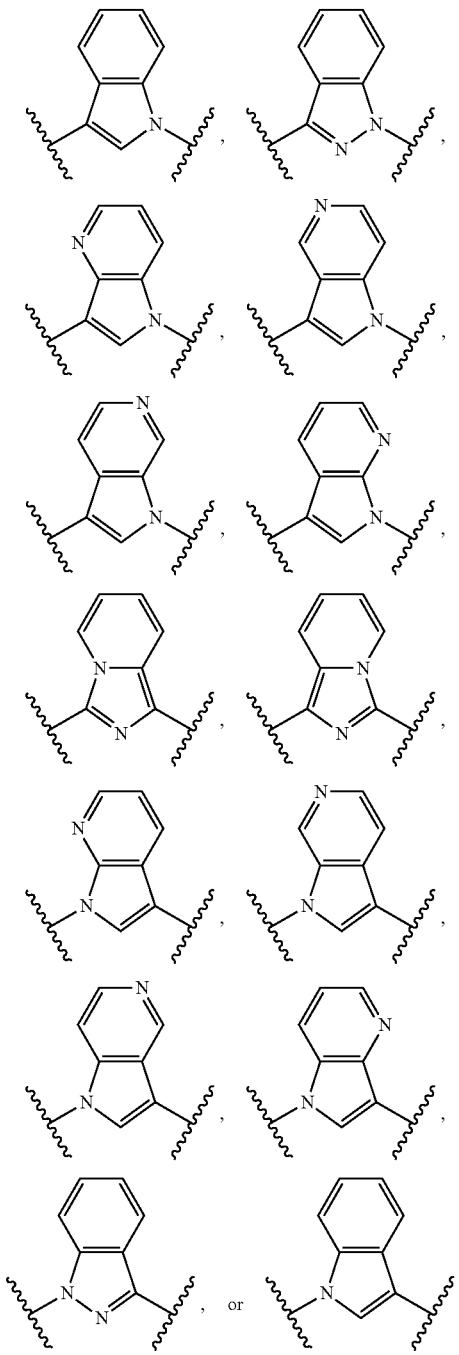

Another embodiment provides the compound of Formula (Ia), or a pharmaceutically acceptable salt thereof, wherein Ring C is chosen from naphthyridine or quinoline wherein the 1,3-substitution occurs at the 2- and 4-position of the ring. Another embodiment provides the compound of Formula (Ia), or a pharmaceutically acceptable salt thereof, wherein Ring C is chosen from:

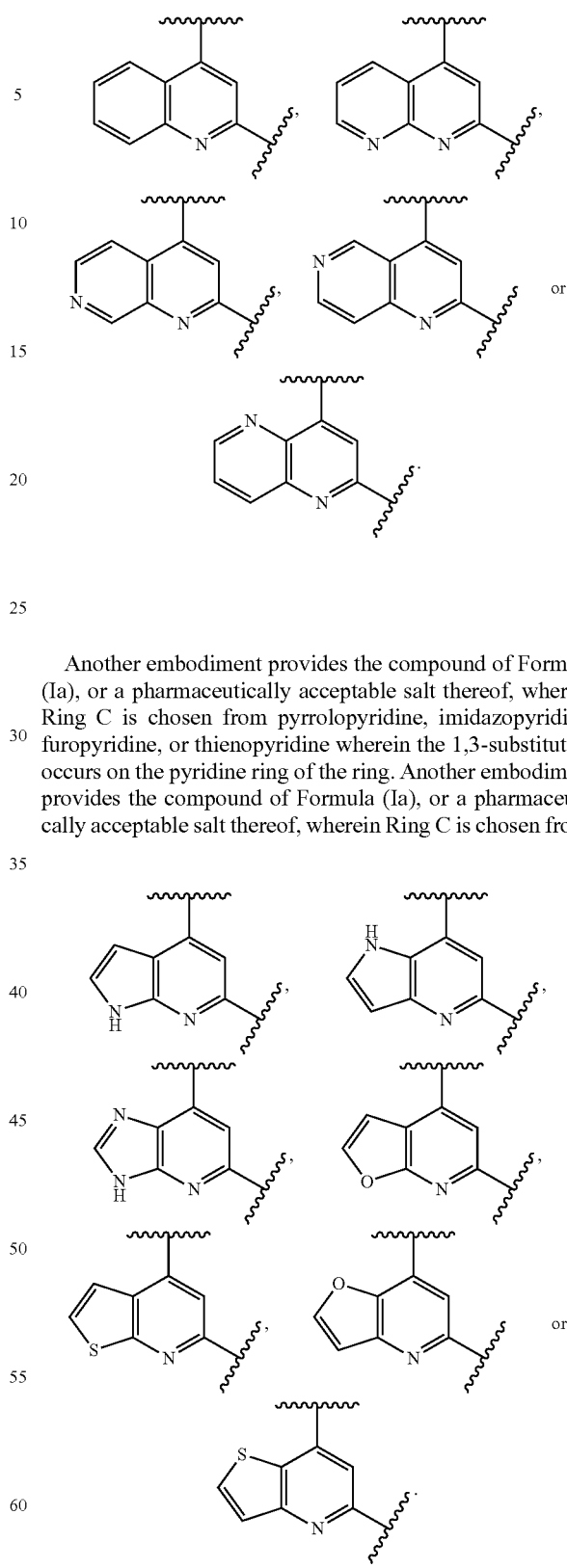

Another embodiment provides the compound of Formula (Ia), or a pharmaceutically acceptable salt thereof, wherein Ring C is chosen from pyrrolopyridine, imidazopyridine, furopyridine, or thienopyridine wherein the 1,3-substitution occurs on the pyridine ring of the ring. Another embodiment provides the compound of Formula (Ia), or a pharmaceutically acceptable salt thereof, wherein Ring C is chosen from:

One embodiment provides a compound, or a pharmaceutically acceptable salt thereof, having the structure of Formula (II):

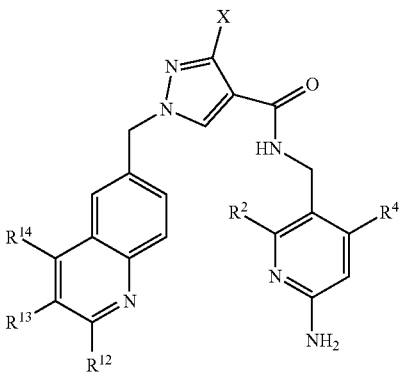

(II)

wherein,

X is selected from —CN, C1-C3alkyl, —O(C1-C3alkyl), —OCF$_3$, —CH$_2$NH$_2$, —CF$_3$, —CF$_2$, —CH$_2$F, —CH$_2$CF$_3$, or C$_2$F$_5$;

R$^2$ and R$^4$ are each independently selected from H or C1-C3alkyl; and

R$^{12}$ is H or C1-C3alkyl; and

R$^{13}$ and R$^{14}$ are each independently H, Cl, F, —CF$_3$, C1-C3alkyl, or C3-C5 cycloalkyl.

Another embodiment provides a compound of Formula (II), or a pharmaceutically acceptable salt thereof, wherein R$^2$ and R$^4$ are methyl, R$^{12}$ and R$^{14}$ are H, R$^{13}$ is Cl, and X is —CN, C1-C3alkyl, —O(C1-C3alkyl), —OCF$_3$, —CH$_2$NH$_2$, —CF$_3$, —C—F$_2$, —CH$_2$F, —CH$_2$CF$_3$, or C$_2$F$_5$.

Another embodiment provides a compound of Formula (II), or a pharmaceutically acceptable salt thereof, wherein R$^2$ and R$^4$ are methyl, R$^{12}$ and R$^{14}$ are H, R$^{13}$ is Cl, and X is —CN, C1-C3alkyl, —O(C1-C3alkyl), —CH$_2$NH$_2$, or —CF$_3$.

Another embodiment provides a compound of Formula (II), or a pharmaceutically acceptable salt thereof, wherein R$^2$ and R$^4$ are methyl, R$^{12}$ and R$^{14}$ are H, R$^{13}$ is Cl, and X is —CN.

Another embodiment provides a compound of Formula (II), or a pharmaceutically acceptable salt thereof, wherein R$^2$ and R$^4$ are methyl, R$^{12}$ and R$^{14}$ are H, R$^{13}$ is Cl, and X is —CF$_3$.

Another embodiment provides a compound of Formula (II), or a pharmaceutically acceptable salt thereof, wherein R$^2$ and R$^4$ are methyl, R$^{12}$ and R$^{14}$ are H, R$^{13}$ is Cl, and X is —CH$_2$NH$_2$.

A compound, or a pharmaceutically acceptable salt thereof, having the structure of Formula (III):

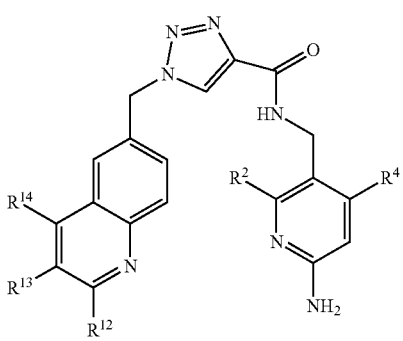

(III)

wherein,

R$^2$ and R$^4$ are each independently selected from H or C1-C3alkyl; and

R$^{12}$ is H or C1-C3alkyl; and

R$^{13}$ and R$^{14}$ are each independently H, Cl, F, —CF$_3$, C1-C3alkyl, or C3-C5 cycloalkyl.

A compound, or a pharmaceutically acceptable salt thereof, having the structure of Formula (IV):

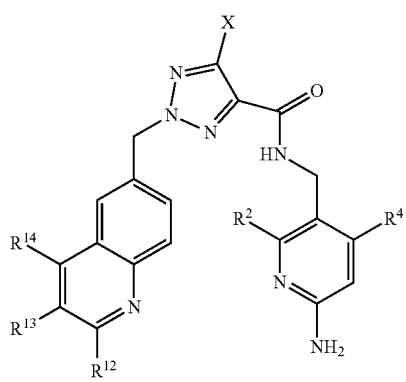

(IV)

wherein,

X is selected from —H, —CN, C1-C3alkyl, —O(C1-C3alkyl), —OCF$_3$, —CH$_2$NH$_2$, —CF$_3$, —CHF$_2$, —CH$_2$F, —CH$_2$CF$_3$, or C$_2$F$_5$;

R$^2$ and R$^4$ are each independently selected from H or C1-C3alkyl; and

R$^{12}$ is H or C1-C3alkyl; and

R$^{13}$ and R$^{14}$ are each independently H, Cl, F, —CF$_3$, C1-C3alkyl, or C3-C5 cycloalkyl.

Another embodiment provides a compound of Formula (IV), or a pharmaceutically acceptable salt thereof, wherein R$^2$ and R$^4$ are methyl, R$^{12}$ and R$^{14}$ are H, R$^{13}$ is Cl, and X is —H, —CN, C1-C3alkyl, —O(C1-C3alkyl), —OCF$_3$, —CH$_2$NH$_2$, —CF$_3$, —CHF$_2$, —CH$_2$F, —CH$_2$CF$_3$, or C$_2$F$_5$.

Another embodiment provides a compound of Formula (IV), or a pharmaceutically acceptable salt thereof, wherein R$^2$ and R$^4$ are methyl, R$^{12}$ and R$^{14}$ are H, R$^{13}$ is Cl, and X is —H, —CN, C1-C3alkyl, —O(C1-C3alkyl), —CH$_2$NH$_2$, or —CF$_3$.

Another embodiment provides a compound of Formula (IV), or a pharmaceutically acceptable salt thereof, wherein R$^2$ and R$^4$ are methyl, R$^{12}$ and R$^{14}$ are H, R$^{13}$ is Cl, and X is —H, —CN, —O(C1-C3alkyl), —CH$_2$NH$_2$, —CF$_3$.

Another embodiment provides a compound of Formula (IV), or a pharmaceutically acceptable salt thereof, wherein R$^2$ and R$^4$ are methyl, R$^{12}$ and R$^{14}$ are H, R$^{13}$ is Cl, and X is —CN, C1-C3alkyl, —O(C1-C3alkyl), —OCF$_3$, —CH$_2$NH$_2$, —CF$_3$, —CHF$_2$, —CH$_2$F, —CH$_2$CF$_3$, or C$_2$F$_5$.

Another embodiment provides a compound of Formula (IV), or a pharmaceutically acceptable salt thereof, wherein R$^2$ and R$^4$ are methyl, R$^{12}$ and R$^{14}$ are H, R$^{13}$ is Cl, and X is —CN, C1-C3alkyl, —O(C1-C3alkyl), —CH$_2$NH$_2$, or —CF$_3$.

A compound, or a pharmaceutically acceptable salt thereof, having the structure of Formula (V):

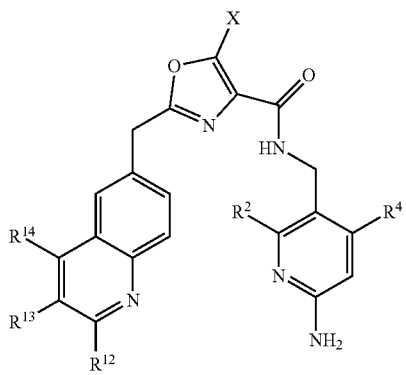

(V)

wherein,

X is selected from —H, —CN, C1-C3alkyl, —O(C1-C3alkyl), —OCF₃, —CH₂NH₂, —CF₃, —CHF₂, —CH₂F, —CH₂CF₃, or C₂F₅;

$R^2$ and $R^4$ are each independently selected from H or C1-C3alkyl; and $R^{12}$ is H or C1-C3alkyl; and $R^{13}$ and $R^{14}$ are each independently H, Cl, F, —CF₃, C1-C3alkyl, or C3-C5 cycloalkyl.

A compound, or a pharmaceutically acceptable salt thereof, having the structure of Formula (VI):

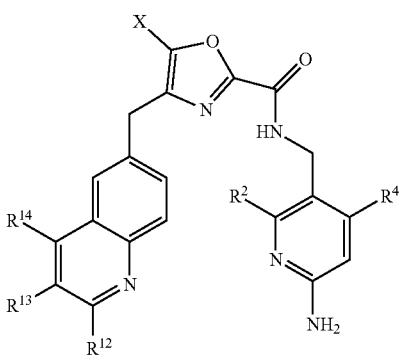

(VI)

wherein,

X is selected from —H, —CN, C1-C3alkyl, —O(C1-C3alkyl), —OCF₃, —CH₂NH₂, —CF₃, —CHF₂, —CH₂F, —CH₂CF₃, or C₂F₅;

$R^2$ and $R^4$ are each independently selected from H or C1-C3alkyl; and $R^{12}$ is H or C1-C3alkyl; and $R^{13}$ and $R^{14}$ are each independently H, Cl, F, —CF₃, C1-C3alkyl, or C3-C5 cycloalkyl.

A compound, or a pharmaceutically acceptable salt thereof, having the structure of Formula (VII):

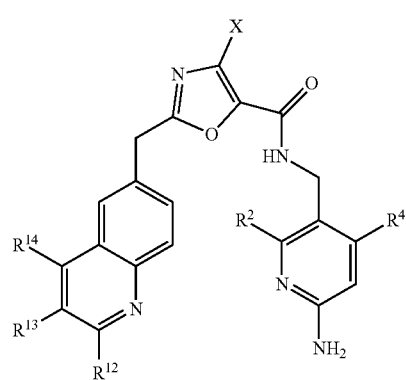

(VII)

wherein,

X is selected from —H, —CN, C1-C3alkyl, —O(C1-C3alkyl), —OCF₃, —CH₂NH₂, —CF₃, —CHF₂, —CH₂F, —CH₂CF₃, or C₂F₅;

$R^2$ and $R^4$ are each independently selected from H or C1-C3alkyl; and $R^{12}$ is H or C1-C3alkyl; and $R^{13}$ and $R^{14}$ are each independently H, Cl, F, —CF₃, C1-C3alkyl, or C3-C5 cycloalkyl.

Another embodiment provides a compound of Formula (VII), or a pharmaceutically acceptable salt thereof, wherein $R^2$ and $R^4$ are methyl, $R^{12}$ and $R^{14}$ are H, $R^{13}$ is Cl, and X is —H, —CN, C1-C3alkyl, —O(C1-C3alkyl), —OCF₃, —CH₂NH₂, —CF₃, —CHF₂, —CH₂F, —CH₂CF₃, or C₂F₅.

Another embodiment provides a compound of Formula (VII), or a pharmaceutically acceptable salt thereof, wherein $R^2$ and $R^4$ are methyl, $R^{12}$ and $R^{14}$ are H, $R^{13}$ is Cl, and X is —H, —CN, C1-C3alkyl, —O(C1-C3alkyl), —CH₂NH₂, or —CF₃.

Another embodiment provides a compound of Formula (VII), or a pharmaceutically acceptable salt thereof, wherein $R^2$ and $R^4$ are methyl, $R^{12}$ and $R^{14}$ are H, $R^{13}$ is Cl, and X is —CN, C1-C3alkyl, —O(C1-C3alkyl), —OCF₃, —CH₂NH₂, —CF₃, —CHF₂, —CH₂F, —CH₂CF₃, or C₂F₅.

Another embodiment provides a compound of Formula (VII), or a pharmaceutically acceptable salt thereof, wherein $R^2$ and $R^4$ are methyl, $R^{12}$ and $R^{14}$ are H, $R^{13}$ is Cl, and X is —CN, C1-C3alkyl, —O(C1-C3alkyl), —CH₂NH₂, or —CF₃.

A compound, or a pharmaceutically acceptable salt thereof, having the structure of Formula (VIII):

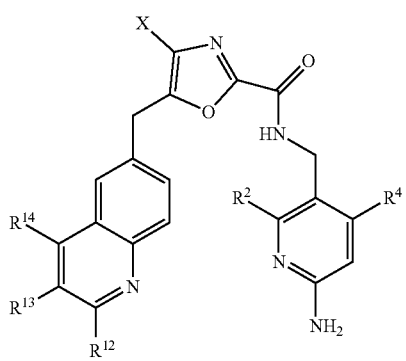

(VIII)

wherein,

X is selected from —H, —CN, C1-C3alkyl, —O(C1-C3alkyl), —OCF₃, —CH₂NH₂, —CF₃, —CHF₂, —CH₂F, —CH₂CF₃, or C₂F₅;

$R^2$ and $R^4$ are each independently selected from H or C1-C3alkyl; and $R^{12}$ is H or C1-C3alkyl; and
$R^{13}$ and $R^{14}$ are each independently H, Cl, F, —CF$_3$, C1-C3alkyl, or C3-C5 cycloalkyl.

A compound, or a pharmaceutically acceptable salt thereof, having the structure of Formula (IX):

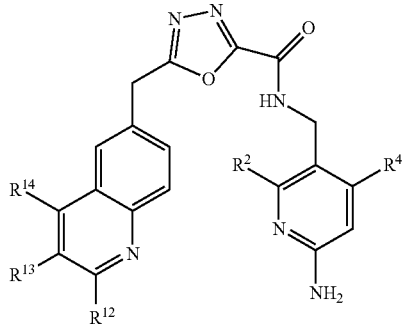

(IX)

wherein,
$R^2$ and $R^4$ are each independently selected from H or C1-C3alkyl; and
$R^{12}$ is H or C1-C3alkyl; and
$R^{13}$ and $R^{14}$ are each independently H, Cl, F, —CF$_3$, C1-C3alkyl, or C3-C5 cycloalkyl.

Another embodiment provides a compound of Formula (IX), or a pharmaceutically acceptable salt thereof, wherein $R^2$ and $R^4$ are methyl, $R^{12}$ and $R^{14}$ are H, and $R^{13}$ is Cl.

A compound, or a pharmaceutically acceptable salt thereof, having the structure of Formula (X):

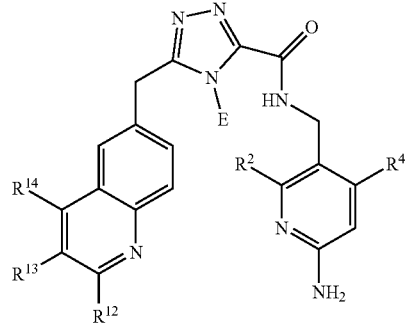

(X)

wherein,
E is H or C1-C3alkyl;
$R^2$ and $R^4$ are each independently selected from H or C1-C3alkyl; and
$R^{12}$ is H or C1-C3alkyl; and
$R^{13}$ and $R^{14}$ are each independently H, Cl, F, —CF$_3$, C1-C3alkyl, or C3-C5 cycloalkyl.

Another embodiment provides a compound of Formula (X), or a pharmaceutically acceptable salt thereof, wherein $R^2$ and $R^4$ are methyl, $R^{12}$ and $R^{14}$ are H, $R^{13}$ is Cl, and E is H.

Another embodiment provides a compound of Formula (X), or a pharmaceutically acceptable salt thereof, wherein $R^2$ and $R^4$ are methyl, $R^{12}$ and $R^{14}$ are H, $R^{13}$ is Cl, and E is methyl.

A compound, or a pharmaceutically acceptable salt thereof, having the structure of Formula (XI):

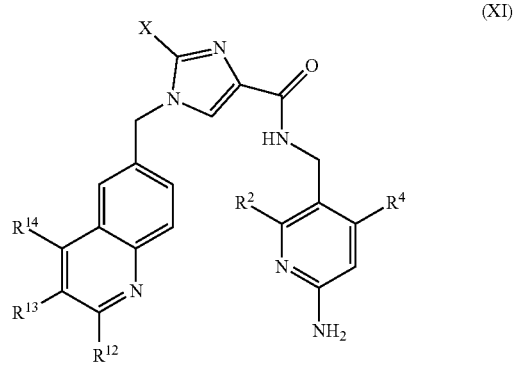

(XI)

wherein,
X is selected from —H, —CN, C1-C3alkyl, —O(C1-C3alkyl), —OCF$_3$, —CH$_2$NH$_2$, —CF$_3$, —CHF$_2$, —CH$_2$F, —CH$_2$CF$_3$, or C$_2$F$_5$;
$R^2$ and $R^4$ are each independently selected from H or C1-C3alkyl; and
$R^{12}$ is H or C1-C3alkyl; and
$R^{13}$ and $R^{14}$ are each independently H, Cl, F, —CF$_3$, C1-C3alkyl, or C3-C5 cycloalkyl.

In some embodiments, the kallikrein inhibitory compound described herein has a structure provided in Table 1.

TABLE 1

| Chemical Synthesis Example | Name | Structure |
|---|---|---|
| 1 | N-((6-amino-2,4-dimethylpyridin-3-yl)methyl)-1-((3-chloroquinolin-6-yl)methyl)-1H-pyrazole-3-carboxamide | 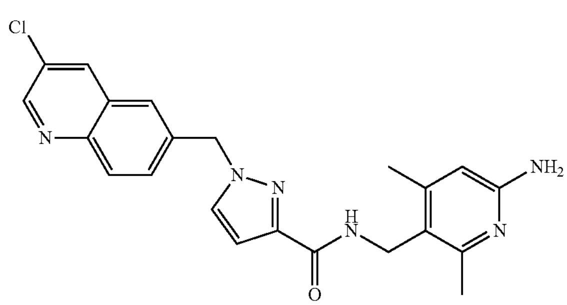 [SMILES: Cc1cc(N)nc(C)c1CNC(=O)c1ccn(Cc2ccc3ncc(Cl)cc3c2)n1] |

TABLE 1-continued

| Chemical Synthesis Example | Name | Structure |
|---|---|---|
| 3 | N-((6-amino-2,4-dimethylpyridin-3-yl)methyl)-1-((3-chloroquinolin-6-yl)methyl)-1H-imidazole-4-carboxamide | 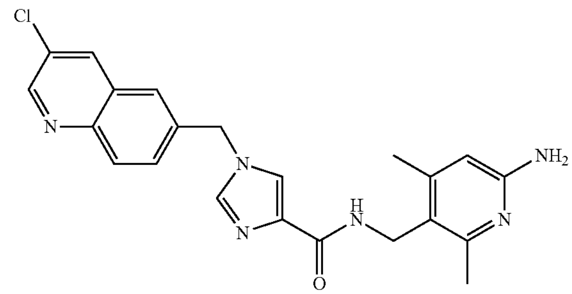 |
| 4 | N-((6-amino-2,4-dimethylpyridin-3-yl)methyl)-1-((3-chloroquinolin-6-yl)methyl)-1H-1,2,4-triazole-3-carboxamide | 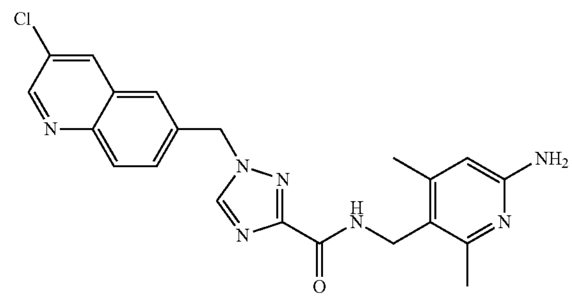 |
| 5 | N-((6-amino-2,4-dimethylpyridin-3-yl)methyl)-2-((3-chloroquinolin-6-yl)methyl)-1H-imidazole-5-carboxamide | 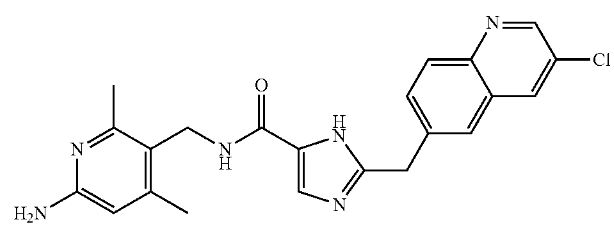 [SMILES: Cc1cc(N)nc(C)c1CNC(=O)c1cnc(Cc2ccc3ncc(Cl)cc3c2)[nH]1] |
| 6 | N-((6-amino-2,4-dimethylpyridin-3-yl)methyl)-3-((3-chloroquinolin-6-yl)methyl)-1,2,4-oxadiazole-5-carboxamide | 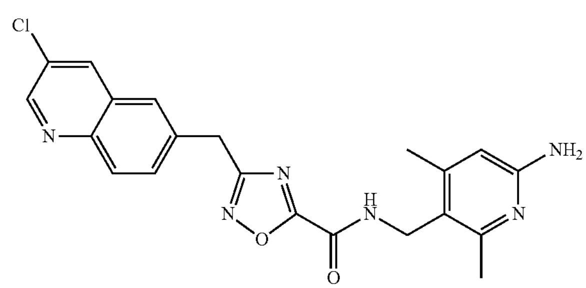 [SMILES: Cc1cc(N)nc(C)c1CNC(=O)c1nc(Cc2ccc3ncc(Cl)cc3c2)no1] |
| 7 | N-((6-amino-2,4-dimethylpyridin-3-yl)methyl)-5-((3-chloroquinolin-6-yl)methyl)-1,2,4-oxadiazole-3-carboxamide | 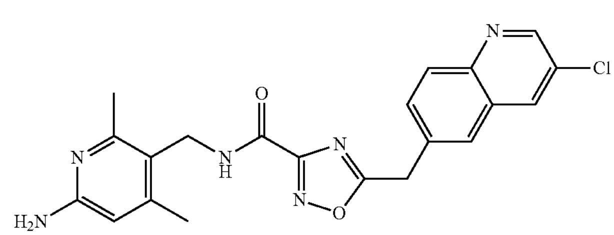 [SMILES: Cc1cc(N)nc(C)c1CNC(=O)c1noc(Cc2ccc3ncc(Cl)cc3c2)n1] |

TABLE 1-continued

| Chemical Synthesis Example | Name | Structure |
|---|---|---|
| 8 | N-((6-amino-2,4-dimethylpyridin-3-yl)methyl)-1-((3-chloroquinolin-6-yl)methyl)-1H-pyrrolo[3,2-b]pyridine-3-carboxamide | 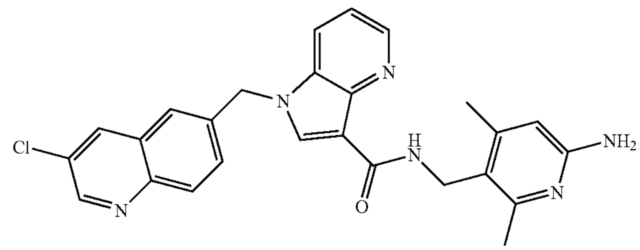 [SMILES: Cc1cc(N)nc(C)c1CNC(=O)c1cn(Cc2ccc3ncc(Cl)cc3c2)c2cccnc12] |
| 9 | N-((6-amino-2,4-dimethylpyridin-3-yl)methyl)-3-((3-chloroquinolin-6-yl)methyl)imidazo[1,5-a]pyridine-1-carboxamide | 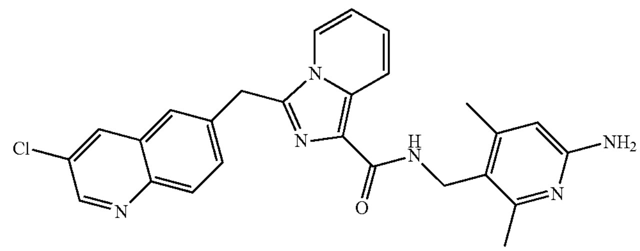 [SMILES: Cc1cc(N)nc(C)c1CNC(=O)c1nc(Cc2ccc3ncc(Cl)cc3c2)n2ccccc12] |
| 10 | N-((6-amino-2,4-dimethylpyridin-3-yl)methyl)-1-((3-chloroquinolin-6-yl)methyl)-1H-1,2,3-triazole-4-carboxamide | 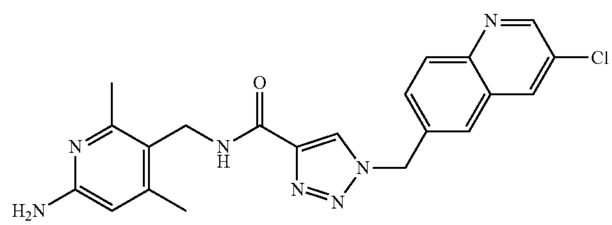 [SMILES: Cc1cc(N)nc(C)c1CNC(=O)c1cn(Cc2ccc3ncc(Cl)cc3c2)nn1] |
| 11 | N-((6-amino-2,4-dimethylpyridin-3-yl)methyl)-1-((3-chloroquinolin-6-yl)methyl)-1H-indole-3-carboxamide | 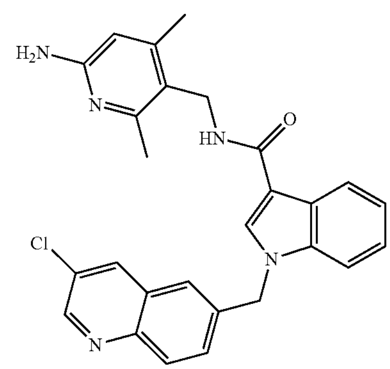 [SMILES: Cc1cc(N)nc(C)c1CNC(=O)c1cn(Cc2ccc3ncc(Cl)cc3c2)c2ccccc12] |
| 12 | N-((6-amino-2,4-dimethylpyridin-3-yl)methyl)-1-((3-chloroquinolin-6-yl)methyl)-1H-pyrrolo[2,3-b]pyridine-3-carboxamide | 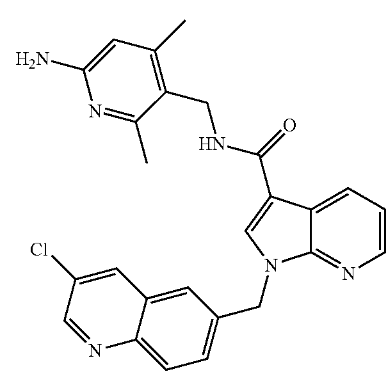 [SMILES: Cc1cc(N)nc(C)c1CNC(=O)c1cn(Cc2ccc3ncc(Cl)cc3c2)c2ncccc12] |

TABLE 1-continued

| Chemical Synthesis Example | Name | Structure |
|---|---|---|
| 13 | N-((6-amino-2,4-dimethylpyridin-3-yl)methyl)-1-((3-chloroquinolin-6-yl)methyl)-1H-indazole-3-carboxamide | 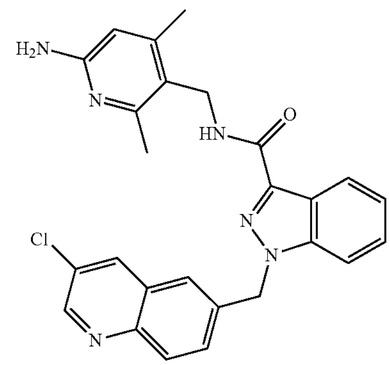 [SMILES: Cc1cc(N)nc(C)c1CNC(=O)c1nn(Cc2ccc3ncc(Cl)cc3c2)c2ccccc12] |
| 14 | N-((6-amino-2,4-dimethylpyridin-3-yl)methyl)-2-((3-chloroquinolin-6-yl)methyl)-2H-indazole-3-carboxamide | 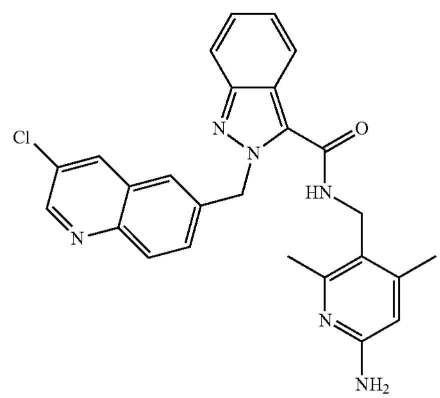 [SMILES: Cc1cc(N)nc(C)c1CNC(=O)c1c2ccccc2nn1Cc1ccc2ncc(Cl)cc2c1] |
| 15 | N-((6-amino-2,4-dimethylpyridin-3-yl)methyl)-1-((3-chloroquinolin-6-yl)methyl)-3-(trifluoromethyl)-1H-pyrazole-4-carboxamide | 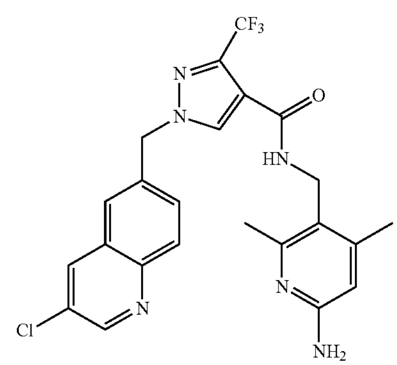 |
| 16 | N-((6-amino-2,4-dimethylpyridin-3-yl)methyl)-1-((3-chloroquinolin-6-yl)methyl)-1H-pyrrolo[2,3-c]pyridine-3-carboxamide | 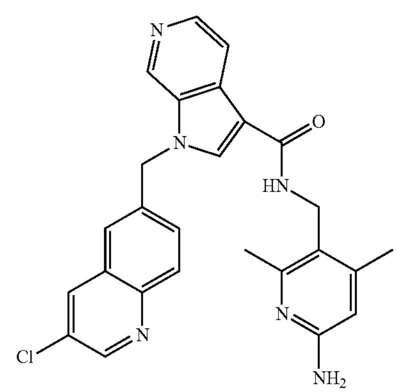 [SMILES: Cc1cc(N)nc(C)c1CNC(=O)c1cn(Cc2ccc3ncc(Cl)cc3c2)c2cnccc12] |

TABLE 1-continued

| Chemical Synthesis Example | Name | Structure |
| --- | --- | --- |
| 17 | 3-amino-N-((6-amino-2,4-dimethylpyridin-3-yl)methyl)-1-((3-chloroquinolin-6-yl)methyl)-1H-pyrazole-4-carboxamide | 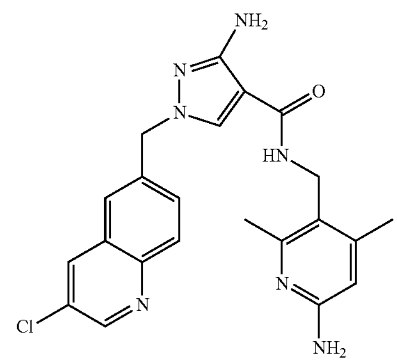 |
| 18 | N-((6-amino-2,4-dimethylpyridin-3-yl)methyl)-1-((3-chloroquinolin-6-yl)methyl)-4-nitro-1H-pyrazole-3-carboxamide | 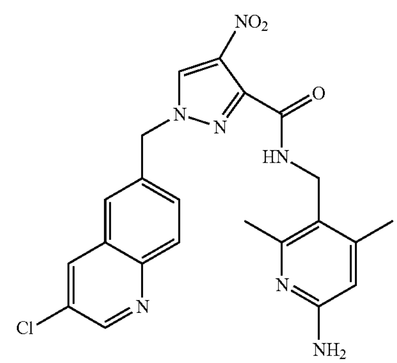 |
| 19 | 4-acetamido-N-((6-amino-2,4-dimethylpyridin-3-yl)methyl)-1-((3-chloroquinolin-6-yl)methyl)-1H-pyrazole-3-carboxamide | 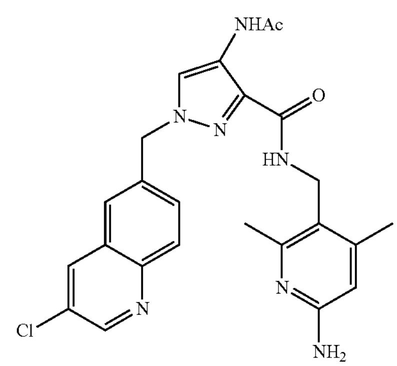 [SMILES: CC(=O)Nc1cn(Cc2ccc3ncc(Cl)cc3c2)nc1C(=O)NCc1c(C)cc(N)nc1C] |
| 20 | 5-amino-N-((6-amino-2,4-dimethylpyridin-3-yl)methyl)-1-((3-chloroquinolin-6-yl)methyl)-1H-1,2,4-triazole-3-carboxamide | 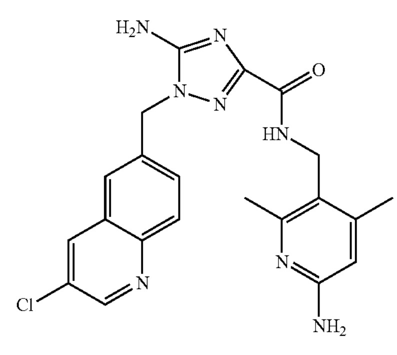 [SMILES: Cc1cc(N)nc(C)c1CNC(=O)c1nc(N)n(Cc2ccc3ncc(Cl)cc3c2)n1] |

TABLE 1-continued

| Chemical Synthesis Example | Name | Structure |
|---|---|---|
| 21 | N-((6-amino-2,4-dimethylpyridin-3-yl)methyl)-2-((3-chloroquinolin-6-yl)methyl)-2H-1,2,3-triazole-4-carboxamide | 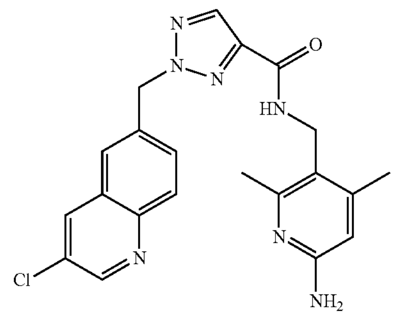 [SMILES: Cc1cc(N)nc(C)c1CNC(=O)c1cnn(Cc2ccc3ncc(Cl)cc3c2)n1] |
| 22 | N-((6-amino-2,4-dimethylpyridin-3-yl)methyl)-1-((3-chloroquinolin-6-yl)methyl)-4-(trifluoromethyl)-1H-pyrazole-3-carboxamide | 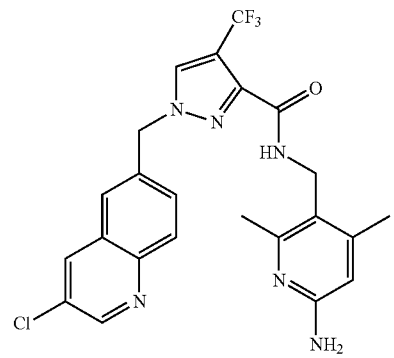 [SMILES: Cc1cc(N)nc(C)c1CNC(=O)c1nn(Cc2ccc3ncc(Cl)cc3c2)cc1C(F)(F)F] |
| 23 | N-((6-amino-2,4-dimethylpyridin-3-yl)methyl)-1-((3-chloroquinolin-6-yl)methyl)imidazo[1,5-a]pyridine-3-carboxamide | 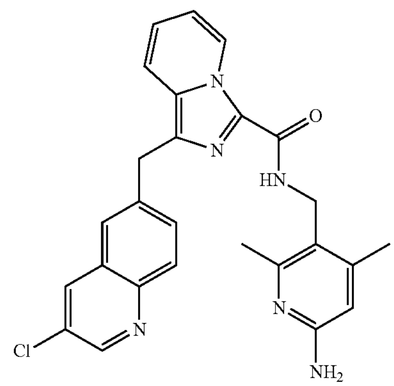 [SMILES: Cc1cc(N)nc(C)c1CNC(=O)c1nc(Cc2ccc3ncc(Cl)cc3c2)c2ccccn12] |
| 24 | 4-amino-N-((6-amino-2,4-dimethylpyridin-3-yl)methyl)-1-((3-chloroquinolin-6-yl)methyl)-1H-pyrazole-3-carboxamide | 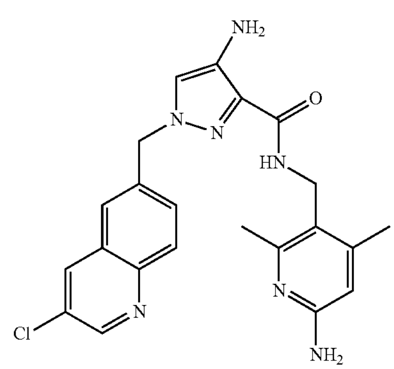 |

TABLE 1-continued

| Chemical Synthesis Example | Name | Structure |
|---|---|---|
| 25 | N-((6-amino-2,4-dimethylpyridin-3-yl)methyl)-1-((3-chloroquinolin-6-yl)methyl)-3-cyano-1H-pyrazole-4-carboxamide | 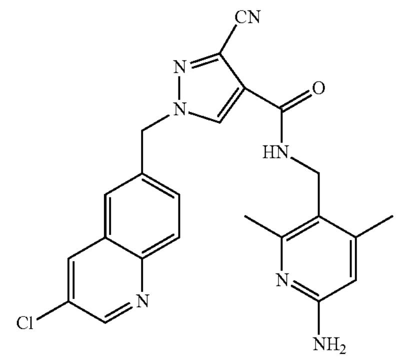 [SMILES: Cc1cc(N)nc(C)c1CNC(=O)c1cn(Cc2ccc3ncc(Cl)cc3c2)nc1C#N] |
| 26 | N4-((6-amino-2,4-dimethylpyridin-3-yl)methyl)-1-((3-chloroquinolin-6-yl)methyl)-1H-pyrazole-3,4-dicarboxamide | 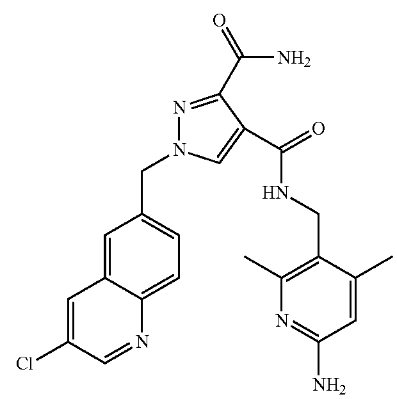 [SMILES: Cc1cc(N)nc(C)c1CNC(=O)c1cn(Cc2ccc3ncc(Cl)cc3c2)nc1C(N)=O] |
| 27 | N-((6-amino-2,4-dimethylpyridin-3-yl)methyl)-3-(aminomethyl)-1-((3-chloroquinolin-6-yl)methyl)-1H-pyrazole-4-carboxamide | 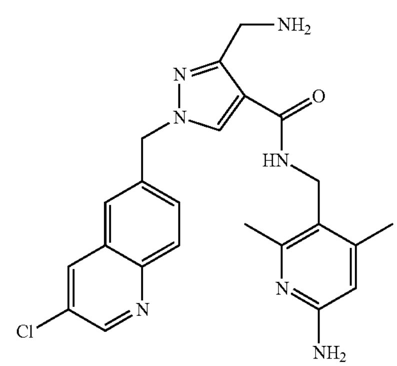 [SMILES: Cc1cc(N)nc(C)c1CNC(=O)c1cn(Cc2ccc3ncc(Cl)cc3c2)nc1CN] |
| 28 | 2-amino-N-((6-amino-2,4-dimethylpyridin-3-yl)methyl)-1-((3-chloroquinolin-6-yl)methyl)-1H-imidazole-4-carboxamide | 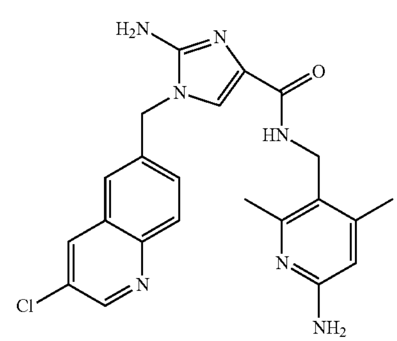 |

TABLE 1-continued

| Chemical Synthesis Example | Name | Structure |
|---|---|---|
| 29 | N-((6-amino-2,4-dimethylpyridin-3-yl)methyl)-2-((3-chloroquinolin-6-yl)methyl)oxazole-4-carboxamide | 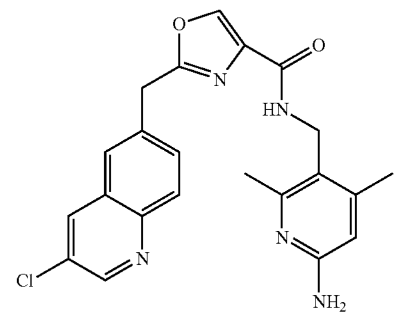 [SMILES: Cc1cc(N)nc(C)c1CNC(=O)c1coc(Cc2ccc3ncc(Cl)cc3c2)n1] |
| 30 | N-((6-amino-2,4-dimethylpyridin-3-yl)methyl)-5-((3-chloroquinolin-6-yl)methyl)-1,3,4-oxadiazole-2-carboxamide | 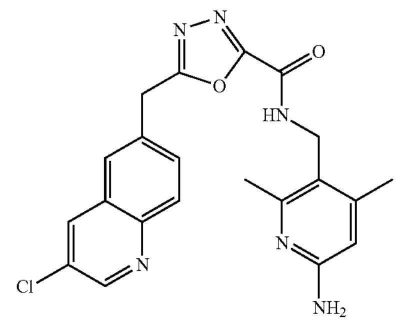 [SMILES: Cc1cc(N)nc(C)c1CNC(=O)c1nnc(Cc2ccc3ncc(Cl)cc3c2)o1] |
| 31 | N-((6-amino-2,4-dimethylpyridin-3-yl)methyl)-5-((3-chloroquinolin-6-yl)methyl)oxazole-2-carboxamide | 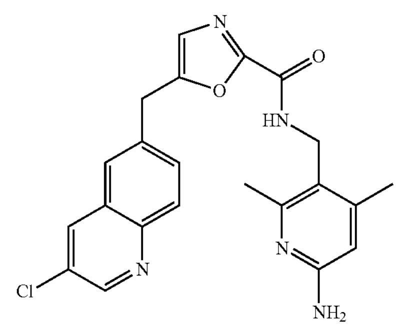 [SMILES: Cc1cc(N)nc(C)c1CNC(=O)c1ncc(Cc2ccc3ncc(Cl)cc3c2)o1] |
| 32 | N-((6-amino-2,4-dimethylpyridin-3-yl)methyl)-7-((3-chloroquinolin-6-yl)methyl)-7H-pyrrolo[2,3-d]pyrimidine-5-carboxamide | 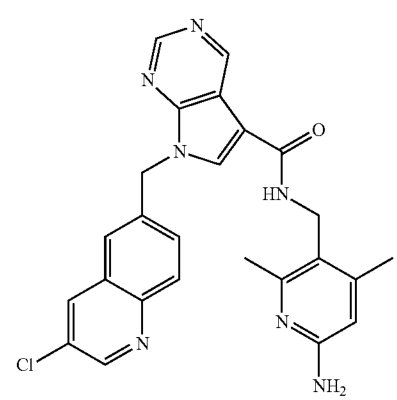 [SMILES: Cc1cc(N)nc(C)c1CNC(=O)c1cn(Cc2ccc3ncc(Cl)cc3c2)c2ncncc12] |

TABLE 1-continued

| Chemical Synthesis Example | Name | Structure |
|---|---|---|
| 33 | 4-amino-N-((6-amino-2,4-dimethylpyridin-3-yl)methyl)-1-((3-chloroquinolin-6-yl)methyl)-1H-indazole-3-carboxamide | 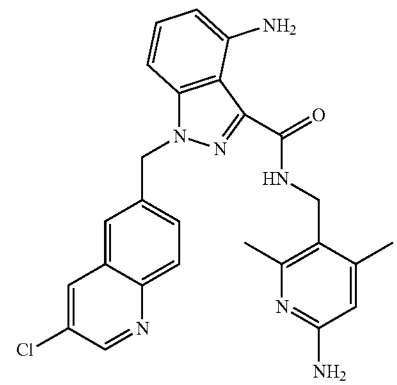 [SMILES: Cc1cc(N)nc(C)c1CNC(=O)c1nn(Cc2ccc3ncc(Cl)cc3c2)c2cccc(N)c12] |
| 34 | 4-amino-N-((6-amino-2,4-dimethylpyridin-3-yl)methyl)-7-((3-chloroquinolin-6-yl)methyl)-7H-pyrrolo[2,3-d]pyrimidine-5-carboxamide | 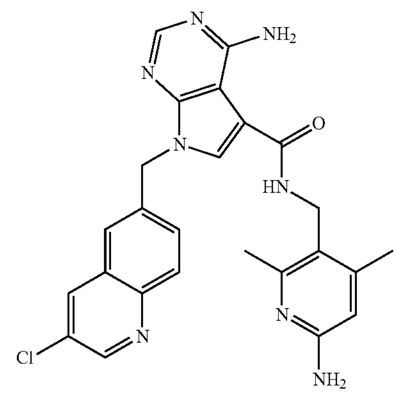 [SMILES: Cc1cc(N)nc(C)c1CNC(=O)c1cn(Cc2ccc3ncc(Cl)cc3c2)c2ncnc(N)c12] |
| 35 | N-((6-amino-2,4-dimethylpyridin-3-yl)methyl)-1-((3-chloroquinolin-6-yl)methyl)-1H-pyrrolo[3,2-c]pyridine-3-carboxamide | 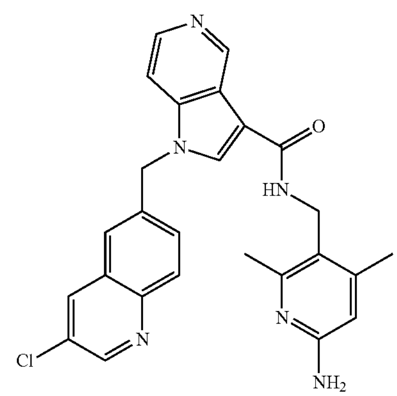 [SMILES: Cc1cc(N)nc(C)c1CNC(=O)c1cn(Cc2ccc3ncc(Cl)cc3c2)c2ccncc12] |
| 36 | N-((6-amino-2,4-dimethylpyridin-3-yl)methyl)-1-((3-chloroquinolin-6-yl)methyl)-4-cyano-1H-pyrazole-3-carboxamide | 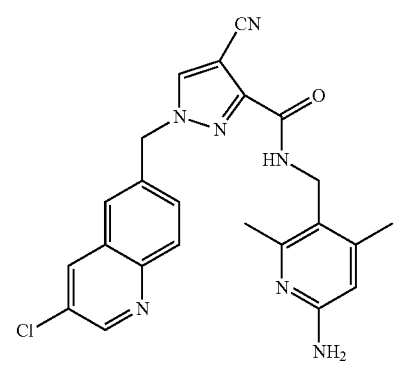 |

TABLE 1-continued

| Chemical Synthesis Example | Name | Structure |
|---|---|---|
| 37 | N-((6-amino-2,4-dimethylpyridin-3-yl)methyl)-2-((3-chloroquinolin-6-yl)methyl)-4-(trifluoromethyl)oxazole-5-carboxamide | 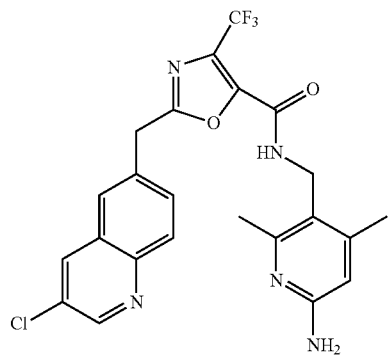 [SMILES: Cc1cc(N)nc(C)c1CNC(=O)c1oc(Cc2ccc3ncc(Cl)cc3c2)nc1C(F)(F)F] |
| 38 | N-((6-amino-2,4-dimethylpyridin-3-yl)methyl)-1-((3-chloroquinolin-6-yl)methyl)-3-methyl-1H-pyrazole-4-carboxamide | 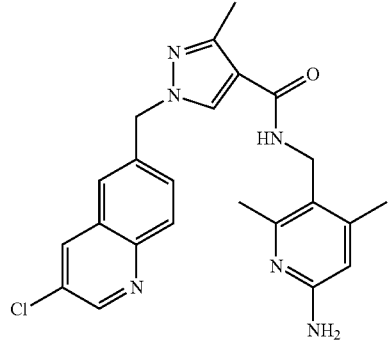 [SMILES: Cc1cc(N)nc(C)c1CNC(=O)c1cn(Cc2ccc3ncc(Cl)cc3c2)nc1C] |
| 39 | N-((6-amino-2,4-dimethylpyridin-3-yl)methyl)-1-((3-chloroquinolin-6-yl)methyl)-3-methoxy-1H-pyrazole-4-carboxamide | 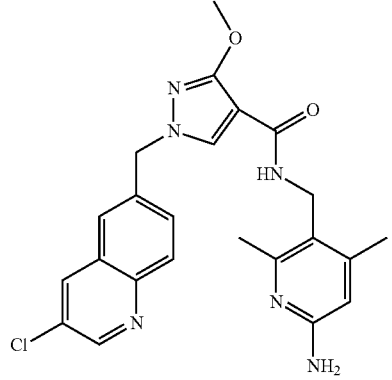 [SMILES: COc1nn(Cc2ccc3ncc(Cl)cc3c2)cc1C(=O)NCc1c(C)cc(N)nc1C] |
| 40 | N-((6-amino-2,4-dimethylpyridin-3-yl)methyl)-1-((3-chloroquinolin-6-yl)methyl)-5-cyano-1H-pyrazole-4-carboxamide | 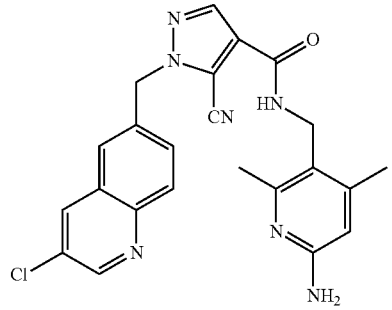 [SMILES: Cc1cc(N)nc(C)c1CNC(=O)c1cnn(Cc2ccc3ncc(Cl)cc3c2)c1C#N] |

TABLE 1-continued

| Chemical Synthesis Example | Name | Structure |
|---|---|---|
| 41 | N-((6-amino-2,4-dimethylpyridin-3-yl)methyl)-5-((3-chloroquinolin-6-yl)methyl)-1H-imidazole-2-carboxamide | 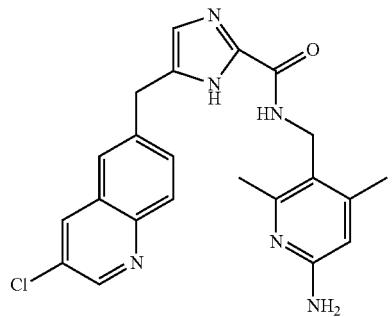 [SMILES: Cc1cc(N)nc(C)c1CNC(=O)c1ncc(Cc2ccc3ncc(Cl)cc3c2)[nH]1] |
| 42 | N-((5-chloro-1H-indazol-3-yl)methyl)-5-((3-chloroquinolin-6-yl)methyl)-1,3,4-oxadiazole-2-carboxamide | 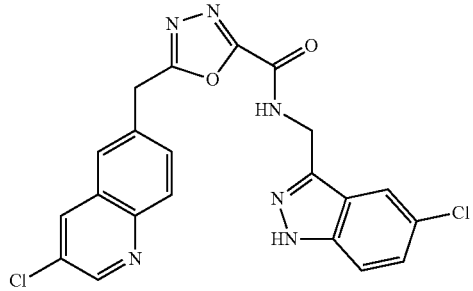 [SMILES: O=C(NCc1n[nH]c2ccc(Cl)cc12)c1nnc(Cc2ccc3ncc(Cl)cc3c2)o1] |
| 43 | N-((3-chloro-4-fluoro-1H-indol-5-yl)methyl)-5-((3-chloroquinolin-6-yl)methyl)-1,3,4-oxadiazole-2-carboxamide | 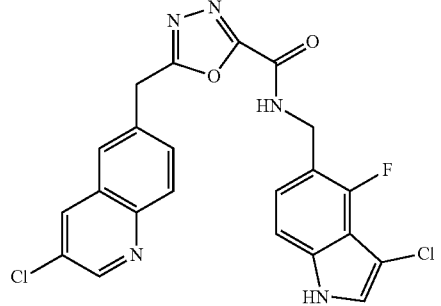 [SMILES: O=C(NCc1ccc2[nH]cc(Cl)c2c1F)c1nnc(Cc2ccc3ncc(Cl)cc3c2)o1] |
| 44 | N-((3-chloro-6-fluoro-1H-indol-5-yl)methyl)-5-((3-chloroquinolin-6-yl)methyl)-1,3,4-oxadiazole-2-carboxamide | 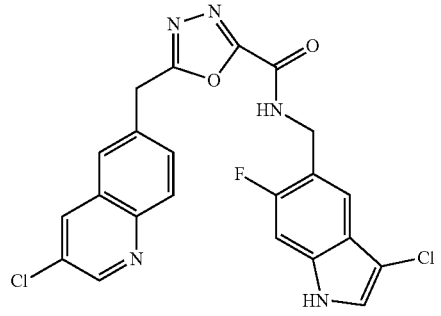 [SMILES: O=C(NCc1cc2c(Cl)c[nH]c2cc1F)c1nnc(Cc2ccc3ncc(Cl)cc3c2)o1] |
| 45 | N-((3-chloro-1H-pyrrolo[2,3-b]pyridin-5-yl)methyl)-5-((3-chloroquinolin-6-yl)methyl)-1,3,4-oxadiazole-2-carboxamide | 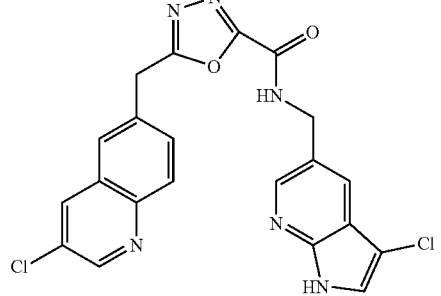 |

TABLE 1-continued

| Chemical Synthesis Example | Name | Structure |
|---|---|---|
| 46 | N-((1-aminoisoquinolin-6-yl)methyl)-5-((3-chloroquinolin-6-yl)methyl)-1,3,4-oxadiazole-2-carboxamide | 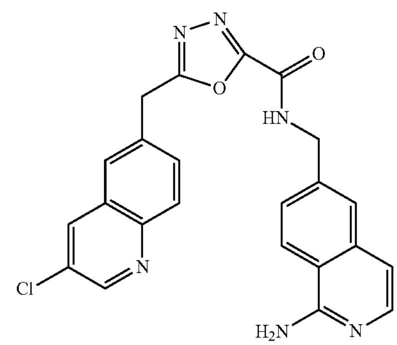 [SMILES: Nc1nccc2cc(CNC(=O)c3nnc(Cc4ccc5ncc(Cl)cc5c4)o3)ccc12] |
| 47 | N-((3-chloro-4-fluoro-1H-indol-5-yl)methyl)-1-((3-chloroquinolin-6-yl)methyl)-3-cyano-1H-pyrazole-4-carboxamide | 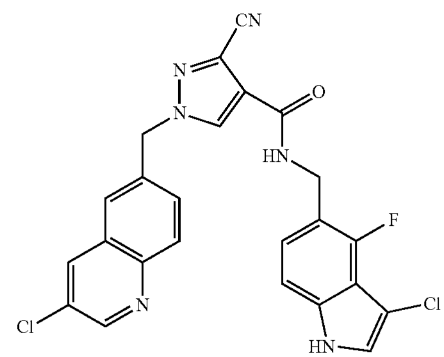 [SMILES: N#Cc1nn(Cc2ccc3ncc(Cl)cc3c2)cc1C(=O)NCc1ccc2[nH]cc(Cl)c2c1F] |
| 48 | N-((5-chloro-1H-indazol-3-yl)methyl)-1-((3-chloroquinolin-6-yl)methyl)-3-cyano-1H-pyrazole-4-carboxamide | 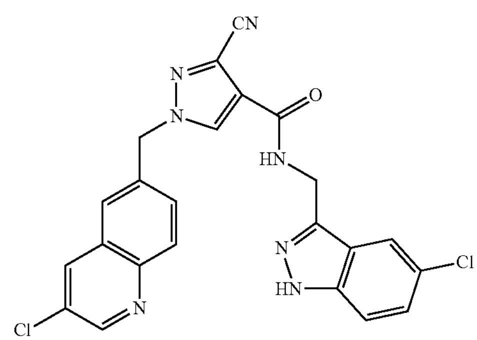 [SMILES: N#Cc1nn(Cc2ccc3ncc(Cl)cc3c2)cc1C(=O)NCc1n[nH]c2ccc(Cl)cc12] |
| 49 | N-((1-aminoisoquinolin-6-yl)methyl)-1-((3-chloroquinolin-6-yl)methyl)-3-cyano-1H-pyrazole-4-carboxamide | 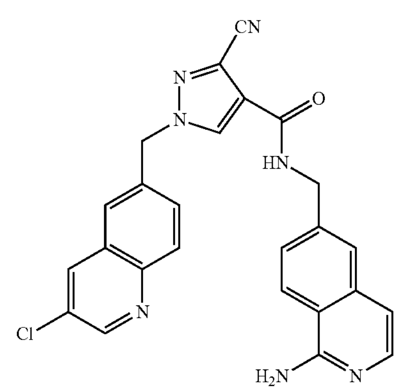 [SMILES: N#Cc1nn(Cc2ccc3ncc(Cl)cc3c2)cc1C(=O)NCc1ccc2c(N)nccc2c1] |

TABLE 1-continued

| Chemical Synthesis Example | Name | Structure |
|---|---|---|
| 50 | N-((3-chloro-1H-pyrrolo[2,3-b]pyridin-5-yl)methyl)-1-((3-chloroquinolin-6-yl)methyl)-3-cyano-1H-pyrazole-4-carboxamide | 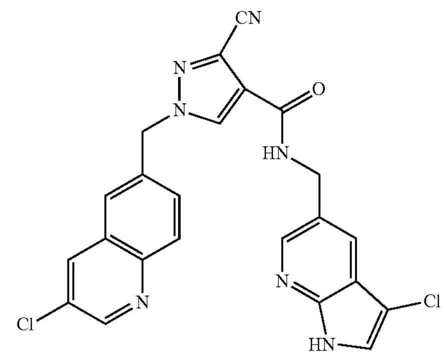 [SMILES: N#Cc1nn(Cc2ccc3ncc(Cl)cc3c2)cc1C(=O)NCc1cnc2[nH]cc(Cl)c2c1] |
| 51 | N-((3-chloro-6-fluoro-1H-indol-5-yl)methyl)-1-((3-chloroquinolin-6-yl)methyl)-3-cyano-1H-pyrazole-4-carboxamide | 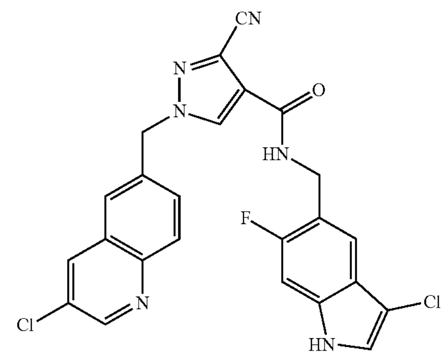 [SMILES: N#Cc1nn(Cc2ccc3ncc(Cl)cc3c2)cc1C(=O)NCc1cc2c(Cl)c[nH]c2cc1F] |
| 52 | N-((6-amino-2,4-dimethylpyridin-3-yl)methyl)-1-((3-chloro-8-fluoroquinolin-6-yl)methyl)-3-cyano-1H-pyrazole-4-carboxamide | 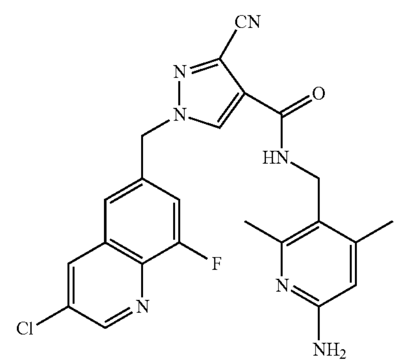 [SMILES: Cc1cc(N)nc(C)c1CNC(=O)c1cn(Cc2cc(F)c3ncc(Cl)cc3c2)nc1C#N] |
| 53 | N-((3-chloro-6-fluoro-1H-indol-5-yl)methyl)-1-((3-chloro-8-fluoroquinolin-6-yl)methyl)-3-cyano-1H-pyrazole-4-carboxamide | 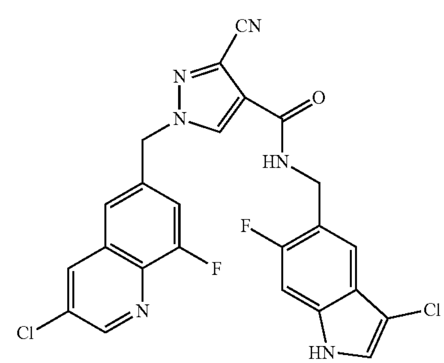 [SMILES: N#Cc1nn(Cc2cc(F)c3ncc(Cl)cc3c2)cc1C(=O)NCc1cc2c(Cl)c[nH]c2cc1F] |

TABLE 1-continued

| Chemical Synthesis Example | Name | Structure |
|---|---|---|
| 54 | N-((1-aminoisoquinolin-6-yl)methyl)-1-((3-chloro-8-fluoroquinolin-6-yl)methyl)-3-cyano-1H-pyrazole-4-carboxamide | 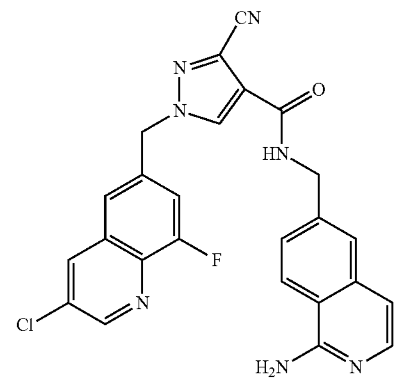 [SMILES: N#Cc1nn(Cc2cc(F)c3ncc(Cl)cc3c2)cc1C(=O)NCc1ccc2c(N)nccc2c1] |
| 55 | N-((5-chloro-1H-indazol-3-yl)methyl)-1-((3-chloro-8-fluoroquinolin-6-yl)methyl)-3-cyano-1H-pyrazole-4-carboxamide | 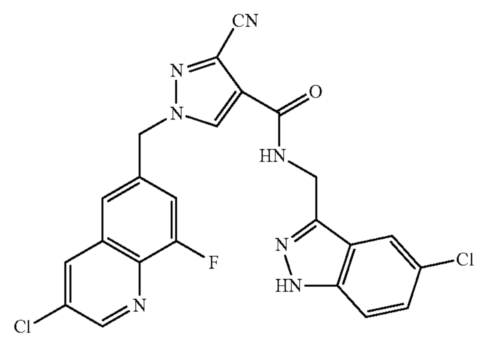 [SMILES: N#Cc1nn(Cc2cc(F)c3ncc(Cl)cc3c2)cc1C(=O)NCc1n[nH]c2ccc(Cl)cc12] |
| 56 | N-((3-chloro-1H-pyrrolo[2,3-b]pyridin-5-yl)methyl)-1-((3-chloro-8-fluoroquinolin-6-yl)methyl)-3-cyano-1H-pyrazole-4-carboxamide | 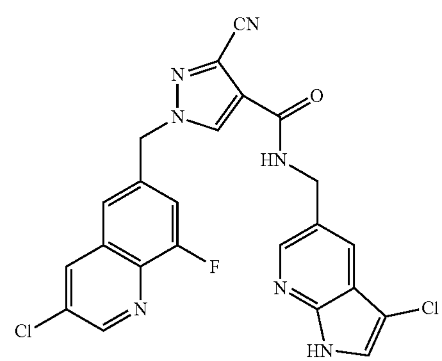 [SMILES: N#Cc1nn(Cc2cc(F)c3ncc(Cl)cc3c2)cc1C(=O)NCc1cnc2[nH]cc(Cl)c2c1] |
| 57 | N-((3-chloro-4-fluoro-1H-indol-5-yl)methyl)-1-((3-chloro-8-fluoroquinolin-6-yl)methyl)-3-cyano-1H-pyrazole-4-carboxamide | 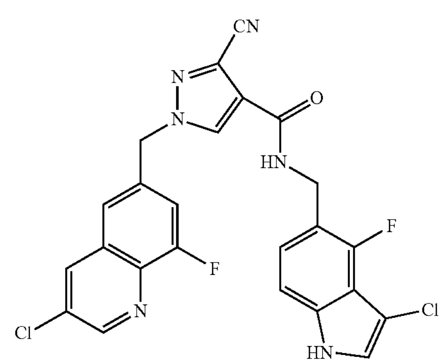 [SMILES: N#Cc1nn(Cc2cc(F)c3ncc(Cl)cc3c2)cc1C(=O)NCc1ccc2[nH]cc(Cl)c2c1F] |

TABLE 1-continued

| Chemical Synthesis Example | Name | Structure |
|---|---|---|
| 58 | N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide | 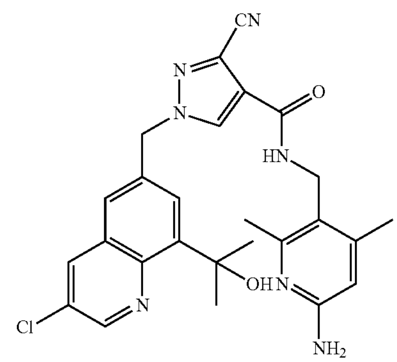 [SMILES: Cc1cc(N)nc(C)c1CNC(=O)c1cn(Cc2cc(C(C)(C)O)c3ncc(Cl)cc3c2)nc1C#N] |
| 59 | N-((1-aminoisoquinolin-6-yl)methyl)-1-((3-chloro-8-(2-hydroxypropan-2-yl)quinolin-6-yl)methyl)-3-cyano-1H-pyrazole-4-carboxamide | 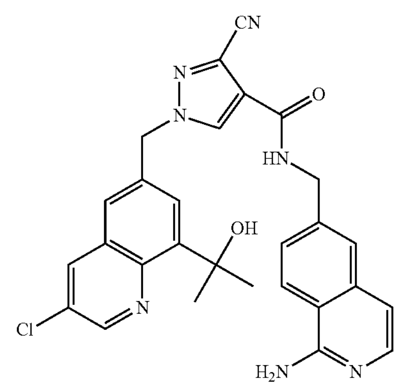 [SMILES: CC(C)(O)c1cc(Cn2cc(C(=O)NCc3ccc4c(N)nccc4c3)c(C#N)n2)cc2cc(Cl)cnc12] |
| 60 | N-((6-amino-2,4-dimethylpyridin-3-yl)methyl)-1-((3-chloro-8-sulfamoylquinolin-6-yl)methyl)-3-cyano-1H-pyrazole-4-carboxamide | 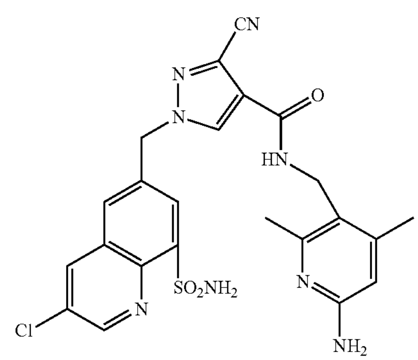 [SMILES: Cc1cc(N)nc(C)c1CNC(=O)c1cn(Cc2cc(S(N)(=O)=O)c3ncc(Cl)cc3c2)nc1C#N] |
| 61 | N-((6-amino-2,4-dimethylpyridin-3-yl)methyl)-3-cyano-1-((3-methyl-8-(methylsulfonyl)quinolin-6-yl)methyl)-1H-pyrazole-4-carboxamide | 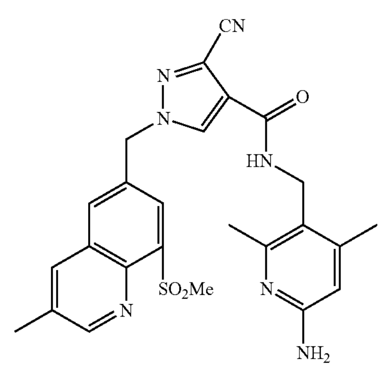 |

TABLE 1-continued

| Chemical Synthesis Example | Name | Structure |
|---|---|---|
| 62 | N-((6-amino-2,4-dimethylpyridin-3-yl)methyl)-3-cyano-1-((8-cyano-3-methylquinolin-6-yl)methyl)-1H-pyrazole-4-carboxamide | 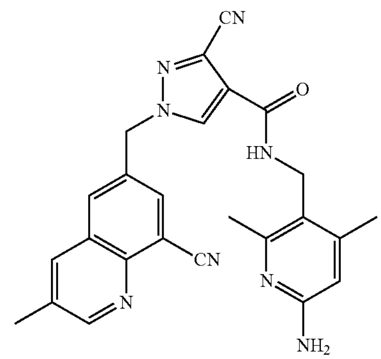 |
| 63 | N4-((6-amino-2,4-dimethylpyridin-3-yl)methyl)-1-((8-cyano-3-methylquinolin-6-yl)methyl)-1H-pyrazole-3,4-dicarboxamide | 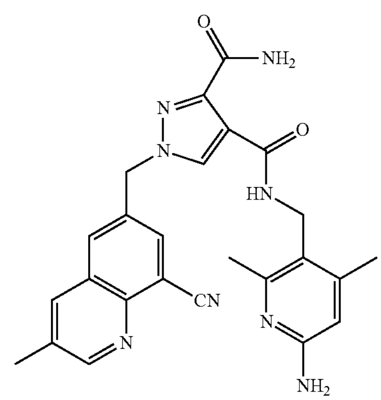 |
| 64 | N-((6-amino-2,4-dimethylpyridin-3-yl)methyl)-1-((3-chloroquinolin-6-yl)methyl)-4-cyano-1H-pyrazole-5-carboxamide | 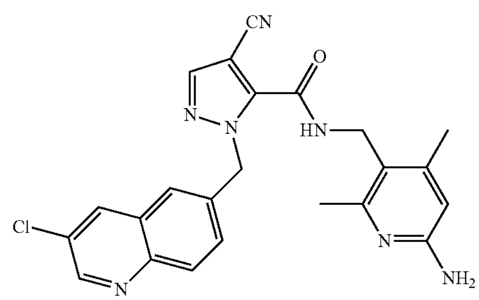 [SMILES: Cc1cc(N)nc(C)c1CNC(=O)c1c(C#N)cnn1Cc1ccc2ncc(Cl)cc2c1] |
| 65 | N-((6-amino-2,4-dimethylpyridin-3-yl)methyl)-3-cyano-1-((3-cyclopropylquinolin-6-yl)methyl)-1H-pyrazole-4-carboxamide | 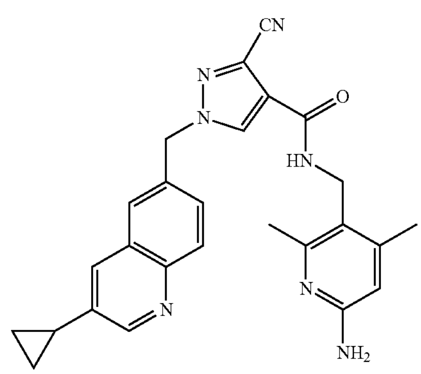 [SMILES: Cc1cc(N)nc(C)c1CNC(=O)c1cn(Cc2ccc3ncc(C4CC4)cc3c2)nc1C#N] |

TABLE 1-continued

| Chemical Synthesis Example | Name | Structure |
|---|---|---|
| 66 | N-((6-amino-2-methylpyridin-3-yl)methyl)-3-cyano-1-((3-cyclopropylquinolin-6-yl)methyl)-1H-pyrazole-4-carboxamide | 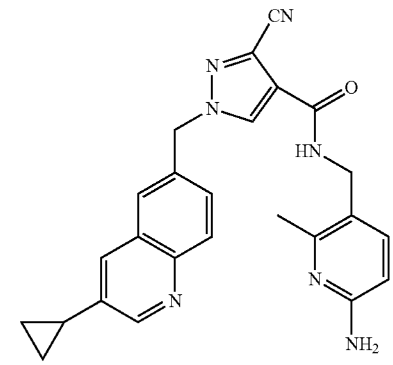 [SMILES: Cc1nc(N)ccc1CNC(=O)c1cn(Cc2ccc3ncc(C4CC4)cc3c2)nc1C#N] |
| 67 | N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide | 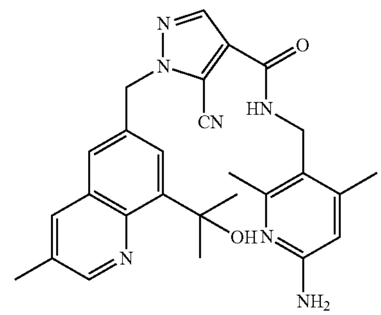 |
| 68 | N-((6-amino-2,4-dimethylpyridin-3-yl)methyl)-1-((3-chloro-8-(methylsulfonyl)quinolin-6-yl)methyl)-3-cyano-1H-pyrazole-4-carboxamide | 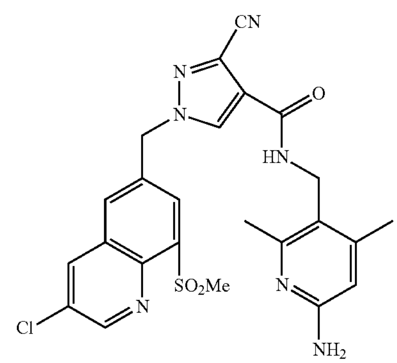 [SMILES: Cc1cc(N)nc(C)c1CNC(=O)c1cn(Cc2cc(S(C)(=O)=O)c3ncc(Cl)cc3c2)nc1C#N] |
| 69 | N-((6-amino-2,4-dimethylpyridin-3-yl)methyl)-1-((3-chloro-8-cyanoquinolin-6-yl)methyl)-3-cyano-1H-pyrazole-4-carboxamide | 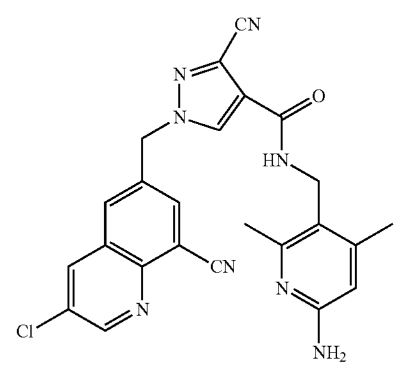 [SMILES: Cc1cc(N)nc(C)c1CNC(=O)c1cn(Cc2cc(C#N)c3ncc(Cl)cc3c2)nc1C#N] |

TABLE 1-continued

| Chemical Synthesis Example | Name | Structure |
|---|---|---|
| 70 | N-((6-amino-2,4-dimethylpyridin-3-yl)methyl)-1-((3-chloro-8-fluoroquinolin-6-yl)methyl)-5-cyano-1H-pyrazole-4-carboxamide | 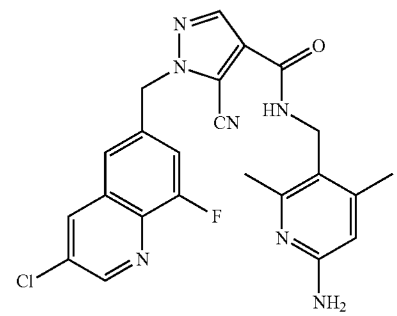 [SMILES: Cc1cc(N)nc(C)c1CNC(=O)c1cnn(Cc2cc(F)c3ncc(Cl)cc3c2)c1C#N] |
| 71 | N4-((6-amino-2,4-dimethylpyridin-3-yl)methyl)-1-((3-chloro-8-fluoroquinolin-6-yl)methyl)-1H-pyrazole-4,5-dicarboxamide | 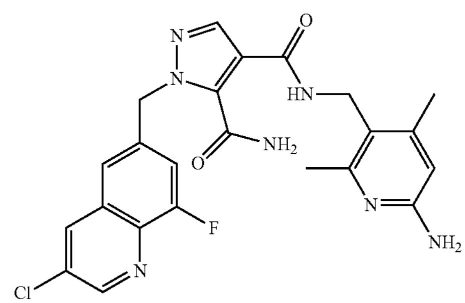 [SMILES: Cc1cc(N)nc(C)c1CNC(=O)c1cnn(Cc2cc(F)c3ncc(Cl)cc3c2)c1C(N)=O] |
| 72 | 6-((4-(((6-amino-2,4-dimethylpyridin-3-yl)methyl)carbamoyl)-3-cyano-1H-pyrazol-1-yl)methyl)-3-chloroquinoline-8-carboxamide | 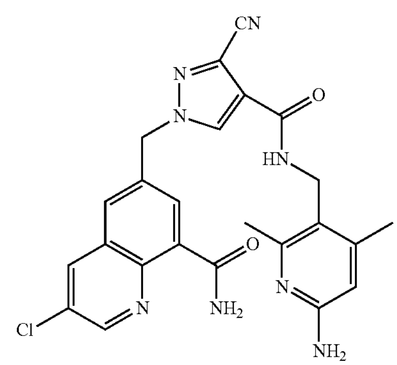 [SMILES: Cc1cc(N)nc(C)c1CNC(=O)c1cn(Cc2cc(C(N)=O)c3ncc(Cl)cc3c2)nc1C#N] |
| 73 | N-((6-amino-2,4-dimethylpyridin-3-yl)methyl)-3-cyano-1-((3-(trifluoromethyl)quinolin-6-yl)methyl)-1H-pyrazole-4-carboxamide | 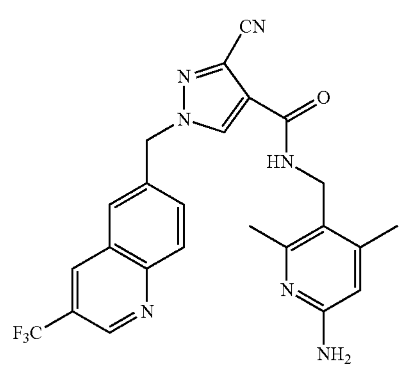 [SMILES: Cc1cc(N)nc(C)c1CNC(=O)c1cn(Cc2ccc3ncc(C(F)(F)F)cc3c2)nc1C#N] |

TABLE 1-continued

| Chemical Synthesis Example | Name | Structure |
|---|---|---|
| 74 | N-((6-amino-2-methylpyridin-3-yl)methyl)-3-cyano-1-((3-(trifluoromethyl)quinolin-6-yl)methyl)-1H-pyrazole-4-carboxamide | 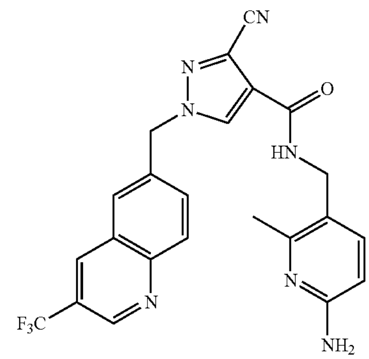 [SMILES: Cc1nc(N)ccc1CNC(=O)c1cn(Cc2ccc3ncc(C(F)(F)F)cc3c2)nc1C#N] |
| 75 | N-((6-amino-2,4-dimethylpyridin-3-yl)methyl)-5-((3-chloro-8-fluoroquinolin-6-yl)methyl)-1,3,4-oxadiazole-2-carboxamide | 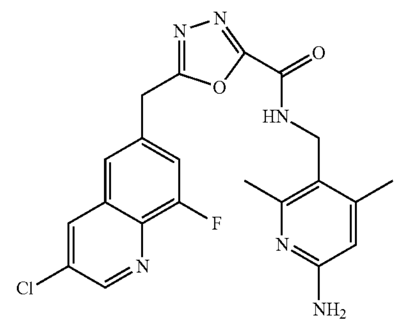 [SMILES: Cc1cc(N)nc(C)c1CNC(=O)c1nnc(Cc2cc(F)c3ncc(Cl)cc3c2)o1] |
| 76 | N-((6-amino-2,4-dimethylpyridin-3-yl)methyl)-1-((3-chloroquinolin-6-yl)methyl)-4-cyano-1H-pyrazolo[4,3-c]pyridine-3-carboxamide | 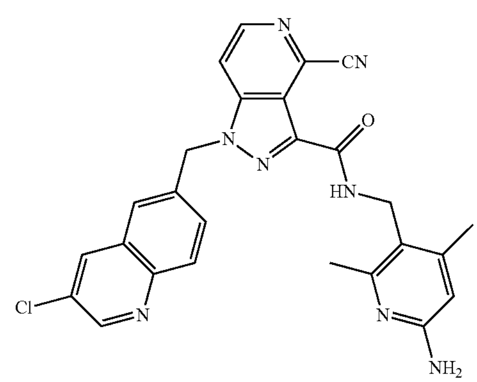 [SMILES: Cc1cc(N)nc(C)c1CNC(=O)c1nn(Cc2ccc3ncc(Cl)cc3c2)c2ccnc(C#N)c12] |
| 77 | N-((6-amino-2-methylpyridin-3-yl)methyl)-1-((3-chloroquinolin-6-yl)methyl)-3-cyano-1H-pyrazole-4-carboxamide | 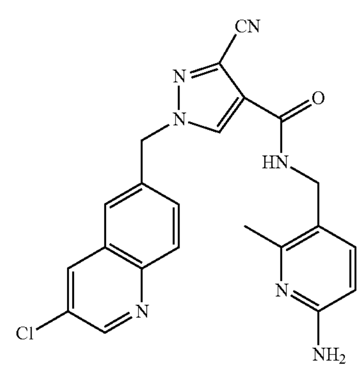 [SMILES: Cc1nc(N)ccc1CNC(=O)c1cn(Cc2ccc3ncc(Cl)cc3c2)nc1C#N] |

TABLE 1-continued

| Chemical Synthesis Example | Name | Structure |
|---|---|---|
| 78 | 6-((4-(((6-amino-2,4-dimethylpyridin-3-yl)methyl)carbamoyl)-3-cyano-1H-pyrazol-1-yl)methyl)-3-methylquinoline-8-carboxamide | 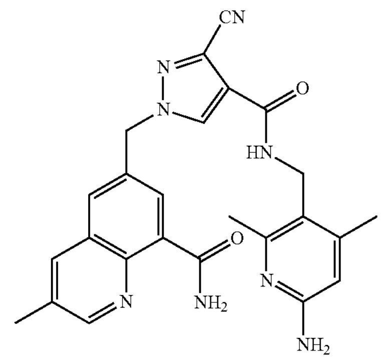 |
| 79 | N-((6-amino-2-methylpyridin-3-yl)methyl)-5-((3-chloroquinolin-6-yl)methyl)-1,3,4-oxadiazole-2-carboxamide | 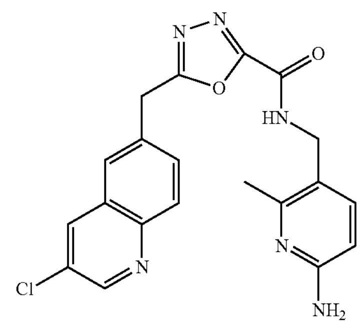 [SMILES: Cc1nc(N)ccc1CNC(=O)c1nnc(Cc2ccc3ncc(Cl)cc3c2)o1] |
| 80 | N-((6-amino-2,4-dimethylpyridin-3-yl)methyl)-2-(3-chloroquinoline-6-carbonyl)oxazole-5-carboxamide | 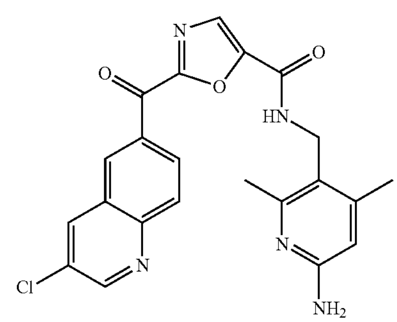 [SMILES: Cc1cc(N)nc(C)c1CNC(=O)c1cnc(C(=O)c2ccc3ncc(Cl)cc3c2)o1] |
| 81 | N-((6-amino-2,4-dimethylpyridin-3-yl)methyl)-3-cyano-1-((3-methylquinolin-6-yl)methyl)-1H-pyrazole-4-carboxamide | 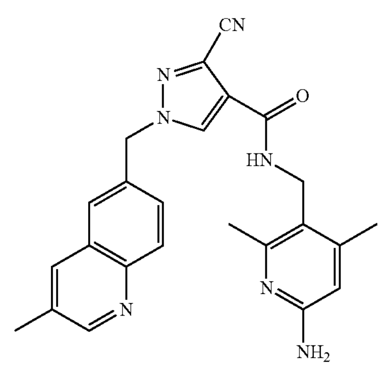 |

TABLE 1-continued

| Chemical Synthesis Example | Name | Structure |
|---|---|---|
| 82 | N-((6-amino-2-methylpyridin-3-yl)methyl)-3-cyano-1-((3-methylquinolin-6-yl)methyl)-1H-pyrazole-4-carboxamide | 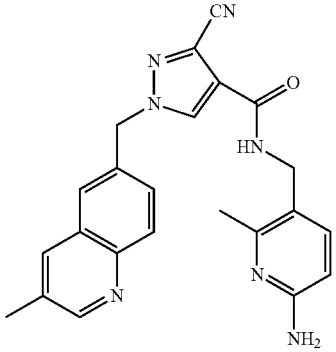 [SMILES: Cc1cnc2ccc(Cn3cc(C(=O)NCc4ccc(N)nc4C)c(C#N)n3)cc2c1] |
| 83 | N-((6-amino-2-methylpyridin-3-yl)methyl)-2-((3-chloroquinolin-6-yl)methyl)oxazole-4-carboxamide | 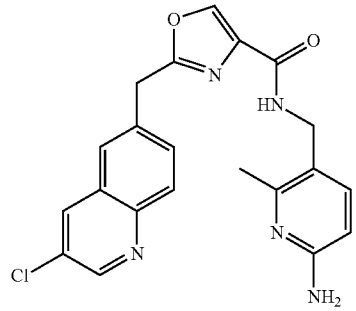 [SMILES: Cc1nc(N)ccc1CNC(=O)c1coc(Cc2ccc3ncc(Cl)cc3c2)n1] |
| 84 | N-((6-amino-2-methylpyridin-3-yl)methyl)-5-((3-chloroquinolin-6-yl)methyl)oxazole-2-carboxamide | 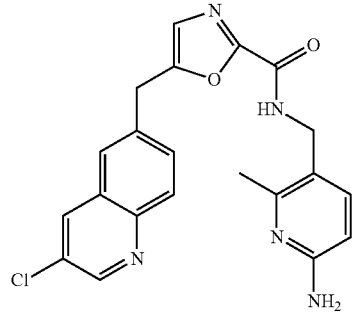 [SMILES: Cc1nc(N)ccc1CNC(=O)c1ncc(Cc2ccc3ncc(Cl)cc3c2)o1] |
| 85 | N-((6-amino-2-methylpyridin-3-yl)methyl)-1-((3-chloroquinolin-6-yl)methyl)-3-methyl-1H-pyrazole-4-carboxamide | 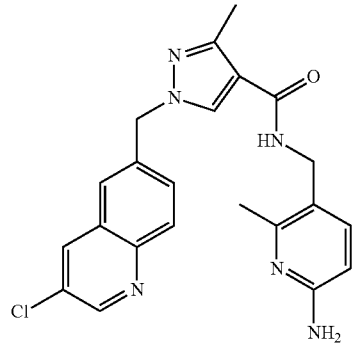 [SMILES: Cc1nc(N)ccc1CNC(=O)c1cn(Cc2ccc3ncc(Cl)cc3c2)nc1C] |

TABLE 1-continued

| Chemical Synthesis Example | Name | Structure |
|---|---|---|
| 86 | N-((6-amino-2,4-dimethylpyridin-3-yl)methyl)-5-((3-chloro-8-(2-hydroxypropan-2-yl)quinolin-6-yl)methyl)-1,3,4-oxadiazole-2-carboxamide | 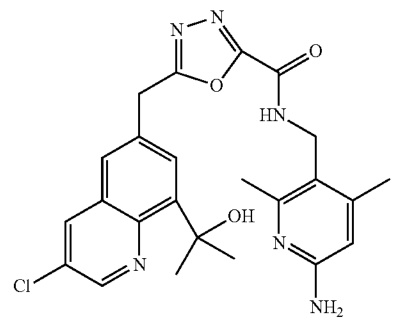 [SMILES: Cc1cc(N)nc(C)c1CNC(=O)c1nnc(Cc2cc(C(C)(C)O)c3ncc(Cl)cc3c2)o1] |
| 87 | N-((6-amino-2,4-dimethylpyridin-3-yl)methyl)-2-((3-chloroquinolin-6-yl)methyl)-4-cyanooxazole-5-carboxamide | 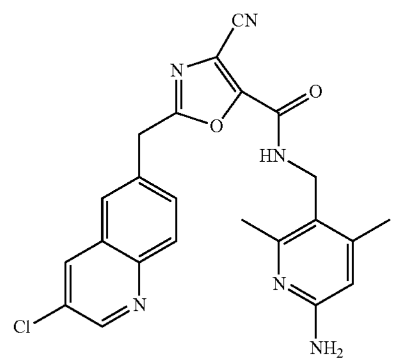 [SMILES: Cc1cc(N)nc(C)c1CNC(=O)c1oc(Cc2ccc3ncc(Cl)cc3c2)nc1C#N] |
| 88 | N-((6-amino-2-methylpyridin-3-yl)methyl)-2-((3-chloroquinolin-6-yl)methyl)-4-cyanooxazole-5-carboxamide | 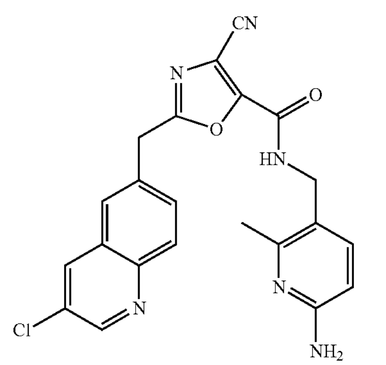 [SMILES: Cc1nc(N)ccc1CNC(=O)c1oc(Cc2ccc3ncc(Cl)cc3c2)nc1C#N] |
| 89 | N-((6-amino-2,4-dimethylpyridin-3-yl)methyl)-2-((3-chloroquinolin-6-yl)methyl)oxazole-5-carboxamide | 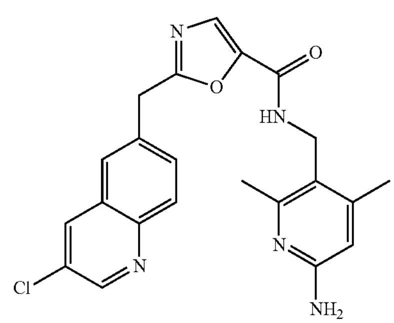 [SMILES: Cc1cc(N)nc(C)c1CNC(=O)c1cnc(Cc2ccc3ncc(Cl)cc3c2)o1] |

TABLE 1-continued

| Chemical Synthesis Example | Name | Structure |
|---|---|---|
| 90 | N-((6-amino-2-methylpyridin-3-yl)methyl)-2-((3-chloroquinolin-6-yl)methyl)oxazole-5-carboxamide | 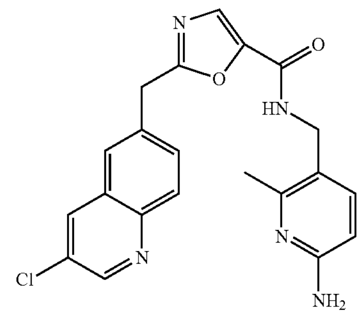 [SMILES: Cc1nc(N)ccc1CNC(=O)c1cnc(Cc2ccc3ncc(Cl)cc3c2)o1] |
| 91 | N-((6-amino-2,4-dimethylpyridin-3-yl)methyl)-1-((3-chloroquinolin-6-yl)methyl)-3-(difluoromethyl)-1H-pyrazole-4-carboxamide | 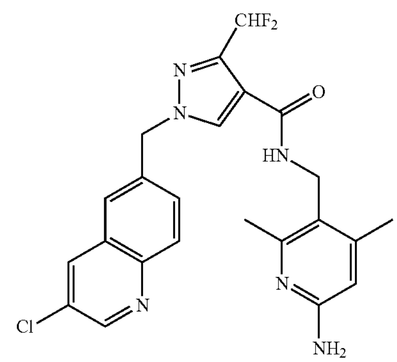 [SMILES: Cc1cc(N)nc(C)c1CNC(=O)c1cn(Cc2ccc3ncc(Cl)cc3c2)nc1C(F)F] |
| 92 | N-((6-amino-2,4-dimethylpyridin-3-yl)methyl)-1-((3-chloroquinolin-6-yl)methyl)-3-(hydroxymethyl)-1H-pyrazole-4-carboxamide | 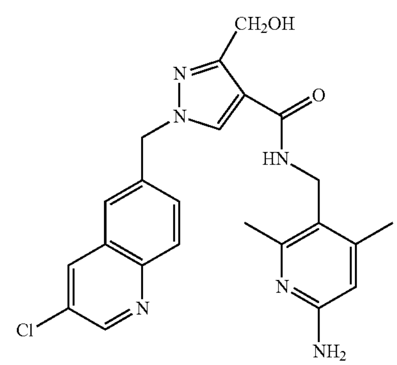 [SMILES: Cc1cc(N)nc(C)c1CNC(=O)c1cn(Cc2ccc3ncc(Cl)cc3c2)nc1CO] |
| 93 | N-((6-amino-2,4-dimethylpyridin-3-yl)methyl)-1-((3-chloroquinolin-6-yl)methyl)-3-(fluoromethyl)-1H-pyrazole-4-carboxamide | 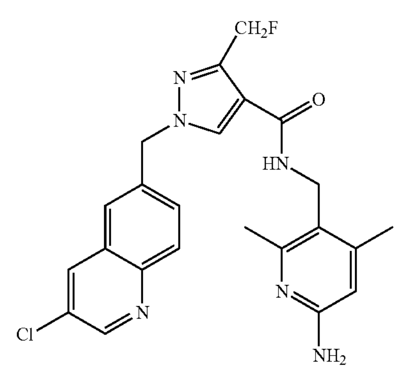 |

TABLE 1-continued

| Chemical Synthesis Example | Name | Structure |
|---|---|---|
| 94 | N-((6-amino-2,4-dimethylpyridin-3-yl)methyl)-1-((3-chloroquinolin-6-yl)methyl)-3-(1-hydroxyethyl)-1H-pyrazole-4-carboxamide | 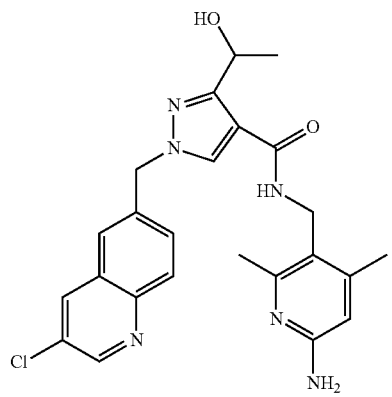 [SMILES: Cc1cc(N)nc(C)c1CNC(=O)c1cn(Cc2ccc3ncc(Cl)cc3c2)nc1C(C)O] |
| 95 | N-((6-amino-2,4-dimethylpyridin-3-yl)methyl)-2-((3-chloroquinolin-6-yl)methyl)-5-cyano-2H-1,2,3-triazole-4-carboxamide | 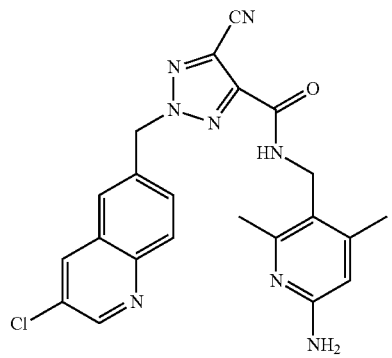 |
| 96 | N-((6-amino-2,4-dimethylpyridin-3-yl)methyl)-5-((3-chloroquinolin-6-yl)methyl)-4H-1,2,4-triazole-3-carboxamide | 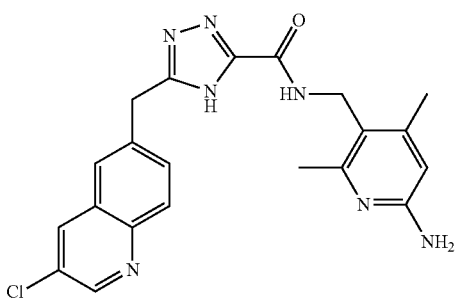 [SMILES: Cc1cc(N)nc(C)c1CNC(=O)c1nnc(Cc2ccc3ncc(Cl)cc3c2)[nH]1] |
| 97 | N-((6-amino-2-methylpyridin-3-yl)methyl)-5-((3-chloroquinolin-6-yl)methyl)-4H-1,2,4-triazole-3-carboxamide | 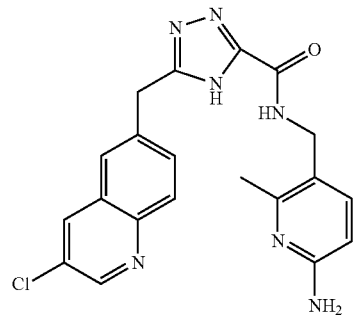 [SMILES: Cc1nc(N)ccc1CNC(=O)c1nnc(Cc2ccc3ncc(Cl)cc3c2)[nH]1] |

TABLE 1-continued

| Chemical Synthesis Example | Name | Structure |
|---|---|---|
| 98 | N-((6-amino-2,4-dimethylpyridin-3-yl)methyl)-5-((3-chloroquinolin-6-yl)methyl)-4-methyl-4H-1,2,4-triazole-3-carboxamide | 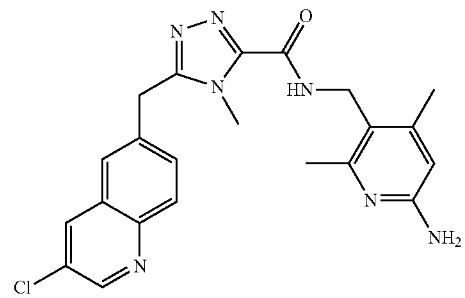 [SMILES: Cc1cc(N)nc(C)c1CNC(=O)c1nnc(Cc2ccc3ncc(Cl)cc3c2)n1C] |
| 99 | N-((6-amino-2,4-dimethylpyridin-3-yl)methyl)-3-((3-chloroquinolin-6-yl)methyl)-1-methyl-1H-1,2,4-triazole-5-carboxamide | 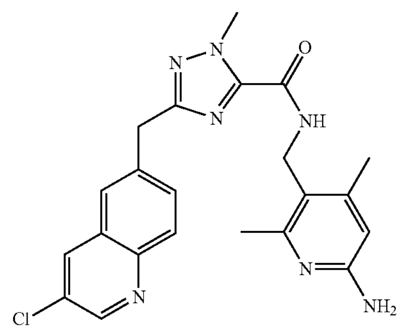 [SMILES: Cc1cc(N)nc(C)c1CNC(=O)c1nc(Cc2ccc3ncc(Cl)cc3c2)nn1C] |
| 100 | N-((6-amino-2,4-dimethylpyridin-3-yl)methyl)-5-bromo-1-((3-chloroquinolin-6-yl)methyl)-1H-1,2,4-triazole-3-carboxamide | 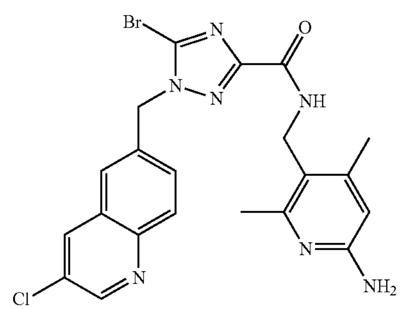 [SMILES: Cc1cc(N)nc(C)c1CNC(=O)c1nc(Br)n(Cc2ccc3ncc(Cl)cc3c2)n1] |
| 101 | N-((6-amino-2,4-dimethylpyridin-3-yl)methyl)-1-((3-chloroquinolin-6-yl)methyl)-5-cyano-1H-1,2,4-triazole-3-carboxamide | 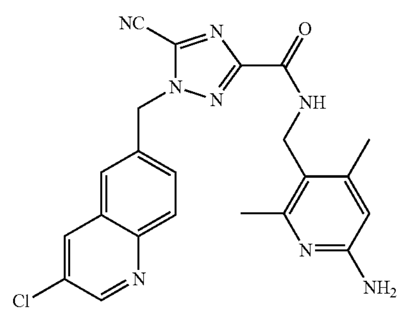 [SMILES: Cc1cc(N)nc(C)c1CNC(=O)c1nc(C#N)n(Cc2ccc3ncc(Cl)cc3c2)n1] |

TABLE 1-continued

| Chemical Synthesis Example | Name | Structure |
|---|---|---|
| 102 | methyl 3-(((6-amino-2,4-dimethylpyridin-3-yl)methyl)carbamoyl)-1-((3-chloroquinolin-6-yl)methyl)-1H-1,2,4-triazole-5-carboxylate | 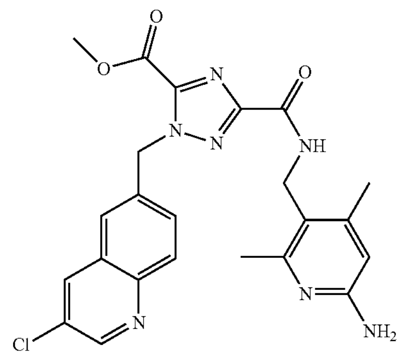 [SMILES: COC(=O)c1nc(C(=O)NCc2c(C)cc(N)nc2C)nn1Cc1ccc2ncc(Cl)cc2c1] |
| 103 | N-((6-amino-2,4-dimethylpyridin-3-yl)methyl)-2-((3-chloroquinolin-6-yl)methyl)-1H-imidazole-4-carboxamide | 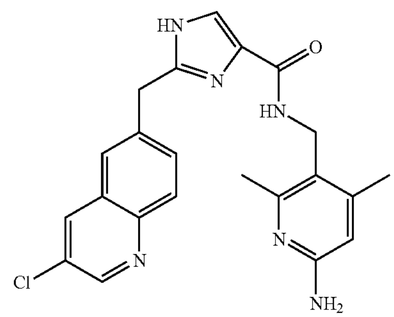 |
| 104 | N-((6-amino-2,4-dimethylpyridin-3-yl)methyl)-2-((3-chloroquinolin-6-yl)methyl)-1-methyl-1H-imidazole-4-carboxamide | 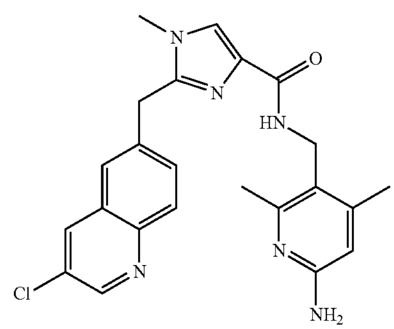 [SMILES: Cc1cc(N)nc(C)c1CNC(=O)c1cn(C)c(Cc2ccc3ncc(Cl)cc3c2)n1] |
| 105 | N-((6-amino-2,4-dimethylpyridin-3-yl)methyl)-2-((3-chloroquinolin-6-yl)methyl)-1-methyl-1H-imidazole-5-carboxamide | 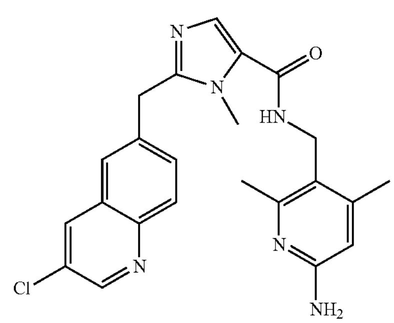 [SMILES: Cc1cc(N)nc(C)c1CNC(=O)c1cnc(Cc2ccc3ncc(Cl)cc3c2)n1C] |

TABLE 1-continued

| Chemical Synthesis Example | Name | Structure |
|---|---|---|
| 106 | N-((6-amino-2,4-dimethylpyridin-3-yl)methyl)-4-bromo-2-((3-chloroquinolin-6-yl)methyl)-1H-imidazole-5-carboxamide | 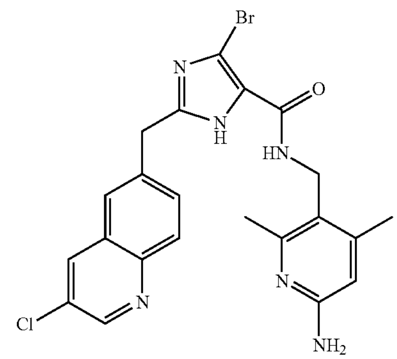 [SMILES: Cc1cc(N)nc(C)c1CNC(=O)c1[nH]c(Cc2ccc3ncc(Cl)cc3c2)nc1Br] |
| 107 | N-((6-amino-2,4-dimethylpyridin-3-yl)methyl)-1-((3-chloroquinolin-6-yl)methyl)-5-cyano-1H-1,2,4-triazole-3-carboxamide | 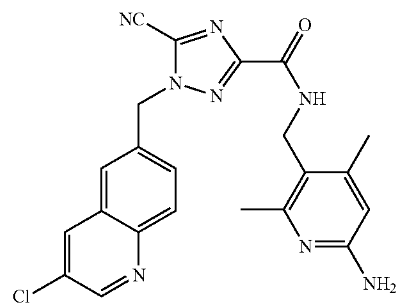 [SMILES: Cc1cc(N)nc(C)c1CNC(=O)c1nc(C#N)n(Cc2ccc3ncc(Cl)cc3c2)n1] |
| 108 | N-((6-amino-2,4-dimethylpyridin-3-yl)methyl)-1-((3-chloroquinolin-6-yl)methyl)-5-cyano-1H-pyrazole-3-carboxamide | 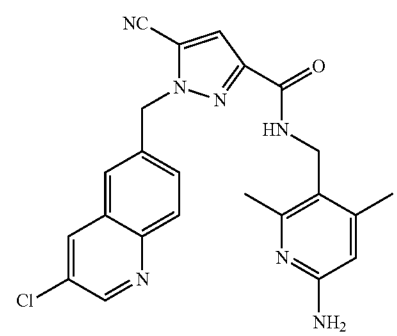 [SMILES: Cc1cc(N)nc(C)c1CNC(=O)c1cc(C#N)n(Cc2ccc3ncc(Cl)cc3c2)n1] |
| 109 | N-((6-amino-2,4-dimethylpyridin-3-yl)methyl)-1-((3-chloroquinolin-6-yl)methyl)-3-cyano-1H-pyrazole-5-carboxamide | 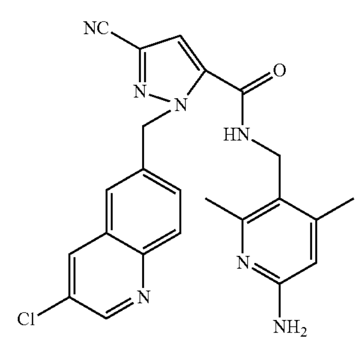 [SMILES: Cc1cc(N)nc(C)c1CNC(=O)c1cc(C#N)nn1Cc1ccc2ncc(Cl)cc2c1] |

TABLE 1-continued

| Chemical Synthesis Example | Name | Structure |
|---|---|---|
| 110 | N-((6-amino-2,4-dimethylpyridin-3-yl)methyl)-1-((3-chloroquinolin-6-yl)methyl)-2-(hydroxymethyl)-1H-imidazole-4-carboxamide | 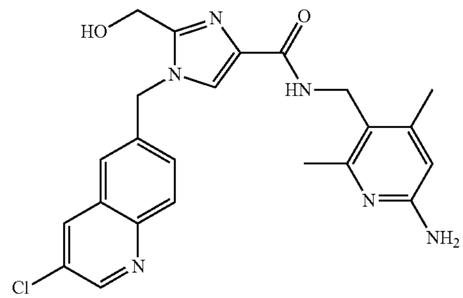 [SMILES: Cc1cc(N)nc(C)c1CNC(=O)c1cn(Cc2ccc3ncc(Cl)cc3c2)c(CO)n1] |
| 111 | N4-((6-amino-2,4-dimethylpyridin-3-yl)methyl)-1-((3-chloroquinolin-6-yl)methyl)-1H-imidazole-2,4-dicarboxamide | 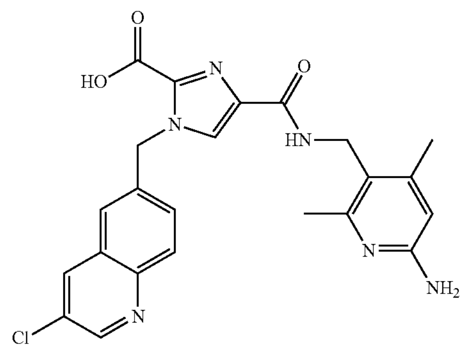 [SMILES: Cc1cc(N)nc(C)c1CNC(=O)c1cn(Cc2ccc3ncc(Cl)cc3c2)c(C(=O)O)n1] |
| 112 | N-((6-amino-2,4-dimethylpyridin-3-yl)methyl)-2-(aminomethyl)-1-((3-chloroquinolin-6-yl)methyl)-1H-imidazole-4-carboxamide | 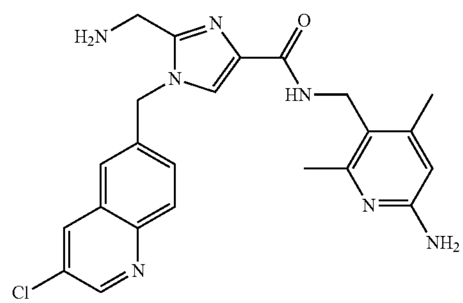 [SMILES: Cc1cc(N)nc(C)c1CNC(=O)c1cn(Cc2ccc3ncc(Cl)cc3c2)c(CN)n1] |
| 113 | N-((6-amino-2,4-dimethylpyridin-3-yl)methyl)-1-((3-chloroquinolin-6-yl)methyl)-2-cyano-1H-imidazole-4-carboxamide | 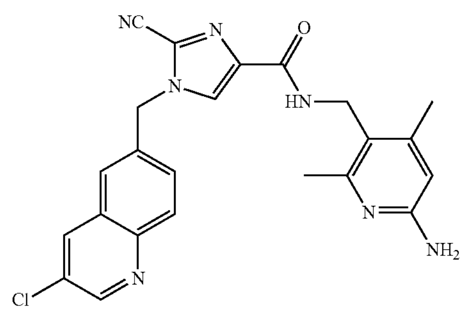 [SMILES: Cc1cc(N)nc(C)c1CNC(=O)c1cn(Cc2ccc3ncc(Cl)cc3c2)c(C#N)n1] |
| 114 | N-((6-amino-2,4-dimethylpyridin-3-yl)methyl)-2-((3-chloroquinolin-6-yl)methyl)oxazole-5-carboxamide | 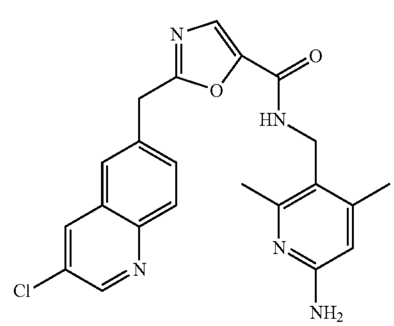 |

TABLE 1-continued

| Chemical Synthesis Example | Name | Structure |
|---|---|---|
| 115 | N-((6-amino-2,4-dimethylpyridin-3-yl)methyl)-2-((3-chloroquinolin-6-yl)methyl)-5-(trifluoromethyl)-2H-1,2,3-triazole-4-carboxamide | 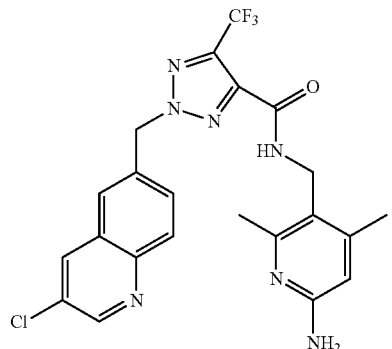 |
| 116 | N-((6-amino-2,4-dimethylpyridin-3-yl)methyl)-1-((3-chloroquinolin-6-yl)methyl)-5-(trifluoromethyl)-1H-pyrazole-3-carboxamide | 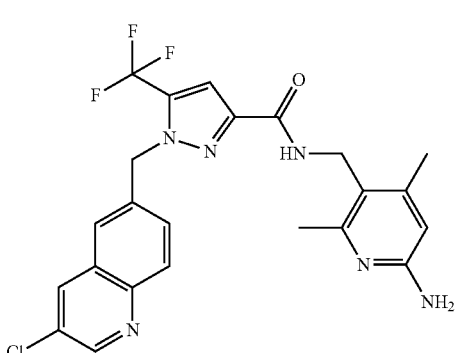 |
| 117 | N-((6-amino-2,4-dimethylpyridin-3-yl)methyl)-5-chloro-1-((3-chloroquinolin-6-yl)methyl)-1H-pyrrolo[2,3-c]pyridine-3-carboxamide | 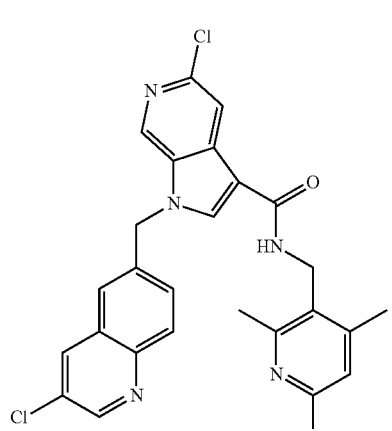 |
| 118 | N-((6-amino-2,4-dimethylpyridin-3-yl)methyl)-1-((3-chloroquinolin-6-yl)methyl)-4-oxo-4,5-dihydro-1H-pyrrolo[3,2-c]pyridine-3-carboxamide | 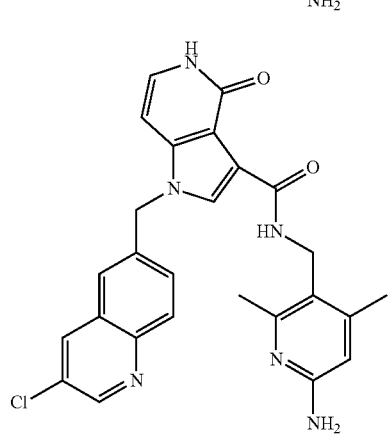 |

TABLE 1-continued

| Chemical Synthesis Example | Name | Structure |
|---|---|---|
| 119 | N-((6-amino-2,4-dimethylpyridin-3-yl)methyl)-4-chloro-1-((3-chloroquinolin-6-yl)methyl)-1H-pyrazolo[4,3-c]pyridine-3-carboxamide | 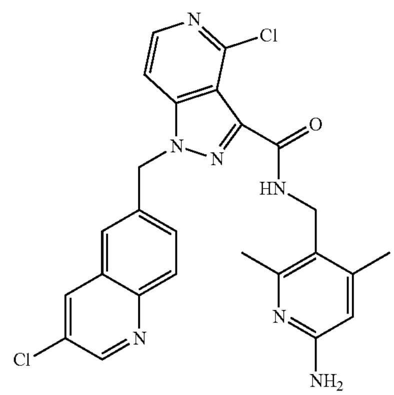 [SMILES: Cc1cc(N)nc(C)c1CNC(=O)c1nn(Cc2ccc3ncc(Cl)cc3c2)c2ccnc(Cl)c12] |
| 120 | N-((6-amino-2,4-dimethylpyridin-3-yl)methyl)-1-((3-chloroquinolin-6-yl)methyl)-4-oxo-4,5-dihydro-1H-pyrazolo[4,3-c]pyridine-3-carboxamide | 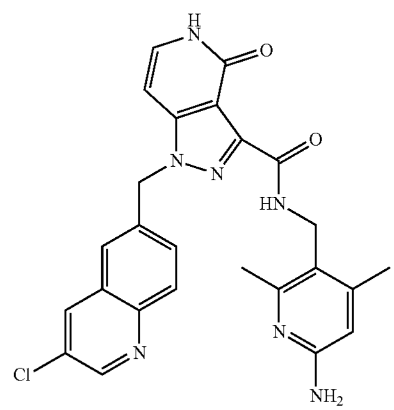 [SMILES: Cc1cc(N)nc(C)c1CNC(=O)c1nn(Cc2ccc3ncc(Cl)cc3c2)c2cc[nH]c(=O)c12] |
| 121 | N-((6-amino-2,4-dimethylpyridin-3-yl)methyl)-1-((3-chloroquinolin-6-yl)methyl)-5-methoxy-1H-pyrrolo[2,3-c]pyridine-3-carboxamide | 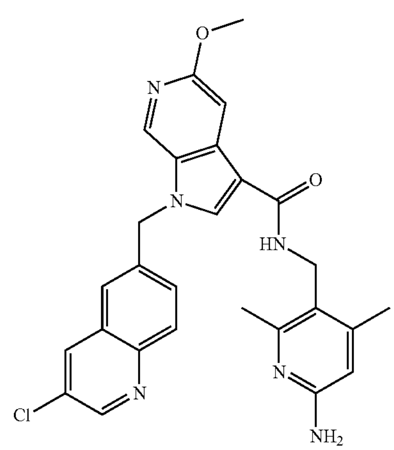 [SMILES: COc1cc2c(C(=O)NCc3c(C)cc(N)nc3C)cn(Cc3ccc4ncc(Cl)cc4c3)c2cn1] |

TABLE 1-continued

| Chemical Synthesis Example | Name | Structure |
|---|---|---|
| 122 | N-((6-amino-2,4-dimethylpyridin-3-yl)methyl)-1-((3-chloroquinolin-6-yl)methyl)-5-methoxy-1H-pyrazolo[3,4-c]pyridine-3-carboxamide | 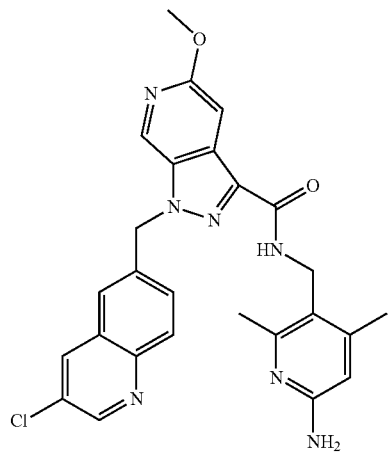 [SMILES: COc1cc2c(C(=O)NCc3c(C)cc(N)nc3C)nn(Cc3ccc4ncc(Cl)cc4c3)c2cn1] |
| 123 | N-((6-amino-2,4-dimethylpyridin-3-yl)methyl)-1-((3-chloroquinolin-6-yl)methyl)-4-cyano-1H-pyrrolo[2,3-c]pyridine-3-carboxamide | 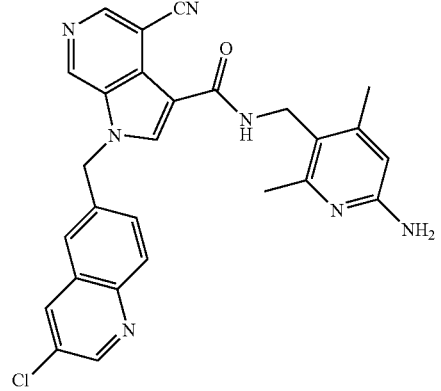 [SMILES: Cc1cc(N)nc(C)c1CNC(=O)c1cn(Cc2ccc3ncc(Cl)cc3c2)c2cncc(C#N)c12] |
| 124 | N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide | 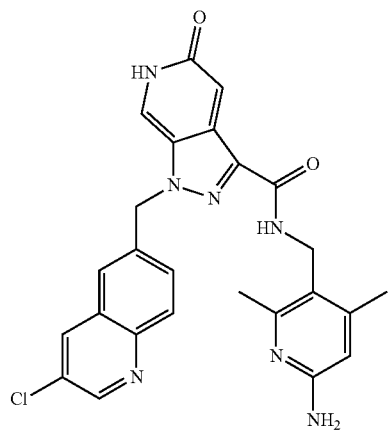 [SMILES: Cc1cc(N)nc(C)c1CNC(=O)c1nn(Cc2ccc3ncc(Cl)cc3c2)c2c[nH]c(=O)cc12] |

TABLE 1-continued

| Chemical Synthesis Example | Name | Structure |
|---|---|---|
| 125 | N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide | 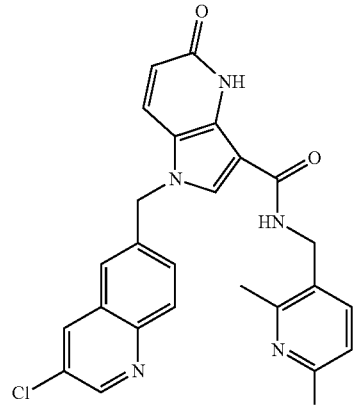 |
| 126 | N-((6-amino-2,4-dimethylpyridin-3-yl)methyl)-1-((3-chloroquinolin-6-yl)methyl)-5-oxo-4,5-dihydro-1H-pyrrolo[3,2-b]pyridine-3-carboxamide | 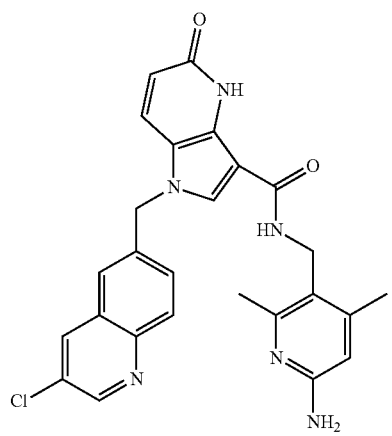 [SMILES: Cc1cc(N)nc(C)c1CNC(=O)c1cn(Cc2ccc3ncc(Cl)cc3c2)c2ccc(=O)[nH]c12] |
| 127 | N-((6-amino-2,4-dimethylpyridin-3-yl)methyl)-1-((3-chloroquinolin-6-yl)methyl)-4-cyano-1H-pyrrolo[2,3-b]pyridine-3-carboxamide | 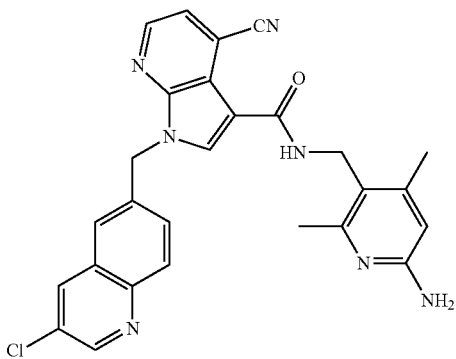 [SMILES: Cc1cc(N)nc(C)c1CNC(=O)c1cn(Cc2ccc3ncc(Cl)cc3c2)c2nccc(C#N)c12] |

TABLE 1-continued

| Chemical Synthesis Example | Name | Structure |
|---|---|---|
| 128 | N-((6-amino-2,4-dimethylpyridin-3-yl)methyl)-1-((3-chloroquinolin-6-yl)methyl)-5-methoxy-1H-pyrrolo[3,2-b]pyridine-3-carboxamide | 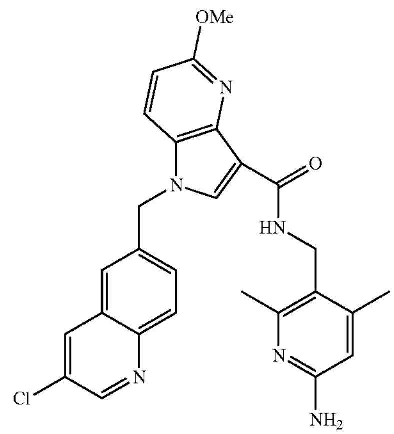 [SMILES: COc1ccc2c(n1)c(C(=O)NCc1c(C)cc(N)nc1C)cn2Cc1ccc2ncc(Cl)cc2c1] |
| 129 | N-((6-amino-2,4-dimethylpyridin-3-yl)methyl)-1-((3-chloroquinolin-6-yl)methyl)-4-cyano-1H-pyrazolo[3,4-c]pyridine-3-carboxamide | 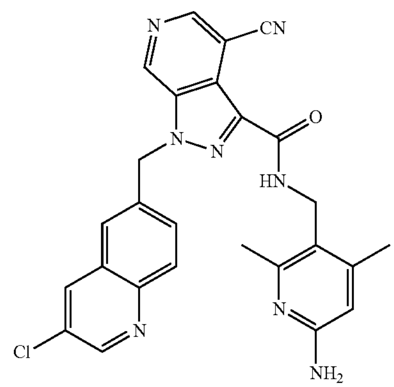 [SMILES: Cc1cc(N)nc(C)c1CNC(=O)c1nn(Cc2ccc3ncc(Cl)cc3c2)c2cncc(C#N)c12] |
| 130 | N-((6-amino-2,4-dimethylpyridin-3-yl)methyl)-1-((3-chloroquinolin-6-yl)methyl)-5-cyano-1H-pyrazolo[3,4-c]pyridine-3-carboxamide | 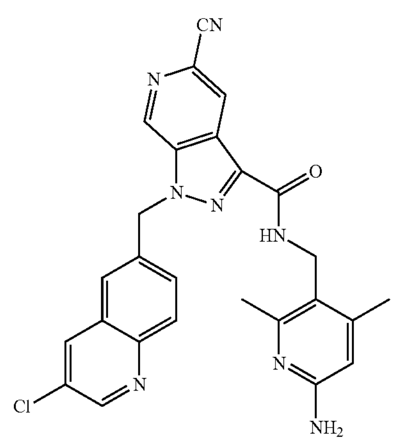 |

TABLE 1-continued

| Chemical Synthesis Example | Name | Structure |
|---|---|---|
| 131 | N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide | 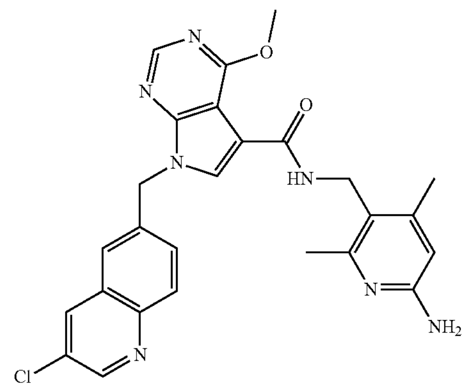 [SMILES: COc1ncnc2c1c(C(=O)NCc1c(C)cc(N)nc1C)cn2Cc1ccc2ncc(Cl)cc2c1] |
| 132 | N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide | 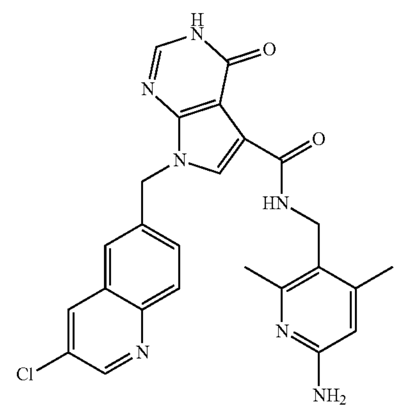 [SMILES: Cc1cc(N)nc(C)c1CNC(=O)c1cn(Cc2ccc3ncc(Cl)cc3c2)c2nc[nH]c(=O)c12] |
| 133 | N-((6-amino-2,4-dimethylpyridin-3-yl)methyl)-1-((3-chloroquinolin-6-yl)methyl)-4-cyano-1H-pyrrolo[3,2-c]pyridine-3-carboxamide | 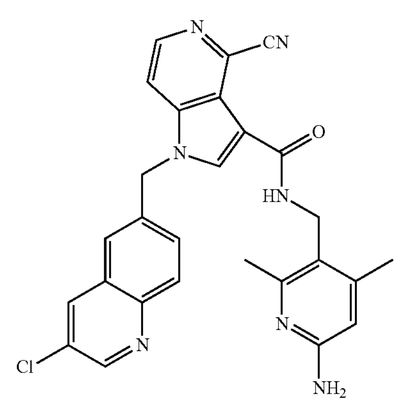 [SMILES: Cc1cc(N)nc(C)c1CNC(=O)c1cn(Cc2ccc3ncc(Cl)cc3c2)c2ccnc(C#N)c12] |

TABLE 1-continued

| Chemical Synthesis Example | Name | Structure |
|---|---|---|
| 134 | N-((6-amino-2,4-dimethylpyridin-3-yl)methyl)-1-((3-chloroquinolin-6-yl)methyl)-5-cyano-1H-pyrrolo[2,3-c]pyridine-3-carboxamide | 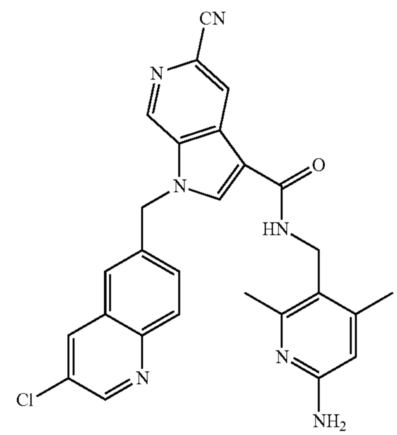 [SMILES: Cc1cc(N)nc(C)c1CNC(=O)c1cn(Cc2ccc3ncc(Cl)cc3c2)c2cnc(C#N)cc12] |
| 135 | N-((6-amino-2,4-dimethylpyridin-3-yl)methyl)-1-((3-chloroquinolin-6-yl)methyl)-5-cyano-1H-pyrrolo[2,3-b]pyridine-3-carboxamide | 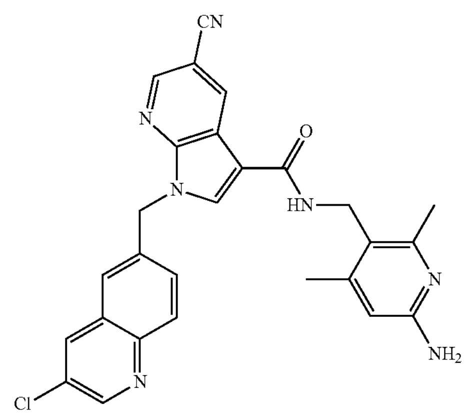 [SMILES: Cc1cc(N)nc(C)c1CNC(=O)c1cn(Cc2ccc3ncc(Cl)cc3c2)c2ncc(C#N)cc12] |
| 136 | N-((6-amino-2,4-dimethylpyridin-3-yl)methyl)-7-((3-chloroquinolin-6-yl)methyl)-4-cyano-7H-pyrrolo[2,3-d]pyrimidine-5-carboxamide | 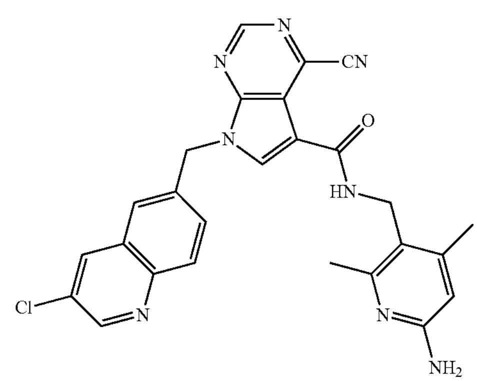 |

TABLE 1-continued

| Chemical Synthesis Example | Name | Structure |
|---|---|---|
| 137 | N-((6-amino-2,4-dimethylpyridin-3-yl)methyl)-1-((3-chloroquinolin-6-yl)methyl)-5-methoxy-1H-pyrazolo[4,3-b]pyridine-3-carboxamide | 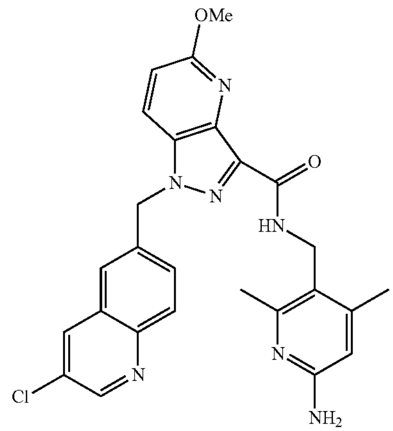 [SMILES: COc1ccc2c(n1)c(C(=O)NCc1c(C)cc(N)nc1C)nn2Cc1ccc2ncc(Cl)cc2c1] |
| 138 | N-((6-amino-2,4-dimethylpyridin-3-yl)methyl)-1-((3-chloroquinolin-6-yl)methyl)-5-oxo-4,5-dihydro-1H-pyrazolo[4,3-b]pyridine-3-carboxamide | 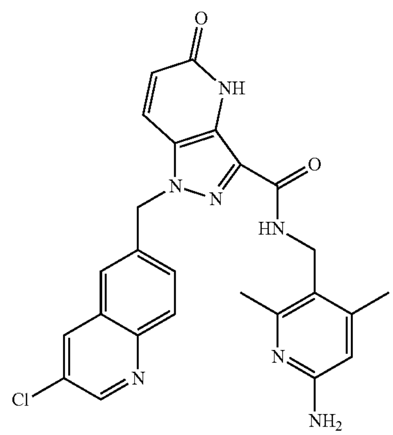 [SMILES: Cc1cc(N)nc(C)c1CNC(=O)c1nn(Cc2ccc3ncc(Cl)cc3c2)c2ccc(=O)[nH]c12] |
| 139 | N-((6-amino-2-methylpyridin-3-yl)methyl)-1-((3-chloroquinolin-6-yl)methyl)-5-oxo-4,5-dihydro-1H-pyrazolo[4,3-b]pyridine-3-carboxamide | 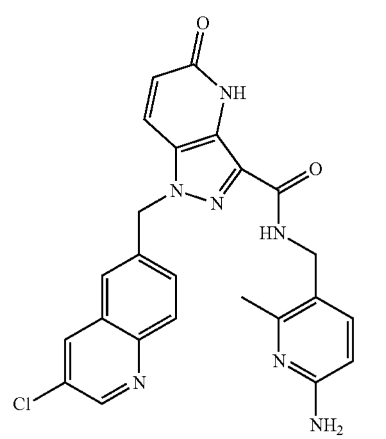 [SMILES: Cc1nc(N)ccc1CNC(=O)c1nn(Cc2ccc3ncc(Cl)cc3c2)c2ccc(=O)[nH]c12] |

TABLE 1-continued

| Chemical Synthesis Example | Name | Structure |
|---|---|---|
| 140 | 4-amino-N-((6-amino-2,4-dimethylpyridin-3-yl)methyl)-2-((3-chloroquinolin-6-yl)methyl)-2H-indazole-3-carboxamide | 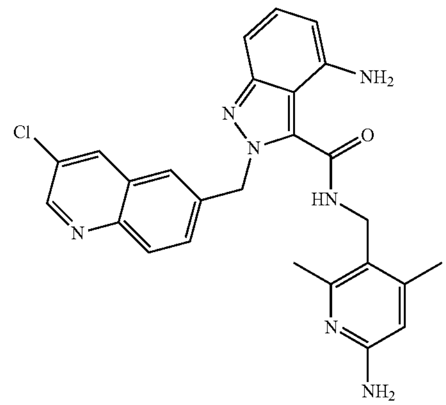 [SMILES: Cc1cc(N)nc(C)c1CNC(=O)c1c2c(N)cccc2nn1Cc1ccc2ncc(Cl)cc2c1] |
| 141 | N-((6-amino-2,4-dimethylpyridin-3-yl)methyl)-1-((3-chloroquinolin-6-yl)methyl)-4-(trifluoromethyl)-1H-1,2,3-triazole-5-carboxamide | 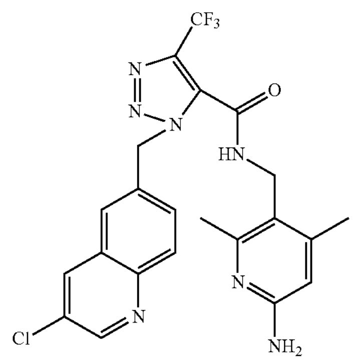 [SMILES: Cc1cc(N)nc(C)c1CNC(=O)c1c(C(F)(F)F)nnn1Cc1ccc2ncc(Cl)cc2c1] |
| 142 | ethyl 3-(((6-amino-2,4-dimethylpyridin-3-yl)methyl)carbamoyl)-1-((3-chloroquinolin-6-yl)methyl)-1H-1,2,4-triazole-5-carboxylate | 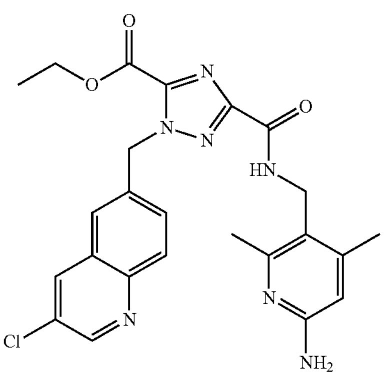 [SMILES: CCOC(=O)c1nc(C(=O)NCc2c(C)cc(N)nc2C)nn1Cc1ccc2ncc(Cl)cc2c1] |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the kallikrein inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the kallikrein inhibitory compound as described herein is administered as a pure chemical. In other embodiments, the kallikrein inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one kallikrein inhibitory compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), (Ia), (II), (III), (IV), (V), (VI), (VII), (IIX), (IX), (X), or (XI), or a pharmaceutically acceptable salt thereof, and a pharmaceutically acceptable excipient.

In certain embodiments, the kallikrein inhibitory compound as described by Formula (I), (Ia), (II), (III), (IV), (V), (VI), (VII), (IIX), (IX), (X), or (XI) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one kallikrein inhibitory compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Kallikrein-Kinin System

Modulation of vascular permeability is important in regulating the passage of small molecules or blood cells between blood vessels and surrounding tissues. Vascular permeability depends upon the physiological states of tissues such as during inflammation, changes in blood pressure, and fluctuations in ion and nutrient gradients. The junctions between the endothelial cells that line blood vessels are the immediate controllers of vascular permeability. The strength of these junctions is tightly regulated by the kinin-kallikrein system of polypeptides and enzymes. Abnormalities in the kinin-kallikrein system lead to a range of pathologies including angioedema, macular edema and brain edema. Angioedema is a potentially fatal blood disorder characterized by swelling that may occur in the face, gastrointestinal tract, extremities, genitals and upper airways. Genetic hereditary angioedema attacks result from the unregulated activation of the kallikrein system with uncontrolled increases in vascular permeability. Currently there is a need for agents that are useful for the treatment of angioedema and for agents that inhibit plasma kallikrein.

The kallikrein-kinin system represents a metabolic cascade that, when activated, triggers the release of vasoactive kinins. The kinin-kallikrein system (KKS) consists of serine proteases involved in the production of kinins, principally bradykinin and Lys-bradykinin (kallidin). The KKS contributes to a variety of physiological processes including inflammation, blood pressure control and coagulation. The activation of this system is particularly important in blood pressure regulation and in inflammatory reactions, due to the ability of bradykinin to elevate vascular permeability and to cause vasodilatation of arteries and veins of the gut, aorta, uterus and urethra. The kinin-kallikrein system, also referred to as the contact system, consists of three serine proenzymes (factor XII (FXII) or Hageman factor, factor IX (FIX), and prekallikrein), and the kinin precursor high molecular weight kinin (HK). Contact activation is triggered by the binding of FXII to a negatively charged surface and involves the formation of α-FXIIa via autocatalysis. Bound α-FXIIa converts prekallikrein into kallikrein. Kallikrein can further convert α-FXIIa to β-FXIIa by an additional cleavage at R334-N335, a positive feedback mechanism that leads to sufficient kallikrein production to drive downstream processes. α-FXIIa consists of a heavy and light chain that are disulphide linked, whereas β-FXIIa lacks the heavy chain and loses its capacity to bind to negatively charged surfaces (Stavrou E, Schmaier A H., Thrombosis Research, 2010, 125(3) pp. 210-215). The N-terminal region of FXII (α-FXIIa heavy chain) shows strong homology with tissue-type plasminogen activator (tPA), with the presence of fibronectin type I, epidermal growth factor, and Kringle domains (Ny et al., Proc Natl Acad Sci USA, 1984, 81(17) pp. 5355-5359; Cool D E, MacGillivray R T, The Journal of Biological Chemistry, 1987, 262(28) pp. 13662-13673). Kallikrein is a trypsin-like serine protease enzyme that cleaves high molecular weight kinin (HK) to produce bradykinin. Bradykinin then binds to the bradykinin 2R receptors (BK2R) on endothelial cells to trigger an increase in vascular permeability.

Protease inhibitors regulate the activation of the contact system. Several known serpins of plasma are C1-inhibitor (C1INH), antithrombin III, α2-macroglobulin, α1-protease inhibitor, and α2-antiplasmin (Kaplan et al., Advances in Immunology, 1997 (66) pp. 225-72; Pixley et al., The Journal of Biological Chemistry, 1985, 260(3) pp. 1723-9). However, C1INH is the major regulator of the intrinsic system, interfering with the activities of factor XIIa and of kallikrein (Cugno et al., The Journal of Laboratory and Clinical Medicine, 1993, 121(1) pp. 38-43). Both C1INH and α2-macroglobulin account for more than 90% of the kallikrein inhibitory activity of plasma. Thus, the FXII-dependent kallikrein-kinin system is tightly regulated by the CINH and when regulation of the FXII-dependent kallikrein-kinin system fails, in a subject, the subject is believed to suffer from hereditary angioedema (HAE) that is characterized by invalidating edema attacks.

Angioedema is a potentially fatal blood disorder characterized by swelling that may occur in the face, gastrointestinal tract, extremities, genitals and upper airways. Angioedema attacks begin in the deeper layers of the skin and mucous membranes with localized blood vessel dilatation and increased permeability. Symptoms of the disease result from the leakage of plasma from blood vessels into surrounding tissues. Genetic hereditary angioedema attacks result from unregulated activation of the kallikrein system with consequent overproduction of bradykinin and uncontrolled increases in vascular permeability. As vascular permeability rises beyond normal, plasma leaks out of the vasculature into surrounding tissue, causing swelling (Mehta D and Malik A B, Physiol. Rev., 86 (1), 279-367, 2006; Sandoval R et al., J Physiol., 533 (pt 2), 433-45, 2001; Kaplan A P and Greaves M W, Angioedema. J. Am. Acad. Dermatol., 2005).

HAE results from mutations in the genes that code for elements of the coagulation and inflammation pathways. The three forms of HAE are distinguished by their underlying causes and levels of the C1-esterase inhibitor (C1INH, serpin peptidase inhibitor, clade G, member 1) protein in the blood, which inhibits the activity of plasma kallikrein. In type I, patients have insufficient levels of functional C1INH, while type II patients have dysfunctional C1INH. While type I and II affect men and women at equal rates, type III, which primarily affects women, results from a mutation in coagulation factor XII (Hageman factor; HAE-FXII). The underlying causes of type I and II HAE are autosomal dominant mutations in C1INH gene (SERPING1 gene) on chromosome 11 (11q12-q13.1).

C1INH accounts for 90% of inhibition of FXIIa and 50% of inhibition of plasma kallikrein (Pixley R A et al., J. Biol. Chem., 260, 1723-9, 1985; Schapira M et al., Biochemistry, 20, 2738-43, 1981). In addition, C1INH also inactivates prekallikrein (Colman R W et al, Blood, 65, 311-8, 1985). When C1INH levels are normal, its activity blocks FXIIa from converting prekallikrein to kallikrein and blocks kallikrein's conversion to HK, thus preventing the production of bradykinin and the edemic episodes. When C1INH levels are low, or levels of dysfunctional C1INH are high, this inhibition fails and the pathogenic process ensues.

In addition to HAE, plasma kallikrein also contributes to non-hereditary angioedema, high altitude cerebral edema, cytotoxic cerebral edema, osmotic cerebral edema, diabetic macular edema (DME), clinically significant macular edema, cystoid macular edema (CME, Gao B B, Nat Med., 13(2), 181-8, 2007), retinal edema, radiation induced edema, lymph edema, glioma-associated edema, allergic edema e.g. airflow obstruction in chronic allergic sinusitis or perennial rhinitis. Other disorders of the plasma kallikrein system include retinopathy and diabetic retinopathy (Liu J and Feener E P, Biol. Chem. 394(3), 319-28, 2013), proliferative and non-proliferative retinopathy (Liu J et al, Invest. Ophthalmol. Vis. Sci., 54(2), 2013), CME following cataract extraction, CME induced by cryotherapy, CME induced by uveitis, CME following vascular occlusion (e.g., central retinal vein occlusion, branch retinal vein occlusion or hemiretinal vein occlusion), complications related to cataract surgery in diabetic retinopathy, hypertensive retinopathy (JA Phillips et al., Hypertension, 53, 175-181, 2009), retinal trauma, dry and wet age-related macular degeneration (AMD), ischemic reperfusion injuries (C Storoni et al., JPET, 381, 849-954, 2006), e.g., in a variety of contexts associated with tissue and/or organ transplantation.

Current treatments for angioedema, and those under development, target different elements in the HAE pathway. Three classes of therapies are currently available: (a) replacement therapy with C1INH concentrates (e.g., Cinryze, Berinert), (b) administration of selective kallikrein inhibitors (e.g., Ecallantide) and (c) bradykinin receptors antagonists (e.g., Firazyr).

Replacement therapies have proven useful for both acute attacks, including emergency situations, such as laryngeal edema (Bork K et al., Transfusion, 45, 1774-1784, 2005; Bork K and Barnstedt S E, Arch. Intern. Med., 161, 714-718, 2001) and prophylaxis. Selective C1INH inhibitors inactivate both α-FXIIa and β-FXIIa molecules active early in the HAE pathway that catalyze the production of kallikrein (Muller F and Renne T, *Curr. Opin. Hematol.*, 15, 516-21, 2008; Cugno M et al., *Trends Mol. Med.* 15(2):69-78, 2009). In addition to HAE, plasma kallikrein inhibitors are considered to be useful in the treatment of other edemas such as macular edema and brain edema, and retinopathy, e.g., retinopathy associated with diabetes and/or hypertension. There is evidence that plasma kallikrein inhibitors are also effective in the treatment of edema formation in diseases, e.g., edema formation related to ischemic reperfusion injuries. The bradykinin receptors antagonists prevent bradykinin from activating the vascular permeability pathway and stop the initiation of swelling.

Methods of Treatment

Disclosed herein are methods of treating diseases or disorders wherein the inhibition of plasma kallikrein is indicated. Such diseases and disorders include but are not limited to angioedema, including hereditary and non-hereditary.

In some embodiments, the methods disclosed herein are useful for the treatment of angioedema. In some embodiments, the angioedema is hereditary angioedema (HAE). One embodiment provides a method of treating angioedema in a patient in need thereof comprising administration of a composition comprising a compound of Formula, (I), (Ia), (II), (III), (IV), (V), (VI), (VII), (VIII), (IX), (X), (XI) or a pharmaceutically acceptable salt thereof. Another embodiment provides the method wherein the angioedema is hereditary angioedema.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

The following abbreviations and terms have the indicated meanings throughout:
AcOH=acetic acid
B$_2$pin$_2$=bis(pinacolato)diboron
Boc=tert-butoxycarbonyl
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
NaOAc=sodium acetate
PE=petroleum ether
Ph=phenyl
Prep=preparative
quant.=quantitative
RP-HPLC=reverse phase-high pressure liquid chromatography
rt or RT=room temperature
THF=tetrahydrofuran
UV=ultraviolet Example 1: Preparation of N-((6-amino-2,4-dimethylpyridin-3-yl)methyl)-1-((3-chloroquinolin-6-yl)methyl)-1H-pyrazole-3-carboxamide

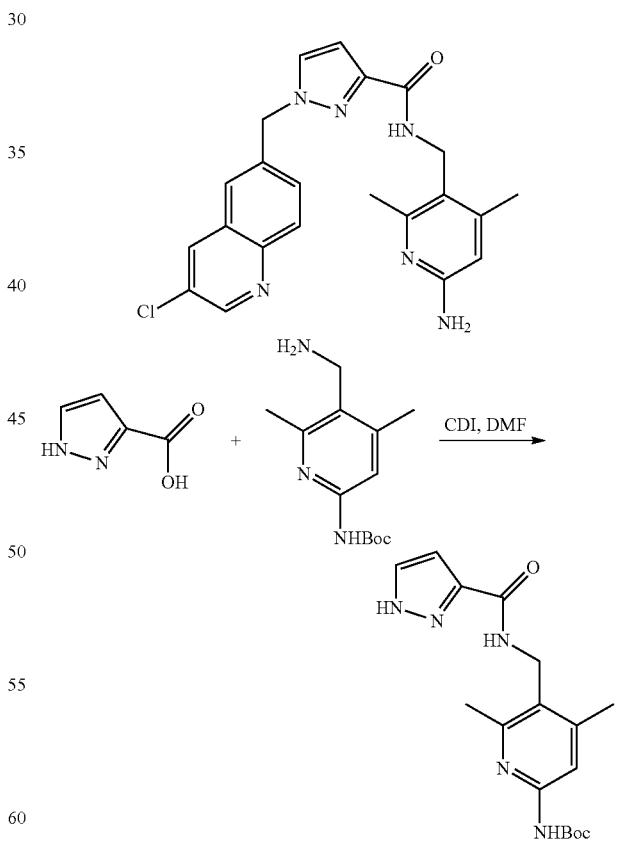

To a solution of 1H-pyrazole-3-carboxylic acid (500 mg, 4.46 mmol, 1 eq) in DMF (20 mL) was added CDI (890 mg, 5.53 mmol, 1.2 eq). The mixture was stirred at rt for 30 min and then (5-aminomethyl-4,6-dimethyl-pyridin-2-yl)-carbamic acid tert-butyl ester (1.38 g, 5.53 mmol, 1.2 eq) was added. After stirring at rt for 3 h, the mixture was concentrated. The resulting residue was washed with water, and the resulting precipitate was collected by filtration to give (4,6-dimethyl-5-{[(1H-pyrazole-3-carbonyl)-amino]-methyl}-pyridin-2-yl)-carbamic acid tert-butyl ester (0.081 g, 52.9%) as a white solid.

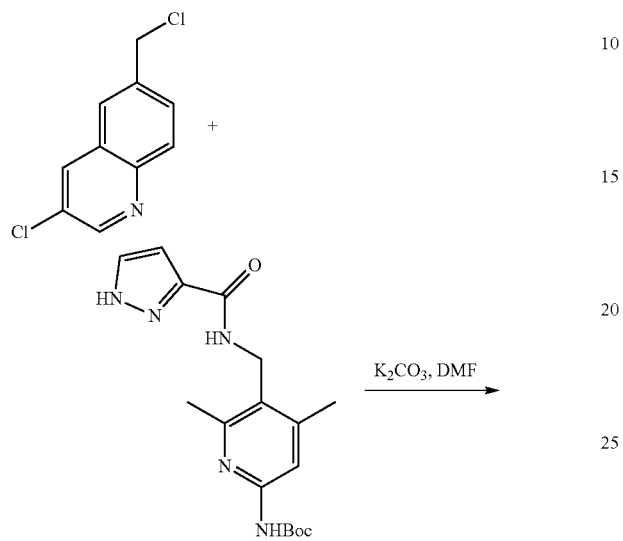

A mixture of (4,6-dimethyl-5-{[(1H-pyrazole-3-carbonyl)-amino]-methyl}-pyridin-2-yl)-carbamic acid tert-butyl ester (200 mg, 0.58 mmol, 1 eq), 3-chloro-6-chloromethyl-quinoline (134 mg, 0.63 mmol, 1.1 eq) and K₂CO₃ (120 mg, 0.87 mmol, 1.5 eq) in DMF (15 mL) was stirred at rt for 8 h, and then concentrated. The resulting residue was washed with water, and the resulting precipitate was collected by filtration to give [5-({[1-(3-chloro-quinolin-6-ylmethyl)-1H-pyrazole-3-carbonyl]-amino}-methyl)-4,6-dimethyl-pyridin-2-yl]-carbamic acid tert-butyl ester (130 mg, 43%) as a white solid.

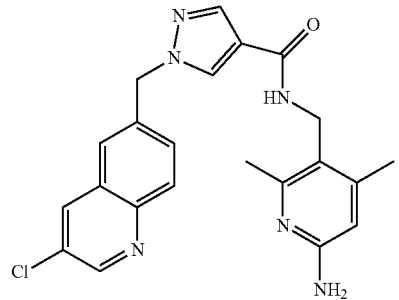

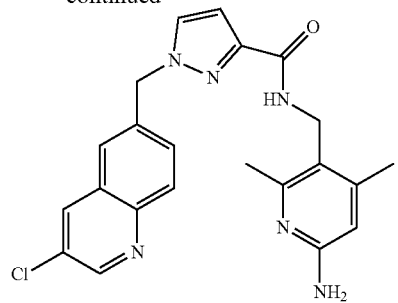

A mixture of [5-({[1-(3-chloro-quinolin-6-ylmethyl)-1H-pyrazole-3-carbonyl]-amino}-methyl)-4,6-dimethyl-pyridin-2-yl]-carbamic acid tert-butyl ester (100 mg, 0.19 mmol, 1 eq) in TFA (2 mL) and DCM (10 mL) was stirred at rt for 12 h, and then concentrated. The resulting residue was diluted with DCM and washed with NaHCO₃ aqueous solution. The organic layer was dried and concentrated to give N-((6-amino-2,4-dimethylpyridin-3-yl)methyl)-1-((3-chloroquinolin-6-yl)methyl)-1H-pyrazole-3-carboxamide (58 mg, 72.5%) as a white solid. LRMS (M+H⁺) m/z calculated 475.2, found 475.8. ¹H NMR (DMSO-d₆, 400 MHz): δ 8.87 (d, 1H), 8.56 (d, 1H), 8.02 (d, 1H), 7.97 (d, 1H), 7.80 (t, 1H), 7.77 (s, 1H), 7.65 (dd, 1H), 6.72 (d, 1H), 6.05 (s, 1H), 5.61 (s, 2H), 5.59 (s, 2H), 4.30 (d, 2H), 2.29 (s, 3H), 2.16 (s, 3H).

Example 2: Preparation of N-((6-amino-2,4-dimethylpyridin-3-yl)methyl)-1-((3-chloroquinolin-6-yl)methyl)-1H-pyrazole-4-carboxamide

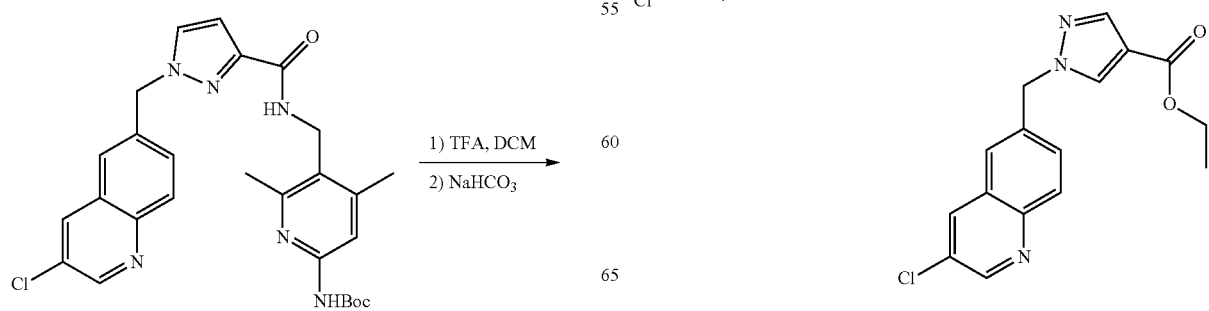

125

To a solution of 3-chloro-6-chloromethyl-quinoline (500 mg, 2.36 mmol, 1.0 eq) and K$_2$CO$_3$ (488 mg, 3.54 mmol, 1.5 eq) in DMF (5 mL) was added 1H-pyrazole-4-carboxylic acid ethyl ester (330 mg, 2.36 mmol, 1.0 eq). The reaction mixture was stirred at rt overnight under N$_2$. The reaction mixture was diluted with H$_2$O, and extracted with EA. The organic layer was washed with H$_2$O, dried over Na$_2$SO$_4$, concentrated and purified by chromatography on silica gel column (PE/EA=3/1, v/v) to give 1-(3-chloro-quinolin-6-ylmethyl)-1H-pyrazole-4-carboxylic acid ethyl ester (665 mg, 89.5%) as a white solid.

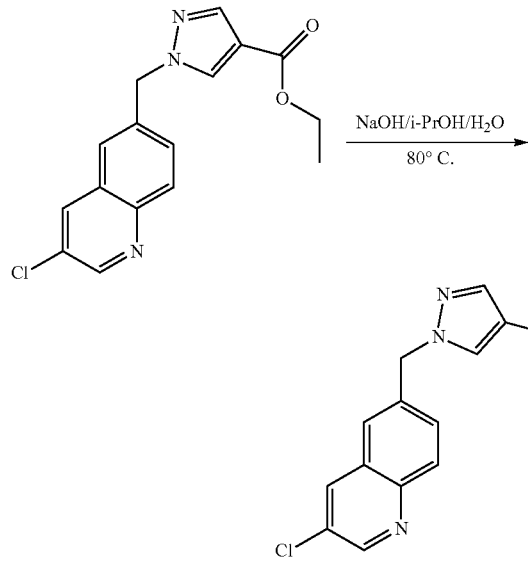

To a solution of 1-(3-chloro-quinolin-6-ylmethyl)-1H-pyrazole-4-carboxylic acid ethyl ester (400 mg, 1.27 mmol, 1.0 eq) in isopropyl alcohol (8 mL) and H$_2$O (5 mL) was added NaOH (508 mg, 12.7 mmol, 10.0 eq). The reaction mixture was stirred at 80° C. overnight. The reaction mixture was acidified with 2 N aq. HCl to pH 1. The mixture was filtered and the solid was rinsed with H$_2$O. The solid was dried in vacuum to give 1-(3-chloro-quinolin-6-ylmethyl)-1H-pyrazole-4-carboxylic acid (270 mg, 77%) as a white solid.

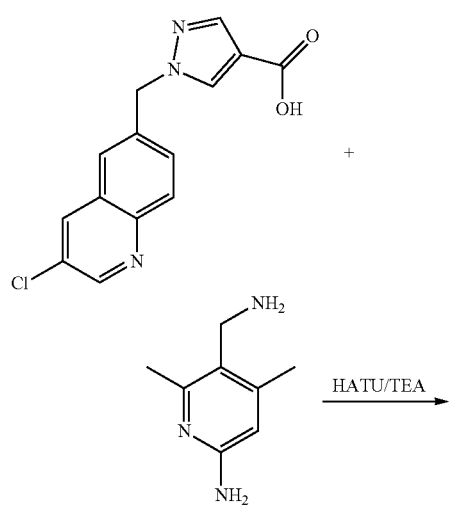

126

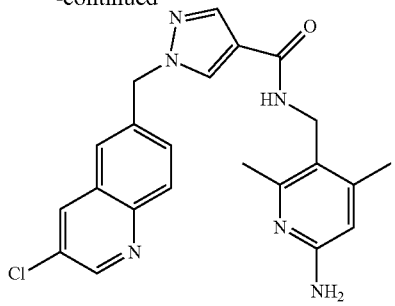

To a solution of 1-(3-chloro-quinolin-6-ylmethyl)-1H-pyrazole-4-carboxylic acid (150 mg, 0.52 mmol, 1.0 eq), 5-aminomethyl-4,6-dimethyl-pyridin-2-ylamine (98 mg, 0.52 mmol, 1.0 eq) and HATU (298 mg, 0.74 mmol, 1.5 eq) in DMF (5 mL) was added TEA (158 mg, 1.57 mmol, 3.0 eq) at 0° C. under N$_2$. The reaction mixture was stirred at rt for 1.5 h. The reaction mixture was purified by Prep-HPLC to give 1-(3-chloro-quinolin-6-ylmethyl)-1H-pyrazole-4-carboxylic acid (6-amino-2,4-dimethyl-pyridin-3-ylmethyl)-amide (78 mg, 35.5%) as a white solid. LRMS (M+H$^+$) m/z calculated 421.1, found 421.1. $^1$H NMR (DMSO-d$_6$, 400 MHz): δ 8.87 (d, 1H), 8.58 (d, 1H), 8.34 (s, 1H), 8.03 (d, 1H), 7.92 (d, 2H), 7.80 (s, 1H), 7.66 (s, 1H), 6.11 (d, 1H), 5.63 (s, 2H), 5.54 (s, 2H), 2.28 (s, 3H), 2.14 (s, 3H).

Example 3: Preparation of N-((6-amino-2,4-dimethylpyridin-3-yl)methyl)-1-((3-chloroquinolin-6-yl)methyl)-1H-imidazole-4-carboxamide

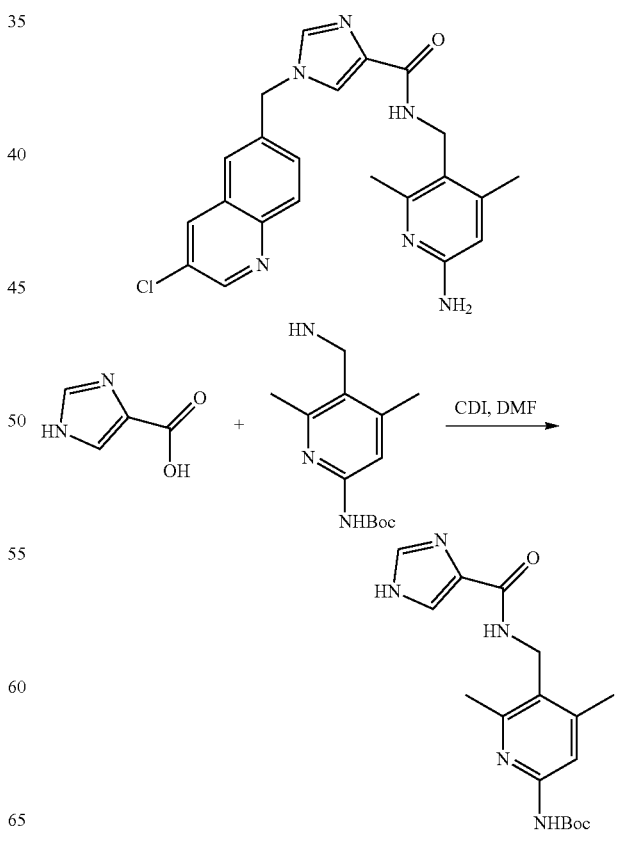

To a solution of 1H-imidazole-4-carboxylic acid (500 mg, 4.46 mmol, 1.0 eq) in DMF (10 mL) was added CDI (867 mg, 5.35 mmol, 1.2 eq) at rt. The solution was stirred at rt for 30 min. Then (5-aminomethyl-4,6-dimethyl-pyridin-2-yl)-carbamic acid tert-butyl ester (1.30 g, 5.35 mmol, 1.2 eq) was added. The mixture was stirred at rt overnight. The mixture was concentrated, and the resulting residue was purified by chromatography on a silica gel column (PE/EA=3/1 to EA) to give tert-butyl (5-((1H-imidazole-4-carboxamido)methyl)-4,6-dimethylpyridin-2-yl)carbamate (400 mg, 26%) as a white solid.

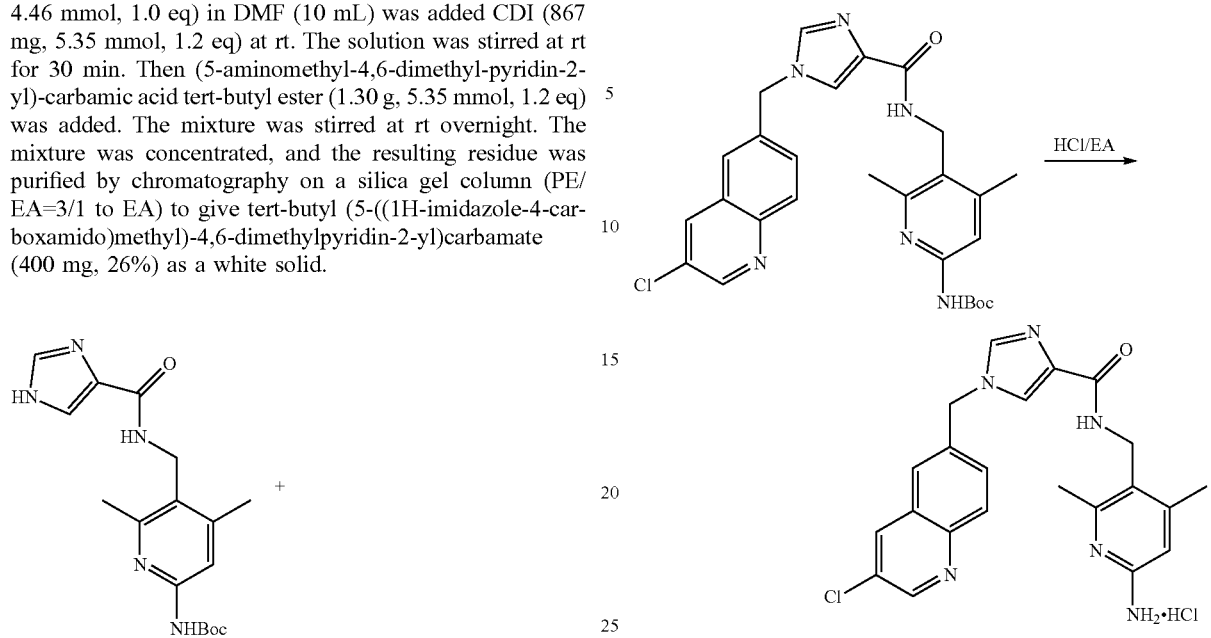

A mixture of tert-butyl (5-((1H-imidazole-4-carboxamido)methyl)-4,6-dimethylpyridin-2-yl)carbamate (200 mg, 3.18 mmol, 1.0 eq), 3-chloro-6-chloromethyl-quinoline (148 mg, 0.70 mmol, 1.2 eq) and K₂CO₃ (240 mg, 1.74 mmol, 3.0 eq) in DMF (6 mL) was stirred at rt overnight. The mixture was poured into water (30 mL). The resulting precipitate was filtered and the solid was dried in vacuo to give tert-butyl (5-((1-((3-chloroquinolin-6-yl)methyl)-1H-imidazole-4-carboxamido)methyl)-4,6-dimethylpyridin-2-yl)carbamate (100 mg, 33%) as a white solid.

To a solution of tert-butyl (5-((1-((3-chloroquinolin-6-yl)methyl)-1H-imidazole-4-carboxamido)methyl)-4,6-dimethylpyridin-2-yl)carbamate (100 mg, 0.19 mmol, 1.0 eq) in DCM (20 mL) was added HCl/EA (10 mL) at rt. The mixture was stirred at rt overnight. The resulting precipitate was filtered and washed with EA (30 mL). The solid was dried in vacuo to give N-((6-amino-2,4-dimethylpyridin-3-yl)methyl)-1-((3-chloroquinolin-6-yl)methyl)-1H-imidazole-4-carboxamide as the hydrochloride salt (60 mg, 70%) as a white solid. LRMS (M+H⁺) m/z calculated 421.2, found 421.1. ¹H NMR (DMSO-d₆, 400 MHz): δ 14.10 (s, 1H), 8.92-8.91 (m, 3H), 8.59 (d, 1H), 8.20 (s, 1H), 8.08 (d, 1H), 7.93 (s, 1H), 7.80-7.68 (m, 3H), 6.64 (s, 1H), 5.61 (s, 2H), 4.33 (d, 2H), 2.53 (s, 3H), 2.37 (s, 3H).

Example 4: Preparation of N-((6-amino-2,4-dimethylpyridin-3-yl)methyl)-1-((3-chloroquinolin-6-yl)methyl)-1H-1,2,4-triazole-3-carboxamide

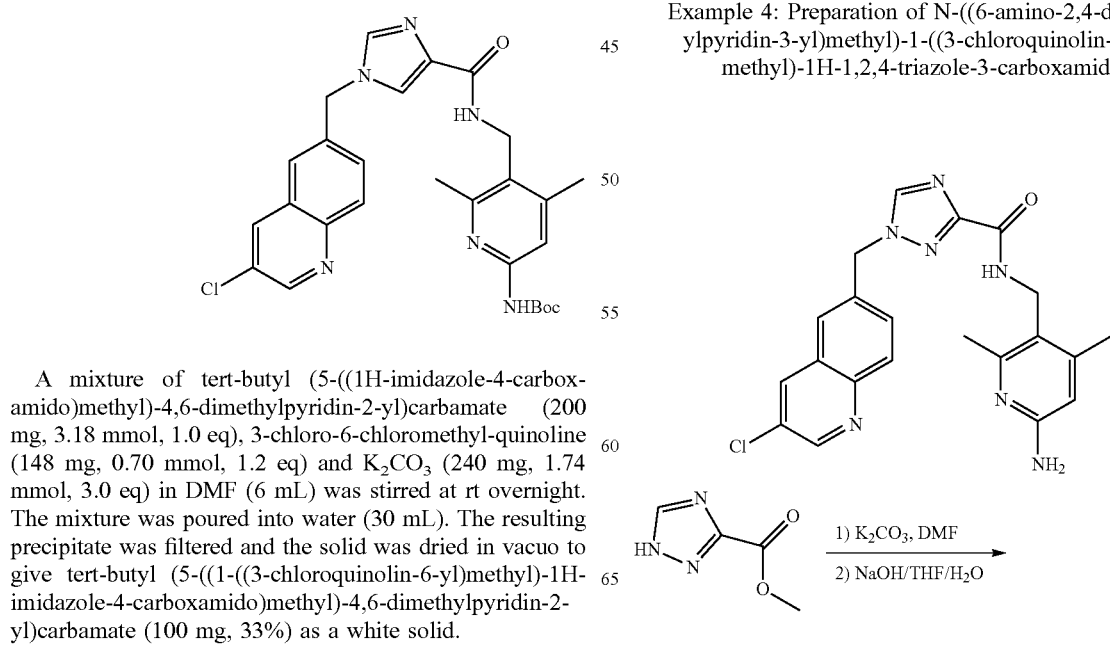

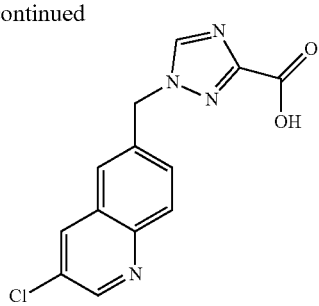

A mixture of 1H-[1,2,4]triazole-3-carboxylic acid methyl ester (640 mg, 5.04 mmol, 1 eq), 3-chloro-6-chloromethyl-quinoline (1.07 g, 5.04 mmol, 1 eq) and K$_2$CO$_3$ (1.38 g, 10.08 mmol, 2 eq) in DMF (12 mL) was stirred at rt for 3 h and then concentrated. The resulting residue was washed with water, and the precipitate was collected by filtration to give 2.7 g of wet white solid. The solid was dissolved in 150 mL of THF and then 5 mL of 3 N NaOH solution was added. The mixture was stirred at rt overnight. THF was removed by evaporation and the aqueous layer was acidified to pH 3 with 3 N HCl solution. The resulting precipitate was collected and dried. The solid was purified by trituration in 60 mL of EtOAc to afford 1-(3-chloro-quinolin-6-ylmethyl)-1H-[1,2,4]triazole-3-carboxylic acid (760 mg, 52.8%) as a white solid.

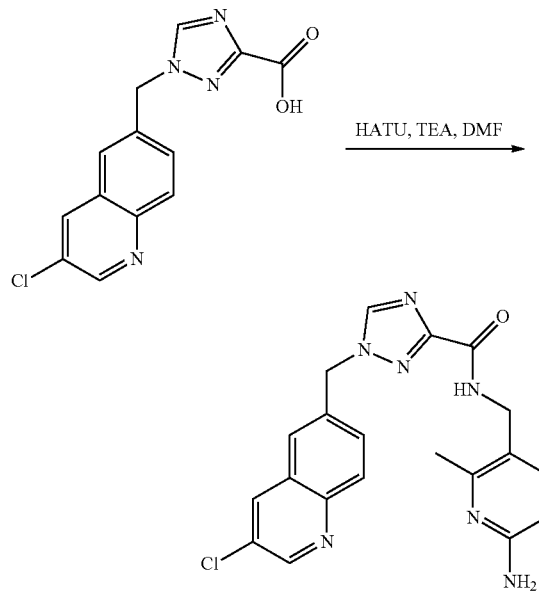

A mixture of 1-(3-chloro-quinolin-6-ylmethyl)-1H-[1,2,4]triazole-3-carboxylic acid (760 mg, 2.64 mmol, 1.0 eq), 5-aminomethyl-4,6-dimethyl-pyridin-2-ylamine (710 mg, 3.17 mmol, 1.2 eq), HATU (1.2 g, 3.17 mmol, 1.2 eq), and TEA (1.5 mL, 10.56 mmol, 4.0 eq) in DMF (30 mL) was stirred at rt overnight. The mixture was poured into 500 mL of water, and the solid was collected by filtration. The solid was triturated in DCM and MeOH (v/v=1/1) at rt for 3 h. After filtration, the filter cake was triturated in DCM and MeOH (v/v=1/1) at reflux overnight to afford N-((6-amino-2,4-dimethylpyridin-3-yl)methyl)-1-((3-chloroquinolin-6-yl)methyl)-1H-1,2,4-triazole-3-carboxamide (662 mg, 59.6%) as a white solid.

LRMS (M+H$^+$) m/z calculated 422.1, found 422.1. $^1$H NMR (DMSO-d$_6$, 400 MHz): δ 8.89 (d, 1H), 8.83 (s, 1H), 8.69 (d, 1H), 8.26 (t, 1H), 8.05 (d, 1H), 7.86 (s, 1H), 7.71 (dd, 1H), 6.11 (s, 1H), 5.73 (s, 2H), 5.66 (s, 2H), 4.32 (d, 2H), 2.30 (s, 3H), 2.17 (s, 3H).

Example 5: Preparation of N-((6-amino-2,4-dimethylpyridin-3-yl)methyl)-2-((3-chloroquinolin-6-yl)methyl)-1H-imidazole-5-carboxamide

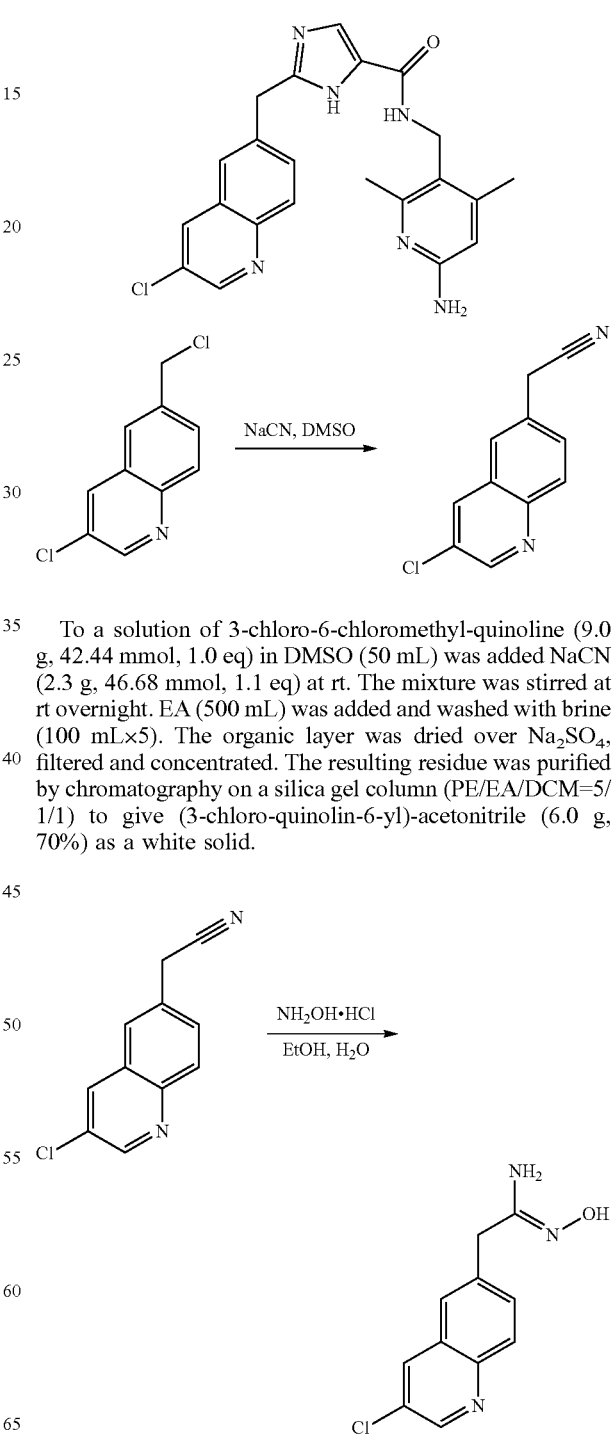

To a solution of 3-chloro-6-chloromethyl-quinoline (9.0 g, 42.44 mmol, 1.0 eq) in DMSO (50 mL) was added NaCN (2.3 g, 46.68 mmol, 1.1 eq) at rt. The mixture was stirred at rt overnight. EA (500 mL) was added and washed with brine (100 mL×5). The organic layer was dried over Na$_2$SO$_4$, filtered and concentrated. The resulting residue was purified by chromatography on a silica gel column (PE/EA/DCM=5/1/1) to give (3-chloro-quinolin-6-yl)-acetonitrile (6.0 g, 70%) as a white solid.

To a solution of (3-chloro-quinolin-6-yl)-acetonitrile (500 mg, 2.47 mmol, 1.0 eq) in EtOH (15 mL) and water (5 mL) were added NH₂OH.HCl (343 mg, 4.93 mmol, 2.0 eq) and Na₂CO₃ (611 mg, 4.93 mmol, 2.0 eq) at rt. The mixture was stirred at 80° C. overnight. The reaction solution was concentrated, and the resulting residue was washed with water (50 mL). The solid was dried in vacuo to give 2-(3-chloro-quinolin-6-yl)-N-hydroxy-acetamidine (540 mg, 93%) as an off-white solid.

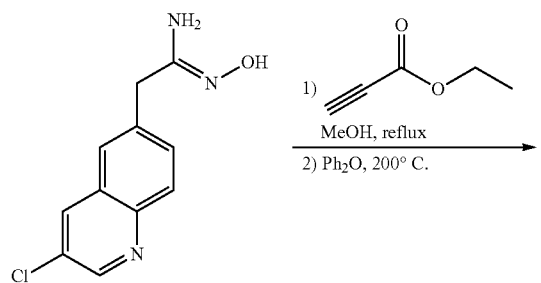

A mixture of 2-(3-chloro-quinolin-6-yl)-N-hydroxy-acetamidine (200 mg, 0.85 mmol, 1.0 eq) and propynoic acid ethyl ester (66 mg, 1.70 mmol, 2.0 eq) in MeOH (20 mL) was stirred at 65° C. for 4 h. The reaction solution was concentrated and Ph₂O (12 mL) was added. The solution was stirred at 200° C. for 1 h. The solution was cooled to rt and PE (100 mL) was added. The brown solid was obtained was filtered and purified by chromatography on a silica gel column (PE/EA=1/1 to EA) to give ethyl 2-((3-chloroquinolin-6-yl)methyl)-1H-imidazole-5-carboxylate (80 mg, 30%) as a brown solid.

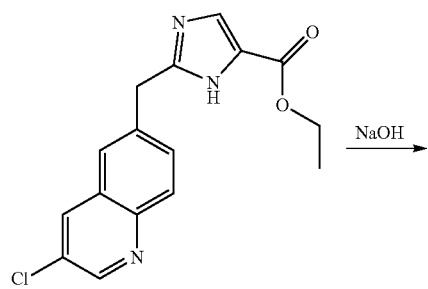

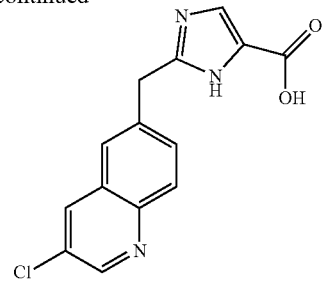

To a solution of ethyl 2-((3-chloroquinolin-6-yl)methyl)-1H-imidazole-5-carboxylate (80 mg, 0.25 mmol, 1.0 eq) in THF (4 mL) was added a solution of NaOH (15 mg, 0.38 mmol, 1.5 eq) in water (4 mL) at rt. The mixture was stirred at 80° C. overnight. The mixture was cooled to rt and neutralized with 1N HCl. The white solid was collected and dried in vacuo to give 2-((3-chloroquinolin-6-yl)methyl)-1H-imidazole-5-carboxylic acid (60 mg, 84%) as a brown solid.

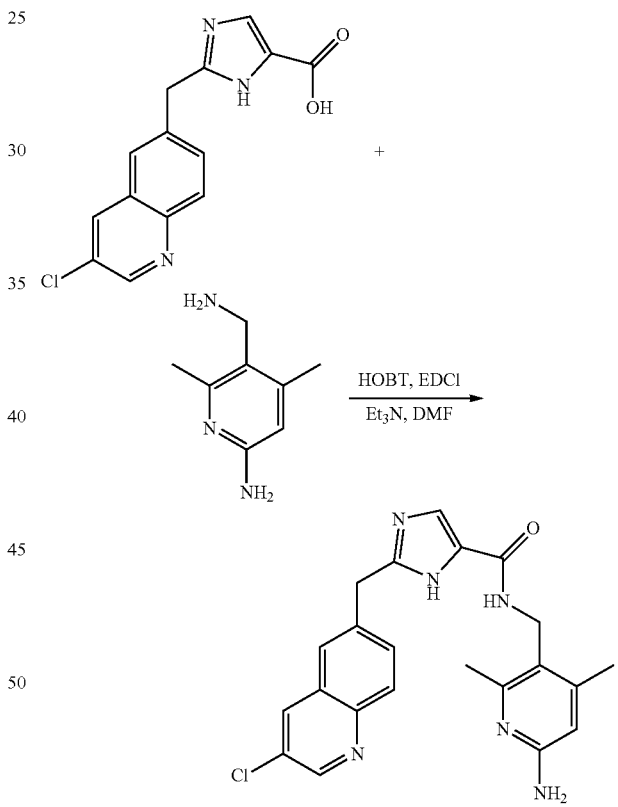

A mixture of 2-((3-chloroquinolin-6-yl)methyl)-1H-imidazole-5-carboxylic acid (60 mg, 0.21 mmol, 1.0 eq), 5-aminomethyl-4,6-dimethyl-pyridin-2-ylamine (47 mg, 0.31 mmol, 1.5 eq), HOBT (42 mg, 0.31 mmol, 1.5 eq), EDCI (59 mg, 0.31 mmol, 1.5 eq) and Et₃N (63 mg, 0.62 mmol, 3.0 eq) in DMF (2 mL) was stirred at rt overnight. The mixture was concentrated, and the resulting residue was purified by Prep-HPLC to give N-((6-amino-2,4-dimethyl-pyridin-3-yl)methyl)-2-((3-chloroquinolin-6-yl)methyl)-1H-imidazole-5-carboxamide (25.0 mg, 28%) as a white solid. LRMS (M+H⁺) m/z calculated 421.2, found 421.1. ¹H NMR (DMSO-d$_6$, 400 MHz): δ 12.36 (s, 1H), 8.83 (d, 1H), 8.53 (s, 1H), 7.98 (d, 1H), 7.75-7.67 (m, 2H), 7.56 (d, 1H), 7.40 (s, 1H), 6.10 (s, 1H), 5.65 (s, 2H), 4.30 (d, 2H), 4.19 (s, 2H), 2.30 (s, 3H), 2.17 (s, 3H).

Example 6: Preparation of N-((6-amino-2,4-dimethylpyridin-3-yl)methyl)-3-((3-chloroquinolin-6-yl)methyl)-1,2,4-oxadiazole-5-carboxamide

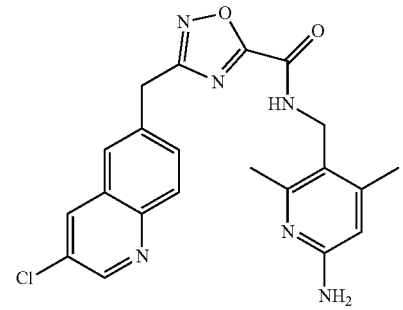

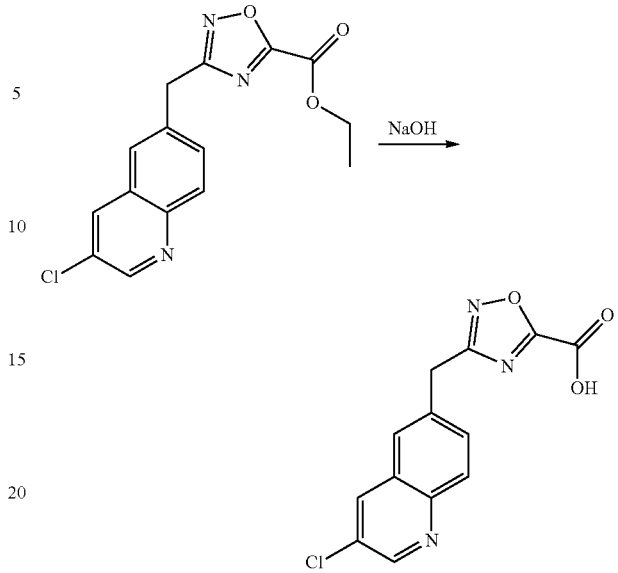

To a solution of ethyl 3-((3-chloroquinolin-6-yl)methyl)-1,2,4-oxadiazole-5-carboxylate (100 mg, 0.31 mmol, 1.0 eq) in THF (4 mL) was added a solution of NaOH (15 mg, 0.38 mmol, 1.5 eq) in water (4 mL) at rt. The mixture was stirred at rt for 1 h. The mixture was neutralized with 1N HCl. The yellow solid was collected and dried in vacuum to give 3-((3-chloroquinolin-6-yl)methyl)-1,2,4-oxadiazole-5-carboxylic acid (60 mg, 84%) as a yellow solid.

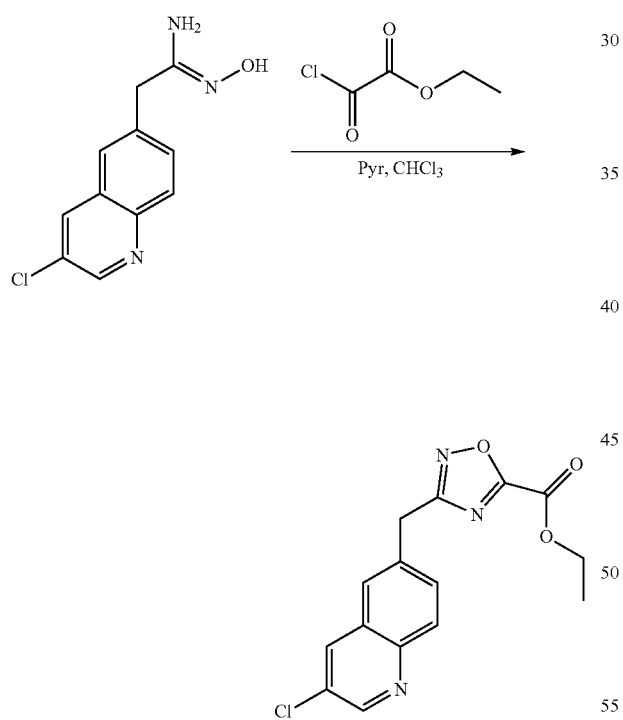

To a solution of 2-(3-chloro-quinolin-6-yl)-N-hydroxyacetamidine (200 mg, 0.84 mmol, 1.0 eq) and pyridine (132 mg, 1.68 mmol, 2.0 eq) in CHCl$_3$ (20 mL) was added chloro-oxo-acetic acid ethyl ester (140 mg, 1.02 mmol, 1.2 eq) at 0° C. The mixture was warmed to rt and heated at 80° C. overnight. The mixture was concentrated, and the resulting residue was purified by chromatography on a silica gel column (PE/EA=3/1) to give ethyl 3-((3-chloroquinolin-6-yl)methyl)-1,2,4-oxadiazole-5-carboxylate (300 mg, 74%) as a white solid.

A mixture of 3-((3-chloroquinolin-6-yl)methyl)-1,2,4-oxadiazole-5-carboxylic acid (60 mg, 0.21 mmol, 1.0 eq), 5-aminomethyl-4,6-dimethyl-pyridin-2-ylamine (47 mg, 0.31 mmol, 1.5 eq), HOBT (42 mg, 0.31 mmol, 1.5 eq), EDCI (59 mg, 0.31 mmol, 1.5 eq) and Et$_3$N (63 mg, 0.62 mmol, 3.0 eq) in DMF (2 mL) was stirred at rt overnight. The mixture was concentrated, and the resulting residue was purified by Prep-HPLC to give N-((6-amino-2,4-dimethyl-pyridin-3-yl)methyl)-3-((3-chloroquinolin-6-yl)methyl)-1,2,4-oxadiazole-5-carboxamide (25.0 mg, 28%) as a white solid. LRMS (M+H$^+$) m/z calculated 423.1, found 423.1. $^1$H NMR (DMSO-d$_6$, 400 MHz): δ 9.42-9.39 (m, 1H), 8.86 (d, 1H), 8.53 (d, 1H), 8.02 (d, 1H), 7.88 (d, 1H), 7.76-7.73 (m, 1H), 6.09 (s, 1H), 5.68 (s, 2H), 4.41 (d, 2H), 4.33 (d, 2H), 2.27 (s, 3H), 2.15 (s, 3H).

Example 7: Preparation of N-((6-amino-2,4-dimethyl$_l$pyridin-3-yl)methyl)-5-((3-chloroquinolin-6-yl)methyl)-1,2,4-oxadiazole-3-carboxamide

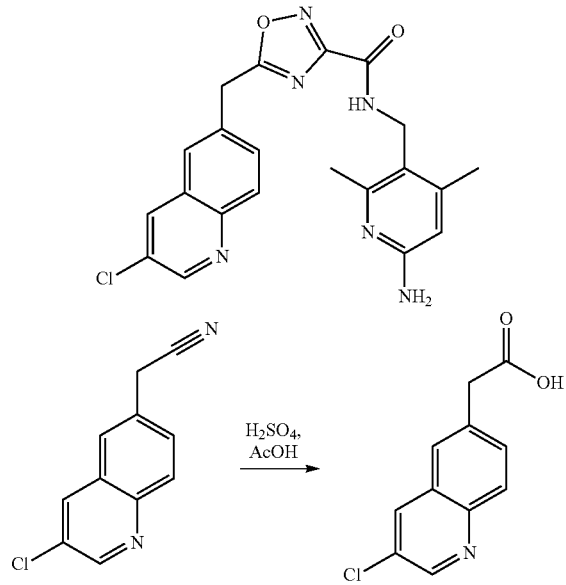

A mixture of (3-chloro-quinolin-6-yl)-acetonitrile (4.30 g, 21.22 mmol, 1.0 eq) in H$_2$SO$_4$ (8 mL), AcOH (8 mL) and water (8 mL) was stirred at 110° C. for overnight. The mixture was concentrated, and the resulting residue was neutralized with 1N NaOH to pH 2. The solid was collected, and dried in vacuum to give 2-(3-chloroquinolin-6-yl)acetic acid (4.2 g, 89%) as a white solid.

A mixture of 2-(3-chloroquinolin-6-yl)acetic acid (500 mg, 2.26 mmol, 1.0 eq) in SOCl$_2$ (6 mL) was stirred at rt for 1 h. The solution was concentrated to give 2-(3-chloroquinolin-6-yl)acetyl chloride (560 mg, crude) as a purple solid, which was used in the next step without further purification.

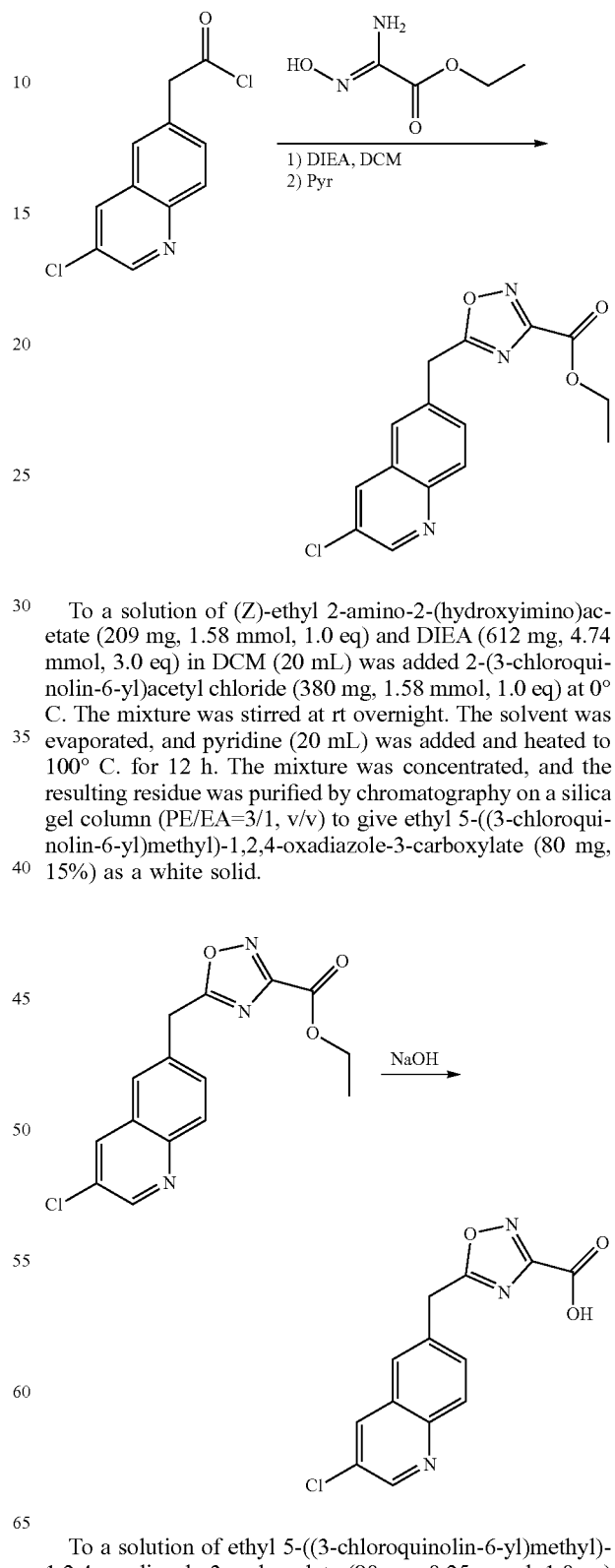

To a solution of (Z)-ethyl 2-amino-2-(hydroxyimino)acetate (209 mg, 1.58 mmol, 1.0 eq) and DIEA (612 mg, 4.74 mmol, 3.0 eq) in DCM (20 mL) was added 2-(3-chloroquinolin-6-yl)acetyl chloride (380 mg, 1.58 mmol, 1.0 eq) at 0° C. The mixture was stirred at rt overnight. The solvent was evaporated, and pyridine (20 mL) was added and heated to 100° C. for 12 h. The mixture was concentrated, and the resulting residue was purified by chromatography on a silica gel column (PE/EA=3/1, v/v) to give ethyl 5-((3-chloroquinolin-6-yl)methyl)-1,2,4-oxadiazole-3-carboxylate (80 mg, 15%) as a white solid.

To a solution of ethyl 5-((3-chloroquinolin-6-yl)methyl)-1,2,4-oxadiazole-3-carboxylate (80 mg, 0.25 mmol, 1.0 eq)

in THF (5 mL) was added a solution of NaOH (15 mg, 0.37 mmol, 1.5 eq) in water (5 mL) at rt. The mixture was stirred at rt for 1 h. The mixture was neutralized with 1N HCl, and then concentrated to give 5-((3-chloroquinolin-6-yl)methyl)-1,2,4-oxadiazole-3-carboxylic acid (100 mg, crude) as a white solid, which was used in the next step without further purification.

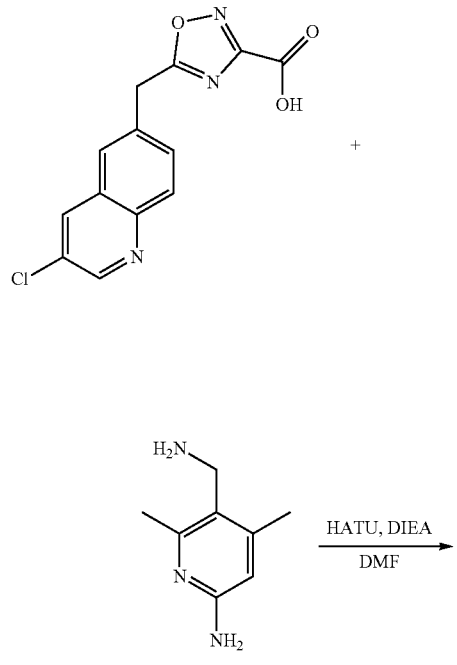

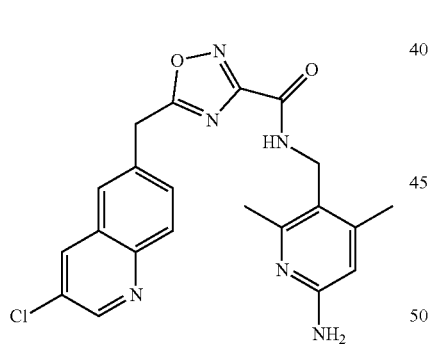

A mixture of 5-((3-chloroquinolin-6-yl)methyl)-1,2,4-oxadiazole-3-carboxylic acid (100 mg crude, 0.34 mmol, 1.0 eq), 5-aminomethyl-4,6-dimethyl-pyridin-2-ylamine (78 mg, 0.52 mmol, 1.5 eq), HATU (197 mg, 0.52 mmol, 1.5 eq) and DIEA (132 mg, 1.02 mmol, 3.0 eq) in DMF (4 mL) was stirred at rt for 2 h. The mixture was concentrated, and the resulting residue was purified by Prep-HPLC to give N-((6-amino-2,4-dimethylpyridin-3-yl)methyl)-5-((3-chloroquinolin-6-yl)methyl)-1,2,4-oxadiazole-3-carboxamide (16.0 mg, 11%) as a white solid. LRMS (M+H$^+$) m/z calculated 423.1, found 423.0. $^1$H NMR (DMSO-d$_6$, 400 MHz): δ 8.99 (m, 1H), 8.57 (d, 1H), 8.05 (d, 1H), 7.95 (s, 1H), 7.80-7.77 (m, 1H), 6.09 (s, 1H), 5.68 (s, 2H), 4.67 (s, 2H), 4.32 (d, 2H), 2.28 (s, 3H), 2.16 (s, 3H).

Example 8: Preparation of N-((6-amino-2,4-dimethylpyridin-3-yl)methyl)-1-((3-chloroquinolin-6-yl)methyl)-1H-pyrrolo[3,2-b]pyridine-3-carboxamide

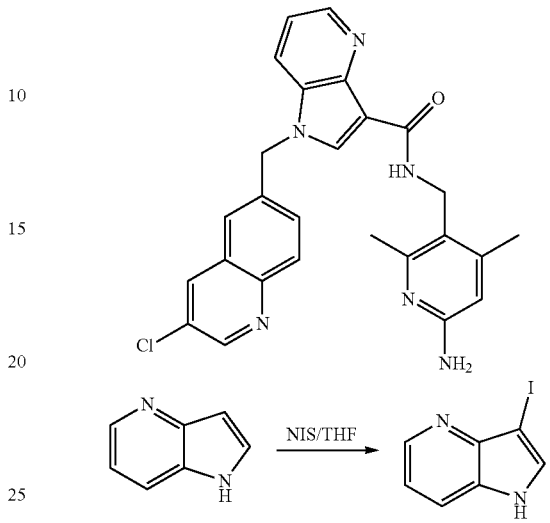

To a solution of 1H-pyrrolo[3,2-b]pyridine (3.0 g, 25.4 mmol, 1.0 eq) in THF (20 mL) was added NIS (6.3 g, 27.9 mmol, 1.1 eq). Precipitation occurred after a few minutes. The stirring was continued at rt overnight. The precipitate was collected by filtration and washed with a small amount of THF. The resulting solid was dried in vacuum to give 3-iodo-1H-pyrrolo[3,2-b]pyridine (5.8 g, 93.5%).

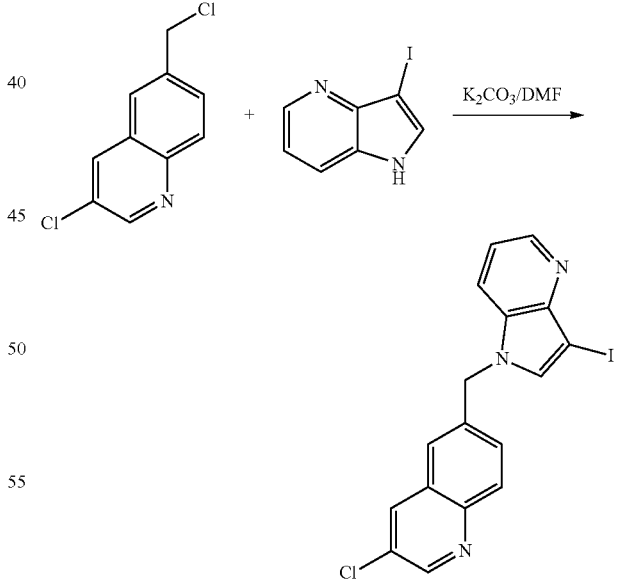

A mixture of 3-iodo-1H-pyrrolo[3,2-b]pyridine (2.1 g, 10 mmol, 1 eq), 3-chloro-6-chloromethyl-quinoline (2.9 g, 12 mmol, 1.2 eq) and K$_2$CO$_3$ (2.8 g, 20 mmol, 2 eq) in DMF (60 mL) was stirred at rt overnight and then concentrated. The residue was washed with water, and the resulting precipitate was collected by filtration to give 3-chloro-6-(3-iodo-pyrrolo[3,2-b]pyridin-1-ylmethyl)-quinoline (2.9 g, 69%).

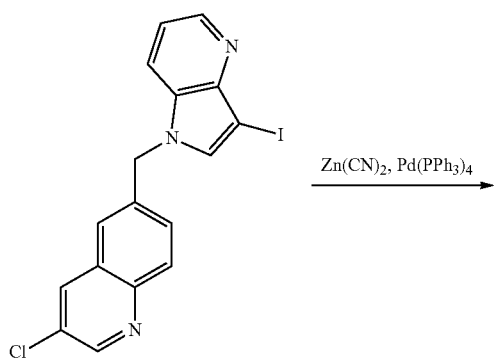

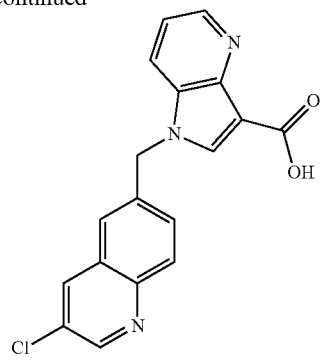

A mixture of 1-(3-chloro-quinolin-6-ylmethyl)-1H-pyrrolo[3,2-b]pyridine-3-carbonitrile (0.8 g, 2.5 mmol, 1 eq), water (2 mL), acetic acid (2 mL) and sulfuric acid (2 mL) was stirred at 100° C., overnight. The mixture was then diluted with water (50 mL), adjusted to pH 4 with 10% NaOH solution. The resulting precipitate was collected by filtration, washed with water and dried under 120° C. for 3 h. The solid was triturated in EtOAc (50 mL) to give 1-(3-chloro-quinolin-6-ylmethyl)-1H-pyrrolo[3,2-b]pyridine-3-carboxylic acid (144 mg, 17.1%).

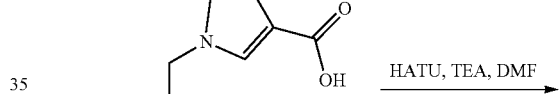

A mixture of 3-chloro-6-(3-iodo-pyrrolo[3,2-b]pyridin-1-ylmethyl)-quinoline (2.9 g, 6.91 mmol, 1 eq), Zn(CN)$_2$ (1.62 g, 13.8 mmol, 2 eq) and Pd(PPh$_3$)$_4$ (0.8 g, 0.69 mmol, 0.1 eq) in DMF (50 mL) was stirred at 130° C. overnight under N$_2$ atmosphere. After cooling to rt, the mixture was concentrated. The resulting residue was purified by chromatography on a silica gel column (PE/EA=3/1 to 1/2, v/v) to give 1-(3-chloro-quinolin-6-ylmethyl)-1H-pyrrolo[3,2-b]pyridine-3-carbonitrile (0.8 g, 36.4%) as an off-white solid.

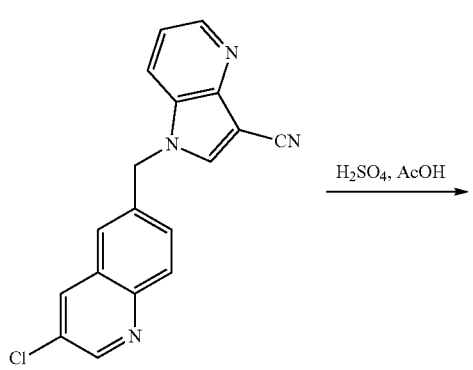

A mixture of 1-(3-chloro-quinolin-6-ylmethyl)-1H-pyrrolo[3,2-b]pyridine-3-carboxylic acid (144 mg, 0.63 mmol, 1.0 eq), 5-aminomethyl-4,6-dimethyl-pyridin-2-ylamine (105 mg, 0.47 mmol, 1.1 eq), HATU (194 mg, 0.51 mmol, 1.2 eq), and TEA (0.24 mL, 1.7 mmol, 4.0 eq) in DMF (4 mL) was stirred at rt overnight. The mixture was concentrated, and the resulting residue was purified by chromatography on a silica gel column (DCM/MeOH=14/1, v/v) to give N-((6-amino-2,4-dimethylpyridin-3-yl)methyl)-1-((3-chloroquinolin-6-yl)methyl)-1H-pyrrolo[3,2-b]pyridine-3- carboxamide (118 mg, 59%). LRMS (M+H⁺) m/z calculated 472.2, found 472.1. ¹H NMR (DMSO-d₆, 300 MHz): δ 8.85 (d, 1H), 8.75 (t, 1H), 8.53 (d, 1H), 8.48 (s, 1H), 8.42 (d, 1H), 8.04 (d, 1H), 8.02 (d, 1H), 7.79 (s, 1H), 7.68 (d, 1H), 7.21 (dd, 1H), 6.16 (s, 1H), 5.80 (s, 2H), 5.75 (s, 2H), 4.48 (d, 2H), 2.47 (s, 3H), 2.26 (s, 3H).

Example 9: Preparation of N-((6-amino-2,4-dimethylpyridin-3-yl)methyl)-3-((3-chloroquinolin-6-yl)methyl)imidazo[1,5-a]pyridine-1-carboxamide

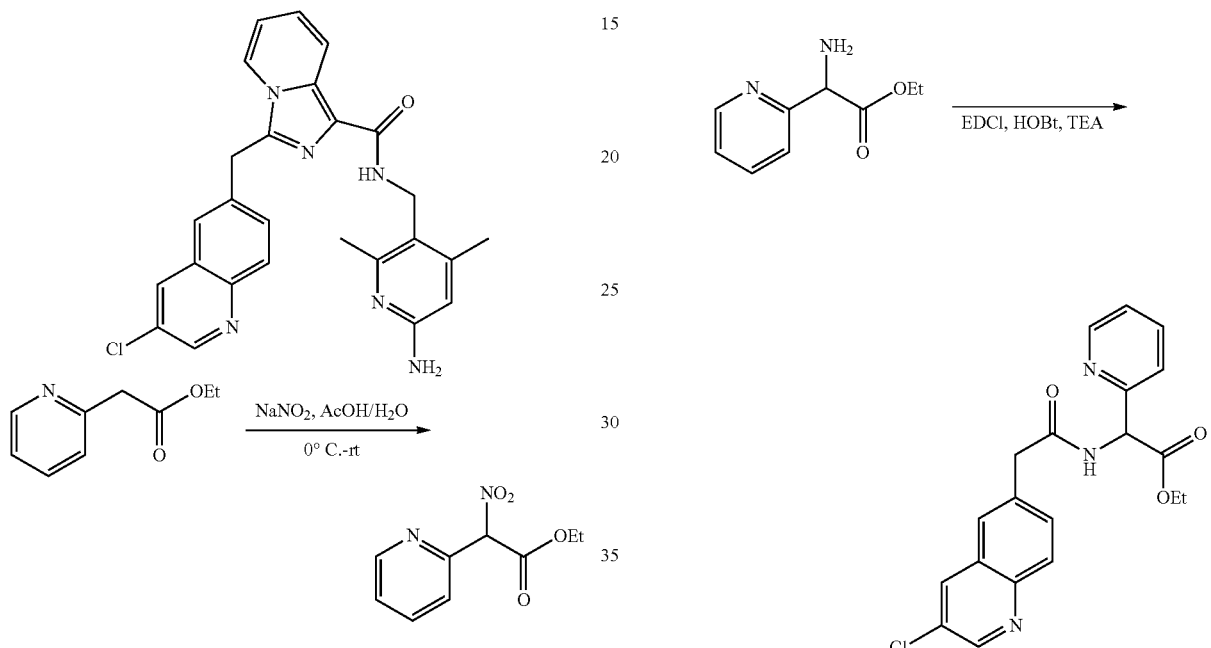

To a solution of pyridin-2-yl-acetic acid ethyl ester (3.3 g, 20 mmol, 1 eq) in glacial acetic acid (10 mL) at 0° C. was added portion-wise a solution of sodium nitrite (1.38 g, 20 mmol, 1 eq) in water (5 mL). The mixture was stirred at ambient temperature for 2 h. Water (30 mL) was added and the mixture was extracted with DCM. The combined organic layers were washed with water, dried over MgSO₄, filtered and concentrated to give nitro-pyridin-2-yl-acetic acid ethyl ester (3.2 g, 76.2%) as an off-white solid.

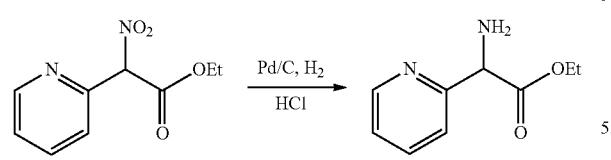

A mixture of nitro-pyridin-2-yl-acetic acid ethyl ester (3.2 g, 15.2 mmol, 1 eq) and 10% Pd/C in MeOH (60 mL) was stirred at rt under N₂ overnight. Then the mixture was filtered and the filtrate was concentrated. The residue was diluted with EA/THF/MeOH (v/v, 4/1/1, 200 mL). 50 mL of 2 N HCl solution in EA was added. The mixture was stirred at rt overnight. The resulting precipitate was collected and dried to give amino-pyridin-2-yl-acetic acid ethyl ester (3.5 g, 91%) as a yellow solid.

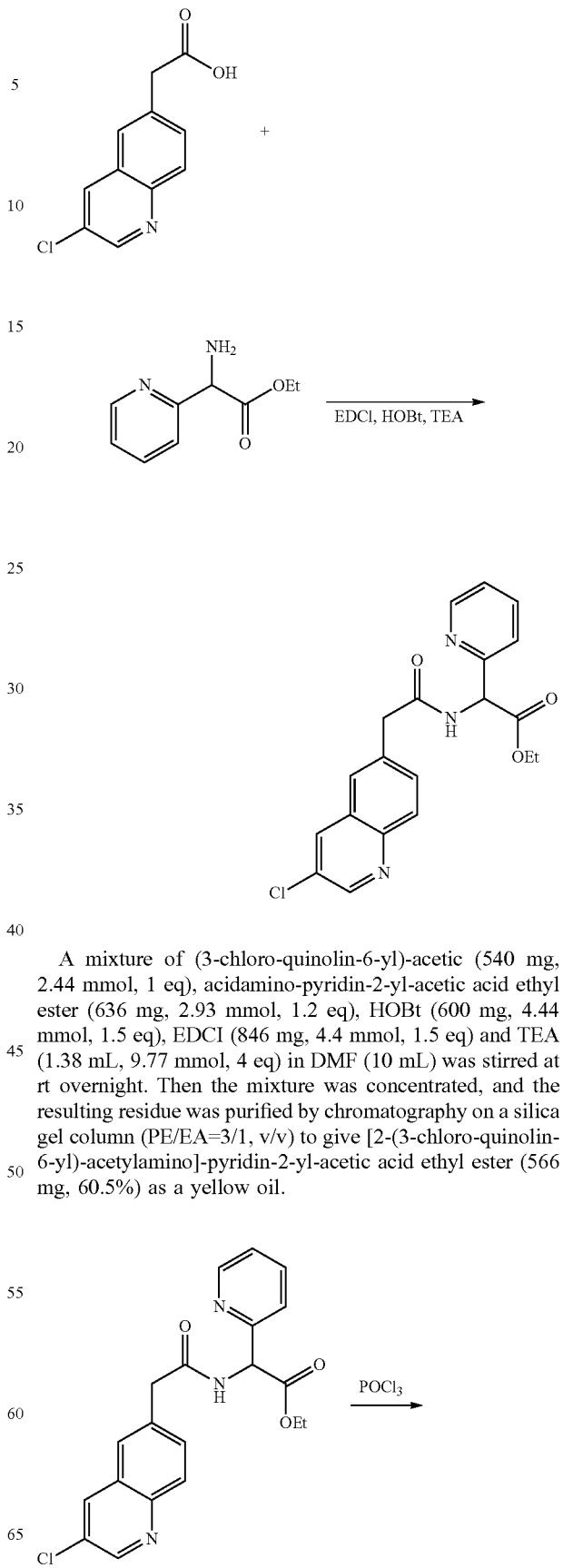

A mixture of (3-chloro-quinolin-6-yl)-acetic (540 mg, 2.44 mmol, 1 eq), acidamino-pyridin-2-yl-acetic acid ethyl ester (636 mg, 2.93 mmol, 1.2 eq), HOBt (600 mg, 4.44 mmol, 1.5 eq), EDCI (846 mg, 4.4 mmol, 1.5 eq) and TEA (1.38 mL, 9.77 mmol, 4 eq) in DMF (10 mL) was stirred at rt overnight. Then the mixture was concentrated, and the resulting residue was purified by chromatography on a silica gel column (PE/EA=3/1, v/v) to give [2-(3-chloro-quinolin-6-yl)-acetylamino]-pyridin-2-yl-acetic acid ethyl ester (566 mg, 60.5%) as a yellow oil.

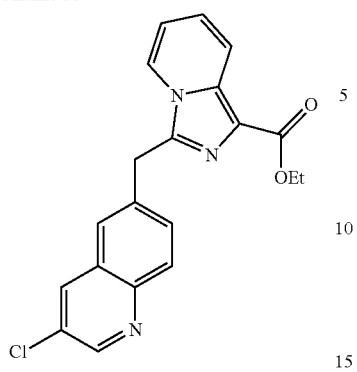

A mixture of [2-(3-chloro-quinolin-6-yl)-acetylamino]-pyridin-2-yl-acetic acid ethyl ester (566 mg, 1.48 mmol, 1 eq) in POCl₃ (50 mL) was stirred at 110° C. overnight. The mixture was concentrated, and the resulting residue was diluted with DCM. The mixture was washed with aq. Na₂CO₃ solution. The organic layer was concentrated, and the resulting residue was purified by chromatography on a silica gel column (PE/EA=1/1, v/v) to give [2-(3-chloro-quinolin-6-yl)-acetylamino]-pyridin-2-yl-acetic acid ethyl ester (512 mg, 94.6%) as a brown oil.

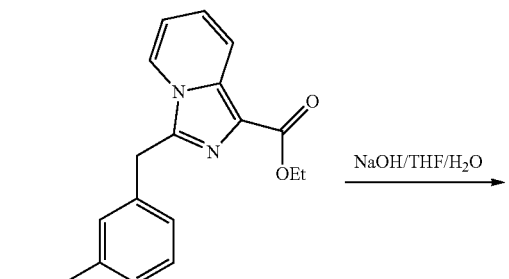

A mixture of [2-(3-chloro-quinolin-6-yl)-acetylamino]-pyridin-2-yl-acetic acid ethyl ester (512 mg, 1.4 mmol, 1 eq) and NaOH (168 mg, 4.2 mmol, 3 eq) in THF/H₂O (5/1, 30 mL) was stirred under reflux overnight. THF was removed by evaporation and the aqueous layer was acidified to pH 2 with 3 N aq. HCl solution. The resulting solid was collected and washed with water and dried under 120° C. for 3 h to give [2-(3-chloro-quinolin-6-yl)-acetylamino]-pyridin-2-yl-acetic acid (252 mg, 53.3%) as a yellow solid.

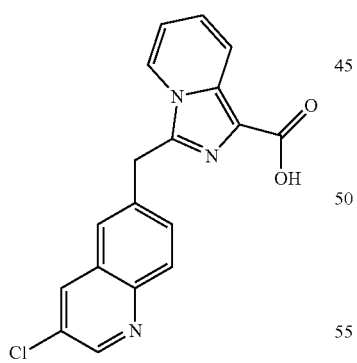

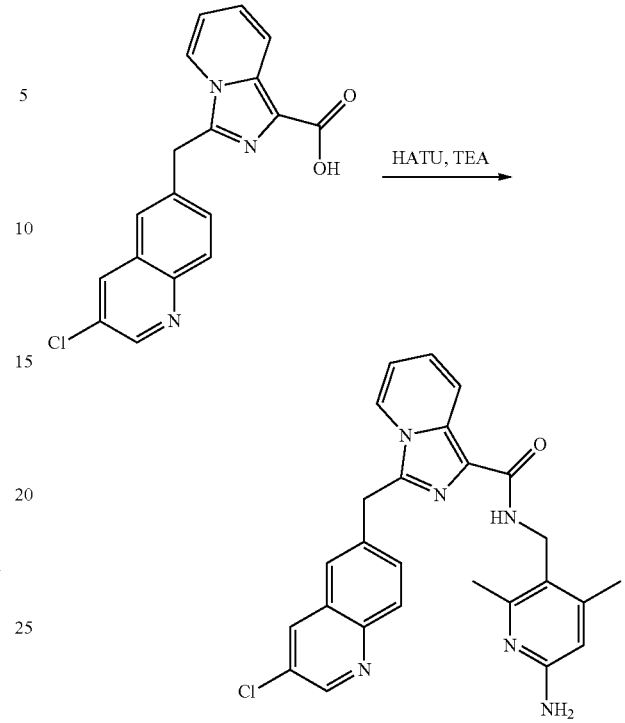

A mixture of 3-(3-chloro-quinolin-6-ylmethyl)-imidazo[1,5-a]pyridine-1-carboxylic acid (252 mg, 0.75 mmol, 1.0 eq), 5-aminomethyl-4,6-dimethyl-pyridin-2-ylamine (184 mg, 0.82 mmol, 1.1 eq), HATU (340 mg, 0.90 mmol, 1.2 eq), and TEA (0.42 mL, 3.0 mmol, 4.0 eq) in DMF (5 mL) was stirred at rt overnight. The mixture was concentrated, and the resulting residue was purified by chromatography on a silica gel column (DCM/MeOH=14/1, v/v) to give N-((6-amino-2,4-dimethylpyridin-3-yl)methyl)-3-((3-chloroquinolin-6-yl)methyl)imidazo[1,5-a]pyridine-1-carboxamide (203 mg, 57.8%) as a yellow solid.

LRMS (M+H⁺) m/z calculated 471.2, found 471.1. ¹H NMR (DMSO-d₆, 300 MHz): δ 8.82 (d, 1H), 8.47 (d, 1H), 8.25 (d, 1H), 8.13 (d, 1H), 7.97 (d, 1H), 7.73 (s, 1H), 7.67 (s, 1H), 7.65 (d, 1H), 7.09 (dd, 1H), 6.83 (dd, 1H), 6.16 (s, 1H), 5.80 (s, 2H), 4.67 (s, 2H), 4.40 (d, 2H), 2.37 (s, 3H), 2.22 (s, 3H).

Example 10: Preparation of N-((6-amino-2,4-dimethylpyridin-3-yl)methyl)-1-((3-chloroquinolin-6-yl)methyl)-1H-1,2,3-triazole-4-carboxamide

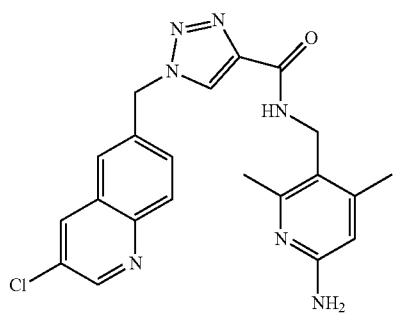

-continued

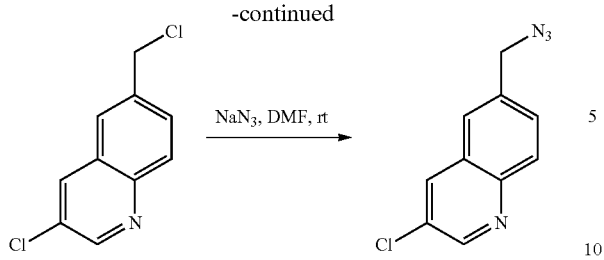

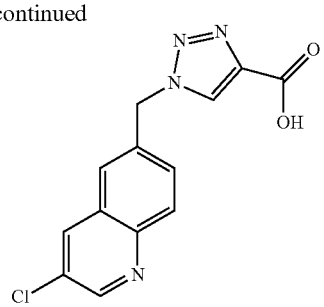

A mixture of 3-chloro-6-chloromethyl-quinoline (2.1 g, 10 mmol, 1.0 eq) and NaN₃ (0.65 g, 10 mmol, 1 eq) in DMF (40 mL) was stirred at rt overnight. The mixture was poured into 400 mL of water. The resulting precipitate was collected by filtration and washed with water. The solid was diluted with EA and dried over Na₂SO₄, and then concentrated to give 6-azidomethyl-3-chloro-quinoline (1.66 g, 76%) as a white solid.

A mixture of 1-(3-chloro-quinolin-6-ylmethyl)-1H-[1,2,3]triazole-4-carboxylic acid ethyl ester (1.25 g, 3.95 mmol, 1 eq) and NaOH (474 mg, 11.85 mmol, 3 eq) in THF/H₂O (3/1, 100 mL) was stirred at rt overnight. THF was removed by evaporation and the aqueous layer was acidified to pH 2 with 1 N aq. HCl solution. The resulting solid was collected and washed with water and dried to give 1-(3-chloro-quinolin-6-ylmethyl)-1H-[1,2,3]triazole-4-carboxylic acid (1.075 g, 94.3%) as a yellow solid.

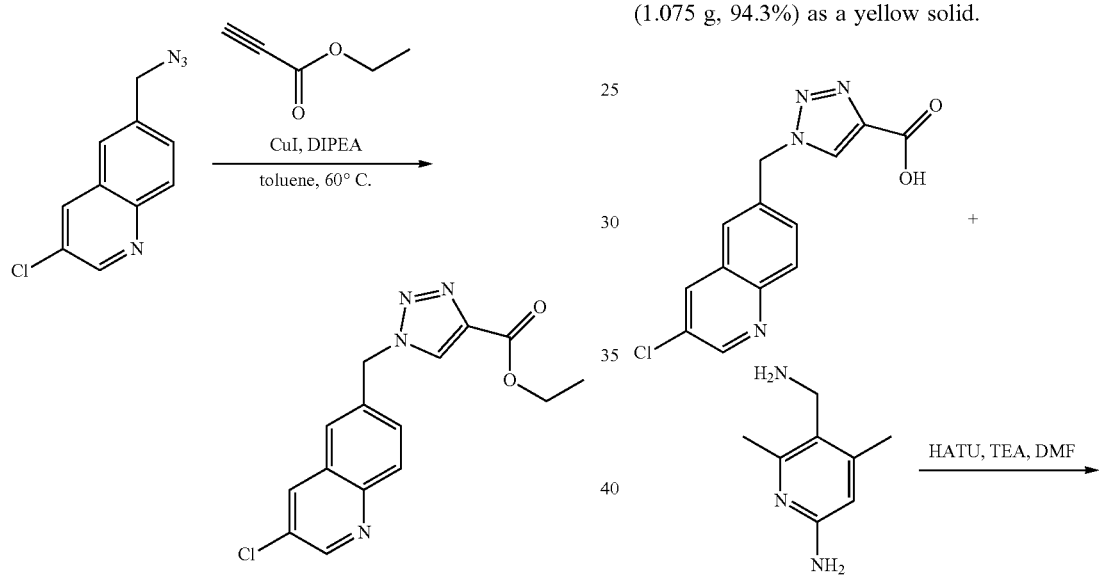

A mixture of 6-azidomethyl-3-chloro-quinoline (439 mg, 2 mmol, 1 eq), propynoic acid ethyl ester (196 mg, 2 mmol, 1 eq), DIPEA (258 mg, 2 mmol, 1 eq) and CuI (38 mg, 0.2 mmol, 0.1 eq) in toluene (40 mL) was stirred at 60° C. for 18 h. The mixture was concentrated, and the resulting residue was purified by chromatography on a silica gel column (PE/EA=1/1, v/v) to give 1-(3-chloro-quinolin-6-ylmethyl)-1H-[1,2,3]triazole-4-carboxylic acid ethyl ester (337 mg, 53.2%) as a white solid.

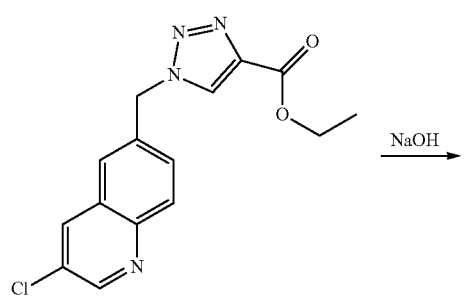

A mixture of 1-(3-chloro-quinolin-6-ylmethyl)-1H-[1,2,3]triazole-4-carboxylic acid (1.075 g, 3.71 mmol, 1.0 eq), 5-aminomethyl-4,6-dimethyl-pyridin-2-ylamine (998 mg, 4.45 mmol, 1.2 eq), HATU (1.69 g, 4.45 mmol, 1.2 eq), and TEA (2.1 mL, 14.8 mmol, 4.0 eq) in DMF (40 mL) was stirred at rt overnight. The mixture was diluted with water (500 mL), and extracted with CHCl₃ (500 mL×3). The combined organic layers were washed with sat. aq. NH₄Cl solution, then dried and concentrated. The resulting residue was triturated with EA/DCM/MeOH (110/20/20, v/v, 150 mL) to give N-((6-amino-2,4-dimethylpyridin-3-yl)methyl)-

1-((3-chloroquinolin-6-yl)methyl)-1H-1,2,3-triazole-4-carboxamide (775 mg, 49.4%) as a yellow solid.

LRMS (M+H⁺) m/z calculated 422.1, found 422.1. ¹H NMR (DMSO-d₆, 300 MHz): δ 8.90 (d, 1H), 8.70 (s, 1H), 8.60 (d, 1H), 8.35 (t, 1H), 8.06 (d, 1H), 7.87 (s, 1H), 7.73 (dd, 1H), 6.10 (s, 1H), 5.86 (s, 2H), 5.64 (s, 2H), 4.32 (d, 2H), 2.33 (s, 3H), 2.18 (s, 3H).

Example 11: Preparation of N-((6-amino-2,4-dimethylpyridin-3-yl)methyl)-1-((3-chloroquinolin-6-yl)methyl)-1H-indole-3-carboxamide

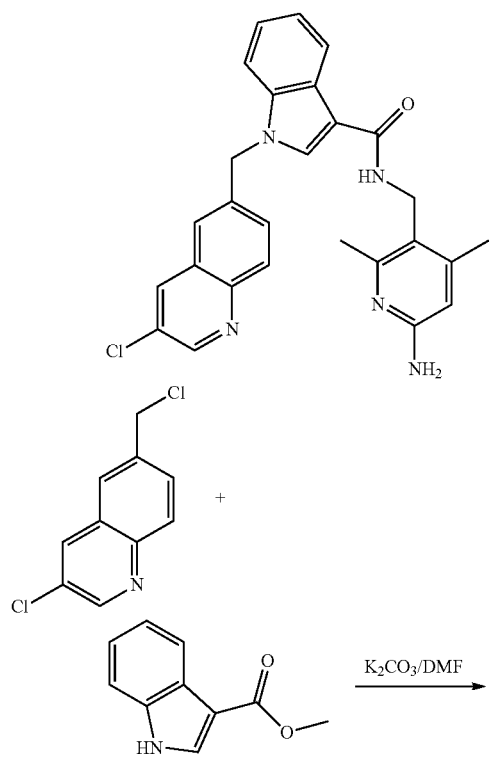

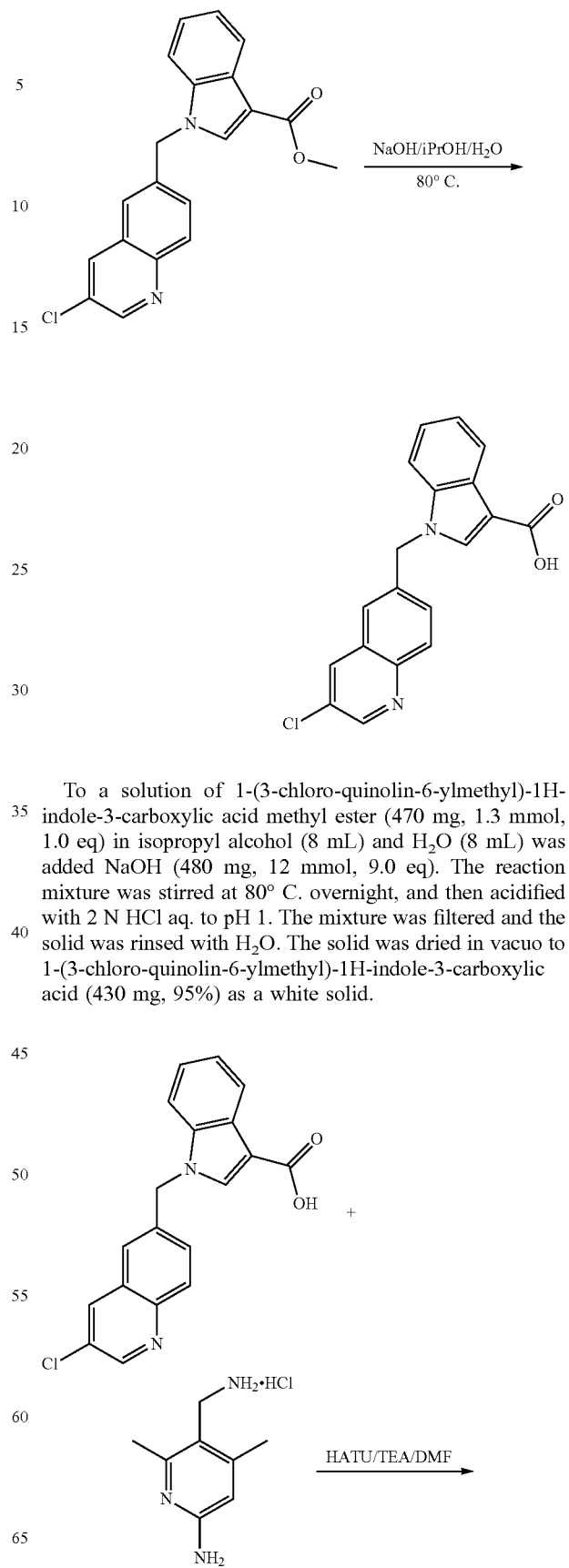

To a solution of 1-(3-chloro-quinolin-6-ylmethyl)-1H-indole-3-carboxylic acid methyl ester (470 mg, 1.3 mmol, 1.0 eq) in isopropyl alcohol (8 mL) and H₂O (8 mL) was added NaOH (480 mg, 12 mmol, 9.0 eq). The reaction mixture was stirred at 80° C. overnight, and then acidified with 2 N HCl aq. to pH 1. The mixture was filtered and the solid was rinsed with H₂O. The solid was dried in vacuo to 1-(3-chloro-quinolin-6-ylmethyl)-1H-indole-3-carboxylic acid (430 mg, 95%) as a white solid.

To a solution of 3-chloro-6-chloromethyl-quinoline (500 mg, 2.36 mmol, 1.0 eq) and K₂CO₃ (488 mg, 3.54 mmol, 1.5 eq) in DMF (5 ml) was added 1H-indole-3-carboxylic acid methyl ester (412 mg, 2.36 mmol, 1.0 eq). The reaction mixture was stirred at rt overnight under N₂, then diluted with H₂O, and filtered. The solid was rinsed with EA and dried in vacuo to give 1-(3-chloro-quinolin-6-ylmethyl)-1H-indole-3-carboxylic acid methyl ester (527 mg, 63.9%) as a white solid.

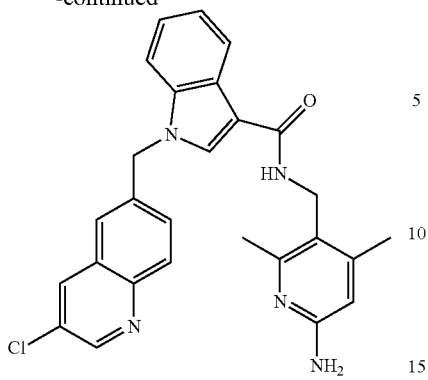

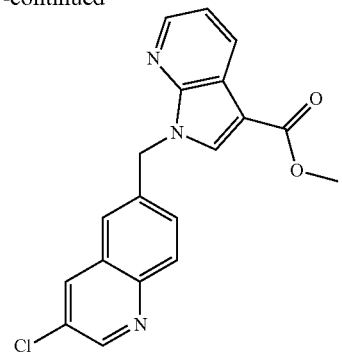

To a solution of 1-(3-chloro-quinolin-6-ylmethyl)-1H-indole-3-carboxylic acid (200 mg, 0.59 mmol, 1.0 eq), 5-aminomethyl-4,6-dimethyl-pyridin-2-ylamine (110 mg, 0.59 mmol, 1.0 eq) and HATU (338 mg, 0.89 mmol, 1.5 eq) in DMF (5 ml) was added TEA (180 mg, 1.78 mmol, 3.0 eq) at 0° C. under $N_2$. The reaction mixture was stirred at rt for 4 h. The reaction mixture was purified by Prep-HPLC to give N-((6-amino-2,4-dimethylpyridin-3-yl)methyl)-1-((3-chloroquinolin-6-yl)methyl)-1H-indole-3-carboxamide (60 mg, 21.6%) as a white solid. LRMS (M+H$^+$) m/z calculated 470.2, found 470.1. $^1$H NMR (DMSO-d$_6$, 400 MHz): δ 8.85 (s, 1H), 8.53 (s, 1H), 8.23-8.18 (m, 2H), 8.01 (d, 1H), 7.80-7.78 (m, 2H), 7.62-7.59 (m, 1H), 7.51-7.49 (m, 1H), 7.15-7.12 (m, 2H), 6.12 (s, 1H), 5.65 (s, 2H), 5.63 (s, 2H), 4.35 (d, 2H), 2.34 (s, 3H), 2.20 (s, 3H).

Example 12: Preparation of N-((6-amino-2,4-dimethylpyridin-3-yl)methyl)-1-((3-chloroquinolin-6-yl)methyl)-1H-pyrrolo[2,3-b]pyridine-3-carboxamide To a solution of 3-chloro-6-chloromethyl-quinoline (500 mg, 2.36 mmol, 1.0 eq) and K$_2$CO$_3$ (488 mg, 3.54 mmol, 1.5 eq) in DMF (5 mL) was added 1H-pyrrolo[2,3-b]pyridine-3-carboxylic acid methyl ester (415 mg, 2.36 mmol, 1.0 eq). The reaction mixture was stirred at rt overnight under $N_2$, then diluted with H$_2$O, and filtered. The solid was rinsed with EA and dried in vacuo to give 1-(3-chloro-quinolin-6-ylmethyl)-1H-pyrrolo[2,3-b]pyridine-3-carboxylic acid methyl ester (490 mg, 59.2%) as a white solid.

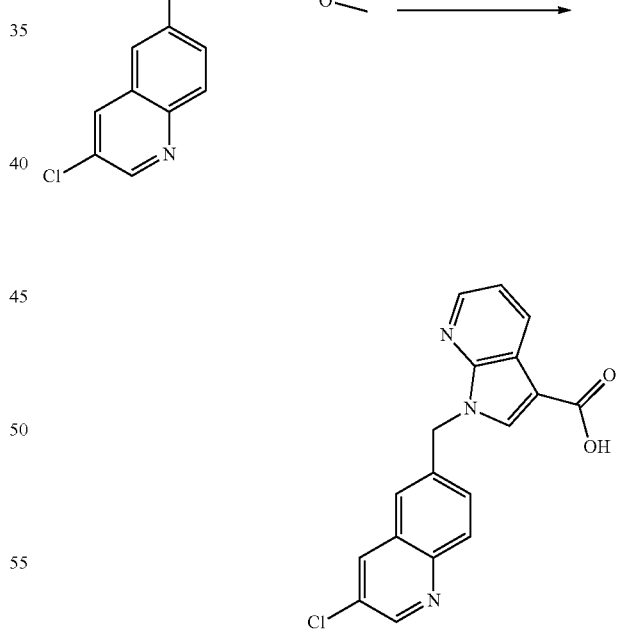

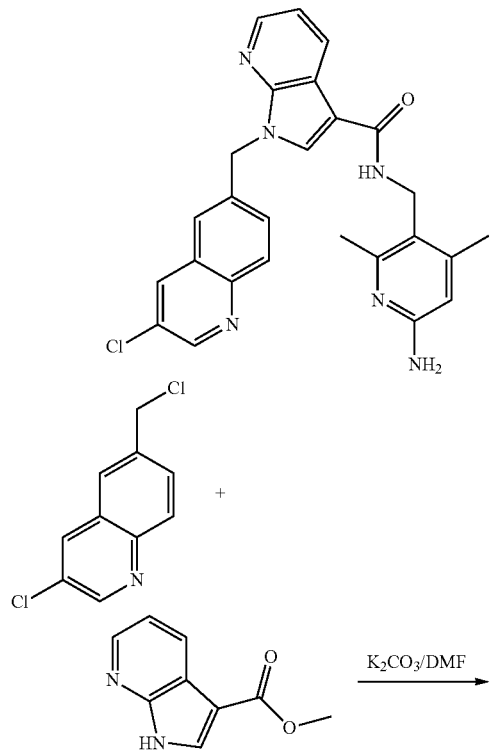

To a solution of compound 1 (220 mg, 0.63 mmol, 1.0 eq) in isopropyl alcohol (4 ml) and H$_2$O (4 mL1) was added NaOH (250 mg, 6.3 mmol, 10.0 eq). The reaction mixture was stirred at 80° C. overnight, and acidified with 2 N HCl aq. to pH 1. The mixture was filtered, and the solid was rinsed with H$_2$O. The solid was dried in vacuo to give 1-(3-chloro-quinolin-6-ylmethyl)-1H-pyrrolo[2,3-b]pyridine-3-carboxylic acid (180 mg, 85%) as a white solid.

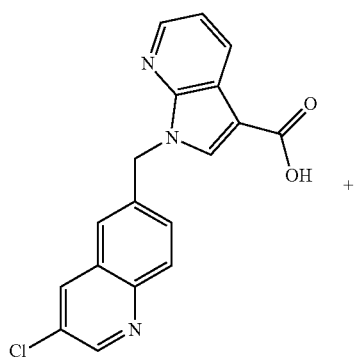

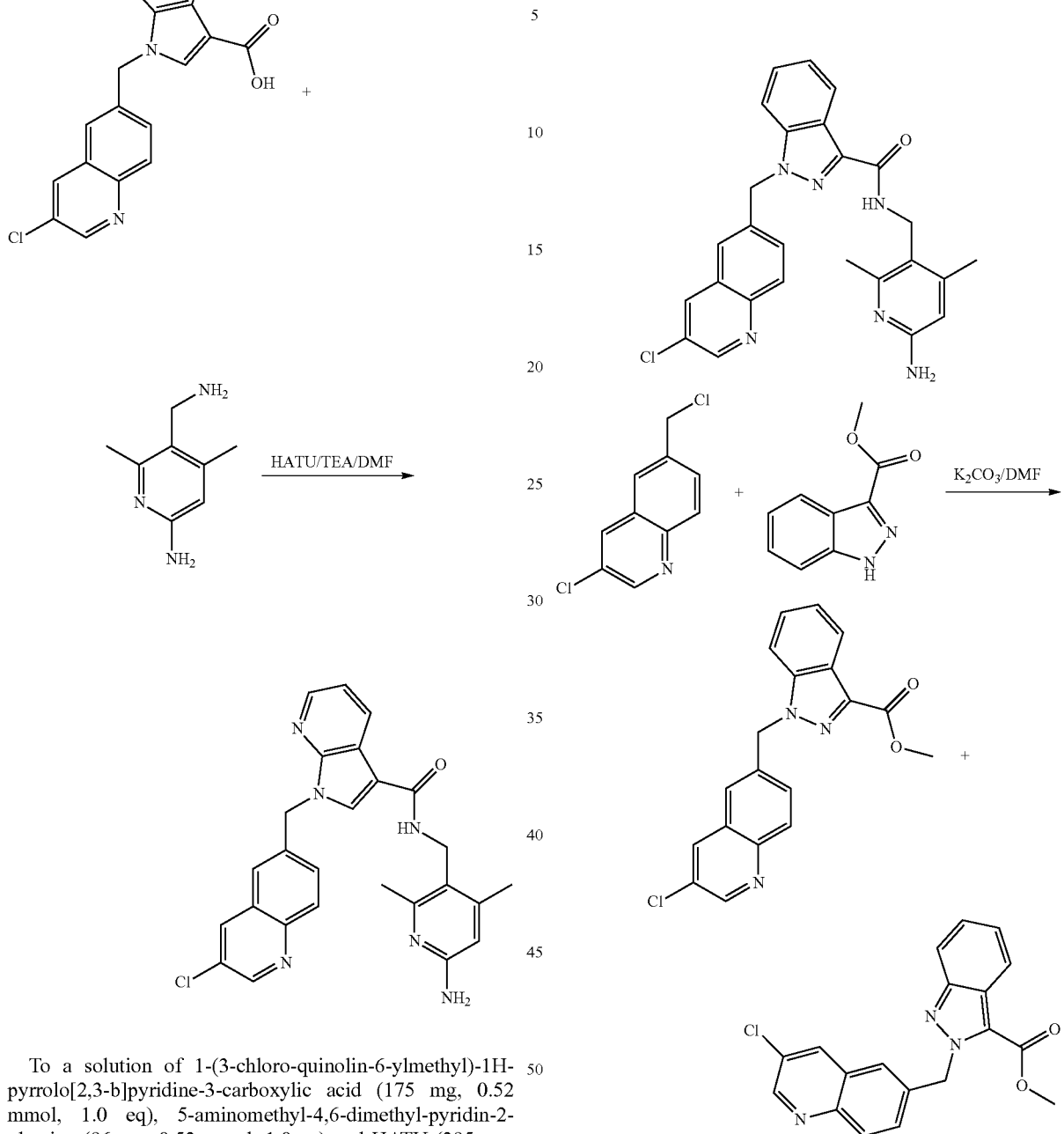

To a solution of 1-(3-chloro-quinolin-6-ylmethyl)-1H-pyrrolo[2,3-b]pyridine-3-carboxylic acid (175 mg, 0.52 mmol, 1.0 eq), 5-aminomethyl-4,6-dimethyl-pyridin-2-ylamine (96 mg, 0.52 mmol, 1.0 eq) and HATU (295 mg, 0.78 mmol, 1.5 eq) in DMF (5 ml) was added TEA (150 mg, 1.55 mmol, 3.0 eq) at 0° C. under $N_2$. The reaction mixture was stirred at rt for 4 h. The reaction mixture was purified by Prep-HPLC to give N-((6-amino-2,4-dimethylpyridin-3-yl)methyl)-1-((3-chloroquinolin-6-yl)methyl)-1H-pyrrolo[2,3-b]pyridine-3-carboxamide (88 mg, 36.2%) as a white solid.

LRMS (M+H$^+$) m/z calculated 471.2, found 471.1. $^1$H NMR (DMSO-d$_6$, 400 MHz): δ 8.85 (s, 1H), 8.55-8.50 (m, 2H), 8.35-8.32 (m, 2H), 8.02 (d, 1H), 7.93 (s, 1H), 7.78 (s, 1H), 7.67-7.65 (m, 1H), 7.26-7.23 (m, 1H), 6.12 (s, 1H), 5.71 (s, 2H), 5.67 (s, 2H), 4.34 (d, 2H), 2.32 (s, 3H), 2.19 (s, 3H).

Example 13: Preparation of N-((6-amino-2,4-dimethylpyridin-3-yl)methyl)-1-((3-chloroquinolin-6-yl)methyl)-1H-indazole-3-carboxamide To a solution of 3-chloro-6-chloromethyl-quinoline (500 mg, 2.36 mmol, 1.0 eq) and K$_2$CO$_3$ (488 mg, 3.54 mmol, 1.5 eq) in DMF (5 mL) was added 1H-indazole-3-carboxylic acid methyl ester (415 mg, 2.36 mmol, 1.0 eq). The reaction mixture was stirred at rt overnight under N$_2$. The reaction mixture was diluted with H$_2$O, extracted with EA. The organic layer was washed with H$_2$O, dried over Na$_2$SO$_4$, concentrated and purified by chromatography on a silica gel column (PE/EA=10/1~3/1, v/v) to give 1-(3-chloro-quinolin-6-ylmethyl)-1H-indazole-3-carboxylic acid methyl ester (450 mg, 54.3%) and 2-(3-chloro-quinolin-6-ylmethyl)-2H-indazole-3-carboxylic acid methyl ester (270 mg, 32.6%).

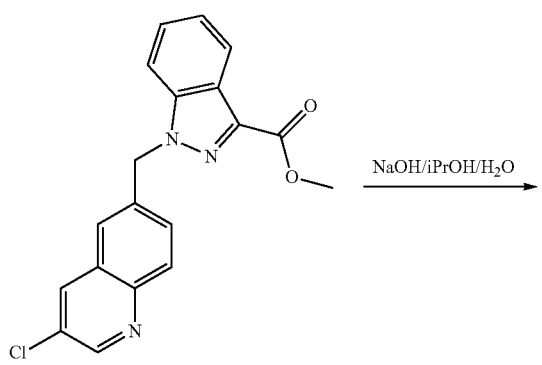

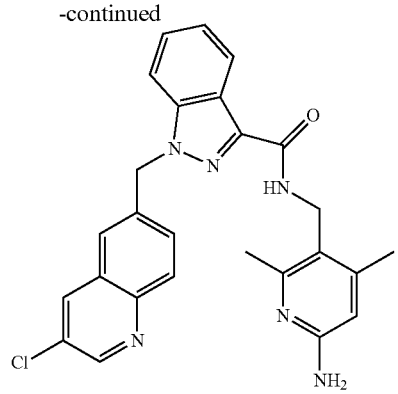

To a solution of 1-(3-chloro-quinolin-6-ylmethyl)-1H-indazole-3-carboxylic acid methyl ester (250 mg, 0.71 mmol, 1.0 eq) in isopropyl alcohol (4 mL) and H₂O (4 mL) was added NaOH (285 mg, 7.1 mmol, 10.0 eq). The reaction mixture was stirred at 80° C. overnight. The reaction mixture was acidified with 2N HCl aq. to pH 1. The mixture was filtered and the solid was rinsed with H₂O. The solid was dried in vacuo to give 1-(3-chloro-quinolin-6-ylmethyl)-1H-indazole-3-carboxylic acid (220 mg, 91%) as a white solid.

To a solution of 1-(3-chloro-quinolin-6-ylmethyl)-1H-indazole-3-carboxylic acid (220 mg, 0.65 mmol, 1.0 eq), 4-aminomethyl-3,5-dimethyl-phenylamine (121 mg, 0.65 mmol, 1.0 eq) and HATU (371 mg, 0.98 mmol, 1.5 eq) in DMF (5 mL) was added TEA (197 mg, 1.95 mmol, 3.0 eq) at 0° C. under N₂. The reaction mixture was stirred at rt for 2 h, and purified by Prep-HPLC to give N-((6-amino-2,4-dimethylpyridin-3-yl)methyl)-1-((3-chloroquinolin-6-yl)methyl)-1H-indazole-3-carboxamide (136 mg, 44%) as a white solid.

LRMS (M+H⁺) m/z calculated 471.2, found 471.1. ¹H NMR (DMSO-d₆, 400 MHz): δ 8.85 (d, 1H), 8.53 (d, 1H), 8.22-8.20 (m, 2H), 8.00 (d, 1H), 7.78-7.75 (m, 2H), 7.65-7.62 (m, 1H), 7.43-7.41 (m, 1H), 7.30-7.26 (m, 1H), 6.11 (s, 1H), 5.94 (s, 2H), 5.64 (s, 2H), 4.42 (d, 2H), 2.35 (s, 3H), 2.23 (s, 3H).

Example 14: Preparation of N-((6-amino-2,4-dimethylpyridin-3-yl)methyl)-2-((3-chloroquinolin-6-yl)methyl)-2H-indazole-3-carboxamide

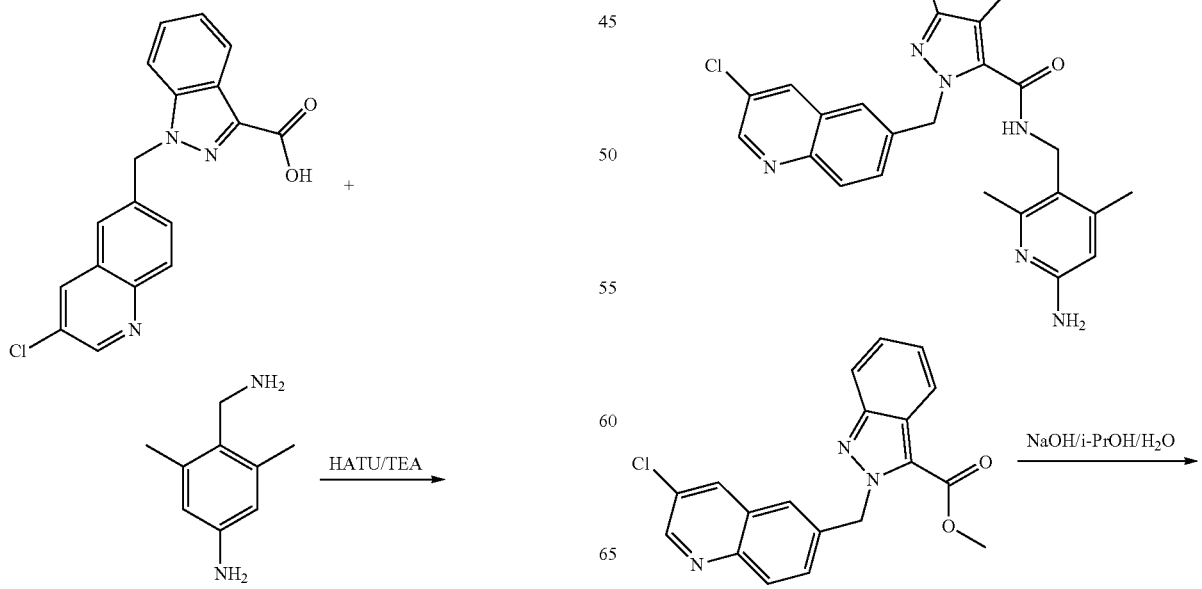

-continued

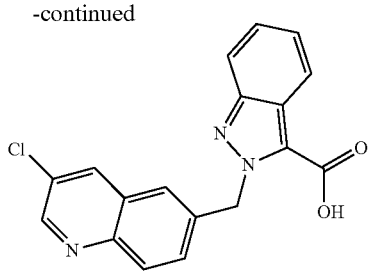

To a solution of 2-(3-chloro-quinolin-6-ylmethyl)-2H-indazole-3-carboxylic acid methyl ester (270 mg, 0.77 mmol, 1.0 eq) in isopropyl alcohol (5 mL) and H₂O (5 mL) was added NaOH (308 mg, 7.7 mmol, 10.0 eq). The reaction mixture was stirred at 80° C. overnight. The reaction mixture was acidified with 2N HCl aq. to pH 1. The mixture was filtered, and the solid was rinsed with H₂O, and dried in vacuo to give 2-(3-chloro-quinolin-6-ylmethyl)-2H-indazole-3-carboxylic acid (200 mg, 77%) as a white solid.

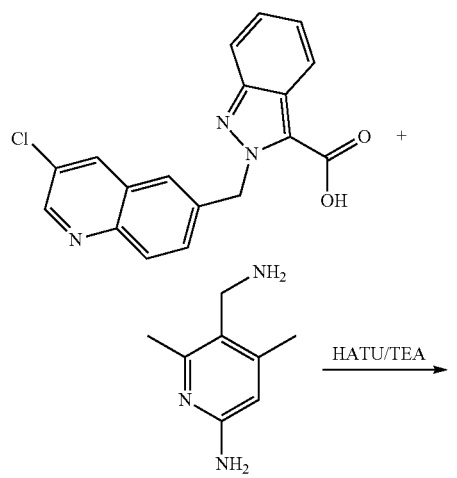

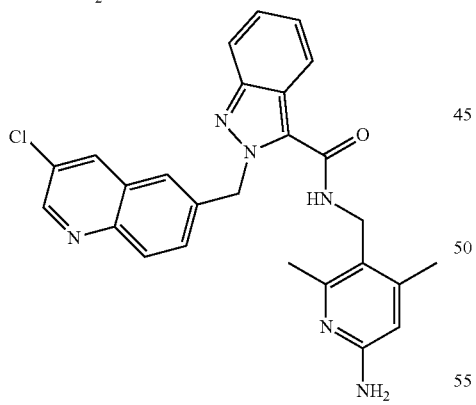

To a solution of 2-(3-chloro-quinolin-6-ylmethyl)-2H-indazole-3-carboxylic acid (200 mg, 0.59 mmol, 1.0 eq), 5-aminomethyl-4,6-dimethyl-pyridin-2-ylamine (110 mg, 0.59 mmol, 1.0 eq) and HATU (337 mg, 0.89 mmol, 1.5 eq) in DMF (5 ml) was added TEA (179 mg, 1.78 mmol, 3.0 eq) at 0° C. under N₂. The reaction mixture was stirred at rt for 2 h, and purified by Prep-HPLC to give N-((6-amino-2,4-dimethylpyridin-3-yl)methyl)-2-((3-chloroquinolin-6-yl)methyl)-2H-indazole-3-carboxamide (47 mg, 17%) as a white solid.

LRMS (M+H⁺) m/z calculated 472.1, found 471.1. ¹H NMR (DMSO-d₆, 400 MHz): δ 8.87 (d, 1H), 8.76-8.74 (m, 1H), 8.53 (d, 1H), 8.80 (d, 1H), 7.78 (s, 1H), 7.70-7.67 (m, 2H), 7.58 (d, 1H), 7.33-7.29 (m, 1H), 7.19-7.16 (m, 1H), 6.10 (s, 3H), 5.65 (s, 2H), 4.39 (d, 2H), 2.25 (s, 3H), 2.12 (s, 3H).

Example 15: Preparation of N-((6-amino-2,4-dimethylpyridin-3-yl)methyl)-1-((3-chloroquinolin-6-yl)methyl)-3-(trifluoromethyl)-1H-pyrazole-4-carboxamide

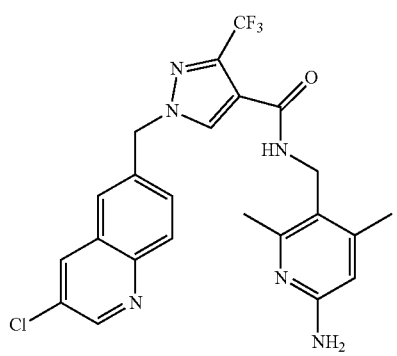

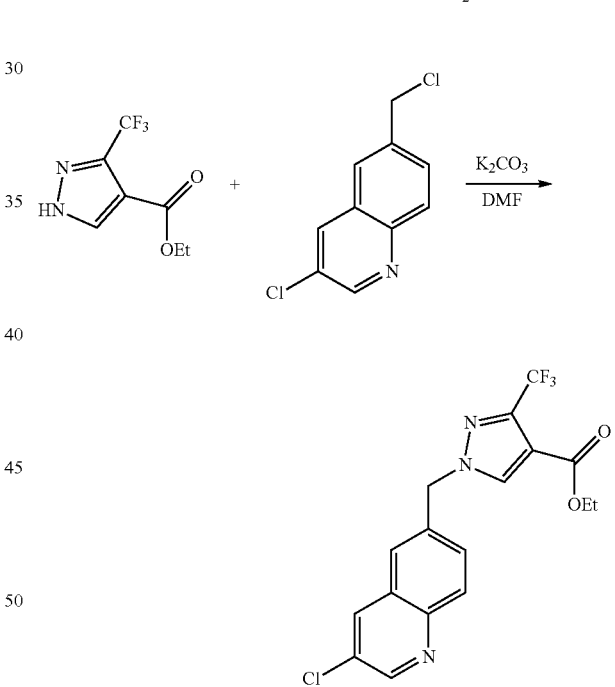

A mixture of 3-trifluoromethyl-1H-pyrazole-4-carboxylic acid ethyl ester (1.0 g, 4.81 mmol, 1.0 eq), 3-chloro-6-chloromethyl-quinoline (1.02 g, 5.77 mmol, 1.2 eq) and K₂CO₃ (994 mg, 7.2 mmol, 1.5 eq) in DMF (20 mL) was stirred at rt overnight. The mixture was concentrated, and the resulting residue was diluted with water. The mixture was extracted with EtOAc. The combined organic layers were dried and concentrated. The resulting residue was purified by chromatography on a silica gel column (DCM/MeOH=40/1, v/v) to give 1-(3-chloro-quinolin-6-ylmethyl)-3-trifluoromethyl-1H-pyrazole-4-carboxylic acid ethyl ester (1.3 g, 70.6%) as a white solid.

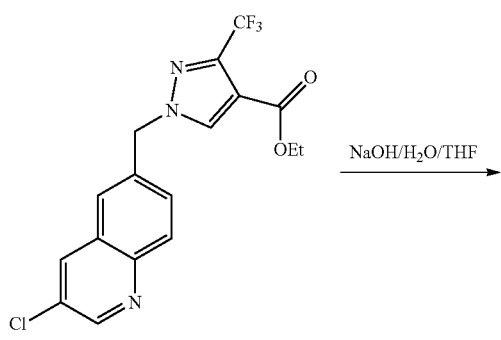

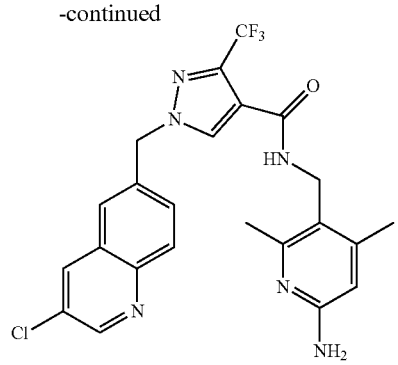

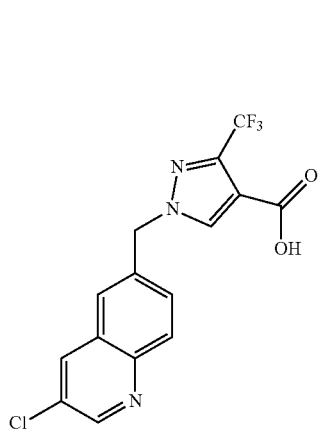

To a solution of 1-(3-chloro-quinolin-6-ylmethyl)-3-trifluoromethyl-1H-pyrazole-4-carboxylic acid ethyl ester (800 mg, 2.09 mmol, 1 eq) in THF (15 mL) was added a solution of NaOH (417 mg, 10.4 mmol, 5 eq) in water (15 mL) at rt. The mixture was stirred at rt for 2 h. The mixture was neutralized with 3N HCl, and the resulting precipitate was collected by filtration. The filter cake was dried to give 1-(3-chloro-quinolin-6-ylmethyl)-3-trifluoromethyl-1H-pyrazole-4-carboxylic acid (0.64 g, 87%) as a white solid.

A mixture of 1-(3-chloro-quinolin-6-ylmethyl)-3-trifluoromethyl-1H-pyrazole-4-carboxylic acid (100 mg crude, 0.28 mmol, 1.0 eq), 5-aminomethyl-4,6-dimethyl-pyridin-2-ylamine (64 mg, 0.34 mmol, 1.2 eq), HATU (160 mg, 0.42 mmol, 1.5 eq) and Et₃N (42 mg, 0.42 mmol, 1.5 eq) in DMF (10 mL) was stirred at rt for 2 h. The mixture was concentrated, and the resulting residue was purified by Prep-HPLC to give N-((6-amino-2,4-dimethylpyridin-3-yl)methyl)-1-((3-chloroquinolin-6-yl)methyl)-3-(trifluoromethyl)-1H-pyrazole-4-carboxamide (52 mg, 38%) as a white solid. LRMS (M+H⁺) m/z calculated 489.1, found 488.9. ¹H NMR (DMSO-d₆, 400 MHz): δ 8.89 (d, 1H), 8.61 (d, 1H), 8.48 (s, 1H), 8.15 (t, 1H), 8.05 (d, 1H), 7.89 (s, 1H), 7.67 (dd, 1H), 6.11 (s, 1H), 5.65 (s, 2H), 5.63 (s, 2H), 4.26 (d, 2H), 2.28 (s, 3H), 2.14 (s, 3H).

Example 16: Preparation of N-((6-amino-2,4-dimethylpyridin-3-yl)methyl)-1-((3-chloroquinolin-6-yl)methyl)-1H-pyrrolo[2,3-c]pyridine-3-carboxamide

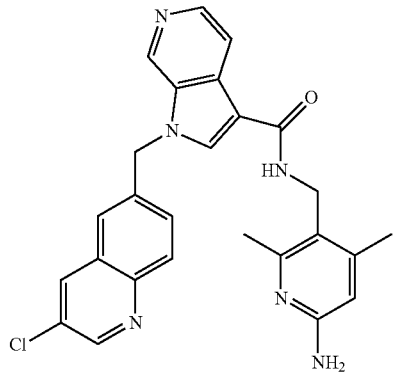

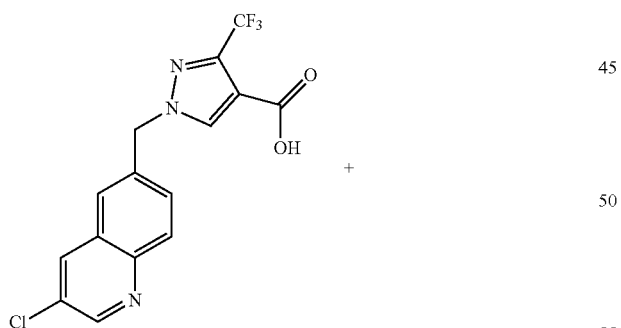

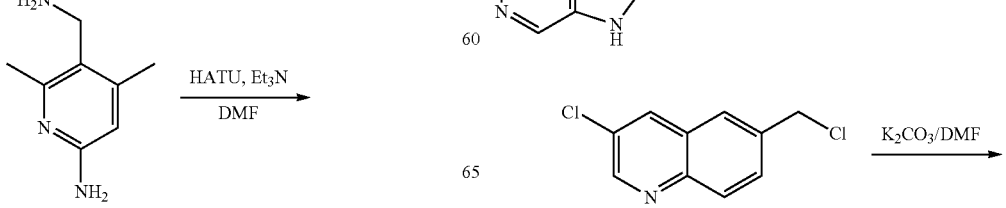

-continued

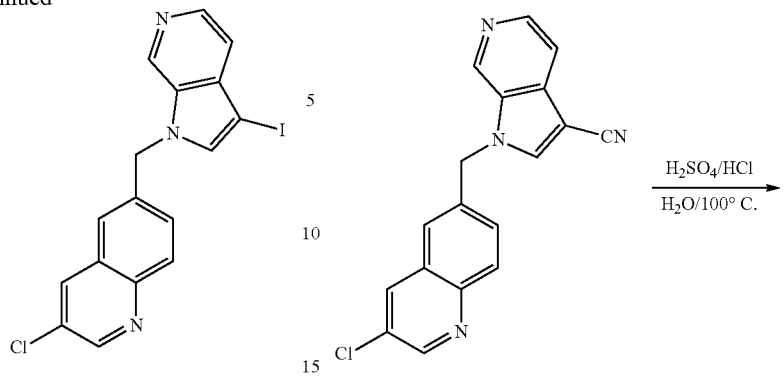

A mixture of 3-iodo-1H-pyrrolo[2,3-c]pyridine (2 g, 8.2 mmol, 1.0 eq), 3-chloro-6-chloromethyl-quinoline (1.74 g, 8.2 mmol, 1.0 eq) and $K_2CO_3$ (1.7 g, 12.3 mmol, 1.5 eq) in DMF (30 mL) was stirred at rt overnight. The reaction mixture was diluted with $H_2O$, and then extracted with EA. The organic layer was washed with water, brine, dried over $Na_2SO_4$, and concentrated. The resulting residue was purified by chromatography on a silica gel column (PE/EA=10/1-1/2, v/v) to give 3-chloro-6-(3-iodo-pyrrolo[2,3-c]pyridin-1-ylmethyl)-quinoline (1.3 g, 38%).

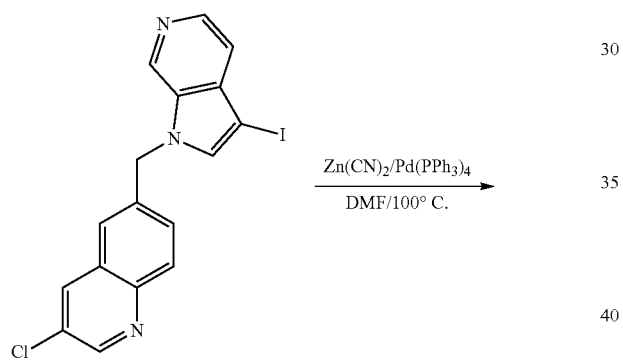

A mixture of 3-chloro-6-(3-iodo-pyrrolo[2,3-c]pyridin-1-ylmethyl)-quinoline (1.3 g, 3.1 mmol, 1.0 eq), $Zn(CN)_2$ (0.73 g, 6.2 mmol, 2.0 eq) and $Pd(PPh_3)_4$ (0.36 g, 0.31 mmol, 0.1 eq) in DMF (15 mL) was stirred at 100° C. overnight. The reaction mixture was diluted with $H_2O$, and then extracted with EA. The organic layer was washed with water, brine, dried over $Na_2SO_4$, and concentrated. The resulting residue was purified by chromatography on a silica gel column (DCM/MeOH=20/1, v/v) to give 1-(3-chloro-quinolin-6-ylmethyl)-1H-pyrrolo[2,3-c]pyridine-3-carbonitrile (0.28 g, 28%).

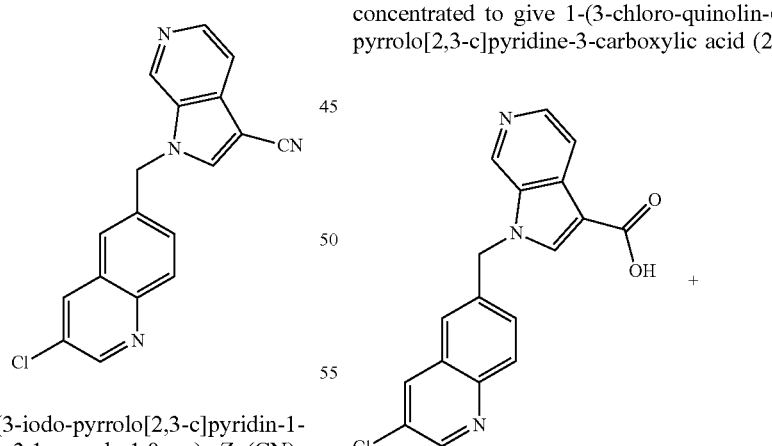

To a solution of 1-((3-chloroquinolin-6-yl)methyl)-1H-pyrrolo[2,3-c]pyridine-3-carbonitrile (275 mg, 0.86 mmol, 1.0 eq) in $H_2SO_4$ (2 mL), HCl (2 mL) and $H_2O$ (2 mL). The reaction mixture was stirred at 110° C. overnight. Then it was diluted with $H_2O$, and extracted with EA. The organic layer was washed with water, brine, dried over $Na_2SO_4$, and concentrated to give 1-(3-chloro-quinolin-6-ylmethyl)-1H-pyrrolo[2,3-c]pyridine-3-carboxylic acid (290 mg).

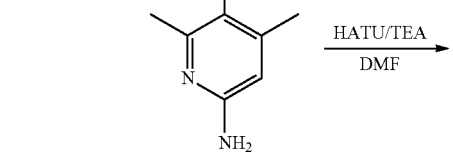

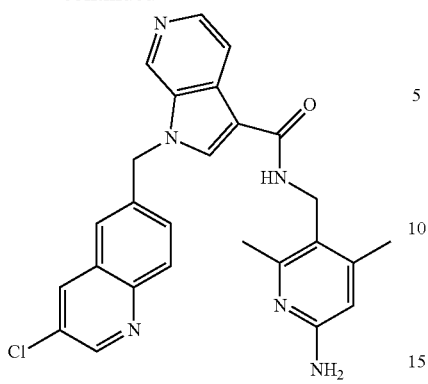

To a solution of 1-(3-chloro-quinolin-6-ylmethyl)-1H-pyrrolo[2,3-c]pyridine-3-carboxylic acid (180 mg, 0.56 mmol, 1.0 eq), 5-aminomethyl-4,6-dimethyl-pyridin-2-ylamine (105 mg, 0.56 mmol, 1.0 eq) and HATU (322 mg, 0.85 mmol, 1.5 eq) in DMF (5 mL) was added TEA (171 mg, 1.69 mmol, 3.0 eq) at 0° C. under $N_2$. The reaction mixture was stirred at rt overnight, then diluted with $H_2O$ and extracted with EA. The organic layer was concentrated. The resulting residue was purified by Prep-HPLC to give N-((6-amino-2,4-dimethylpyridin-3-yl)methyl)-1-((3-chloroquinolin-6-yl)methyl)-1H-pyrrolo[2,3-c]pyridine-3-carboxamide (45 mg, 17.7%) as a white solid. LRMS (M+H$^+$) m/z calculated 471.2, found 471.0. $^1$H NMR (DMSO-d$_6$, 400 MHz): δ 8.91 (s, 1H), 8.86 (d, 1H), 8.56 (d, 1H), 8.41 (s, 1H), 8.26 (d, 1H), 8.08-8.10 (m, 2H), 7.94 (d, 1H), 7.64 (s, 1H), 7.6 (d, 1H), 6.12 (s, 2H), 5.63 (s, 2H), 4.34 (d, 2H), 2.32 (s, 3H), 2.19 (s, 3H).

Example 17: Preparation of 3-amino-N-((6-amino-2,4-dimethylpyridin-3-yl)methyl)-1-((3-chloroquinolin-6-yl)methyl)-1H-pyrazole-4-carboxamide

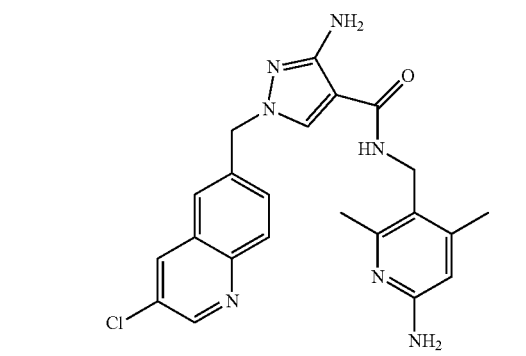

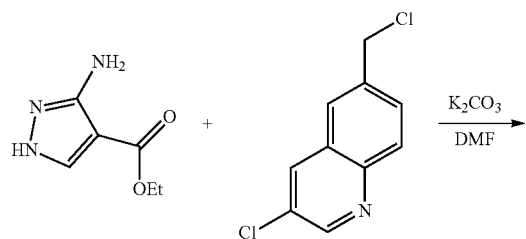

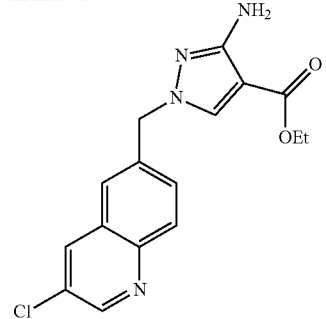

A mixture of 3-amino-1H-pyrazole-4-carboxylic acid ethyl ester (1.0 g, 6.45 mmol, 1.0 eq), 3-chloro-6-chloromethyl-quinoline (1.64 g, 7.74 mmol, 1.2 eq) and $K_2CO_3$ (1.34 g, 9.68 mmol, 1.5 eq) in DMF (20 mL) was stirred at rt overnight. The mixture was concentrated, and the resulting residue was diluted with water. The mixture was extracted with EtOAc. The combined organic layers were dried and concentrated to give 3-amino-1-(3-chloro-quinolin-6-ylmethyl)-1H-pyrazole-4-carboxylic acid ethyl ester (2.2 g).

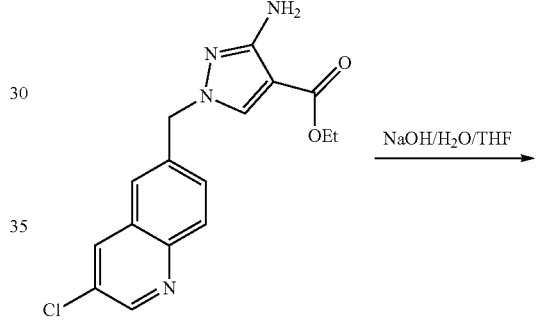

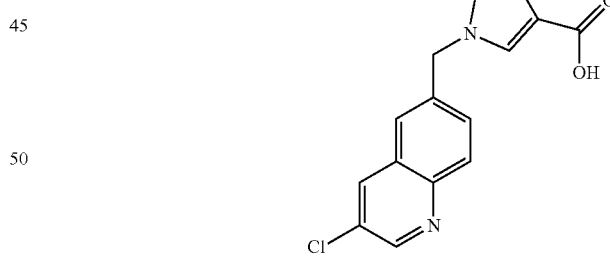

To a solution of 3-amino-1-(3-chloro-quinolin-6-ylmethyl)-1H-pyrazole-4-carboxylic acid ethyl ester (500 mg, 1.51 mmol, 1 eq) in THF (15 mL) was added a solution of NaOH (302 mg, 7.55 mmol, 5 eq) in water (15 mL) at rt. The mixture was stirred at rt for 2 h, and then neutralized with 3N HCl and the resulting precipitate was collected by filtration. The filter cake was dried to give 3-amino-1-(3-chloro-quinolin-6-ylmethyl)-1H-pyrazole-4-carboxylic acid (0.22 g, 44%) as a white solid.

163

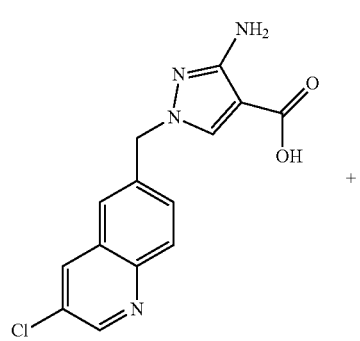

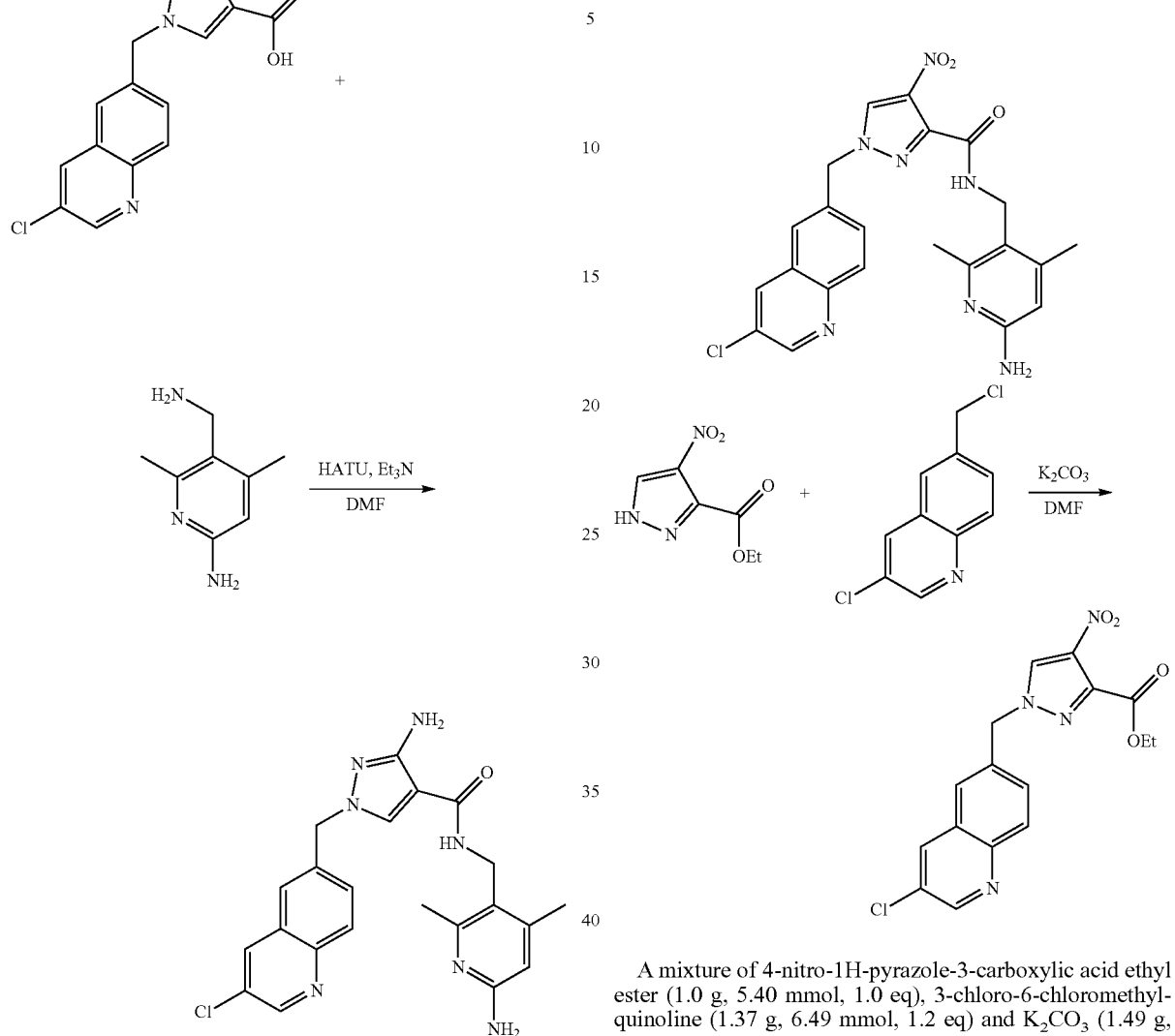

A mixture of 3-amino-1-(3-chloro-quinolin-6-ylmethyl)-1H-pyrazole-4-carboxylic acid (80 mg, 0.26 mmol, 1.0 eq), 5-aminomethyl-4,6-dimethyl-pyridin-2-ylamine (59 mg, 0.31 mmol, 1.2 eq), HATU (148 mg, 0.39 mmol, 1.5 eq) and Et$_3$N (104 mg, 1.04 mmol, 4.0 eq) in DMF (10 mL) was stirred at rt for 2 h, and then concentrated, The resulting residue was purified by Prep-HPLC to give 3-amino-N-((6-amino-2,4-dimethylpyridin-3-yl)methyl)-1-((3-chloroquinolin-6-yl)methyl)-1H-pyrazole-4-carboxamide (15 mg, 13%) as a white solid. LRMS (M+H$^+$) m/z calculated 436.2, found 436.0. $^1$H NMR (DMSO-d$_6$, 400 MHz): δ 8.87 (d, 1H), 8.58 (d, 1H), 8.10 (s, 1H), 8.03 (d, 1H), 7.79 (s, 1H), 7.63 (d, 1H), 7.61 (d, 1H), 6.15 (s, 1H), 5.76 (s, 2H), 5.43 (s, 2H), 5.26 (d, 2H), 4.23 (d, 2H), 2.30 (s, 3H), 2.17 (s, 3H).

164

Example 18: Preparation of N-((6-amino-2,4-dimethylpyridin-3-yl)methyl)-1-((3-chloroquinolin-6-yl)methyl)-4-nitro-1H-pyrazole-3-carboxamide A mixture of 4-nitro-1H-pyrazole-3-carboxylic acid ethyl ester (1.0 g, 5.40 mmol, 1.0 eq), 3-chloro-6-chloromethyl-quinoline (1.37 g, 6.49 mmol, 1.2 eq) and K$_2$CO$_3$ (1.49 g, 10.8 mmol, 2.0 eq) in DMF (20 mL) was stirred at rt overnight. The mixture was concentrated, and the resulting residue was diluted with water. The mixture was extracted with EtOAc. The combined organic layers were dried and concentrated. The resulting residue was purified by chromatography on silica gel column (DCM/MeOH=40/1, v/v) to give 1-(3-chloro-quinolin-6-ylmethyl)-4-nitro-1H-pyrazole-3-carboxylic acid ethyl ester (1.68 g, 86%).

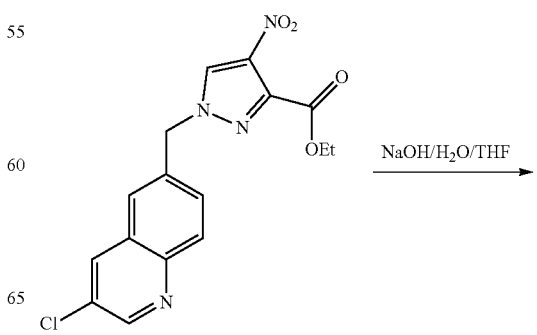

-continued

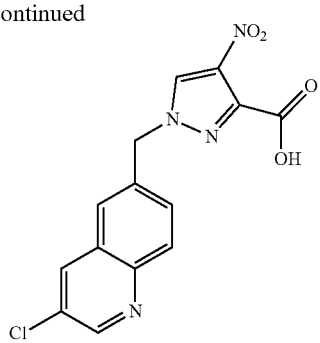

To a solution of 1-(3-chloro-quinolin-6-ylmethyl)-4-nitro-1H-pyrazole-3-carboxylic acid ethyl ester (680 mg, 1.88 mmol, 1 eq) in THF (15 mL) was added a solution of NaOH (377 mg, 9.42 mmol, 5 eq) in water (15 mL) at rt. The mixture was stirred at rt for 2 h, and then neutralized with 3N HCl. The resulting precipitate was collected by filtration. The filter cake was dried to give 1-(3-chloro-quinolin-6-ylmethyl)-4-nitro-1H-pyrazole-3-carboxylic acid (494 mg, 79%).

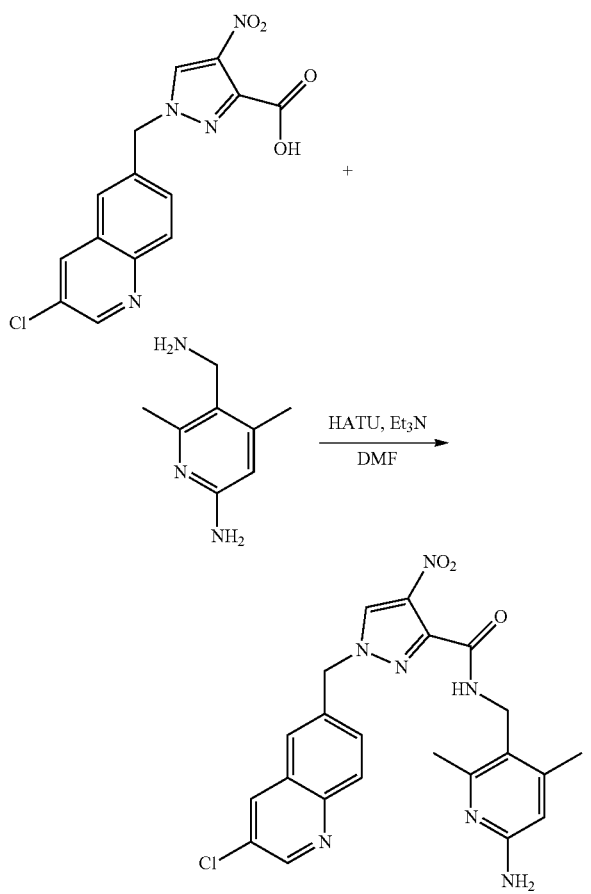

A mixture of 1-(3-chloro-quinolin-6-ylmethyl)-4-nitro-1H-pyrazole-3-carboxylic acid (100 mg, 0.30 mmol, 1.0 eq), 5-aminomethyl-4,6-dimethyl-pyridin-2-ylamine 63.5 mg, 0.36 mmol, 1.2 eq), HATU (171 mg, 0.45 mmol, 1.5 eq) and Et$_3$N (0.15 mL, 1.2 mmol, 4.0 eq) in DMF (10 mL) was stirred at rt for 3 h. The mixture was concentrated, and the resulting residue was purified by Prep-HPLC to give N-((6-amino-2,4-dimethylpyridin-3-yl)methyl)-1-((3-chloroquinolin-6-yl)methyl)-4-nitro-1H-pyrazole-3-carboxamide (150 mg, 93.7%). LRMS (M+H$^+$) m/z calculated 466.1, found 465.9. $^1$H NMR (DMSO-d$_6$, 400 MHz): δ 9.09 (s, 1H), 8.90 (d, 1H), 8.59 (s, 1H), 8.57 (d, 1H), 8.06 (d, 1H), 7.92 (s, 1H), 7.77 (d, 1H), 6.10 (s, 1H), 5.67 (s, 2H), 5.60 (s, 2H), 4.29 (d, 2H), 2.29 (s, 3H), 2.16 (s, 3H).

Example 19: Preparation of 4-acetamido-N-((6-amino-2,4-dimethylpyridin-3-yl)methyl)-1-((3-chloroquinolin-6-yl)methyl)-1H-pyrazole-3-carboxamide

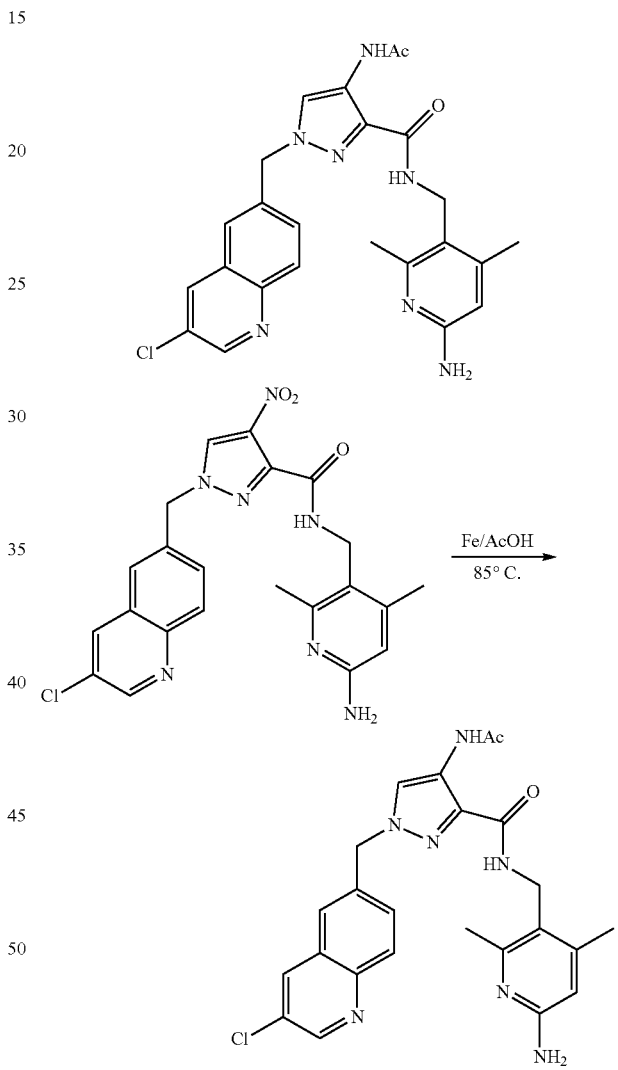

A mixture of 1-(3-chloro-quinolin-6-ylmethyl)-4-nitro-1H-pyrazole-3-carboxylic acid (6-amino-2,4-dimethyl-pyridin-3-ylmethyl)-amide (100 mg, 0.21 mmol, 1 eq) and ferrous powder (60 mg, 1.07 mmol, 5 eq) in AcOH (5 mL) was stirred at 85° C. for 3 h. After cooling to rt, the mixture was filtered, and the filtrate was concentrated. The resulting residue was diluted with DCM and washed with sat. NaHCO$_3$ solution. The organic layer was concentrated. The resulting residue was purified by Prep-HPLC to give 4-acetamido-N-((6-amino-2,4-dimethylpyridin-3-yl)methyl)-1-((3-chloroquinolin-6-yl)methyl)-1H-pyrazole-3-carboxamide (20 mg, 19.5%) as a white solid. LRMS (M+H⁺) m/z calculated 478.2, found 478.0. ¹H NMR (DMSO-d6, 400 MHz): δ 9.65 (s, 1H), 8.87 (d, 1H), 8.57 (d, 1H), 8.39 (s, 1H), 8.09 (t, 1H), 8.02 (d, 1H), 7.77 (d, 1H), 7.63 (dd, 1H), 6.10 (s, 1H), 5.66 (s, 2H), 5.58 (s, 2H), 4.34 (d, 2H), 2.31 (s, 3H), 2.18 (s, 3H), 2.10 (s, 3H).

Example 20: Preparation of 5-amino-N-((6-amino-2,4-dimethylpyridin-3-yl)methyl)-1-((3-chloroquinolin-6-yl)methyl)-1H-1,2,4-triazole-3-carboxamide

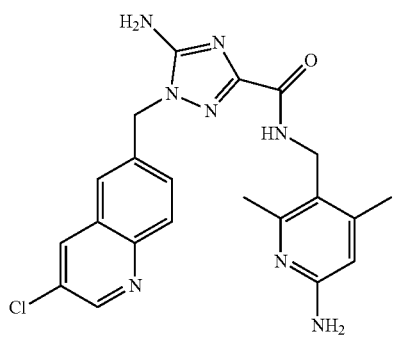

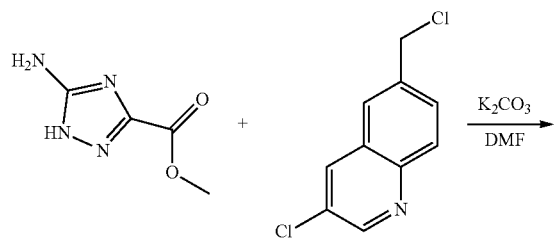

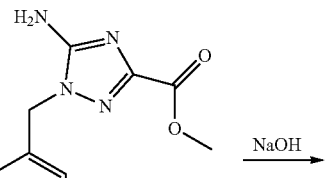

A mixture of 5-amino-1H-[1,2,4]triazole-3-carboxylic acid methyl ester (1.0 g, 7.04 mmol, 1.0 eq), 3-chloro-6-chloromethyl-quinoline (2.2 g, 10.55 mmol, 1.5 eq) and K₂CO₃ (2.9 g, 21.12 mmol, 3.0 eq) in DMF (30 mL) was stirred at rt for overnight. The mixture was filtered, and the filtrate was concentrated. The resulting residue was washed with water (20 mL) and MeOH (20 mL) to give methyl 5-amino-1-((3-chloroquinolin-6-yl)methyl)-1H-1,2,4-triazole-3-carboxylate (1.8 g, 82%). LRMS (M+H⁺) m/z calculated 318.1, found 318.1.

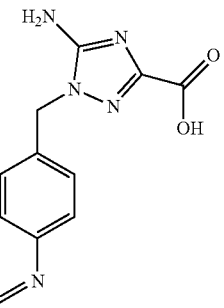

To a solution of methyl 5-amino-1-((3-chloroquinolin-6-yl)methyl)-1H-1,2,4-triazole-3-carboxylate (100 mg, 0.32 mmol, 1.0 eq) in THF (10 mL) was added a solution of NaOH (19 mg, 0.47 mmol, 1.5 eq) in water (10 mL) at rt. The mixture was stirred at rt for 2 h. The mixture was neutralized with 1N HCl, and concentrated to give 5-amino-1-((3-chloroquinolin-6-yl)methyl)-1H-1,2,4-triazole-3-carboxylic acid (100 mg, crude). LRMS (M+H⁺) m/z calculated 304.1, found 304.1.

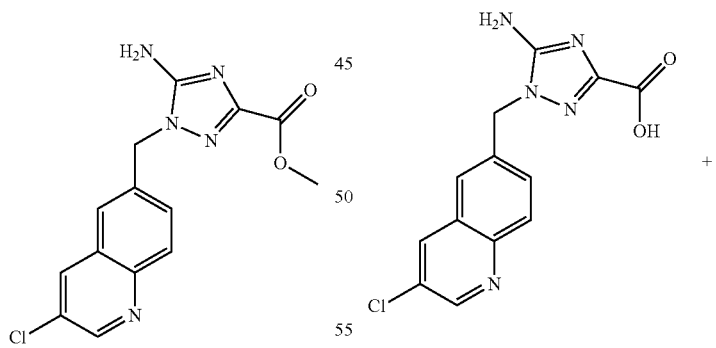

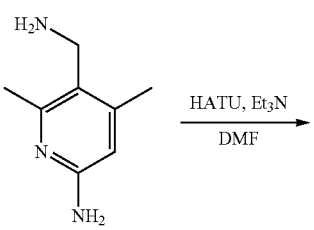

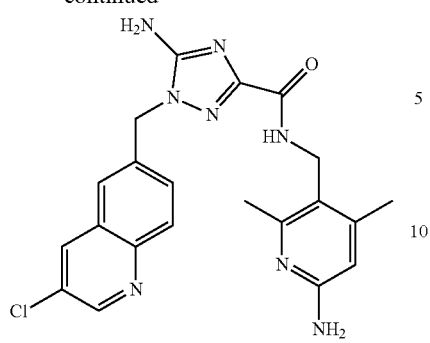

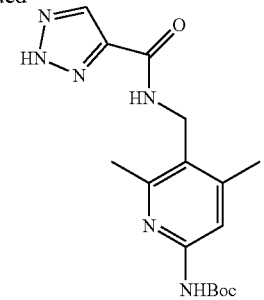

A mixture of 5-amino-1-((3-chloroquinolin-6-yl)methyl)-1H-1,2,4-triazole-3-carboxylic acid (100 mg crude, 0.30 mmol, 1.0 eq), 5-aminomethyl-4,6-dimethyl-pyridin-2-ylamine (68 mg, 0.45 mmol, 1.5 eq), HATU (171 mg, 0.45 mmol, 1.5 eq) and Et₃N (91 mg, 0.90 mmol, 3.0 eq) in DMF (4 mL) was stirred at rt for 2 h. The mixture was concentrated, and the resulting residue was purified by Prep-HPLC to give 5-amino-N-((6-amino-2,4-dimethylpyridin-3-yl)methyl)-1-((3-chloroquinolin-6-yl)methyl)-1H-1,2,4-triazole-3-carboxamide (8.0 mg, 6%). LRMS (M+H⁺) m/z calculated 437.1, found 437.0. ¹H NMR (DMSO-d₆, 400 MHz): δ 8.87 (s, 1H), 8.59 (s, 1H), 8.04 (d, 1H), 7.73-7.62 (m, 3H), 6.60 (s, 2H), 6.11 (s, 1H), 5.72 (br, 2H), 5.38 (s, 2H), 4.28 (d, 2H), 2.29 (s, 3H), 2.17 (s, 3H).

Example 21: Preparation of N-((6-amino-2,4-dimethylpyridin-3-yl)methyl)-2-((3-chloroquinolin-6-yl)methyl)-2H-1,2,3-triazole-4-carboxamide N-((6-amino-2,4-dimethylpyridin-3-yl)methyl)-2-((3-chloroquinolin-6-yl)methyl)-2H-1,2,3-triazole-4-carboxamide

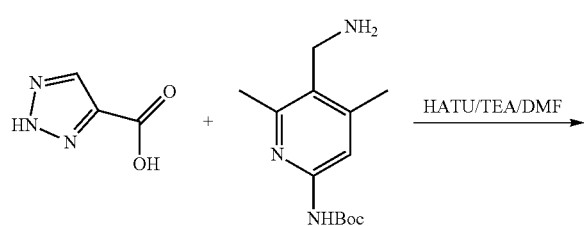

HATU/TEA/DMF

To a mixture of 2H-[1,2,3]triazole-4-carboxylic acid (0.5 g, 4.42 mmol, 1.0 eq) and (5-aminomethyl-4,6-dimethyl-pyridin-2-yl)-carbamic acid tert-butyl ester (1.09 g, 4.86 mmol, 1.1 eq) in DMF was added HATU (2.0 g, 5.3 mmol, 1.2 eq) and TEA (1.35 g, 13.3 mmol, 3.0 eq). The mixture was stirred at rt overnight. Then DMF was removed by evaporation and the resulting residue was purified by chromatography on silica gel column (PE/EA=3/1 to 0/1, v/v) to give (4,6-dimethyl-5-{[(2H-[1,2,3]triazole-4-carbonyl)-amino]-methyl}-pyridin-2-yl)-carbamic acid tert-butyl ester (1.4 g, 91%) as a white solid.

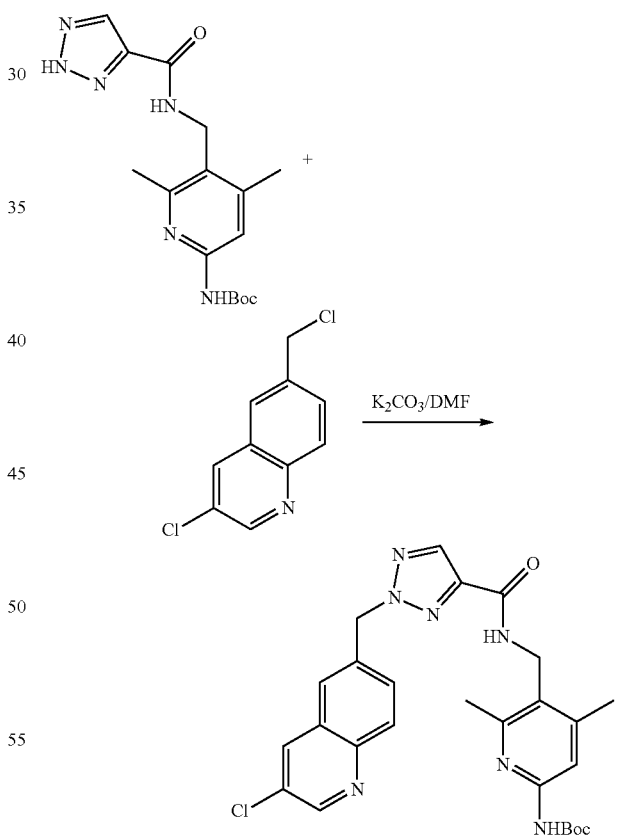

A mixture of (4,6-dimethyl-5-{[(2H-[1,2,3]triazole-4-carbonyl)-amino]-methyl}-pyridin-2-yl)-carbamic acid tert-butyl ester (0.692 g, 2 mmol, 1.0 eq), 3-chloro-6-chloromethyl-quinoline (0.424 g, 2 mmol, 1.0 eq) and K2CO3 (0.55 g, 4 mmol, 2.0 eq) in DMF (20 mL) was stirred at rt for 2 days. DMF was removed by evaporation and the resulting residue was diluted with CH2Cl2 (250 mL). The organic layer was washed with water (100 mL×2), dried, and concentrated. The resulting residue was purified by chromatography on silica gel column (PE/EA=3/1 to 1/1, v/v) to give [5-({[2-(3-chloro-quinolin-6-ylmethyl)-2H-[1,2,3]triazole-4-carbonyl]-amino}-methyl)-4,6-dimethyl-pyridin-2-yl]-carbamic acid tert-butyl ester (180 mg, 17%) as white solid.

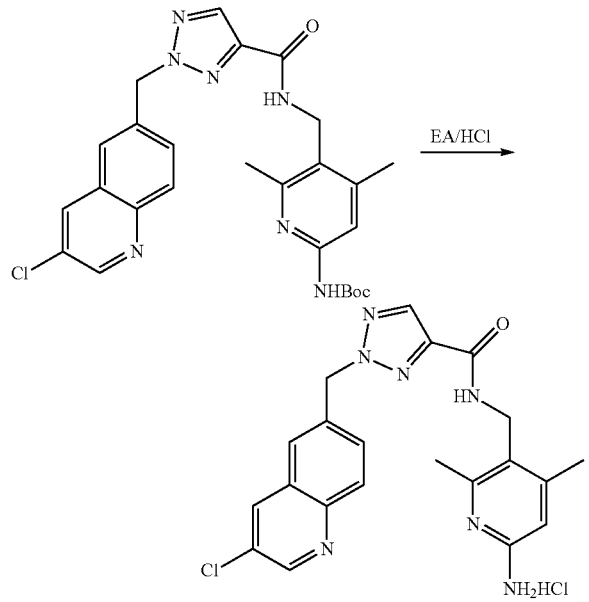

To a solution of [5-({[2-(3-chloro-quinolin-6-ylmethyl)-2H-[1,2,3]triazole-4-carbonyl]-amino}-methyl)-4,6-dimethyl-pyridin-2-yl]-carbamic acid tert-butyl ester (180 mg, 0.35 mmol, 1.0 eq) in EA was added HCl/EA solution. The mixture was stirred at rt for 4 h, and the resulting precipitate was obtained by filtered, dried to give N-((6-amino-2,4-dimethylpyridin-3-yl)methyl)-2-((3-chloroquinolin-6-yl)methyl)-2H-1,2,3-triazole-4-carboxamide (100 mg, 63%) as a white solid. LRMS (M+H+) m/z calculated 422.1, found 422.0. 1H NMR (DMSO-d6, 400 MHz): δ 14.2 (s, 1H), 8.87-8.90 (m, 2H), 8.75 (s, 1H), 8.60-8.61 (d, 1H), 8.05-8.07 (d, 1H), 7.89 (s, 1H), 7.68-7.76 (m, 3H), 6.64 (s, 1H), 5.89 (s, 2H), 4.33 (d, 2H), 2.53 (s, 3H), 2.37 (s, 3H).

Example 22: Preparation of N-((6-amino-2,4-dimethylpyridin-3-yl)methyl)-1-((3-chloroquinolin-6-yl)methyl)-4-(trifluoromethyl)-1H-pyrazole-3-carboxamide

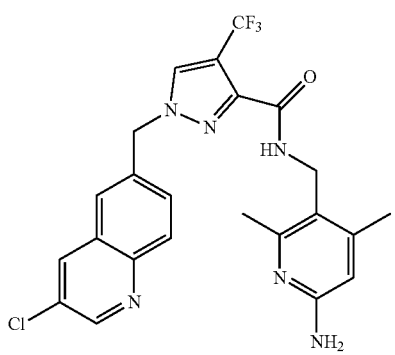

N-((6-amino-2,4-dimethylpyridin-3-yl)methyl)-1-((3-chloroquinolin-6-yl)methyl)-4-(trifluoromethyl)-1H-pyrazole-3-carboxamide

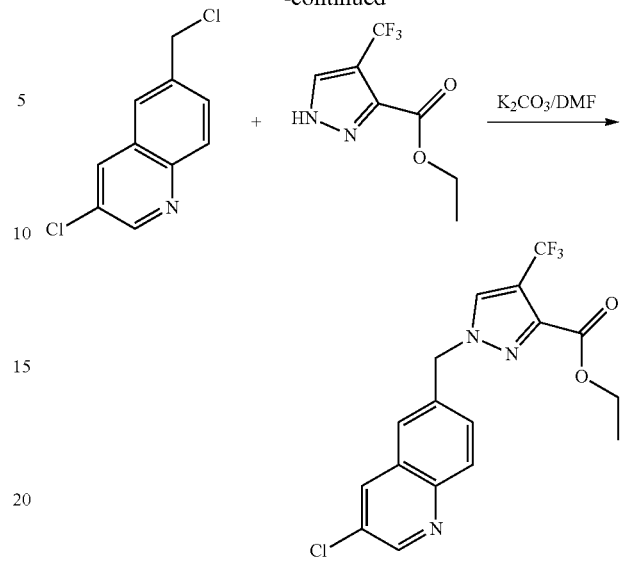

A mixture of 4-trifluoromethyl-1H-pyrazole-3-carboxylic acid ethyl ester (0.36 g, 1.73 mmol, 1.0 eq), 3-chloro-6-chloromethyl-quinoline (0.367 g, 1.73 mmol, 1.0 eq) and K2CO3 (0.477 g, 3.46 mmol, 2.0 eq) in DMF (20 mL) was stirred at rt overnight. DMF was removed by evaporation and the resulting residue was diluted with 200 mL of DCM, washed with water. The organic layer was dried, and concentrated. The resulting residue was purified by chromatography on a silica gel column (PE/EA=6/1 to 3/1, v/v) to give 1-(3-chloro-quinolin-6-ylmethyl)-4-trifluoromethyl-1H-pyrazole-3-carboxylic acid ethyl ester (0.41 g, 61%) as a white solid.

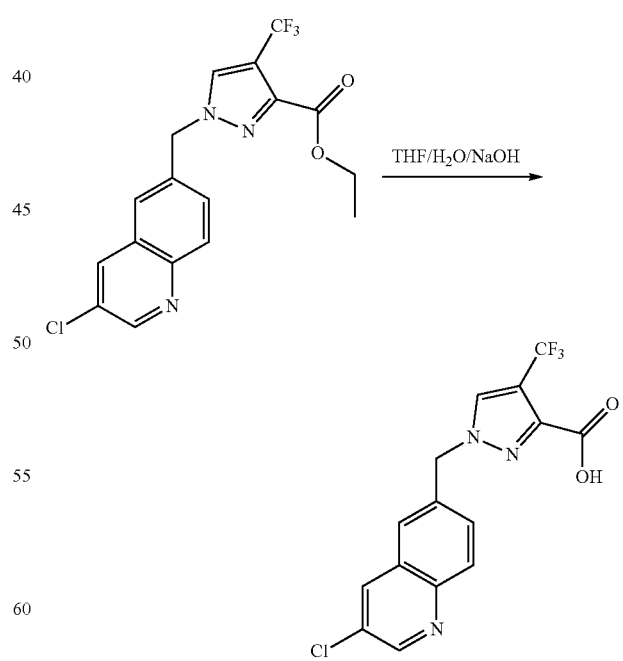

To a solution of 1-(3-chloro-quinolin-6-ylmethyl)-4-trifluoromethyl-1H-pyrazole-3-carboxylic acid ethyl ester (0.41 g, 1.06 mmol, 1.0 eq) in THF (10 mL) and H2O (2 mL) was added NaOH (0.127 g, 3.18 mmol, 3.0 eq). The mixture was stirred at 60° C. for 4 h. THF was removed and the aqueous layer was adjusted with 6 N HCl to pH 1.0. The resulting precipitate was collected by filtered, washed with water, dried to give 1-(3-chloro-quinolin-6-ylmethyl)-4-trifluoromethyl-1H-pyrazole-3-carboxylic acid (0.32 g, 84%).

Example 23: Preparation of N-((6-amino-2,4-dimethylpyridin-3-yl)methyl)-1-((3-chloroquinolin-6-yl)methyl)imidazo[1,5-a]pyridine-3-carboxamide

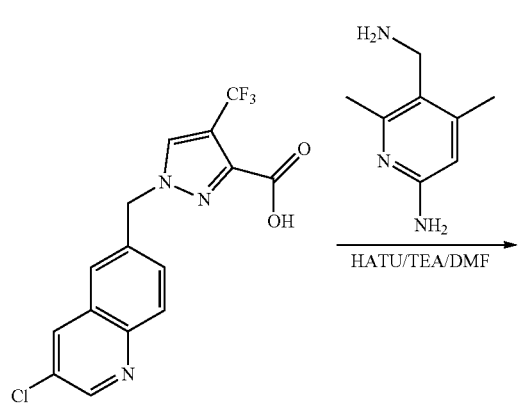

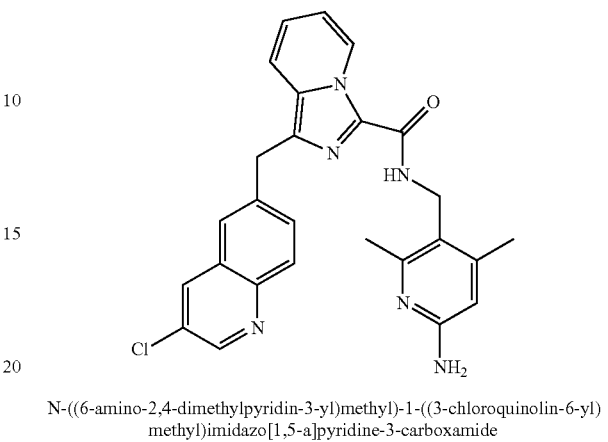

N-((6-amino-2,4-dimethylpyridin-3-yl)methyl)-1-((3-chloroquinolin-6-yl)methyl)imidazo[1,5-a]pyridine-3-carboxamide

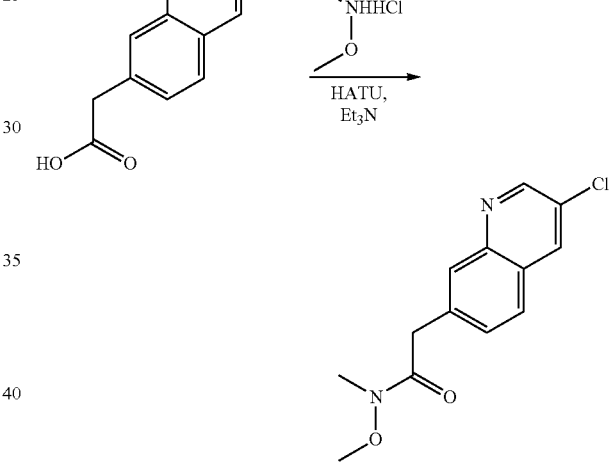

To a mixture of 1-(3-chloro-quinolin-6-ylmethyl)-4-trifluoromethyl-1H-pyrazole-3-carboxylic acid (0.32 g, 0.89 mmol, 1.0 eq), 5-(aminomethyl)-4,6-dimethylpyridin-2-amine (0.24 g, 1.07 mmol, 1.2 eq) and HATU (0.407 g, 1.07 mmol, 1.2 eq) in 20 mL of DMF was added TEA (0.269 g, 2.67 mmol, 3.0 eq). The reaction mixture was stirred at rt overnight. DMF was removed by evaporation and the resulting residue was diluted with 200 mL of DCM and washed with sat. NH4Cl aqueous solution. The organic layer was dried over anhydrous Na2SO4, filtered, and concentrated. The resulting residue was purified by chromatography on a silica gel column (DCM/MeOH=1/0 to 15/1, v/v) to give N-((6-amino-2,4-dimethylpyridin-3-yl)methyl)-1-((3-chloroquinolin-6-yl)methyl)-4-(trifluoromethyl)-1H-pyrazole-3-carboxamide (180 mg, 41%) as a white solid. LRMS (M+H+) m/z calculated 489.1, found 489.0. 1H NMR (DMSO-d6, 400 MHz): δ 8.89 (s, 1H), 8.59-8.63 (m, 2H), 8.15-8.17 (m, 1H), 8.04-8.06 (m, 1H), 7.85 (s, 1H), 7.70-7.72 (m, 1H), 6.10 (s, 1H), 5.62-5.67 (m, 4H), 4.30-4.31 (m, 2H), 2.28 (s, 3H), 2.16 (s, 3H).

A mixture of (3-chloro-quinolin-7-yl)-acetic acid (1.0 g, 4.51 mmol, 1.0 eq), O, N-dimethyl-hydroxylamine (660 mg, 6.77 mmol, 1.5 eq), HATU (2.6 g, 6.77 mmol, 1.5 eq) and Et3N (1.4 g, 13.53 mmol, 3.0 eq) in DMF (8 mL) was stirred at rt for 2 h. The mixture was concentrated and the resulting residue was purified by chromatography on silica gel column (PE/EA=3/1, v/v) to afford 2-(3-chloro-quinolin-7-yl)-N-methoxy-N-methyl-acetamide (1.2 g, 100%) as a colorless oil. LRMS (M+H+) m/z calculated 265.1, found 265.1.

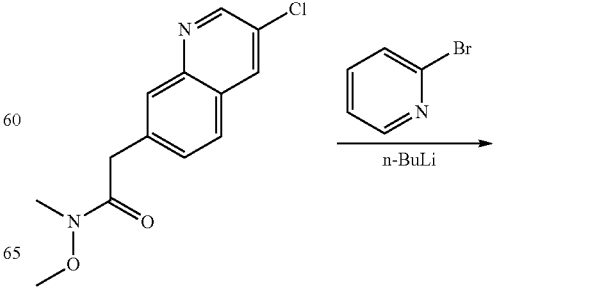

-continued

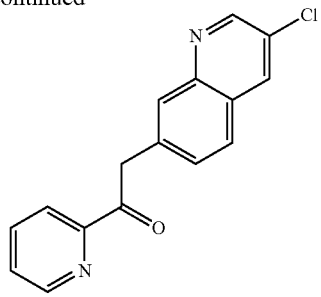

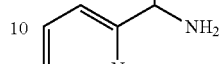

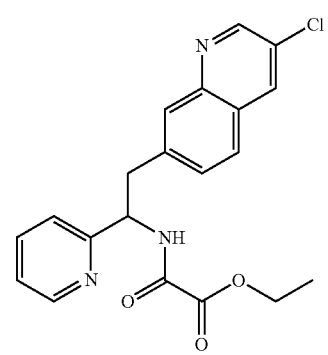

To a solution of 2-bromo-pyridine (859 mg, 5.44 mmol, 1.2 eq) in THF (40 mL) was added n-BuLi (2.2 mL, 5.44 mmol, 1.2 eq) at −78° C. The solution was stirred at −78° C. for 1 h. Then a solution of 2-(3-chloro-quinolin-7-yl)-N-methoxy-N-methyl-acetamide (1.2 g, 4.53 mmol, 1.0 eq) in THF (10 mL) was added at −78° C. The mixture was warmed to rt and stirred for 3 h. The reaction solution was quenched with NH4Cl aq. and extracted with EA (100 mL×2). The combined organic layers were dried over Na2SO4, filtered and concentrated. The resulting residue was purified by chromatography on silica gel column (PE/EA=4/1, v/v) to afford 2-(3-chloro-quinolin-7-yl)-1-pyridin-2-yl-ethanone (600 mg, 46%) as a colorless oil. LRMS (M+H+) m/z calculated 283.1, found 283.1.

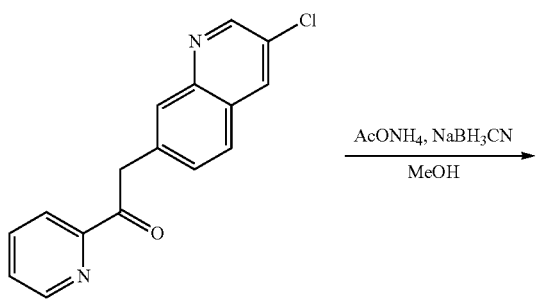

To a solution of 2-(3-chloro-quinolin-7-yl)-1-pyridin-2-yl-ethylamine (300 mg crude, 1.05 mmol, 1.0 eq) in DCM (20 mL) was added Et3N (318 mg, 3.15 mmol, 3.0 eq) and chloro-oxo-acetic acid ethyl ester (287 mg, 2.10 mmol, 2.0 eq) at 0° C. The solution was stirred at 0° C. for 2 h. The mixture was concentrated and the resulting residue was purified by chromatography on silica gel column (PE/EA=3/1, v/v) to afford N-[2-(3-chloro-quinolin-7-yl)-1-pyridin-2-yl-ethyl]-oxalamic acid ethyl ester (120 mg, 30%) as a colorless oil.

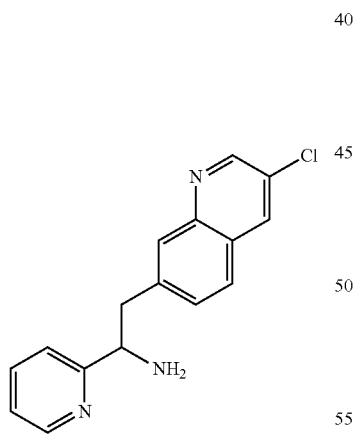

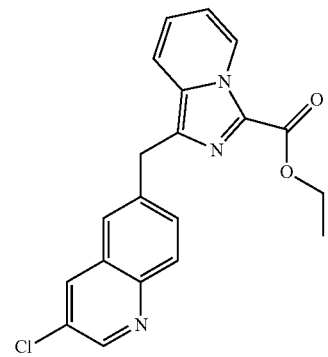

To a solution of 2-(3-chloro-quinolin-7-yl)-1-pyridin-2-yl-ethanone (300 mg, 1.06 mmol, 1.0 eq) in MeOH (30 mL) was added NH4OAc (1.6 g, 21.22 mmol, 20.0 eq) and NaBH3CN (99 mg, 1.59 mmol, 1.5 eq) at rt. The solution was stirred at rt overnight. Then DCM (100 mL) was added and the mixture was washed with water (20 mL×2). The organic layers were dried over Na2SO4, filtered and concentrated. The resulting residue (300 mg, crude) was used in next step directly without further purification. LRMS (M+H+) m/z calculated 284.1, found 284.1.

A mixture of N-[2-(3-chloro-quinolin-7-yl)-1-pyridin-2-yl-ethyl]-oxalamic acid ethyl ester (120 mg, 0.31 mmol, 1.0 eq) in POCl3 (4 mL) was stirred at 100° C. overnight. The mixture was concentrated and EA (50 mL) was added. The mixture was washed with NaHCO₃ aq. (10 mL×4). The organic layer was dried over Na2SO4, filtered and concentrated. The resulting residue was purified by chromatography on silica gel column (PE/EA=2/1, v/v) to afford 1-(3-chloro-quinolin-6-ylmethyl)-imidazo[1,5-a]pyridine-3-carboxylic acid ethyl ester (40 mg, 35%) as a white solid.

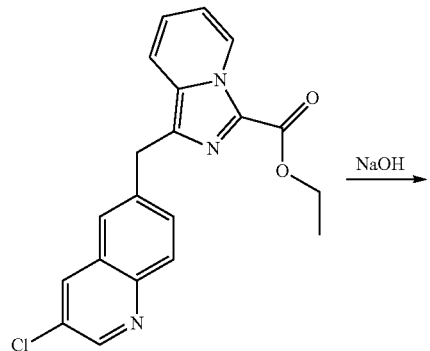

To a solution of 1-(3-chloro-quinolin-6-ylmethyl)-imidazo[1,5-a]pyridine-3-carboxylic acid ethyl ester (40 mg, 0.11 mmol, 1.0 eq) in THF (5 mL) was added a solution of NaOH (7.0 mg, 0.16 mmol, 1.5 eq) in water (5 mL) at rt. The solution was stirred at rt overnight. The reaction solution was neutralized with 1N HCl. The mixture was concentrated and the resulting residue (40 mg crude) was used in next step directly without further purification.

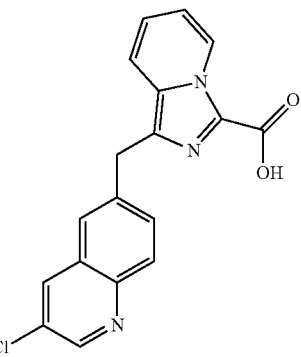

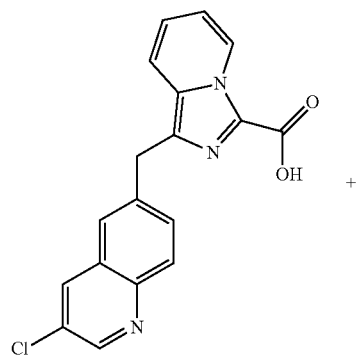

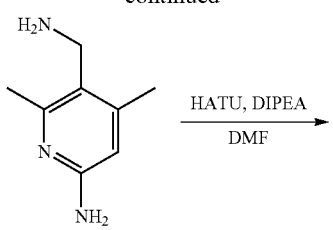

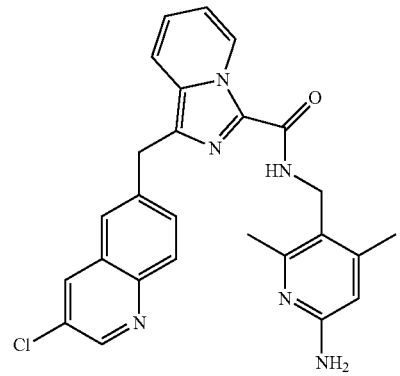

A mixture of 1-(3-Chloro-quinolin-6-ylmethyl)-imidazo[1,5-a]pyridine-3-carboxylic acid (40 mg, 0.12 mmol, 1.0 eq), 5-(aminomethyl)-4,6-dimethylpyridin-2-amine (27 mg, 0.18 mmol, 1.5 eq), HATU (68 mg, 0.18 mmol, 1.5 eq) and DIPEA (46 mg, 0.36 mmol, 3.0 eq) in DMF (2 mL) was stirred at rt for 2 h. The mixture was concentrated and the resulting residue was purified by prep-HPLC to afford N-((6-amino-2,4-dimethylpyridin-3-yl)methyl)-1-((3-chloroquinolin-6-yl)methyl)imidazo[1,5-a]pyridine-3-carboxamide (10.0 mg, 18%) as a white solid. LRMS (M+H+) m/z calculated 471.2, found 471.0. 1H NMR (DMSO-d6, 400 MHz): δ 9.35 (d, 1H), 8.80 (s, 1H), 8.47 (s, 1H), 8.17-8.15 (m, 1H), 7.93 (d, 1H), 7.77-7.76 (m, 2H), 7.69 (d, 1H), 7.03-6.92 (m, 2H), 6.09 (s, 1H), 5.62 (s, 2H), 4.45 (s, 2H), 4.39 (d, 2H), 2.34 (s, 3H), 2.21 (s, 3H).

Example 24: Preparation of 4-amino-N-((6-amino-2,4-dimethylpyridin-3-yl)methyl)-1-((3-chloroquinolin-6-yl)methyl)-1H-pyrazole-3-carboxamide

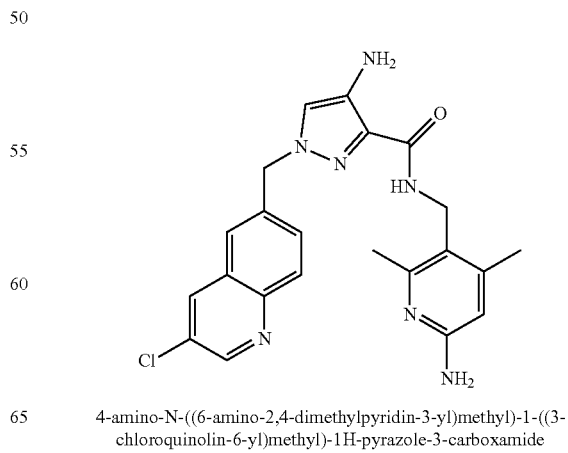

4-amino-N-((6-amino-2,4-dimethylpyridin-3-yl)methyl)-1-((3-chloroquinolin-6-yl)methyl)-1H-pyrazole-3-carboxamide -continued

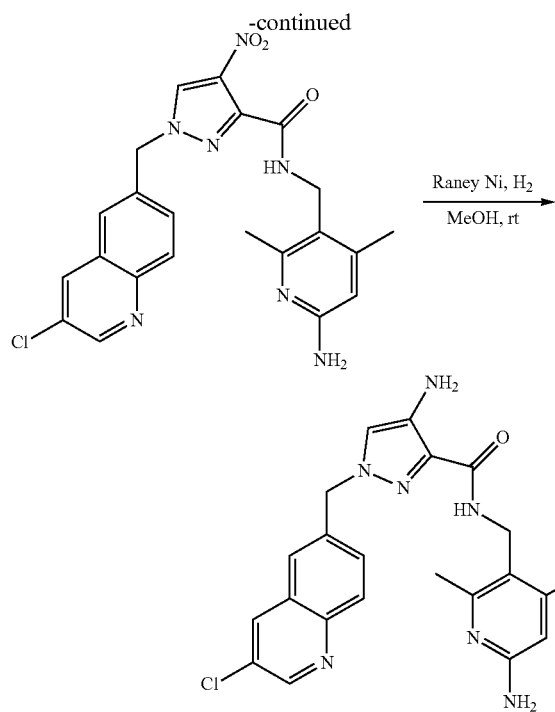

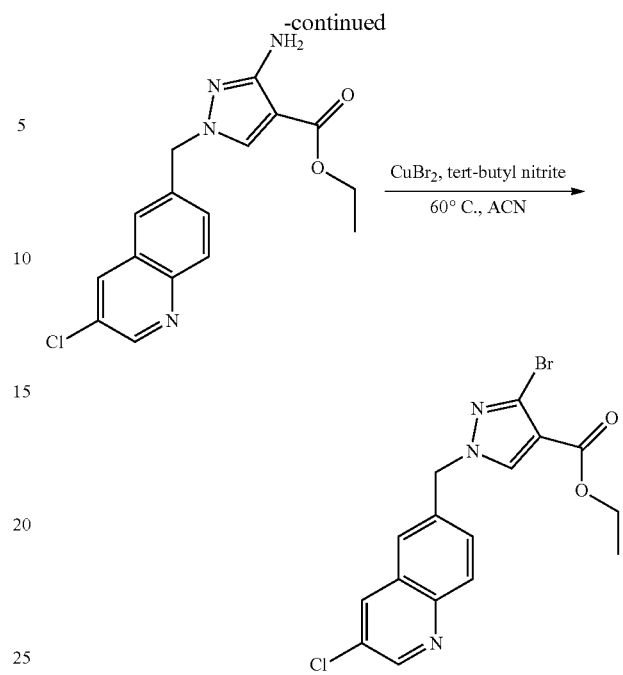

A mixture of N-((6-amino-2,4-dimethylpyridin-3-yl)methyl)-1-((3-chloroquinolin-6-yl)methyl)-4-nitro-1H-pyrazole-3-carboxamide4-nitro-1H-pyrazole-3-carboxylic acid ethyl ester (80 mg, 0.17 mmol, 1.0 eq) and Raney Ni (50 mg) in MeOH (10 mL) was stirred at rt under H2 atmosphere for 1 h. Raney Ni was removed by filtration and the filtrate was concentrated. The resulting residue was purified by Prep-HPLC to give 4-amino-N-((6-amino-2,4-dimethylpyridin-3-yl)methyl)-1-((3-chloroquinolin-6-yl)methyl)-1H-pyrazole-3-carboxamide (22 mg, 30%) as a white solid. LRMS (M+H+) m/z calculated 436.2, found 471.0. 1H NMR (DMSO-d6, 400 MHz): δ 8.86 (d, 1H), 8.56 (s, 1H), 8.01 (d, 1H), 7.76 (s, 1H), 7.62 (dd, 1H), 7.41 (t, 1H), 7.24 (s, 1H), 6.09 (s, 1H), 5.59 (s, 2H), 5.41 (s, 2H), 4.69 (s, 2H), 4.30 (d, 2H), 2.30 (s, 3H), 2.17 (s, 3H).

Example 25: Preparation of N-((6-amino-2,4-dimethylpyridin-3-yl)methyl)-1-((3-chloroquinolin-6-yl)methyl)-3-cyano-1H-pyrazole-4-carboxamide

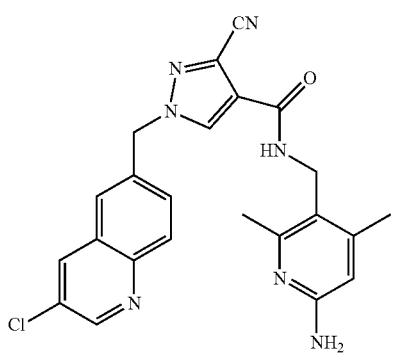

N-((6-amino-2,4-dimethylpyridin-3-yl)methyl)-1-((3-chloroquinolin-6-yl)methyl)-3-cyano-1H-pyrazole-4-carboxamide To a stirred mixture of 3-amino-1-(3-chloro-quinolin-6-ylmethyl)-1H-pyrazole-4-carboxylic acid ethyl ester (1.0 g, 3 mmol, 1 eq) and CuBr2 (1.34 g, 6 mmol, 2 eq) in dry ACN (40 mL) was added tert-butyl nitrite (0.47 g, 4.5 mmol, 1.5 eq) drop wise. Then the mixture was stirred at 60° C. for 4 h. The reaction was quenched with water and extracted with EA. The combined organic layers were dried and concentrated. The resulting residue was purified by chromatography on silica gel column (PE/EA=4/1, v/v) to afford 3-bromo-1-(3-chloro-quinolin-6-ylmethyl)-1H-pyrazole-4-carboxylic acid ethyl ester (400 mg, 37%) as a white solid.

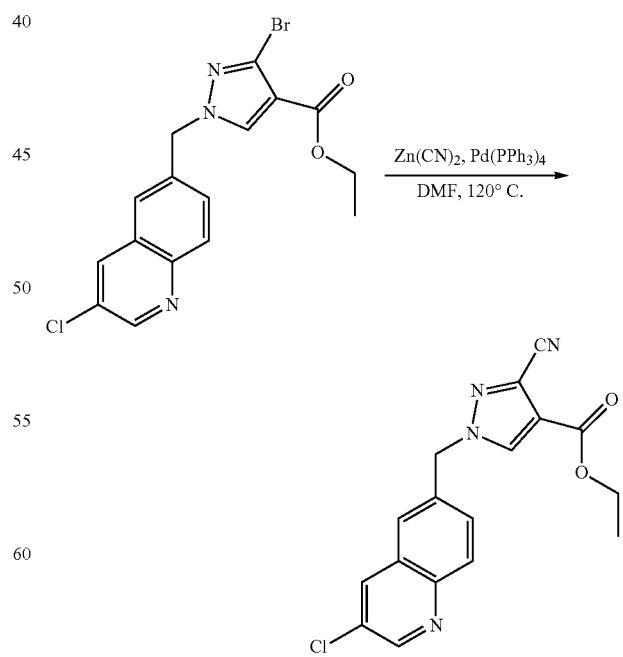

A mixture of 3-bromo-1-(3-chloro-quinolin-6-ylmethyl)-1H-pyrazole-4-carboxylic acid ethyl ester (100 mg, 0.25 mmol, 1 eq), Zn(CN)2 (70 mg, 0.63 mmol, 2.5 eq) and Pd(PPh3)4 (117 mg, 0.1 mmol, 0.4 eq) in DMF (15 mL) was stirred at 120° C. overnight. After cooling to rt, the mixture was concentrated, and the resulting residue was purified by chromatography on silica gel column (PE/EA=3/1, v/v) to afford 1-(3-chloro-quinolin-6-ylmethyl)-3-cyano-1H-pyrazole-4-carboxylic acid ethyl ester (12 mg, 15%) as a white solid.

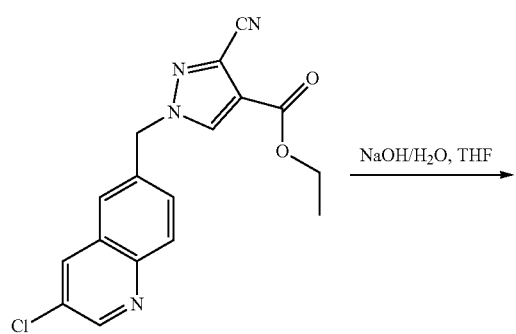

To a solution of 1-(3-chloro-quinolin-6-ylmethyl)-3-cyano-1H-pyrazole-4-carboxylic acid ethyl ester (100 mg, 0.29 mmol, 1.0 eq) in THF (5 mL) and H2O (2 mL) was added NaOH (40 mg, 1 mmol, 3.0 eq). The mixture was stirred at 60° C. for 4 h. THF was removed and the aqueous layer was adjusted with 6 N HCl to pH 1.0. The resulting precipitate was collected by filtered, washed with water and dried to give 1-(3-chloro-quinolin-6-ylmethyl)-3-cyano-1H-pyrazole-4-carboxylic acid (80 mg, 87%).

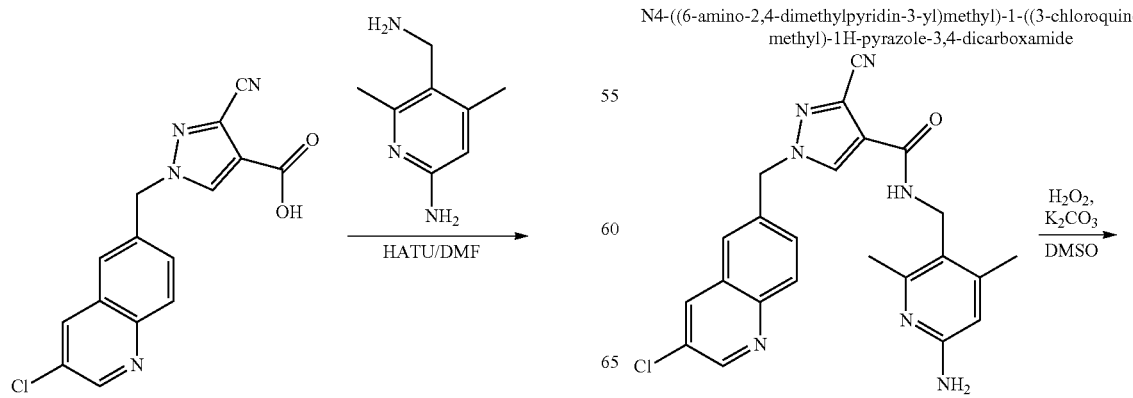

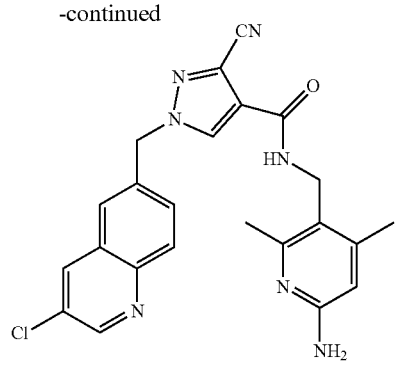

A mixture of 1-(3-chloro-quinolin-6-ylmethyl)-3-cyano-1H-pyrazole-4-carboxylic acid (80 mg, 0.25 mmol, 1.0 eq), 5-aminomethyl-4,6-dimethyl-pyridin-2-ylamine (57 mg, 0.30 mmol, 1.2 eq), HATU (143 mg, 0.38 mmol, 1.5 eq) and TEA (63 mg, 0.63 mmol, 2.5 eq) in DMF (2 mL) was stirred at rt for 5 h. The mixture was concentrated and the resulting residue was purified by prep-HPLC to afford N-((6-amino-2,4-dimethylpyridin-3-yl)methyl)-1-((3-chloroquinolin-6-yl)methyl)-3-cyano-1H-pyrazole-4-carboxamide (30 mg, 26%) as a white solid. LRMS (M+H+) m/z calculated 446.1, found 446.0. 1H NMR (DMSO-d6, 400 MHz): δ 8.90 (d, 1H), 8.61 (d, 1H), 8.57 (s, 1H), 8.24 (t, 1H), 8.06 (d, 1H), 7.86 (d, 1H), 7.70 (dd, 1H), 6.11 (s, 1H), 5.68 (s, 2H), 5.65 (s, 2H), 4.28 (d, 2H), 2.28 (s, 3H), 2.15 (s, 3H).

Example 26: Preparation of N4-((6-amino-2,4-dimethylpyridin-3-yl)methyl)-1-((3-chloroquinolin-6-yl)methyl)-1H-pyrazole-3,4-dicarboxamide

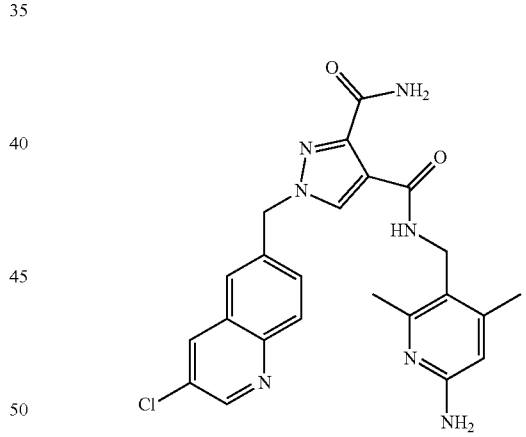

N4-((6-amino-2,4-dimethylpyridin-3-yl)methyl)-1-((3-chloroquinolin-6-yl)methyl)-1H-pyrazole-3,4-dicarboxamide

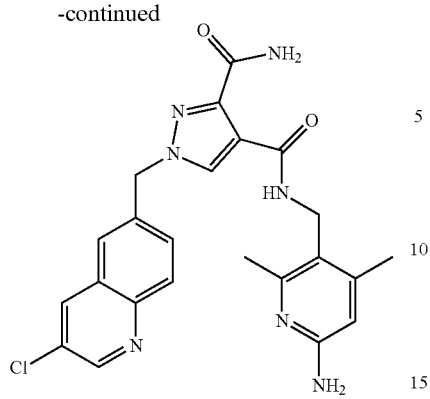

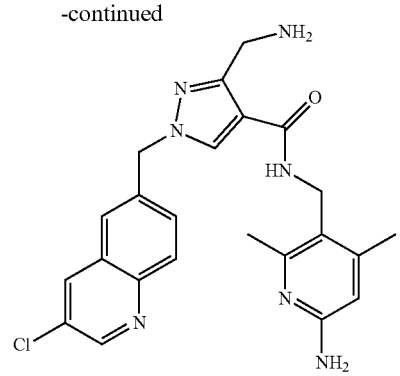

A mixture of N-((6-amino-2,4-dimethylpyridin-3-yl)methyl)-1-((3-chloroquinolin-6-yl)methyl)-3-cyano-1H-pyrazole-4-carboxamide (80 mg, 0.18 mmol, 1.0 eq), H2O2 (2 mL) and K2CO3 (37.2 mg, 0.27 mmol, 1.5 eq) in DMSO (4 mL) was stirred at rt 40 min. Then the mixture was filtered and the filtrate was concentrated. The resulting residue was purified by prep-HPLC to afford N4-((6-amino-2,4-dimethylpyridin-3-yl)methyl)-1-((3-chloroquinolin-6-yl)methyl)-1H-pyrazole-3,4-dicarboxamide (25.4 mg, 30%) as a white solid. LRMS (M+H+) m/z calculated 464.2, found 464.0. 1H NMR (DMSO-d6, 400 MHz): δ 10.58 (t, 1H), 8.88 (d, 1H), 8.58 (d, 1H), 8.50 (s, 1H), 8.05 (d, 1H), 7.98 (s, 1H), 7.78 (s, 2H), 7.71 (d, 1H), 6.10 (s, 1H), 5.65 (s, 4H), 4.32 (d, 2H), 2.32 (s, 3H), 2.20 (s, 3H).

A mixture of N-((6-amino-2,4-dimethylpyridin-3-yl)methyl)-1-((3-chloroquinolin-6-yl)methyl)-3-cyano-1H-pyrazole-4-carboxamide (50 mg, 0.11 mmol, 1.0 eq), Et3N (11 mg, 0.11 mmol, 1.0 eq) and Raney Ni (50 mg) in NH3.H2O (3 mL) and MeOH (6 mL) was stirred under H2 atmosphere at rt for 12 h. Raney Ni was removed by filtration and the filtrate was concentrated. The resulting residue was purified by prep-HPLC to give N-((6-amino-2,4-dimethylpyridin-3-yl)methyl)-3-(aminomethyl)-1-((3-chloroquinolin-6-yl)methyl)-1H-pyrazole-4-carboxamide (4.9 mg, 9%) as a white solid. LRMS (M+H+) m/z calculated 450.2, found 450.0. 1H NMR (DMSO-d6, 400 MHz): δ 10.58 (t, 1H), 8.88 (d, 1H), 8.58 (d, 1H), 8.50 (s, 1H), 8.05 (d, 1H), 7.98 (s, 1H), 7.78 (s, 2H), 7.71 (d, 1H), 6.10 (s, 1H), 5.65 (s, 4H), 4.32 (d, 2H), 2.32 (s, 3H), 2.20 (s, 3H).

Example 27: Preparation of N-((6-amino-2,4-dimethylpyridin-3-yl)methyl)-3-(aminomethyl)-1-((3-chloroquinolin-6-yl)methyl)-1H-pyrazole-4-carboxamide Example 28: Preparation of 2-amino-N-((6-amino-2,4-dimethylpyridin-3-yl)methyl)-1-((3-chloroquinolin-6-yl)methyl)-1H-imidazole-4-carboxamide

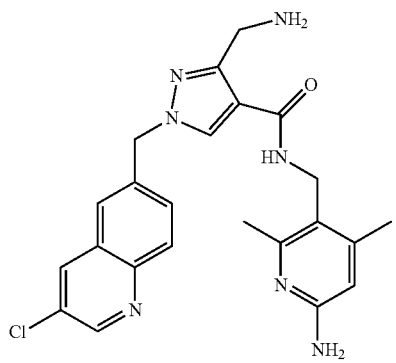

N-((6-amino-2,4-dimethylpyridin-3-yl)methyl)-3-(aminomethyl)-1-((3-chloroquinolin-6-yl)methyl)-1H-pyrazole-4-carboxamide

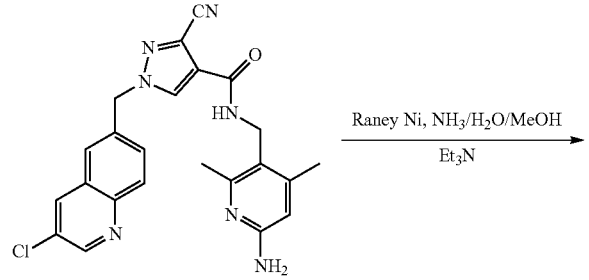

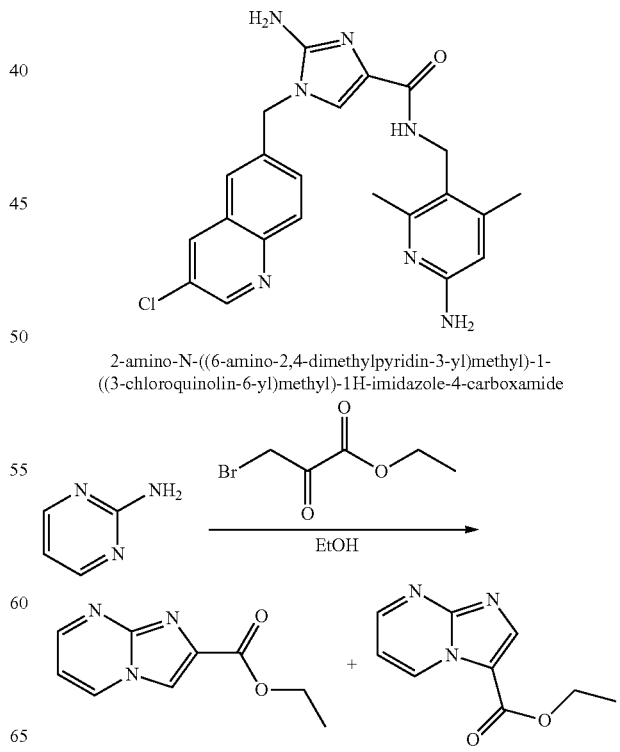

2-amino-N-((6-amino-2,4-dimethylpyridin-3-yl)methyl)-1-((3-chloroquinolin-6-yl)methyl)-1H-imidazole-4-carboxamide A mixture of pyrimidin-2-ylamine (2.0 g, 21.1 mmol, 1.0 eq) and 3-bromo-2-oxo-propionic acid ethyl ester (5.13 g, 21.1 mmol, 1.0 eq) in EtOH (30 mL) was stirred at 75° C. overnight. The reaction mixture was concentrated and the resulting residue was purified by chromatography on a silica gel column (DCM/MeOH=20/1, v/v) to give a mixture of imidazo[1,2-a]pyrimidine-2-carboxylic acid ethyl ester and imidazo[1,2-a]pyrimidine-3-carboxylic acid ethyl ester (3.05 g, 76%0) as a yellow solid.

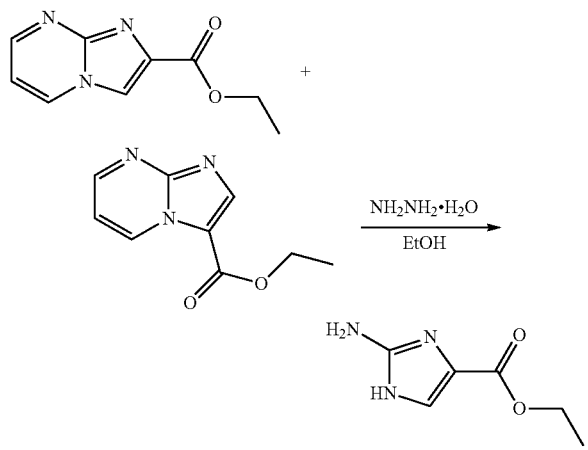

To a mixture of imidazo[1,2-a]pyrimidine-2-carboxylic acid ethyl ester and imidazo[1,2-a]pyrimidine-3-carboxylic acid ethyl ester (500 mg, 2.62 mmol, 1.0 eq) in EtOH (20 mL) was added hydrazine hydrate (180 mg, 2.88 mmol, 1.1 eq). The reaction mixture was heated at 75° C. overnight. The reaction mixture was concentrated and the resulting residue was purified by chromatography on a silica gel column (DCM/MeOH=20/1, v/v) to give 2-amino-1H-imidazole-4-carboxylic acid ethyl ester (220 mg, 54%) as a yellow solid.

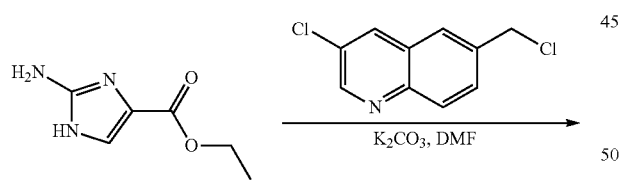

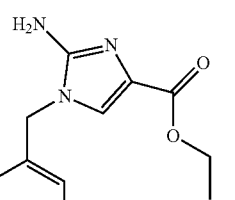

-continued

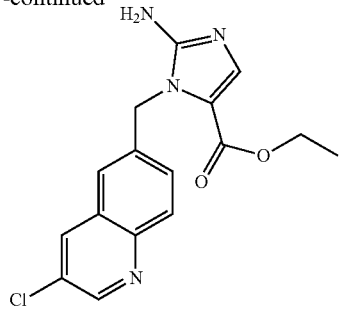

The mixture of 2-amino-1H-imidazole-4-carboxylic acid ethyl ester (220 mg, 1.42 mmol, 1.0 eq), 3-chloro-6-chloromethyl-quinoline (301 mg, 1.42 mmol, 1.0 eq) and K2CO3 (294 mg, 2.13 mmol, 1.5 eq) in DMF (8 mL) was stirred at 50° C. overnight. The reaction mixture was diluted with water and extracted with EA. The combined organic layers was dried and concentrated. The resulting residue was purified by chromatography on a silica gel column (DCM/MeOH=20/1, v/v) to give 2-amino-1-(3-chloro-quinolin-6-ylmethyl)-1H-imidazole-4-carboxylic acid ethyl ester (100 mg, 21%) and 2-amino-3-(3-chloro-quinolin-6-ylmethyl)-3H-imidazole-4-carboxylic acid ethyl ester (120 mg, 26%) as a yellow solid.

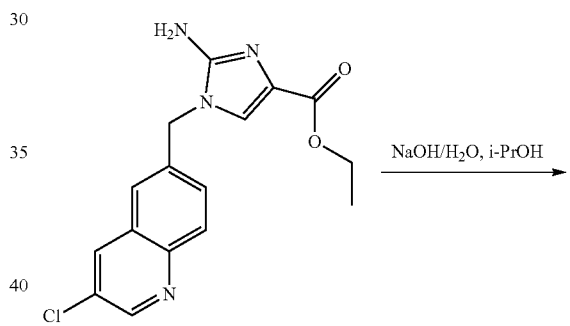

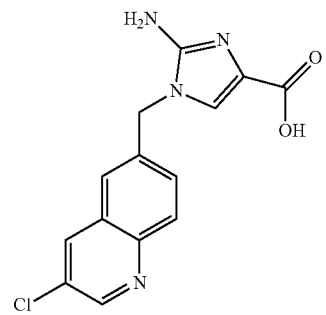

To a solution of 2-amino-1-(3-chloro-quinolin-6-ylmethyl)-1H-imidazole-4-carboxylic acid ethyl ester (300 mg, 0.91 mmol, 1.0 eq) in isopropyl alcohol (20 mL) and H2O (10 mL) was added NaOH (364 mg, 9.1 mmol, 10.0 eq). The reaction mixture was stirred at 85° C. for 3 h. The reaction mixture was acidified to pH 1 with 2 N HCl. The mixture was concentrated to give 2-amino-1-(3-chloro-quinolin-6-ylmethyl)-1H-imidazole-4-carboxylic acid (270 mg, 98%), which was used directly without further purification.

Example 29: Preparation of N-((6-amino-2,4-dimethylpyridin-3-yl)methyl)-2-((3-chloroquinolin-6-yl)methyl)oxazole-4-carboxamide

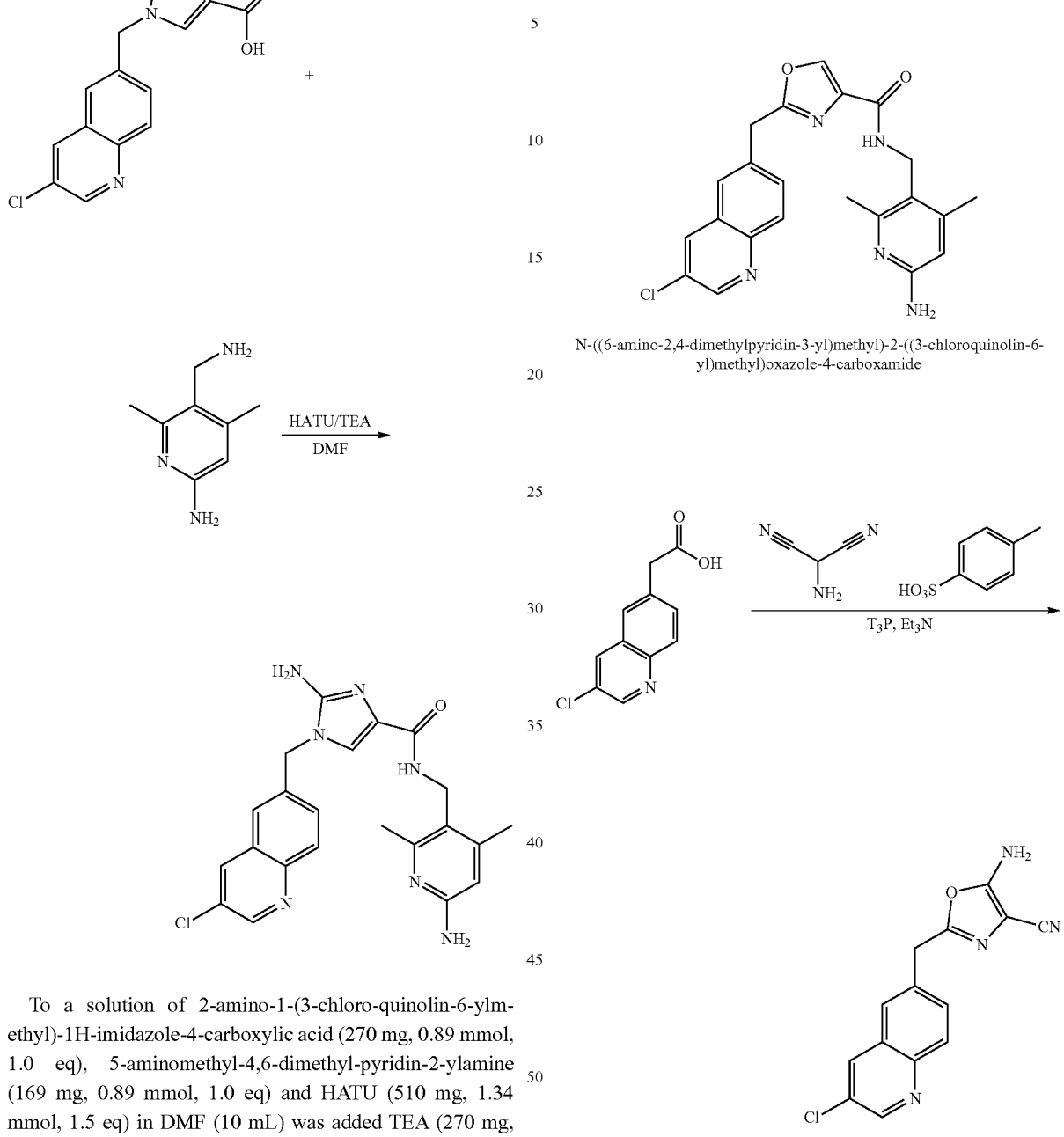

N-((6-amino-2,4-dimethylpyridin-3-yl)methyl)-2-((3-chloroquinolin-6-yl)methyl)oxazole-4-carboxamide To a solution of 2-amino-1-(3-chloro-quinolin-6-ylmethyl)-1H-imidazole-4-carboxylic acid (270 mg, 0.89 mmol, 1.0 eq), 5-aminomethyl-4,6-dimethyl-pyridin-2-ylamine (169 mg, 0.89 mmol, 1.0 eq) and HATU (510 mg, 1.34 mmol, 1.5 eq) in DMF (10 mL) was added TEA (270 mg, 2.68 mmol, 3.0 eq) at 0° C. under N2. The reaction mixture was stirred at rt overnight. The reaction mixture was diluted with H2O and extracted with EA. The combined organic layers were dried and concentrated. The resulting residue was purified by prep-HPLC to give 2-amino-1-(3-chloro-quinolin-6-ylmethyl)-1H-imidazole-4-carboxylic acid (6-amino-2,4-dimethyl-pyridin-3-ylmethyl)-amide (30 mg, 7.7%) as a white solid. LRMS (M+H+) m/z calculated 436.2, found 436.0. 1H NMR (DMSO-d6, 400 MHz): δ 8.86 (s, 1H), 8.56 (s, 1H), 8.04 (d, 1H), 7.71 (s, 1H), 7.64 (d, 1H), 7.22 (s, 1H), 6.96 (s, 1H), 6.10 (s, 1H), 5.74 (s, 2H), 5.64 (s, 2H), 5.20 (s, 2H), 4.26 (d, 2H), 2.29 (s, 3H), 2.16 (s, 3H).

A mixture of (3-chloro-quinolin-6-yl)-acetic acid (3.3 g, 0.015 mol, 1.0 eq), 2-aminopropanedinitrile,4-methylbenzenesulfonic acid (4.6 g, 0.018 mol, 1.2 eq), T3P (9.5 g, 0.03 mol, 2.0 eq) and Et3N (3.0 g, 0.03 mol, 2.0 eq) in DMF was stirred at rt overnight. The solvent was removed by evaporation, and the resulting residue was diluted with DCM (600 mL) and washed with water (150 mL×2). The organic layer was dried and concentrated. The resulting residue was triturated with 100 mL of PE/EA (1/1, v/v), filtered, and dried to give 5-amino-2-((3-chloro-quinolin-6-yl)methyl)-oxazole-4-carbonitrile (2.4 g, 56%) as a white solid.

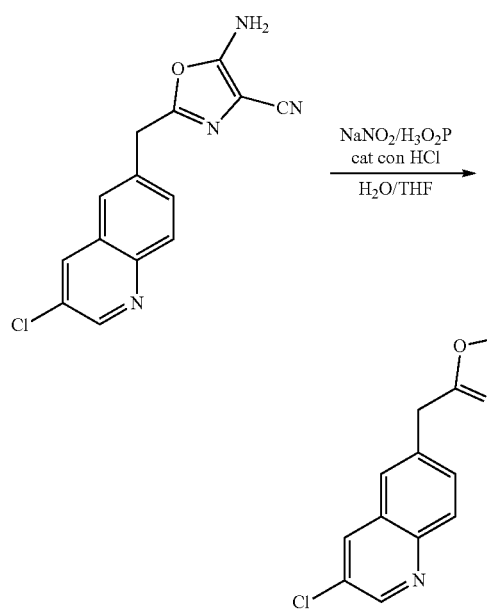

A solution of 5-amino-2-((3-chloro-quinolin-6-yl)methyl)-oxazole-4-carbonitrile (0.8 g, 2.81 mmol, 1.0 eq) in THF (40 mL) was added to a pre-cooled (−20° C.) and stirred solution of hypophosphorous acid (50%, 12 mL) containing a few drops of hydrochloric acid. To the above clear solution was added a solution of NaNO2 (0.97 g, 14.1 mmol, 5.0 eq) in water (10 mL) slowly, then the stirring was continued for 4 h at −20° C. The reaction solution was adjusted to pH 6 by careful addition of 10% aqueous NaOH. The final reaction mixture was extracted with EA and dried, concentrated and the crude residue was purified by chromatography on a silica gel column (PE/EA=9/1 to 4/1, v/v) to give 2-((3-chloro-quinolin-6-yl)methyl)-oxazole-4-carbonitrile (200 mg, 26.5%) as a white solid.

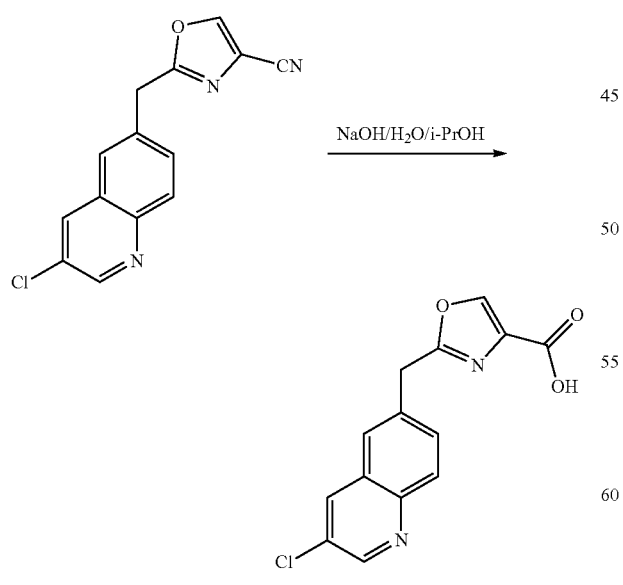

A mixture of 2-(3-chloro-quinolin-6-ylmethyl)-oxazole-4-carbonitrile (54 mg, 0.2 mmol, 1.0 eq), and NaOH (48 mg, 1.2 mmol, 6 eq) in H2O (1 mL) and i-PrOH (5 mL) was stirred under refluxing overnight. i-PrOH was removed and the resulting residue was adjusted to pH 2 with 1 N HCl. The resulting precipitate was filtered and dried to give 2-((3-chloro-quinolin-6-yl)methyl)-oxazole-4-carboxylic acid (41 mg, 72%) as a gray solid.

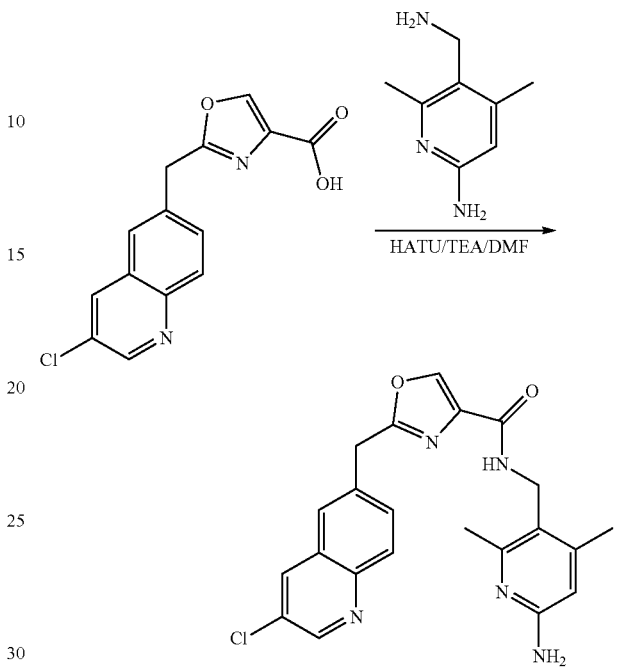

To a mixture of 2-((3-chloro-quinolin-6-yl)methyl)-oxazole-4-carboxylic acid (41 mg, 0.14 mmol, 1.0 eq), 5-aminomethyl-4,6-dimethyl-pyridin-2-ylamine (25 mg, 0.11 mmol, 0.8 eq), and HATU (46 mg, 0.12 mmol, 0.86 eq) in DMF was added TEA (30 mg, 0.3 mmol, 2.1 eq). The reaction mixture was stirred at rt overnight. DMF was removed by evaporation. The resulting residue was diluted with DCM. The combined organic layers were washed with sat aq NH4Cl, dried and concentrated. The resulting residue was purified by pre-HPLC to give N-((6-amino-2,4-dimethylpyridin-3-yl)methyl)-2-((3-chloroquinolin-6-yl)methyl)oxazole-4-carboxamide (10 mg, 17%) as a white solid. LRMS (M+H+) m/z calculated 422.1, found 422.0. 1H NMR (DMSO-d6, 400 MHz): δ 8.86 (d, 1H), 8.54 (t, 2H), 7.98-8.03 (m, 2H), 7.86 (s, 1H), 7.71-7.73 (m, 1H), 6.11 (s, 1H), 5.67 (s, 2H), 4.40 (s, 2H), 4.31 (s, 2H), 2.30 (s, 3H), 2.17 (s, 3H).

Example 30: Preparation of N-((6-amino-2,4-dimethylpyridin-3-yl)methyl)-5-((3-chloroquinolin-6-yl)methyl)-1,3,4-oxadiazole-2-carboxamide N-((6-amino-2,4-dimethylpyridin-3-yl)methyl)-5-((3-chloroquinolin-6-yl)methyl)-1,3,4-oxadiazole-2-carboxamide -continued

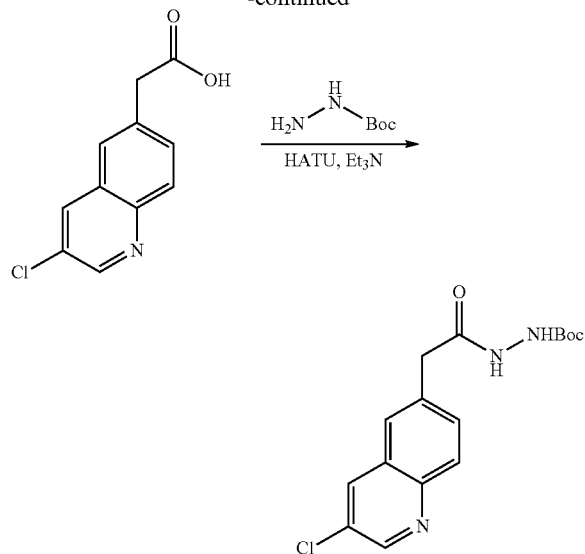

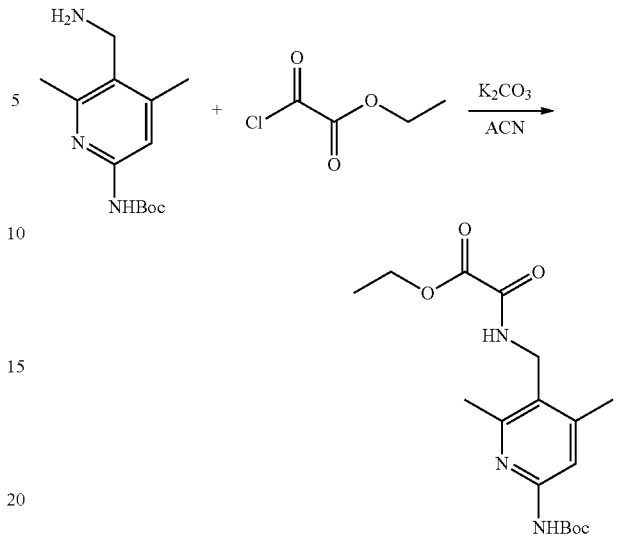

A mixture of (3-chloro-quinolin-6-yl)-acetic acid (1.0 g, 4.51 mmol, 1.0 eq), hydrazinecarboxylic acid tert-butyl ester (894 mg, 6.77 mmol, 1.5 eq), HATU (2.6 g, 6.77 mmol, 1.5 eq) and Et3N (1.4 g, 13.53 mmol, 3.0 eq) in DMF (20 mL) was stirred at rt overnight. Water (50 mL) was added. The resulting precipitate was filtered and dried in vacuo to afford N'-[2-(3-chloro-quinolin-6-yl)-acetyl]-hydrazinecarboxylic acid tert-butyl ester (1.3 g, crude) as a white solid.

To a solution of (5-aminomethyl-4,6-dimethyl-pyridin-2-yl)-carbamic acid tert-butyl ester (251 mg, 1.0 mmol, 1.0 eq) and K2CO3 (414 mg, 3.0 mmol, 3.0 eq) in ACN (20 mL) was added chloro-oxo-acetic acid ethyl ester (164 mg, 1.2 mmol, 1.2 eq) at 0° C. The solution was stirred at rt overnight. The reaction solution was concentrated and the resulting residue was purified by chromatography on a silica gel column (PE/EA=3/1, v/v) to afford N-(6-tert-Butoxycarbonylamino-2,4-dimethyl-pyridin-3-ylmethyl)-oxalamic acid ethyl ester (300 mg, 85%) as a white solid.

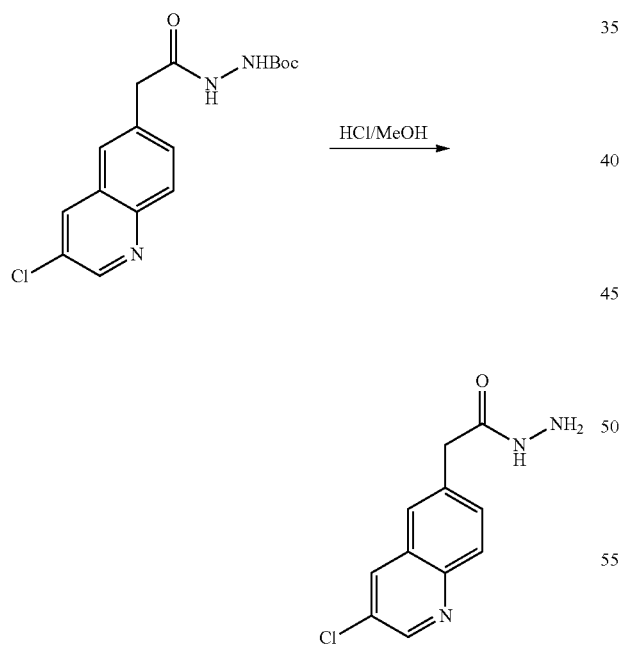

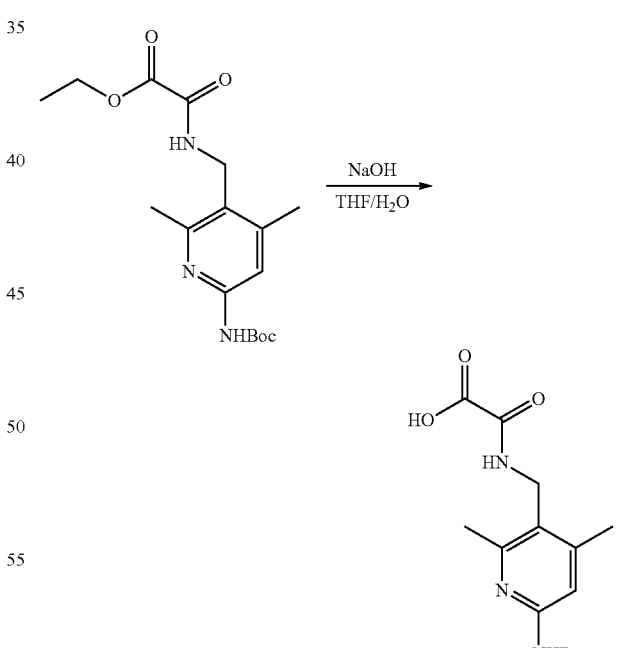

To a solution of N'-[2-(3-chloro-quinolin-6-yl)-acetyl]-hydrazinecarboxylic acid tert-butyl ester (1.3 g, 3.87 mmol, 1.0 eq) in MeOH (20 mL) was added HCl/MeOH (20 mL) at rt. The solution was stirred at rt overnight. The resulting precipitate was filtered and dried in vacuo to afford (3-chloro-quinolin-6-yl)-acetic acid hydrazide (1.0 g, 95%) as a white solid.

To a solution of N-(6-tert-butoxycarbonylamino-2,4-dimethyl-pyridin-3-ylmethyl)-oxalamic acid ethyl ester (300 mg, 0.85 mmol, 1.0 eq) in THF (20 mL) was added a solution of NaOH (51.0 mg, 1.28 mmol, 1.5 eq) in water (20 mL) at rt. The solution was stirred at rt for 2 h. The reaction solution was neutralized with 1 N HCl and extracted with EA (30 mL×3). The combined organic layers were dried over Na2SO4, filtered and concentrated. The resulting residue was used in next step directly without further purification (250 mg, 91%) as a white solid.

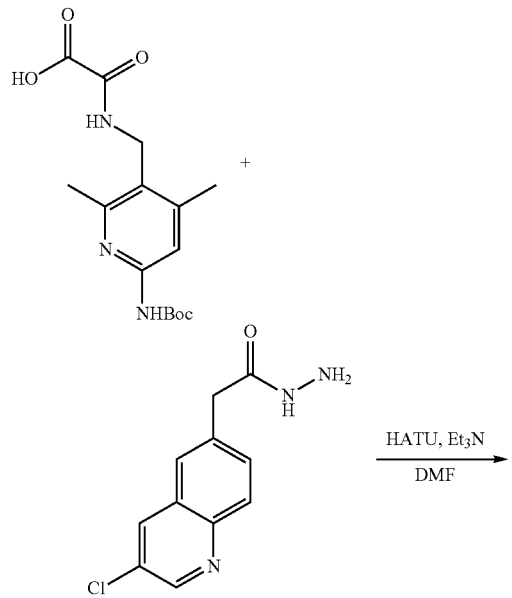

A mixture of N-(6-tert-butoxycarbonylamino-2,4-dimethyl-pyridin-3-ylmethyl)-oxalamic acid (350 mg, 1.08 mmol, 1.0 eq), (3-chloro-quinolin-6-yl)-acetic acid hydrazide (306 mg, 1.29 mmol, 1.5 eq), HATU (615 mg, 1.62 mmol, 1.5 eq) and Et3N (327 mg, 3.24 mmol, 3.0 eq) in DMF (10 mL) was stirred at rt for 2 h. The mixture was concentrated and the resulting residue was purified by chromatography on a silica gel column (PE/EA=2/1, v/v) to EA to afford {5-[({N'-[2-(3-chloro-quinolin-6-yl)-acetyl]-hydrazinooxalyl}-amino)-methyl]-4,6-dimethyl-pyridin-2-yl}-carbamic acid tert-butyl ester (250 mg, 43%) as a white solid.

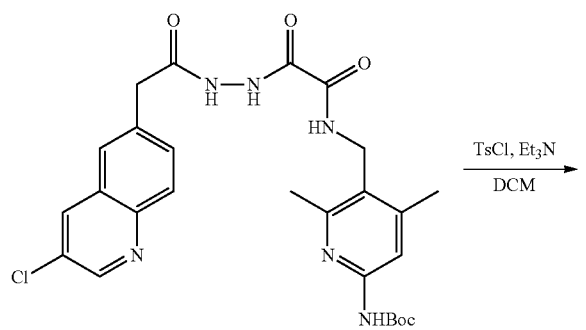

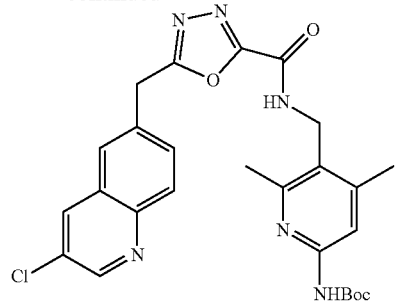

To a solution of {5-[({N'-[2-(3-chloro-quinolin-6-yl)-acetyl]-hydrazinooxalyl}-amino)-methyl]-4,6-dimethyl-pyridin-2-yl}-carbamic acid tert-butyl ester (250 mg, 0.46 mmol, 1.0 eq) and Et3N (60 mg, 0.60 mmol, 1.3 eq) in DCM (20 mL) was added TsCl (105 mg, 0.55 mmol, 1.2 eq) at rt. The solution was stirred at rt overnight. The reaction solution was concentrated and the resulting residue was purified by chromatography on a silica gel column (PE/EA=1/1, v/v) to afford [5-({[5-(3-chloro-quinolin-6-ylmethyl)-[1,3,4]oxadiazole-2-carbonyl]-amino}-methyl)-4,6-dimethyl-pyridin-2-yl]-carbamic acid tert-butyl ester (120 mg, 48%) as a white solid.

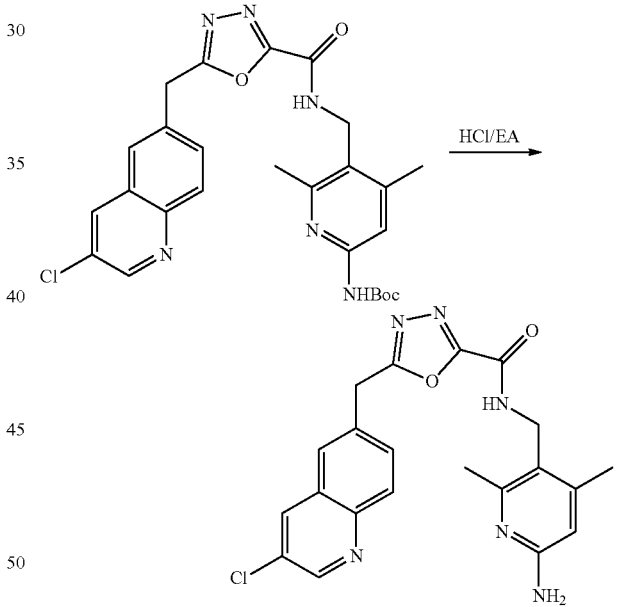

To a solution of [5-({[5-(3-chloro-quinolin-6-ylmethyl)-[1,3,4]oxadiazole-2-carbonyl]-amino}-methyl)-4,6-dimethyl-pyridin-2-yl]-carbamic acid tert-butyl ester (20 mg, 0.04 mmol, 1.0 eq) in EA (5 mL) was added HCl/EA (10 mL) at rt. The solution was stirred at rt overnight. The mixture was concentrated and the resulting residue was purified by prep-HPLC to afford N-((6-amino-2,4-dimethylpyridin-3-yl)methyl)-5-((3-chloroquinolin-6-yl)methyl)-1,3,4-oxadiazole-2-carboxamide (4.0 mg, 23%) as a white solid. LRMS (M+H+) m/z calculated 423.1, found 423.0. 1H NMR (DMSO-d6, 400 MHz): δ 9.31-9.29 (m, 1H), 8.88 (d, 1H), 8.56 (d, 1H), 8.05 (d, 1H), 7.93 (s, 1H), 7.78-7.76 (m, 1H), 6.09 (s, 1H), 5.66 (s, 2H), 4.59 (s, 2H), 4.33 (d, 2H), 2.28 (s, 3H), 2.16 (s, 3H).

Example 31: Preparation of N-((6-amino-2,4-dimethylpyridin-3-yl)methyl)-5-((3-chloroquinolin-6-yl)methyl)oxazole-2-carboxamide

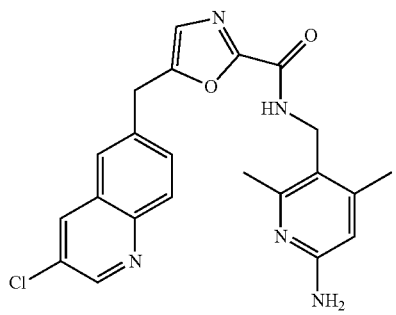

N-((6-amino-2,4-dimethylpyridin-3-yl)methyl)-5-((3-chloroquinolin-6-yl)methyl)oxazole-2-carboxamide

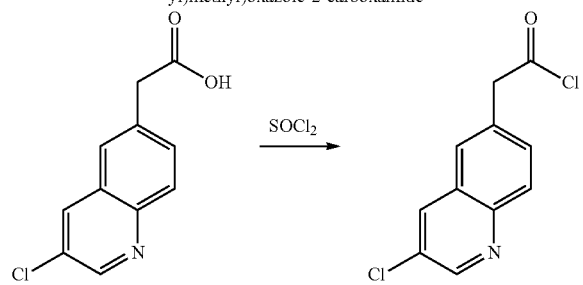

A mixture of (3-chloro-quinolin-6-yl)-acetic acid (3.0 g, 13.53 mmol, 1.0 eq) in SOCl2 (20 mL) was stirred at rt for 1 h. The mixture was concentrated, and the resulting residue was used in the next step directly without further purification (3.2 g, crude).

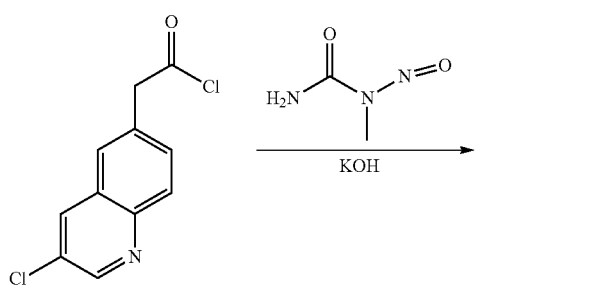

To a solution of KOH (4.9 g, 87.94 mmol, 6.5 eq) in water (50 mL) and Et2O (200 mL) was added 1-ethyl-1-nitrosourea (8.4 g, 81.21 mmol, 6.0 eq) at 0° C. The solution was stirred at 0° C.° C. for 30 min. The organic layer was separated and dried over Na2SO4.

To a solution of (3-chloro-quinolin-6-yl)-acetyl chloride (3.2 g crude, 13.53 mmol, 1.0 eq) in THF (100 mL) was added the above Et2O solution at 0° C. The solution was stirred at 0° C.° C. for 2 h. The reaction solution was concentrated, and the resulting residue was purified by chromatography on a silica gel column (PE/EA=4/1, v/v) to afford 1-(3-chloro-quinolin-6-yl)-3-diazo-propan-2-one (2.5 g, 76%) as a white solid.

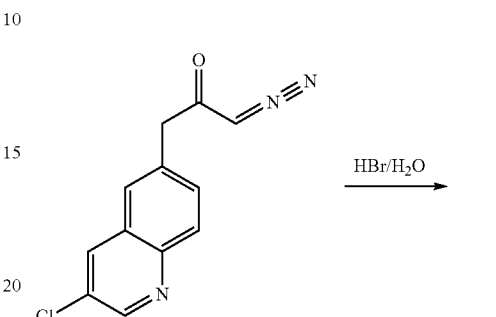

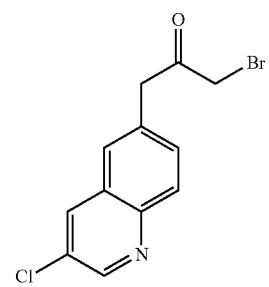

To a solution of 1-(3-chloro-quinolin-6-yl)-3-diazo-propan-2-one (2.5 g, 10.18 mmol, 1.0 eq) in THF (100 mL) was added HBr (6 mL) at 0° C. The solution was stirred at 0° C. for 2 h. The reaction solution was neutralized with aq. NaHCO3 and extracted with EA (100 mL×2). The organic layers were dried over Na2SO4, filtered and concentrated. The resulting residue was purified by chromatography on silica gel column (PE/EA=6/1, v/v) to afford 1-bromo-3-(3-chloro-quinolin-6-yl)-propan-2-one (2.0 g, 67%) as a yellow solid.

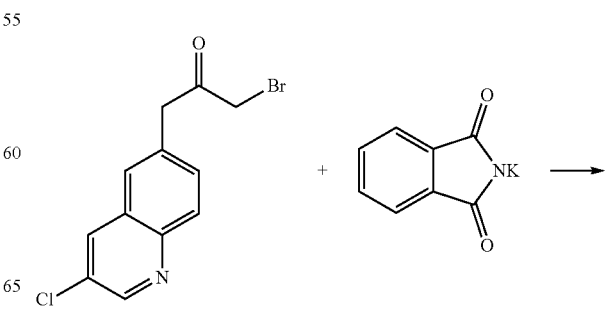

-continued

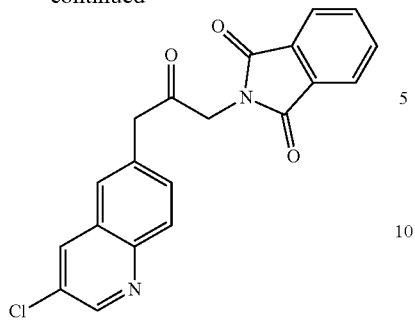

To a solution of 1-bromo-3-(3-chloro-quinolin-6-yl)-propan-2-one (600 mg, 2.01 mmol, 1.0 eq) in acetonitrile (20 mL) was added potassium phthalimide (409 mg, 2.21 mmol, 1.1 eq) at rt. The solution was stirred at rt for 2 h. The reaction solution was filtered and the solid was dried in vacuo to afford 2-[3-(3-chloro-quinolin-6-yl)-2-oxo-propyl]-isoindole-1,3-dione (570 mg, crude) as a brown solid.

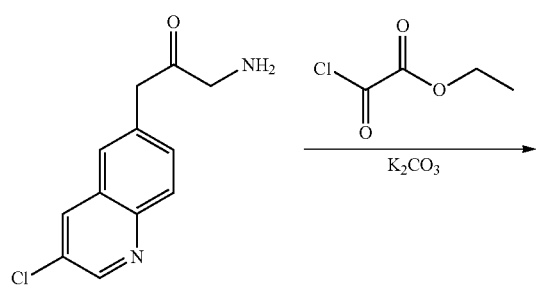

A solution of 2-[3-(3-chloro-quinolin-6-yl)-2-oxo-propyl]-isoindole-1,3-dione (600 mg, 2.01 mmol, 1.0 eq) in conc. HCl (20 mL) was stirred at 100° C. overnight. The reaction solution was concentrated. The resulting residue was used in the next step directly without further purification (600 mg, crude).

-continued

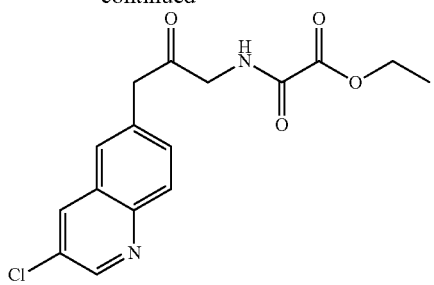

To a solution of 1-amino-3-(3-chloro-quinolin-6-yl)-propan-2-one (600 mg crude, 2.21 mmol, 1.0 eq) and K2CO3 (915 mg, 6.63 mmol, 3.0 eq) in acetonitrile (20 mL) was added chloro-oxo-acetic acid ethyl ester (362 mg, 2.66 mmol, 1.2 eq) at 0° C. The solution was stirred at 0° C. for 2 h. The mixture was filtered and the filtrate was concentrated. The resulting residue was purified by chromatography on a silica gel column (PE/EA=3/1, v/v) to afford N-[3-(3-chloro-quinolin-6-yl)-2-oxo-propyl]-oxalamic acid ethyl ester (120 mg, 16%) as a yellow solid.

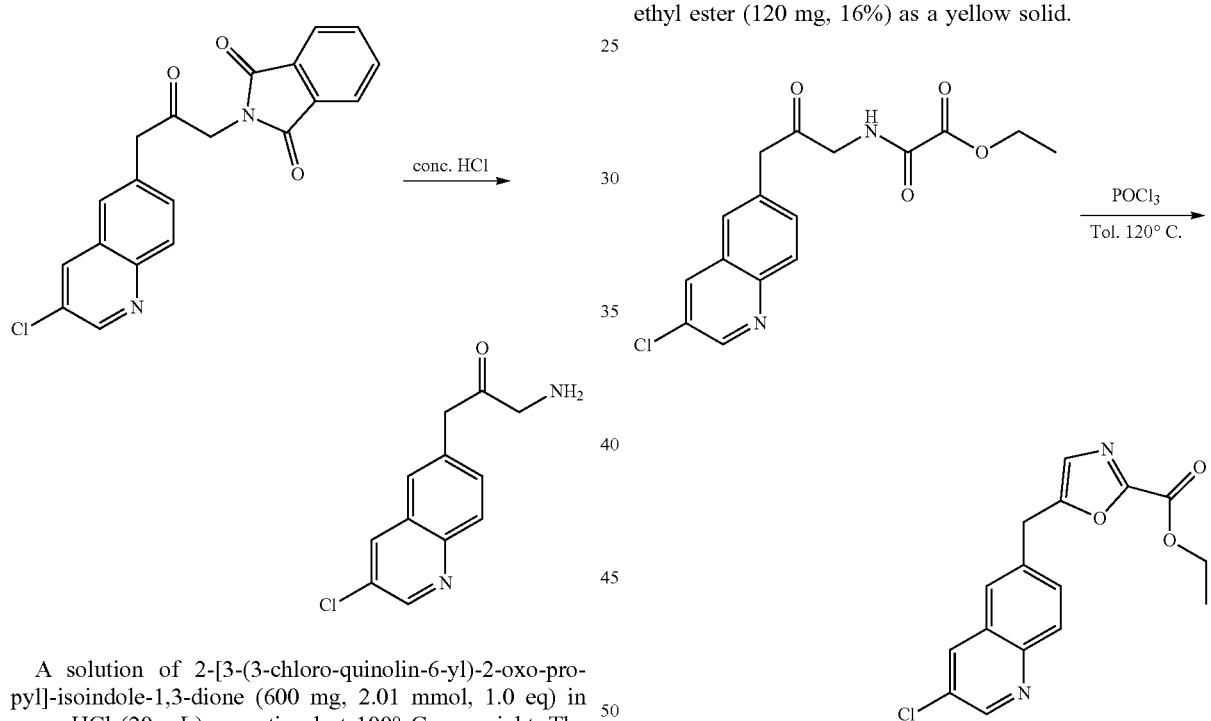

To a solution of N-[3-(3-chloro-quinolin-6-yl)-2-oxo-propyl]-oxalamic acid ethyl ester (120 mg, 0.36 mmol, 1.0 eq) in toluene (20 mL) was added POCl3 (110 mg, 0.72 mmol, 2.0 eq) at 0° C. The solution was stirred at 120° C. for 2 h. The mixture was concentrated. Then NaHCO3 aq. was added and extracted with EA (30 mL×3). The organic layers were dried over Na2SO4, filtered and concentrated. The resulting residue was purified by chromatography on silica gel column (PE/EA=3/1, v/v) to afford 5-(3-chloro-quinolin-6-ylmethyl)-oxazole-2-carboxylic acid ethyl ester (90 mg, 79%) as a white solid.

199

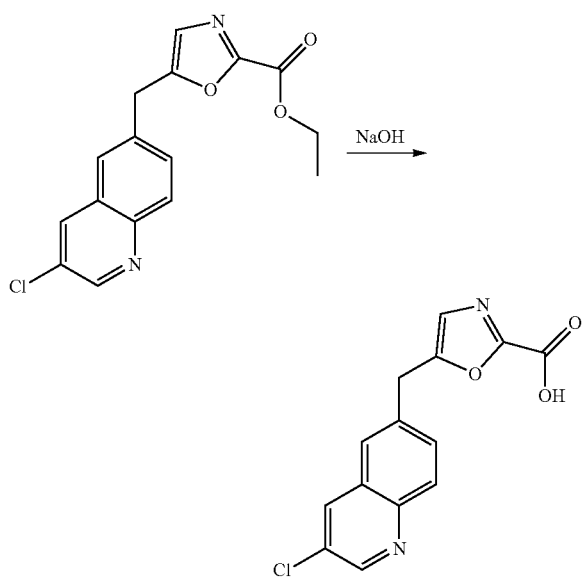

To a solution of 5-(3-chloro-quinolin-6-ylmethyl)-oxazole-2-carboxylic acid ethyl ester (90 mg, 0.28 mmol, 1.0 eq) in THF (5 mL) was added a solution of NaOH (17 mg, 0.43 mmol, 1.5 eq) in water (5 mL) at rt. The solution was stirred at rt for 1 h. The reaction solution was neutralized with 1 N HCl. The mixture was concentrated to afford 5-(3-chloro-quinolin-6-ylmethyl)-oxazole-2-carboxylic acid (100 mg crude) as a white solid.

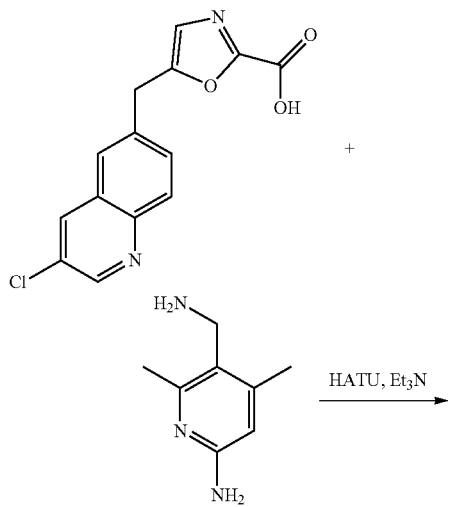

200

A mixture of 5-(3-chloro-quinolin-6-ylmethyl)-oxazole-2-carboxylic acid (100 mg crude, 0.35 mmol, 1.0 eq), 5-aminomethyl-4,6-dimethyl-pyridin-2-ylamine (78 mg, 0.52 mmol, 1.5 eq), HATU (198 mg, 0.52 mmol, 1.5 eq) and Et3N (106 mg, 1.05 mmol, 3.0 eq) in DMF (6 mL) was stirred at rt for 2 h. The mixture was concentrated and the resulting residue was purified by prep-HPLC to afford 5-(3-chloro-quinolin-6-ylmethyl)-oxazole-2-carboxylic acid (6-amino-2,4-dimethyl-pyridin-3-ylmethyl)-amide (5.0 mg, 3%) as a white solid. LRMS (M+H+) m/z calculated 422.1, found 422.0. 1H NMR (DMSO-d6, 400 MHz): δ 8.86 (d, 1H), 8.78-8.76 (m, 1H), 8.55 (d, 1H), 8.04 (d, 1H), 7.84 (d, 1H), 7.72-7.69 (m, 1H), 7.17 (s, 1H), 6.09 (s, 1H), 5.64 (s, 2H), 4.35 (s, 2H), 4.30 (d, 2H), 2.28 (s, 3H), 2.16 (s, 3H).

Example 32: Preparation of N-((6-amino-2,4-dimethylpyridin-3-yl)methyl)-7-((3-chloroquinolin-6-yl)methyl)-7H-pyrrolo[2,3-d]pyrimidine-5-carboxamide

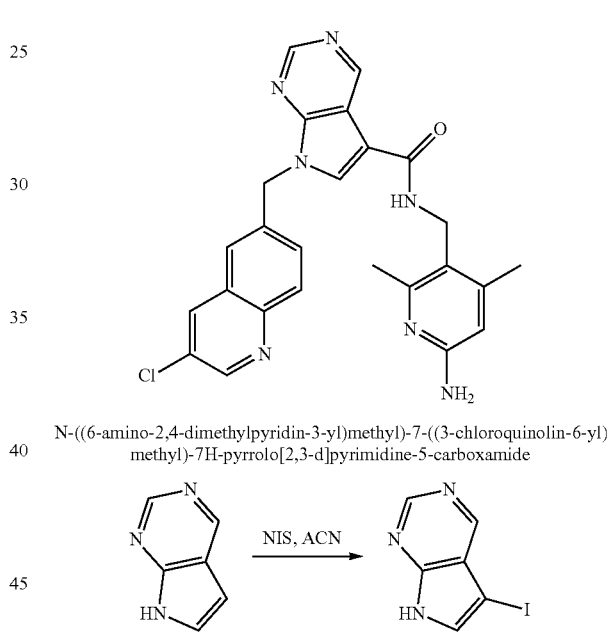

N-((6-amino-2,4-dimethylpyridin-3-yl)methyl)-7-((3-chloroquinolin-6-yl)methyl)-7H-pyrrolo[2,3-d]pyrimidine-5-carboxamide To a solution of 7H-pyrrolo[2,3-d]pyrimidine (2.17 g, 18.2 mmol, 1.0 eq) in CH3CN (45 mL) was added NIS (4.3 g, 19.1 mmol, 1.0 eq) at rt. The solution was stirred at rt for 2 h. The mixture was filtered and the solid was dried in vacuo to give 5-iodo-7H-pyrrolo[2,3-d]pyrimidine (4.24 g, 95%).

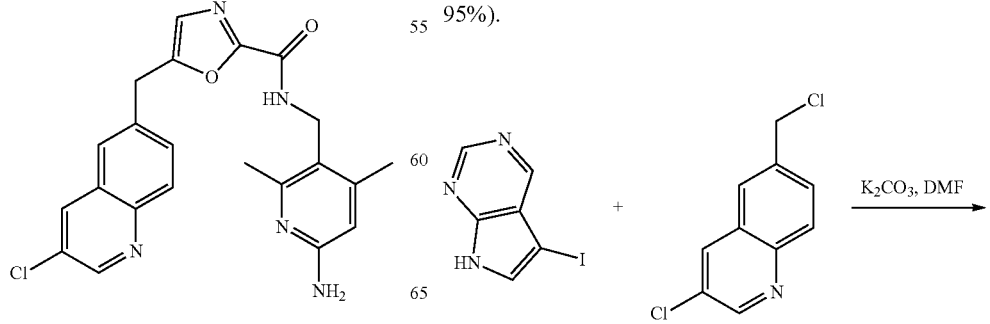

-continued

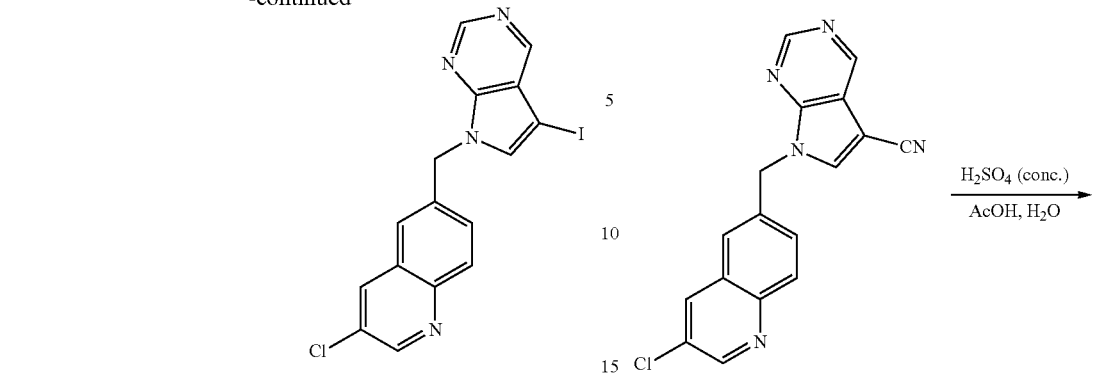

A mixture of 5-iodo-7H-pyrrolo[2,3-d]pyrimidine (1 g, 4.08 mmol, 1.0 eq), 3-chloro-6-chloromethyl-quinoline (1.039 g, 4.90 mmol, 1.2 eq) and K2CO3 (1.689 g, 12.24 mmol, 3.0 eq) in DMF (6 mL) was stirred at rt for 2 h. The mixture was poured into water (30 mL), and the resulting precipitate was collected by filtration. The white solid was dried in vacuo to give 3-chloro-6-(5-iodo-pyrrolo[2,3-d]pyrimidin-7-ylmethyl)-quinoline (1.52 g, 88.9%).

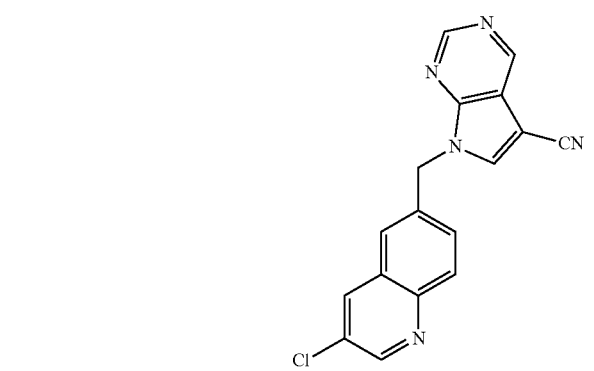

A mixture of 3-chloro-6-(5-iodo-pyrrolo[2,3-d]pyrimidin-7-ylmethyl)-quinoline (1.5 g, 3.57 mmol, 1.0 eq), Zn(CN)2 (0.84 g, 7.14 mmol, 2.0 eq) and Pd(PPh3)4 (0.41 g, 0.357 mmol, 0.1 eq) in DMF (50 mL) was stirred at rt overnight. The mixture was concentrated and the resulting residue was purified by column chromatography on silica gel (PE/EA=2/1~1/1, v/v) to give 7-(3-chloro-quinolin-6-ylmethyl)-7H-pyrrolo[2,3-d]pyrimidine-5-carbonitrile (350 mg, 35%) as a yellow solid.

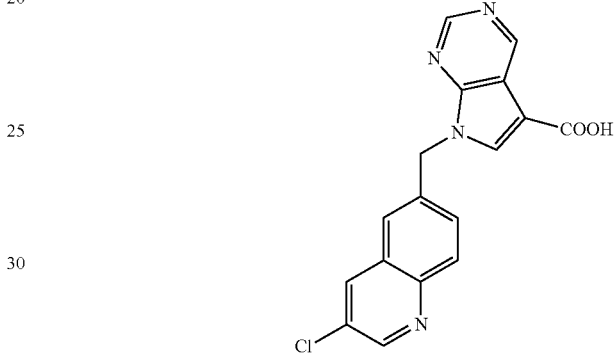

A mixture of 7-(3-chloro-quinolin-6-ylmethyl)-7H-pyrrolo[2,3-d]pyrimidine-5-carbonitrile (400 mg, 1.25 mmol, 1.0 eq), H2SO4 (1 mL) and AcOH (1 mL) in H2O (1 mL) was stirred at 110° C. for 2 h. The mixture was cooled to rt. H2O was added and the mixture was neutralized with aq. NaOH (10%) to pH 5. The resulting precipitate was filtered, washed with H2O and dried in vacuo to give 7-(3-chloro-quinolin-6-ylmethyl)-7H-pyrrolo[2,3-d]pyrimidine-5-carboxylic acid (390 mg, 92.3%) as a white solid.

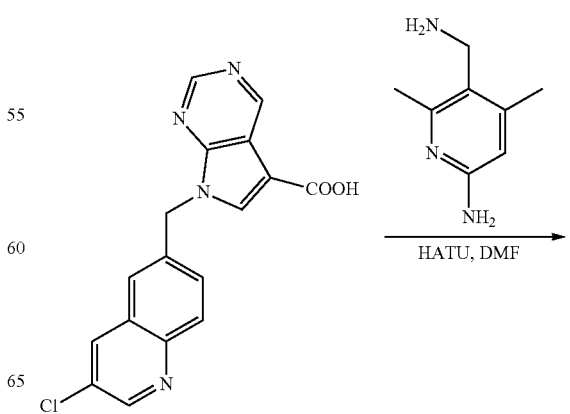

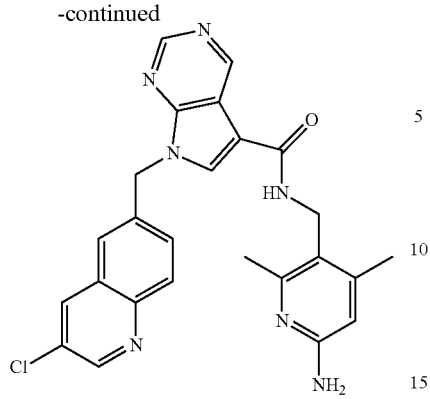
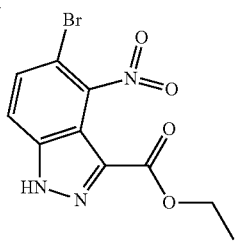

A mixture of 7-(3-chloro-quinolin-6-ylmethyl)-7H-pyrrolo[2,3-d]pyrimidine-5-carboxylic acid (190 mg, 0.56 mmol, 1.0 eq), 5-aminomethyl-4,6-dimethyl-pyridin-2-ylamine (127 mg, 0.67 mmol, 1.2 eq), HATU (319 mg, 0.84 mmol, 1.5 eq) and Et3N (169 mg, 1.68 mmol, 3.0 eq) in DMF (10 mL) was stirred at rt overnight. H2O was added, and the resulting precipitate was filtered, washed with H2O and dried in vacuo. The solid was further purified by trituration with MeOH twice to give N-((6-amino-2,4-dimethylpyridin-3-yl)methyl)-7-((3-chloroquinolin-6-yl)methyl)-7H-pyrrolo[2,3-d]pyrimidine-5-carboxamide (76 mg, 29%). LRMS (M+H+) m/z calculated 472.2, found 471.9. 1H NMR (DMSO-d6, 400 MHz): δ 9.43 (s, 1H), 8.90 (s, 1H), 8.85 (d, 1H), 8.55 (s, 1H), 8.38 (s, 1H), 8.11 (t, 1H), 8.02 (d, 1H), 7.78 (s, 1H), 7.69 (dd, 1H), 6.13 (s, 1H), 5.71 (s, 2H), 5.66 (s, 2H), 4.35 (d, 2H), 2.32 (s, 3H), 2.19 (s, 3H).

Example 33: Preparation of 4-amino-N-((6-amino-2,4-dimethylpyridin-3-yl)methyl)-1-((3-chloroquinolin-6-yl)methyl)-1H-indazole-3-carboxamide A solution of 5-bromo-1H-indazole-3-carboxylic acid ethyl ester (1.5 g, 5.6 mmol, 1.0 eq) in conc. H2SO4 (20 mL) was cooled to 0° C. A mixture of 70 percent HNO3 (1.1 mL) and conc. H2SO4 (3 mL) was added drop wise and the reaction was maintained for 1 h at 0° C. The mixture was poured into 100 mL of ice water and the solid was collected by filtration and dried in vacuo to give 5-bromo-4-nitro-1H-indazole-3-carboxylic acid ethyl ester (1.6 g, 91%) as a yellow solid.

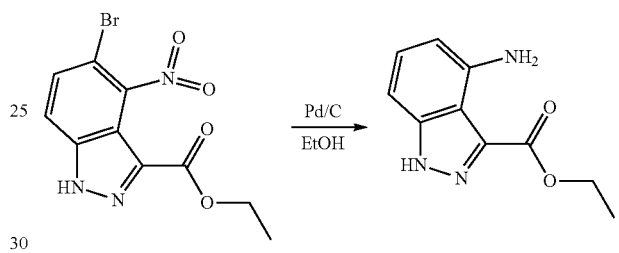

To a solution of 5-bromo-4-nitro-1H-indazole-3-carboxylic acid ethyl ester (1.6 g, 5.1 mmol, 1.0 eq) in EtOH (80 mL) was added Pd/C (320 mg). The reaction mixture was stirred at rt under 50 psi H2 for 5 h. The reaction was filtered and concentrated. The resulting residue was purified by chromatography on a silica gel column (DCM/MeOH=50/1, v/v) to give 4-amino-1H-indazole-3-carboxylic acid ethyl ester (255 mg, 24%) as a yellow solid.

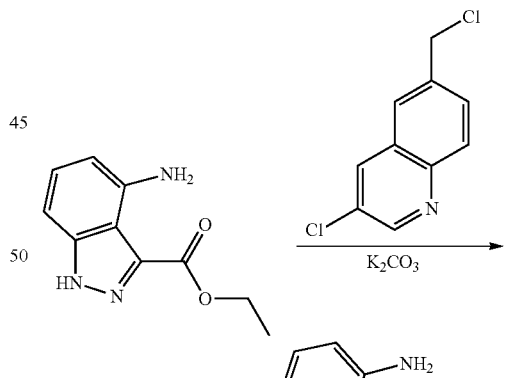

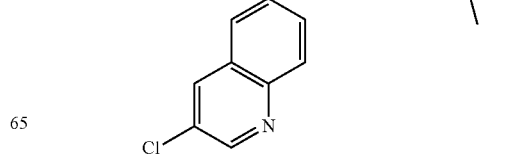

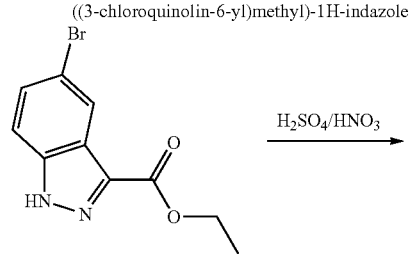

4-amino-N-((6-amino-2,4-dimethylpyridin-3-yl)methyl)-1-((3-chloroquinolin-6-yl)methyl)-1H-indazole-3-carboxamide 205
-continued

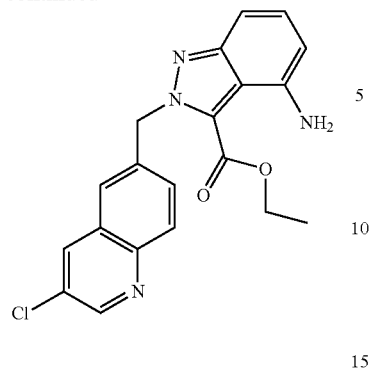

206
-continued

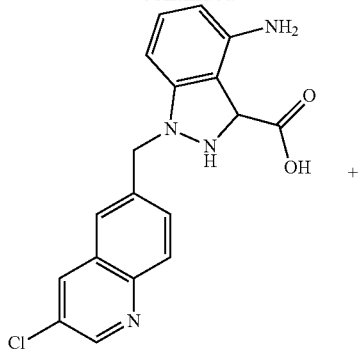

To a mixture of 4-amino-1H-indazole-3-carboxylic acid ethyl ester (255 mg, 1.24 mmol, 1.0 eq) and 3-chloro-6-chloromethyl-quinoline (264 mg, 1.24 mmol, 1.0 eq) in DMF (8 mL) was added K2CO3 (257 mg, 1.87 mmol, 1.5 eq). The reaction mixture was stirred at rt overnight. The reaction mixture was diluted with water and extracted with EA. The combined organic layers were washed with water, brine and dried over Na2SO4, filtered, and concentrated. The resulting residue was purified by chromatography on a silica gel column (DCM/MeOH=20/1, v/v) to give 4-amino-1-(3-chloro-quinolin-6-ylmethyl)-2,3-dihydro-1H-indazole-3-carboxylic acid ethyl ester and 4-amino-2-(3-chloro-quinolin-6-ylmethyl)-2,3-dihydro-1H-indazole-3-carboxylic acid ethyl ester in total 300 mg (63%) as a yellow solid.

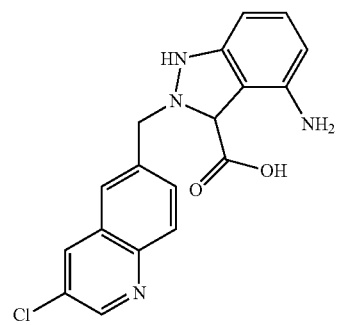

To a solution of 4-amino-1-(3-chloro-quinolin-6-ylmethyl)-2,3-dihydro-1H-indazole-3-carboxylic acid ethyl ester and 4-amino-2-(3-chloro-quinolin-6-ylmethyl)-2,3-dihydro-1H-indazole-3-carboxylic acid ethyl ester (150 mg, 0.39 mmol, 1.0 eq) in isopropyl alcohol (8 mL) and H2O (4 mL) was added NaOH (158 mg, 3.9 mmol, 10.0 eq). The reaction mixture was stirred at 85° C. for 3 h. The reaction mixture was acidified to pH 1 with 2 N HCl. The mixture was concentrated to give 4-amino-1-(3-chloro-quinolin-6-ylmethyl)-2,3-dihydro-1H-indazole-3-carboxylic acid and 4-amino-2-(3-chloro-quinolin-6-ylmethyl)-2,3-dihydro-1H-indazole-3-carboxylic acid (135 mg, 97%), which were used directly without further purification.

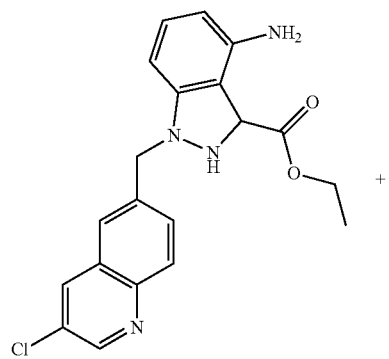

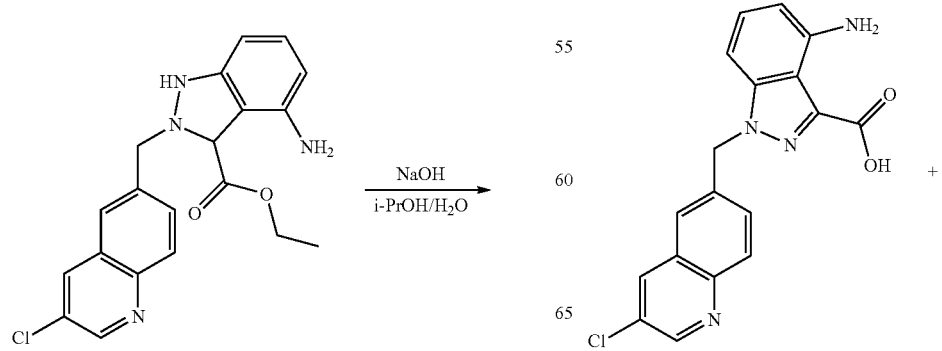

-continued

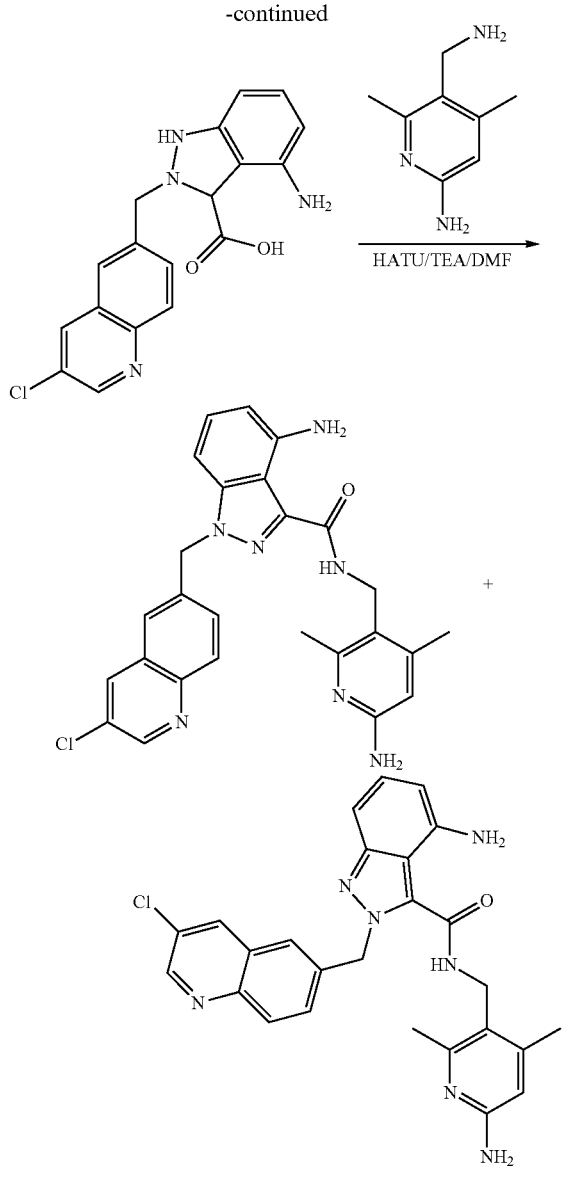

5.68 (s, 2H), 4.40 (d, 2H), 2.35 (s, 3H), 2.22 (s, 3H). The latter, LRMS (M+H+) m/z calculated 486.2, found 486.0. 1H NMR (DMSO-d6, 400 MHz): δ 9.09 (t, 1H), 8.86 (d, 1H), 8.48 (d, 1H), 7.97 (d 1H), 7.58 (s, 1H), 7.51 (d, 1H), 7.01 (dd, 1H), 6.85 (d, 1H), 6.20 (d, 1H), 6.14 (s, 1H), 5.88 (s, 2H), 5.36 (s, 2H), 4.38 (d, 2H), 2.25 (s, 3H), 2.10 (s, 3H).

Example 34: Preparation of 4-amino-7-(3-chloro-quinolin-6-ylmethyl)-7H-pyrrolo[2,3-d]pyrimidine-5-carboxylic acid (6-amino-2,4-dimethyl-pyridin-3-ylmethyl)-amide

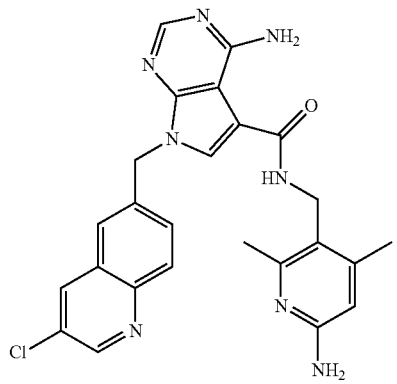

4-amino-N-((6-amino-2,4-dimethylpyridin-3-yl)methyl)-7-((3-chloroquinolin-6-yl)methyl)-7H-pyrrolo[2,3-d]pyrimidine-5-carboxamide

To a solution of 4-amino-1-(3-chloro-quinolin-6-ylmethyl)-2,3-dihydro-1H-indazole-3-carboxylic acid, 4-amino-2-(3-chloro-quinolin-6-ylmethyl)-2,3-dihydro-1H-indazole-3-carboxylic acid (135 mg, 0.39 mmol, 1.0 eq), 5-aminomethyl-4,6-dimethyl-pyridin-2-ylamine (74 mg, 0.39 mmol, 1.0 eq) and HATU (223 mg, 0.59 mmol, 1.5 eq) in DMF (10 mL) was added TEA (119 mg, 0.18 mmol, 3.0 eq) at 0° C. under N2. The reaction mixture was stirred at rt overnight. The reaction mixture was diluted with H2O and extracted with EA. The combined organic layers were dried and concentrated. The resulting residue was purified by prep-HPLC to give 4-amino-1-(3-chloro-quinolin-6-ylmethyl)-2,3-dihydro-1H-indazole-3-carboxylic acid (6-amino-2,4-dimethyl-pyridin-3-ylmethyl)-amide (40 mg, 22%) and 4-amino-2-(3-chloro-quinolin-6-ylmethyl)-2H-indazole-3-carboxylic acid (6-amino-2,4-dimethyl-pyridin-3-ylmethyl)-amide (10 mg, 5%). The former, LRMS (M+H+) m/z calculated 486.2, found 486.0. 1H NMR (DMSO-d6, 400 MHz): δ 8.84 (d, 1H), 8.52 (d, 1H), 8.32 (t, 1H), 7.99 (d 1H), 7.75 (s, 1H), 7.62 (dd, 1H), 7.06 (dd, 1H), 6.92 (s, 2H), 6.68 (d, 1H), 6.26 (d, 1H), 6.12 (s, 1H), 5.80 (s, 2H), To a solution of 7H-pyrrolo[2,3-d]pyrimidin-4-ylamine (1.3 g, 9.7 mmol, 1.0 eq) in CHCl3 (45 mL) was added NIS (2.18 g, 9.7 mmol, 1.0 eq) at rt. The solution was refluxed for 2 h. The precipitate was filtered and dried in vacuo to give 5-iodo-7H-pyrrolo[2,3-d]pyrimidin-4-ylamine (2.09 g, 83%) as a white solid.

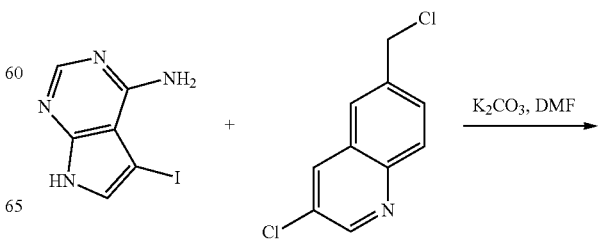

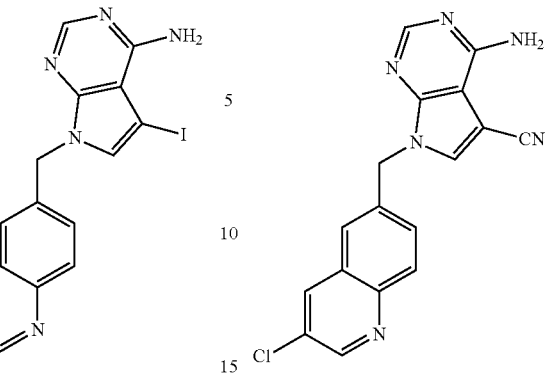

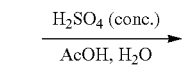

A mixture of 5-iodo-7H-pyrrolo[2,3-d]pyrimidin-4-ylamine (1 g, 3.85 mmol, 1.0 eq), 3-chloro-6-chloromethyl-quinoline (0.98 g, 4.62 mmol, 1.2 eq) and K2CO3 (1.59 g, 11.52 mmol, 3.0 eq) in DMF (6 mL) was stirred at rt for 2 h. The mixture was poured into water (30 mL), and the resulting precipitate was collected by filtration. The white solid was dried in vacuo to give 7-(3-chloro-quinolin-6-ylmethyl)-5-iodo-7H-pyrrolo[2,3-d]pyrimidin-4-ylamine (1.47 g, 88%).

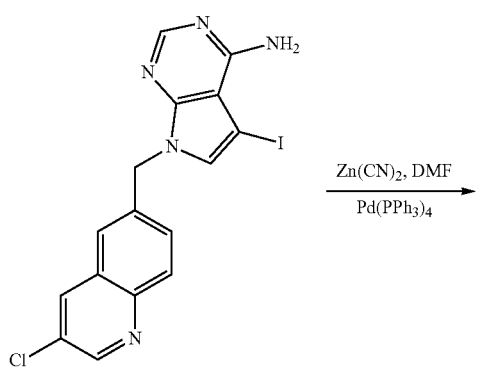

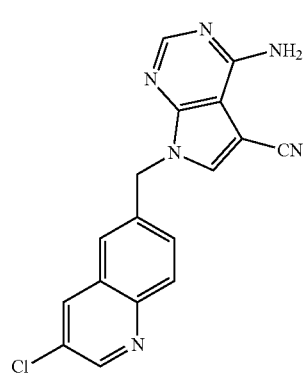

A mixture of 7-(3-chloro-quinolin-6-ylmethyl)-5-iodo-7H-pyrrolo[2,3-d]pyrimidin-4-ylamine (1.47 g, 3.37 mmol, 1.0 eq), Zn(CN)2 (0.80 g, 6.74 mmol, 2.0 eq) and Pd(PPh3)4 (0.40 g, 0.337 mmol, 0.1 eq) in DMF (50 mL) was stirred at rt overnight. The precipitate was filtered off and the filtrate was concentrated. The residue was tritutated with MeOH to give 4-amino-7-(3-chloro-quinolin-6-ylmethyl)-7H-pyrrolo[2,3-d]pyrimidine-5-carbonitrile (1 g, 88.9%) as a white solid.

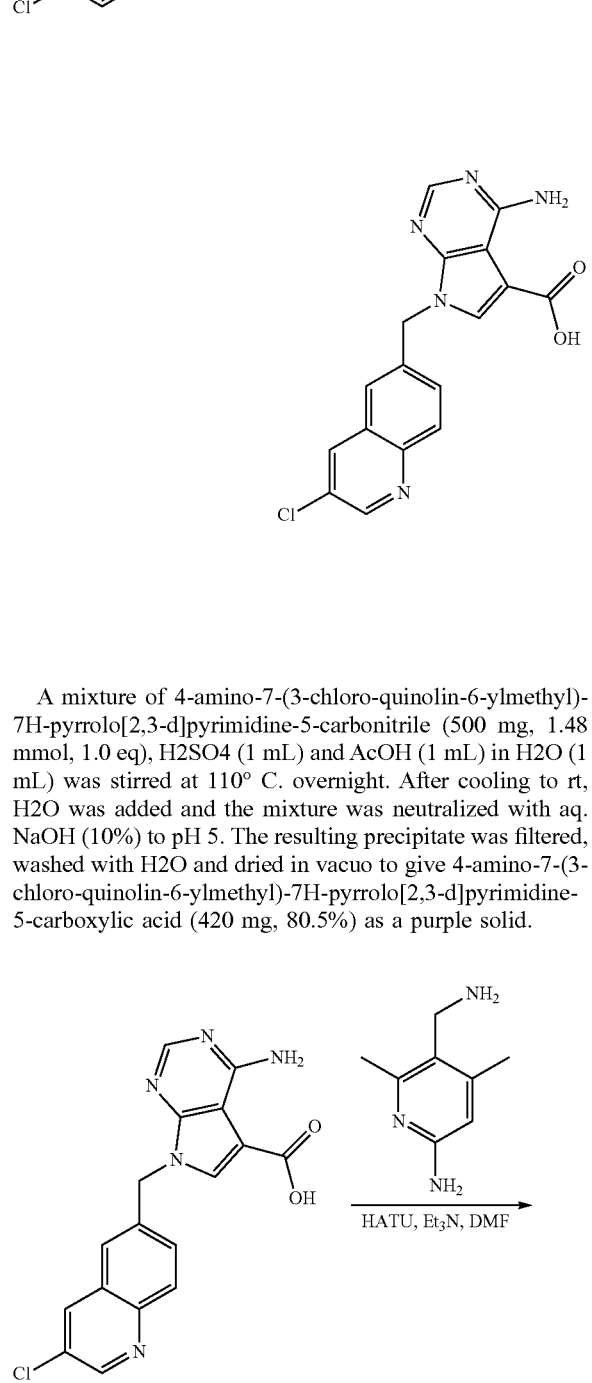

A mixture of 4-amino-7-(3-chloro-quinolin-6-ylmethyl)-7H-pyrrolo[2,3-d]pyrimidine-5-carbonitrile (500 mg, 1.48 mmol, 1.0 eq), H2SO4 (1 mL) and AcOH (1 mL) in H2O (1 mL) was stirred at 110° C. overnight. After cooling to rt, H2O was added and the mixture was neutralized with aq. NaOH (10%) to pH 5. The resulting precipitate was filtered, washed with H2O and dried in vacuo to give 4-amino-7-(3-chloro-quinolin-6-ylmethyl)-7H-pyrrolo[2,3-d]pyrimidine-5-carboxylic acid (420 mg, 80.5%) as a purple solid.

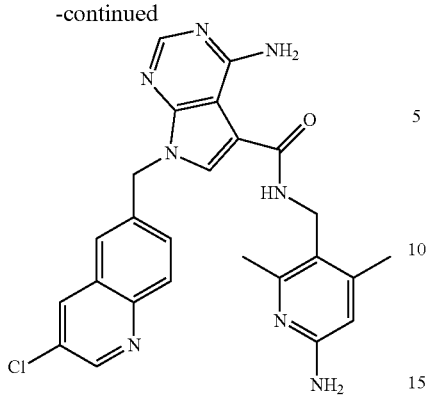

A mixture of 4-amino-7-(3-chloro-quinolin-6-ylmethyl)-7H-pyrrolo[2,3-d]pyrimidine-5-carboxylic acid (200 mg, 0.57 mmol, 1.0 eq), 5-aminomethyl-4,6-dimethyl-pyridin-2-ylamine (128 mg, 0.68 mmol, 1.2 eq), HATU (325 mg, 0.85 mmol, 1.5 eq) and Et3N (173 mg, 1.71 mmol, 3.0 eq) in DMF (10 mL) was stirred at rt overnight. H2O was added, and the resulting precipitate was filtered, washed with H2O and dried in vacuo. The solid was further purified by trituration with MeOH twice to give 4-amino-N-((6-amino-2,4-dimethylpyridin-3-yl)methyl)-7-((3-chloroquinolin-6-yl)methyl)-7H-pyrrolo[2,3-d]pyrimidine-5-carboxamide (20 mg, 7%) as an off-white solid. LRMS (M+H+) m/z calculated 487.2, found 487.0. 1H NMR (DMSO-d6, 400 MHz): δ 8.86 (d, 1H), 8.56 (d, 1H), 8.21 (t, 1H), 8.12 (s, 1H), 8.11 (s, 1H), 8.11 (t, 1H), 8.02 (d, 1H), 7.73 (s, 1H), 7.66 (dd, 1H), 6.15 (s, 1H), 5.70 (s, 2H), 5.57 (s, 2H), 4.35 (d, 2H), 2.31 (s, 3H), 2.18 (s, 3H).

Example 35: Preparation of N-((6-amino-2,4-dimethylpyridin-3-yl)methyl)-1-((3-chloroquinolin-6-yl)methyl)-1H-pyrrolo[3,2-c]pyridine-3-carboxamide

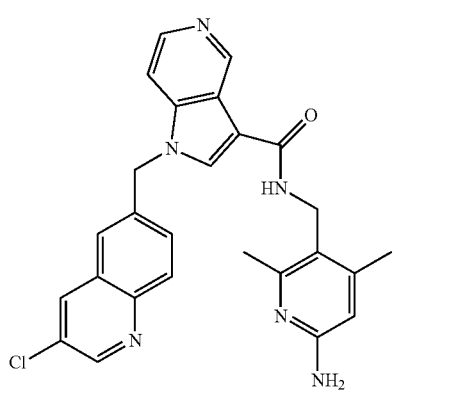

N-((6-amino-2,4-dimethylpyridin-3-yl)methyl)-1-((3-chloroquinolin-6-yl)methyl)-1H-pyrrolo[3,2-c]pyridine-3-carboxamide

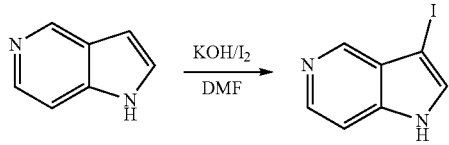

To a solution of 1H-pyrrolo[3,2-c]pyridine (5.76 g, 48.8 mmol, 1.0 eq) in DMF (30 mL) was added KOH (10.39 g, 185.5 mmol, 3.8 eq). The reaction mixture was stirred at rt for 15 min. The reaction mixture was cooled to 0° C. and a solution of 12 (12.4 g, 48.8 mmol, 1.0 eq) in DMF (15 mL) was added. After stirring for 15 min at rt, the reaction mixture was poured into water. The mixture was filtered and the solid was rinsed with water. The yellow solid was dried in vacuo to give 3-iodo-1H-pyrrolo[3,2-c]pyridine (9.9 g, 83%).

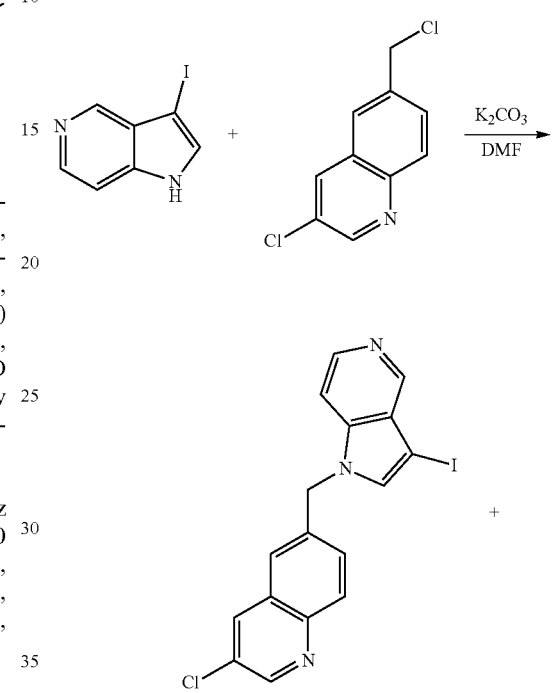

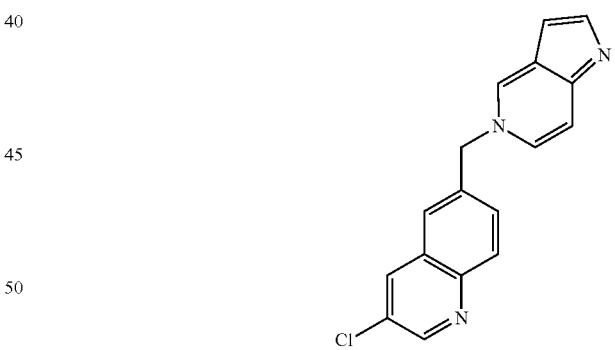

To a mixture of 3-iodo-1H-pyrrolo[3,2-c]pyridine (5.76 g, 23.6 mmol, 1.0 eq) and 3-chloro-6-chloromethyl-quinoline (5.0 g, 23.6 mmol, 1.0 eq) in DMF (50 mL) was added K2CO3 (4.88 g, 35.3 mmol, 1.5 eq). The reaction mixture was stirred at rt overnight. The reaction mixture was diluted with water and extracted with EA. The combined organic layers were washed with water, brine and dried over Na2SO4. The mixture was filtered, concentrated and purified by chromatography on a silica gel column (DCM/MeOH=50/1, v/v) to give 3-chloro-6-(3-iodo-pyrrolo[3,2-c]pyridin-1-ylmethyl)-quinoline (1.45 g, 15%) and 3-chloro-6-(3-iodo-pyrrolo[3,2-c]pyridin-5-ylmethyl)-quinoline (1.45 g, 15%).

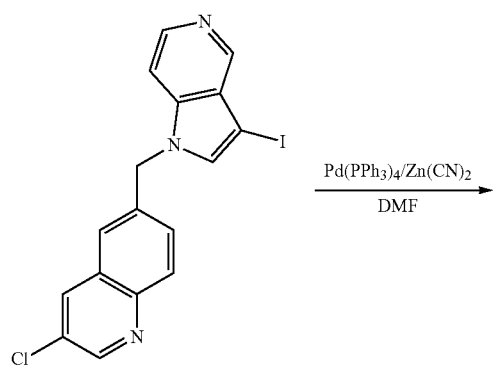

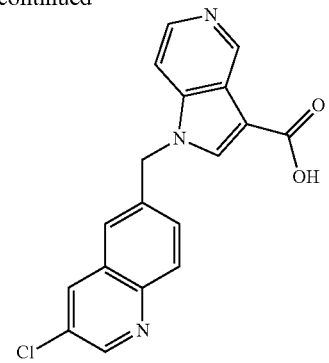

To a solution of 1-(3-chloro-quinolin-6-ylmethyl)-1H-pyrrolo[3,2-c]pyridine-3-carbonitrile (270 mg, 0.85 mmol, 1.0 eq) in conc. H2SO4 (2 mL), AcOH (2 mL) and H2O (2 mL) was stirred at 110° C. overnight. It was alkalized to pH 4 with NaOH aq. and extracted with EA. The combined organic layers were washed with water, brine and dried over Na2SO4, filtered, and concentrated to give 1-(3-chloro-quinolin-6-ylmethyl)-1H-pyrrolo[3,2-c]pyridine-3-carboxylic acid (180 mg, 63%) without further purification.

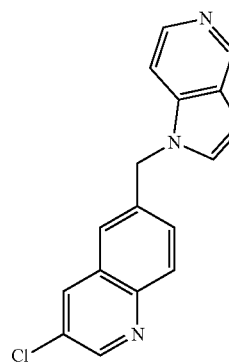

The mixture of 3-chloro-6-(3-iodo-pyrrolo[3,2-c]pyridin-1-ylmethyl)-quinoline (1.45 g, 3.5 mmol, 1.0 eq), Zn(CN)2 (0.8 g, 6.9 mmol, 2.0 eq) and Pd(PPh3)4 (0.4 g, 0.35 mmol, 0.1 eq) in DMF (15 mL) was stirred at 100° C. overnight. Then it was diluted with water and extracted with EA. The combined organic layers were washed with water, brine and dried over Na2SO4, filtered, and concentrated. The resulting residue was purified by chromatography on a silica gel column (DCM/MeOH=50/1, v/v) to give 1-(3-chloro-quinolin-6-ylmethyl)-1H-pyrrolo[3,2-c]pyridine-3-carbonitrile (270 mg, 25%) as a yellow solid.

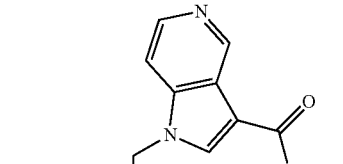

To a solution of 1-(3-chloro-quinolin-6-ylmethyl)-1H-pyrrolo[3,2-c]pyridine-3-carboxylic acid (180 mg, 0.53 mmol, 1.0 eq), (5-aminomethyl-4,6-dimethyl-pyridin-2-yl)- carbamic acid tert-butyl ester (134 mg, 0.53 mmol, 1.0 eq) and HATU (304 mg, 0.8 mmol, 1.5 eq) in DMF (10 mL) was added TEA (161 mg, 1.6 mmol, 3.0 eq) at 0° C. under N2. The reaction mixture was stirred at rt overnight. The reaction mixture was diluted with H2O and extracted with EA. The combined organic layers were dried and concentrated. The resulting residue was purified by chromatography on a silica gel column (DCM/MeOH=20/1, v/v) to give [4-({[1-(3-chloro-quinolin-6-ylmethyl)-1H-pyrrolo[3,2-c]pyridine-3-carbonyl]-amino}-methyl)-3,5-dimethyl-phenyl]-carbamic acid tert-butyl ester (180 mg, 59%) as a yellow solid.

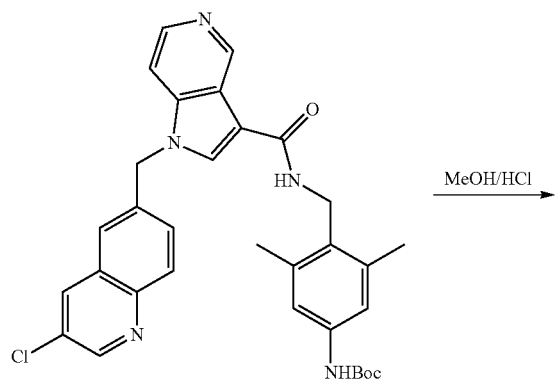

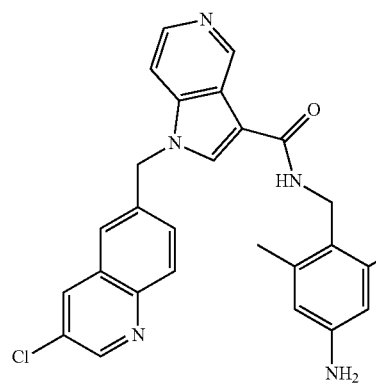

To a solution of [4-({[1-(3-chloro-quinolin-6-ylmethyl)-1H-pyrrolo[3,2-c]pyridine-3-carbonyl]-amino}-methyl)-3,5-dimethyl-phenyl]-carbamic acid tert-butyl ester (180 mg, 0.32 mmol, 1.0 eq) in MeOH (5 mL) was added 4 N MeOH/HCl (10 mL). The reaction mixture was stirred at rt for 2 h. The reaction mixture was filtered and the residue was rinsed with EA. The solid was dried in vacuo to give N-((6-amino-2,4-dimethylpyridin-3-yl)methyl)-1-((3-chloroquinolin-6-yl)methyl)-1H-pyrrolo[3,2-c]pyridine-3-carboxamide (100 mg, 68%). LRMS (M+H+) m/z calculated 471.2, found 471.0. 1H NMR (DMSO-d6, 400 MHz): δ 11.34 (s, 1H), 9.52 (s, 1H), 9.01 (t, 1H), 8.91 (s, 1H), 8.89 (s, 1H), 8.61 (d, 1H), 8.54 (d, 1H), 8.35 (d, 1H), 8.05 (d, 1H), 7.87 (d, 1H), 7.75 (s, 2H), 7.72 (s, 1H), 6.67 (s, 1H), 5.94 (s, 2H), 4.38 (d, 2H), 2.59 (s, 3H), 2.43 (s, 3H).

Example 36: Preparation of N-((6-amino-2,4-dimethylpyridin-3-yl)methyl)-1-((3-chloroquinolin-6-yl)methyl)-4-cyano-1H-pyrazole-3-carboxamide

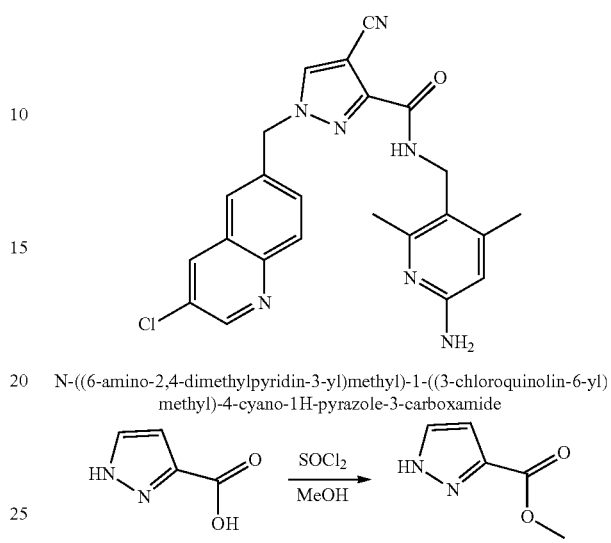

N-((6-amino-2,4-dimethylpyridin-3-yl)methyl)-1-((3-chloroquinolin-6-yl)methyl)-4-cyano-1H-pyrazole-3-carboxamide

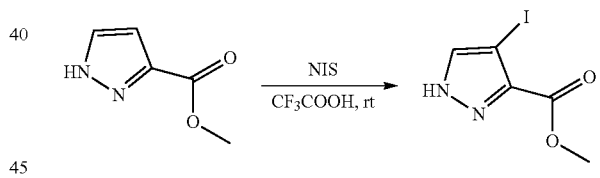

To a stirred solution of 1H-pyrazole-3-carboxylic acid (2 g, 17.8 mmol, 1 eq) in MeOH (20 mL) was added thionyl chloride (2.5 mL, 35.5 mmol, 2 eq). The mixture was stirred at 40° C. for 5 h, and then concentrated. The resulting residue was diluted with DCM and washed with saturated aqueous NaHCO3 solution. The organic layer was separated, dried and concentrated. The resulting residue was purified by chromatography on a silica gel column (PE/EA=1/3, v/v) to give 1H-pyrazole-3-carboxylic acid methyl ester (1.8 g, 79.6%) as a white solid.

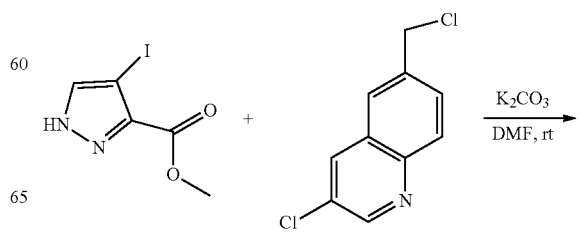

To a solution of 1H-pyrazole-3-carboxylic acid methyl ester (0.5 g, 4.3 mmol, 1.1 eq) and NIS (0.97 g, 3.9 mmol, 1 eq) in CH3CN (15 mL) was added CF3COOH (0.1 mL). The mixture was stirred at rt for 3 h, and then concentrated. The resulting residue was partitioned between EtOAc and 5% NaHCO3. The organic layer was separated, dried over Na2SO4, filtrated, and concentrated. The resulting residue was purified by chromatography on a silica gel column to give 4-iodo-1H-pyrazole-3-carboxylic acid methyl ester (0.61 g, 61%).

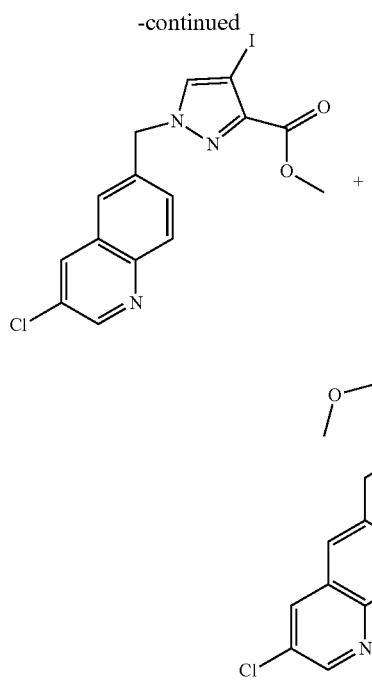

A mixture of 4-iodo-1H-pyrazole-3-carboxylic acid methyl ester (0.3 g, 1.2 mmol, 1 eq), 3-chloro-6-chloromethyl-quinoline (0.3 g, 1.42 mmol, 1.2 eq), and K2CO3 (0.33 g, 2.4 mmol, 2 eq) in DMF (15 mL) was stirred at rt for 12 h, and then concentrated. The resulting residue was washed with water, and extracted with CH2Cl2 (3×100 mL). The organic layers were concentrated and the resulting residue was purified by chromatography on a silica gel column (PE/EA=1/3, v/v) to give 1-(3-chloro-quinolin-6-ylmethyl)-4-iodo-1H-pyrazole-3-carboxylic acid methyl ester (0.32 g, 63%) and 2-(3-chloro-quinolin-6-ylmethyl)-4-iodo-2H-pyrazole-3-carboxylic acid methyl ester (0.18 g, 35.5%).

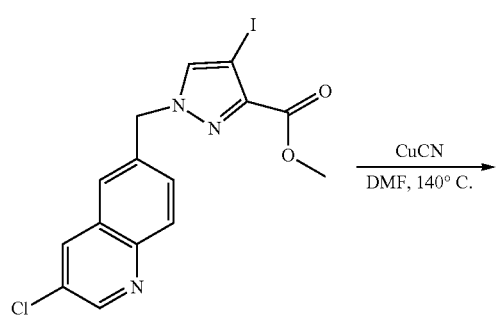

To a solution of 1-(3-chloro-quinolin-6-ylmethyl)-4-iodo-1H-pyrazole-3-carboxylic acid methyl ester (0.32 g, 0.7 mmol, 1 eq) in DMF (15 mL) was added CuCN (0.33 g, 3.73 mmol, 5.3 eq). The mixture was stirred in sealed tube at 135° C. for 20 h. After cooling to rt, the mixture was filtered and the filtrate was concentrated. The resulting residue was purified by chromatography on a silica gel column (PE/EA=1/3, v/v) to give 1-(3-chloro-quinolin-6-ylmethyl)-4-cyano-1H-pyrazole-3-carboxylic acid methyl ester (60 mg, 24.5%).

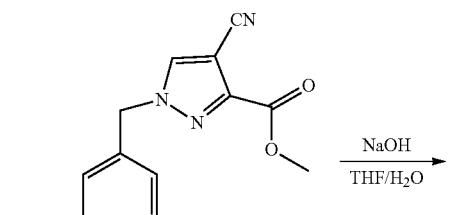

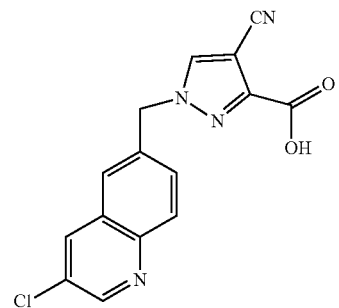

To a stirred solution of 1-(3-chloro-quinolin-6-ylmethyl)-4-cyano-1H-pyrazole-3-carboxylic acid methyl ester (60 mg, 0.18 mmol, 1 eq) in THF/H2O (3 mL/3 mL) was added NaOH (30 mg, 0.74 mmol, 4 eq) in THF/H2O (3 mL/3 mL). The mixture was stirred at rt for 2 h, then adjusted to pH=3 with HCl (1 N). The mixture was concentrated, and the resulting precipitate was filtered. The solid was dried under reduce pressure to give 1-(3-chloro-quinolin-6-ylmethyl)-4-cyano-1H-pyrazole-3-carboxylic acid (50 mg, 87.7%).

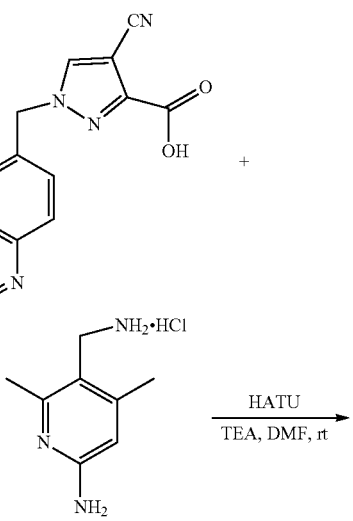

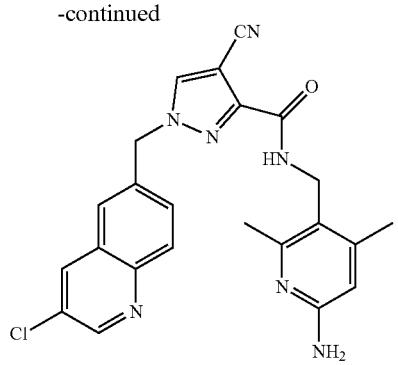

A mixture of 1-(3-chloro-quinolin-6-ylmethyl)-4-cyano-1H-pyrazole-3-carboxylic acid (50 mg, 0.16 mmol, 1 eq) and 5-aminomethyl-4,6-dimethyl-pyridin-2-ylamine (36 mg, 0.19 mmol, 1.2 eq), HATU (91 mg, 0.24 mmol, 1.5 eq) and TEA (48 mg, 0.48 mmol, 3 eq) in DMF (5 mL) was stirred at rt for 2 h, and then concentrated. The resulting residue was purified by per-HPLC to give N-((6-amino-2,4-dimethylpyridin-3-yl)methyl)-1-((3-chloroquinolin-6-yl)methyl)-4-cyano-1H-pyrazole-3-carboxamide (23.2 mg, 32.4%) as white solid. LRMS (M+H+) m/z calculated 446.1, found 446.0. 1H NMR (DMSO-d6, 400 MHz): δ 8.89 (d, 1H), 8.84 (s, 1H), 8.58 (d, 1H), 8.31 (t, 1H), 8.05 (d, 1H), 7.78 (s, 1H), 7.70 (dd, 1H), 6.09 (s, 1H), 5.66 (s, 2H), 5.64 (s, 2H), 4.31 (d, 2H), 2.29 (s, 3H), 2.17 (s, 3H).

Example 37: Preparation of N-((6-amino-2,4-dimethylpyridin-3-yl)methyl)-2-((3-chloroquinolin-6-yl)methyl)-4-(trifluoromethyl)oxazole-5-carboxamide

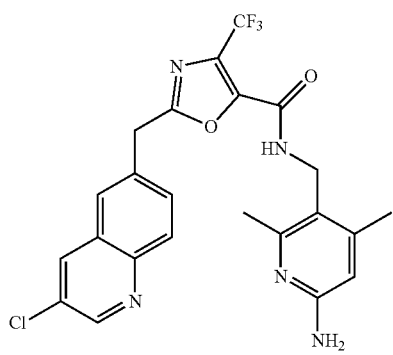

N-((6-amino-2,4-dimethylpyridin-3-yl)methyl)-2-((3-chloroquinolin-6-yl)methyl)-4-(trifluoromethyl)oxazole-5-carboxamide

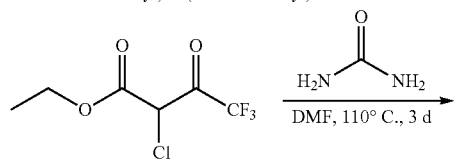

A mixture of 2-chloro-4,4,4-trifluoro-3-oxo-butyric acid ethyl ester (2.5 g, 11.4 mmol, 1 eq) and urea (3.43 g, 57.2 mmol, 5 eq) in dry DMF (4 mL) was heated at 110° C. for 3 days. After cooling to rt, the orange slurry was poured into 25 mL of water. The solid was collected by filtration. The crude product was triturated in EA/PE (1/3, v/v, 20 mL) to give ethyl 2-amino-4-(trifluoromethyl)oxazole-5-carboxylate (1.8 g, 71%) as slightly yellow solid.

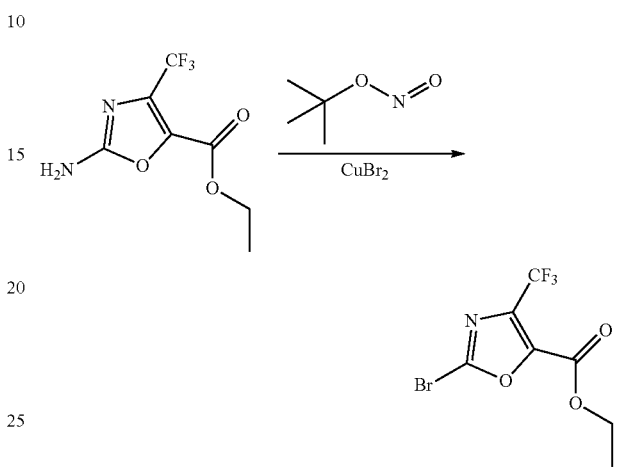

To a mixture of ethyl 2-amino-4-(trifluoromethyl)oxazole-5-carboxylate (1.8 g, 8.0 mmol, 1 eq) and CuBr2 (2.14 g, 9.6 mmol, 1.2 eq) in dry MeCN (15 mL) was added t-butylnitrite slowly. The reaction mixture was warmed slowly from 0° C. to rt under a nitrogen atmosphere. After stirring at rt for 2.5 h, the mixture was diluted with saturated NH4Cl aqueous solution and extracted with EA twice. The combined organic layers were dried and concentrated. The resulting residue was purified by chromatography on a silica gel column to give ethyl 2-bromo-4-(trifluoromethyl)oxazole-5-carboxylate (1.2 g, 52%) as a colorless oil.

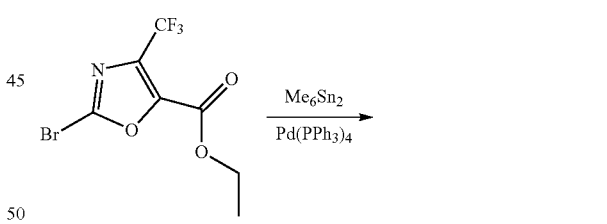

A mixture of ethyl 2-bromo-4-(trifluoromethyl)oxazole-5-carboxylate (500 mg, 1.74 mmol, 1 eq), Me6Sn2 (626 mg, 3.48 mmol, 2 eq) and Pd(PPh3)4 (100 mg, 0.087 mmol, 0.05 eq) in toluene (10 mL) was heated at 100° C. under nitrogen atmosphere for 16 h. After cooling to rt, the mixture was concentrated and the resulting residue was directly used in the next step.

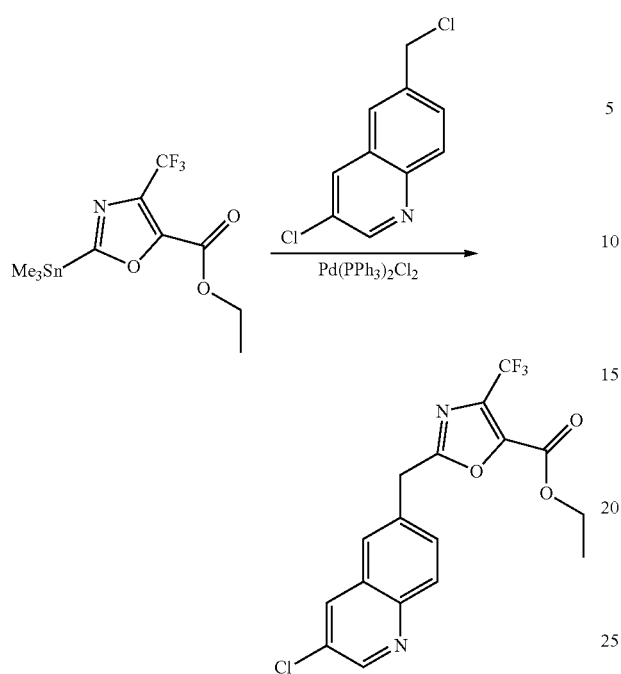

A mixture of ethyl 4-(trifluoromethyl)-2-(trimethylstannyl)oxazole-5-carboxylate (647 mg, 1.74 mmol, 1 eq), 3-chloro-6-chloromethyl-quinoline (367 mg, 1.74 mmol, 1 eq) and Pd(PPh3)2Cl2 (122 mg, 0.17 mmol, 0.05 eq) in dioxane (12 mL) was heated at 95° C. under nitrogen atmosphere for 4.5 h. After cooling to rt, the mixture was concentrated and the resulting residue was purified by chromatography on a silica gel column (EA/PE=1/10, v/v) to give ethyl 2-((3-chloroquinolin-6-yl)methyl)-4-(trifluoromethyl)oxazole-5-carboxylate (80 mg, 12% for 2 steps).

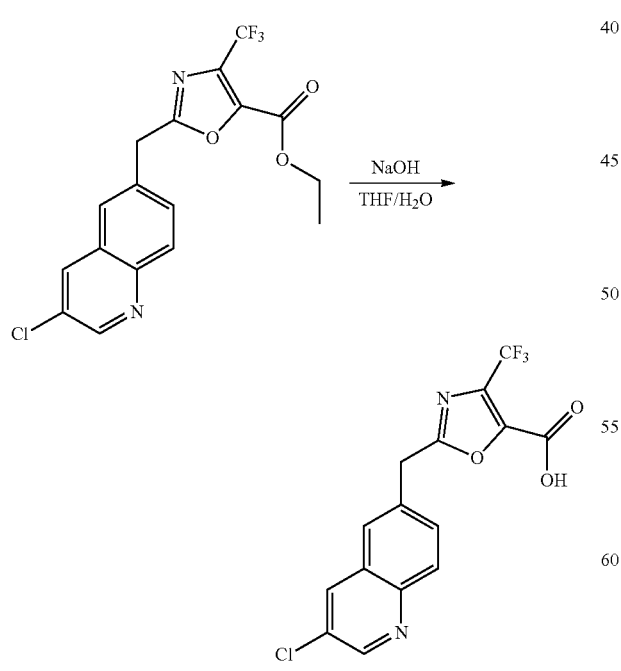

To a solution of ethyl 2-((3-chloroquinolin-6-yl)methyl)-4-(trifluoromethyl)oxazole-5-carboxylate (80 mg, 0.21 mmol, 1.0 eq) in THF (2 mL) was added a solution of NaOH (13 mg, 0.31 mmol, 1.5 eq) in H2O (2 mL) at rt. The solution was stirred at rt for 2 h, and then neutralized with HCl (1 N). The mixture was concentrated to give 2-(3-chloro-quinolin-6-ylmethyl)-4-trifluoromethyl-oxazole-5-carboxylic acid (100 mg crude) as a yellow solid, which was used in the next step without further purification.

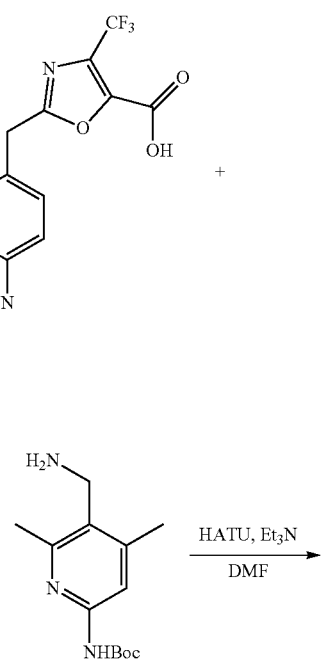

A mixture of 2-(3-chloro-quinolin-6-ylmethyl)-4-trifluoromethyl-oxazole-5-carboxylic acid (100 mg crude, 0.21 mmol, 1 eq), tert-butyl (5-(aminomethyl)-4,6-dimethylpyridin-2-yl)carbamate (79 mg, 0.32 mmol, 1.5 eq), HATU (122 mg, 0.32 mmol, 1.5 eq) and Et3N (64 mg, 0.63 mmol, 3.0 eq) in DMF (6 mL) was stirred at rt for 2 h. The mixture was concentrated, and the residue was purified by TLC-plate (DCM/MeOH=20/1) to give tert-butyl (5-((2-((3-chloroquinolin-6-yl)methyl)-4-(trifluoromethyl)oxazole-5-carboxamido)methyl)-4,6-dimethylpyridin-2-yl)carbamate (40 mg, 32%) as a white solid.

223

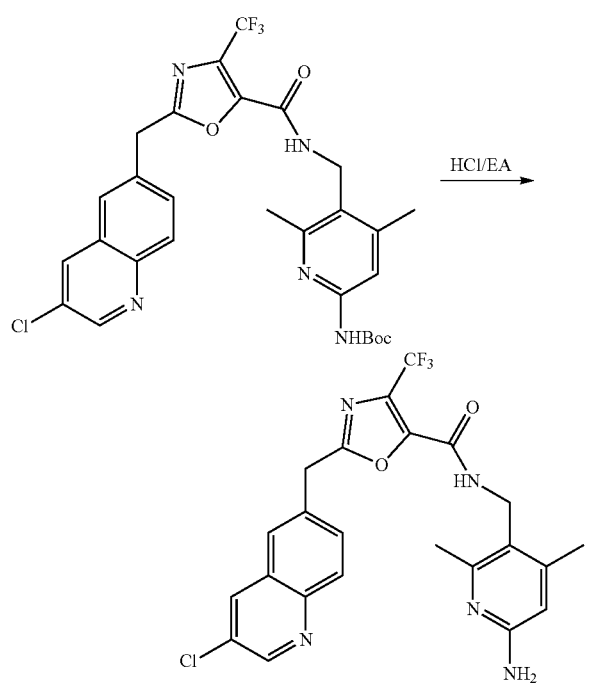

To a solution of tert-butyl (5-((2-((3-chloroquinolin-6-yl)methyl)-4-(trifluoromethyl)oxazole-5-carboxamido)methyl)-4,6-dimethylpyridin-2-yl)carbamate (40 mg, 0.07 mmol, 1.0 eq) in EA (10 mL) was added HCl/EA (10 mL). The solution was stirred at rt overnight. The reaction solution was concentrated and the resulting residue was purified by prep-HPLC to give N-((6-amino-2,4-dimethylpyridin-3-yl)methyl)-2-((3-chloroquinolin-6-yl)methyl)-4-(trifluoromethyl)oxazole-5-carboxamide (7 mg, 21%) as a white solid. LRMS (M+H+) m/z calculated 490.1, found 489.9. 1H NMR (DMSO-d6, 400 MHz): δ 8.88-8.87 (m, 2H), 8.56 (d, 1H), 8.04 (d, 1H), 7.91 (d, 1H), 7.78-7.75 (m, 1H), 6.12 (s, 1H), 5.72 (br. s., 2H), 4.48 (s, 2H), 4.31 (d, 2H), 2.28 (s, 3H), 2.16 (s, 3H).

Example 38: Preparation of N-((6-amino-2,4-dimethylpyridin-3-yl)methyl)-1-((3-chloroquinolin-6-yl)methyl)-3-methyl-1H-pyrazole-4-carboxamide

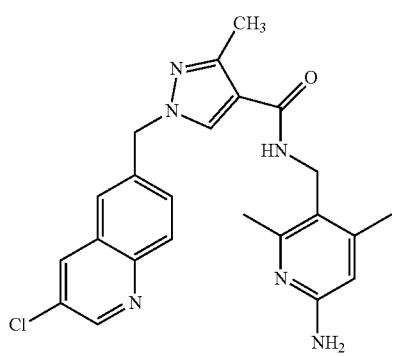

N-((6-amino-2,4-dimethylpyridin-3-yl)methyl)-1-((3-chloroquinolin-6-yl)methyl)-3-methyl-1H-pyrazole-4-carboxamide

224

-continued

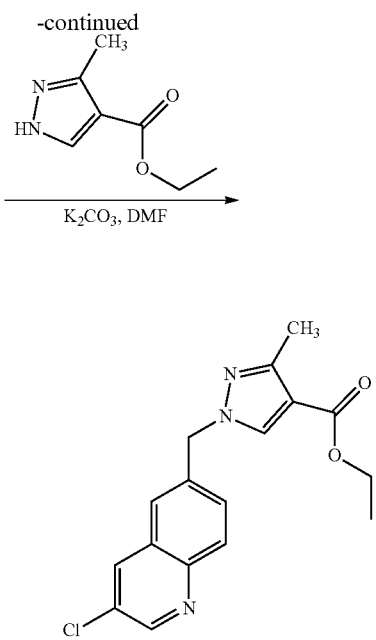

A mixture of ethyl 3-methyl-1H-pyrazole-4-carboxylate (400 mg, 2.6 mmol, 1 eq), 3-chloro-6-chloromethyl-quinoline (753 mg, 3.6 mmol, 1.4 eq) and K2CO3 (672 mg, 4.9 mmol, 1.9 eq) in DMF (6 mL) was stirred at rt overnight. Then the mixture was concentrated and the residue was diluted with water. The mixture was extracted with EA, and the combined organic layers were dried and concentrated. The resulting residue was purified by chromatography on a silica gel column (PE/EA=2/1, v/v) to afford a white solid, which was triturated in PE/EA (10/1, v/v) to give ethyl 1-((3-chloroquinolin-6-yl)methyl)-3-methyl-1H-pyrazole-4-carboxylate (430 mg, 50%) as a white solid.

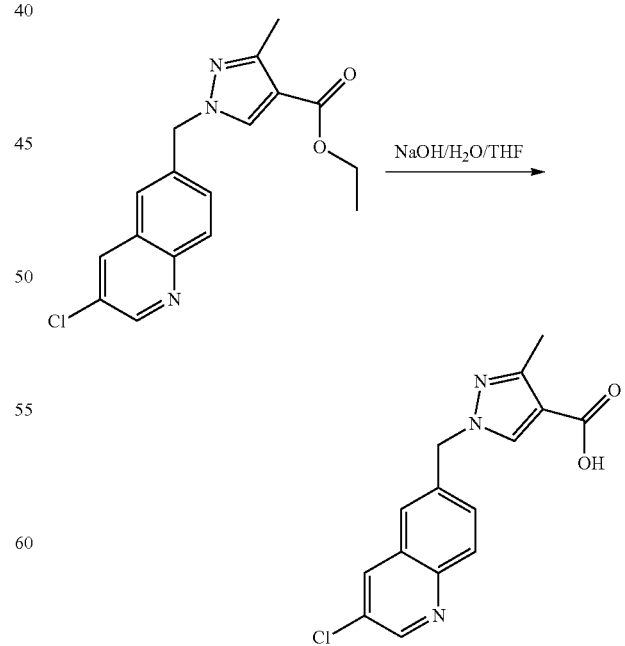

A mixture of ethyl 1-((3-chloroquinolin-6-yl)methyl)-3-methyl-1H-pyrazole-4-carboxylate (200 mg, 0.61 mmol, 1 eq) and NaOH (60 mg, 1.5 mmol, 2.46 eq) in i-PrOH/H2O (15 mL, v/v=2/1) was stirred at 100° C. for 36 h. After cooling to rt, the mixture was neutralized to pH 5 with HCl (1 N). The resulting precipitate was collected by filtration to give 1-(3-chloro-quinolin-6-ylmethyl)-3-methyl-1H-pyrazole-4-carboxylic acid (149 mg, 81%) as a white solid

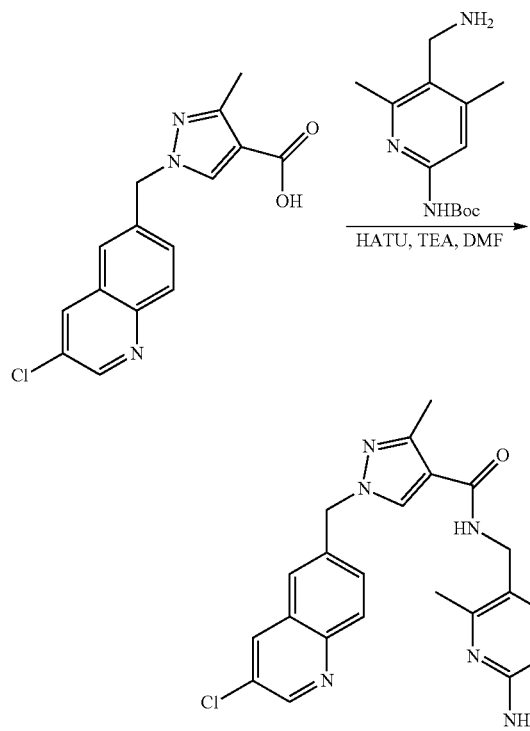

A mixture of 1-(3-chloro-quinolin-6-ylmethyl)-3-methyl-1H-pyrazole-4-carboxylic acid (230 mg, 0.76 mmol, 1.0 eq), tert-butyl (5-(aminomethyl)-4,6-dimethylpyridin-2-yl)carbamate (230 mg, 0.91 mmol, 1.2 eq), HATU (435 mg, 1.14 mmol, 1.5 eq) and TEA (0.32 mL, 2.28 mmol, 3.0 eq) in DMF (10 mL) was stirred at rt overnight. The mixture was concentrated, and the residue was diluted with water. The mixture was extracted with EA and the combined organic layers were dried and concentrated. The resulting residue was purified by chromatography on a silica gel column (EA) to afford tert-butyl (5-((1-((3-chloroquinolin-6-yl)methyl)-3-methyl-1H-pyrazole-4-carboxamido)methyl)-4,6-dimethylpyridin-2-yl)carbamate (230 mg, 57%) as a white solid.

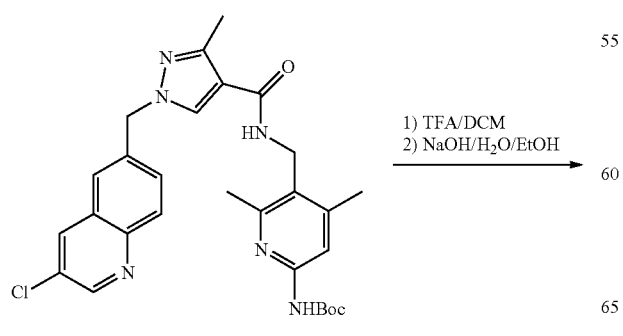

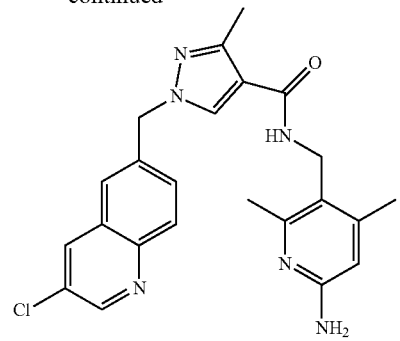

A mixture of tert-butyl (5-((1-((3-chloroquinolin-6-yl)methyl)-3-methyl-1H-pyrazole-4-carboxamido)methyl)-4,6-dimethylpyridin-2-yl)carbamate (230 mg, 0.43 mmol) in TFA/DCM (10 mL, v/v=1/1) was stirred at rt for 3 h. The mixture was concentrated to remove volatile solvent. The resulting residue was suspended in EtOH (5 mL). A solution of 1 N NaOH solution (5 mL) was added and the resulting mixture was stirred at rt for 3 h. The resulting precipitate was collected by filtration and washed with H2O. The white solid was dried under reduced pressure to give N-((6-amino-2,4-dimethylpyridin-3-yl)methyl)-1-((3-chloroquinolin-6-yl)methyl)-3-methyl-1H-pyrazole-4-carboxamide (84.4 mg, 45%). LRMS (M+H+) m/z calculated 435.2, found 435.0. 1H NMR (DMSO-d6, 400 MHz): δ 8.87 (d, 1H), 8.58 (d, 1H), 8.26 (s, 1H), 8.03 (d, 1H), 7.82 (d, 1H), 7.73 (t, 1H), 7.63 (dd, 1H), 6.12 (s, 1H), 5.68 (s, 2H), 5.44 (s, 2H), 4.23 (d, 2H), 2.32 (s, 3H), 2.29 (s, 3H), 2.16 (s, 3H).

Example 39: Preparation of N-((6-amino-2,4-dimethylpyridin-3-yl)methyl)-1-((3-chloroquinolin-6-yl)methyl)-3-methoxy-1H-pyrazole-4-carboxamide

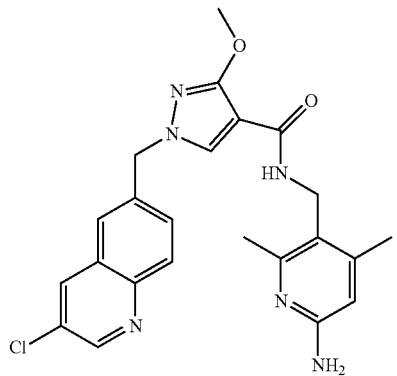

N-((6-amino-2,4-dimethylpyridin-3-yl)methyl)-1-((3-chloroquinolin-6-yl)methyl)-3-methoxy-1H-pyrazole-4-carboxamide

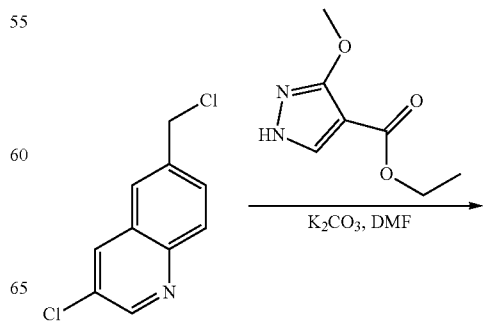

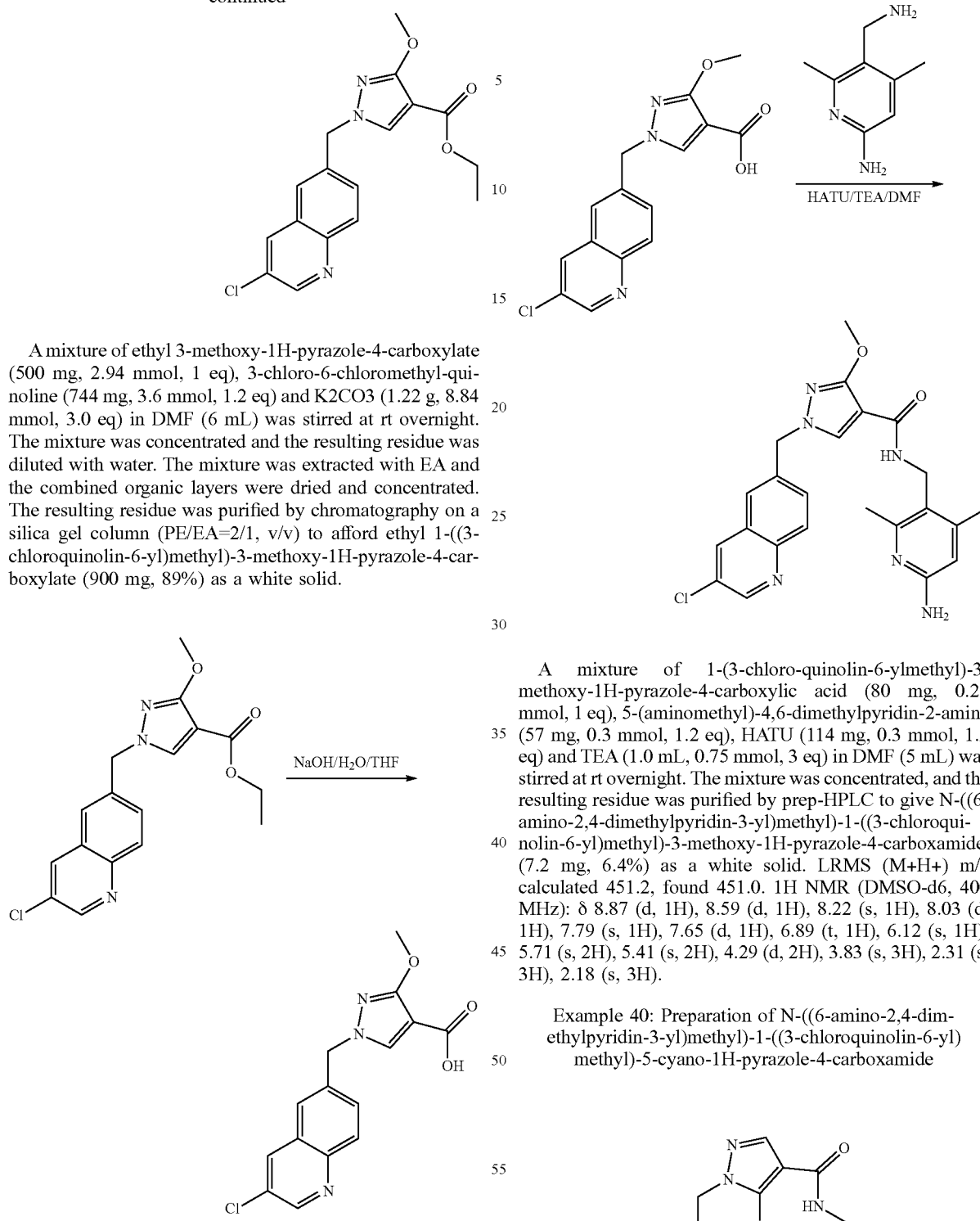

A mixture of ethyl 3-methoxy-1H-pyrazole-4-carboxylate (500 mg, 2.94 mmol, 1 eq), 3-chloro-6-chloromethyl-quinoline (744 mg, 3.6 mmol, 1.2 eq) and K2CO3 (1.22 g, 8.84 mmol, 3.0 eq) in DMF (6 mL) was stirred at rt overnight. The mixture was concentrated and the resulting residue was diluted with water. The mixture was extracted with EA and the combined organic layers were dried and concentrated. The resulting residue was purified by chromatography on a silica gel column (PE/EA=2/1, v/v) to afford ethyl 1-((3-chloroquinolin-6-yl)methyl)-3-methoxy-1H-pyrazole-4-carboxylate (900 mg, 89%) as a white solid.

A mixture of ethyl 1-((3-chloroquinolin-6-yl)methyl)-3-methoxy-1H-pyrazole-4-carboxylate (200 mg, 0.58 mmol, 1 eq) and NaOH (60 mg, 1.5 mmol, 2.59 eq) in i-PrOH/H2O (15 mL, v/v=2/1) was stirred at 100° C. for 36 h. After cooling to rt, the mixture was neutralized to pH 5 with HCl (1 N). The resulting precipitate was collected by filtration to give 1-(3-chloro-quinolin-6-ylmethyl)-3-methoxy-1H-pyrazole-4-carboxylic acid (156 mg, 85%) as a white solid.

A mixture of 1-(3-chloro-quinolin-6-ylmethyl)-3-methoxy-1H-pyrazole-4-carboxylic acid (80 mg, 0.25 mmol, 1 eq), 5-(aminomethyl)-4,6-dimethylpyridin-2-amine (57 mg, 0.3 mmol, 1.2 eq), HATU (114 mg, 0.3 mmol, 1.2 eq) and TEA (1.0 mL, 0.75 mmol, 3 eq) in DMF (5 mL) was stirred at rt overnight. The mixture was concentrated, and the resulting residue was purified by prep-HPLC to give N-((6-amino-2,4-dimethylpyridin-3-yl)methyl)-1-((3-chloroquinolin-6-yl)methyl)-3-methoxy-1H-pyrazole-4-carboxamide (7.2 mg, 6.4%) as a white solid. LRMS (M+H+) m/z calculated 451.2, found 451.0. 1H NMR (DMSO-d6, 400 MHz): δ 8.87 (d, 1H), 8.59 (d, 1H), 8.22 (s, 1H), 8.03 (d, 1H), 7.79 (s, 1H), 7.65 (d, 1H), 6.89 (t, 1H), 6.12 (s, 1H), 5.71 (s, 2H), 5.41 (s, 2H), 4.29 (d, 2H), 3.83 (s, 3H), 2.31 (s, 3H), 2.18 (s, 3H).

Example 40: Preparation of N-((6-amino-2,4-dimethylpyridin-3-yl)methyl)-1-((3-chloroquinolin-6-yl)methyl)-5-cyano-1H-pyrazole-4-carboxamide N-((6-amino-2,4-dimethylpyridin-3-yl)methyl)-1-((3-chloroquinolin-6-yl)methyl)-5-cyano-1H-pyrazole-4-carboxamide -continued

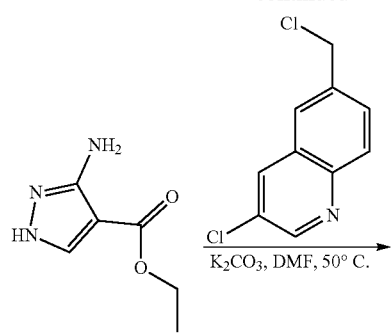

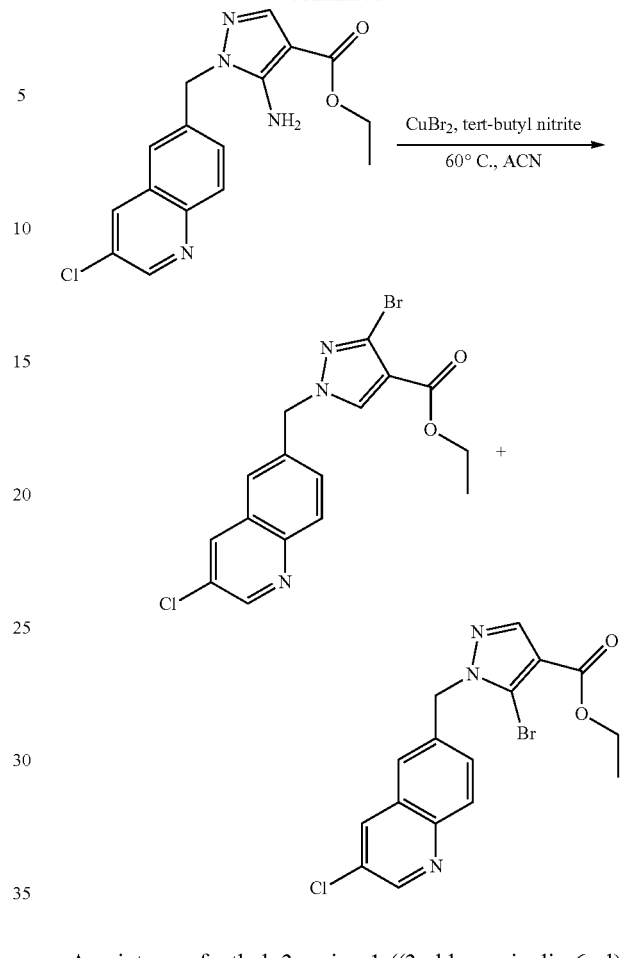

To a solution of ethyl 3-amino-1H-pyrazole-4-carboxylate (45 g, 0.29 mol, 1.0 eq) and 3-chloro-6-chloromethyl-quinoline (61.5 g, 0.29 mol, 1.0 eq) in DMF (900 mL) was added K2CO3 (80.0 g, 0.58 mol, 2.0 eq). The mixture was stirred at 50° C. for 18 h, and then concentrated. The resulting residue was portioned with water. The yellow solid was filtered and triturated with PE/EA (1500 mL, v/v=2/1) to give ethyl 3-amino-1-((3-chloroquinolin-6-yl)methyl)-1H-pyrazole-4-carboxylate and ethyl 5-amino-1-((3-chloroquinolin-6-yl)methyl)-1H-pyrazole-4-carboxylate (69 g, 72%).

A mixture of ethyl 3-amino-1-((3-chloroquinolin-6-yl)methyl)-1H-pyrazole-4-carboxylate and ethyl 5-amino-1-((3-chloroquinolin-6-yl)methyl)-1H-pyrazole-4-carboxylate (62.4 g, 0.189 mol, 1.0 eq), tert-butyl nitrite (29.2 g, 0.284 mol, 1.5 eq), and CuBr2 (84.3 g, 0.378 mol, 2.0 eq) in ACN (2000 mL) was stirred at 60° C. for 18 h. The reaction solution was cooled to rt, adjusted to pH 3~4 with HCl (1 N) and stirred for 30 min. The reaction solution was further adjusted to pH 7 with NaOH (1 N), mixed with 5 L of water, and extracted with EA (5 L×2). The organic layers were combined and concentrated, and the resulting residue was purified by chromatography on a silica gel column (PE/EA=9/1 to 6/1, v/v) to give ethyl 5-bromo-1-((3-chloroquinolin-6-yl)methyl)-1H-pyrazole-4-carboxylate (8.3 g, 11%) and ethyl 3-bromo-1-((3-chloroquinolin-6-yl)methyl)-1H-pyrazole-4-carboxylate (12.0 g, 16%).

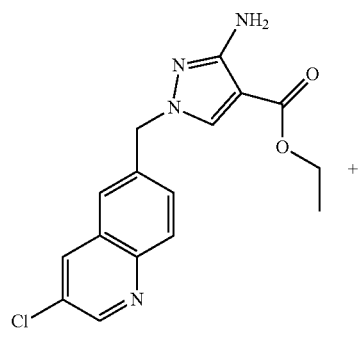

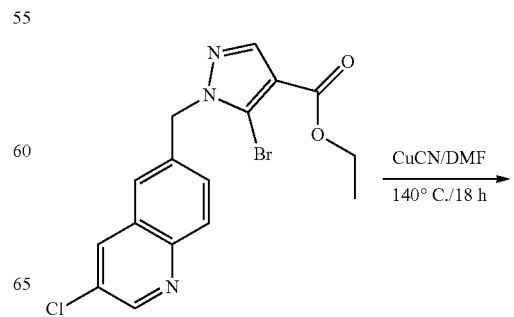

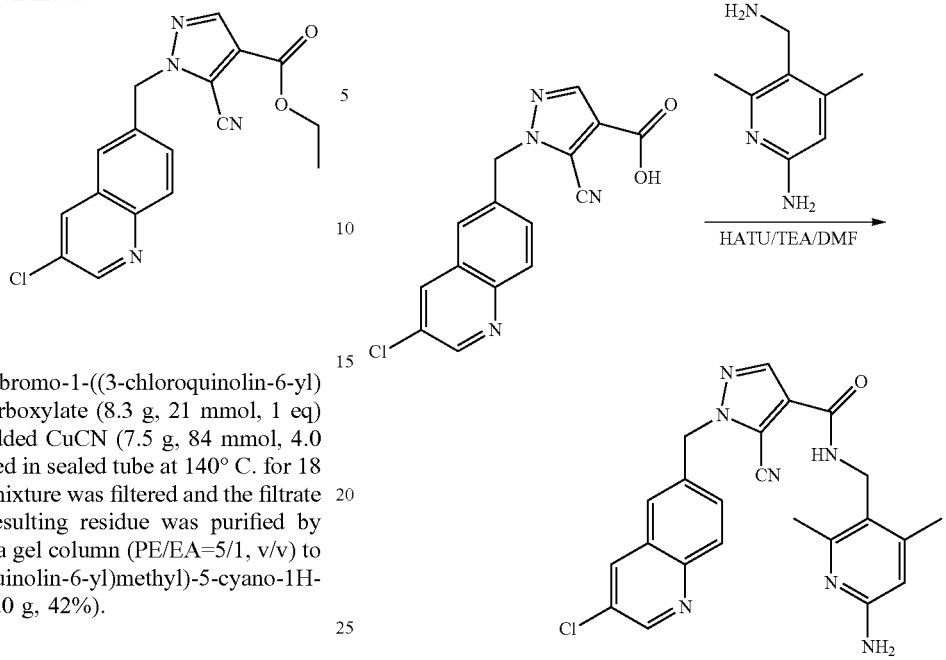

To a solution of ethyl 5-bromo-1-((3-chloroquinolin-6-yl)methyl)-1H-pyrazole-4-carboxylate (8.3 g, 21 mmol, 1 eq) in DMF (160 mL) was added CuCN (7.5 g, 84 mmol, 4.0 eq). The mixture was stirred in sealed tube at 140° C. for 18 h. After cooling to rt, the mixture was filtered and the filtrate was concentrated. The resulting residue was purified by chromatography on a silica gel column (PE/EA=5/1, v/v) to give ethyl 1-((3-chloroquinolin-6-yl)methyl)-5-cyano-1H-pyrazole-4-carboxylate (3.0 g, 42%).

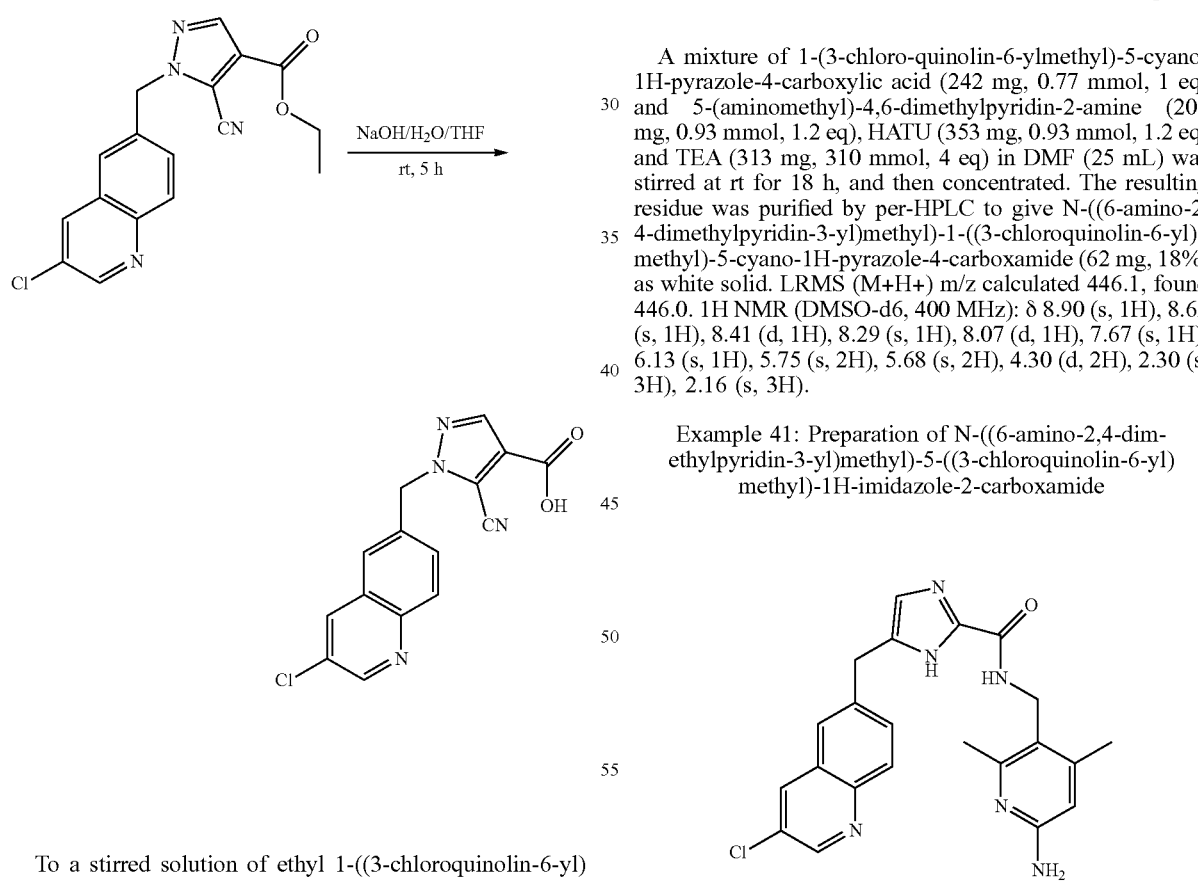

To a stirred solution of ethyl 1-((3-chloroquinolin-6-yl)methyl)-5-cyano-1H-pyrazole-4-carboxylate (340 mg, 1.0 mmol, 1 eq) in THF/H2O (20 mL/10 mL) was added NaOH (80 mg, 2.0 mmol, 2 eq) in H2O (3 mL). The mixture was stirred at rt for 2 h, then adjusted to pH 3 with HCl (1 N), and concentrated. The resulting precipitate was filtered. The solid was dried under reduce pressure to give 1-(3-chloro-quinolin-6-ylmethyl)-5-cyano-1H-pyrazole-4-carboxylic acid (242 mg, 77.3%).

A mixture of 1-(3-chloro-quinolin-6-ylmethyl)-5-cyano-1H-pyrazole-4-carboxylic acid (242 mg, 0.77 mmol, 1 eq) and 5-(aminomethyl)-4,6-dimethylpyridin-2-amine (208 mg, 0.93 mmol, 1.2 eq), HATU (353 mg, 0.93 mmol, 1.2 eq) and TEA (313 mg, 310 mmol, 4 eq) in DMF (25 mL) was stirred at rt for 18 h, and then concentrated. The resulting residue was purified by per-HPLC to give N-((6-amino-2,4-dimethylpyridin-3-yl)methyl)-1-((3-chloroquinolin-6-yl)methyl)-5-cyano-1H-pyrazole-4-carboxamide (62 mg, 18%) as white solid. LRMS (M+H+) m/z calculated 446.1, found 446.0. 1H NMR (DMSO-d6, 400 MHz): δ 8.90 (s, 1H), 8.62 (s, 1H), 8.41 (d, 1H), 8.29 (s, 1H), 8.07 (d, 1H), 7.67 (s, 1H), 6.13 (s, 1H), 5.75 (s, 2H), 5.68 (s, 2H), 4.30 (d, 2H), 2.30 (s, 3H), 2.16 (s, 3H).

Example 41: Preparation of N-((6-amino-2,4-dimethylpyridin-3-yl)methyl)-5-((3-chloroquinolin-6-yl)methyl)-1H-imidazole-2-carboxamide N-((6-amino-2,4-dimethylpyridin-3-yl)methyl)-5-((3-chloroquinolin-6-yl)methyl)-1H-imidazole-2-carboxamide

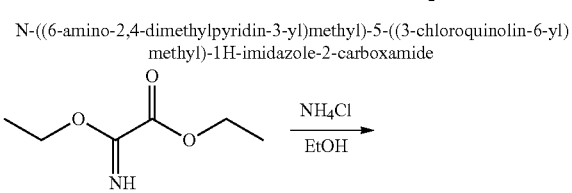

-continued

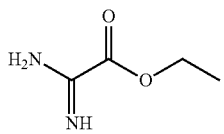

A mixture of ethyl 2-ethoxy-2-iminoacetate (2.5 g, 17.22 mmol, 1.0 eq) and NH4Cl (738 mg, 13.78 mmol, 0.8 eq) in EtOH (60 mL) was stirred at rt overnight. The reaction solution was filtered. The filtrate was concentrated and the residue was washed with acetone. The resulting residue was dried in vacuo to afford ethyl 2-amino-2-iminoacetate (1.8 g, 69%) as a white solid. 1H NMR (DMSO-d6, 300 MHz): δ 9.76 (br, 4H), 4.35 (q, 2H), 1.31 (t, 3H).

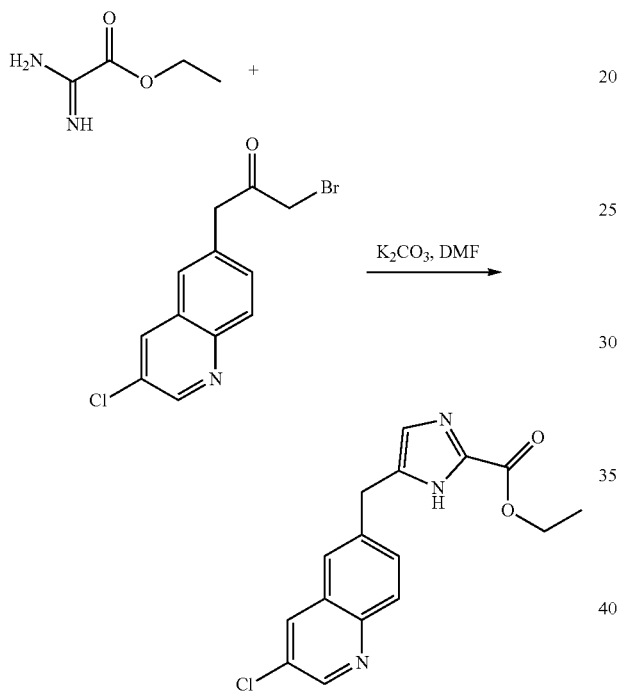

A mixture of 1-bromo-3-(3-chloroquinolin-6-yl)propan-2-one (1.0 g, 3.35 mmol, 1.0 eq), ethyl 2-amino-2-iminoacetate (389 mg, 3.35 mmol, 1.0 eq) and K2CO3 (925 mg, 6.70 mmol, 2.0 eq) in DMF (10 mL) was stirred at 50° C. for overnight. The mixture was concentrated, and the resulting residue was purified by chromatography on a silica gel column (PE/EA=3/1, v/v) to afford ethyl 5-((3-chloroquinolin-6-yl)methyl)-1H-imidazole-2-carboxylate (120 mg, 11%) as a white solid.

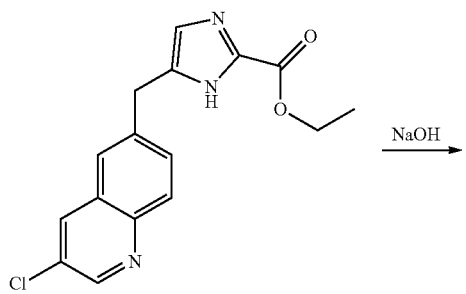

-continued

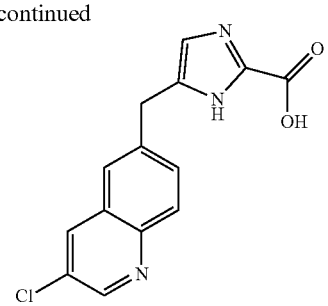

To a solution of ethyl 5-((3-chloroquinolin-6-yl)methyl)-1H-imidazole-2-carboxylate (120 mg, 0.38 mmol, 1.0 eq) in THF (10 mL) was added a solution of NaOH (30 mg, 0.76 mmol, 2.0 eq) in H2O (10 mL) at rt. The mixture was stirred at rt overnight. The solution was neutralized with HCl (1 N). The mixture was concentrated to afford 5-(3-chloro-quinolin-6-ylmethyl)-1H-imidazole-2-carboxylic acid (120 mg, crude) as a yellow solid.

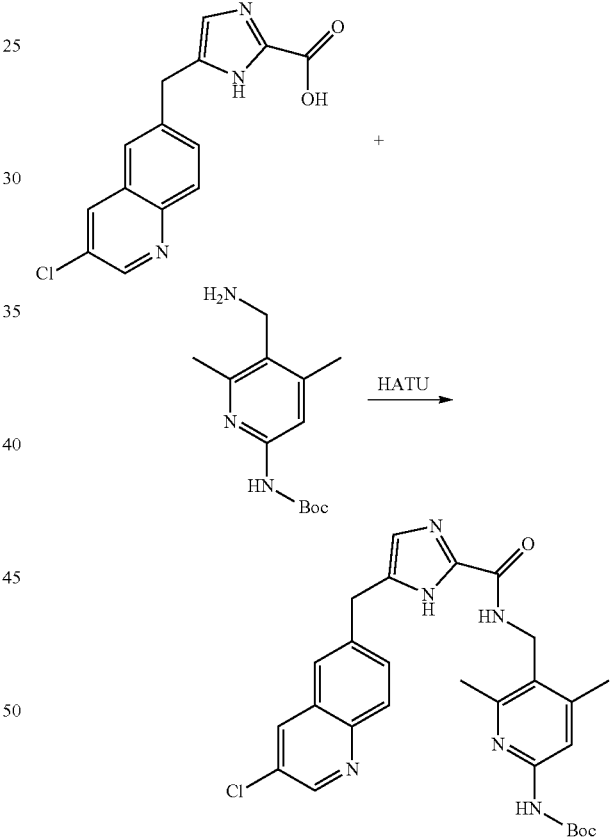

A mixture of 5-(3-chloro-quinolin-6-ylmethyl)-1H-imidazole-2-carboxylic acid (120 mg crude, 0.38 mmol, 1.0 eq), tert-butyl (5-(aminomethyl)-4,6-dimethylpyridin-2-yl)carbamate (143 mg, 0.57 mmol, 1.5 eq), HATU (216 mg, 0.57 mmol, 1.5 eq) and Et3N (115 mg, 1.14 mmol, 3.0 eq) in DMF (4 mL) was stirred at rt for 2 h. The mixture was concentrated, and the resulting residue was purified by chromatography on a silica gel column (DCM/MeOH=20/1, v/v) to afford tert-butyl (5-((5-((3-chloroquinolin-6-yl)methyl)-1H-imidazole-2-carboxamido)methyl)-4,6-dimethylpyridin-2-yl)carbamate (40 mg, 20%) as a white solid.

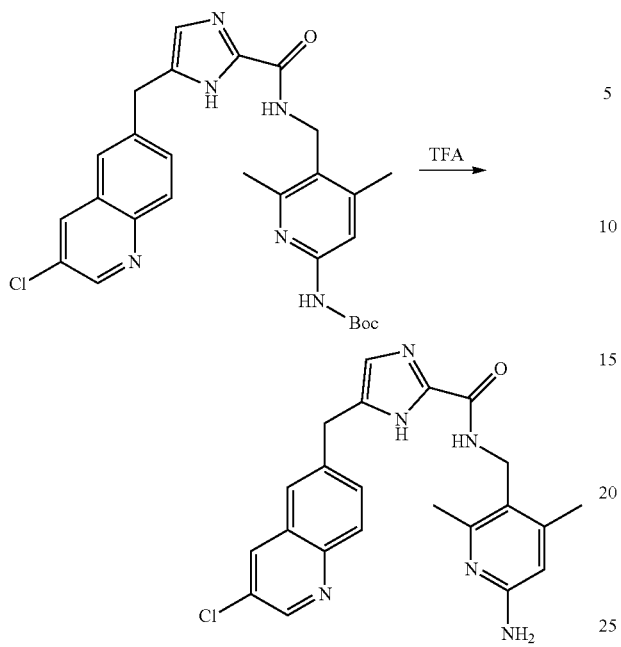

To a solution of tert-butyl (5-((5-((3-chloroquinolin-6-yl)methyl)-1H-imidazole-2-carboxamido)methyl)-4,6-dimethylpyridin-2-yl)carbamate (40 mg, 0.077 mmol, 1.0 eq) in DCM (4 mL) was added TFA (2 mL) at rt. The mixture was stirred at rt overnight. The solution was concentrated, and the resulting residue was purified by prep-HPLC to afford N-((6-amino-2,4-dimethylpyridin-3-yl)methyl)-5-((3-chloroquinolin-6-yl)methyl)-1H-imidazole-2-carboxamide (15 mg, 47%) as a white solid. LRMS (M+H+) m/z calculated 421.1, found 421.0. 1H NMR (DMSO-d6, 400 MHz): δ 13.02 (s, 0.4H), 12.84 (s, 0.6H), 8.82 (d, 0.4H), 8.80 (d, 0.6H), 8.51 (d, 0.4H), 8.48 (d, 0.6H), 8.04 (t, 1H), 7.97 (d, 0.4H), 7.95 (d, 0.6H), 7.77 (s, 0.4H), 7.75 (s, 0.6H), 7.71-7.67 (m, 1H), 7.06 (d, 0.6H), 6.79 (s, 0.4H), 6.09 (s, 1H), 5.66 (s, 2H), 4.30 (d, 2H), 4.13 (s, 0.8H), 4.04 (s, 1.2H), 2.31 (s, 1.2H), 2.30 (s, 1.8H), 2.19 (s, 1.2H), 2.18 (s, 1.8H).

Example 42: Preparation of N-((5-chloro-1H-indazol-3-yl)methyl)-5-((3-chloroquinolin-6-yl)methyl)-1,3,4-oxadiazole-2-carboxamide

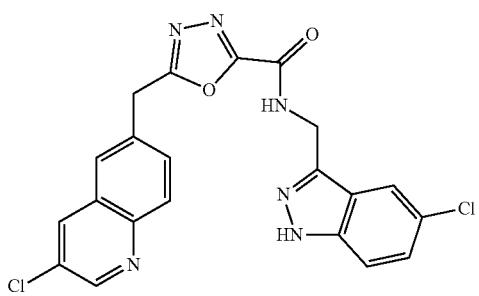

N-((5-chloro-1H-indazol-3-yl)methyl)-5-((3-chloroquinolin-6-yl)methyl)-1,3,4-oxadiazole-2-carboxamide

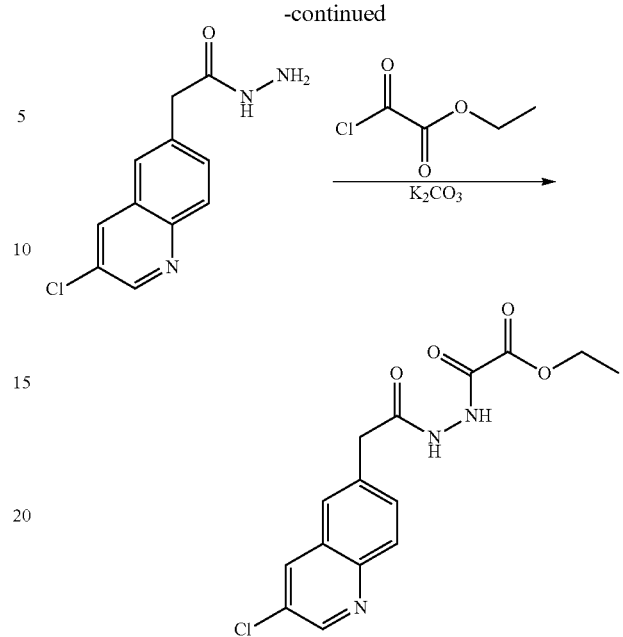

To a solution of (3-chloro-quinolin-6-yl)-acetic acid hydrazide (1.5 g, 5.51 mmol, 1.0 eq) and K2CO3 (2.3 g, 16.53 mmol, 3.0 eq) in ACN (40 mL) was added chloro-oxo-acetic acid ethyl ester (1.5 g, 11.02 mmol, 2.0 eq) at rt. The mixture was stirred at rt for 2 days. Water (30 mL) was added and the formed precipitate was filtered. The solid was washed with water (20 mL), MeOH (20 mL) and EA (20 mL) sequentially and dried in vacuo to afford {N'-[2-(3-chloro-quinolin-6-yl)-acetyl]-hydrazino}-oxo-acetic acid ethyl ester (1.4 g, 78%) as a white solid.

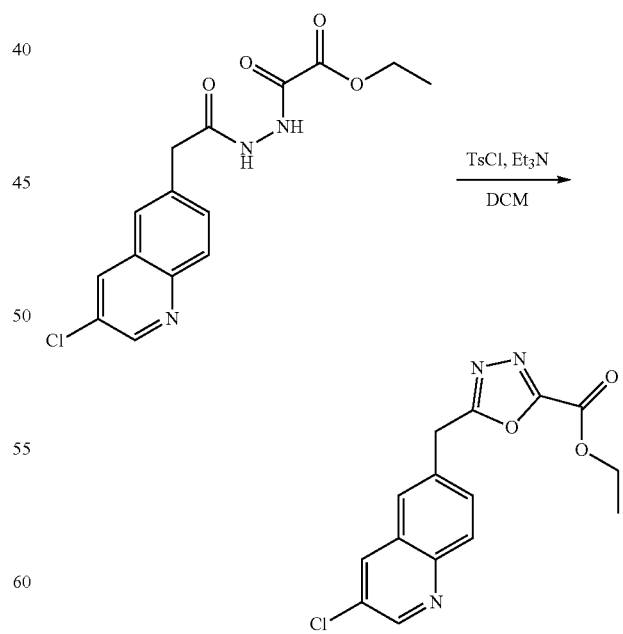

To a solution of {N'-[2-(3-chloro-quinolin-6-yl)-acetyl]-hydrazino}-oxo-acetic acid ethyl ester (1.4 g, 4.17 mmol, 1.0 eq) in DCM (40 mL) was added TsCl (953 mg, 5.00 mmol, 1.2 eq) and Et3N (547 mg, 5.42 mmol, 1.3 eq) at rt.

The mixture was stirred at rt overnight. The mixture was concentrated and the resulting residue was purified by chromatography on a silica gel column (PE/EA=3/1, v/v) to afford 5-(3-chloro-quinolin-6-ylmethyl)-[1,3,4]oxadiazole-2-carboxylic acid ethyl ester (950 mg, 72%) as a white solid.

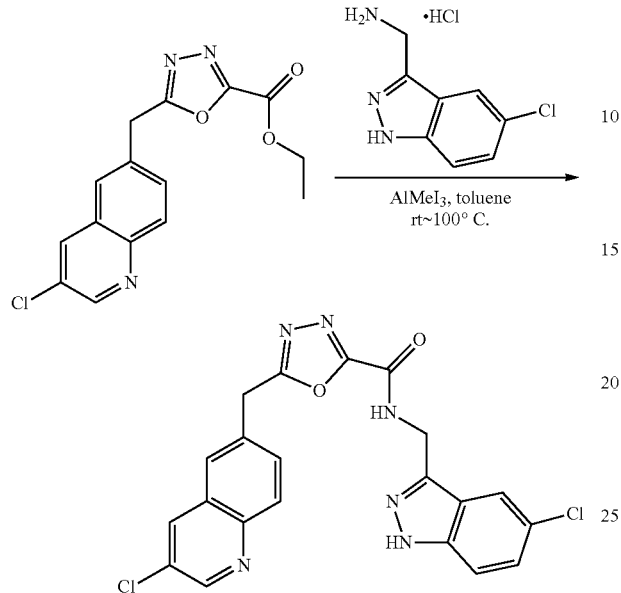

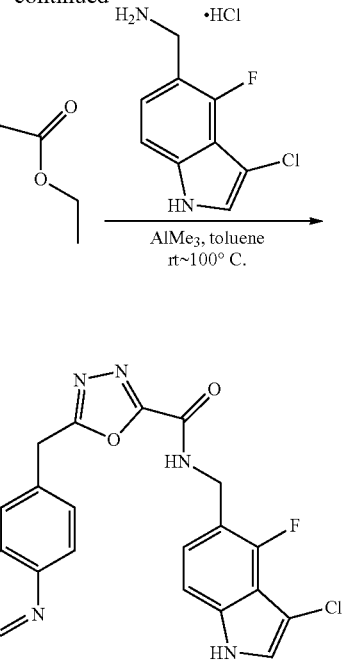

To a solution of (5-chloro-1H-indazol-3-yl)methanamine hydrochloride (213 mg, 0.98 mmol, 3.1 eq) in toluene (10 mL) was added AlMe3 (2 M in toluene, 0.5 mL, 0.98 mmol, 3.1 eq) at 0° C. The mixture was stirred at rt for 1 h. Then 5-(3-chloro-quinolin-6-ylmethyl)-[1,3,4]oxadiazole-2-carboxylic acid ethyl ester mixture (100 mg, 0.31 mmol, 1.0 eq) was added and heated at 100° C. overnight. After cooling to rt, water (10 mL) was added and the mixture was extracted with EA (30 mL×3). The organic layers were dried over Na2SO4, filtered and concentrated. The resulting residue was purified by chromatography on a silica gel column (PE/EA=1/1 to EA, v/v) to afford N-((5-chloro-1H-indazol-3-yl)methyl)-5-((3-chloroquinolin-6-yl)methyl)-1,3,4-oxadiazole-2-carboxamide (10 mg, 7%) as a white solid. LRMS (M+H+) m/z calculated 453.1, found 452.9.

1H NMR (DMSO-d6, 400 MHz): δ 13.07 (s, 1H), 9.91 (t, 1H), 8.88 (d, 1H), 8.56 (d, 1H), 8.04 (d, 1H), 7.96 (d, 1H), 7.92 (d, 1H), 7.77 (dd, 1H), 7.33 (dd, 1H), 4.74 (d, 2H), 4.60 (s, 2H).

Example 43: Preparation of N-((3-chloro-4-fluoro-1H-indol-5-yl)methyl)-5-((3-chloroquinolin-6-yl)methyl)-1,3,4-oxadiazole-2-carboxamide To a solution of (3-chloro-4-fluoro-1H-indol-5-yl)methanamine hydrochloride (229 mg, 0.98 mmol, 3.1 eq) in toluene (10 mL) was added AlMe3 (2 M in toluene, 0.5 mL, 0.98 mmol, 3.1 eq) at 0° C. The mixture was stirred at rt for 1 h. Then 5-(3-chloro-quinolin-6-ylmethyl)-[1,3,4]oxadiazole-2-carboxylic acid ethyl ester mixture (100 mg, 0.31 mmol, 1.0 eq) was added and heated at 100° C. overnight. After cooling to rt, water (10 mL) was added and the mixture was extracted with EA (30 mL×3). The organic layers were dried over Na2SO4, filtered and concentrated. The resulting residue was purified by chromatography on a silica gel column (PE/EA=1/1 to EA, v/v) to afford N-((3-chloro-4-fluoro-1H-indol-5-yl)methyl)-5-((3-chloroquinolin-6-yl)methyl)-1,3,4-oxadiazole-2-carboxamide (55 mg, 38%) as a white solid. LRMS (M+H+) m/z calculated 470.1, found 469.9. 1H NMR (DMSO-d6, 400 MHz): δ 11.57 (s, 1H), 9.77 (t, 1H), 8.88 (d, 1H), 8.56 (d, 1H), 8.04 (d, 1H), 7.92 (d, 1H), 7.79-7.76 (m, 1H), 7.50 (d, 1H), 7.19-7.12 (m, 2H), 4.60 (s, 2H), 4.54 (d, 2H).

Example 44: Preparation of N-((3-chloro-6-fluoro-1H-indol-5-yl)methyl)-5-((3-chloroquinolin-6-yl)methyl)-1,3,4-oxadiazole-2-carboxamide

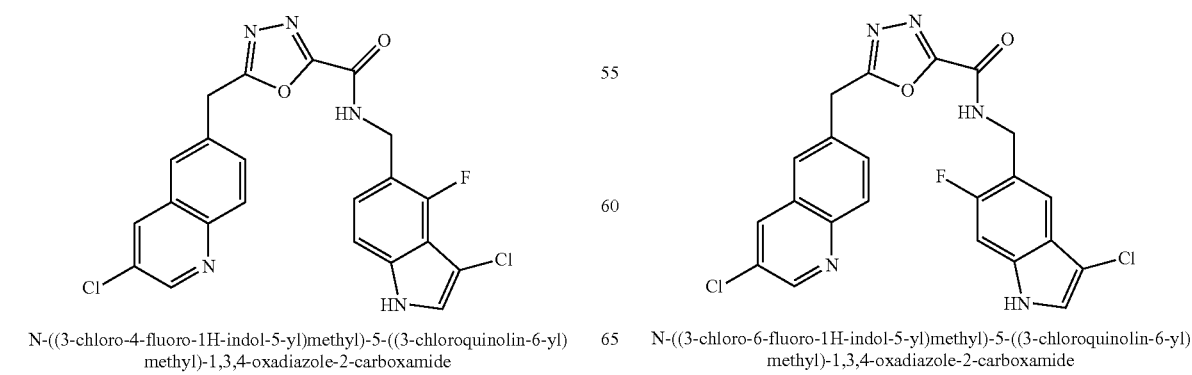

N-((3-chloro-4-fluoro-1H-indol-5-yl)methyl)-5-((3-chloroquinolin-6-yl)methyl)-1,3,4-oxadiazole-2-carboxamide N-((3-chloro-6-fluoro-1H-indol-5-yl)methyl)-5-((3-chloroquinolin-6-yl)methyl)-1,3,4-oxadiazole-2-carboxamide -continued

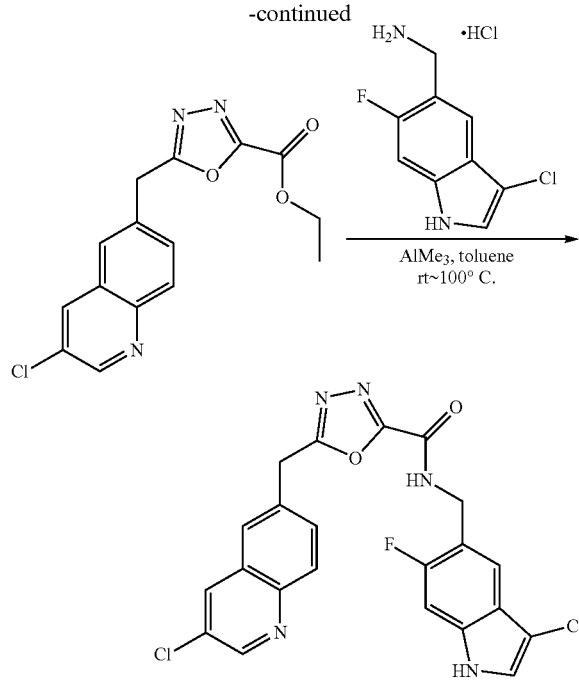

To a solution of (3-chloro-6-fluoro-1H-indol-5-yl)methanamine hydrochloride (342 mg, 1.46 mmol, 3.1 eq) in toluene (15 mL) was added AlMe3 (2 M in toluene, 0.73 mL, 1.46 mmol, 3.1 eq) at 0° C. The mixture was stirred at rt for 1 h. Then 5-(3-chloro-quinolin-6-ylmethyl)-[1,3,4]oxadiazole-2-carboxylic acid ethyl ester mixture (150 mg, 0.47 mmol, 1.0 eq) was added and heated at 100° C. overnight. After cooling to rt, water (10 mL) was added and the mixture was extracted with EA (30 mL×3). The organic layers were dried over Na2SO4, filtered and concentrated. The resulting residue was purified by chromatography on a silica gel column (PE/EA=1/1 to EA, v/v) to afford N-((3-chloro-6-fluoro-1H-indol-5-yl)methyl)-5-((3-chloroquinolin-6-yl) methyl)-1,3,4-oxadiazole-2-carboxamide (70 mg, 32%) as a white solid. LRMS (M+H+) m/z calculated 470.1, found 469.9. 1H NMR (DMSO-d6, 400 MHz): δ 11.39 (s, 1H), 9.80 (t, 1H), 8.88 (d, 1H), 8.56 (d, 1H), 8.05 (d, 1H), 7.94 (d, 1H), 7.78 (dd, 1H), 7.51-7.46 (m, 2H), 7.22 (d, 1H), 4.61 (s, 2H), 4.56 (d, 2H).

Example 45: Preparation of N-((3-chloro-1H-pyrrolo[2,3-b]pyridin-5-yl)methyl)-5-((3-chloroquinolin-6-yl)methyl)-1,3,4-oxadiazole-2-carboxamide

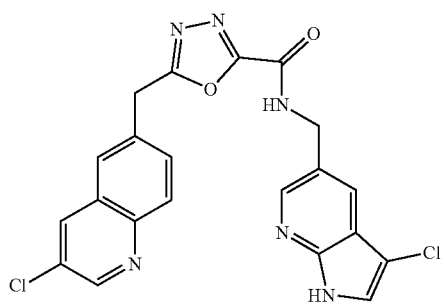

N-((3-chloro-1H-pyrrolo[2,3-b]pyridin-5-yl)methyl)-5-((3-chloroquinolin-6-yl)methyl)-1,3,4-oxadiazole-2-carboxamide -continued

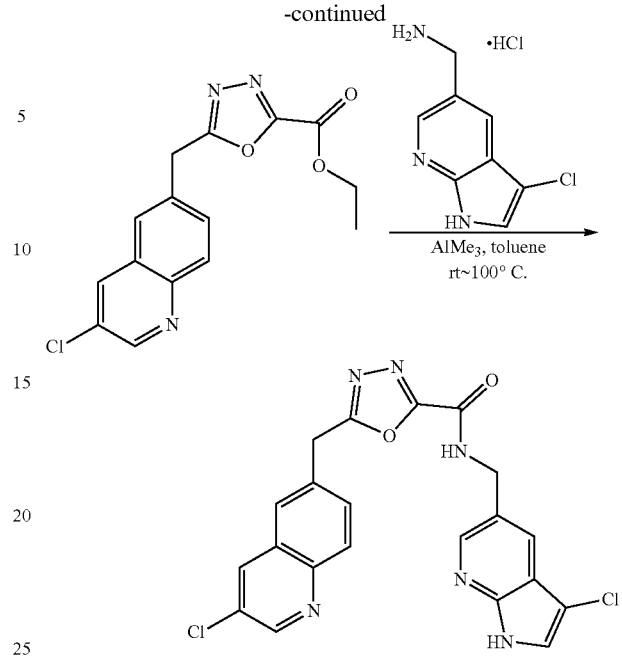

To a solution of (3-chloro-1H-pyrrolo[2,3-b]pyridin-5-yl) methanamine hydrochloride (317 mg, 1.46 mmol, 3.1 eq) in toluene (15 mL) was added AlMe3 (2 M in toluene, 0.73 mL, 1.46 mmol, 3.1 eq) at 0° C. The mixture was stirred at rt for 1 h. Then 5-(3-chloro-quinolin-6-ylmethyl)-[1,3,4]oxadiazole-2-carboxylic acid ethyl ester (150 mg, 0.47 mmol, 1.0 eq) was added and heated at 100° C. overnight. After cooling to rt, water (10 mL) was added and the mixture was extracted with EA (30 mL×3). The organic layers were dried over Na2SO4, filtered and concentrated. The resulting residue was purified by chromatography on a silica gel column (PE/EA=1/1 to EA, v/v) to afford N-((3-chloro-1H-pyrrolo[2,3-b]pyridin-5-yl)methyl)-5-((3-chloroquinolin-6-yl) methyl)-1,3,4-oxadiazole-2-carboxamide (32 mg, 15%) as a white solid. LRMS (M+H+) m/z calculated 453.1, found 452.9. 1H NMR (DMSO-d6, 400 MHz): δ 11.96 (s, 1H), 9.88 (t, 1H), 8.88 (d, 1H), 8.56 (d, 1H), 8.30 (d, 1H), 8.05 (d, 1H), 7.92-7.89 (m, 2H), 7.78-7.76 (m, 1H), 7.67 (d, 1H), 4.60 (s, 2H), 4.56 (d, 2H).

Example 46: Preparation of N-((1-aminoisoquinolin-6-yl)methyl)-5-((3-chloroquinolin-6-yl)methyl)-1,3,4-oxadiazole-2-carboxamide

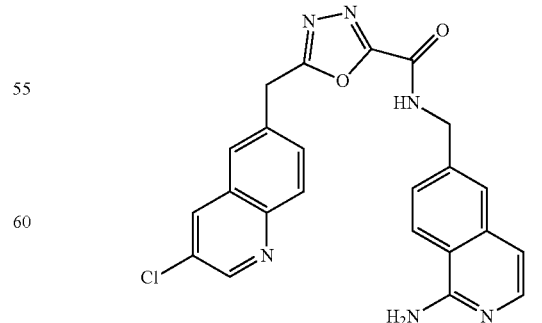

N-((1-aminoisoquinolin-6-yl)methyl)-5-((3-chloroquinolin-6-yl)methyl)-1,3,4-oxadiazole-2-carboxamide -continued

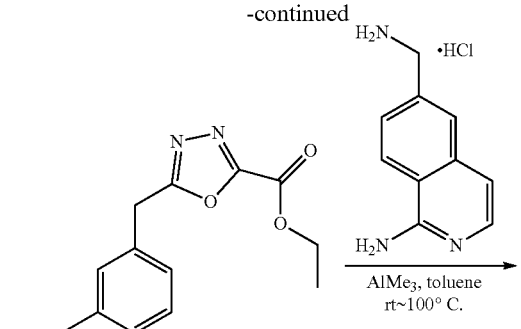

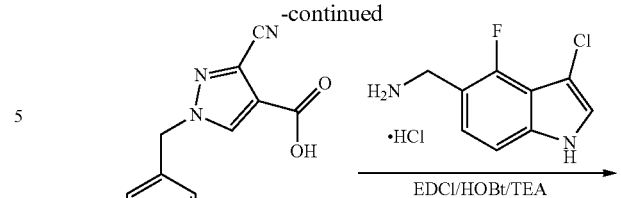

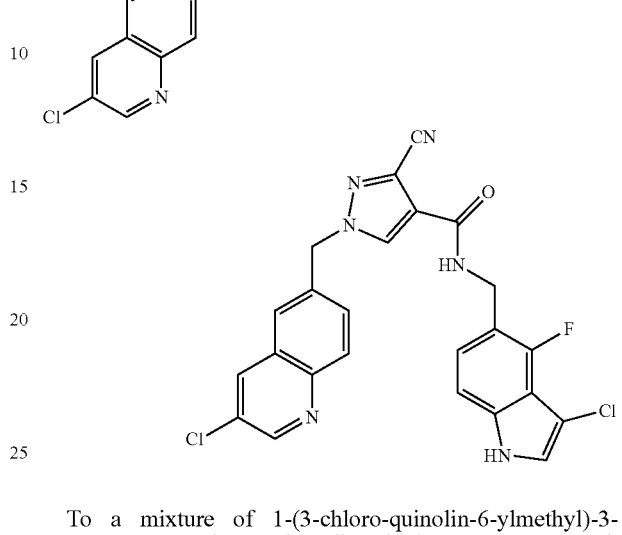

To a solution of 6-aminomethyl-isoquinolin-1-ylamine hydrochloride (205 mg, 0.98 mmol, 3.1 eq) in toluene (10 mL) was added AlMe3 (2 M in toluene, 0.5 mL, 0.98 mmol, 3.1 eq) at 0° C. The mixture was stirred at rt for 1 h. Then 5-(3-chloro-quinolin-6-ylmethyl)-[1,3,4]oxadiazole-2-carboxylic acid ethyl ester (100 mg, 0.31 mmol, 1.0 eq) was added and heated at 100° C. overnight. After cooling to rt, water (10 mL) was added and the mixture was extracted with EA (30 mL*3). The organic layers were dried over Na2SO4, filtered and concentrated. The resulting residue was purified by chromatography on a silica gel column (PE/EA=1/1 to EA, v/v) to afford N-((1-aminoisoquinolin-6-yl)methyl)-5-((3-chloroquinolin-6-yl)methyl)-1,3,4-oxadiazole-2-carboxamide (13 mg, 9.4%) as a white solid. LRMS (M+H+) m/z calculated 445.1, found 445.0. 1H NMR (DMSO-d6, 400 MHz): δ 9.92 (t, 1H), 8.89 (d, 1H), 8.57 (d, 1H), 8.14 (d, 1H), 8.06 (d, 1H), 7.94 (d, 1H), 7.81-7.75 (m, 2H), 7.57 (s, 1H), 7.42-7.39 (m, 1H), 6.80 (s, 2H), 4.62 (s, 2H), 4.57 (d, 2H).

Example 47: Preparation of N-((3-chloro-4-fluoro-1H-indol-5-yl)methyl)-1-((3-chloroquinolin-6-yl)methyl)-3-cyano-1H-pyrazole-4-carboxamide To a mixture of 1-(3-chloro-quinolin-6-ylmethyl)-3-cyano-1H-pyrazole-4-carboxylic acid (100 mg, 0.32 mmol, 1.0 eq) in DMF (5 mL) was added (3-chloro-4-fluoro-1H-indol-5-yl)methanamine hydrochloride (75 mg, 0.32 mmol, 1.0 eq), EDCI (92 mg, 0.48 mmol, 1.5 eq) and HOBt (65 mg, 0.48 mmol, 1.5 eq) and TEA (97 mg, 0.96 mmol, 3.0 eq). The mixture was stirred at 50° C. overnight. Then the mixture was diluted with H2O and extracted with EA. The combined organic layers were washed with NaHCO3 aq, NH4Cl aq, brine, dried over Na2SO4, filtrated and concentrated. The resulting residue was purified by prep-HPLC to give N-((3-chloro-4-fluoro-1H-indol-5-yl)methyl)-1-((3-chloroquinolin-6-yl)methyl)-3-cyano-1H-pyrazole-4-carboxamide (45 mg, 12%) as a white solid. LRMS (M+H+) m/z calculated 493.1, found 492.9. 1H NMR (DMSO-d6, 400 MHz): δ 11.58 (s, 1H), 8.89 (d, 1H), 8.84 (s, 1H), 8.61 (s, 1H), 8.55 (s, 1H), 8.06 (d, 1H), 7.86 (s, 1H), 7.71 (d, 1H), 7.51 (s, 1H), 7.19 (d, 1H), 7.14 (d, 1H), 5.70 (s, 1H), 4.50 (d, 2H).

Example 48: Preparation of N-((5-chloro-1H-indazol-3-yl)methyl)-1-((3-chloroquinolin-6-yl)methyl)-3-cyano-1H-pyrazole-4-carboxamide

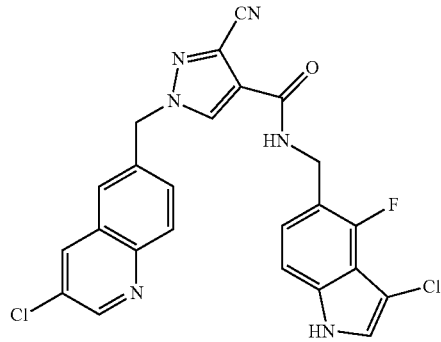

N-((3-chloro-4-fluoro-1H-indol-5-yl)methyl)-1-((3-chloroquinolin-6-yl)methyl)-3-cyano-1H-pyrazole-4-carboxamide

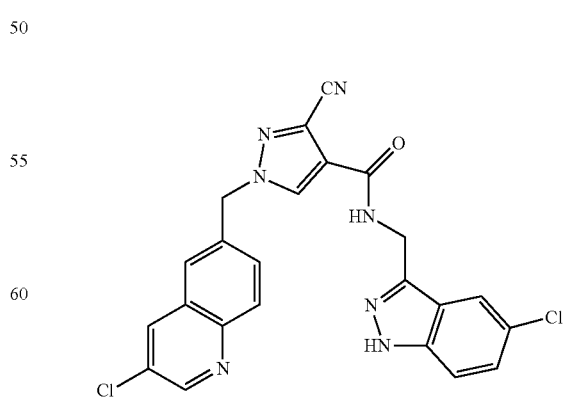

N-((5-chloro-1H-indazol-3-yl)methyl)-1-((3-chloroquinolin-6-yl)methyl)-3-cyano-1H-pyrazole-4-carboxamide

243

-continued

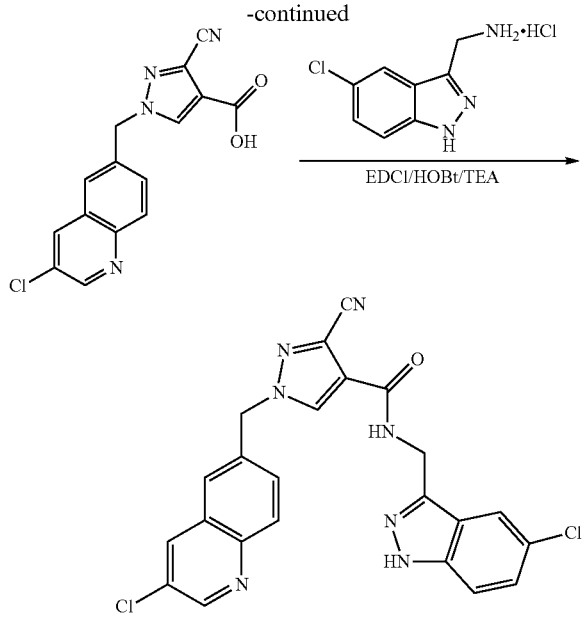

EDCl/HOBt/TEA

To a mixture of 1-(3-chloro-quinolin-6-ylmethyl)-3-cyano-1H-pyrazole-4-carboxylic acid (200 mg, 0.64 mmol, 1.0 eq) in DMF (8 mL) was added (5-chloro-1H-indazol-3-yl)methanamine hydrochloride (141 mg, 0.64 mmol, 1.0 eq), EDCI (184 mg, 0.96 mmol, 1.5 eq) and HOBt (130 mg, 0.96 mmol, 1.5 eq) and TEA (194 mg, 1.92 mmol, 3.0 eq). The mixture was stirred at 50° C. overnight. Then the mixture was diluted with H2O and extracted with EA. The combined organic layers were washed with NaHCO3 aq, NH4Cl aq, brine, dried over Na2SO4, filtrated and concentrated. The resulting residue was purified by prep-HPLC to give N-((5-chloro-1H-indazol-3-yl)methyl)-1-((3-chloroquinolin-6-yl)methyl)-3-cyano-1H-pyrazole-4-carboxamide (35 mg, 12%) as a white solid. LRMS (M+H+) m/z calculated 476.1, found 475.9. 1H NMR (DMSO-d6, 400 MHz): δ 13.10 (s, 1H), 9.03 (s, 1H), 8.91 (s, 1H), 8.61 (s, 1H), 8.55 (d, 1H), 7.88 (d, 2H), 7.71 (d, 1H), 7.53 (d, 1H), 7.33 (d, 1H), 5.71 (s, 2H), 4.72 (d, 2H).

Example 49: Preparation of N-((1-aminoisoquinolin-6-yl)methyl)-1-((3-chloroquinolin-6-yl)methyl)-3-cyano-1H-pyrazole-4-carboxamide

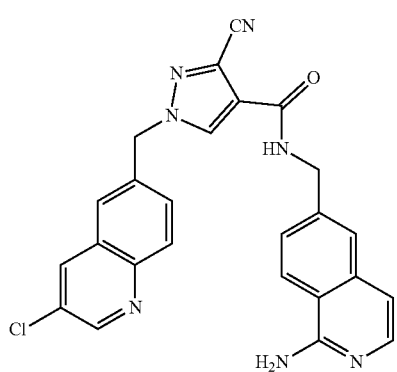

N-((1-aminoisoquinolin-6-yl)methyl)-1-((3-chloroquinolin-6-yl)methyl)-3-cyano-1H-pyrazole-4-carboxamide

244

-continued

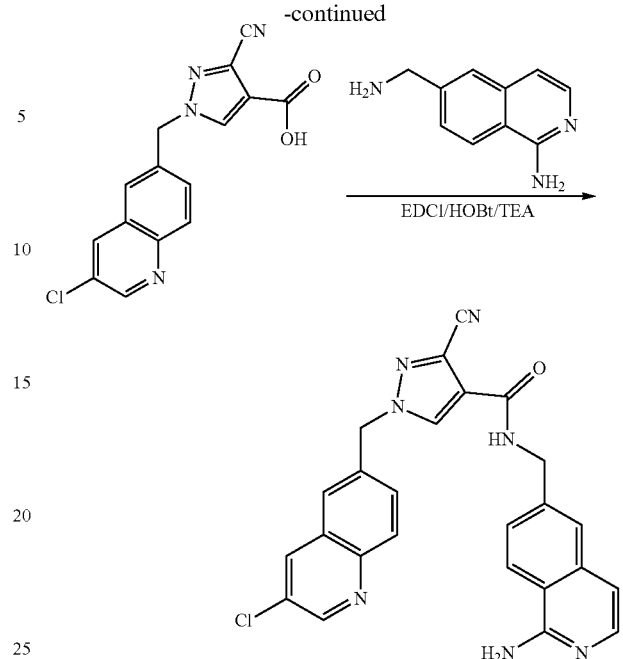

EDCl/HOBt/TEA

To a mixture of 1-(3-chloro-quinolin-6-ylmethyl)-3-cyano-1H-pyrazole-4-carboxylic acid (200 mg, 0.64 mmol, 1.0 eq) in DMF (8 mL) was added 6-aminomethyl-isoquinolin-1-ylamine (111 mg, 0.64 mmol, 1.0 eq), EDCI (184 mg, 0.96 mmol, 1.5 eq) and HOBt (130 mg, 0.96 mmol, 1.5 eq) and TEA (194 mg, 1.92 mmol, 3.0 eq). The mixture was stirred at 50° C. overnight. Then the mixture was diluted with H2O and extracted with EA. The combined organic layers were washed with aq. NaHCO3, aq. NH4Cl, brine, dried over Na2SO4, filtrated and concentrated. The resulting residue was purified by prep-HPLC to give N-((1-aminoisoquinolin-6-yl)methyl)-1-((3-chloroquinolin-6-yl)methyl)-3-cyano-1H-pyrazole-4-carboxamide (102 mg, 34%) as a white solid. LRMS (M+H+) m/z calculated 468.1, found 468.0. 1H NMR (DMSO-d6, 400 MHz): δ13.38 (s, 1H), 9.36 (s, 1H), 9.17 (s, 2H), 8.92 (s, 1H), 8.75 (s, 1H), 8.64 (s, 1H), 8.58 (d, 1H), 8.09 (d, 1H), 7.92 (s, 1H), 7.91 (s, 1H), 7.74 (d, 3H), 7.20 (d, 1H), 5.76 (s, 2H), 4.62 (d, 2H).

Example 50: Preparation of N-((3-chloro-1H-pyrrolo[2,3-b]pyridin-5-yl)methyl)-1-((3-chloroquinolin-6-yl)methyl)-3-cyano-1H-pyrazole-4-carboxamide

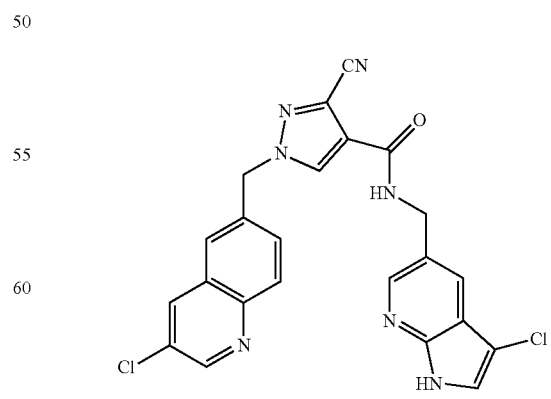

N-((3-chloro-1H-pyrrolo[2,3-b]pyridin-5-yl)methyl)-1-((3-chloroquinolin-6-yl)methyl)-3-cyano-1H-pyrazole-4-carboxamide

245

-continued

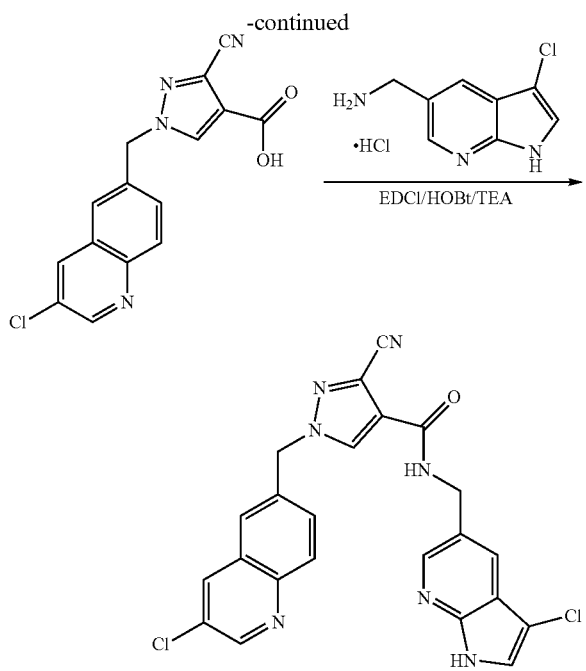

To a mixture of 1-(3-chloro-quinolin-6-ylmethyl)-3-cyano-1H-pyrazole-4-carboxylic acid (200 mg, 0.64 mmol, 1.0 eq) in DMF (8 mL) was added (3-chloro-1H-pyrrolo[2,3-b]pyridin-5-yl)methanamine hydrochloride (139 mg, 0.64 mmol, 1.0 eq), EDCI (184 mg, 0.96 mmol, 1.5 eq) and HOBt (130 mg, 0.96 mmol, 1.5 eq) and TEA (194 mg, 1.92 mmol, 3.0 eq). The mixture was stirred at 50° C. overnight. Then the mixture was diluted with H2O and extracted with EA. The combined organic layers were washed with NaHCO₃ aq, NH4Cl aq, brine, dried over Na2SO4, filtrated and concentrated. The resulting residue was purified by prep-HPLC to give N-((3-chloro-1H-pyrrolo[2,3-b]pyridin-5-yl)methyl)-1-((3-chloroquinolin-6-yl)methyl)-3-cyano-1H-pyrazole-4-carboxamide (55 mg, 18%) as a white solid. LRMS (M+H+) m/z calculated 476.1, found 475.8. 1H NMR (DMSO-d6, 400 MHz): δ11.97 (s, 1H), 8.96 (s, 1H), 8.90 (s, 1H), 8.61 (s, 1H), 8.55 (s, 1H), 8.29 (s, 1H), 8.07 (d, 1H), 7.71 (s, 2H), 7.69 (d, 2H), 5.72 (s, 2H), 4.54 (d, 2H).

Example 51: Preparation of N-((3-chloro-6-fluoro-1H-indol-5-yl)methyl)-1-((3-chloroquinolin-6-yl)methyl)-3-cyano-1H-pyrazole-4-carboxamide

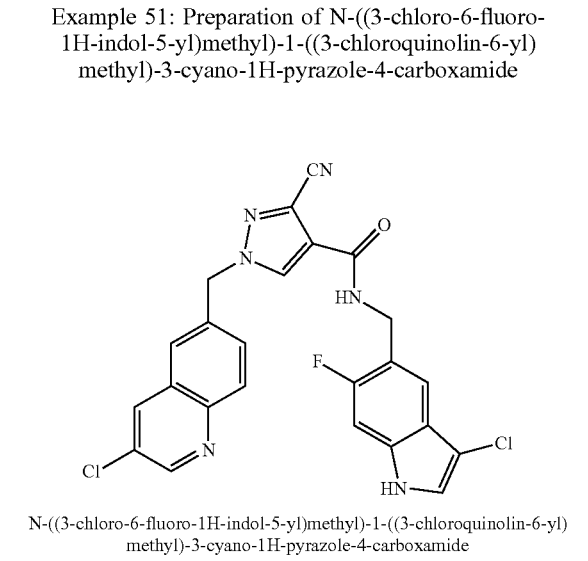

N-((3-chloro-6-fluoro-1H-indol-5-yl)methyl)-1-((3-chloroquinolin-6-yl)methyl)-3-cyano-1H-pyrazole-4-carboxamide

246

-continued

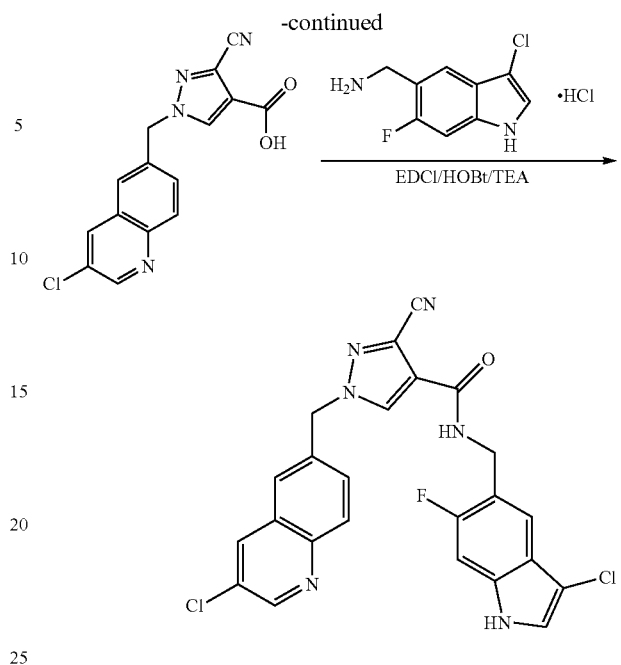

To a mixture of 1-(3-chloro-quinolin-6-ylmethyl)-3-cyano-1H-pyrazole-4-carboxylic acid (200 mg, 0.64 mmol, 1.0 eq) in DMF (8 mL) was added (3-chloro-6-fluoro-1H-indol-5-yl)methanamine hydrochloride (150 mg, 0.64 mmol, 1.0 eq), EDCI (184 mg, 0.96 mmol, 1.5 eq) and HOBt (130 mg, 0.96 mmol, 1.5 eq) and TEA (194 mg, 1.92 mmol, 3.0 eq). The mixture was stirred at 50° C. overnight. Then the mixture was diluted with H2O and extracted with EA. The combined organic layers were washed with NaHCO₃ aq, NH4Cl aq, brine, dried over Na2SO4, filtrated and concentrated. The resulting residue was purified by prep-HPLC to give N-((3-chloro-6-fluoro-1H-indol-5-yl)methyl)-1-((3-chloroquinolin-6-yl)methyl)-3-cyano-1H-pyrazole-4-carboxamide (75 mg, 24%) as a white solid. LRMS (M+H+) m/z calculated 493.1, found 492.9. 1H NMR (DMSO-d6, 400 MHz): δ 11.40 (s, 1H), 8.89 (d, 2H), 8.62 (s, 1H), 8.58 (s, 1 H), 8.06 (d, 1H), 7.87 (s, 1H), 7.72 (d, 1H), 7.51 (s, 1H), 7.45 (d, 1H), 7.22 (d, 1H), 5.72 (s, 2H), 4.52 (d, 2H).

Example 52: Preparation of N-((6-amino-2,4-dimethylpyridin-3-yl)methyl)-1-((3-chloro-8-fluoroquinolin-6-yl)methyl)-3-cyano-1H-pyrazole-4-carboxamide

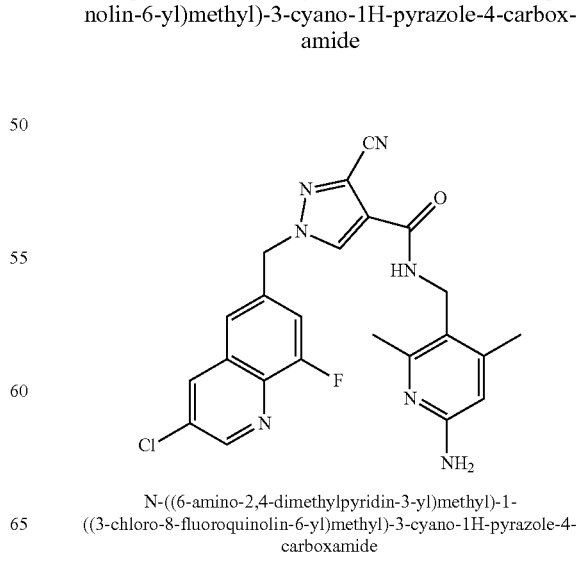

N-((6-amino-2,4-dimethylpyridin-3-yl)methyl)-1-((3-chloro-8-fluoroquinolin-6-yl)methyl)-3-cyano-1H-pyrazole-4-carboxamide

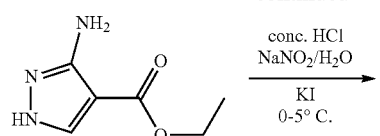

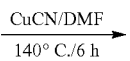

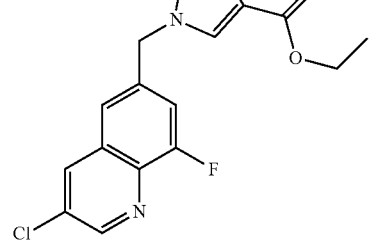

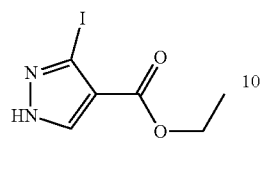

To a stirred of 3-amino-1H-pyrazole-4-carboxylic acid ethyl ester (50.0 g, 0.322 mol, 1.0 eq) in concentrated HCl (450 mL) was added a solution of sodium nitrite (44.4 g, 0.644 mol, 2.0 eq) in water (120 mL) over 25 min at 0° C. To the resulting reaction mixture was added a solution of KI (134 g, 0.805 mmol, 2.5 eq) in water (280 mL) over 20 min. The reaction mixture was stirred for 30 min further, then extracted with EA and the combined organic extracts were washed with Na2S2O3, dried over Na2SO4 and concentrated under reduce pressure to give 3-iodo-1H-pyrazole-4-carboxylic acid ethyl ester (52.2 g, 61%) as a light yellow solid.

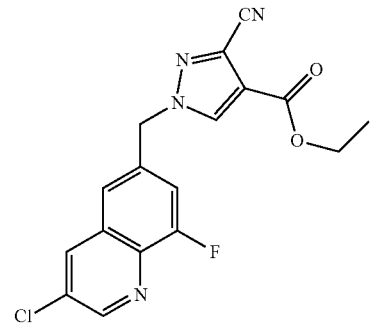

A mixture of 1-(3-chloro-8-fluoro-quinolin-6-ylmethyl)-3-iodo-1H-pyrazole-4-carboxylic acid ethyl ester (1.5 g, 3.3 mmol, 1.0 eq) and CuCN (0.35 g, 4 mmol, 1.2 eq) in DMF (45 mL) was stirred at 140° C. for 6 h under nitrogen. After cooling, the mixture was poured into a mixture of conc. NH3.H2O (50 mL), H2O (200 mL) and EA (100 mL) with stirring. The aqueous layer was extracted with EA, dried and concentrated. The residue was purified by chromatography on a silica gel column (PE/EA/DCM=4/1/0.5, v/v) to give 1-(3-chloro-8-fluoro-quinolin-6-ylmethyl)-3-cyano-1H-pyrazole-4-carboxylic acid ethyl ester (0.75 g, 64%).

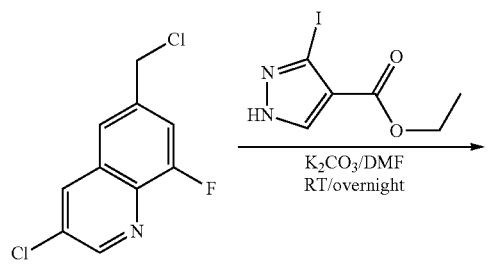

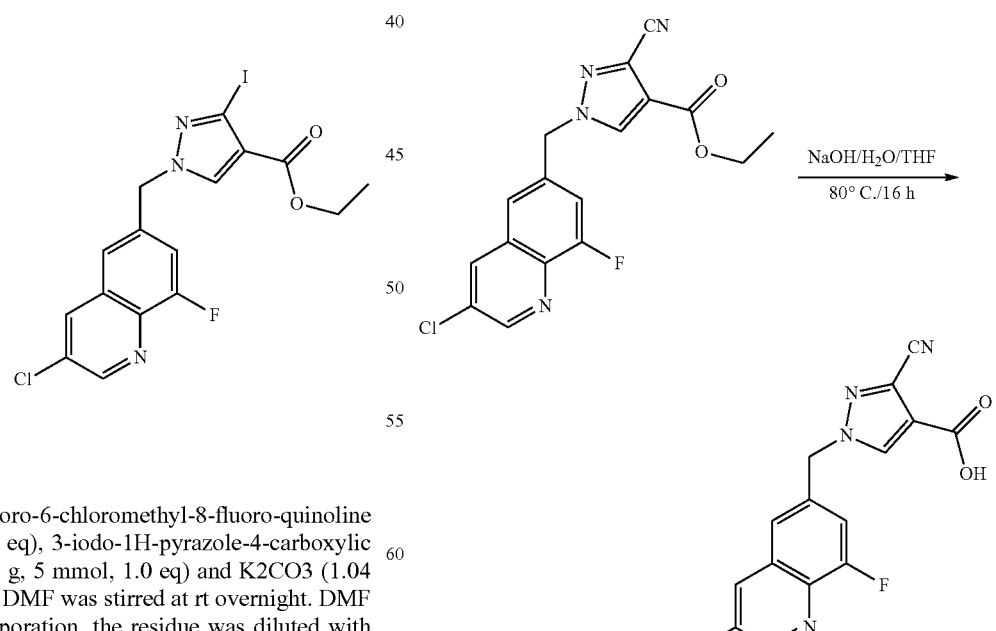

A mixture of 3-chloro-6-chloromethyl-8-fluoro-quinoline (1.33 g, 5 mmol, 1.0 eq), 3-iodo-1H-pyrazole-4-carboxylic acid ethyl ester (1.15 g, 5 mmol, 1.0 eq) and K2CO3 (1.04 g, 8 mmol, 1.5 eq) in DMF was stirred at rt overnight. DMF was removed by evaporation, the residue was diluted with DCM, washed with water, dried and purified by chromatography on a silica gel column (PE/EA=9/1 to 3/1, v/v) to give 1-(3-chloro-8-fluoro-quinolin-6-ylmethyl)-3-iodo-1H-pyrazole-4-carboxylic acid ethyl ester (1.5 g, 85%).

To a mixture of 1-(3-chloro-8-fluoro-quinolin-6-ylmethyl)-3-cyano-1H-pyrazole-4-carboxylic acid ethyl ester (540 mg, 1.5 mmol, 1.0 eq) in THF/H2O (25 mL/20 mL) was added NaOH (240 mg, 6.0 mmol, 4.0 eq. The mixture was stirred at 80° C. overnight. THF was removed by evaporation. The aqueous layer was adjusted to pH 2 with 1 N HCl. The precipitate was collected by filtration, washed with water and dried to give 1-(3-chloro-8-fluoro-quinolin-6-ylmethyl)-3-cyano-1H-pyrazole-4-carboxylic acid (0.446 g, 90%) as a white solid.

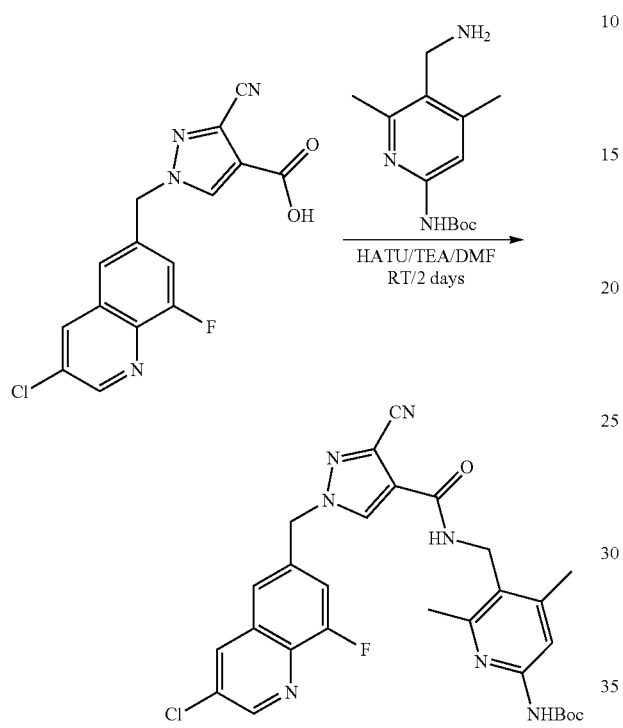

A mixture of 1-(3-chloro-8-fluoro-quinolin-6-ylmethyl)-3-cyano-1H-pyrazole-4-carboxylic acid (0.446 g, 1.35 mmol, 1.0 eq), tert-butyl (5-(aminomethyl)-4,6-dimethylpyridin-2-yl)carbamate (0.339 g, 1.35 mmol, 1.0 eq), TEA (0.41 g, 4.05 mmol, 3.0 eq) and HATU (0.616 g, 1.62 mmol, 1.2 eq) in DMF (30 mL) was stirred at rt for 2 days. DMF was removed by evaporation and the residue was diluted with DCM, washed with sat. aqueous NH4Cl, dried, concentrated, and purified by chromatography on a silica gel column (PE/EA=1/1 to DCM/MeOH=20/1) v/v) to give 0.5 g of mixture which was purified by pre-HPLC to give tert-butyl (5-((1-((3-chloro-8-fluoroquinolin-6-yl)methyl)-3-cyano-1H-pyrazole-4-carboxamido)methyl)-4,6-dimethylpyridin-2-yl)carbamate (342 mg, 45%) as a white solid.

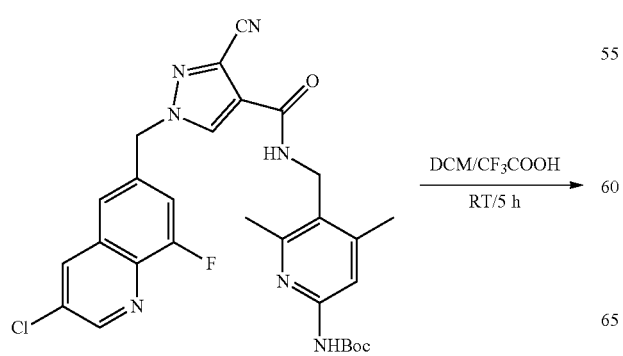

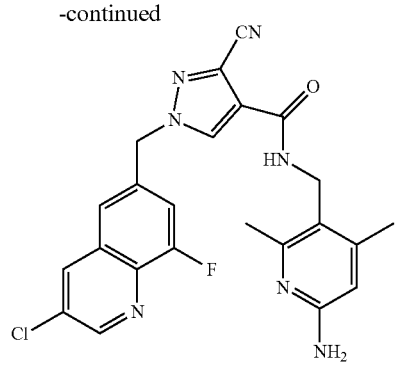

A mixture of tert-butyl (5-((1-((3-chloro-8-fluoroquinolin-6-yl)methyl)-3-cyano-1H-pyrazole-4-carboxamido)methyl)-4,6-dimethylpyridin-2-yl)carbamate (342 mg, 0.61 mmol) in DCM/CF3COOH (10 mL/10 mL) was stirred at rt for 5 h. The volatile was removed, and the residue was diluted with ethanol (20 mL), added sat aqueous Na2CO3 to pH 9, and stirred at rt overnight. After filtration, the solid was washed with water, and dried at 110° C. for 5 h to give N-((6-amino-2,4-dimethylpyridin-3-yl)methyl)-1-((3-chloro-8-fluoroquinolin-6-yl)methyl)-3-cyano-1H-pyrazole-4-carboxamide (100 mg, 36%). LRMS (M+H+) m/z calculated 464.1, found 464.1. 1H NMR (DMSO-d6, 400 MHz): δ 8.96 (d, 1H), 8.71 (s, 1H), 8.57 (s, 1H), 8.28 (t, 1H), 7.67 (s, 1H), 7.61 (dd, 1H), 7.73 (s, 1H), 6.12 (s, 1H), 5.71 (s, 2H), 5.67 (s, 2H), 4.28 (d, 2H), 2.29 (s, 3H), 2.16 (s, 3H).

Example 53: Preparation of N-((3-chloro-6-fluoro-1H-indol-5-yl)methyl)-1-((3-chloro-8-fluoroquinolin-6-yl)methyl)-3-cyano-1H-pyrazole-4-carboxamide

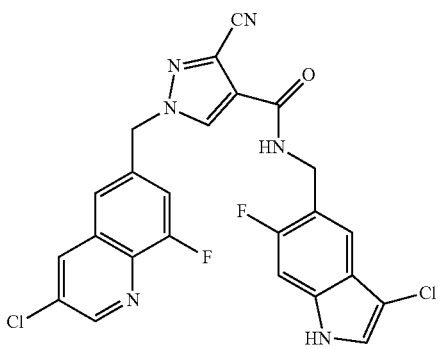

N-((3-chloro-6-fluoro-1H-indol-5-yl)methyl)-1-((3-chloro-8-fluoroquinolin-6-yl)methyl)-3-cyano-1H-pyrazole-4-carboxamide

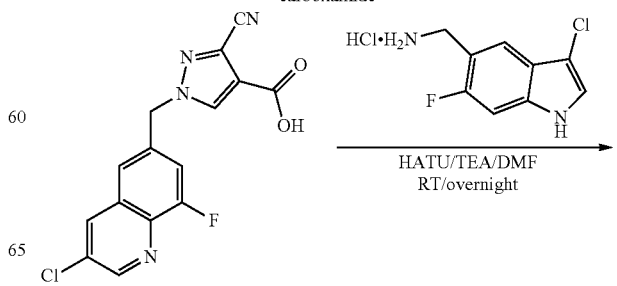

251
-continued

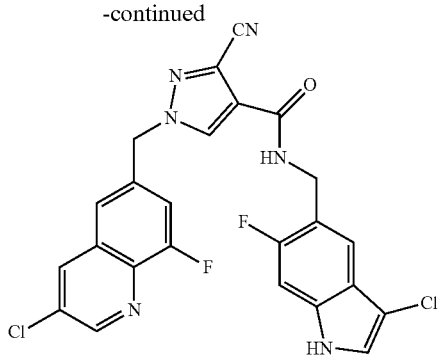

A mixture of 1-(3-chloro-8-fluoro-quinolin-6-ylmethyl)-3-cyano-1H-pyrazole-4-carboxylic acid (100 mg, 0.303 mmol, 1.0 eq), (3-chloro-6-fluoro-1H-indol-5-yl)methanamine hydrochloride (86 mg, 0.364 mmol, 1.2 eq), TEA (153 mg, 1.52 mmol, 5.0 eq) and HATU (150 mg, 0.394 mmol, 1.3 eq) in DMF (10 mL) was stirred ar rt overnight. The mixture was diluted with water (40 mL), extracted with DCM (150 mL). The combined organic layers were washed with water, dried and concentrated. The residue was purified by pre-HPLC to give N-((3-chloro-6-fluoro-1H-indol-5-yl)methyl)-1-((3-chloro-8-fluoroquinolin-6-yl)methyl)-3-cyano-1H-pyrazole-4-carboxamide (24 mg, 16%) as a white solid. LRMS (M−H+) m/z calculated 509.1, found 509.0. 1H NMR (DMSO-d6, 400 MHz): δ 11.41 (s, 1H), 8.96 (d, 1H), 8.88 (t, 1H), 8.71 (s, 1H), 8.58 (s, 1H), 7.68 (s, 1H), 7.64 (d, 1H), 7.51 (d, 1H), 7.46 (d, 1H), 7.22 (d, 1H), 5.71 (s, 2H), 4.52 (d, 2H).

Example 54: Preparation of N-((1-aminoisoquinolin-6-yl)methyl)-1-((3-chloro-8-fluoroquinolin-6-yl)methyl)-3-cyano-1H-pyrazole-4-carboxamide 252
-continued

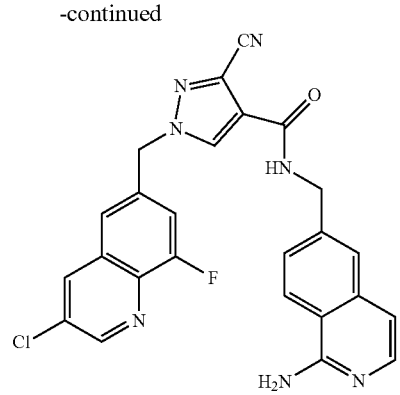

A suspension of 1-(3-chloro-8-fluoro-quinolin-6-ylmethyl)-3-cyano-1H-pyrazole-4-carboxylic acid (100 mg, 0.303 mmol, 1.0 eq), 6-aminomethyl-isoquinolin-1-ylamine hydrochloride (76 mg, 0.364 mmol, 1.2 eq), TEA (153 mg, 1.52 mmol, 5.0 eq) and HATU (150 mg, 0.394 mmol, 1.3 eq) in DMF (10 mL) was stirred ar rt overnight. The mixture was diluted with water (100 mL) and a white precipitate formed, which was purified by pre-HPLC to give N-((1-aminoisoquinolin-6-yl)methyl)-1-((3-chloro-8-fluoroquinolin-6-yl)methyl)-3-cyano-1H-pyrazole-4-carboxamide (34 mg, 23%). 1H NMR (DMSO-d6, 300 MHz): δ 9.03 (s, 1H), 8.95 (s, 1H), 8.70 (s, 1H), 8.59 (s, 1H), 8.19 (s, 1H), 7.75-7.61 (m, 4H), 7.39 (s, 1H), 6.85 (s, 1H), 6.80 (s, 2H), 5.72 (s, 2H), 4.54 (s, 2H). LRMS (M−H+) m/z calculated 486.1, found 485.9.

Example 55: Preparation of N-((5-chloro-1H-indazol-3-yl)methyl)-1-((3-chloro-8-fluoroquinolin-6-yl)methyl)-3-cyano-1H-pyrazole-4-carboxamide

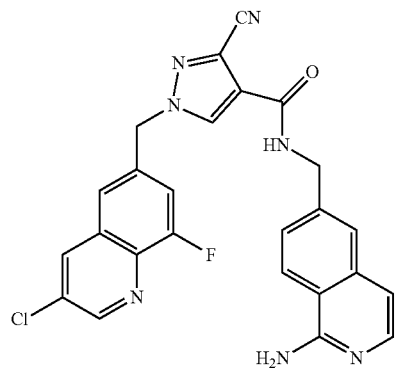

N-((1-aminoisoquinolin-6-yl)methyl)-1-((3-chloro-8-fluoroquinolin-6-yl)methyl)-3-cyano-1H-pyrazole-4-carboxamide

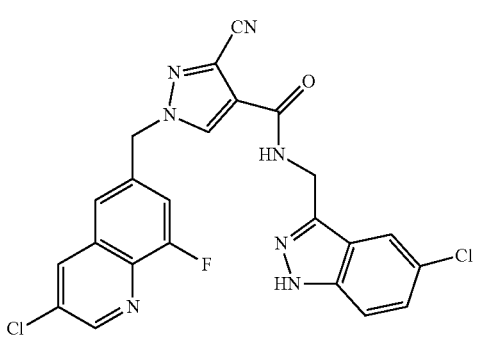

N-((5-chloro-1H-indazol-3-yl)methyl)-1-((3-chloro-8-fluoroquinolin-6-yl)methyl)-3-cyano-1H-pyrazole-4-carboxamide

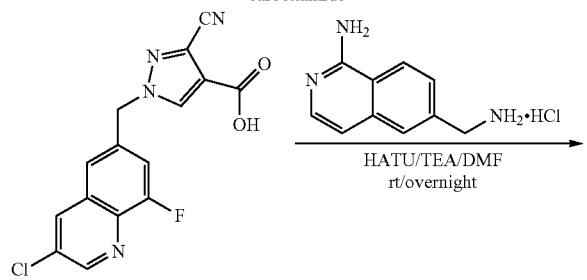

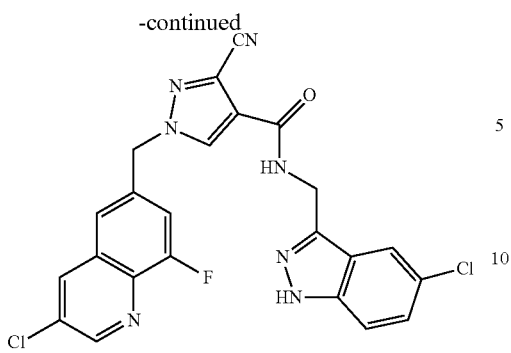

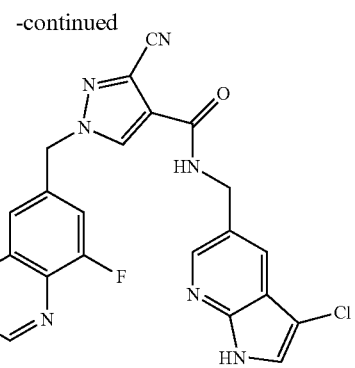

A suspension mixture of 1-(3-chloro-8-fluoro-quinolin-6-ylmethyl)-3-cyano-1H-pyrazole-4-carboxylic acid (100 mg, 0.303 mmol, 1.0 eq), (5-chloro-1H-indazol-3-yl)methanamine hydrochloride (93 mg, 0.364 mmol, 1.2 eq), TEA (153 mg, 1.52 mmol, 5.0 eq) and HATU (150 mg, 0.394 mmol, 1.3 eq) in DMF (10 mL) was stirred ar rt overnight. The mixture was diluted with water (100 mL) and a white precipitate formed, which was purified by pre-HPLC to give N-((5-chloro-1H-indazol-3-yl)methyl)-1-((3-chloro-8-fluoroquinolin-6-yl)methyl)-3-cyano-1H-pyrazole-4-carboxamide (10 mg, 7%). 1H NMR (DMSO-d6, 300 MHz): δ 13.1 (s, 1H), 9.01 (s, 1H), 8.95 (s, 1H), 8.69 (s, 1H), 8.51 (s, 1H), 7.87 (s, 1H), 7.67 (s, 1H), 7.63 (d, 1H), 7.51 (d, 1H), 7.34 (s, 1H), 5.68 (s, 2H), 4.72 (d, 2H). LRMS (M−H+) m/z calculated 494.1, found 493.9.

Example 56: Preparation of N-((3-chloro-1H-pyrrolo[2,3-b]pyridin-5-yl)methyl)-1-((3-chloro-8-fluoroquinolin-6-yl)methyl)-3-cyano-1H-pyrazole-4-carboxamide A suspension of 1-(3-chloro-8-fluoro-quinolin-6-ylmethyl)-3-cyano-1H-pyrazole-4-carboxylic acid (100 mg, 0.303 mmol, 1.0 eq), (3-chloro-1H-pyrrolo[2,3-b]pyridin-5-yl)methanamine hydrochloride (79 mg, 0.364 mmol, 1.2 eq), TEA (153 mg, 1.52 mmol, 5.0 eq) and HATU (150 mg, 0.394 mmol, 1.3 eq) in DMF (10 mL) was stirred ar rt overnight. The reaction mixture was poured onto water (120 mL) and a white precipitate formed, which was purified by pre-HPLC to give N-((3-chloro-1H-pyrrolo[2,3-b]pyridin-5-yl)methyl)-1-((3-chloro-8-fluoroquinolin-6-yl)methyl)-3-cyano-1H-pyrazole-4-carboxamide (27 mg, 18%). 1H NMR (DMSO-d6, 300 MHz): δ 11.97 (s, 1H), 8.96 (s, 2H), 8.69 (s, 1H), 8.53 (s, 1H), 8.28 (s, 1H), 7.85 (s, 1H), 7.66 (s, 2H), 7.64 (s, 1H), 5.68 (s, 2H), 4.52 (d, 2H). LRMS (M−H+) m/z calculated 494.1, found 493.9.

Example 57: Preparation of N-((3-chloro-4-fluoro-1H-indol-5-yl)methyl)-1-((3-chloro-8-fluoroquinolin-6-yl)methyl)-3-cyano-1H-pyrazole-4-carboxamide

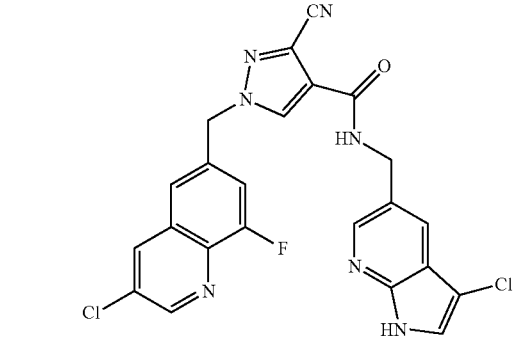

N-((3-chloro-1H-pyrrolo[2,3-b]pyridin-5-yl)methyl)-1-((3-chloro-8-fluoroquinolin-6-yl)methyl)-3-cyano-1H-pyrazole-4-carboxamide

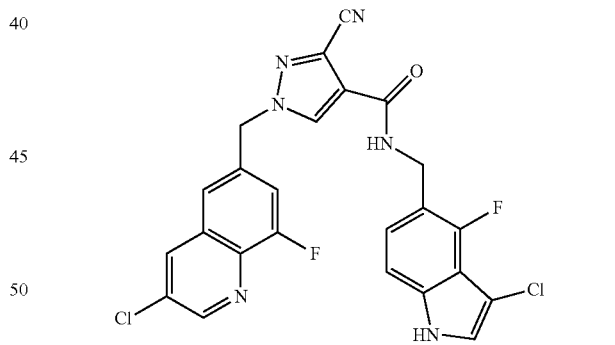

N-((3-chloro-4-fluoro-1H-indol-5-yl)methyl)-1-((3-chloro-8-fluoroquinolin-6-yl)methyl)-3-cyano-1H-pyrazole-4-carboxamide

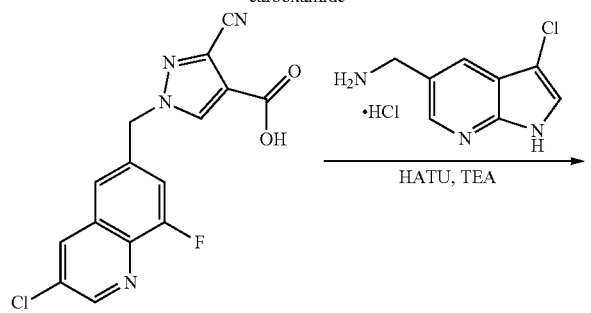

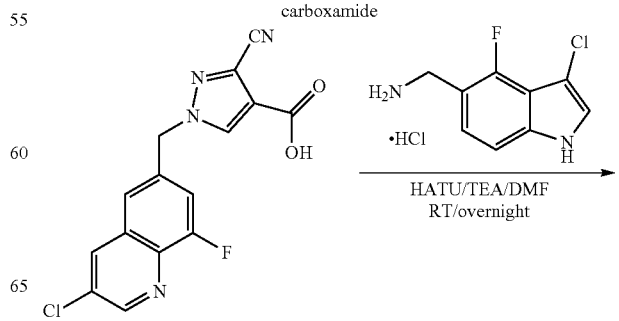

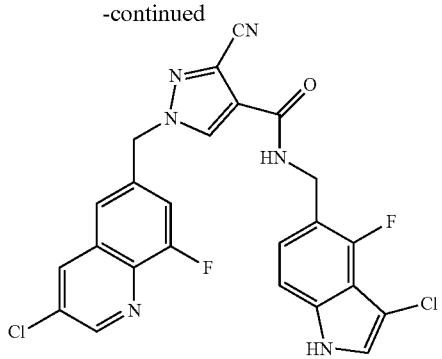

A suspension of 1-(3-chloro-8-fluoro-quinolin-6-ylmethyl)-3-cyano-1H-pyrazole-4-carboxylic acid (100 mg, 0.303 mmol, 1.0 eq), (3-chloro-4-fluoro-1H-indol-5-yl)methanamine hydrochloride (85 mg, 0.364 mmol, 1.2 eq), TEA (153 mg, 1.52 mmol, 5.0 eq) and HATU (150 mg, 0.394 mmol, 1.3 eq) in DMF (10 mL) was stirred ar rt overnight. The mixture was diluted with 200 mL of CHCl3/MeOH (v/v=9/1), washed with sat. aqueous NH4Cl (100 mL×2), dried and concentrated. The residue was purified by chromatography on a silica gel column (DCM/MeOH=40/1, v/v) to give 50 mg of mixture which was triturated in DCM/EA/MeOH (30 mL, v/v/v=2/2/1) to provide N-((3-chloro-4-fluoro-1H-indol-5-yl)methyl)-1-((3-chloro-8-fluoroquinolin-6-yl)methyl)-3-cyano-1H-pyrazole-4-carboxamide (47 mg, 30%). LRMS (M−H+) m/z calculated 511.1, found 510.8. 1H NMR (DMSO-d6, 300 MHz): δ 11.59 (s, 1H), 8.95 (s, 1 H), 8.86 (t, 1H), 8.70 (s, 1H), 8.55 (s, 1H), 7.67 (s, 1H), 7.60 (d, 1H), 7.51 (s, 1H), 7.21-7.13 (m, 2H), 5.67 (s, 2H), 4.50 (d, 2H).

Example 58: Preparation of N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide

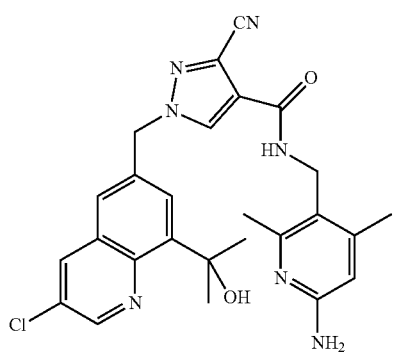

N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide

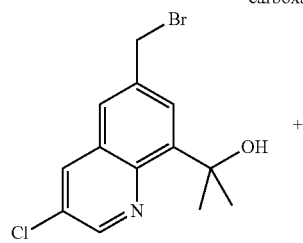

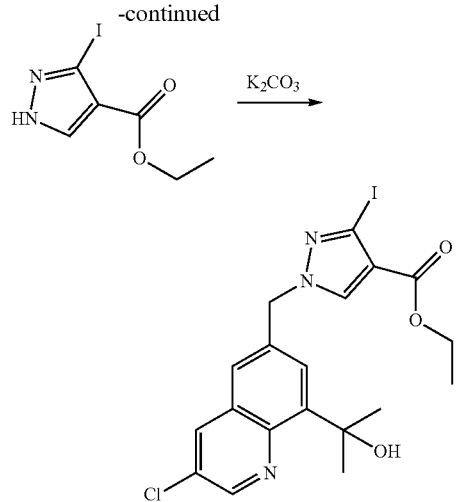

A mixture of 2-(6-bromomethyl-3-chloro-quinolin-8-yl)-propan-2-ol (1.0 g, 3.18 mmol, 1.0 eq), 3-iodo-1H-pyrazole-4-carboxylic acid ethyl ester (845 mg, 3.18 mmol, 1.0 eq) and K2CO3 (658 mg, 4.77 mmol, 1.5 eq) in DMF (20 mL) was stirred at rt overnight. The mixture was concentrated and the resulting residue was purified by chromatography on a silica gel column (PE/EA=3/1, v/v) to afford 1-[3-chloro-8-(1-hydroxy-1-methyl-ethyl)-quinolin-6-ylmethyl]-3-iodo-1H-pyrazole-4-carboxylic acid ethyl ester (1.1 g, 70%) as a white solid.

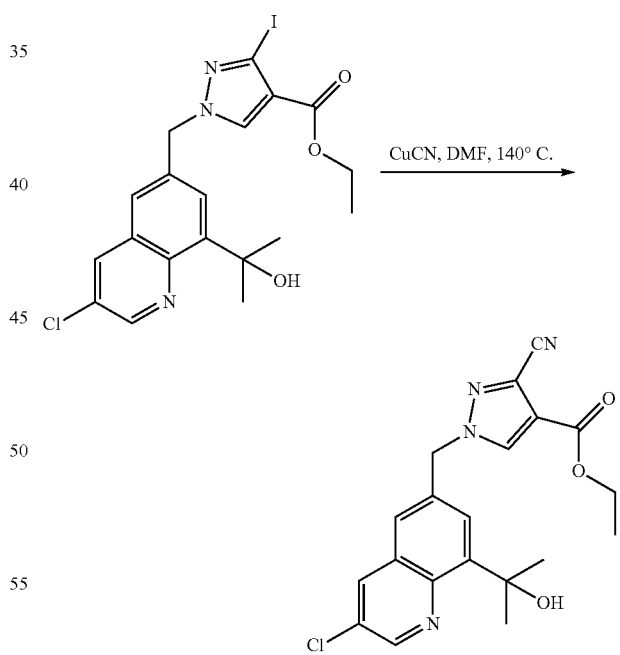

A mixture of 1-[3-chloro-8-(1-hydroxy-1-methyl-ethyl)-quinolin-6-ylmethyl]-3-iodo-1H-pyrazole-4-carboxylic acid ethyl ester (900 mg, 1.80 mmol, 1.0 eq) and CuCN (242 mg, 2.70 mmol, 1.5 eq) in DMF (20 mL) was stirred at 140° C. for 6 h. The solution was poured into water/NH3.H2O (50 mL/20 mL) and extracted with EA (50 mL×2). The organic layers were dried over Na2SO4, filtered and concentrated. The resulting residue was purified by chromatography on a silica column (PE/EA=3/1, v/v) to afford 1-[3-chloro-8-(1-hydroxy-1-methyl-ethyl)-quinolin-6-ylmethyl]-3-cyano-1H-pyrazole-4-carboxylic acid ethyl ester (350 mg, 49%) as a white solid.

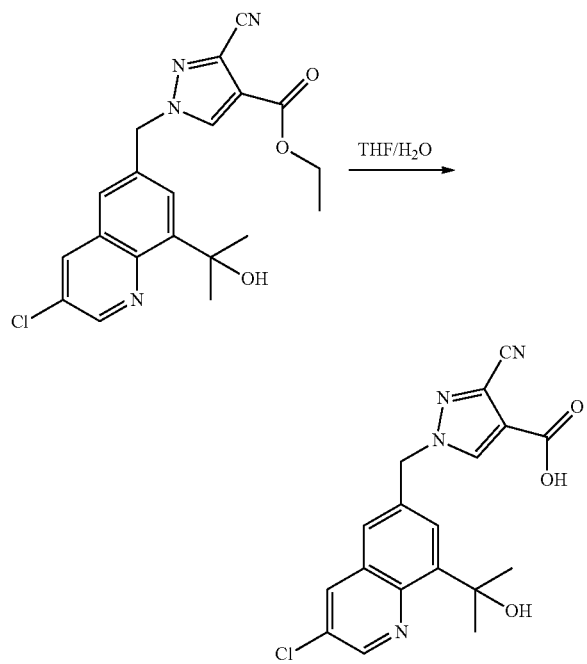

To a solution of 1-[3-chloro-8-(1-hydroxy-1-methyl-ethyl)-quinolin-6-ylmethyl]-3-cyano-1H-pyrazole-4-carboxylic acid ethyl ester (100 mg, 0.25 mmol, 1.0 eq) in THF (4 mL) and water (4 mL) was added NaOH (40 mg, 1.0 mmol, 4.0 eq) at rt. The solution was stirred at 80° C. overnight. The mixture was neutralized with 1N HCl and concentrated to give 1-[3-chloro-8-(1-hydroxy-1-methyl-ethyl)-quinolin-6-ylmethyl]-3-cyano-1H-pyrazole-4-carboxylic acid (110 mg, crude) which was used in next step directly.

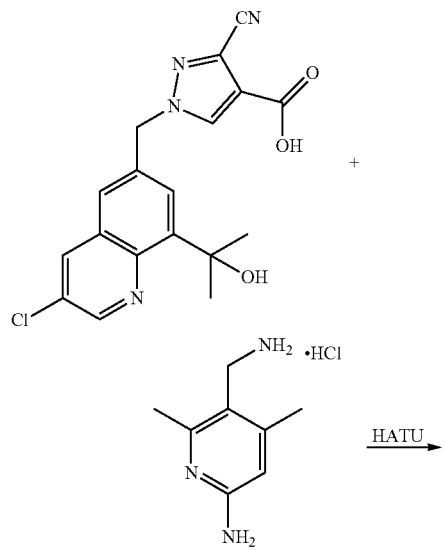

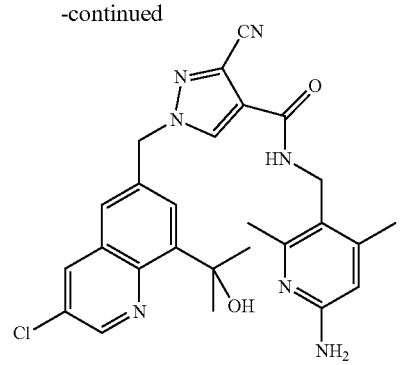

A mixture of 1-[3-chloro-8-(1-hydroxy-1-methyl-ethyl)-quinolin-6-ylmethyl]-3-cyano-1H-pyrazole-4-carboxylic acid (110 mg, crude, 0.25 mmol, 1.0 eq), 5-aminomethyl-4,6-dimethyl-pyridin-2-ylamine hydrochloride (69 mg, 0.37 mmol, 1.5 eq), HATU (142 mg, 0.37 mmol, 1.5 eq) and Et3N (76 mg, 0.75 mmol, 3.0 eq) in DMF (4 mL) was stirred at rt overnight. The mixture was concentrated and the residue was purified by prep-HPLC to afford N-((6-amino-2,4-dimethylpyridin-3-yl)methyl)-1-((3-chloro-8-(2-hydroxy-propan-2-yl)quinolin-6-yl)methyl)-3-cyano-1H-pyrazole-4-carboxamide (56 mg, 44%) as a white solid. LRMS (M+H+) m/z calculated 504.2, found 504.2. 1H NMR (DMSO-d6, 400 MHz): δ 8.92 (d, 1H), 8.61 (d, 1H), 8.57 (s, 1H), 8.30 (t, 1H), 7.92 (d, 1H), 7.67 (d, 1H), 6.11 (s, 1H), 5.74 (s, 1H), 5.72 (s, 2H), 5.67 (s, 2H), 4.27 (d, 2H), 2.28 (s, 3H), 2.15 (s, 3H), 1.72 (s, 6H).

Example 59: Preparation of N-((1-aminoisoquinolin-6-yl)methyl)-1-((3-chloro-8-(2-hydroxypropan-2-yl)quinolin-6-yl)methyl)-3-cyano-1H-pyrazole-4-carboxamide

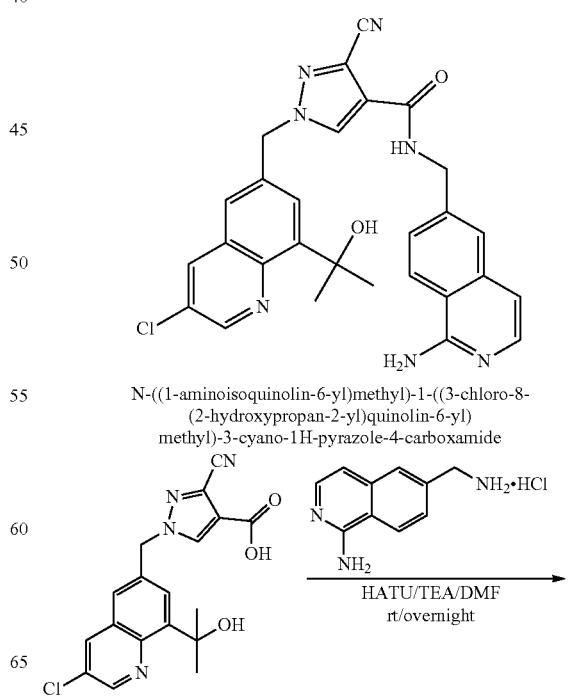

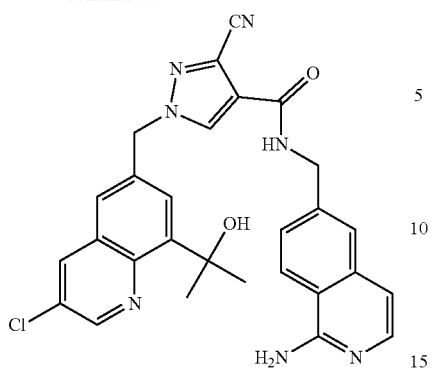

A suspension of 1-[3-chloro-8-(1-hydroxy-1-methyl-ethyl)-quinolin-6-ylmethyl]-3-cyano-1H-pyrazole-4-carboxylic acid (100 mg, 0.27 mmol, 1.0 eq), 6-aminomethyl-isoquinolin-1-ylamine hydrochloride (67 mg, 0.32 mmol, 1.2 eq), TEA (109 mg, 1.08 mmol, 4.0 eq) and HATU (133 mg, 0.35 mmol, 1.3 eq) in DMF (10 mL) was stirred at rt overnight. The mixture was diluted with DCM (200 mL), washed with sat aq NH4Cl (100 mL×2). The combined organic layers were dried and concentrated. The resulting residue was purified by chromatography on a silica gel column (DCM/MeOH=30/1, v/v) to give 80 mg of mixture, which was further purified by pre-HPLC to give N-((1-aminoisoquinolin-6-yl)methyl)-1-((3-chloro-8-(2-hydroxypropan-2-yl)quinolin-6-yl)methyl)-3-cyano-1H-pyrazole-4-carboxamide (14 mg, 10%) as a white solid. LRMS (M+H+) m/z calculated 526.2, found 526.0. 1H NMR (DMSO-d6, 400 MHz) δ 9.12 (t, 1H), 8.94 (s, 1H), 8.64 (s, 1H), 8.63 (s, 1H), 8.23 (d, 1H), 7.97 (s, 1H), 7.75 (s, 1H), 7.72 (s, 1H), 7.63 (s, 1H), 7.47 (d, 1H), 7.32 (s, 2H), 6.95 (s, 1H), 5.79 (s, 1H), 5.74 (s, 2H), 4.58 (d, 2H), 1.74 (s, 6H).

Example 60: Preparation of N-((6-amino-2,4-dimethylpyridin-3-yl)methyl)-1-((3-chloro-8-sulfamoylquinolin-6-yl)methyl)-3-cyano-1H-pyrazole-4-carboxamide

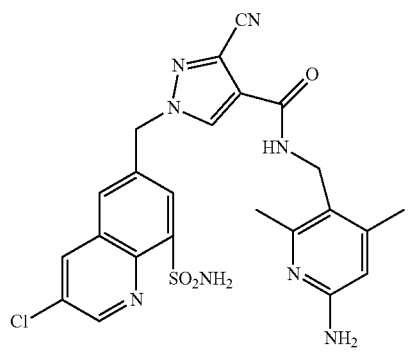

N-((6-amino-2,4-dimethylpyridin-3-yl)methyl)-1-((3-chloro-8-sulfamoylquinolin-6-yl)methyl)-3-cyano-1H-pyrazole-4-carboxamide

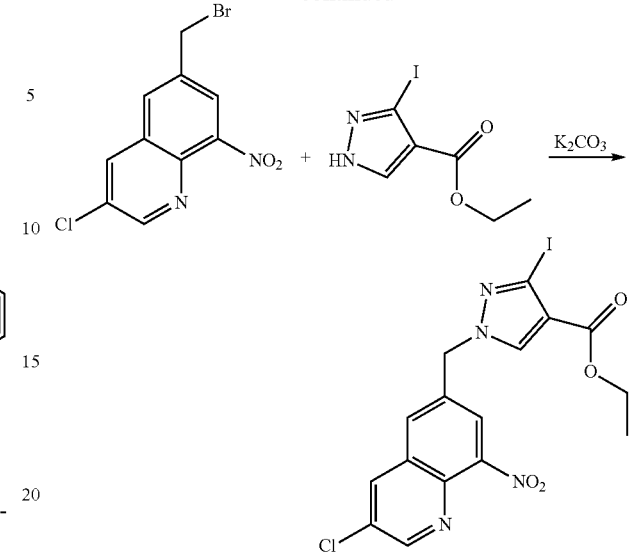

A mixture of 6-bromomethyl-3-chloro-8-nitro-quinoline (1.0 g, 3.56 mmol, 1.0 eq), 3-iodo-1H-pyrazole-4-carboxylic acid ethyl ester (946 mg, 3.56 mmol, 1.0 eq) and K2CO3 (737 mg, 5.34 mmol, 1.5 eq) in DMF (20 mL) was stirred at rt overnight. The mixture was concentrated and the residue was purified by chromatography on a silica gel column (PE/EA=4/1, v/v) to afford 1-(3-chloro-8-nitro-quinolin-6-ylmethyl)-3-iodo-1H-pyrazole-4-carboxylic acid ethyl ester (900 mg, 52%) as a yellow solid.

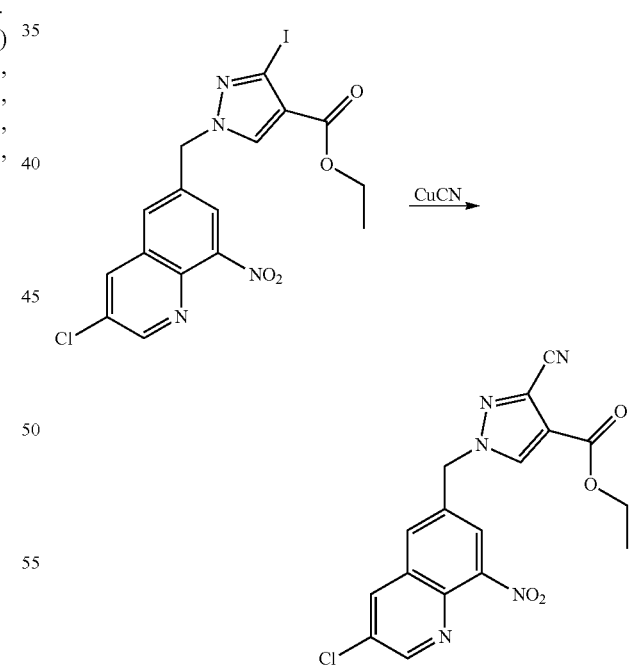

A mixture of 1-(3-chloro-8-nitro-quinolin-6-ylmethyl)-3-iodo-1H-pyrazole-4-carboxylic acid ethyl ester (700 mg, 1.40 mmol, 1.0 eq) and CuCN (188 mg, 2.10 mmol, 1.5 eq) in DMF (20 mL) was stirred at 140° C. for 6 h. The solution was poured into water/NH3.H2O (40 mL/20 mL) and extracted with EA (50 mL×2). The organic layers were dried over Na2SO4, filtered and concentrated. The resulting residue was purified by chromatography on a silica gel column (PE/EA=3/1, v/v) to afford 1-(3-chloro-8-nitro-quinolin-6-ylmethyl)-3-cyano-1H-pyrazole-4-carboxylic acid ethyl ester (300 mg, 54%) as a yellow solid.

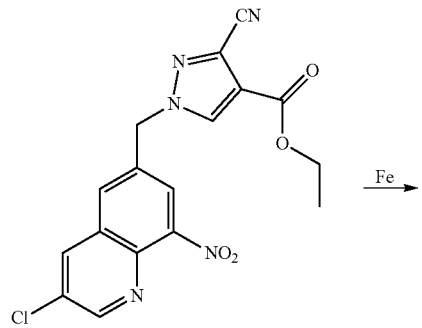

To a solution of 1-(3-chloro-8-nitro-quinolin-6-ylmethyl)-3-cyano-1H-pyrazole-4-carboxylic acid ethyl ester (300 mg, 0.78 mmol, 1.0 eq) in AcOH (20 mL) was added Fe (218 mg, 3.89 mmol, 5.0 eq) at rt. The mixture was stirred at 80° C. for 30 min. The mixture was concentrated. The resulting residue was purified by chromatography on a silica gel column (PE/EA=3/1, v/v) to give 1-(8-amino-3-chloro-quinolin-6-ylmethyl)-3-cyano-1H-pyrazole-4-carboxylic acid ethyl ester (200 mg, 72%) as a yellow solid.

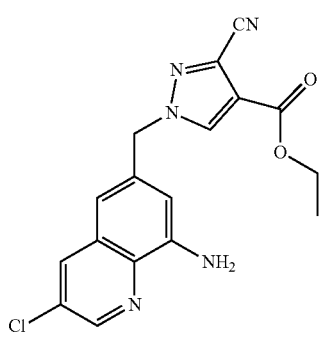

To a solution of 1-(8-amino-3-chloro-quinolin-6-ylmethyl)-3-cyano-1H-pyrazole-4-carboxylic acid ethyl ester (100 mg, 0.28 mmol, 1.0 eq) in H2SO4 (1.5 mL) was added a solution of NaNO2 (19 mg, 0.28 mmol, 1.0 eq) in H2O (2 mL) at 0° C. The mixture was stirred at 0° C. for 1 h.

To another flask was added H2O (2 mL) and SOCl2 (166 mg, 1.40 mmol, 5.0 eq) dropwise at 0° C. The mixture was stirred at 0° C. for 10 min. After that, CuCl (30.0 mg, 0.028 mmol, 0.1 eq) and the above solution were added to the mixture at 0° C. The mixture was stirred at 0° C. for 2 h. The mixture was concentrated and the residue was used to next step directly without further purification. The crude product was dissolved in dioxane (10 mL) and to the solution was added NH3.H2O (2 mL) at 0° C. The mixture was stirred at rt for 1 h and then concentrated. The resulting residue was purified by chromatography on a silica gel column (PE/EA=3/1, v/v) to give 1-(3-chloro-8-sulfamoyl-quinolin-6-ylmethyl)-3-cyano-1H-pyrazole-4-carboxylic acid ethyl ester (40 mg, 34%) as a yellow solid.

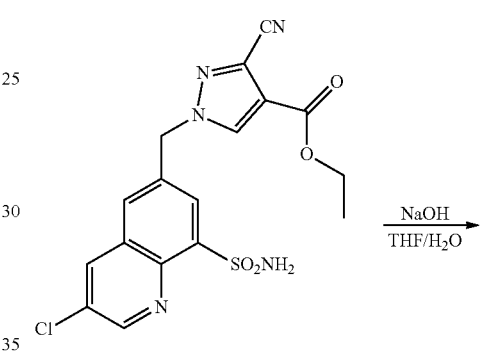

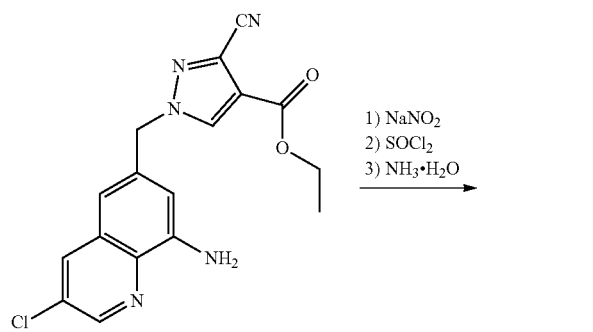

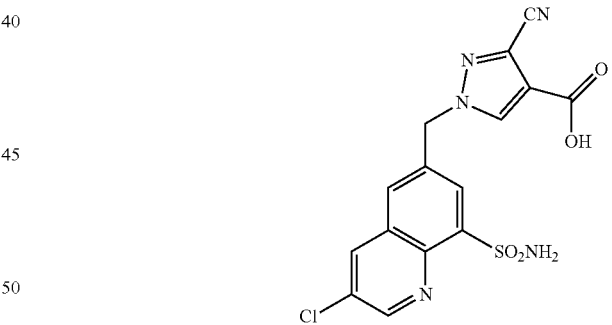

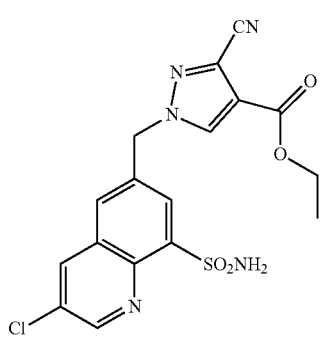

To a solution of 1-(3-chloro-8-sulfamoyl-quinolin-6-ylmethyl)-3-cyano-1H-pyrazole-4-carboxylic acid ethyl ester (40 mg, 0.095 mmol, 1.0 eq) in THF (5 mL) and water (5 mL) was added NaOH (38 mg, 0.95 mmol, 10.0 eq) at rt. The solution was stirred at 80° C. overnight. The mixture was neutralized with 1 N HCl and concentrated to give 1-(3-chloro-8-sulfamoyl-quinolin-6-ylmethyl)-3-cyano-1H-pyrazole-4-carboxylic acid (50 mg, crude) which was used in next step directly.

263

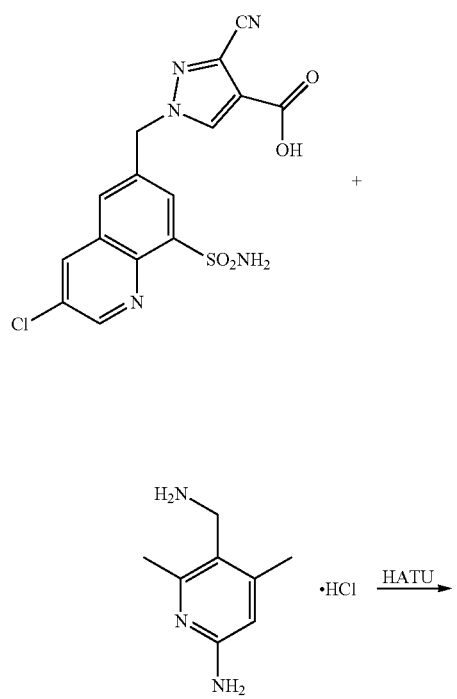

+

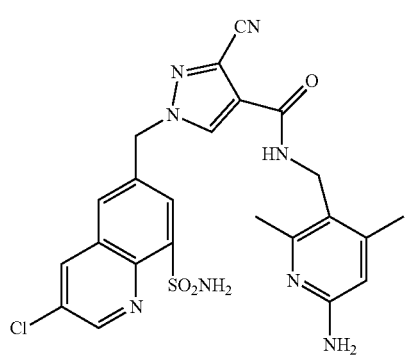

A mixture of 1-(3-chloro-8-sulfamoyl-quinolin-6-ylmethyl)-3-cyano-1H-pyrazole-4-carboxylic acid (50 mg crude, 0.095 mmol, 1.0 eq), 5-aminomethyl-4,6-dimethylpyridin-2-ylamine hydrochloride (26 mg, 0.14 mmol, 1.5 eq), HATU (53 mg, 0.14 mmol, 1.5 eq) and Et3N (28 mg, 0.28 mmol, 3.0 eq) in DMF (4 mL) was stirred at rt for overnight. The mixture was concentrated and the residue was purified by prep-HPLC to afford N-((6-amino-2,4-dimethylpyridin-3-yl)methyl)-1-((3-chloro-8-sulfamoylquinolin-6-yl)methyl)-3-cyano-1H-pyrazole-4-carboxamide (9 mg, 18%) as a white solid. LRMS (M+H+) m/z calculated 525.1, found 524.9. 1H NMR (DMSO-d6, 400 MHz): δ 9.03 (d, 1H), 8.80 (d, 1H), 8.63 (s, 1H), 8.35 (d, 1H), 8.23 (d, 1H), 8.11 (s, 1H), 7.35 (s, 2H), 6.11 (s, 1H), 5.77 (s, 1H), 5.72 (s, 2H), 4.28 (d, 2H), 2.29 (s, 3H), 2.15 (s, 3H).

264

Example 61: Preparation of N-((6-amino-2,4-dimethylpyridin-3-yl)methyl)-3-cyano-1-((3-methyl-8-(methylsulfonyl)quinolin-6-yl)methyl)-1H-pyrazole-4-carboxamide

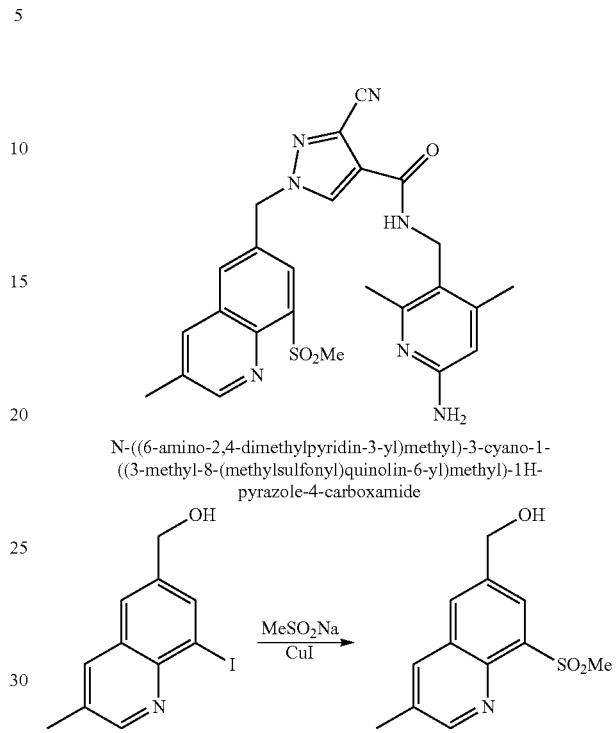

N-((6-amino-2,4-dimethylpyridin-3-yl)methyl)-3-cyano-1-((3-methyl-8-(methylsulfonyl)quinolin-6-yl)methyl)-1H-pyrazole-4-carboxamide A mixture of (8-iodo-3-methyl-quinolin-6-yl)-methanol (5 g, 16.7 mmol, 1 eq), MeSO2Na (2.03 g, 20 mmol, 1.2 eq), CuI (317 mg, 1.67 mmol, 0.1 eq) and sodium pyrrolidine-2-carboxylate (457 mg, 3.34 mmol, 2 eq) was stirred in DMSO (33 mL) at 110° C. under N2 overnight. After the reaction was completed, the mixture was extracted with DCM (100 mL×3). The combined organic layers were concentrated and purified by chromatography on a silica gel column (PE/DCM/EA=1/1/1, v/v/v) to give (8-methanesulfonyl-3-methyl-quinolin-6-yl)-methanol (2.03 g, 48.5%) as a white solid.

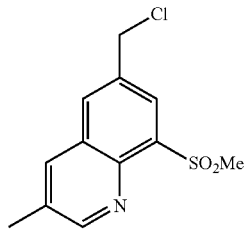

A mixture of (8-methanesulfonyl-3-methyl-quinolin-6-yl)-methanol (1 g, 4 mmol) in SOCl2 (20 mL) was stirred at rt for 3 h. After the reaction was completed, the solvent was evaporated, diluted with DCM and washed with aq. NaHCO₃. The combined organic layers were concentrated and dried in vacuo to give 6-chloromethyl-8-methanesulfonyl-3-methyl-quinoline (1.03 g, 96.3%) as a white solid.

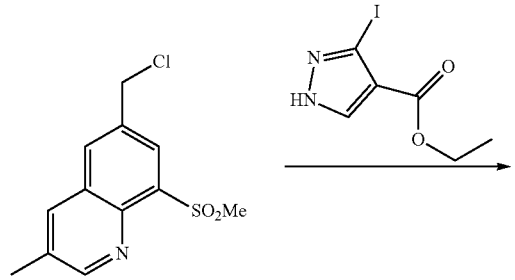

A mixture of 6-chloromethyl-8-methanesulfonyl-3-methyl-quinoline (1.03 g, 3.83 mmol, 1 eq), 3-iodo-1H-pyrazole-4-carboxylic acid ethyl ester (1.22 g, 4.59 mmol, 1.2 eq) and K2CO3 (1.58 g, 11.49 mmol, 3 eq) in DMF (6 mL) was stirred at rt overnight. After the reaction was completed, the mixture solution was diluted with water and extracted with EA (50 mL×3). The combined organic layers were concentrated and purified by chromatography on a silica gel column (PE/EA=5/1, v/v) to give 3-iodo-1-(8-methanesulfonyl-3-methyl-quinolin-6-ylmethyl)-1H-pyrazole-4-carboxylic acid ethyl ester (1.15 g, 60.2%) as a white solid.

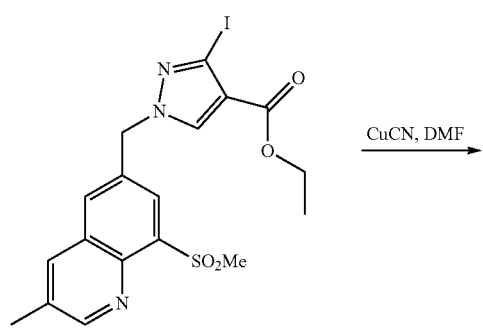

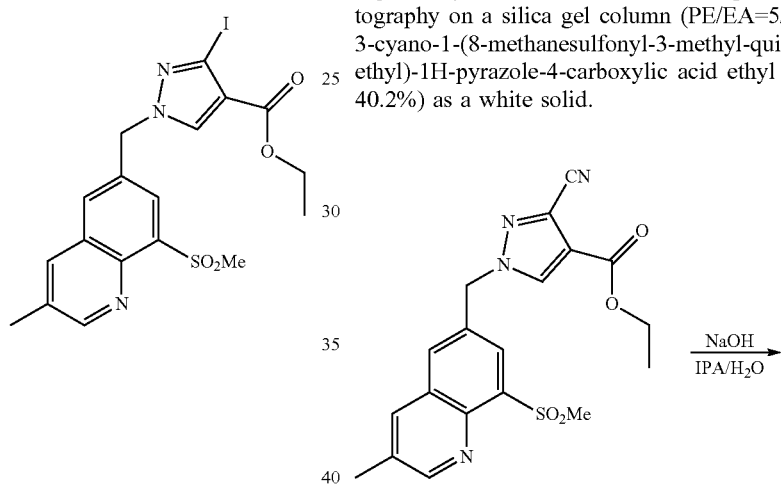

A mixture of 3-iodo-1-(8-methanesulfonyl-3-methyl-quinolin-6-ylmethyl)-1H-pyrazole-4-carboxylic acid ethyl ester (500 mg, 1 mmol, 1 eq) and CuCN (102 mg, 1.2 mmol, 1.2 eq) in DMF (6 mL) was stirred at 140° C. overnight. After the reaction was completed, the mixture was diluted with H2O, and extracted with DCM (50 mL×3). The combined organic layers were concentrated and purified by chromatography on a silica gel column (PE/EA=5/1, v/v) to give 3-cyano-1-(8-methanesulfonyl-3-methyl-quinolin-6-ylmethyl)-1H-pyrazole-4-carboxylic acid ethyl ester (140 mg, 40.2%) as a white solid.

A mixture of 3-cyano-1-(8-methanesulfonyl-3-methyl-quinolin-6-ylmethyl)-1H-pyrazole-4-carboxylic acid ethyl ester (160 mg, 0.4 mmol, 1 eq) and NaOH (48 mg, 1.2 mmol, 3 eq) in IPA (6 mL) and H2O (4 mL) was stirred at 100° C. for 30 min. The solvent was evaporated and neutralized with 1 N of HCl to pH 5. Then a white precipitate formed, which was filtered and dried in vacuo to give 3-cyano-1-(8-methanesulfonyl-3-methyl-quinolin-6-ylmethyl)-1H-pyrazole-4-carboxylic acid (210 mg, crude) as a white solid.

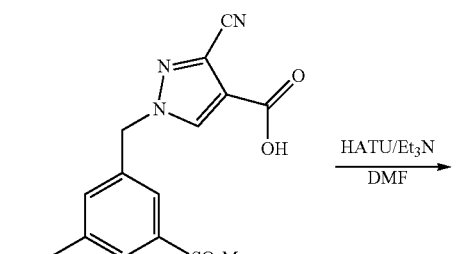

A mixture of 3-cyano-1-(8-methanesulfonyl-3-methyl-quinolin-6-ylmethyl)-1H-pyrazole-4-carboxylic acid (210 mg, 0.57 mmol, 1 eq), (5-aminomethyl-4,6-dimethyl-pyridin-2-yl)-carbamic acid tert-butyl ester (171 mg, 0.68 mmol, 1.2 eq), HATU (325 mg, 0.855 mmol, 1.5 eq), Et3N (0.25 mL, 1.71 mmol, 3 eq) in DMF (6 mL) was stirred at rt overnight. After the reaction was completed, the mixture was diluted with H2O and extracted with DCM (30 mL×3). The combined organic layers were concentrated and purified by chromatography on a silica gel column (PE/EA=5/1, v/v) to give [5-({[3-cyano-1-(8-methanesulfonyl-3-methyl-quinolin-6-ylmethyl)-1H-pyrazole-4-carbonyl]-amino}-methyl)-4,6-dimethyl-pyridin-2-yl]-carbamic acid tert-butyl ester (100 mg, 41.5%) as a white solid.

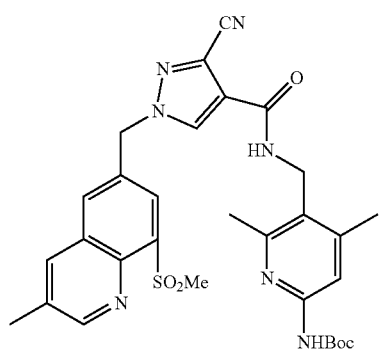

A mixture of [5-({[3-cyano-1-(8-methanesulfonyl-3-methyl-quinolin-6-ylmethyl)-1H-pyrazole-4-carbonyl]-amino}-methyl)-4,6-dimethyl-pyridin-2-yl]-carbamic acid tert-butyl ester (100 mg, 0.16 mmol) in TFA (10 mL) was stirred at rt for 0.5 h. After the reaction was completed, the solvent was evaporated and the resulting residue was purified by prep-HPLC to give N-((6-amino-2,4-dimethylpyridin-3-yl)methyl)-3-cyano-1-((3-methyl-8-(methylsulfonyl)quinolin-6-yl)methyl)-1H-pyrazole-4-carboxamide (26 mg, 31%) as a white solid. LRMS (M+H+) m/z calculated 504.2, found 504.0. 1H NMR (DMSO-d6, 400 MHz): δ 8.99 (d, 1H), 8.61 (s, 1H), 8.37 (s, 1H), 8.36 (s, 1H), 8.26 (d, 1H), 8.15 (d, 1H), 6.16 (s, 1H), 5.79 (s, 2H), 5.77 (s, 2H), 4.27 (d, 2H), 3.59 (s, 3H), 2.53 (s, 3H), 2.31 (s, 3H), 2.17 (s, 3H).

Example 62: Preparation of N-((6-amino-2,4-dimethylpyridin-3-yl)methyl)-3-cyano-1-((8-cyano-3-methylquinolin-6-yl)methyl)-1H-pyrazole-4-carboxamide

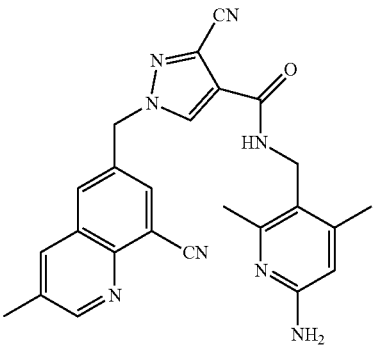

N-((6-amino-2,4-dimethylpyridin-3-yl)methyl)-3-cyano-1-((8-cyano-3-methylquinolin-6-yl)methyl)-1H-pyrazole-4-carboxamide

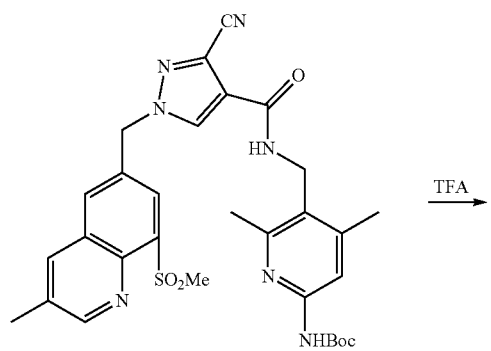

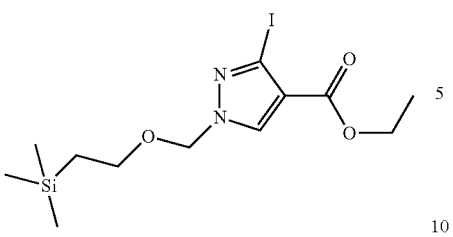

To a solution of 3-iodo-1H-pyrazole-4-carboxylic acid ethyl ester (20.0 g, 75 mmol, 1.0 eq) in THF was added NaH (6.0 g, 150 mmol, 2.0 eq) at 0° C. The mixture was stirred at 0° C. for 1 h. SEM-Cl (12.5 g, 113 mmol, 1.5 eq) was added, and the reaction mixture was stirred at rt overnight. The mixture was poured into water (800 mL) and extracted with EA (800 mL×2). The combined organic layers were washed with water, dried, concentrated and purified by chromatography on a silica gel column (PE/EA=20/1, v/v) to give 3-iodo-1-(2-trimethylsilanyl-ethoxymethyl)-1H-pyrazole-4-carboxylic acid ethyl ester (25.7 g, 86%) as a yellow oil.

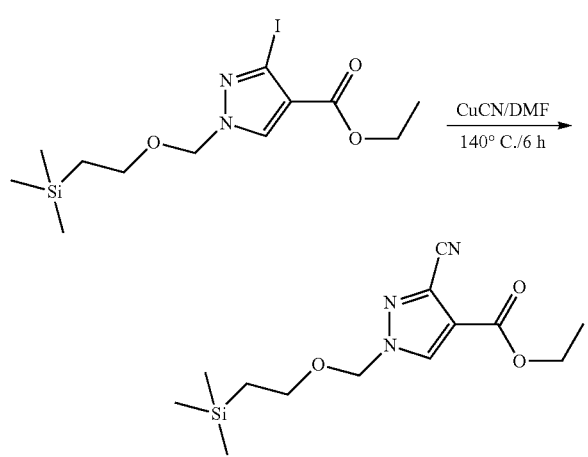

A mixture of 3-iodo-1-(2-trimethylsilanyl-ethoxymethyl)-1H-pyrazole-4-carboxylic acid ethyl ester (25.7 g, 65 mmol, 1.0 eq) and CuCN (7.0 g, 78 mmol, 1.2 eq) in DMF (300 mL) was stirred at 140° C. for 6 h. The solution was poured into water/NH3.H2O (800 mL/200 mL) and extracted with EA. The combined organic layers were washed with water, dried and concentrated. The resulting residue was purified by chromatography on a silica gel column (PE/EA/DCM=10/1/0.5 to 5/1/0.4, v/v) to give 3-cyano-1-(2-trimethylsilanyl-ethoxymethyl)-1H-pyrazole-4-carboxylic acid ethyl ester (8.6 g, 45%).

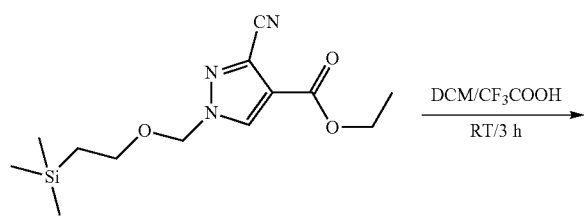

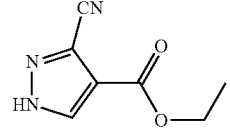

A mixture of 3-cyano-1-(2-trimethylsilanyl-ethoxymethyl)-1H-pyrazole-4-carboxylic acid ethyl ester (8.6 g, 29 mmol, 1.0 eq) in DCM/CF3COOH (100 mL/100 mL) was stirred at rt for 3 h. The volatile was removed by evaporation and the residue was diluted with water. The aqueous layer was adjusted to pH 9 with sat. aqueous Na2CO3 and extracted with DCM (200 mL×5). The combined organic layers were dried, concentrated and purified by chromatography on a silica gel column (PE/EA=4/1 to 2/1, v/v) to give 3-cyano-1H-pyrazole-4-carboxylic acid ethyl ester as a white solid (4.5 g, 94%) as a white solid.

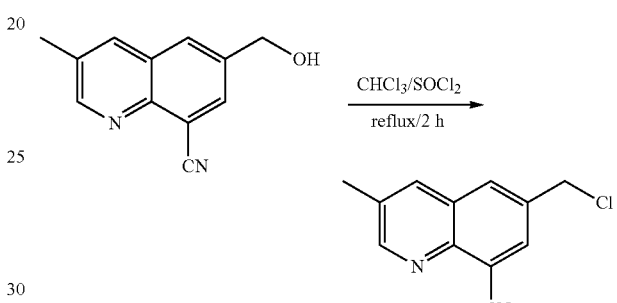

A mixture of 6-hydroxymethyl-3-methyl-quinoline-8-carbonitrile (660 mg, 3.3 mmol, 1.0 eq) and SOCl2 (10 mL) in CHCl3 (40 mL) was stirred under reflux for 2 h. The solvent was removed and the residue was diluted with H2O, adjusted to pH 8~9 with sat. aqueous NaHCO$_3$, extracted with DCM (100 mL). The combined organic layers were washed with H2O, dried and concentrated to give 6-chloromethyl-3-methyl-quinoline-8-carbonitrile (598 mg, 83%).

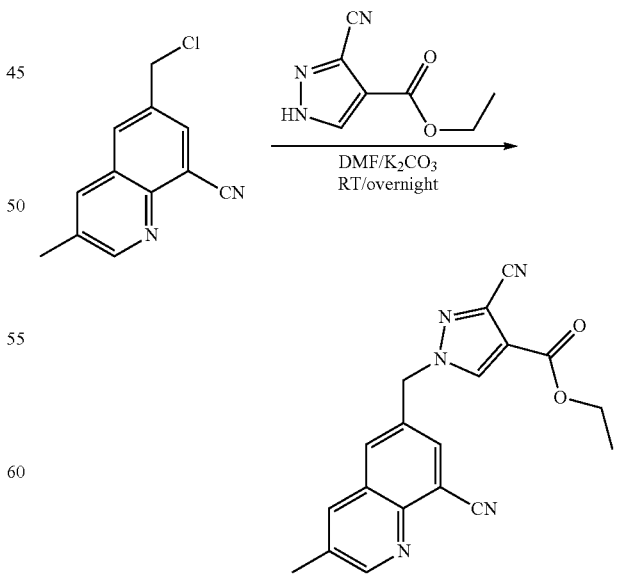

A mixture of 6-chloromethyl-3-methyl-quinoline-8-carbonitrile (297 mg, 1.37 mmol, 1.0 eq), 3-cyano-1H-pyrazole-4-carboxylic acid ethyl este (226 mg, 1.37 mmol, 1.0 eq) and K2CO3 (378 g, 2.74 mmol, 2.0 eq) in DMF (10 mL) was stirred at rt overnight. DMF was removed by evaporation and the residue was diluted with DCM, washed with water, dried, concentrated and purified by chromatography on a silica gel column (PE/EA=2/1, v/v) to give 3-cyano-1-(8-cyano-3-methyl-quinolin-6-ylmethyl)-1H-pyrazole-4-carboxylic acid ethyl ester (200 mg, 42.3%).

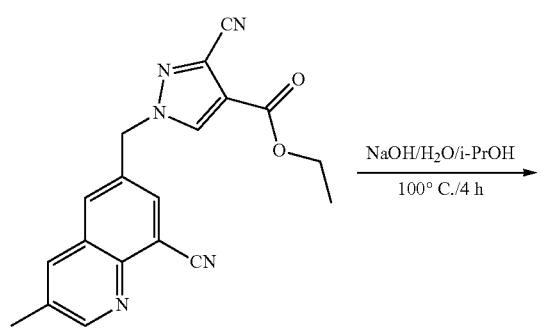

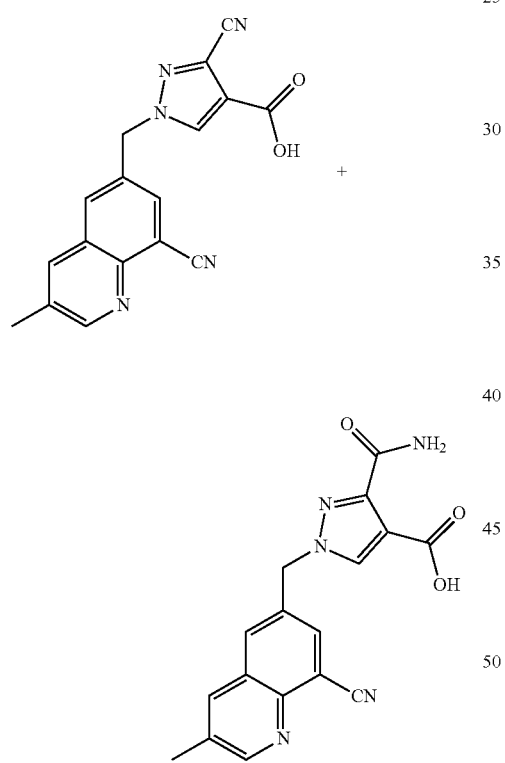

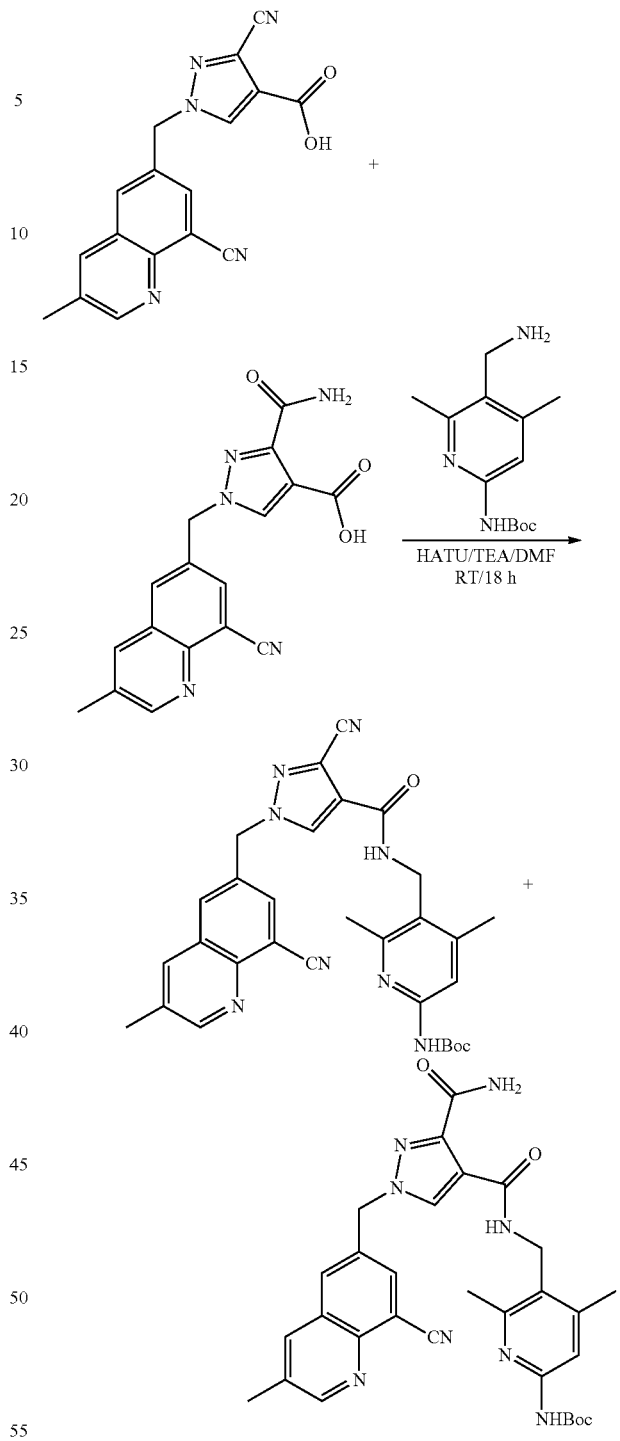

A mixture of 3-cyano-1-(8-cyano-3-methyl-quinolin-6-ylmethyl)-1H-pyrazole-4-carboxylic acid ethyl ester (200 mg, 0.58 mmol, 1.0 eq), and NaOH (0.35 g, 8.7 mmol, 15.0 eq) in 50 mL of i-PrOH/H2O (50 mL, 1/1, v/v) was stirred under reflux for 4 h. LCMS analysis showed the reaction contained 3-cyano-1-((8-cyano-3-methylquinolin-6-yl)methyl)-1H-pyrazole-4-carboxylic acid (75%) and 3-carbamoyl-1-((8-cyano-3-methylquinolin-6-yl)methyl)-1H-pyrazole-4-carboxylic acid (23%). i-PrOH was removed by evaporation, the aqueous layer was adjusted to pH 3 with 1 N HCl. The white precipitate was filtered, washed with water, dried to give 215 mg of mixture.

A mixture of 3-cyano-1-(8-cyano-3-methyl-quinolin-6-ylmethyl)-1H-pyrazole-4-carboxylic acid and 3-carbamoyl-1-((8-cyano-3-methylquinolin-6-yl)methyl)-1H-pyrazole-4-carboxylic acid (215 mg, ca. 0.68 mmol, 1.0 eq), (5-aminomethyl-4,6-dimethyl-pyridin-2-yl)-carbamic acid tert-butyl ester (203 mg, 0.81 mmol, 1.2 eq), TEA (0.21 g, 2.04 mmol, 3.0 eq) and HATU (334 mg, 0.88 mmol, 1.3 eq) in DMF (10 mL) was stirred at rt overnight. The reaction mixture was diluted with DCM (300 mL), washed with sat aq NH4Cl (100 mL×2). The combined organics were dried, concentrated and purified by chromatography on a silica gel column (DCM/MeOH=50/1, v/v) to give 240 mg of crude mixture. The mixture was purified by pre-HPLC to afford 186 mg of tert-butyl (5-((3-cyano-1-((8-cyano-3-methylquinolin-6-yl)methyl)-1H-pyrazole-4-carboxamido)methyl)-4,6-dimethylpyridin-2-yl)carbamate (49.3% yield) and 15 mg of tert-butyl (5-((3-carbamoyl-1-((8-cyano-3-methylquinolin-6-yl)methyl)-1H-pyrazole-4-carboxamido)methyl)-4,6-dimethylpyridin-2-yl)carbamate (4%, yield).

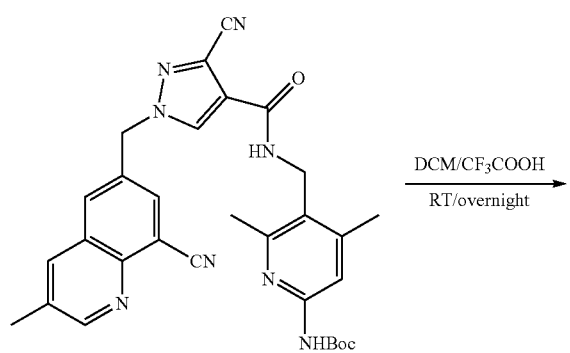

A solution of tert-butyl (5-((3-cyano-1-((8-cyano-3-methylquinolin-6-yl)methyl)-1H-pyrazole-4-carboxamido)methyl)-4,6-dimethylpyridin-2-yl)carbamate (186 mg, 0.34 mmol, 1.0 eq) in DCM (25 mL) and CF3COOH (25 mL) was stirred at rt overnight. LCMS analysis showed the reaction was complete. The solvent was removed by evaporation, and the resulting residue was diluted in ethanol (20 mL), adjusted to pH 9 with aq. Na2CO3 and stirred at rt for 5 h. The resulting precipitate was filtered, washed with water, and dried at 120° C. for 3 h to give N-((6-amino-2,4-dimethylpyridin-3-yl)methyl)-3-cyano-1-((8-cyano-3-methylquinolin-6-yl)methyl)-1H-pyrazole-4-carboxamide (117 mg, 77%) as a white solid. LRMS (M+H+) m/z calculated 451.2, found 451.0. 1H NMR (DMSO-d6, 300 MHz): δ 8.95 (s, 1H), 8.56 (s, 1H), 8.32 (s, 1H), 8.26 (s, 1H), 8.23 (s, 2H), 8.13 (s, 1H), 6.01 (s, 1H), 5.68 (s, 4H), 4.26 (d, 2H), 2.27 (s, 3H), 2.14 (s, 3H).

Example 63: Preparation of N4-((6-amino-2,4-dimethylpyridin-3-yl)methyl)-1-((8-cyano-3-methylquinolin-6-yl)methyl)-1H-pyrazole-3,4-dicarboxamide

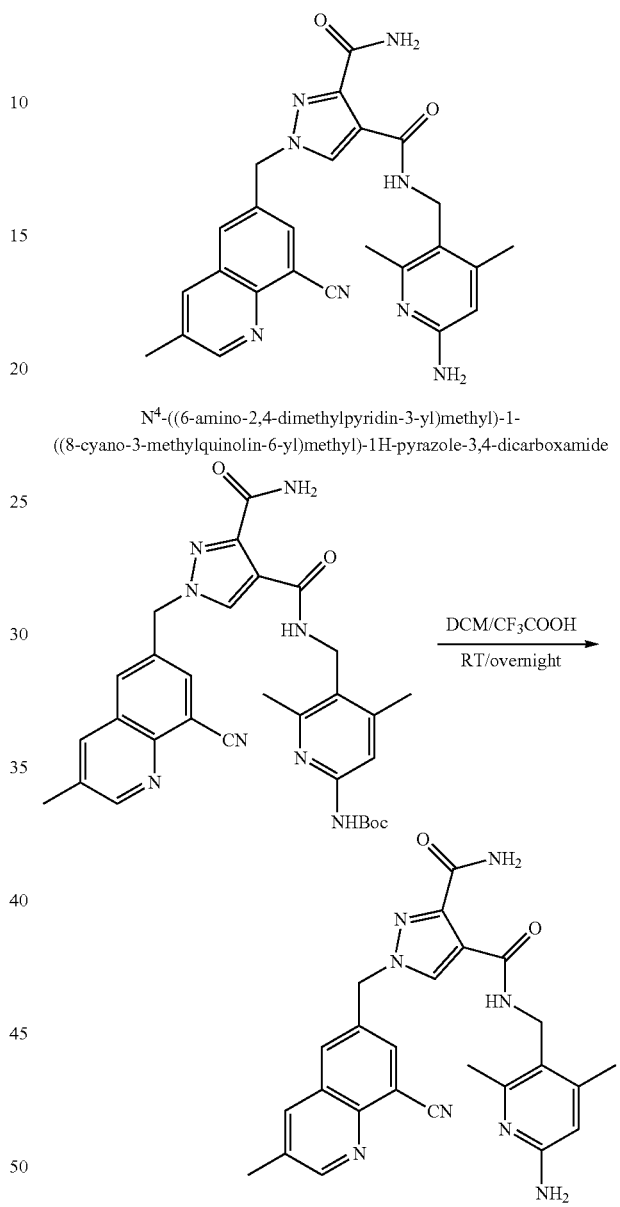

N$^4$-((6-amino-2,4-dimethylpyridin-3-yl)methyl)-1-((8-cyano-3-methylquinolin-6-yl)methyl)-1H-pyrazole-3,4-dicarboxamide A solution of tert-butyl (5-((3-carbamoyl-1-((8-cyano-3-methylquinolin-6-yl)methyl)-1H-pyrazole-4-carboxamido)methyl)-4,6-dimethylpyridin-2-yl)carbamate (11 mg, 0.019 mmol, 1.0 eq) in DCM (5 mL) and CF3COOH (5 mL) was stirred at rt overnight. LCMS analysis showed the reaction was complete. The solvent was removed by evaporation, and the resulting residue was diluted in ethanol (5 mL), adjusted to pH 9 with aqueous Na2CO3 and stirred at rt for 5 h. The resulting precipitate was filtered, washed with water, and dried at 120° C. for 3 h to give N4-((6-amino-2,4-dimethylpyridin-3-yl)methyl)-1-((8-cyano-3-methylquinolin-6-yl)methyl)-1H-pyrazole-3,4-dicarboxamide (2 mg, 16%) as a white solid. LRMS (M+H+) m/z calculated 469.2, found 469.3. 1H NMR (DMSO-d6, 300 MHz): δ 10.62 (s, 1H), 8.93 (s, 1H), 8.54 (s, 1H), 8.32 (s, 1H), 8.29 (s, 1H), 8.06 (s, 2H), 7.84 (s, 1H), 6.09 (s, 1H), 5.65 (s, 2H), 5.62 (s, 2H), 4.31 (d, 2H), 2.31 (s, 3H), 2.18 (s, 3H).

Example 64: Preparation of N-((6-amino-2,4-dimethylpyridin-3-yl)methyl)-1-((3-chloroquinolin-6-yl)methyl)-4-cyano-1H-pyrazole-5-carboxamide

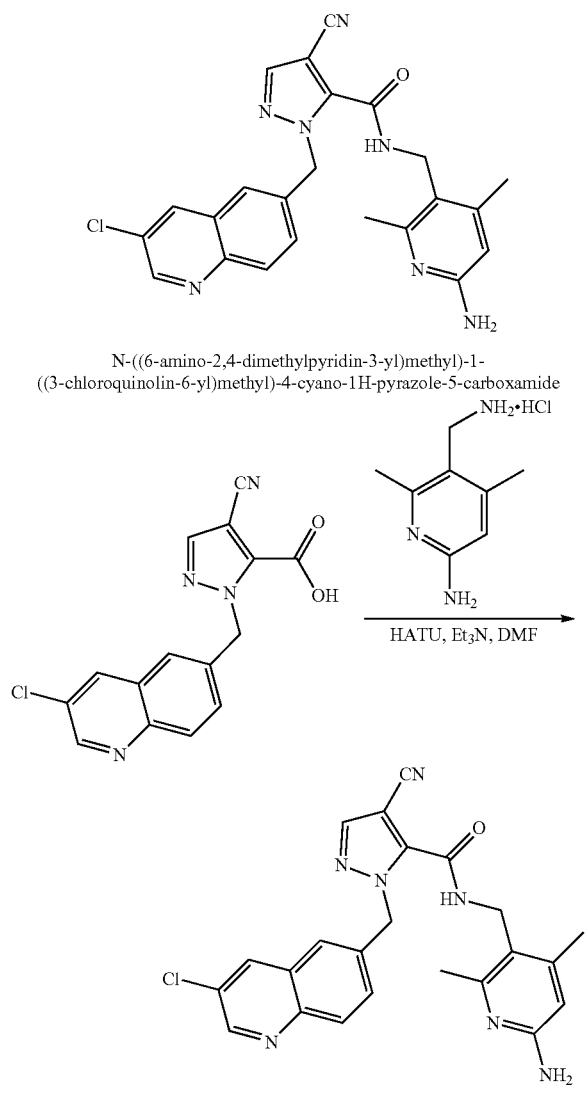

A mixture of 2-(3-chloro-quinolin-6-ylmethyl)-4-cyano-2H-pyrazole-3-carboxylic acid (95 mg, 0.30 mmol, 1.0 eq), 5-aminomethyl-6-methyl-pyridin-2-ylamine hydrochloride (67 mg, 0.36 mmol, 1.2 eq), HATU (139 mg, 0.36 mmol, 1.2 eq) and Et3N (0.12 mL, 0.9 mmol, 3.0 eq) in DMF (6 mL) was stirred at rt overnight. After the reaction was completed, the mixture solution was purified by prep-HPLC to give N-((6-amino-2,4-dimethylpyridin-3-yl)methyl)-1-((3-chloroquinolin-6-yl)methyl)-4-cyano-1H-pyrazole-5-carboxamide (75 mg, 55%) as a white solid. LCMS (M+H+) m/z calculated 446.1, found 446.0. 1H NMR (DMSO-d6, 400 MHz) δ 9.04 (t, 1H), 8.89 (s, 1H), 8.51 (s, 1H), 8.18 (s, 1H), 8.02 (d, 1H) 7.65 (s, 1H), 7.63 (s, 1H), 6.08 (s, 1H), 5.74 (s, 2H), 5.69 (s, 2H), 4.24 (d, 2H), 2.16 (s, 3H), 2.03 (s, 3H).

Example 65: Preparation of N-((6-amino-2,4-dimethylpyridin-3-yl)methyl)-3-cyano-1-((3-cyclopropylquinolin-6-yl)methyl)-1H-pyrazole-4-carboxamide

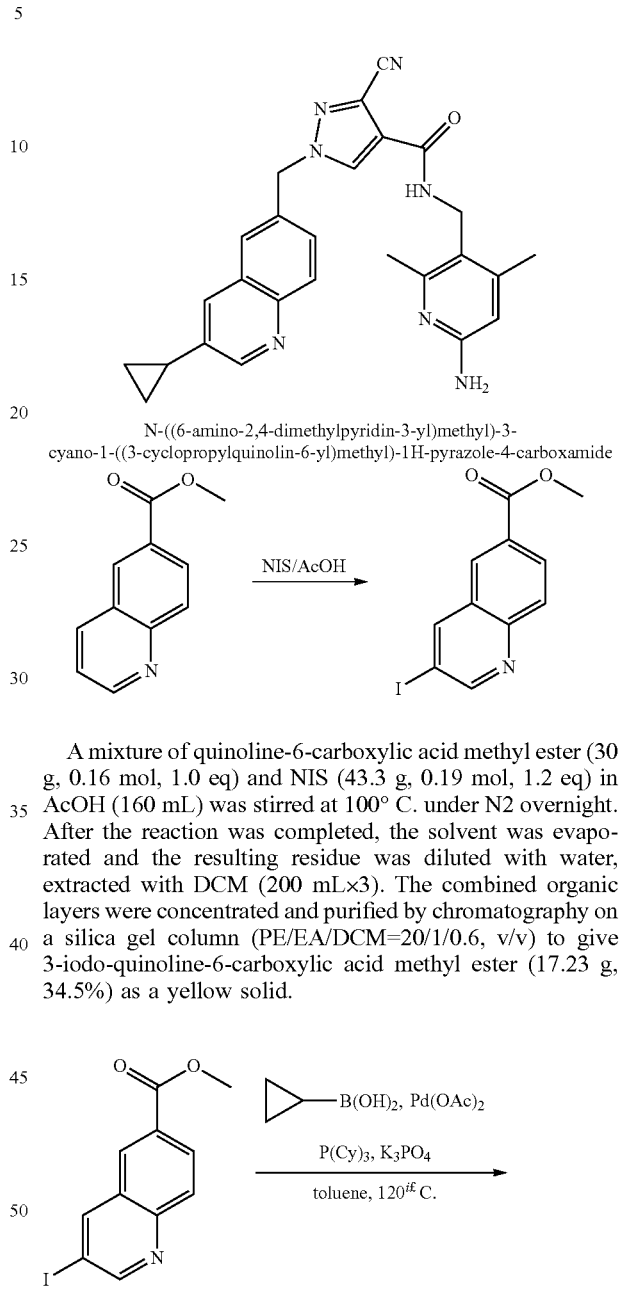

A mixture of quinoline-6-carboxylic acid methyl ester (30 g, 0.16 mol, 1.0 eq) and NIS (43.3 g, 0.19 mol, 1.2 eq) in AcOH (160 mL) was stirred at 100° C. under N2 overnight. After the reaction was completed, the solvent was evaporated and the resulting residue was diluted with water, extracted with DCM (200 mL×3). The combined organic layers were concentrated and purified by chromatography on a silica gel column (PE/EA/DCM=20/1/0.6, v/v) to give 3-iodo-quinoline-6-carboxylic acid methyl ester (17.23 g, 34.5%) as a yellow solid.

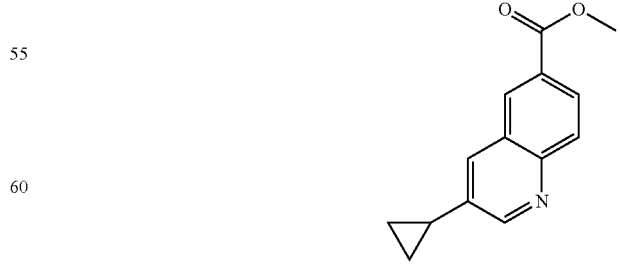

A mixture of 3-iodo-quinoline-6-carboxylic acid methyl ester (2 g, 6.41 mmol, 1.0 eq), cyclopropylboronic acid (770 mg, 8.97 mmol, 1.4 eq), K3PO4 (4.08 g, 19.23 mmol, 3.0 eq), Pd(OAc)2 (143 mg, 0.63 mmol, 0.1 eq), P(Cy)3 (358 mg, 1.28 mmol, 0.2 eq) in toluene (45 mL) and H2O (2 mL) was stirred at 120° C. under N2 overnight. After the reaction was completed, the mixture was extracted with EA (100 mL×3). The combined organic layers were concentrated and purified by chromatography on a silica gel column (PE/EA=10/1, v/v) to give 3-cyclopropyl-quinoline-6-carboxylic acid methyl ester (770 mg, 53%) as a yellow solid.

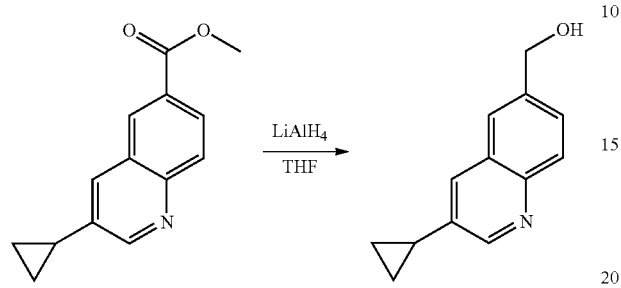

A mixture of 3-cyclopropyl-quinoline-6-carboxylic acid methyl ester (770 mg, 3.39 mmol, 1.0 eq) and LiAlH4 (3.4 mL, 3.4 mmol, 1.0 eq) in THF (20 mL) was stirred at 0° C. under N2 for 3 h. After the reaction was completed, the mixture solution was quenched with aqueous Rochelie' salt (20 mL), then extracted with EA (50 mL×3). The combined organic layers were concentrated and purified by chromatography on a silica gel column (PE/EA=2/1, v/v) to give (3-cyclopropyl-quinolin-6-yl)-methanol (600 mg, 89%) as a white solid.

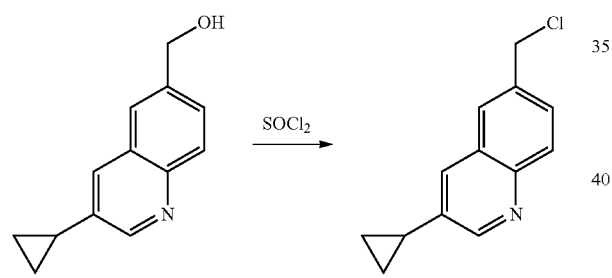

A mixture of (3-cyclopropyl-quinolin-6-yl)-methanol (600 mg, 3 mmol, 1.0 eq), in SOCl2 (20 mL) was stirred at rt for 3 h. Then the solvent was evaporated in vacuo and the resulting residue was diluted with DCM and washed with saturated NaHCO₃ (50 mL). The combined organic layers were concentrated and dried in vacuo to give 6-chloromethyl-3-cyclopropyl-quinoline (550 mg, 84.5%) as a yellow oil.

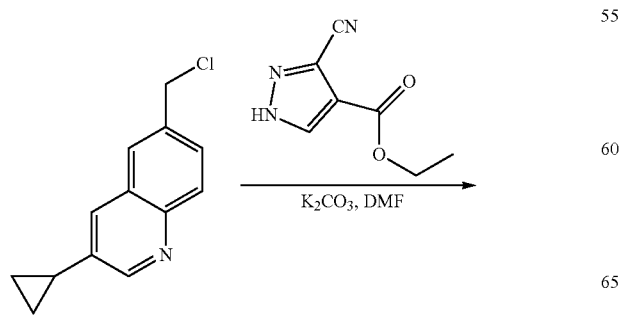

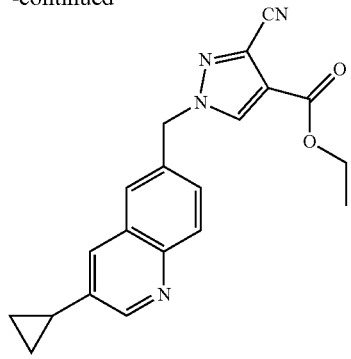

A mixture of 6-chloromethyl-3-cyclopropyl-quinoline (550 mg, 2.5 mmol, 1.4 eq), 3-cyano-1H-pyrazole-4-carboxylic acid ethyl ester (300 mg, 1.8 mmol, 1.0 eq), and K2CO3 (745 mg, 5.4 mmol, 3.0 eq) in DMF (6 mL) was stirred at rt overnight. After the reaction was completed, the reaction solution was diluted with H2O and extracted with DCM (30 mL×3). The combined organic layers were concentrated and purified by chromatography on silica gel column (PE/EA=2/1, v/v) to give 3-cyano-1-(3-cyclopropyl-quinolin-6-ylmethyl)-1H-pyrazole-4-carboxylic acid ethyl ester (380 mg, 61%) as a yellow oil.

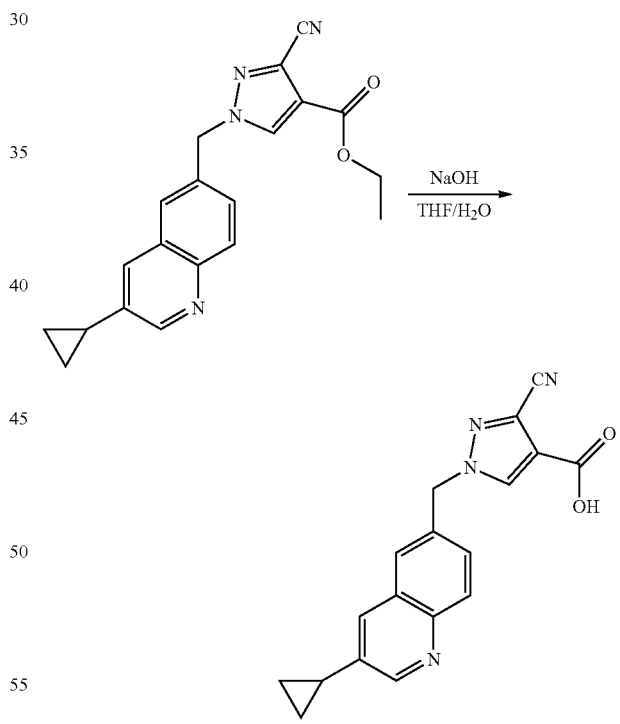

A mixture of 3-cyano-1-(3-cyclopropyl-quinolin-6-ylmethyl)-1H-pyrazole-4-carboxylic acid ethyl ester (380 mg, 1.1 mmol, 1.0 eq) and NaOH (132 mg, 3.3 mmol, 3.0 eq) in THF (6 ml) and H2O (6 mL) was stirred at 80° C. for 1 h. THF was removed by evaporation, and the aqueous was neutralized with 1 N HCl to pH 5. Then a white precipitate was formed, which was filtered and dried in vacuo to give 3-cyano-1-(3-cyclopropyl-quinolin-6-ylmethyl)-1H-pyrazole-4-carboxylic acid (220 mg, 63%).

279

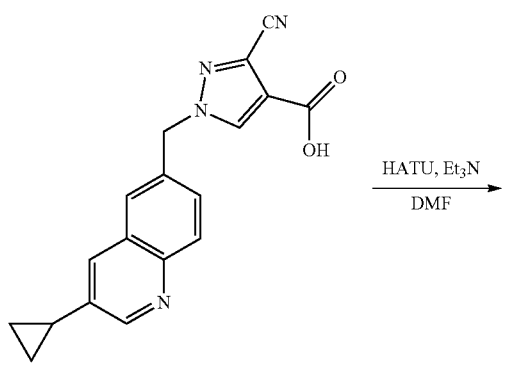

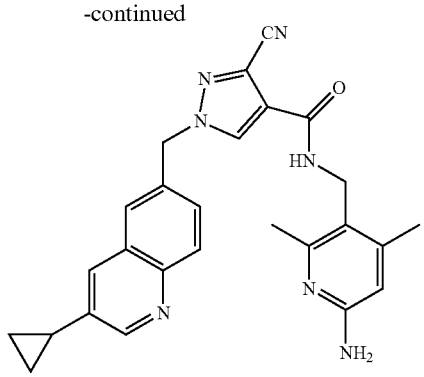

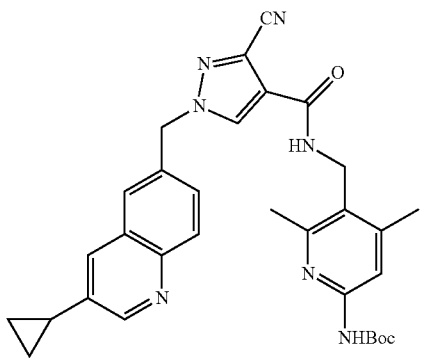

A mixture of 3-cyano-1-(3-cyclopropyl-quinolin-6-ylmethyl)-1H-pyrazole-4-carboxylic acid (220 mg, 0.69 mmol, 1.0 eq), (5-aminomethyl-4,6-dimethyl-pyridin-2-yl)-carbamic acid tert-butyl ester (208 mg, 0.83 mmol, 1.2 eq), HATU (393 mg, 1.03 mmol, 1.5 eq), and Et3N (0.29 mL, 2.07 mmol, 3.0 eq) in DMF (6 mL) was stirred at rt overnight. After the reaction was completed, the reaction was diluted with H2O and extracted with DCM (30 mL×3). The combined organic layers were concentrated and purified by chromatography a on silica gel column (DCM/MeOH=30/1, v/v) to give tert-butyl (5-((3-cyano-1-((3-cyclopropylquinolin-6-yl)methyl)-1H-pyrazole-4-carboxamido)methyl)-4,6-dimethylpyridin-2-yl)carbamate (420 mg, 79%) as a white solid.

280

-continued

A solution of tert-butyl (5-((3-cyano-1-((3-cyclopropylquinolin-6-yl)methyl)-1H-pyrazole-4-carboxamido) methyl)-4,6-dimethylpyridin-2-yl)carbamate (420 mg, 0.76 mmol, 1.0 eq) in TFA (6 mL) and DCM (6 mL) was stirred at rt overnight. Then TFA and DCM were evaporated. The resulting residue was diluted with EtOH (5 mL). It was neutralized to pH 8 with 1 N aqueous NaOH. Then a white precipitate was formed, which was filtered and dried in vacuo to give N-((6-amino-2,4-dimethylpyridin-3-yl)methyl)-3-cyano-1-((3-cyclopropylquinolin-6-yl)methyl)-1H-pyrazole-4-carboxamide (70 mg, 20%) as a white solid. LRMS (M+H+) m/z calculated 452.2, found 452.1. 1H NMR (DMSO-d6, 400 MHz) δ 8.76 (s, 1H), 8.54 (s, 1H), 8.27 (s, 1H), 7.94 (d, 2H), 7.72 (s, 1H), 7.54~7.56 (m, 1H), 6.12 (s, 1H), 5.73 (s, 2H), 5.63 (s, 2H), 4.27 (s, 2H), 2.28 (s, 3H), 2.12 (s, 3H), 1.98 (s, 1H), 1.09~1.05 (m, 2H), 0.89~0.85 (m, 2H).

Example 66: Preparation of N-((6-amino-2-methylpyridin-3-yl)methyl)-3-cyano-1-((3-cyclopropylquinolin-6-yl)methyl)-1H-pyrazole-4-carboxamide

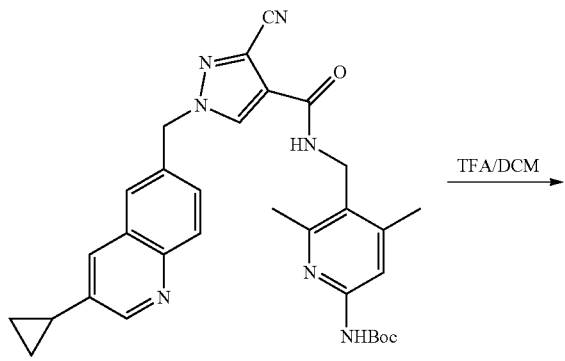

TFA/DCM

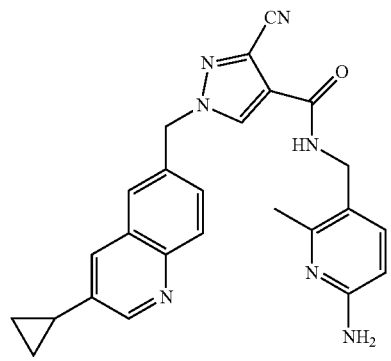

N-((6-amino-2-methylpyridin-3-yl)methyl)-3-cyano-1-((3-cyrlopropylquinolin-6-yl)methyl)-1H-pyrazole-4-carboxamide

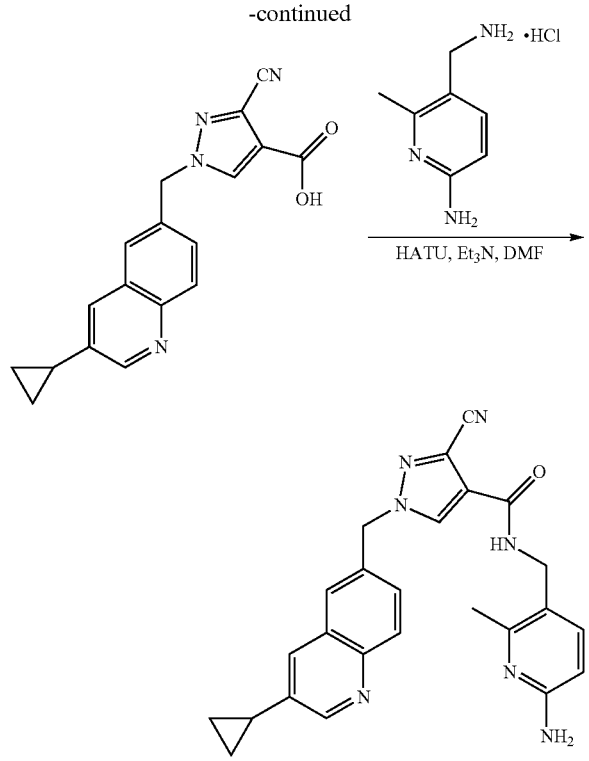

A mixture of 3-cyano-1-(3-cyclopropyl-quinolin-6-ylmethyl)-1H-pyrazole-4-carboxylic acid (80 mg, 0.25 mmol, 1.0 eq), 5-aminomethyl-6-methyl-pyridin-2-ylamine hydrochloride (52 mg, 0.30 mmol, 1.2 eq), HATU (285 mg, 0.75 mmol, 1.5 eq) and Et3N (0.21 mL, 1.5 mmol, 3.0 eq) in DMF (6 mL) was stirred at rt overnight. After the reaction was completed, the mixture solution was purified by prep-HPLC to give N-((6-amino-2-methylpyridin-3-yl)methyl)-3-cyano-1-((3-cyclopropylquinolin-6-yl)methyl)-1H-pyrazole-4-carboxamide (59 mg, 54%) as a white solid. LRMS (M+H+) m/z calculated 438.2, found 438.0. 1H NMR (DMSO-d6, 400 MHz) δ 8.87 (s, 1H), 8.59 (t, 1H), 8.53 (s, 1H), 7.98 (d, 2H), 7.73 (s, 1H) 7.58 (d, 1H), 7.23 (d, 1H), 6.23 (d, 1H), 5.75 (s, 2H), 5.66 (s, 2H), 4.22 (d, 2H), 2.25 (s, 3H), 2.01~1.98 (m, 1H), 1.07~1.09 (t, 2H), 0.88~0.87 (t, 2H).

Example 67: Preparation of N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide

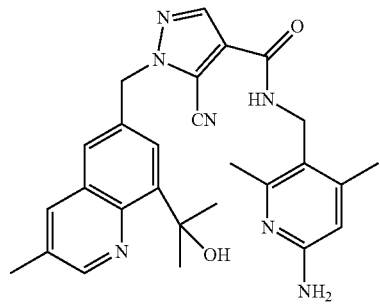

N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide

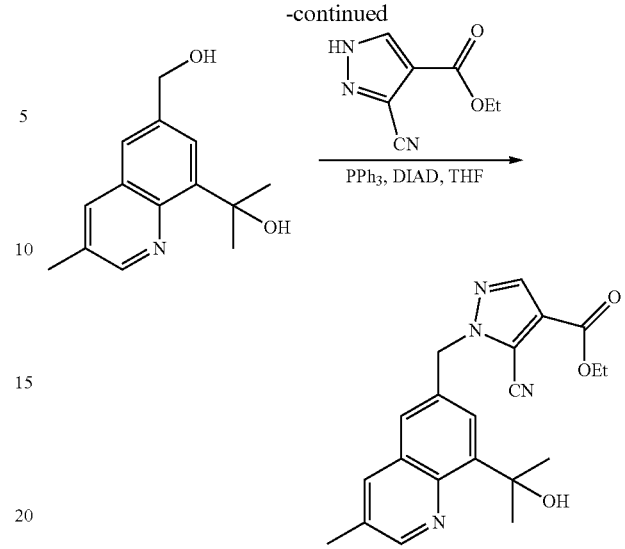

To a mixture of 2-(6-hydroxymethyl-3-methyl-quinolin-8-yl)-propan-2-ol (380 mg, 1.65 mmol, 1 eq), 3-cyano-1H-pyrazole-4-carboxylic acid ethyl ester (271 mg, 1.65 mmol, 1 eq) and PPh3 (519 mg, 1.98 mmol, 1.2 eq) in dry THF (12 mL) was added DIAD (0.39 mL, 1.98 mmol, 1.2 eq) dropwise under N2 at 0° C. The mixture was stirred at rt for 3 h. The mixture was concentrated and the residue was partitioned between DCM and water. The organic layer was dried and concentrated. The resulting residue was purified by chromatography on a silica gel column (PE/EA=5/1, v/v) to give 5-cyano-1-[8-(1-hydroxy-1-methyl-ethyl)-3-methyl-quinolin-6-ylmethyl]-1H-pyrazole-4-carboxylic acid ethyl ester (200 mg, 32%).

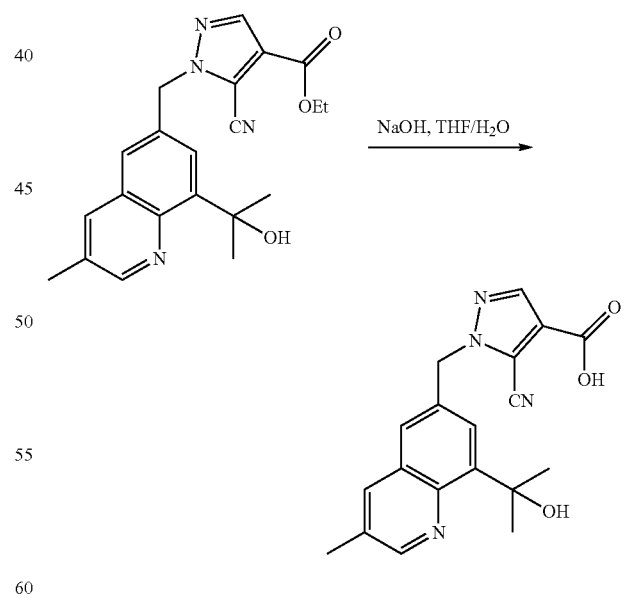

A mixture of 5-cyano-1-[8-(1-hydroxy-1-methyl-ethyl)-3-methyl-quinolin-6-ylmethyl]-1H-pyrazole-4-carboxylic acid ethyl ester (200 mg, 0.53 mmol, 1.0 eq) and NaOH (64 mg, 1.6 mmol, 3 eq) in THF (5 mL) and H2O (5 mL) was stirred at 80° C. for 1 h. THF was removed by evaporation, and the aqueous was neutralized with 1 N HCl to pH 5. Then a white precipitate formed, which was filtered and dried in vacuo to give 5-cyano-1-[8-(1-hydroxy-1-methyl-ethyl)-3-methyl-quinolin-6-ylmethyl]-1H-pyrazole-4-carboxylic acid (120 mg, 620).

Example 68: Preparation of N-((6-amino-2,4-dimethylpyridin-3-yl)methyl)-1-((3-chloro-8-(methylsulfonyl)quinolin-6-yl)methyl)-3-cyano-1H-pyrazole-4-carboxamide

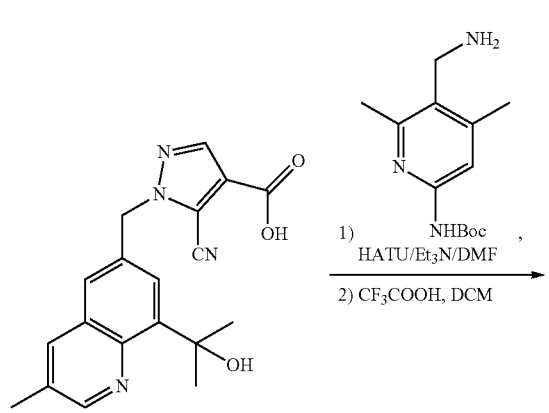

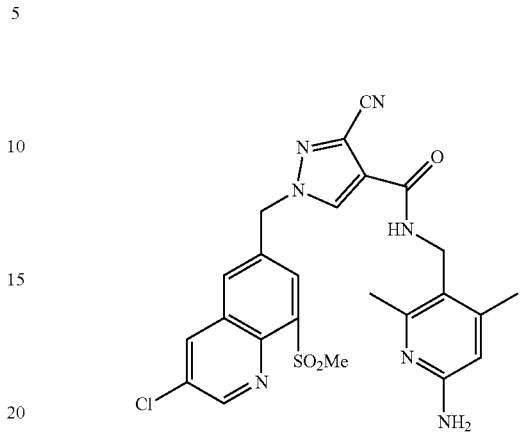

N-((6-amino-2,4-dimethylpyridin-3-yl)methyl)-1-((3-chloro-8-(methylsulfonyl)quinolin-6-yl)methyl)-3-cyano-1H-pyrazole-4-carboxamide

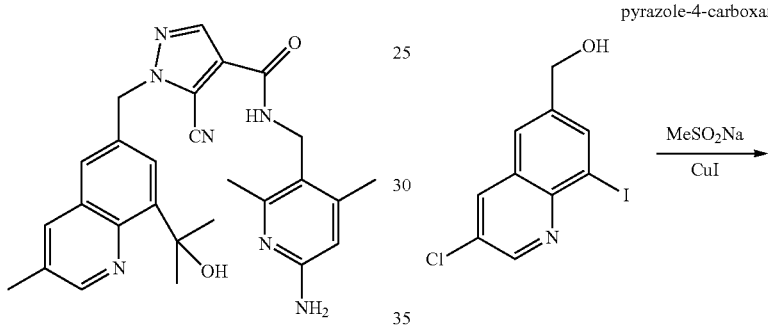

A mixture of 5-cyano-1-[8-(1-hydroxy-1-methyl-ethyl)-3-methyl-quinolin-6-ylmethyl]-1H-pyrazole-4-carboxylic acid (120 mg, 0.34 mmol, 1 eq), (5-aminomethyl-4,6-dimethyl-pyridin-2-yl)-carbamic acid tert-butyl ester (103 mg, 0.41 mmol, 1.2 eq), Et3N (104 mg, 1.03 mmol, 3 eq) and HATU (163 mg, 0.43 mmol, 1.3 eq) in DMF (10 mL) was stirred at rt overnight. The reaction mixture was diluted with 100 mL of water, extracted with DCM. The combined organic layers were dried, concentrated, purified by chromatography on a silica gel column (DCM/MeOH=60/1, v/v) to give 120 mg of mixture, which was purified by pre-HPLC to give tert-butyl (5-((5-cyano-1-((8-(2-hydroxypropan-2-yl)-3-methylquinolin-6-yl)methyl)-1H-pyrazole-4-carboxamido)methyl)-4,6-dimethylpyridin-2-yl)carbamate (40 mg, 20%). The white solid (40 mg, 0.068 mmol, 1.0 eq) was dissolved in DCM/CF3COOH (20 mL/20 mL) and stirred at rt overnight. The mixture was concentrated and the resulting residue was diluted with ethanol/water (6 mL/40 mL) and adjusted to pH 10 with aqueous Na2CO3. The mixture was stirred at rt for 2 h. The formed precipitate was filtered, washed with water and dried at 110° C. for 4 h to give N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide (23 mg, 14%) as a white solid. LRMS (M+H+) m/z calculated 484.2, found 484.1. 1H NMR (DMSO-d6, 400 MHz) δ 8.79 (s, 1H), 8.42 (t, 1H), 8.29 (s, 1H), 8.17 (s, 1H), 7.77 (s, 1H) 7.55 (s, 1H), 6.35 (s, 1H), 6.12 (s, 1H), 5.72 (s, 2H), 5.70 (s, 2H), 4.31 (d, 2H), 2.47 (s, 3H), 2.30 (s, 3H), 2.16 (s, 3H), 1.70 (s, 6H).

A mixture of (3-chloro-8-iodo-quinolin-6-yl)-methanol (5 g, 15.67 mmol, 1.0 eq), sodium methanesulfinate (2.57 g, 18.8 mmol, 1.2 eq), CuI (595 mg, 3.13 mmol, 0.2 eq) and sodium pyrrolidine-2-carboxylate (159 mg, 1.57 mmol, 0.1 eq) in DMSO (30 mL) was stirred at 110° C. under N2 overnight. After the reaction was completed, the mixture was diluted with water and extracted with DCM (100 mL×3). The combined organic layers were concentrated and purified by chromatography on a silica gel column (DCM) to give (3-chloro-8-methanesulfonyl-quinolin-6-yl)-methanol (1.2 g, 28.6%) as a white solid.

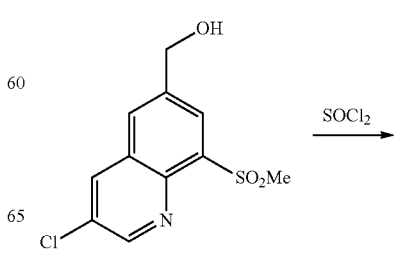

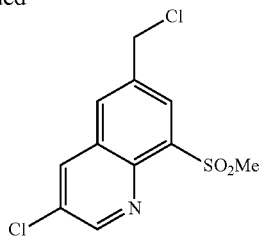

A mixture of (3-chloro-8-methanesulfonyl-quinolin-6-yl)-methanol (2.62 g, 1.0 eq) in SOCl2 (20 mL) was stirred at rt for 3 h. After the reaction was completed, the solvent was evaporated. The resulting residue was diluted with H2O and extracted with DCM (30 mL×3). The combined organic layers were concentrated and purified by chromatography on a silica gel column (DCM) to give 3-chloro-6-chloromethyl-8-methanesulfonyl-quinoline (1.2 g, 43%) as a white solid.

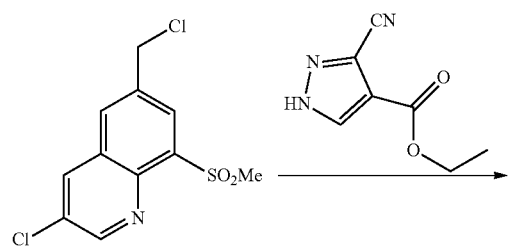

A mixture of 3-chloro-6-chloromethyl-8-methanesulfonyl-quinoline (450 mg, 1.56 mmol, 1.0 eq), 3-cyano-1H-pyrazole-4-carboxylic acid ethyl ester (256 mg, 1.56 mmol, 1.0 eq) and K2CO3 (430 mg, 3.12 mmol, 2.0 eq) in DMF (6 mL) was stirred at rt overnight. After the reaction was completed, the mixture solution was diluted with water and extracted with DCM (30 mL×3). The combined organic layers were concentrated and purified by chromatography on a silica gel column (PE/EA=5/1, v/v) to give 1-(3-chloro-8-methanesulfonyl-quinolin-6-ylmethyl)-3-cyano-1H-pyrazole-4-carboxylic acid ethyl ester (220 mg, 33.7%) as a white solid.

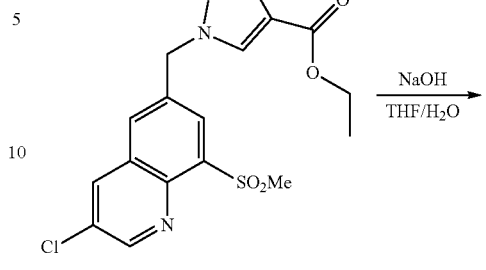

A mixture of 1-(3-chloro-8-methanesulfonyl-quinolin-6-ylmethyl)-3-cyano-1H-pyrazole-4-carboxylic acid ethyl ester (220 mg, 0.53 mmol, 1.0 eq) and NaOH (63 mg, 1.58 mmol, 3.0 eq) in THF (6 mL) and H2O (4 mL) was stirred at 80° C. for 1 h. THF was evaporated and the aqueous layer was neutralized with 1 N HCl to pH 5. Then a white precipitate formed, which was filtered and dried in vacuo to give 1-(3-chloro-8-methanesulfonyl-quinolin-6-ylmethyl)-3-cyano-1H-pyrazole-4-carboxylic acid (100 mg, 48.5%) as a white solid.

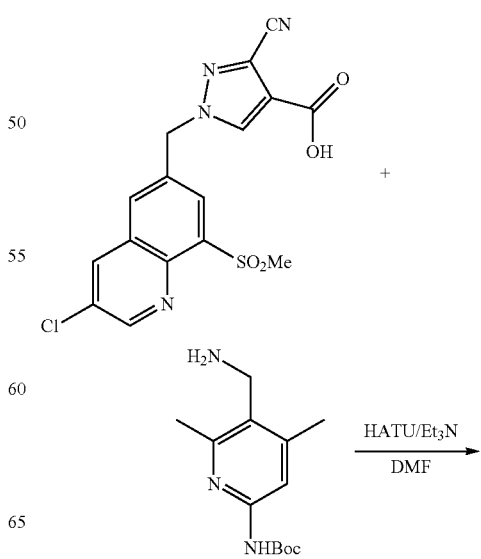

-continued

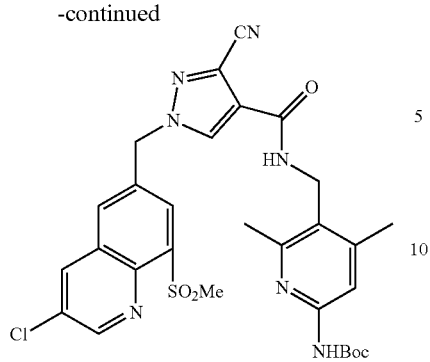

A mixture of 1-(3-chloro-8-methanesulfonyl-quinolin-6-ylmethyl)-3-cyano-1H-pyrazole-4-carboxylic acid (100 mg, 0.25 mmol, 1.0 eq), (5-aminomethyl-4,6-dimethyl-pyridin-2-yl)-carbamic acid tert-butyl ester (77 mg, 0.38 mmol, 1.2 eq), HATU (143 mg, 0.38 mmol, 1.5 eq) and Et3N (0.1 mL, 0.75 mmol, 3.0 eq) in DMF (6 mL) was stirred at rt overnight. Then the solvent was evaporated and the resulting residue was purified by chromatography on a silica gel column (PE/EA=5/1, v/v) to give tert-butyl (5-((1-((3-chloro-8-(methylsulfonyl)quinolin-6-yl)methyl)-3-cyano-1H-pyrazole-4-carboxamido)methyl)-4,6-dimethylpyridin-2-yl)carbamate (90 mg, 58%) as a white solid.

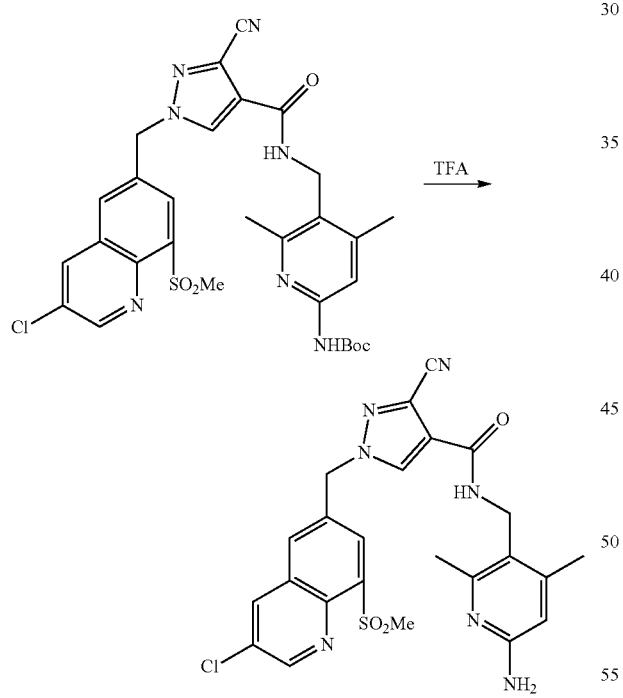

A solution of tert-butyl (5-((1-((3-chloro-8-(methylsulfonyl)quinolin-6-yl)methyl)-3-cyano-1H-pyrazole-4-carboxamido)methyl)-4,6-dimethylpyridin-2-yl)carbamate (90 mg, 0.14 mmol, 1.0 eq) in TFA (6 mL) was stirred at rt for 1 h. After the solvent was evaporated, the resulting residue was diluted with EtOH (5 mL) and neutralized to pH 9 with aqueous NaOH. Then a white precipitate formed, which was filtered and dried in vacuo to give N-((6-amino-2,4-dimethylpyridin-3-yl)methyl)-1-((3-chloro-8-(methylsulfonyl)quinolin-6-yl)methyl)-3-cyano-1H-pyrazole-4-carboxamide (30 mg, 41%) as a white solid. LRMS (M+H+) m/z calculated 524.1, found 524.0. 1H NMR (DMSO-d6, 400 MHz) δ 9.13 (s, 1H), 8.84 (s, 1H), 8.62 (s, 1H), 8.36 (d, 2H), 8.17 (s, 1H), 6.16 (s, 1H), 5.81 (s, 4H), 4.27 (d, 2H), 3.58 (s, 3H), 2.30 (s, 3H), 2.17 (s, 3H).

Example 69: Preparation of N-((6-amino-2,4-dimethylpyridin-3-yl)methyl)-1-((3-chloro-8-cyanoquinolin-6-yl)methyl)-3-cyano-1H-pyrazole-4-carboxamide

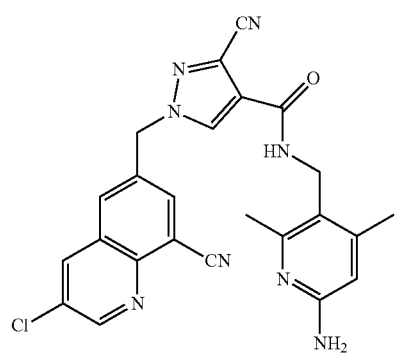

N-((6-amino-2,4-dimethylpyridin-3-yl)methyl)-1-((3-chloro-8-cyanoquinolin-6-yl)methyl)-3-cyano-1H-pyrazole-4-carboxamide

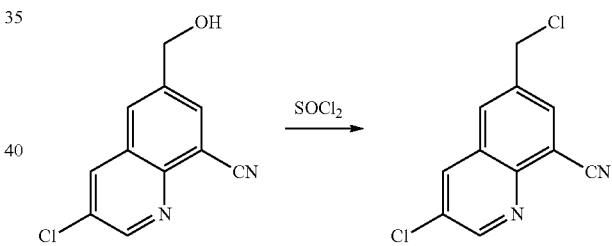

A mixture of 3-chloro-6-hydroxymethyl-quinoline-8-carbonitrile (1.11 g, 5.09 mmol, 1.0 eq) in SOCl2 (20 mL) was stirred at rt for 3 h. LCMS showed the reaction was completed. The solvent was evaporated in vacuo, and the resulting residue was diluted with DCM and washed with saturated NaHCO3. The combined organic layers were concentrated to give 3-chloro-6-chloromethyl-quinoline-8-carbonitrile (1.23 g, 99%) as a white solid.

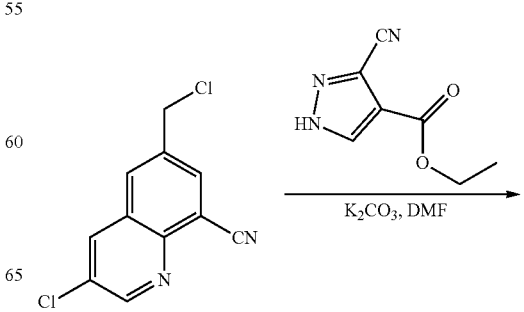

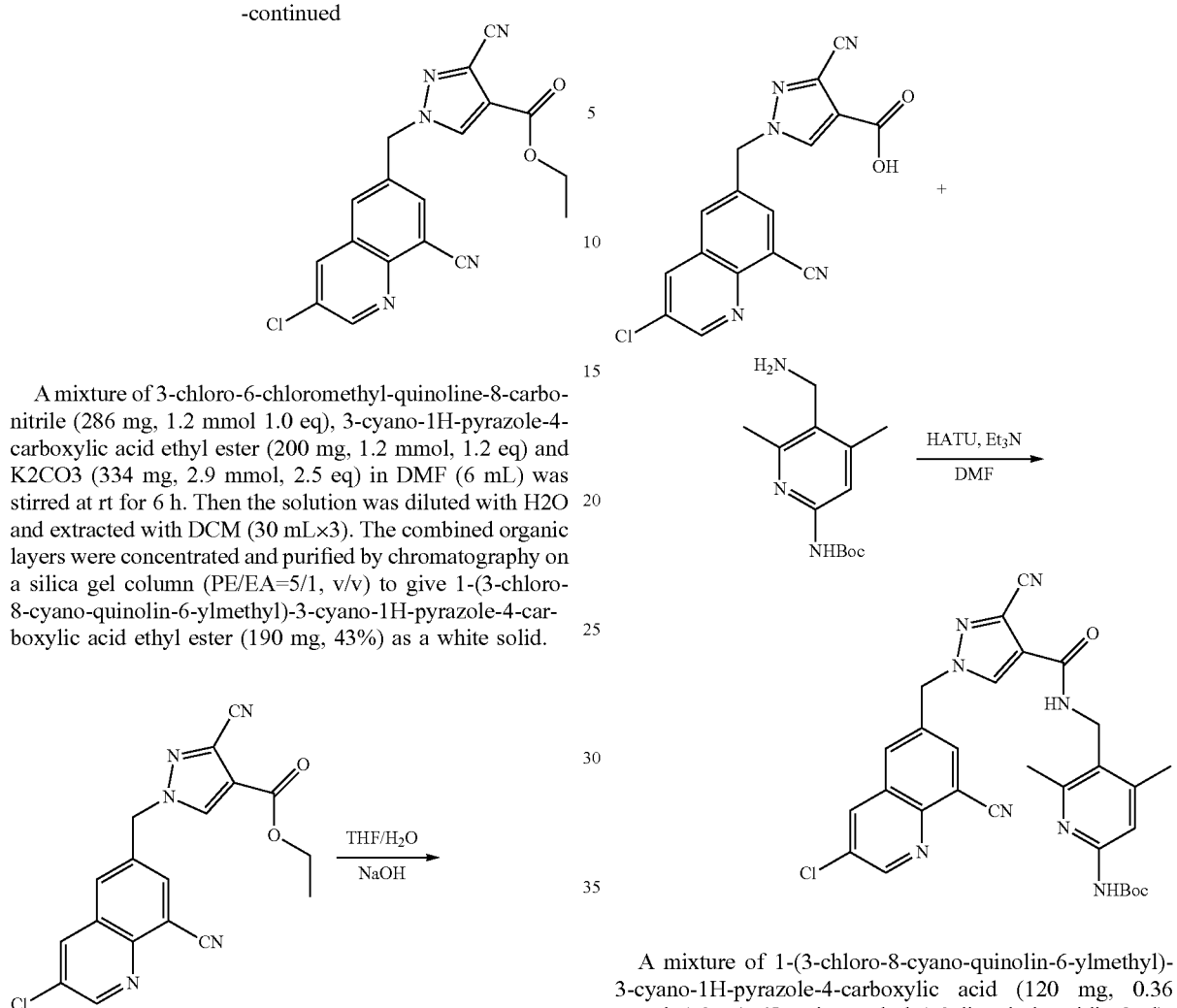

A mixture of 3-chloro-6-chloromethyl-quinoline-8-carbonitrile (286 mg, 1.2 mmol 1.0 eq), 3-cyano-1H-pyrazole-4-carboxylic acid ethyl ester (200 mg, 1.2 mmol, 1.2 eq) and K2CO3 (334 mg, 2.9 mmol, 2.5 eq) in DMF (6 mL) was stirred at rt for 6 h. Then the solution was diluted with H2O and extracted with DCM (30 mL×3). The combined organic layers were concentrated and purified by chromatography on a silica gel column (PE/EA=5/1, v/v) to give 1-(3-chloro-8-cyano-quinolin-6-ylmethyl)-3-cyano-1H-pyrazole-4-carboxylic acid ethyl ester (190 mg, 43%) as a white solid.

A mixture of 1-(3-chloro-8-cyano-quinolin-6-ylmethyl)-3-cyano-1H-pyrazole-4-carboxylic acid ethyl ester (190 mg, 0.52 mmol, 1.0 eq) and NaOH (62 mg, 1.55 mmol, 3.0 eq) in THF (6 mL) and H2O (4 mL) was stirred at 80° C. for 1 h. After the solvent was evaporated, the resulting residue was diluted with EtOH (5 mL) and neutralized with aqueous NaOH. Then a white precipitate formed, which was filtered and dried in vacuo to give 1-(3-chloro-8-cyano-quinolin-6-ylmethyl)-3-cyano-1H-pyrazole-4-carboxylic acid (90 mg, 51%) as a white solid.

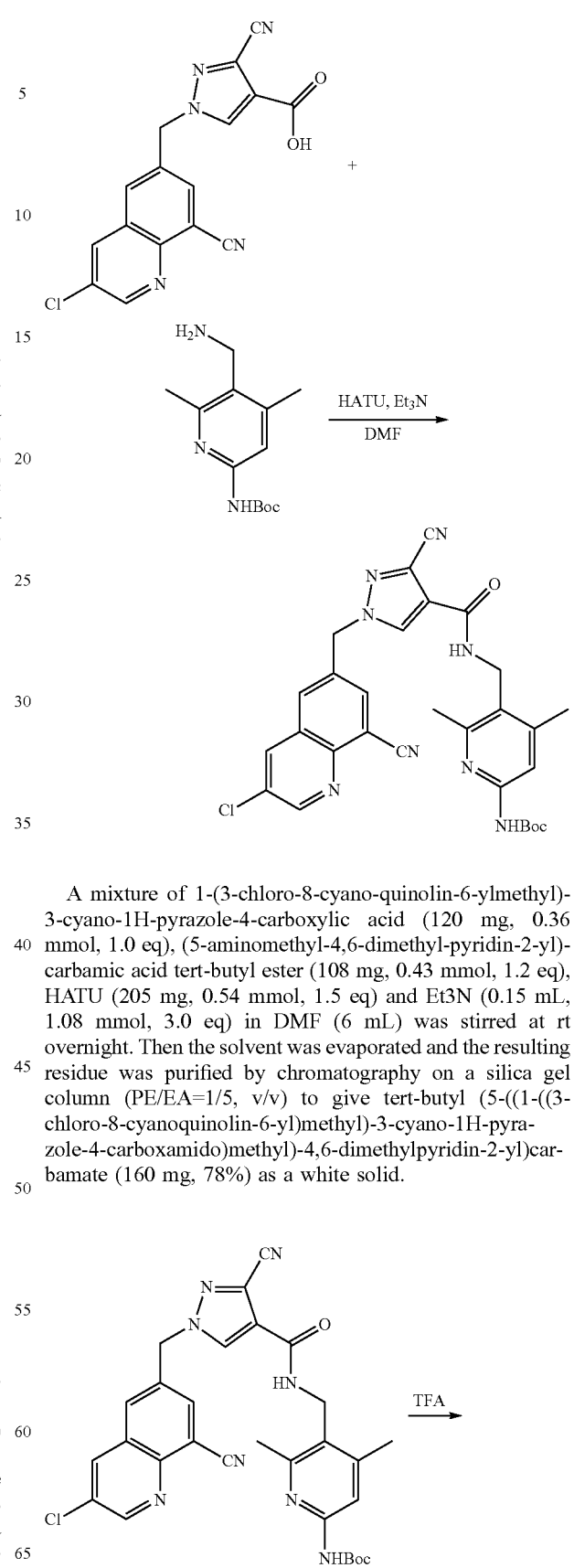

A mixture of 1-(3-chloro-8-cyano-quinolin-6-ylmethyl)-3-cyano-1H-pyrazole-4-carboxylic acid (120 mg, 0.36 mmol, 1.0 eq), (5-aminomethyl-4,6-dimethyl-pyridin-2-yl)-carbamic acid tert-butyl ester (108 mg, 0.43 mmol, 1.2 eq), HATU (205 mg, 0.54 mmol, 1.5 eq) and Et3N (0.15 mL, 1.08 mmol, 3.0 eq) in DMF (6 mL) was stirred at rt overnight. Then the solvent was evaporated and the resulting residue was purified by chromatography on a silica gel column (PE/EA=1/5, v/v) to give tert-butyl (5-((1-((3-chloro-8-cyanoquinolin-6-yl)methyl)-3-cyano-1H-pyrazole-4-carboxamido)methyl)-4,6-dimethylpyridin-2-yl)carbamate (160 mg, 78%) as a white solid.

-continued

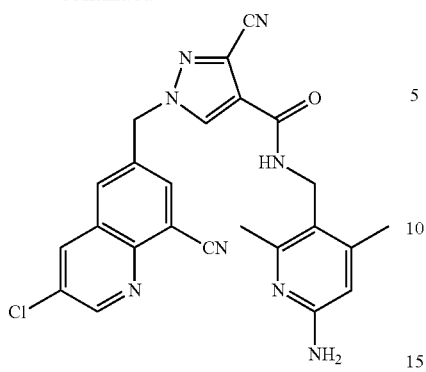

A solution of tert-butyl (5-((1-((3-chloro-8-cyanoquinolin-6-yl)methyl)-3-cyano-1H-pyrazole-4-carboxamido)methyl)-4,6-dimethylpyridin-2-yl)carbamate (160 mg, 0.28 mmol, 1.0 eq) in TFA (10 mL) was stirred at rt for 1 h. After the solvent was evaporated, the resulting residue was diluted with EtOH (5 mL) and neutralized to pH 9 with aqueous NaOH. Then a white precipitate formed, which was filtered and dried in vacuo to give N-((6-amino-2,4-dimethylpyridin-3-yl)methyl)-1-((3-chloro-8-cyanoquinolin-6-yl)methyl)-3-cyano-1H-pyrazole-4-carboxamide (30 mg, 23%) as a yellow solid. LRMS (M+H+) m/z calculated 471.1, found 471.2. 1H NMR (DMSO-d6, 400 MHz) δ 9.11 (s, 1H), 8.81 (s, 1H), 8.58 (s, 1H), 8.39 (s, 1H), 8.23 (s, 1H), 8.16 (s, 1H), 6.12 (s, 1H), 5.72 (s, 4H), 4.28 (d, 2H), 2.29 (s, 3H), 2.15 (s, 3H).

Example 70: Preparation of N-((6-amino-2,4-dimethylpyridin-3-yl)methyl)-1-((3-chloro-8-fluoroquinolin-6-yl)methyl)-5-cyano-1H-pyrazole-4-carboxamide

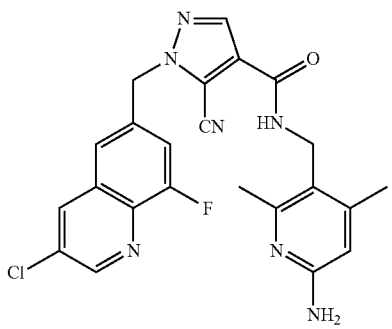

N-((6-amino-2,4-dimethylpyridin-3-yl)methyl)-1-((3-chloro-8-fluoroquinolin-6-yl)methyl)-5-cyano-1H-pyrazole-4-carboxamide

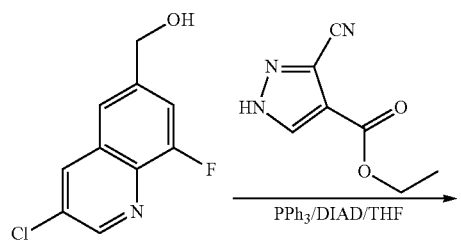

-continued

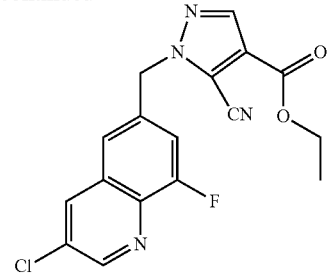

To a mixture of (3-chloro-8-fluoro-quinolin-6-yl)-methanol (844 mg, 4 mmol, 1.0 eq), 3-cyano-1H-pyrazole-4-carboxylic acid ethyl ester (660 mg, 4 mmol, 1.0 eq) and PPh3 (1.26 g, 4.8 mmol, 1.2 eq) in THF (60 mL) was added DIAD (0.97 g, 4.8 mmol, 1.2 eq) under nitrogen at 0° C. The resulting mixture was stirred at rt overnight and then concentrated. The resulting residue was purified by chromatography on a silica gel column (PE/EA=5/1, v/v) to give 1-(3-chloro-8-fluoro-quinolin-6-ylmethyl)-5-cyano-1H-pyrazole-4-carboxylic acid ethyl ester as a white solid (140 mg, 10%).

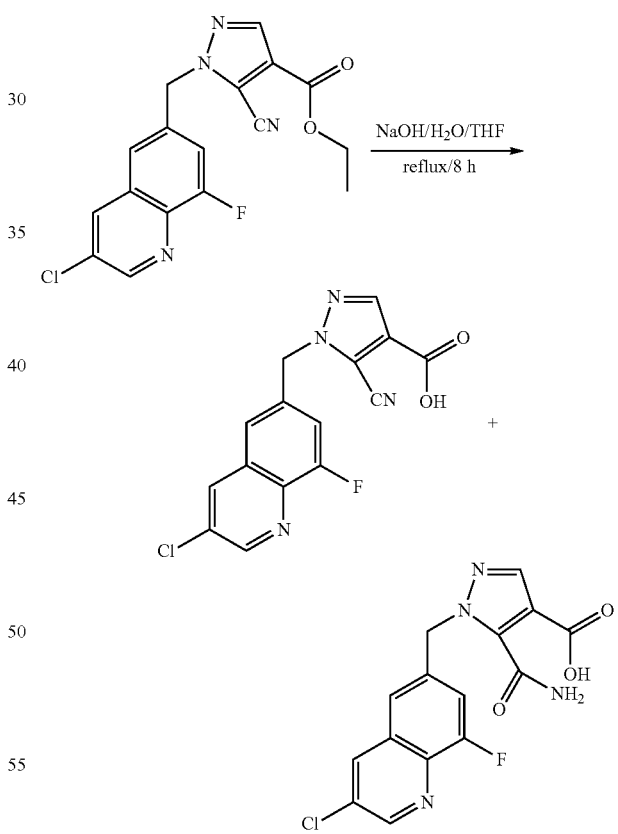

A mixture of 1-(3-chloro-8-fluoro-quinolin-6-ylmethyl)-5-cyano-1H-pyrazole-4-carboxylic acid ethyl ester (160 mg, 0.446 mmol, 1.0 eq) and NaOH (142 mg, 3.57 mmol, 8.0 eq) in water (10 mL) and THF (20 mL) was stirred under reflux for 8 h. THF was removed by evaporation and the aqueous layer was adjusted to pH 2 with 1 N HCl. Then a white precipitate formed, which was filtered and dried in vacuo at 110° C. for 4 h to give 1-((3-chloro-8-fluoroquinolin-6-yl)

methyl)-5-cyano-1H-pyrazole-4-carboxylic acid and 5-carbamoyl-1-((3-chloro-8-fluoroquinolin-6-yl)methyl)-1H-pyrazole-4-carboxylic acid as a yellow solid. (117 mg, ca. 80%).

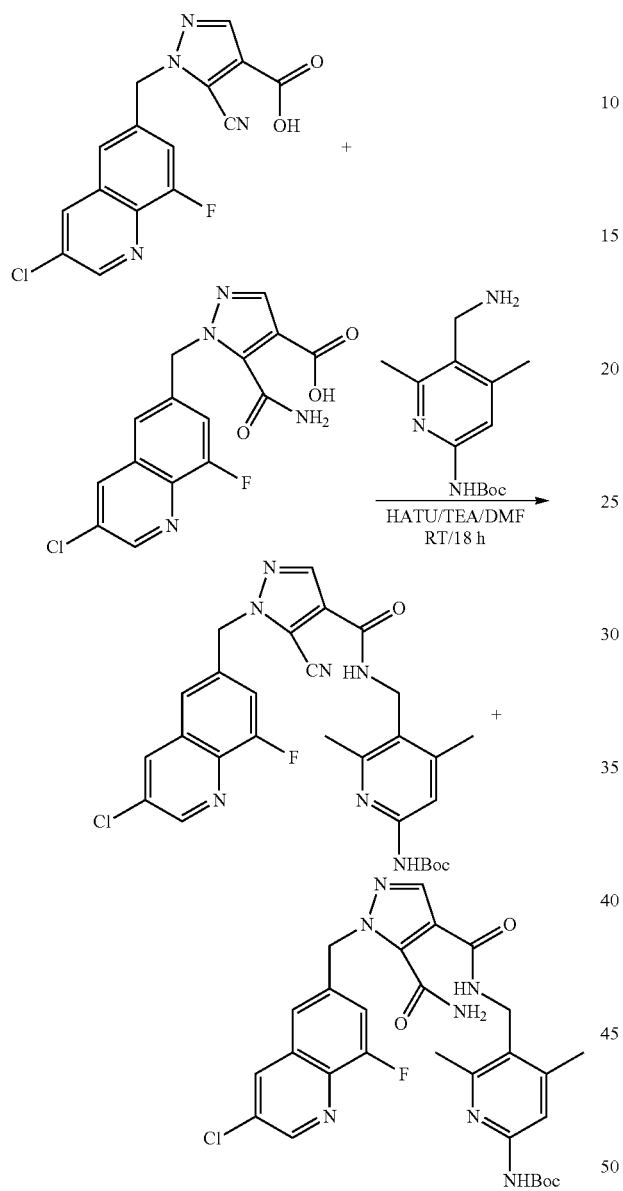

A mixture of 1-(3-chloro-8-fluoro-quinolin-6-ylmethyl)-5-cyano-1H-pyrazole-4-carboxylic acid (117 mg, 0.355 mmol, 1.0 eq), (5-aminomethyl-4,6-dimethyl-pyridin-2-yl)-carbamic acid tert-butyl ester (107 mg, 0.426 mmol, 1.2 eq), Et3N (0.15 mL, 1.05 mmol, 3 eq) and HATU (175 mg, 0.462 mmol, 1.3 eq) in DMF (10 mL) was stirred at rt overnight. The reaction mixture was diluted with CH2Cl2, washed with aqueous NH4Cl (100 mL×2). The combined organic layers were dried and concentrated. The resulting residue was purified by chromatography on a silica gel column (DCM/MeOH=60/1, v/v) to give 160 mg of crude mixture, which was further purified by pre-HPLC to give tert-butyl (5-((1-((3-chloro-8-fluoroquinolin-6-yl)methyl)-5-cyano-1H-pyrazole-4-carboxamido)methyl)-4,6-dimethylpyridin-2-yl)carbamate (30 mg) and tert-butyl (5-((5-carbamoyl-1-((3-chloro-8-fluoroquinolin-6-yl)methyl)-1H-pyrazole-4-carboxamido)methyl)-4,6-dimethylpyridin-2-yl)carbamate (41 mg).

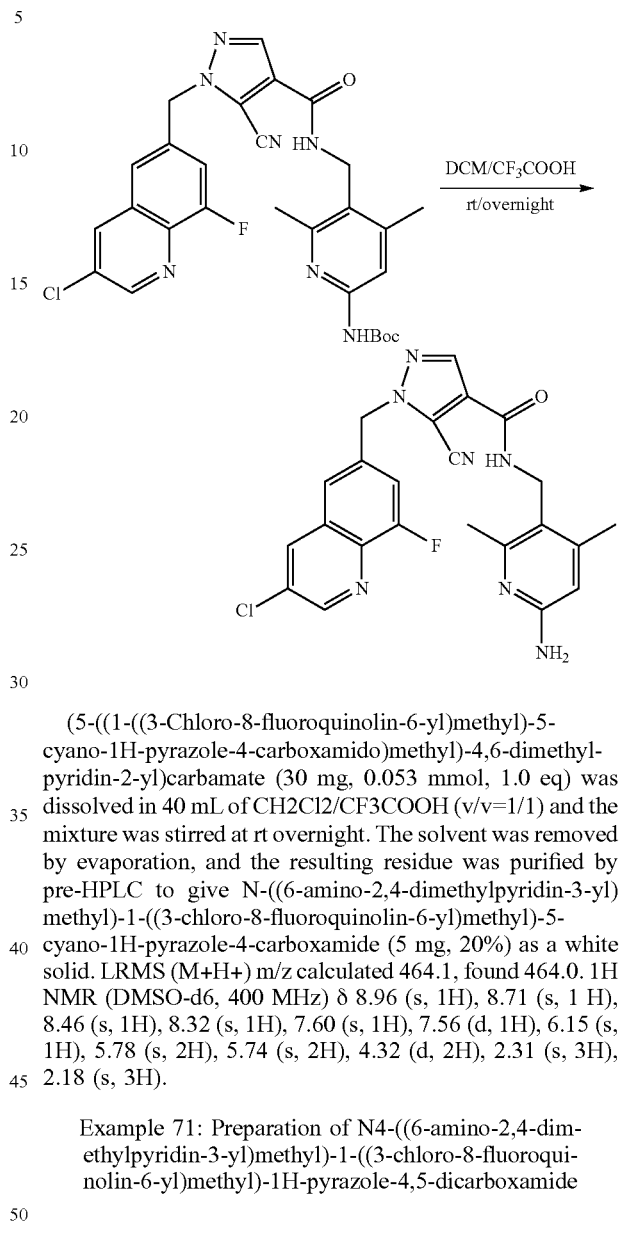

(5-((1-((3-Chloro-8-fluoroquinolin-6-yl)methyl)-5-cyano-1H-pyrazole-4-carboxamido)methyl)-4,6-dimethyl-pyridin-2-yl)carbamate (30 mg, 0.053 mmol, 1.0 eq) was dissolved in 40 mL of CH2Cl2/CF3COOH (v/v=1/1) and the mixture was stirred at rt overnight. The solvent was removed by evaporation, and the resulting residue was purified by pre-HPLC to give N-((6-amino-2,4-dimethylpyridin-3-yl)methyl)-1-((3-chloro-8-fluoroquinolin-6-yl)methyl)-5-cyano-1H-pyrazole-4-carboxamide (5 mg, 20%) as a white solid. LRMS (M+H+) m/z calculated 464.1, found 464.0. 1H NMR (DMSO-d6, 400 MHz) δ 8.96 (s, 1H), 8.71 (s, 1 H), 8.46 (s, 1H), 8.32 (s, 1H), 7.60 (s, 1H), 7.56 (d, 1H), 6.15 (s, 1H), 5.78 (s, 2H), 5.74 (s, 2H), 4.32 (d, 2H), 2.31 (s, 3H), 2.18 (s, 3H).

Example 71: Preparation of N4-((6-amino-2,4-dimethylpyridin-3-yl)methyl)-1-((3-chloro-8-fluoroquinolin-6-yl)methyl)-1H-pyrazole-4,5-dicarboxamide

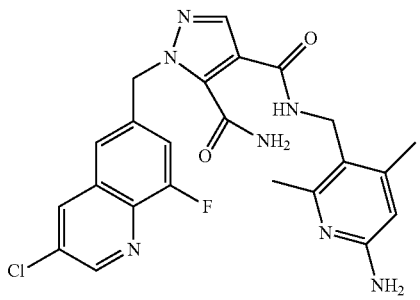

N4-((6-amino-2,4-dimethylpyridin-3-yl)methyl)-1-((3-chloro-8-fluoroquinolin-6-yl)methyl)-1H-pyrazole-4,5-dicarboxamide

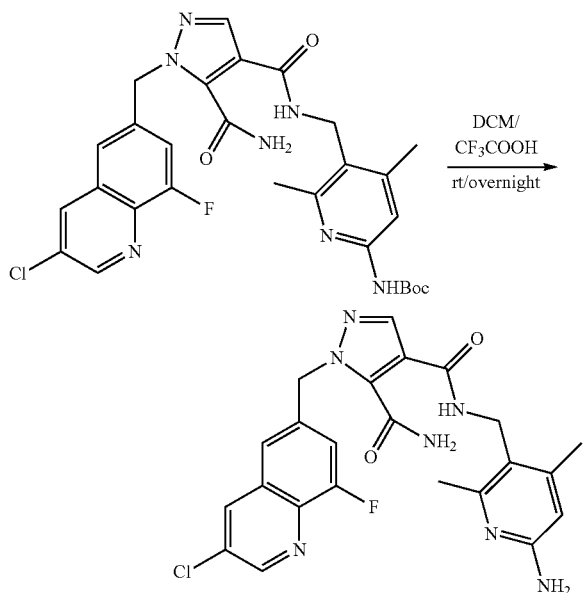

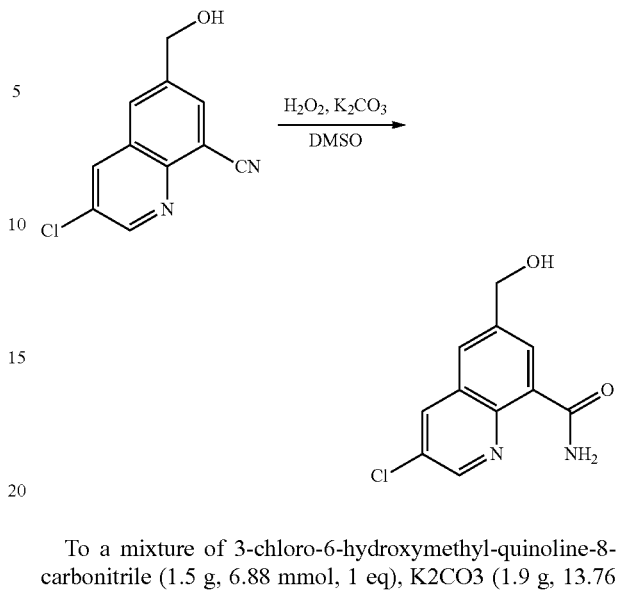

tert-Butyl (5-((5-carbamoyl-1-((3-chloro-8-fluoroquinolin-6-yl)methyl)-1H-pyrazole-4-carboxamido)methyl)-4,6-dimethylpyridin-2-yl)carbamate (41 mg, 0.07 mmol, 1.0 eq) was dissolved in 40 mL of CH2Cl2/CF3COOH (v/v=1/1) and the reaction mixture was stirred at rt overnight. The solvent was removed by evaporation, and the resulting residue was purified by pre-HPLC to give N4-(((6-amino-2,4-dimethylpyridin-3-yl)methyl)-1-((3-chloro-8-fluoroquinolin-6-yl)methyl)-1H-pyrazole-4,5-dicarboxamide (8 mg, 24%). LRMS (M+H+) m/z calculated 482.1, found 482.0. 1H NMR (DMSO-d6, 400 MHz) δ 9.96 (s, 1H), 8.92 (s, 1H), 8.65 (s, 1H), 8.59 (s, 1H), 8.10 (s, 1H), 7.95 (d, 1H), 7.49 (s, 1H), 7.45 (d, 1H), 6.18 (s, 1H), 5.94 (s, 2H), 5.91 (s, 2H), 4.33 (s, 2H), 2.34 (s, 3H), 2.20 (s, 3H).

Example 72: Preparation of 6-((4-(((6-amino-2,4-dimethylpyridin-3-yl)methyl)carbamoyl)-3-cyano-1H-pyrazol-1-yl)methyl)-3-chloroquinoline-8-carboxamide

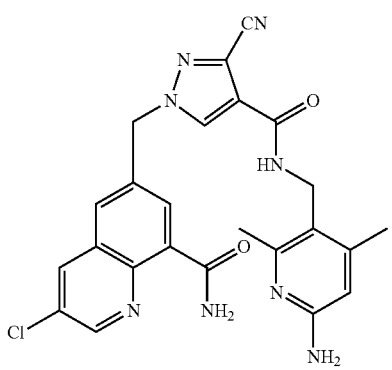

6-((4-(((6-amino-2,4-dimethylpyridin-3-yl)methyl)carbamoyl)-3-cyano-1H-pyrazole-1-yl)methyl)-3-chloroquinoline-8-carboxamide To a mixture of 3-chloro-6-hydroxymethyl-quinoline-8-carbonitrile (1.5 g, 6.88 mmol, 1 eq), K2CO3 (1.9 g, 13.76 mmol, 2 eq) in DMSO (20 mL) was added H2O2 (3 mL, 30%) at 0° C. The mixture was stirred at rt overnight. Then the reaction mixture was diluted with water, the resulting precipitate was collected by filtration, washed with water and EA subsequently. The obtained solid was dried under reduced pressure to give 3-chloro-6-hydroxymethyl-quinoline-8-carboxylic acid amide (750 mg, 46%).

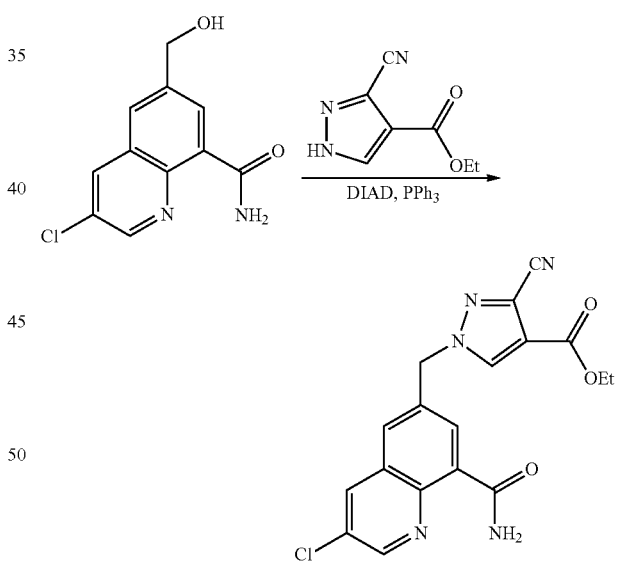

To a mixture of 3-chloro-6-hydroxymethyl-quinoline-8-carboxylic acid amide (430 mg, 1.82 mmol, 1 eq), 3-cyano-1H-pyrazole-4-carboxylic acid ethyl ester (300 mg, 1.82 mmol, 1 eq) and PPh3 (572 mg, 2.18 mmol, 1.2 eq) in DMF (15 mL) was added DIAD (0.4 mL, 2.0 mmol, 1.1 eq) at 0° C. The mixture was stirred at rt overnight. Then the reaction mixture was concentrated and the resulting residue was purified by chromatography on a silica gel column (PE/EA=3/1, v/v) to give 1-(8-carbamoyl-3-chloro-quinolin-6-ylmethyl)-3-cyano-1H-pyrazole-4-carboxylic acid ethyl ester (350 mg, 50%) as a white solid.

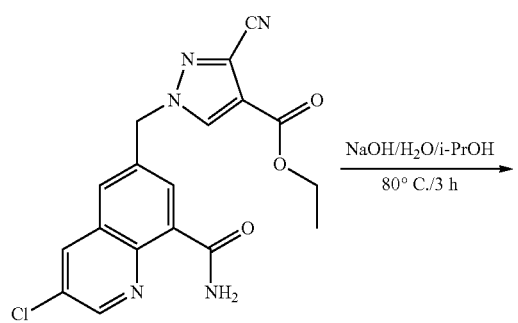

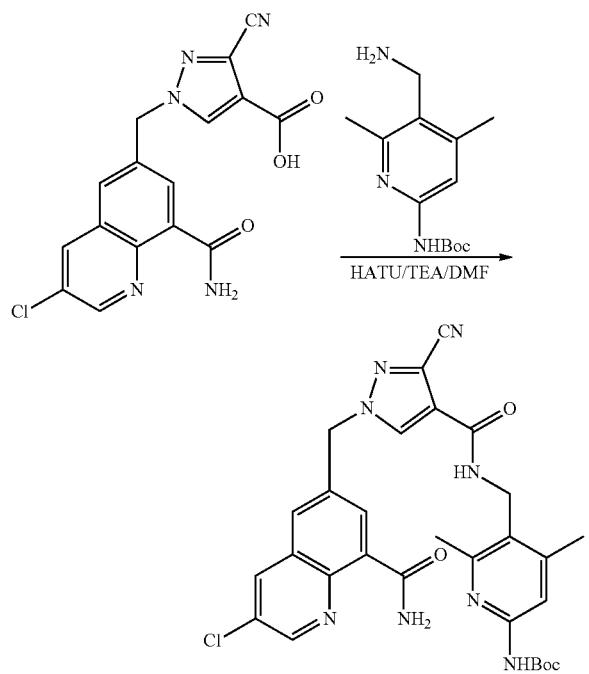

A mixture of 1-(8-carbamoyl-3-chloro-quinolin-6-ylmethyl)-3-cyano-1H-pyrazole-4-carboxylic acid ethyl ester (245 mg, 0.638 mmol, 1.0 eq) and NaOH (128 mg, 3.19 mmol, 5.0 eq) in i-PrOH (15 mL) and water (5 mL) was stirred at 80° C. for 3 h. The solvent was removed by evaporation, and the residue was diluted with water. The aqueous layer was adjusted to pH 2 with 1 N HCl. Then a white precipitate formed, which was filtered and dried in vacuo at 110° C. for 4 h to give 1-(8-carbamoyl-3-chloro-quinolin-6-ylmethyl)-3-cyano-1H-pyrazole-4-carboxylic acid (155 mg, 68%).

A mixture of 1-(8-carbamoyl-3-chloro-quinolin-6-ylmethyl)-3-cyano-1H-pyrazole-4-carboxylic acid (155 mg, 0.437 mmol, 1.0 eq), (5-aminomethyl-4,6-dimethyl-pyridin-2-yl)-carbamic acid tert-butyl ester (132 mg, 0.524 mmol, 1.2 eq), TEA (0.18 mL, 1.31 mmol, 3 eq) and HATU (216 mg, 0.568 mmol, 1.3 eq) in DMF (10 mL) was stirred at rt overnight. The reaction mixture was diluted with 150 mL of CH2Cl2, washed with aqueous NH4Cl (100 mL×2). The combined organic layers were dried and concentrated. The resulting residue was purified by chromatography on a silica gel column (DCM/MeOH=50/1 to 20/1, v/v) to give 49 mg of mixture, which was further purified by pre-HPLC to give tert-butyl (5-((1-((8-carbamoyl-3-chloroquinolin-6-yl)methyl)-3-cyano-1H-pyrazole-4-carboxamido)methyl)-4,6-dimethylpyridin-2-yl)carbamate (10 mg, 4%).

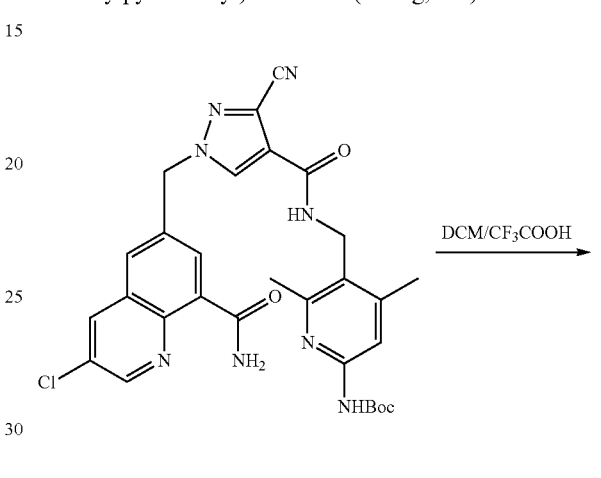

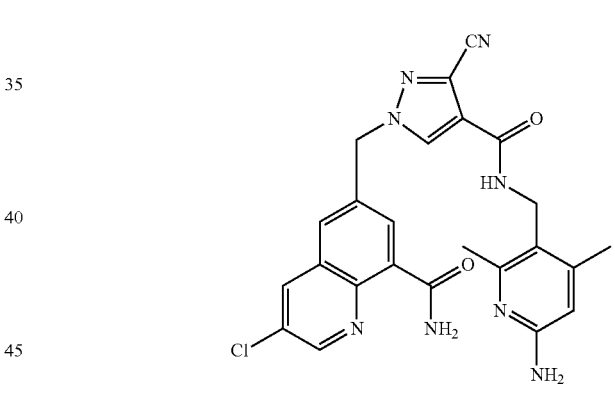

tert-butyl (5-((1-((8-carbamoyl-3-chloroquinolin-6-yl)methyl)-3-cyano-1H-pyrazole-4-carboxamido)methyl)-4,6-dimethylpyridin-2-yl)carbamate (10 mg) was dissolved in DCM/CF3COOH (30 mL, v/v=1/1). The mixture was stirred at rt overnight. The solvent was removed by evaporation, and the resulting residue was diluted with water, adjusted to pH 10 with aqueous NaOH. The resulting precipitate was collected by filtration and further purified by pre-HPLC to give 6-((4-(((6-amino-2,4-dimethylpyridin-3-yl)methyl)carbamoyl)-3-cyano-1H-pyrazol-1-yl)methyl)-3-chloroquinoline-8-carboxamide (2 mg, 1%) as a white solid. LRMS (M+H+) m/z calculated 489.1, found 489.0. 1H NMR (DMSO-d6, 400 MHz) δ 9.50 (s, 1H), 8.95 (s, 1H), 8.70 (s, 1H), 8.53 (s, 1H), 8.32 (s, 1H), 8.22 (t, 1H), 7.95 (s, 1H), 7.93 (s, 1H), 6.02 (s, 1H), 5.66 (s, 2H), 5.60 (s, 2H), 4.19 (d, 2H), 2.20 (s, 3H), 2.06 (s, 3H).

Example 73: Preparation of N-((6-amino-2,4-dimethylpyridin-3-yl)methyl)-3-cyano-1-((3-(trifluoromethyl)quinolin-6-yl)methyl)-1H-pyrazole-4-carboxamide

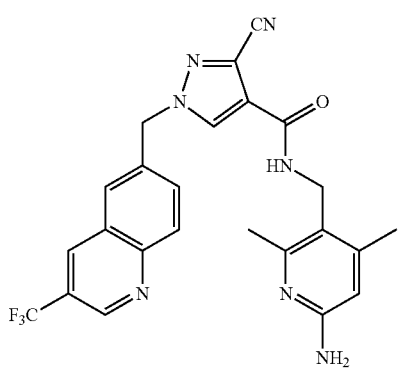

N-((6-amino-2,4-dimethylpyridin-3-yl)methyl)-
3-cyano-1-((3-trifluoromethyl)quinolin-6-yl)methyl)-1H-
pyrazole-4-carboxamide

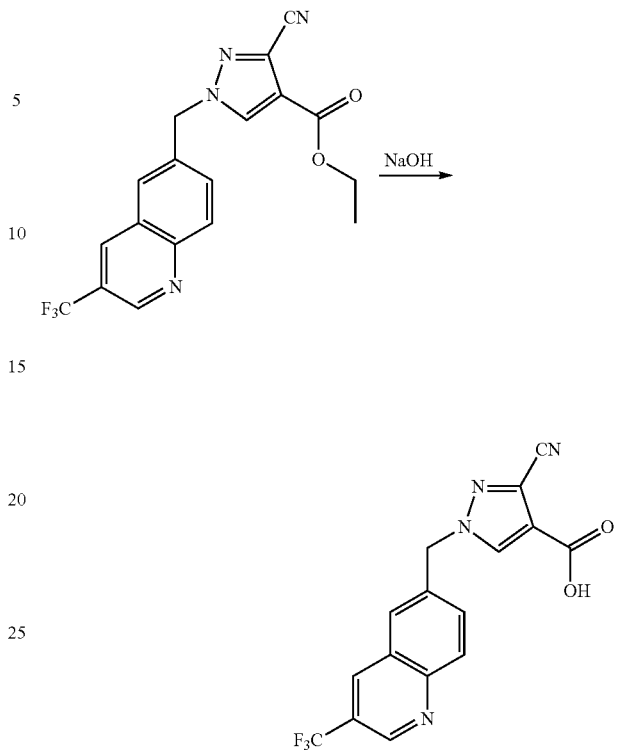

To a solution of 3-cyano-1-(3-trifluoromethyl-quinolin-6-ylmethyl)-1H-pyrazole-4-carboxylic acid ethyl ester (100 mg, 0.27 mmol, 1.0 eq) in THF (4 mL) and water (4 mL) was added NaOH (107 mg, 2.7 mmol, 10.0 eq) at rt. The reaction mixture was stirred at 80° C. for 2 h. The mixture was neutralized to pH 3 with 1N HCl, then a white precipitate formed, which was filtered and dried in vacuo to give 3-cyano-1-(3-trifluoromethyl-quinolin-6-ylmethyl)-1H-pyrazole-4-carboxylic acid (70 mg, 75%) as a white solid.

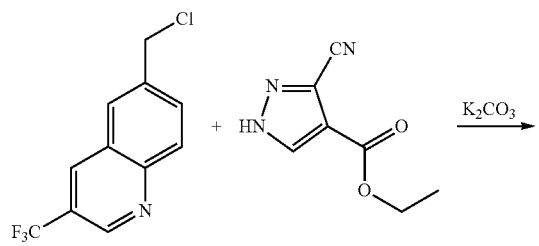

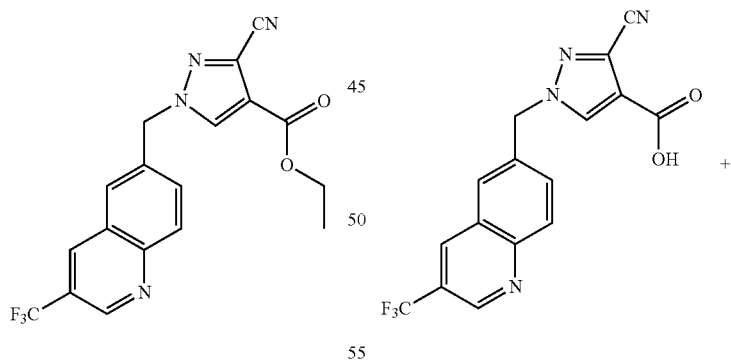

A mixture of 6-chloromethyl-3-trifluoromethyl-quinoline (300 mg, 1.22 mmol, 1.0 eq), 3-cyano-1H-pyrazole-4-carboxylic acid ethyl ester (202 mg, 1.22 mmol, 1.0 eq) and K2CO3 (337 mg, 2.44 mmol, 2.0 eq) in DMF (10 mL) was stirred at rt overnight. The mixture was concentrated and the resulting residue was purified by chromatography on a silica gel column (PE/EA=3/1, v/v) to give 3-cyano-1-(3-trifluoromethyl-quinolin-6-ylmethyl)-1H-pyrazole-4-carboxylic acid ethyl ester (350 mg, 76%) as a white solid.

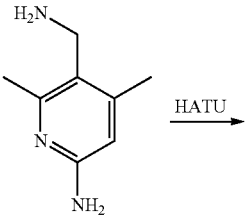

-continued

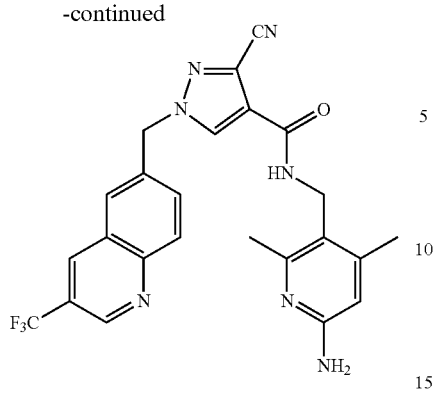

A mixture of 3-cyano-1-(3-trifluoromethyl-quinolin-6-yl-methyl)-1H-pyrazole-4-carboxylic acid (70 mg, 0.20 mmol, 1.0 eq), 5-aminomethyl-4,6-dimethyl-pyridin-2-ylamine hydrochloride (56 mg, 0.30 mmol, 1.5 eq), HATU (114 mg, 0.30 mmol, 1.5 eq) and Et3N (60 mg, 0.60 mmol, 3.0 eq) in DMF (4 mL) was stirred at rt overnight. The mixture was concentrated and the residue was purified by prep-HPLC to afford 3-cyano-1-(3-trifluoromethyl-quinolin-6-ylmethyl)-1H-pyrazole-4-carboxylic acid (6-amino-2,4-dimethyl-pyridin-3-ylmethyl)-amide (50 mg, 53%) as a white solid. LRMS (M+H+) m/z calculated 480.2, found 480.0. 1H NMR (DMSO-d6, 400 MHz): δ 9.21 (d, 1H), 8.99 (s, 1H), 8.59 (s, 1H), 8.29 (t, 1H), 8.17 (d, 1H), 8.03 (s, 1H), 7.88-7.85 (m, 1H), 6.11 (s, 1H), 5.74 (s, 1H), 5.70 (s, 2H), 4.27 (d, 2H), 2.28 (s, 3H), 2.15 (s, 3H).

Example 74: Preparation of N-((6-amino-2-methyl-pyridin-3-yl)methyl)-3-cyano-1-((3-(trifluoromethyl)quinolin-6-yl)methyl)-1H-pyrazole-4-carboxamide

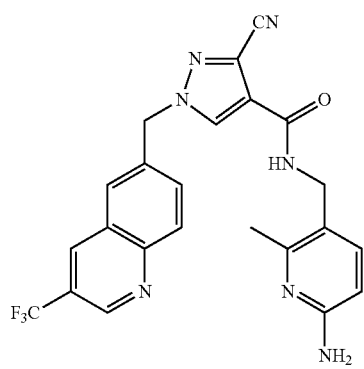

N-((6-amino-2-methylpyridin-3-yl)methyl)-3-cyano-1-((3-trifluoromethyl)quinolin-6-yl)methyl)-1H-pyrazole-4-carboxamide

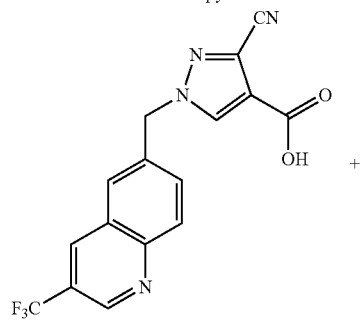

+

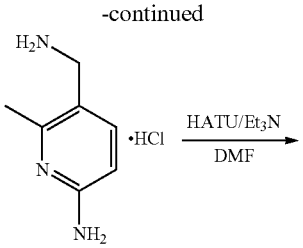

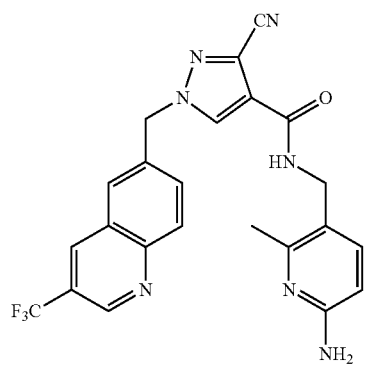

A mixture of 3-cyano-1-(3-trifluoromethyl-quinolin-6-yl-methyl)-1H-pyrazole-4-carboxylic acid (110 mg, 0.32 mmol, 1.0 eq), 5-aminomethyl-6-methyl-pyridin-2-ylamine hydrochloride (66 mg, 0.38 mmol, 1.2 1.2 eq), HATU (182 mg, 0.48 mmol, 1.5 eq) and Et3N (0.23 mL, 1.6 mmol, 3.0 eq) in DMF (6 mL) was stirred at rt overnight. After the reaction was concentrated, the resulting residue was purified by prep-HPLC to give N-((6-amino-2-methylpyridin-3-yl)methyl)-3-cyano-1-((3-(trifluoromethyl)quinolin-6-yl)methyl)-1H-pyrazole-4-carboxamide (59 mg, 40%) as a white solid. LRMS (M+H+) m/z calculated 466.2, found 466.2. 1H NMR (DMSO-d6, 400 MHz) δ 9.20 (s, 1H), 8.99 (s, 1H), 8.61 (d, 2H), 8.19 (d, 1H), 8.03 (s, 1H) 7.89 (d, 1H), 7.24 (d, 1H), 6.23 (d, 2H), 5.75 (s, 4H), 4.22 (d, 2H), 2.26 (s, 3H).

Example 75: Preparation of N-((6-amino-2,4-dimethylpyridin-3-yl)methyl)-5-((3-chloro-8-fluoroquinolin-6-yl)methyl)-1,3,4-oxadiazole-2-carboxamide

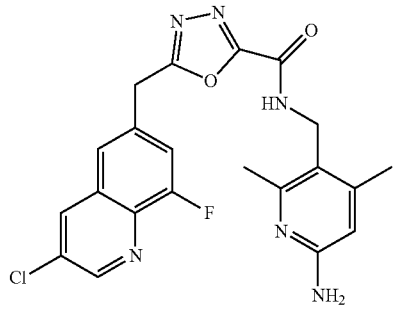

N-((6-amino-2,4-dimethylpyridin-3-yl)methyl)-5-((3-chloro-8-fluoroquinolin-6-yl)methyl)-1,3,4-oxadiazole-2-carboxamide

303

-continued

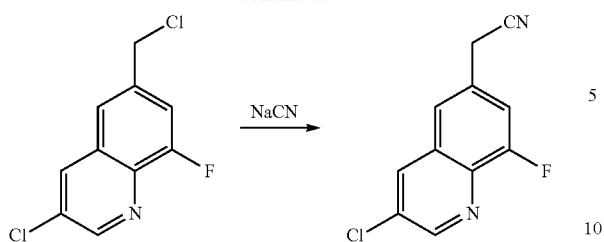

To a solution of 3-chloro-6-chloromethyl-8-fluoro-quinoline (2.7 g, 11.74 mmol, 1.0 eq) in DMSO (20 mL) was added NaCN (575 mg, 11.74 mmol, 1.0 eq) at rt. The mixture was stirred at rt overnight. EA (300 mL) was added and the mixture was washed with brine (30 mL×4). The organic layer was dried over Na2SO4, filtered and concentrated. The resulting residue was purified by chromatography on a silica gel column (PE/EA=3/1, v/v) to give (3-chloro-8-fluoro-quinolin-6-yl)-acetonitrile (800 mg, 31%) as a yellow solid.

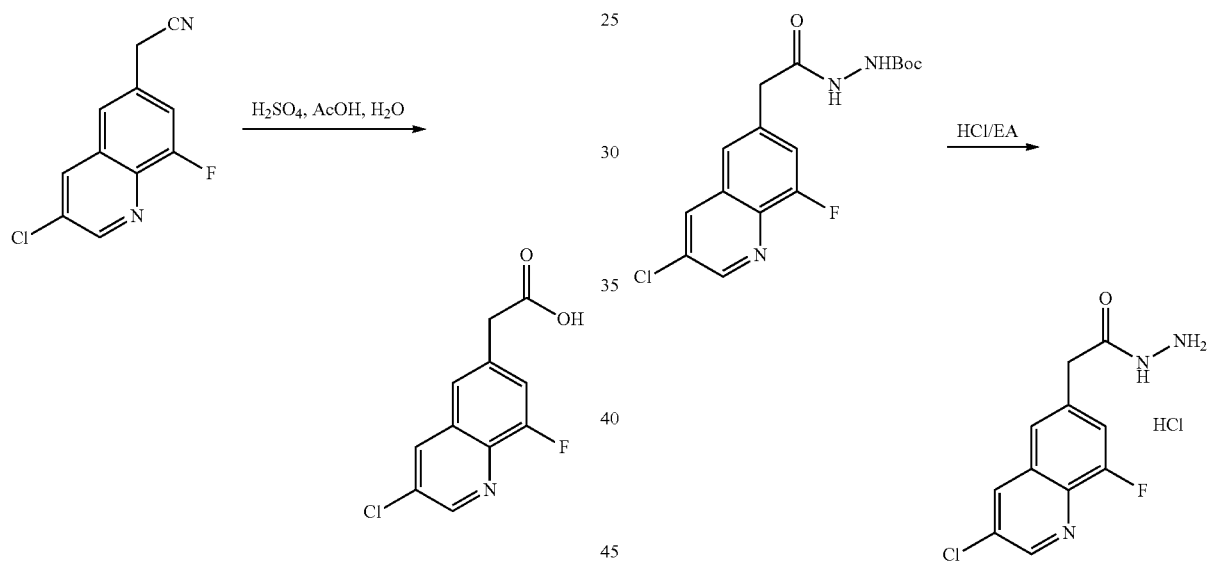

A mixture of (3-chloro-8-fluoro-quinolin-6-yl)-acetonitrile (800 mg, 3.62 mmol, 1.0 eq) in H2SO4 (8 mL), AcOH (8 mL) and water (8 mL) was stirred at 110° C. overnight. The mixture was concentrated and the resulting residue was adjusted to pH 2 with 1N NaOH. A white solid was formed, which was filtered and dried in vacuo to give (3-chloro-8-fluoro-quinolin-6-yl)-acetic acid (800 mg, 92%) as a white solid.

304

-continued

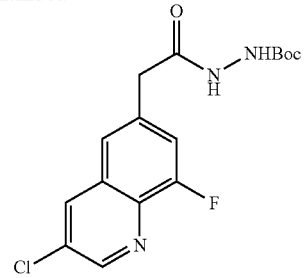

A mixture of (3-chloro-8-fluoro-quinolin-6-yl)-acetic acid (800 mg, 3.34 mmol, 1.0 eq), hydrazinecarboxylic acid tert-butyl ester (661 mg, 5.01 mmol, 1.5 eq), HATU (1.9 g, 5.01 mmol, 1.5 eq) and Et3N (1.0 g, 10.02 mmol, 3.0 eq) in DMF (15 mL) was stirred at rt for 2 h. Water (30 mL) was added. A white solid was formed, which was filtered and dried in vacuo to give tert-butyl 2-(2-(3-chloro-8-fluoroquinolin-6-yl)acetyl)hydrazinecarboxylate (760 mg, 64%) as a white solid.

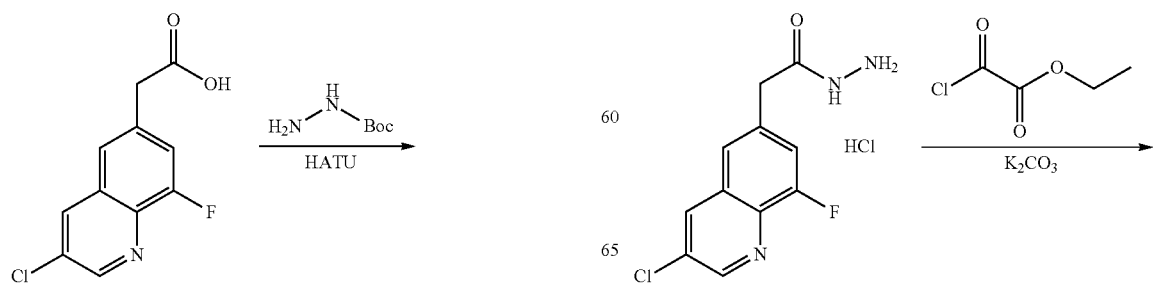

To a solution of tert-butyl 2-(2-(3-chloro-8-fluoroquinolin-6-yl)acetyl)hydrazinecarboxylate (760 mg, 2.15 mmol, 1.0 eq) in EA (20 mL) was added HCl/EA (20 mL) at rt. The mixture was stirred at rt overnight. The mixture was filtered and the solid was washed with EA, and then dried in vacuo to give (3-chloro-8-fluoro-quinolin-6-yl)-acetic acid hydrazide (800 mg, crude) as a white solid.

-continued

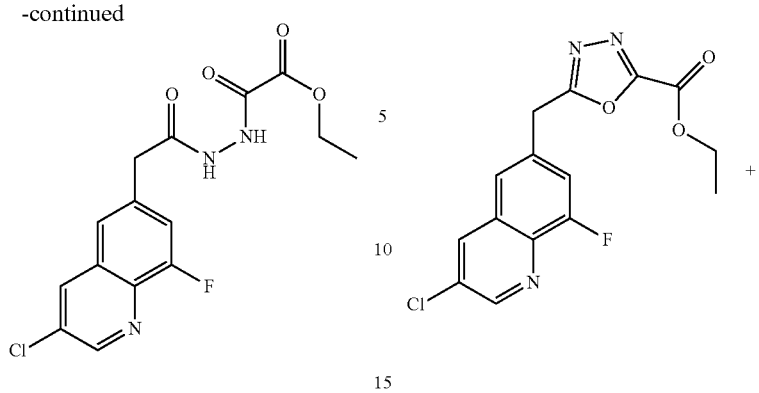

To a solution of (3-chloro-8-fluoro-quinolin-6-yl)-acetic acid hydrazide (800 mg, 2.76 mmol, 1.0 eq) and K2CO3 (1.1 g, 8.28 mmol, 3.0 eq) in ACN (40 mL) was added chloro-oxo-acetic acid ethyl ester (565 mg, 4.14 mmol, 1.5 eq) at rt. The mixture was stirred at rt overnight. Water (20 mL) was added and a white precipitate was formed, which was filtered, and washed with water (20 mL), MeOH (20 mL) and EA (20 mL) subsequently. Then the solid was dried in vacuo to afford ethyl 2-(2-(2-(3-chloro-8-fluoroquinolin-6-yl)acetyl)hydrazinyl)-2-oxoacetate (650 mg, 67%) as a white solid.

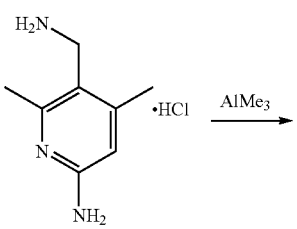

To a solution of ethyl 2-(2-(2-(3-chloro-8-fluoroquinolin-6-yl)acetyl)hydrazinyl)-2-oxoacetate (650 mg, 1.84 mmol, 1.0 eq) in DCM (30 mL) was added TsCl (455 mg, 2.39 mmol, 1.3 eq) and Et3N (280 mg, 2.76 mmol, 1.5 eq) at rt. The mixture was stirred at rt overnight. The mixture was concentrated and the resulting residue was purified by chromatography on a silica gel column (PE/EA=1/1, v/v) to afford 5-(3-chloro-8-fluoro-quinolin-6-ylmethyl)-[1,3,4]oxadiazole-2-carboxylic acid ethyl ester (400 mg, 65%) as a white solid.

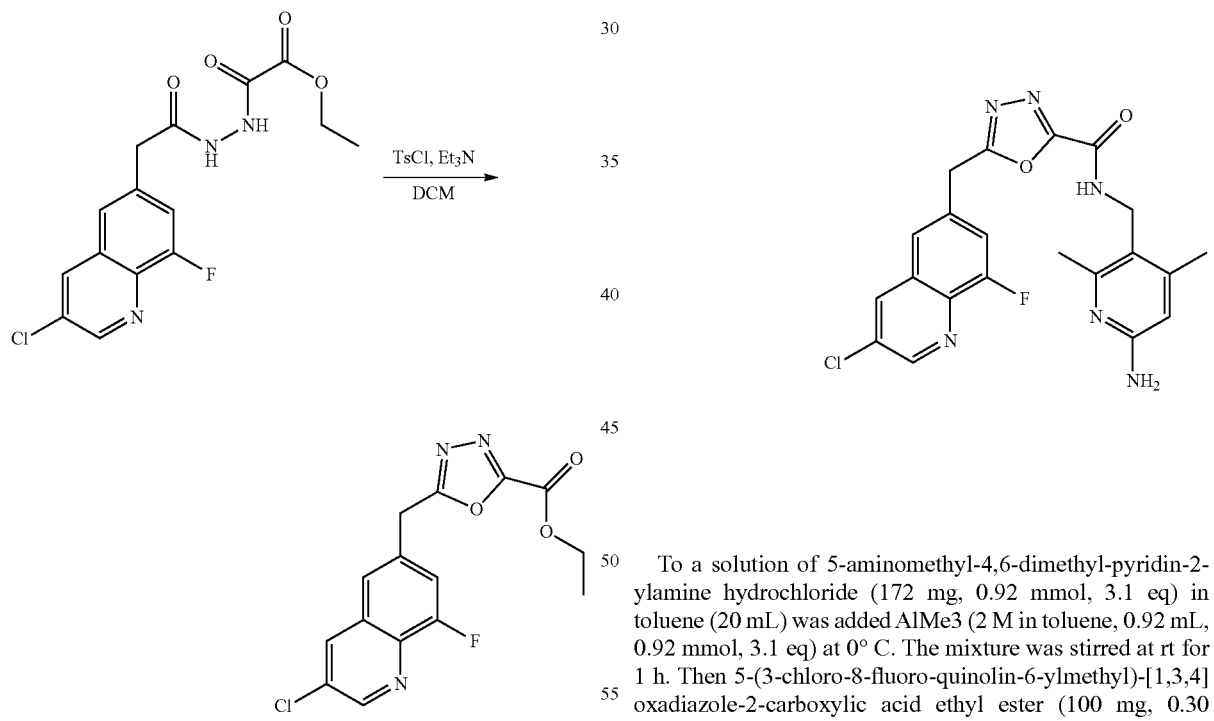

To a solution of 5-aminomethyl-4,6-dimethyl-pyridin-2-ylamine hydrochloride (172 mg, 0.92 mmol, 3.1 eq) in toluene (20 mL) was added AlMe3 (2 M in toluene, 0.92 mL, 0.92 mmol, 3.1 eq) at 0° C. The mixture was stirred at rt for 1 h. Then 5-(3-chloro-8-fluoro-quinolin-6-ylmethyl)-[1,3,4]oxadiazole-2-carboxylic acid ethyl ester (100 mg, 0.30 mmol, 1.0 eq) was added and heated at 120° C. overnight. The mixture was concentrated and the resulting residue was purified by chromatography on a silica gel column (DCM/MeOH=1/1, v/v) to afford N-((6-amino-2,4-dimethylpyridin-3-yl)methyl)-5-((3-chloro-8-fluoroquinolin-6-yl)methyl)-1,3,4-oxadiazole-2-carboxamide (10 mg, 7%) as a white solid. LRMS (M+H+) m/z calculated 441.1, found 441.0. 1H NMR (DMSO-d6, 400 MHz): δ 9.36 (t, 1H), 8.94 (d, 1H), 8.67 (s, 1H), 7.77 (s, 1H), 7.69 (dd, 1H), 6.10 (s, 1H), 5.72 (s, 2H), 4.59 (s, 2H), 4.34 (d, 2H), 2.29 (s, 3H), 2.17 (s, 3H).

Example 76: Preparation of compound N-((6-amino-2,4-dimethylpyridin-3-yl)methyl)-1-((3-chloroquinolin-6-yl)methyl)-4-cyano-1H-pyrazolo[4,3-c]pyridine-3-carboxamide

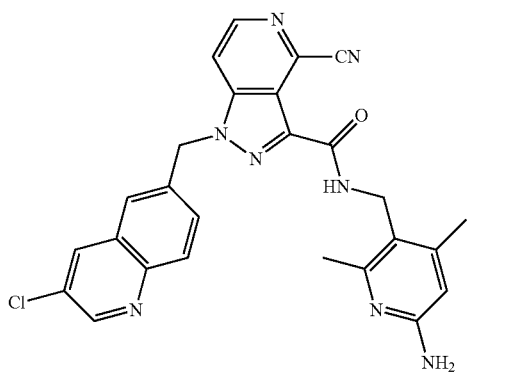

N-((6-amino-2,4-dimethylpyridin-3-yl)methyl)-1-((3-chloroquinolin-6-yl)methyl)-4-cyano-1H-pyrazolo[4,3-c]pyridine-3-carboxamide

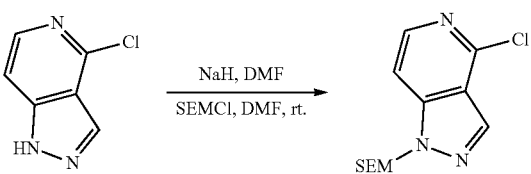

To a solution of 4-chloro-1H-pyrazolo[4,3-c]pyridine (1.0 g, 6.5 mmol, 1.0 eq) in THF (20.0 mL) at 0° C. was added NaH (60% in mineral oil, 0.52 g, 13 mmol, 2.0 eq). The mixture was stirred at 0° C. for 30 mins. then SEMCl (1.3 g, 7.8 mmol, 1.2 eq) was added. The mixture was stirred at rt overnight. After the reaction was complete, water was added to quench the reaction, which was extracted with ethyl acetate. The organic layer was washed with brine, dried over Na2SO4 and filtered. The filtrate was concentrated in vacuo and The resulting residue was purified by column chromatography (PE:EA=3:1) to provide 4-chloro-1-((2-(trimethylsilyl)ethoxy)methyl)-1H-pyrazolo[4,3-c]-pyridine (1.2 g, 65%) as yellow oil.

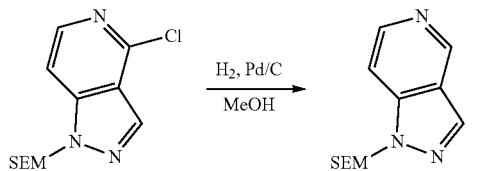 [SMILES: "MeOH" ; C[Si](C)(C)CCOCn1ncc2c(Cl)nccc21 ; "H2, Pd/C" ; C[Si](C)(C)CCOCn1ncc2cnccc21]

To a solution of 4-chloro-1-((2-(trimethylsilyl)ethoxy)methyl)-1H-pyrazolo[4,3-c]-pyridine (1.2 g, 4.2 mmol, 1.0 eq) in MeOH (25.0 mL) was added 10% Pd/C (0.6 g). The mixture was hydrogenated under 1 atm H2 for 16.0 h, then filtered. The filtrate was concentrated in vacuo to provide 1-((2-(trimethylsilyl)ethoxy)methyl)-1H-pyrazolo [4,3-c]-pyridine (800 mg, 76%) as colorless oil, used directly in the next step. LCMS (M+H+) m/z calculated 250.2, found 250.2.

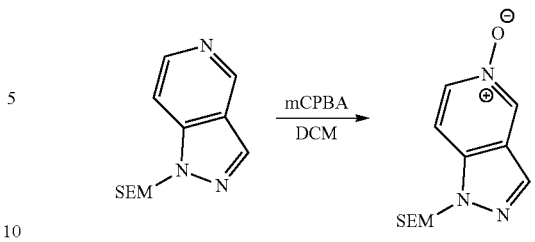

To a solution of 1-((2-(trimethylsilyl)ethoxy)methyl)-1H-pyrazolo[4,3-c]pyridine (430.0 mg, 1.73 mmol, 1.0 eq) in DCM (10.0 mL) was added m-CPBA (700.0 mg, 3.45 mmol, 2.0 eq). The mixture was stirred at rt for 16.0 h. After the reaction was complete, DCM was added to dilute the reaction. And aq. Na2S2O4 was added to quench the reaction. The organic layer was washed with sat. aq. NaHCO3, brine, dried over Na2SO4 and filtered. The filtrate was concentrated in vacuo and The resulting residue was purified by column chromatography on silica gel (EA) to provide 1-((2-(trimethylsilyl)ethoxy)methyl)-1H-pyrazolo[4,3-c]pyridine 5-oxide (200 mg, 45%). LCMS (M+H+) m/z calculated 266.2 found 266.2.

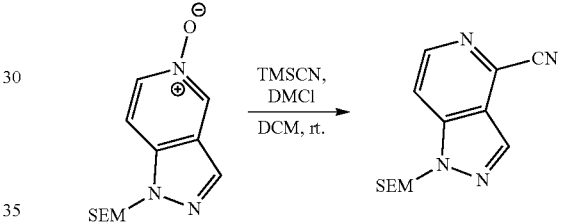

To a solution of 1-((2-(trimethylsilyl)ethoxy)methyl)-1H-pyrazolo[4,3-c]pyridine 5-oxide (200 mg, 0.75 mmol, 1.0 eq) in DCM (10.0 mL) was added TMSCN (225.0 mg, 2.25 mmol, 3.0 eq) and DMCI (160.0 mg, 1.5 mmol, 2.0 eq). The mixture was stirred at 22° C. for 24.0 h. After the reaction was complete, it was quenched with water, extracted with DCM. The organic layer was washed with sat. aq. NaHCO3, brine, dried over Na2SO4 and filtered. The filtrate was concentrated in vacuo, and the resulting residue was purified by column chromatography (PE:EA=2:1) to provide 1-((2-(trimethylsilyl)ethoxy)methyl)-1H-pyrazolo[4,3-c]pyridine-4-carbonitrile (200.0 mg, 95%) as yellow oil. LCMS (M+H+) m/z calculated 275.2 found 275.2.

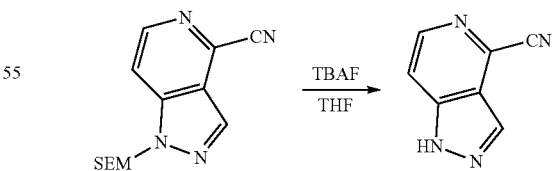

1-((2-(Trimethylsilyl)ethoxy)methyl)-1H-pyrazolo[4,3-c]pyridine-4-carbonitrile (200.0 mg, 0.73 mmol, 1.0 eq) was dissolved in 1M TBAF (8.0 mL, 8.0 mmol, 1.1 eq). The mixture was stirred at rt for 16.0 h. After the reaction was complete, the solvent was removed. The resulting residue was purified by column chromatography on silica gel (PE:EA=2:1) to provide 1H-pyrazolo[4,3-c]pyridine-4-carbonitrile (80.0 mg, 75%) as a white solid. LCMS (M+H+) m/z calculated 145.2 found 145.2.

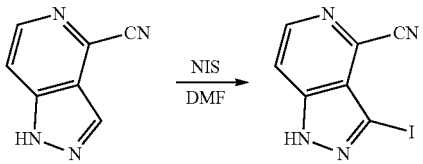

To a solution of 1H-pyrazolo[4,3-c]pyridine-4-carbonitrile (80.0 mg, 0.55 mmol, 1.0 eq) in DMF (3.0 mL) at 25° C. was added NIS (125.0 mg, 0.55 mmol, 1.0 eq). The mixture was stirred at 25° C. for 16 h. After the reaction was complete, the mixture was extracted by EA and the organic layer was washed with brine, dried over Na2SO4 and filtered. The filtrate was concentrated in vacuo and The resulting residue was purified by column chromatography on silica gel (PE:EA=2:1) to provide 3-iodo-5-methoxy-1H-pyrazolo[4,3-b]pyridine (300.0 mg, 2.0 mmol) as a white solid. LCMS (M+H+) m/z calculated 271.2, found 271.2.

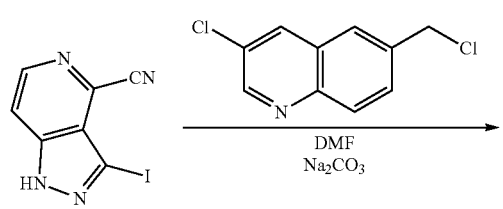

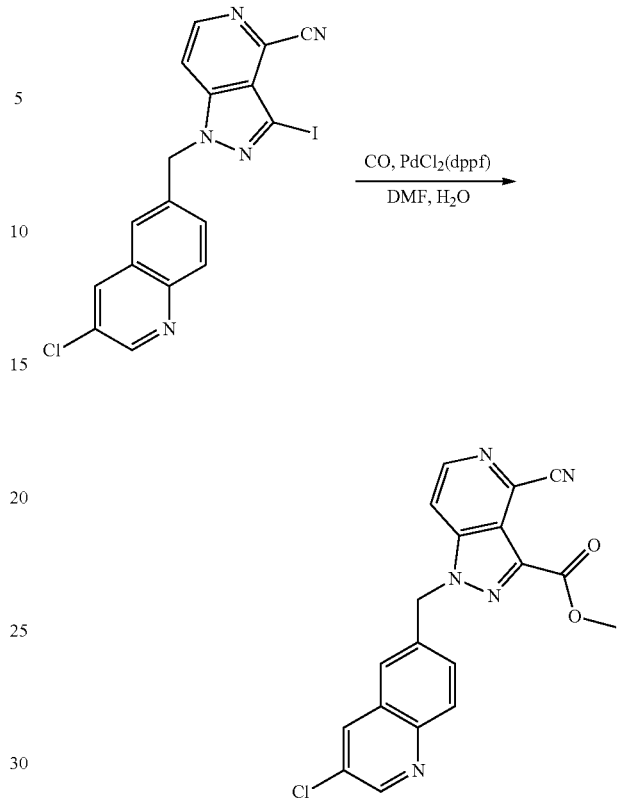

A mixture of 3-iodo-1H-pyrazolo[4,3-c]pyridine-4-carbonitrile (135.0 mg, 0.5 mmol, 1.0 eq), 3-chloro-6-(chloromethyl)quinoline (135.0 mg, 0.55 mmol, 1.1 eq) and Na2CO3 (133.0 mg, 1.25 mmol, 2.5 eq) in DMF (10.0 mL) was stirred under N2 at 70° C. for 16.0 h. After the reaction was complete, the mixture was cooled to rt and extracted by EA. The combined organic layers were washed with brine, dried over Na2SO4 and filtered. The filtrate was concentrated in vacuo and The resulting residue was purified by column chromatography (PE:EA=1:1) to provide 1-((3-chloroquinolin-6-yl)methyl)-3-iodo-1H-pyrazolo[4,3-c]pyridine-4-carbonitrile (120.0 mg, 54%). LCMS (M+H+) m/z calculated 446.2 found 446.2.

A mixture of 1-((3-chloroquinolin-6-yl)methyl)-3-iodo-1H-pyrazolo[4,3-c]pyridine-4-carbonitrile (120.0 mg, 0.27 mmol, 1.0 eq), Et3N (80.0 mg, 0.8 mmol, 3.0 eq) in MeOH (3.0 mL) and DMF (3.0 mL) was degassed with CO.PdCl2 (dppf).CH2Cl2 (20.0 mg, 0.027 mmol, 0.1 eq) was added. The mixture was stirred at 70° C. at CO atmosphere for 16.0 h. After the reaction was complete, the mixture was cooled to rt and extracted by EA. The combined organic layers were washed with brine, dried over Na2SO4 and filtered. The filtrate was concentrated in vacuo. The resulting residue was purified by prep-TLC (PE:EA=1:1) to provide methyl 1-((3-chloroquinolin-6-yl)methyl)-4-cyano-1H-pyrazolo[4,3-c]pyridine-3-carboxylate (80.0 mg, 80%) as gray solid. LCMS (M+H+) m/z calculated 378.2, found 378.2.

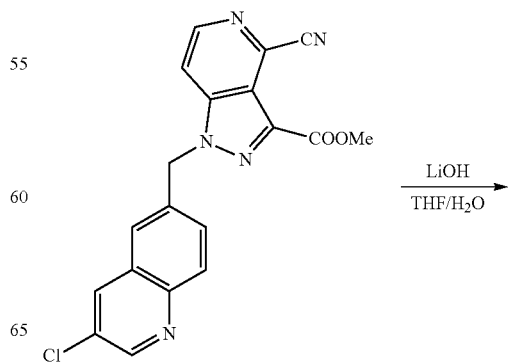

-continued

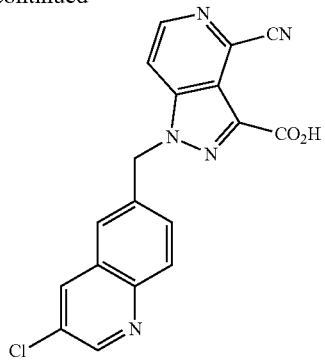

To a solution of methyl 1-((3-chloroquinolin-6-yl)methyl)-4-cyano-1H-pyrazolo [4,3-c]pyridine-3-carboxylate (60.0 mg, 0.16 mmol, 1.0 eq) in THF (4.0 mL) was added LiOH.H2O (65.0 mg, 1.6 mmol, in 1 mL of water, 10 eq). The mixture was stirred at 20° C. for 16 h. Then EA and water was added. 1M aq. HCl was added to adjust till pH=1. The organic layer was separated, dried over Na2SO4 and filtered. The filtrate was concentrated in vacuo to provide 1-((3-chloroquinolin-6-yl)methyl)-4-cyano-1H-pyrazolo[4, 3-c]pyridine-3-carboxylic acid (40.0 mg, 69%). LCMS (M+H+) m/z calculated 364.2, found 364.2.

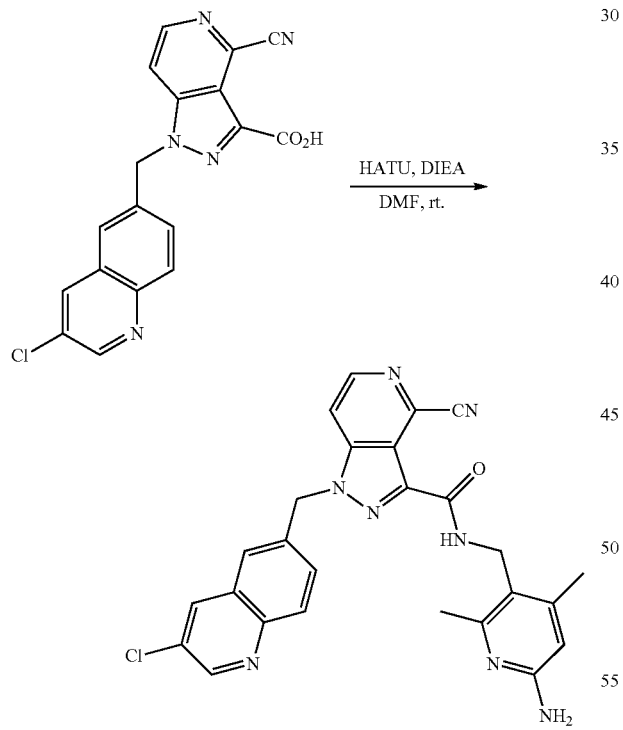

To a solution of 1-((3-chloroquinolin-6-yl)methyl)-4-cyano-1H-pyrazolo [4,3-c] pyridine-3-carboxylic acid (40.0 mg, 0.11 mmol, 1.0 eq), 5-(aminomethyl)-4,6-dimethylpyridin-2-amine (24.0 mg, 0.16 mmol, 1.5 eq) and HATU (60.0 mg, 0.16 mmol, 1.5 eq) in DMF (5.0 mL) at rt was added DIEA (72.0 mg, 0.55 mmol, 5.0 eq). The mixture was stirred at 20° C. for 16.0 h. After the reaction was complete, the mixture was extracted by EA, dried over Na2SO4 and filtered. The filtrate was concentrated in vacuo. The resulting residue was purified by prep-HPLC to provide N-((6-amino-2,4-dimethylpyridin-3-yl)methyl)-1-((3-chloroquinolin-6-yl)methyl)-4-cyano-1H-pyrazolo[4,3-c]pyridine-3-carboxamide (12.0 mg, 22%) as a white solid. 1H NMR (DMSO-d6, 400 MHz) δ 8.86 (s, 1H), 8.66 (t, 1H), 8.63 (d, 1H), 8.51 (d, 1H), 8.23 (d, 1H), 8.02 (d, 1H), 7.75 (s, 1H), 7.67 (d, 1H), 6.13 (s, 1H), 6.04 (s, 2H), 5.71 (brs, 2H), 4.44 (s, 2H), 2.32 (s, 3H), 2.21 (s, 3H). LCMS (M+H+) m/z calculated 497.2, found 497.2.

° C. Example 77: Preparation of N-((6-amino-2-methylpyridin-3-yl)methyl)-1-((3-chloroquinolin-6-yl)methyl)-3-cyano-1H-pyrazole-4-carboxamide

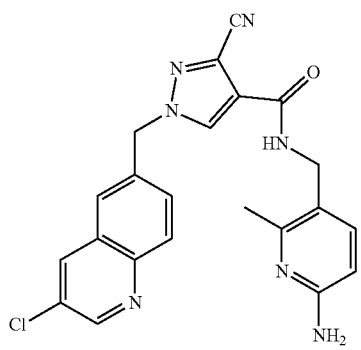

N-((6-amino-2-methylpyridin-3-yl)methyl-1-((3-chloroquinolin-6-yl)methyl)-3-cyano-1H-pyrazole-4-carboxamide

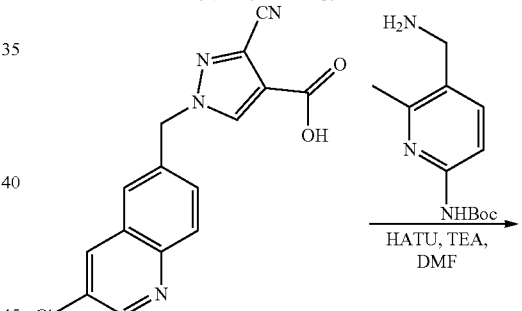

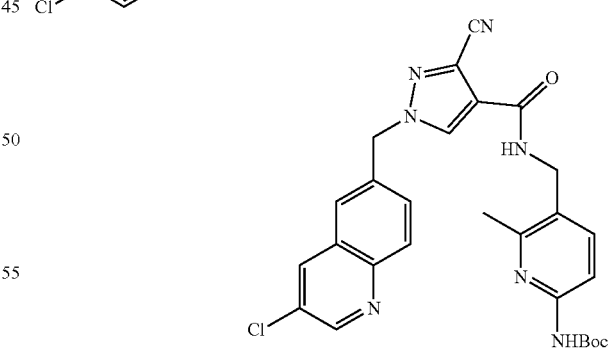

A mixture of 1-((3-chloroquinolin-6-yl)methyl)-3-cyano-1H-pyrazole-4-carboxylic acid (4 g, 12.8 mmol), (5-aminomethyl-6-methyl-pyridin-2-yl)-carbamic acid tert-butyl ester (3.64 g, 15.36 mmol), HATU (7.3 g, 19.2 mmol) and Et3N (5.5 mL, 38.4 mmol) in DMF (30 mL) was stirred at rt overnight. After the reaction was completed, DMF was evaporated and the resulting residue was purified by chromatography on a silica gel column (DCM/MeOH=50/1, v/v)

to give tert-butyl (5-((1-((3-chloroquinolin-6-yl)methyl)-3-cyano-1H-pyrazole-4-carboxamido)methyl)-6-methylpyridin-2-yl)carbamate (1.5 g, 22%) as a white solid.

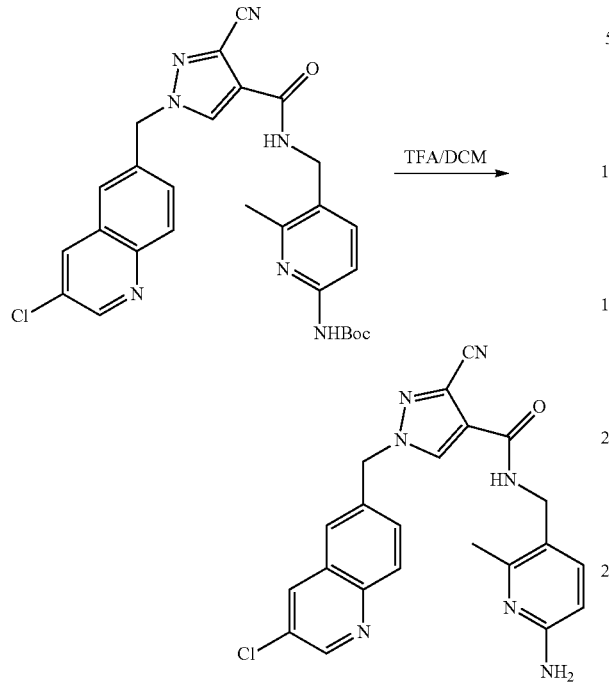

tert-Butyl (5-((1-((3-chloroquinolin-6-yl)methyl)-3-cyano-1H-pyrazole-4-carboxamido)methyl)-6-methylpyridin-2-yl)carbamate (1.5 g, 2.82 mmol) was dissolved in DCM (20 mL), then TFA (20 mL) was added. The mixture solution was stirred at rt overnight. After the reaction was completed, the solvents were evaporated and the resulting residue was diluted with EtOH (5 mL). The mixture was adjusted to pH 9 with aqueous NaOH. A white precipitate formed, which was filtered and dried in vacuo to give N-((6-amino-2-methylpyridin-3-yl)methyl)-1-((3-chloroquinolin-6-yl)methyl)-3-cyano-1H-pyrazole-4-carboxamide (980 mg, 80%) as a white solid. LRMS (M+H+) m/z calculated 432.1, found 432.0. 1H NMR (DMSO-d6, 400 MHz): δ 8.94 (s, 1H), 8.63 (s, 1H), 8.62 (t, 1H), 8.55 (s, 1H), 8.07 (d, 1H), 7.87 (s, 1H), 7.72 (d, 1H), 7.24 (d, 1H), 6.24 (d, 1H), 5.78 (s, 2H), 5.71 (s, 2H), 4.23 (d, 2H), 2.27 (s, 3H).

Example 78: Preparation of 6-((4-(((6-amino-2,4-dimethylpyridin-3-yl)methyl)carbamoyl)-3-cyano-1H-pyrazol-1-yl)methyl)-3-methylquinoline-8-carboxamide

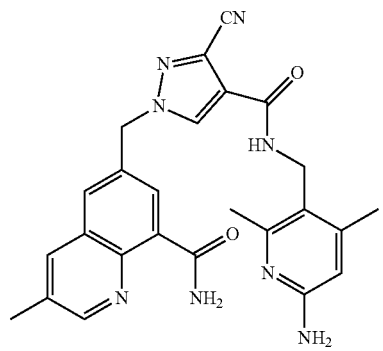

6-((4-(((6-amino-2,4-dimethylpyridin-3-yl)methyl)carbamoyl)-3-cyano-1H-pyrazol-1-yl)methyl)-3-methylquinoline-8-carboxamide

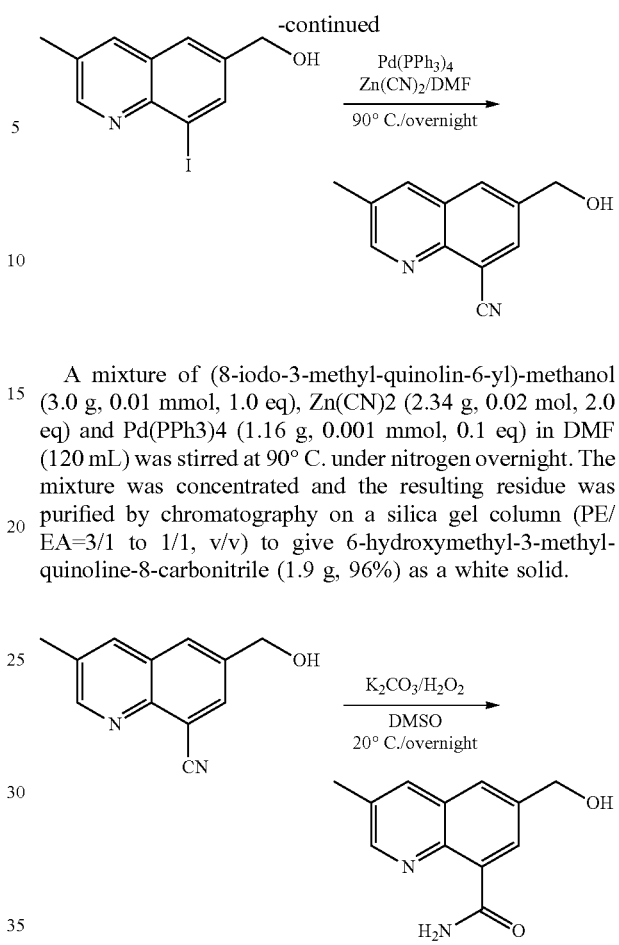

A mixture of (8-iodo-3-methyl-quinolin-6-yl)-methanol (3.0 g, 0.01 mmol, 1.0 eq), Zn(CN)2 (2.34 g, 0.02 mol, 2.0 eq) and Pd(PPh3)4 (1.16 g, 0.001 mmol, 0.1 eq) in DMF (120 mL) was stirred at 90° C. under nitrogen overnight. The mixture was concentrated and the resulting residue was purified by chromatography on a silica gel column (PE/EA=3/1 to 1/1, v/v) to give 6-hydroxymethyl-3-methyl-quinoline-8-carbonitrile (1.9 g, 96%) as a white solid.

A mixture of 6-hydroxymethyl-3-methyl-quinoline-8-carbonitrile (1.9 g, 9.6 mmol, 1.0 eq), K2CO3 (2.65 g, 19.2 mmol, 2.0 eq) and H2O2 (4.5 mL) (30%) in DMSO (30 mL) stirred at 20° C. overnight. Then the mixture was diluted with water (100 mL), and the precipitate was filtered, dried at 120° C. for 4 h. The filtrate was extracted with DCM (200 mL×4). The combined organics were washed with water (150 mL×2), dried and concentrated. The resulting residue was triturated in PE/EA (40 mL, v/v=1/1). The two batches were combined to give 6-hydroxymethyl-3-methyl-quinoline-8-carboxylic acid amide (1.84 g, 85%) as a white solid.

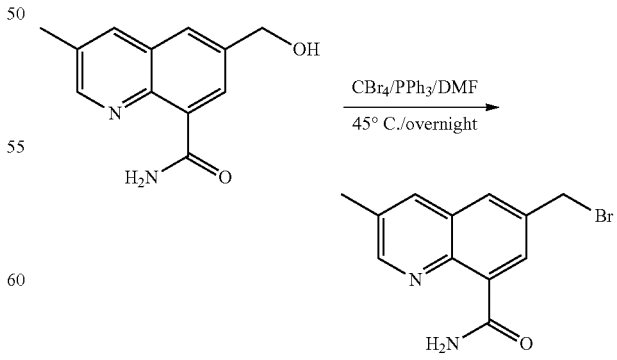

A mixture of 6-hydroxymethyl-3-methyl-quinoline-8-carboxylic acid amide (1.18 g, 5.46 mmol, 1.0 eq), CBr4 (2.26 g, 6.83 mmol, 1.25 eq) and PPh3 (1.79 g, 6.83 mmol, 1.25 eq) in dry DMF (50 mL) was stirred at 45° C. overnight under nitrogen. The reaction mixture was purified by chromatography on a silica gel column (PE/EA=4/1 to 3/1, v/v) to give 6-bromomethyl-3-methyl-quinoline-8-carboxylic acid amide (170 mg, 10%).

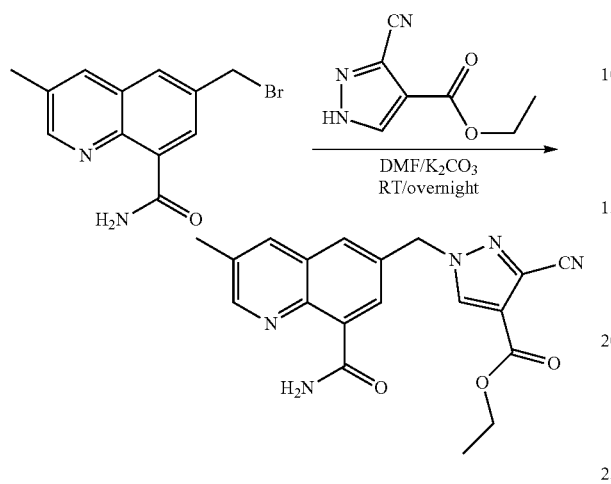

A mixture of 6-bromomethyl-3-methyl-quinoline-8-carboxylic acid amide (170 mg, 0.61 mmol, 1 eq), 3-cyano-1H-pyrazole-4-carboxylic acid ethyl este (101 mg, 0.61 mmol, 1.0 eq) and K2CO3 (168 mg, 1.22 mmol, 2.0 eq) in DMF (10 mL) was stirred at rt overnight. The reaction mixture was diluted with water (160 mL) and extracted with CHCl3 (200 mL×2). The combined organic layers were washed with water, dried and concentrated. The resulting residue was purified by chromatography on a silica gel column (PE/EA=2/1 to DCM/MeOH=15/1, v/v) to give 1-(8-carbamoyl-3-methyl-quinolin-6-ylmethyl)-3-cyano-1H-pyrazole-4-carboxylic acid ethyl ester (250 mg, 71%).

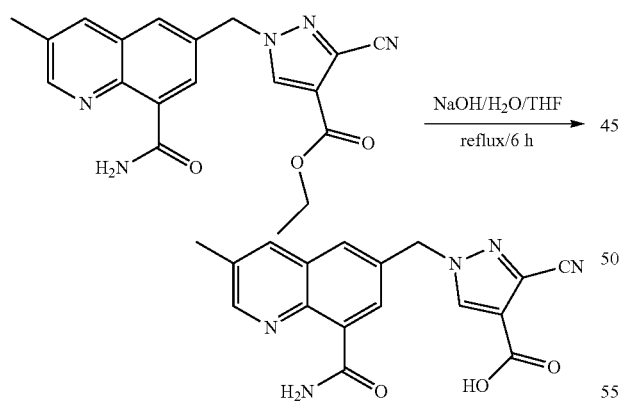

To a solution of 1-(8-carbamoyl-3-methyl-quinolin-6-ylmethyl)-3-cyano-1H-pyrazole-4-carboxylic acid ethyl ester (200 mg, 0.55 mmol, 1.0 eq) in THF (10 mL) was added aq NaOH (220 mg, 5.5 mmol, 10.0 eq) (5 mL). The mixture was stirred under reflux for 6 h. THF was removed by evaporation, and the aqueous layer was adjusted pH 2 with 1N HCl. A white solid precipitate formed, which was filtered, washed with water and dried at 110° C. for 4 h to give 1-(8-carbamoyl-3-methyl-quinolin-6-ylmethyl)-3-cyano-1H-pyrazole-4-carboxylic acid (124 mg, 67%).

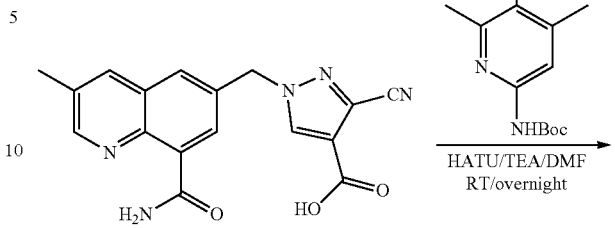

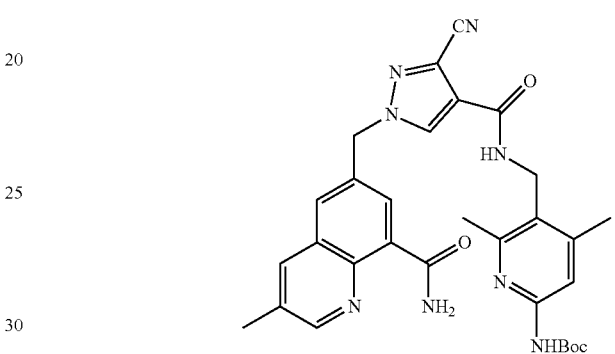

A mixture of 1-(8-carbamoyl-3-methyl-quinolin-6-ylmethyl)-3-cyano-1H-pyrazole-4-carboxylic acid (124 mg, 0.37 mmol, 1.0 eq), (5-aminomethyl-4,6-dimethyl-pyridin-2-yl)-carbamic acid tert-butyl ester (112 mg, 0.44 mmol, 1.2 eq), TEA (112 mg, 1.11 mmol, 3.0 eq) and HATU (183 mg, 0.48 mmol, 1.3 eq) in DMF (10 mL) was stirred at rt overnight. DMF was removed by evaporation and the resulting residue was diluted with 200 mL of DCM, washed with aqueous NH4Cl (100 mL×2). The organic layer was concentrated and the resulting residue was purified by chromatography on a silica gel column (DCM/MeOH=50/1, v/v) to give 66 mg of crude mixture, which was further purified by pre-HPLC to give tert-butyl (5-((1-((8-carbamoyl-3-methylquinolin-6-yl)methyl)-3-cyano-1H-pyrazole-4-carboxamido)methyl)-4,6-dimethylpyridin-2-yl)carbamate (21 mg, 10%).

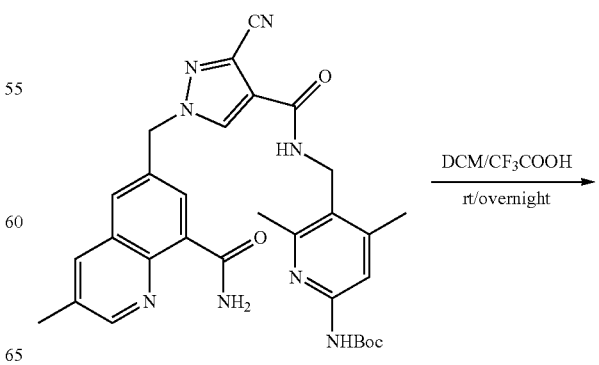

-continued

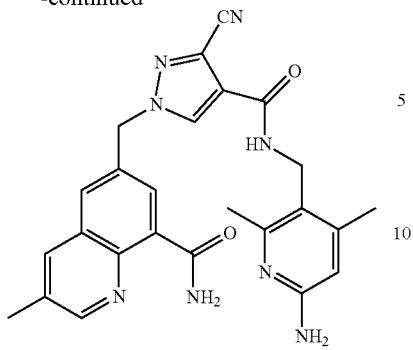

tert-Butyl (5-((1-((8-carbamoyl-3-methylquinolin-6-yl)methyl)-3-cyano-1H-pyrazole-4-carboxamido)methyl)-4,6-dimethylpyridin-2-yl)carbamate (21 mg, 0.037 mmol, 1.0 eq) was dissolved in DCM/CF3COOH (1/1) (20 mL). The mixture was stirred at rt overnight. The solvent was removed by evaporation, and the resulting residue was diluted with water and adjusted to pH 10 with aqueous NaOH. A white precipitate formed, which was collected by filtration. The solid was purified by pre-HPLC to give 6-((4-(((6-amino-2,4-dimethylpyridin-3-yl)methyl)carbamoyl)-3-cyano-1H-pyrazol-1-yl)methyl)-3-methylquinoline-8-carboxamide (13 mg, 77%) as a white solid. LRMS (M+H+) m/z calculated 469.2, found 469.2. 1H NMR (DMSO-d6, 400 MHz): δ 10.16 (s, 1H), 8.91 (s, 1H), 8.59 (s, 1H), 8.40 (s, 1H), 8.33 (s, 2H), 7.99 (s, 2H), 6.18 (s, 1H), 5.95 (s, 2H), 5.72 (s, 2H), 4.28 (d, 2H), 2.50 (s, 3H), 2.31 (s, 3H), 2.18 (s, 3H).

Example 79: Preparation of N-((6-amino-2-methyl-pyridin-3-yl)methyl)-5-((3-chloroquinolin-6-yl)methyl)-1,3,4-oxadiazole-2-carboxamide To a solution of 5-aminomethyl-6-methyl-pyridin-2-ylamine hydrochloride (163 mg, 0.94 mmol, 3.0 eq) in toluene (20 mL) was added AlMe3 (2 M in toluene, 0.5 mL, 1.08 mmol, 3.5 eq) at 0° C. The mixture was stirred at rt for 1 h. Then 5-(3-chloro-quinolin-6-ylmethyl)-[1,3,4]oxadiazole-2-carboxylic acid ethyl ester mixture (100 mg, 0.31 mmol, 1.0 eq) was added and heated to 100° C. overnight. The mixture was cooled to rt and water (10 mL) was added. The mixture was extracted with DCM/MeOH (v/v=10/1, 30 mL×3). The organic layers were dried over Na2SO4, filtered and concentrated. The resulting residue was purified by prep-HPLC to afford N-((6-amino-2-methylpyridin-3-yl)methyl)-5-((3-chloroquinolin-6-yl)methyl)-1,3,4-oxadiazole-2-carboxamide (14 mg, 11%) as a white solid. LRMS (M+H+) m/z calculated 409.1, found 408.9. 1H NMR (DMSO-d6, 400 MHz): δ 9.61 (t, 1H), 8.89 (d, 1H), 8.57 (d, 1H), 8.05 (d, 1H), 7.93 (s, 1H), 7.79-7.76 (1H, m), 7.25 (d, 1H), 6.22 (d, 1H), 5.78 (s, 2H), 4.60 (s, 2H), 4.25 (d, 2H), 2.28 (s, 3H).

Example 80: Preparation of N-((6-amino-2,4-dimethylpyridin-3-yl)methyl)-2-(3-chloroquinoline-6-carbonyl)oxazole-5-carboxamide

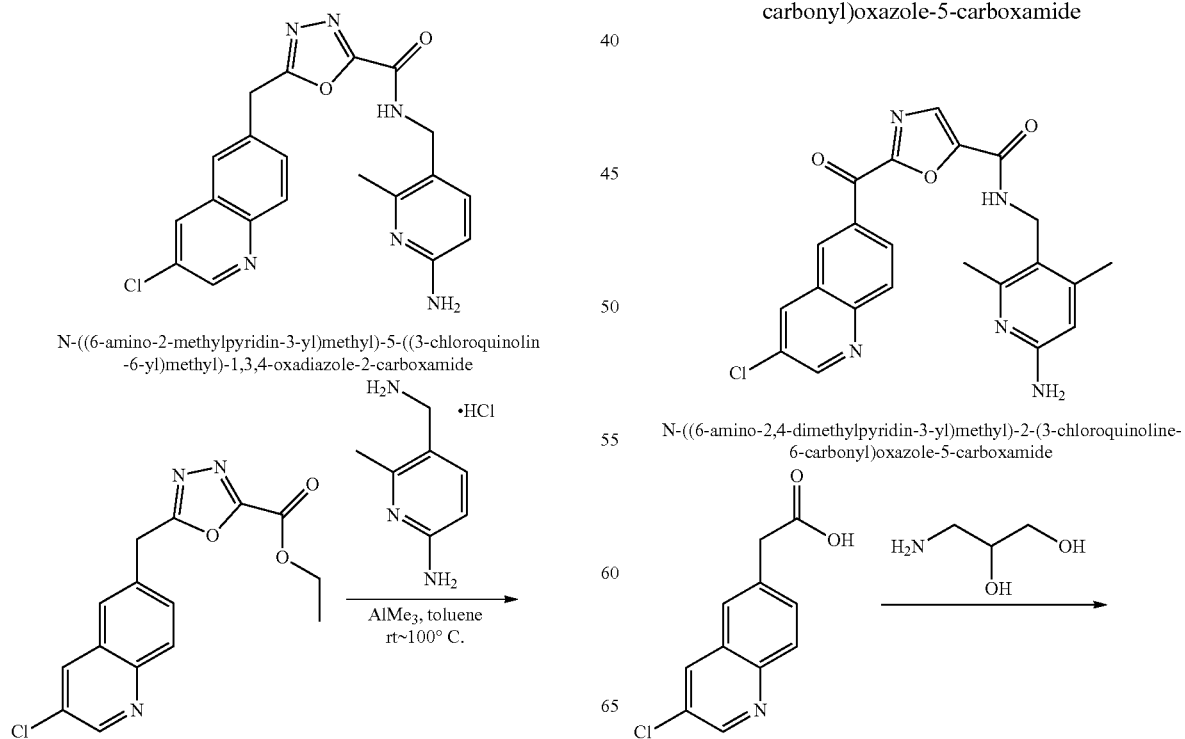

319

-continued

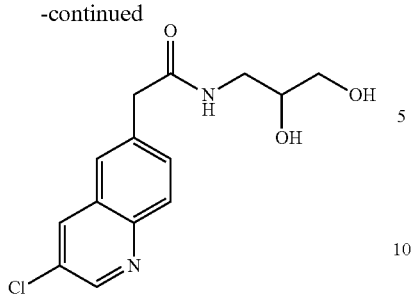

A mixture of (3-chloro-quinolin-6-yl)-acetic acid (2.35 g, 10.60 mmol, 1.0 eq), 3-amino-propane-1,2-diol (1.4 g, 15.90 mmol, 1.5 eq), HATU (6.0 g, 15.90 mmol, 1.5 eq) and Et3N (3.2 g, 31.8 mmol, 3.0 eq) in DMF (20 mL) was stirred at rt overnight. The mixture was concentrated and the resulting residue was washed with EA, dried in vacuo to afford 2-(3-chloro-quinolin-6-yl)-N-(2,3-dihydroxy-propyl)-acetamide (2.7 g, 86%) as a white solid.

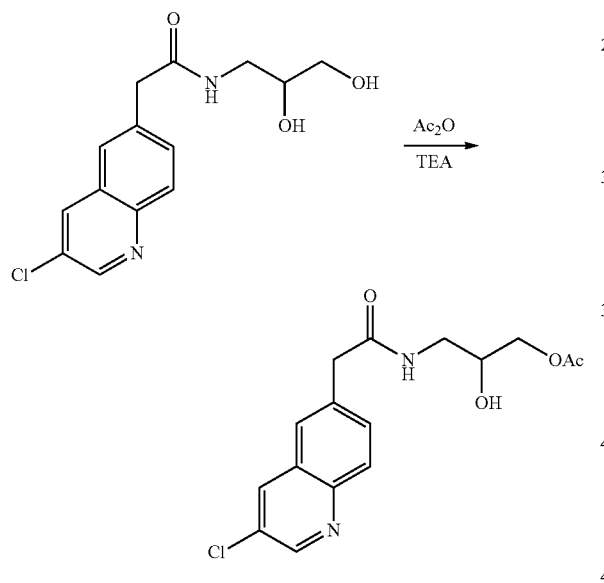

To a solution of 2-(3-chloro-quinolin-6-yl)-N-(2,3-dihydroxy-propyl)-acetamide (2.7 g, 9.16 mmol, 1.0 eq) in DCM (50 mL) was added Ac2O (1.4 g, 13.74 mmol, 1.5 eq) at rt. The mixture was stirred at 45° C. for 6 h. The mixture was concentrated and the resulting residue was purified by chromatography on a silica gel column (DCM/MeOH=20/1, v/v) to afford 3-(2-(3-chloroquinolin-6-yl)acetamido)-2-hydroxypropyl acetate (1.2 g, 39%) as a white solid.

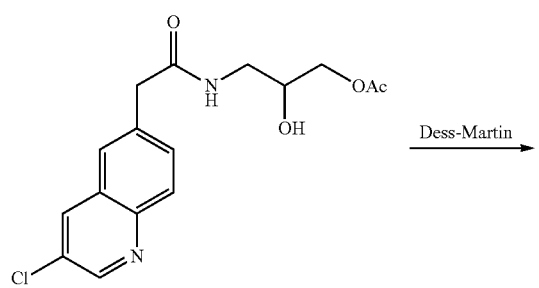

320

-continued

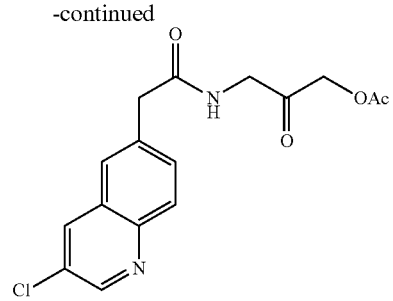

To a solution of 3-(2-(3-chloroquinolin-6-yl)acetamido)-2-hydroxypropyl acetate (1.2 g, 3.56 mmol, 1.0 eq) in DCM (20 mL) was added Dess-Martin (2.3 g, 5.34 mmol, 1.5 eq) at rt. The mixture was stirred at rt overnight. The reaction was quenched with aqueous solution of Na2SO3 and extracted with DCM (50 mL×2). The organic layers were dried over Na2SO4, filtered and concentrated. The resulting residue was purified by chromatography on a silica gel column (DCM/MeOH=30/1, v/v) to afford 3-(2-(3-chloroquinolin-6-yl)acetamido)-2-oxopropyl acetate (800 mg, 67%) as a white solid.

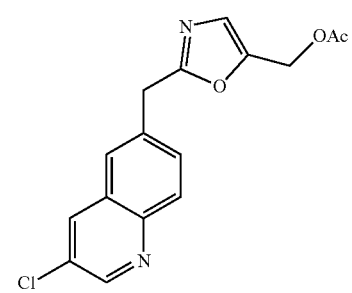

A mixture of 3-(2-(3-chloroquinolin-6-yl)acetamido)-2-oxopropyl acetate (800 mg, 2.39 mmol, 1.0 eq) and POCl3 (733 mg, 4.78 mmol, 2.0 eq) in toluene (100 mL) was stirred at 120° C. overnight. After concentration, the resulting residue was diluted with EA and washed with NaHCO3 aqueous solution. The organic layers were dried over Na2SO4, filtered and concentrated. The resulting residue was purified by chromatography on a silica gel column (PE/EA=3/1, v/v) to afford (2-((3-chloroquinolin-6-yl)methyl)oxazol-5-yl)methyl acetate (100 mg, 13%) as a yellow solid.

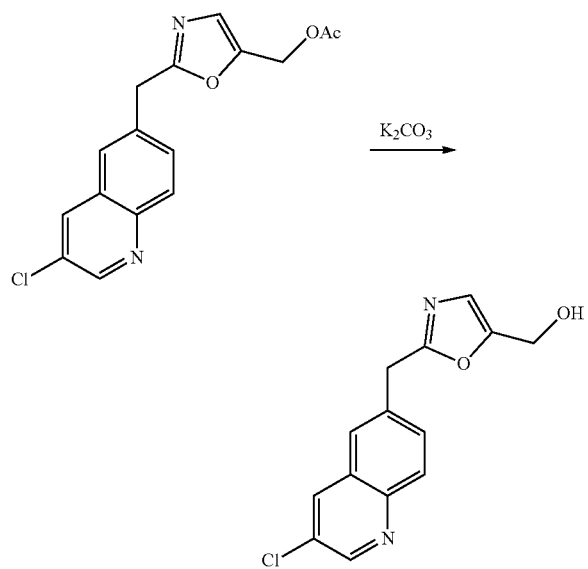

To a solution of (2-((3-chloroquinolin-6-yl)methyl)oxazol-5-yl)methyl acetate (100 mg, 0.32 mmol, 1.0 eq) in MeOH (4 mL) was added K2CO3 (87 mg, 0.63 mmol, 2.0 eq) at rt. The mixture was stirred at rt overnight. The mixture was filtered and the filtrate was concentrated. The resulting residue was used in next step directly.

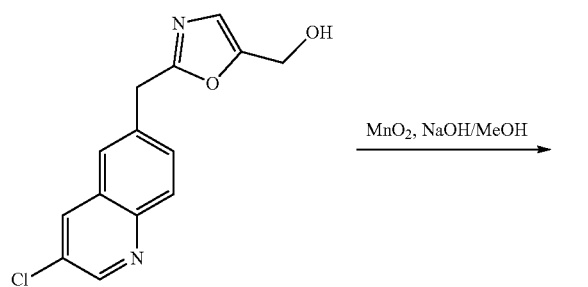

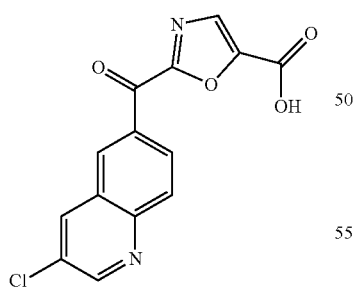

To a solution of 2-(3-chloroquinoline-6-carbonyl)oxazole-5-carboxylic acid (50 mg, crude, 0.18 mmol, 1.0 eq) in MeOH (6 mL) was added MnO2 (237 mg, 2.73 mmol, 5.0 eq) and NaOH (7.2 mg, 0.18 mmol, 1.0 eq) at rt. The mixture was stirred at 35° C. overnight. The mixture was filtered and the filtrate was concentrated. The resulting residue was used in next step directly. LRMS (M+H+) m/z calculated 303.0, found 303.0.

A mixture of 2-(3-chloro-quinoline-6-carbonyl)-oxazole-5-carboxylic acid (50 mg, crude, 0.18 mmol, 1.0 eq), 5-aminomethyl-4,6-dimethyl-pyridin-2-ylamine hydrochloride (51 mg, 0.27 mmol, 1.5 eq), HATU (103 mg, 0.27 mmol, 1.5 eq) and Et3N (54 mg, 0.54 mmol, 3.0 eq) in DMF (2 mL) was stirred at rt for 2 h. The mixture was concentrated and the resulting residue was purified by prep-HPLC to afford N-((6-amino-2,4-dimethylpyridin-3-yl)methyl)-2-(3-chloroquinoline-6-carbonyl)oxazole-5-carboxamide (3 mg, 4%) as a yellow solid. LRMS (M+H+) m/z calculated 436.1, found 435.9. 1H NMR (DMSO-d6, 400 MHz): δ 9.12 (d, 1H), 9.07 (d, 1H), 8.94 (t, 1H), 8.89 (d, 1H), 8.57-8.55 (m, 1H), 8.23-8.18 (m, 2H), 6.14 (s, 1H), 5.72 (s, 2H), 4.38 (d, 2H), 2.32 (s, 3H), 2.19 (s, 3H).

Example 81: Preparation of N-((6-amino-2,4-dimethylpyridin-3-yl)methyl)-3-cyano-1-((3-methylquinolin-6-yl)methyl)-1H-pyrazole-4-carboxamide

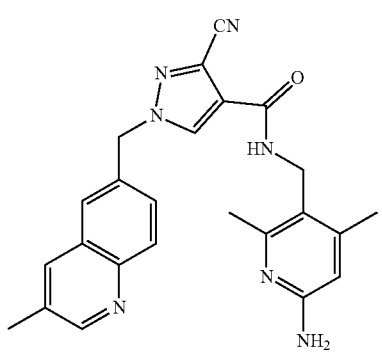

N-((6-amino-2,4-dimethylpyridin-3-yl)methyl-3-cyano-1-((3-methylquinolin-6-yl)methyl)-1H-pyrazole-4-carboxamide

323

-continued

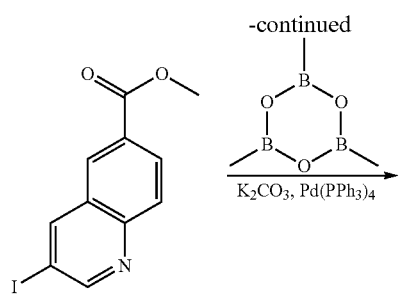

A mixture of 3-iodo-quinoline-6-carboxylic acid methyl ester (3.5 g, 11.22 mmol, 1.0 eq), trimethyloxine (1.73 mL, 12.34 mmol, 1.1 eq), K2CO3 (4.64 g, 33.66 mmol, 3.0 eq) and Pd(PPh3)4 (1.3 g, 1.122 mmol, 0.1 eq) in 1,4-dioxane (82 mL) was stirred at 100° C. overnight under N2. After cooling to rt, the mixture was diluted with EA (50 mL) and washed with H2O. The organic layer was dried over Na2SO4, filtered and evaporated. The crude product was purified by chromatography on a silica gel column (PE/EA=20/1, v/v) to give 3-methyl-quinoline-6-carboxylic acid methyl ester (1.5 g, 67%) as a yellow solid.

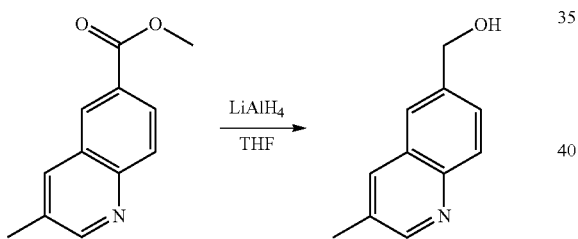

A mixture of 3-methyl-quinoline-6-carboxylic acid methyl ester (1.5 g, 7.46 mmol, 1.0 eq) and LiAlH4 (7.46 mL, 7.46 mmol, 1.0 eq) was stirred in 30 mL at 0° C. under N2 for 3 h. After the reaction was completed, the mixture solution was quenched with saturated potassium sodium tartrate tetrahydrate aqueous solution (30 mL). The mixture was extracted with EA (60 mL×3). The combined organic layers were concentrated and purified by chromatography on a silica gel column (PE/EA=2/1, v/v) to give (3-methyl-quinolin-6-yl)-methanol (650 mg, 51%) as a white solid.

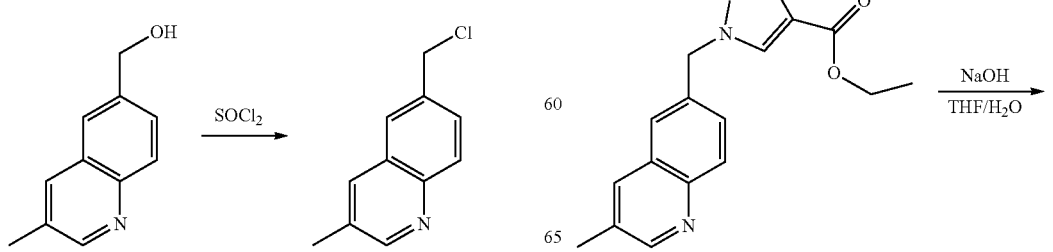

324

A mixture of (3-methyl-quinolin-6-yl)-methanol (650 mg, 3.78 mmol, 1.0 eq) in SOCl2 (10 mL) was stirred at rt for 3 h. After the reaction was completed, the solvent was evaporated to give 6-chloromethyl-3-methyl-quinoline (540 mg, 75%) as a yellow solid.

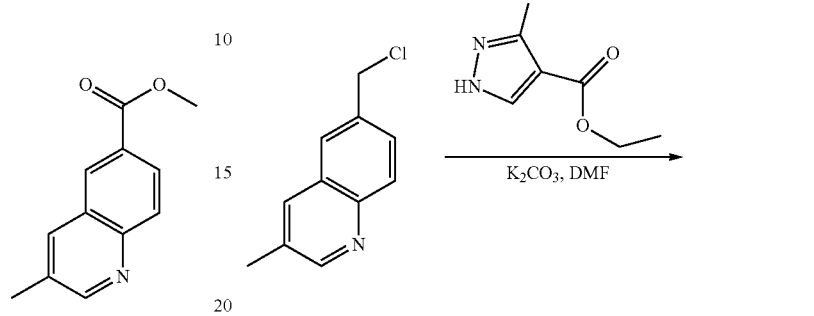

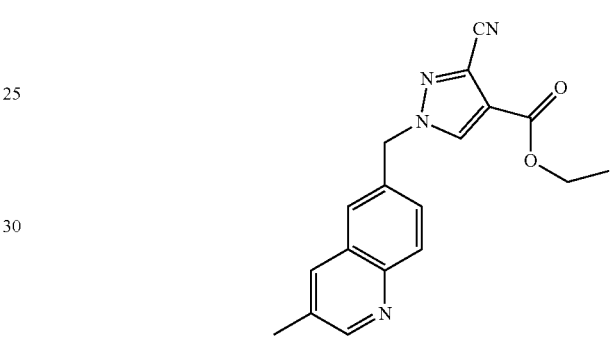

A mixture of 6-chloromethyl-3-methyl-quinoline (250 mg, 1.31 mmol, 1.0 eq), 3-cyano-1H-pyrazole-4-carboxylic acid ethyl ester (216 mg, 1.31 mmol, 1.0 eq) and K2CO3 (1.08 g, 7.86 mmol, 6.0 eq) in DMF (6 mL) was stirred at rt overnight. After the reaction was completed, the mixture solution was diluted with H2O and extracted with DCM (30 mL×3). The combined organic layers were concentrated and purified by chromatography on a silica gel column (PE/EA=2/1, v/v) to give 3-cyano-1-(3-methyl-quinolin-6-ylmethyl)-1H-pyrazole-4-carboxylic acid ethyl ester (360 mg, 82%) as a white solid.

-continued

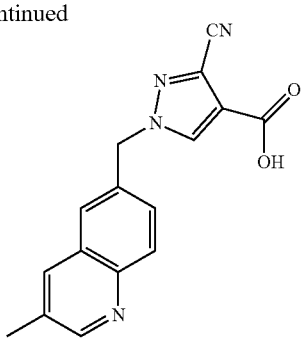

A mixture of 3-cyano-1-(3-methyl-quinolin-6-ylmethyl)-1H-pyrazole-4-carboxylic acid ethyl ester (360 mg, 1.13 mmol, 1.0 eq) and NaOH (135 mg, 3.39 mmol, 3.0 eq) in THF (5 mL) and H2O (5 mL) was stirred at rt overnight. After the reaction was completed, the solvent were evaporated and adjusted to pH 3 with 1 N HCl. Then a white precipitate formed, which was filtered and dried in vacuo to give 3-cyano-1-(3-methyl-quinolin-6-ylmethyl)-1H-pyrazole-4-carboxylic acid (260 mg, 78.8%) as a white solid.

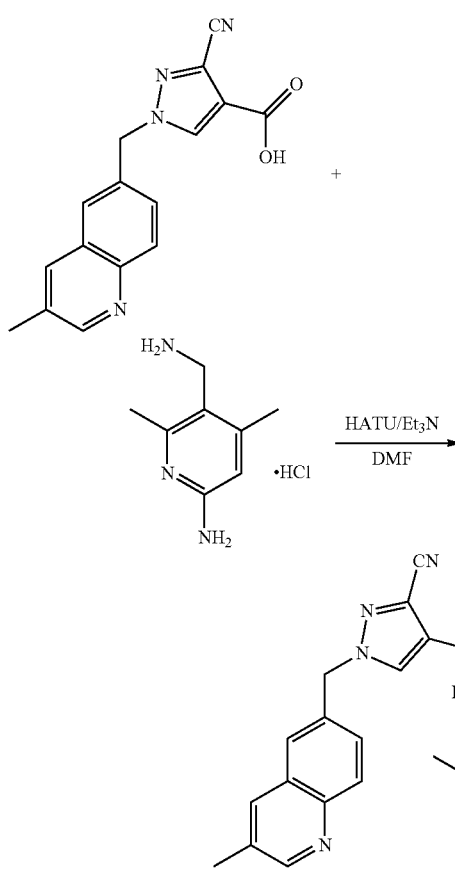

A mixture of 3-cyano-1-(3-methyl-quinolin-6-ylmethyl)-1H-pyrazole-4-carboxylic acid (130 mg, 0.44 mmol, 1.0 eq), 5-aminomethyl-4,6-dimethyl-pyridin-2-ylamine hydrochloride (99 mg, 0.528 mmol, 1.2 mmol), HATU (251 mg, 0.66 mmol, 1.5 eq) and Et3N (0.37 mL, 2.64 mmol, 3.0 eq) in DMF (6 mL) was stirred at rt overnight. After the reaction was completed, the mixture solution was purified by chromatography on a silica gel column (DCM/MeOH=10/1, v/v) to give 50 mg of crude product, which was further purified by prep-HPLC to give N-((6-amino-2,4-dimethylpyridin-3-yl)methyl)-3-cyano-1-((3-methylquinolin-6-yl)methyl)-1H-pyrazole-4-carboxamide (13 mg, 7%) as a white solid. LRMS (M+H+) m/z calculated 426.2, found 426.0. 1H NMR (DMSO-d6, 400 MHz) δ 8.78 (s, 1H), 8.54 (s, 1H), 8.25 (t, 1H), 8.13 (s, 1H), 7.98 (d, 1H) 7.79 (s, 1H), 7.58 (d, 1H), 6.11 (s, 1H), 5.70 (s, 2H), 5.64 (s, 2H), 4.26 (d, 2H), 2.44 (s, 3H), 2.29 (s, 3H), 2.14 (s, 3H).

Example 82: Preparation of N-((6-amino-2-methyl-pyridin-3-yl)methyl)-3-cyano-1-((3-methylquinolin-6-yl)methyl)-1H-pyrazole-4-carboxamide

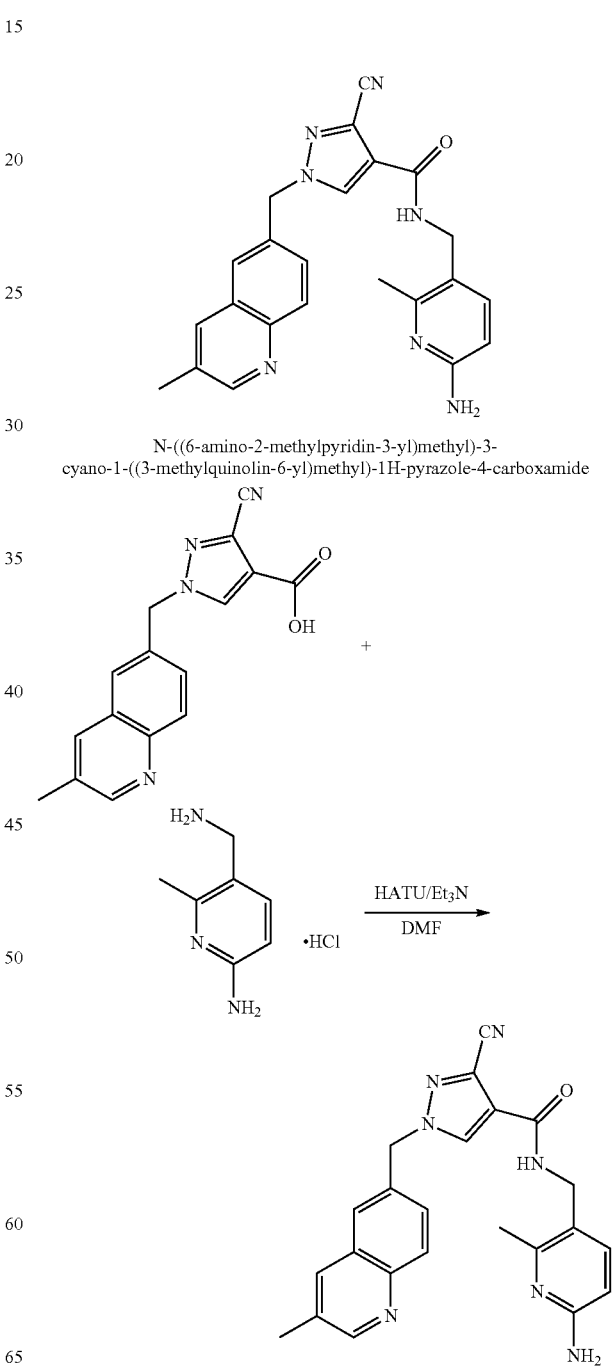

N-((6-amino-2-methylpyridin-3-yl)methyl)-3-cyano-1-((3-methylquinolin-6-yl)methyl)-1H-pyrazole-4-carboxamide A mixture of 3-cyano-1-(3-methyl-quinolin-6-ylmethyl)-1H-pyrazole-4-carboxylic acid (130 mg, 0.44 mmol, 1.0 eq), 5-aminomethyl-6-methyl-pyridin-2-ylamine hydrochloride (91 mg, 0.528 mmol, 1.2 mmol), HATU (251 mg, 0.66 mmol, 1.5 eq) and Et3N (0.37 mL, 2.64 mmol, 3.0 eq) in DMF (6 mL) was stirred at rt overnight. After the reaction was completed, the mixture solution was purified by chromatography on a silica gel column (DCM/MeOH=10/1, v/v) to give 65 mg of crude product, which was purified by prep-HPLC to give N-((6-amino-2-methylpyridin-3-yl)methyl)-3-cyano-1-((3-methylquinolin-6-yl)methyl)-1H-pyrazole-4-carboxamide (25 mg, 14%) as a white solid. LRMS (M+H+) m/z calculated 412.2, found 412.0. 1H NMR (DMSO-d6, 400 MHz) δ 8.78 (s, 1H), 8.58 (t, 1H), 8.52 (s, 1H), 8.14 (s, 1H), 7.99 (d, 1H) 7.81 (s, 1H), 7.59 (d, 1H), 7.24 (d, 1H), 6.22 (d, 1H), 5.78 (s, 2H), 5.66 (s, 2H), 4.22 (d, 2H), 2.50 (s, 3H), 2.25 (s, 3H).

Example 83: Preparation of N-((6-amino-2-methyl-pyridin-3-yl)methyl)-2-((3-chloroquinolin-6-yl)methyl)oxazole-4-carboxamide

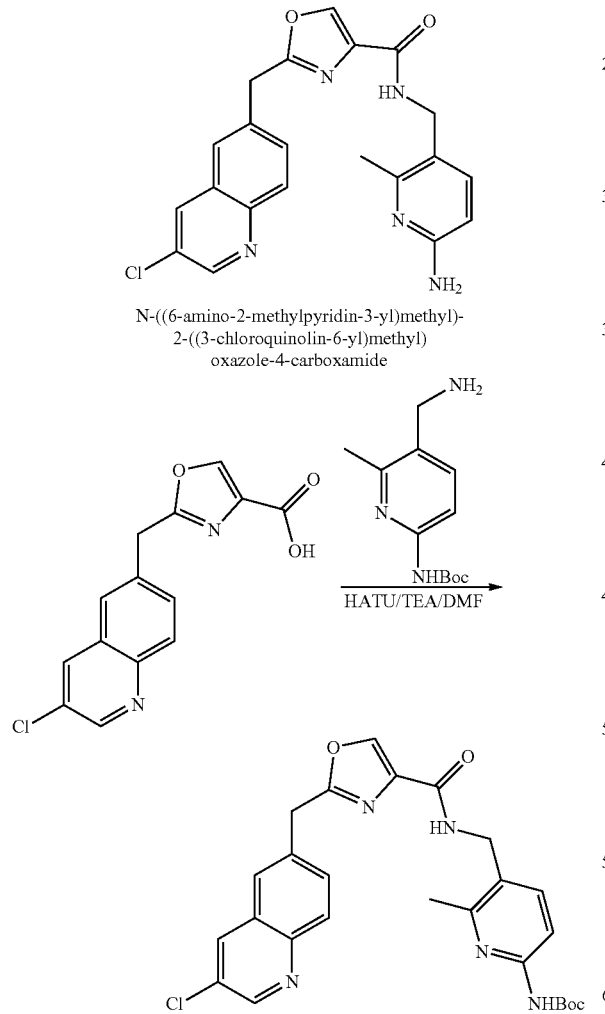

N-((6-amino-2-methylpyridin-3-yl)methyl)-2-((3-chloroquinolin-6-yl)methyl)oxazole-4-carboxamide A mixture of 2-(3-chloro-quinolin-6-ylmethyl)-oxazole-4-carboxylic acid (1.00 g, 3.47 mmol, 1.0 eq), (5-aminomethyl-6-methyl-pyridin-2-yl)-carbamic acid tert-butyl ester (0.82 g, 3.47 mmol, 1.0 eq), TEA (1.05 g, 10.4 mmol, 3.0 eq) and HATU (1.58 g, 4.16 mmol, 1.2 eq) in DMF (20 mL) was stirred at rt overnight. After evaporation to remove DMF, the resulting residue was diluted with 200 mL of DCM and washed with saturated NH4Cl aqueous solution (100 mL×2). The organic layer was concentrated and the resulting residue was purified by chromatography on a silica gel column (DCM/MeOH=30/1, v/v) to give tert-butyl (5-((2-((3-chloroquinolin-6-yl)methyl)oxazole-4-carboxamido)methyl)-6-methylpyridin-2-yl)carbamate (590 mg, 34%).

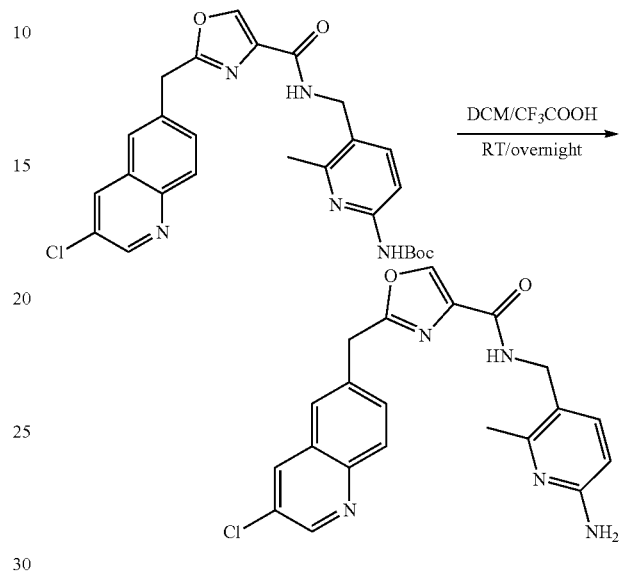

A solution of tert-butyl (5-((2-((3-chloroquinolin-6-yl)methyl)oxazole-4-carboxamido)methyl)-6-methylpyridin-2-yl)carbamate (590 mg, 1.13 mmol, 1.0 eq) in CH2Cl2 (5 mL) and CF3COOH (5 mL) was stirred at rt overnight. The solvent was removed and the resulting residue was diluted with water. The aqueous layer was adjusted to pH 9 with saturated Na2CO3 aqueous solution. Then a white precipitate formed, which was collected by filtration. The solid was purified by pre-HPLC to give N-((6-amino-2-methylpyridin-3-yl)methyl)-2-((3-chloroquinolin-6-yl)methyl)oxazole-4-carboxamide (237 mg, 17%) as a white solid. LRMS (M+H+) m/z calculated 408.1, found 408.0. 1H NMR (DMSO-d6, 400 MHz) δ 8.86 (s, 1H), 8.56 (s, 1H), 8.54 (s, 1H), 8.48 (s, 1H), 8.03 (d, 1H), 7.86 (s, 1H), 7.73 (d, 1H), 7.22 (d, 1H), 6.18 (d, 1H), 5.71 (s, 2H), 4.42 (s, 2H), 4.23 (d, 2H), 2.26 (s, 3H).

Example 84: Preparation of N-((6-amino-2-methyl-pyridin-3-yl)methyl)-5-((3-chloroquinolin-6-yl)methyl)oxazole-2-carboxamide

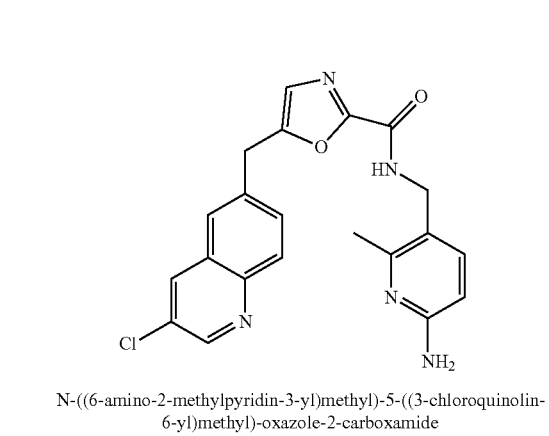

N-((6-amino-2-methylpyridin-3-yl)methyl)-5-((3-chloroquinolin-6-yl)methyl)-oxazole-2-carboxamide -continued

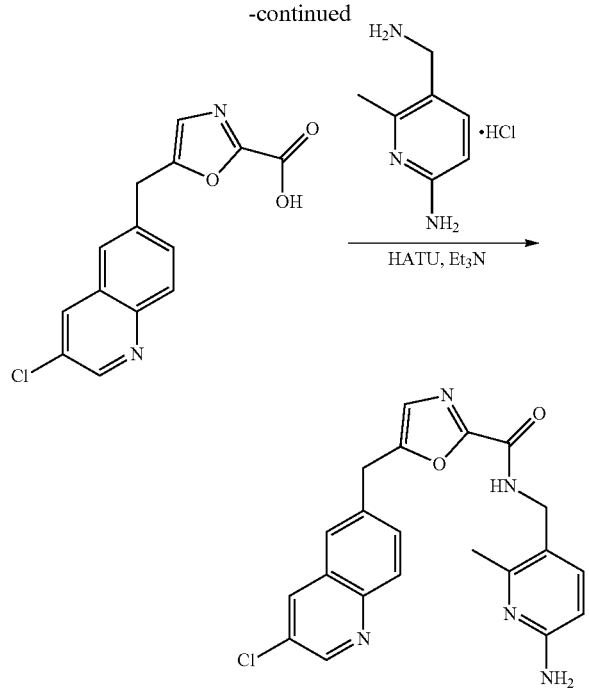

A mixture of 5-(3-chloro-quinolin-6-ylmethyl)-oxazole-2-carboxylic acid (140 mg, 0.48 mmol, 1.0 eq), 5-aminomethyl-6-methyl-pyridin-2-ylamine hydrochloride (126 mg, 0.73 mmol, 1.5 eq), HATU (277 mg, 0.73 mmol, 1.5 eq) and Et3N (145 mg, 1.44 mmol, 3.0 eq) in DMF (4 mL) was stirred at rt overnight. The mixture was concentrated and the resulting residue was purified by chromatography on a silica gel column (DCM/MeOH=10/1, v/v) to afford N-((6-amino-2-methylpyridin-3-yl)methyl)-5-((3-chloroquinolin-6-yl)methyl)oxazole-2-carboxamide (30 mg, 15%) as a white solid. LRMS (M+H+) m/z calculated 408.1, found 408.2. 1H NMR (DMSO-d6, 400 MHz): δ 13.88 (s, 1H), 9.42 (t, 1H), 8.87 (d, 1H), 8.56 (d, 1H), 8.03 (d, 1H), 7.85 (s, 1H), 7.79 (d, 1H), 7.72-7.6 (m, 3H), 7.24 (s, 1H), 6.77 (d, 1H), 4.36 (s, 2H), 4.25 (d, 2H), 2.47 (s, 3H).

Example 85: Preparation of N-((6-amino-2-methyl-pyridin-3-yl)methyl)-1-((3-chloroquinolin-6-yl)methyl)-3-methyl-1H-pyrazole-4-carboxamide N-((6-amino-2-methylpyridin-3-yl)methyl)-1-((3-chloroquinolin-6-yl)methyl)-3-methyl-1H-pyrazole-4-carboxamide -continued

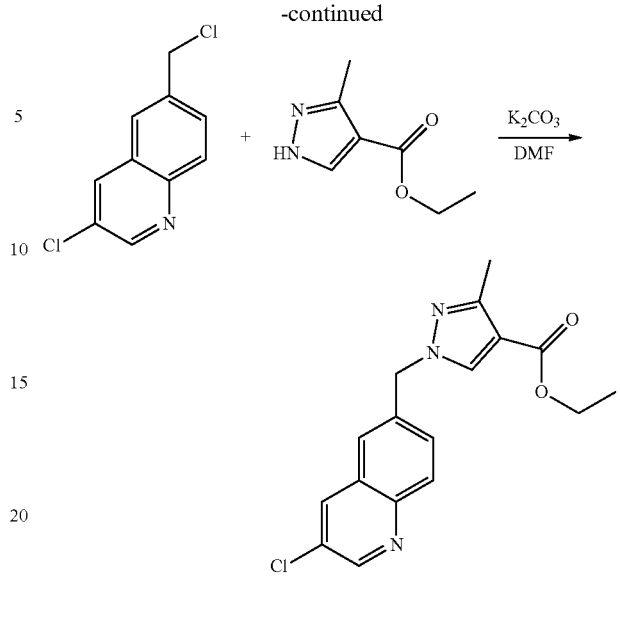

A mixture of 3-chloro-6-chloromethyl-quinoline (753 mg, 3.6 mmol), 3-methyl-1H-pyrazole-4-carboxylic acid ethyl ester (400 mg, 2.6 mmol) and K2CO3 (672 mg, 4.9 mmol) in DMF (15 mL) was stirred at rt overnight. After the reaction was completed, the reaction mixture was concentrated. The resulting residue was diluted with water and extracted with EA (20 mL×3). The combined organic layers were concentrated and purified by chromatography on a silica gel column (PE/EA=5/1 to 2/1, v/v) to give 1-(3-chloro-quinolin-6-ylmethyl)-3-methyl-1H-pyrazole-4-carboxylic acid ethyl ester (840 mg, 98%) as a white solid.

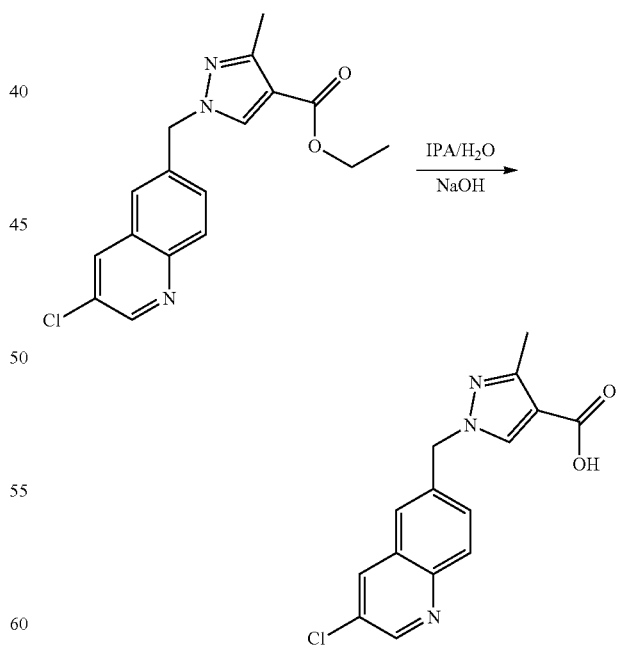

A mixture of 1-(3-chloro-quinolin-6-ylmethyl)-3-methyl-1H-pyrazole-4-carboxylic acid ethyl ester (200 mg, 0.61 mmol) and NaOH (60 mg, 1.52 mmol) in IPA/H2O (15 mL, v/v=1/1) was stirred at 100° C. for 36 h. After the reaction was completed, the reaction solution was neutralized to pH 5 with 1 N HCl. Then a white precipitate formed, which was filtered and dried in vacuo to give 1-(3-chloro-quinolin-6-ylmethyl)-3-methyl-1H-pyrazole-4-carboxylic acid (0.23 g, 1) as a white solid.

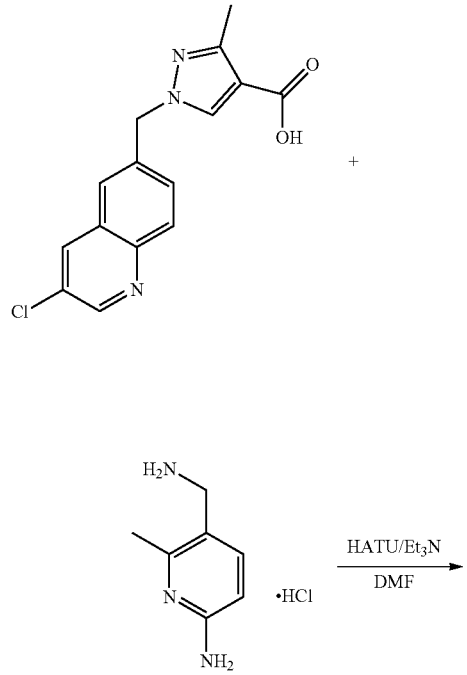

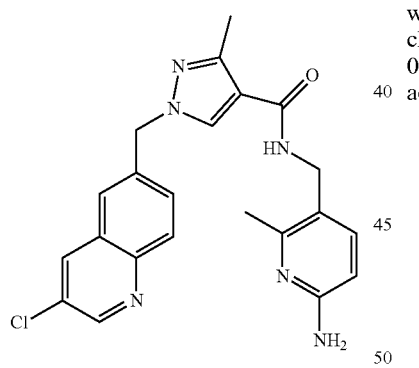

A mixture of 1-(3-chloro-quinolin-6-ylmethyl)-3-methyl-1H-pyrazole-4-carboxylic acid (100 mg, 0.33 mmol, 1.0 eq), 5-aminomethyl-6-methyl-pyridin-2-ylamine hydrochloride (69 mg, 0.40 mmol, 1.2 eq), HATU (188 mg, 1.50 mmol, 1.5 eq) and Et3N (0.14 mL, 1.0 mmol, 3.0 eq) in DMF (6 mL) was stirred at rt overnight. After the reaction was completed, the solvents were evaporated, and the resulting residue was purified by prep-HPLC to give N-((6-amino-2-methylpyridin-3-yl)methyl)-1-((3-chloroquinolin-6-yl)methyl)-3-methyl-1H-pyrazole-4-carboxamide (13.5 mg, 9.7%) as a white solid. LRMS (M+H+) m/z calculated 421.1, found 421.0. 1H NMR (DMSO-d6, 400 MHz) δ 8.88 (s, 1H), 8.59 (s, 1H), 8.258 (s, 1H), 8.08 (t, 1H), 8.05 (d, 1H) 7.81 (s, 1H), 7.64 (d, 1H), 7.22 (d, 1H), 6.23 (d, 1H), 5.68 (s, 2H), 5.46 (s, 2H), 4.18 (d, 2H), 2.31 (s, 3H), 2.25 (s, 3H).

Example 86: Preparation of N-((6-amino-2,4-dimethylpyridin-3-yl)methyl)-5-((3-chloro-8-(2-hydroxypropan-2-yl)quinolin-6-yl)methyl)-1,3,4-oxadiazole-2-carboxamide

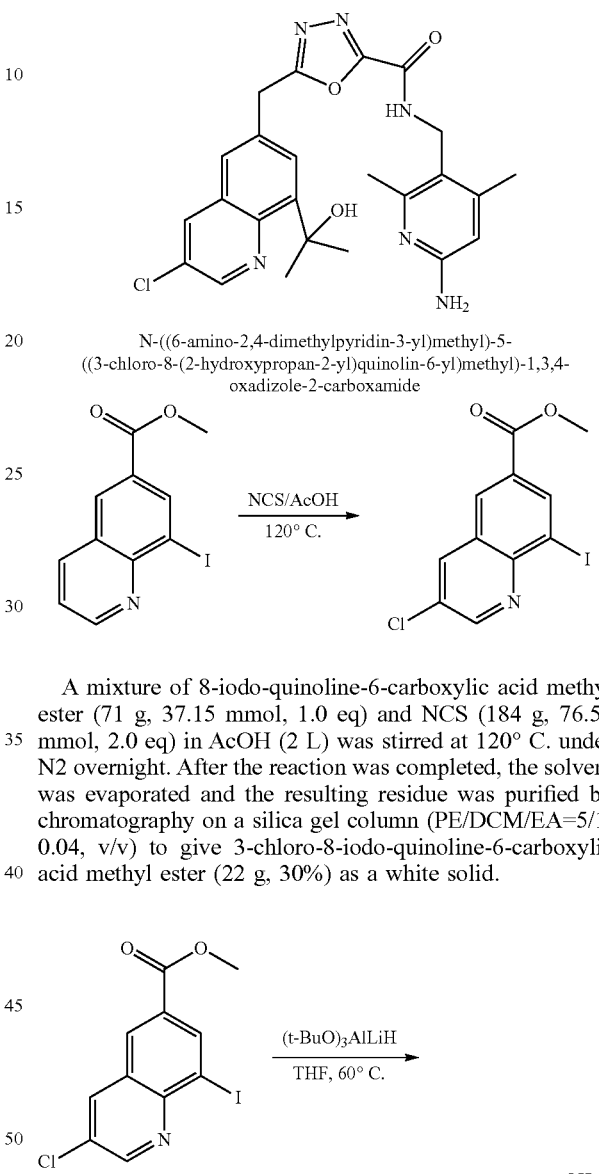

N-((6-amino-2,4-dimethylpyridin-3-yl)methyl)-5-((3-chloro-8-(2-hydroxypropan-2-yl)quinolin-6-yl)methyl)-1,3,4-oxadizole-2-carboxamide A mixture of 8-iodo-quinoline-6-carboxylic acid methyl ester (71 g, 37.15 mmol, 1.0 eq) and NCS (184 g, 76.59 mmol, 2.0 eq) in AcOH (2 L) was stirred at 120° C. under N2 overnight. After the reaction was completed, the solvent was evaporated and the resulting residue was purified by chromatography on a silica gel column (PE/DCM/EA=5/1/0.04, v/v) to give 3-chloro-8-iodo-quinoline-6-carboxylic acid methyl ester (22 g, 30%) as a white solid.

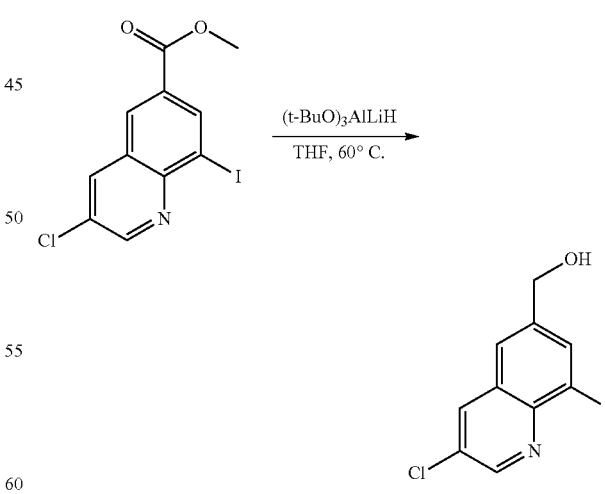

A mixture of 3-chloro-8-iodo-quinoline-6-carboxylic acid methyl ester (20 g, 57.6 mmol, 1.0 eq), (t-BuO)3AlLiH (44 g, 173 mmol, 3.0 eq) in THF (800 mL) was stirred at 60° C. overnight. After the reaction was completed, the reaction was quenched with saturated potassium sodium tartrate tetrahydrate aqueous solution (100 mL). Then the mixture was extracted with EA (500 mL×3). The combined organic layers were concentrated and purified by chromatography on a silica gel column (PE/DCM/EA=2/1/1, v/v) to give (3-chloro-8-iodo-quinolin-6-yl)-methanol (18 g, 98%) as a white solid.

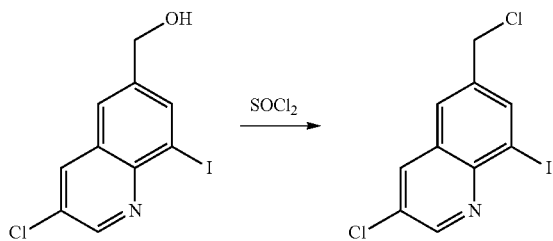 [SMILES: OCc1cc(I)c2ncc(Cl)cc2c1 ; "SOCl2" ; ClCc1cc(I)c2ncc(Cl)cc2c1]

A solution of (3-chloro-8-iodo-quinolin-6-yl)-methanol (11.0 g, 31.3 mmol, 1.0 eq) in SOCl2 (20 mL) was stirred at rt for 3 h. After the reaction was completed, the solvent was evaporated. The resulting residue was diluted with saturated NaHCO₃ aqueous solution and extracted with DCM (30 mL×5). The combined organic layers were concentrated and purified by chromatography on a silica gel column (PE/DCM/EA=20/1/1, v/v) to give 3-chloro-6-chloromethyl-8-iodo-quinoline (10 g, 91%) as a white solid.

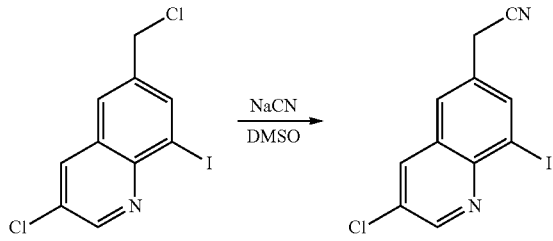

A mixture of 3-chloro-6-chloromethyl-8-iodo-quinoline (9 g, 26.7 mmol, 1.0 eq) and NaCN (1.3 g, 26.7 mmol, 1.0 eq) in DMSO (150 mL) was stirred at rt overnight. After the reaction was completed, the mixture solution was diluted with H2O and extracted with DCM (100 mL×3). The combined organic layers were concentrated and purified by chromatography on a silica gel column (PE/DCM/EA=5/1/1, v/v/v) to give (3-chloro-8-iodo-quinolin-6-yl)-acetonitrile (6.7 g, 76.5%) as a white solid.

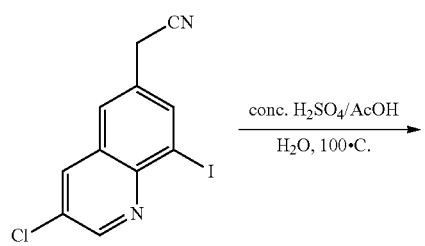

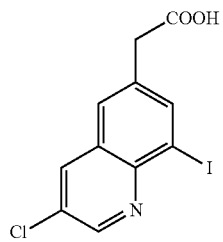

A mixture of (3-chloro-8-iodo-quinolin-6-yl)-acetonitrile (5.7 g, 17.38 mmol, 1.0 eq) in conc. H2SO4 (20 mL), AcOH (20 mL) and H2O (20 mL) was stirred at 100° C. overnight. After the reaction was completed, the mixture solution was adjusted to pH 3 with 1 N NaOH. Then a white precipitate was formed, which was filtered and dried in vacuo to give (3-chloro-8-iodo-quinolin-6-yl)-acetic acid (6.14 g, 1) as a white solid.

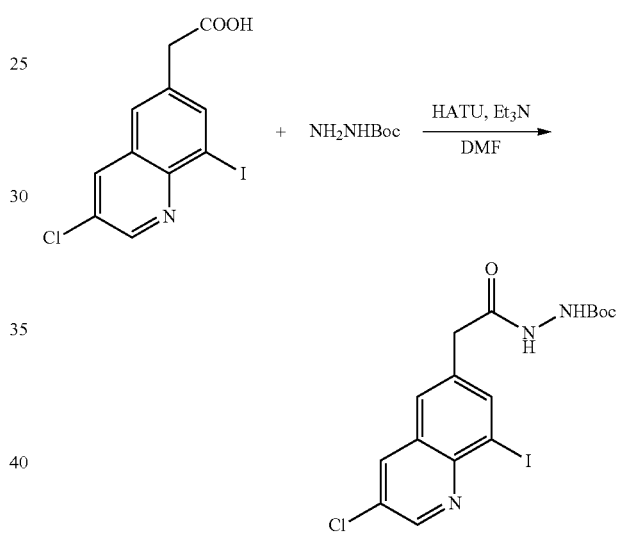

A mixture of (3-chloro-8-iodo-quinolin-6-yl)-acetic acid (6.14 g, 17.7 mmol, 1.0 eq), hydrazinecarboxylic acid tert-butyl ester (2.8 g, 21.2 mmol, 1.2 eq), HATU (10 g, 26.55 mmol, 1.5 eq) and Et3N (7.5 mL, 53.1 mmol, 3.0 eq) in DMF (50 mL) was stirred at rt overnight. After the reaction was completed, H2O was added and a white precipitate formed, which was filtered and dried in vacuo to give tert-butyl 2-(2-(3-chloro-8-iodoquinolin-6-yl)acetyl)hydrazinecarboxylate (8.9 g, 1) as a white solid.

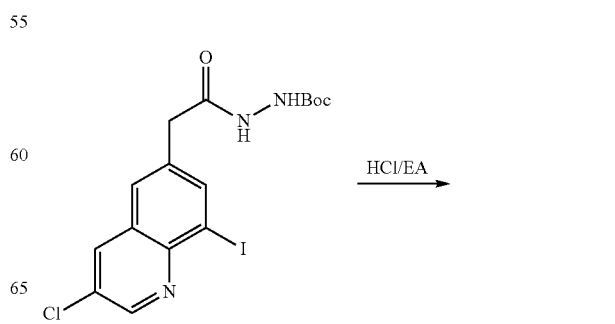

-continued

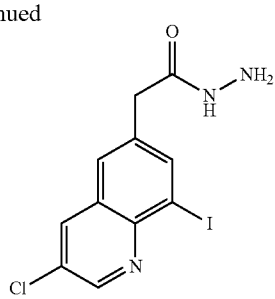

To a solution of tert-butyl 2-(2-(3-chloro-8-iodoquinolin-6-yl)acetyl)hydrazinecarboxylate (8.9 g, 24.65 mmol, 1.0 eq) in EA (150 mL) was added a solution of HCl in EA (4N, 150 mL). The mixture solution was stirred at rt overnight. Then a white precipitate was formed, which was filtered and dried in vacuo to give (3-chloro-8-iodo-quinolin-6-yl)-acetic acid hydrazide (6.92 g, 78%) as a white solid.

A mixture of (5-aminomethyl-4,6-dimethyl-pyridin-2-yl)-carbamic acid tert-butyl ester (5 g, 19.92 mmol, 1.0 eq), chloro-oxo-acetic acid ethyl ester (2.67 mL, 23.9 mmol, 1.2 eq) and K2CO3 (5.5 g, 39.384 mmol, 2.0 eq) in CH3CN (100 mL) was stirred at rt overnight. After the reaction was completed, CH3CN was evaporated. The resulting residue was washed with H2O and extracted with DCM (100 mL×3). The combined organic layers were concentrated and dried in vacuo to give ethyl 2-(((6-((tert-butoxycarbonyl)amino)-2,4-dimethylpyridin-3-yl)methyl)amino)-2-oxoacetate (7.55 g, 1) as a white solid.

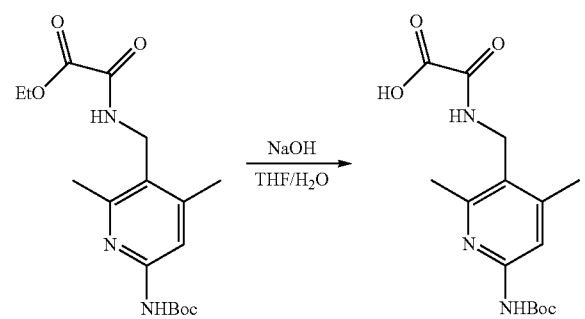

A mixture of ethyl 2-(((6-((tert-butoxycarbonyl)amino)-2,4-dimethylpyridin-3-yl)methyl)amino)-2-oxoacetate (7.55 g, 21.51 mmol, 1.0 eq) and NaOH (1.72 g, 43.02 mmol, 2.0 eq) in THF (50 mL) and H2O (50 mL) was stirred at rt for 1 h. After the reaction was completed, THF was evaporated, and the aqueous layer was neutralized to pH 5 with 1 N HCl. Then a white precipitate formed, which was filtered and dried in vacuo to give 2-(((6-((tert-butoxycarbonyl)amino)-2,4-dimethylpyridin-3-yl)methyl)amino)-2-oxoacetic acid (5.2 g, 74.8%) as a white solid.

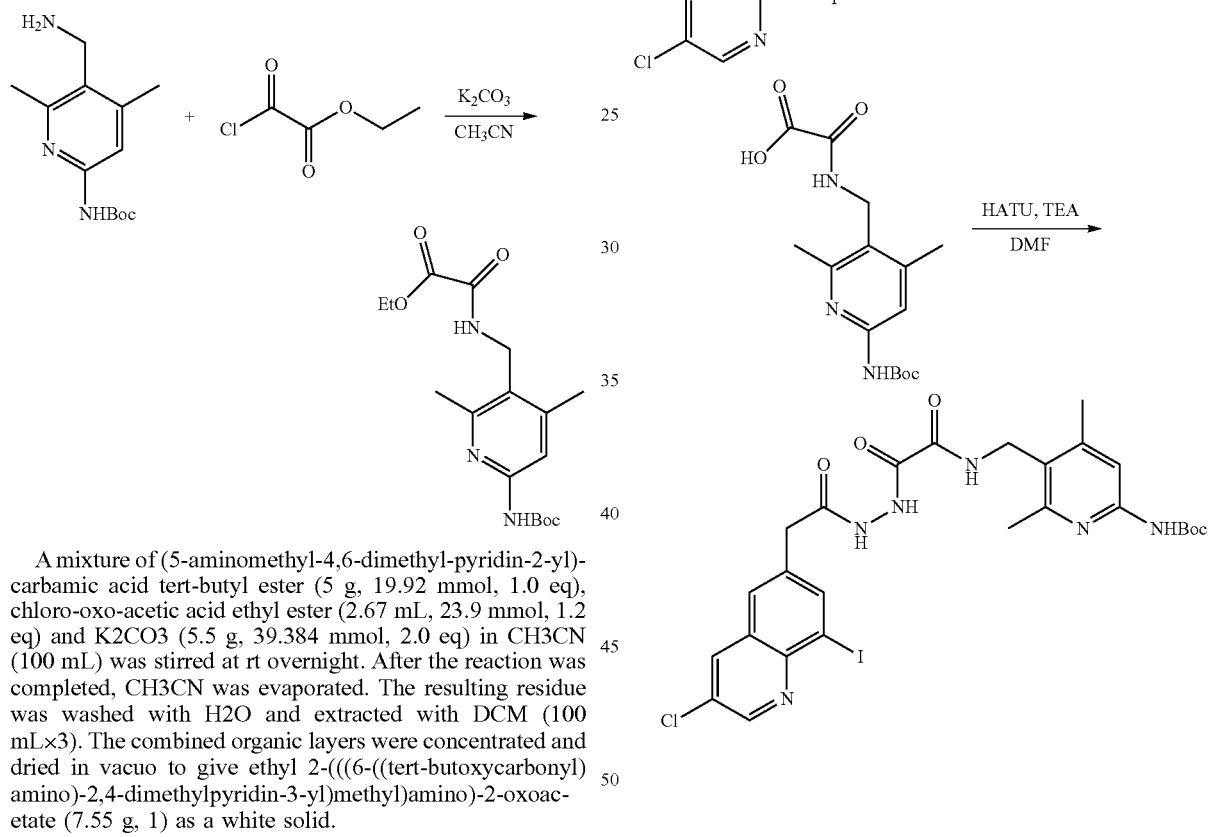

A mixture of (3-chloro-8-iodo-quinolin-6-yl)-acetic acid hydrazide (2 g, 5.54 mmol, 1.0 eq), 2-(((6-((tert-butoxycarbonyl)amino)-2,4-dimethylpyridin-3-yl)methyl)amino)-2-oxoacetic acid (2.14 g, 6.65 mmol, 1.2 eq), HATU (3.16 g, 8.31 mmol, 1.5 eq) and TEA (2.3 mL, 16.62 mmol, 3.0 eq) in DMF (20 mL) was stirred at rt overnight. After the reaction was completed, DMF was evaporated, and the resulting residue was diluted with DCM. The combined organic layers were dried and concentrated. The resulting residue was purified by chromatography on a silica gel column (DCM/MeOH=10/1, v/v) to give tert-butyl (5-((2-(2-(2-(3-chloro-8-iodoquinolin-6-yl)acetyl)hydrazinyl)-2-oxoacetamido)methyl)-4,6-dimethylpyridin-2-yl)carbamate (700 mg, 20%) as a yellow solid.

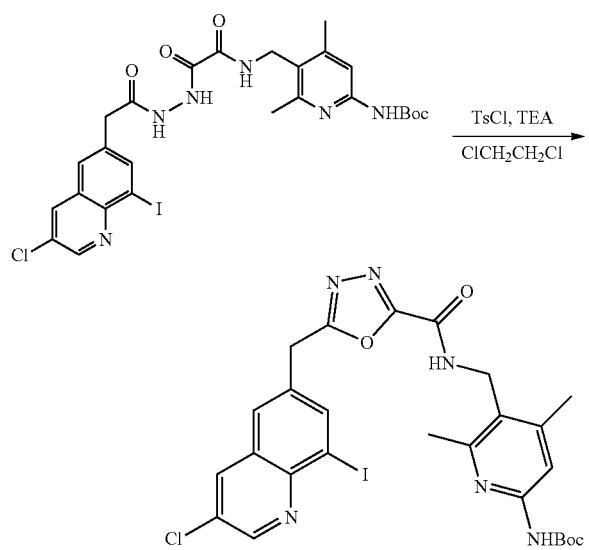

A mixture of tert-butyl (5-((2-(2-(2-(3-chloro-8-iodoquinolin-6-yl)acetyl)hydrazinyl)-2-oxoacetamido)methyl)-4,6-dimethylpyridin-2-yl)carbamate (700 mg, 1.05 mmol, 1.0 eq), TsCl (500 mg, 2.63 mmol, 2.5 eq) and TEA (0.45 mL, 3.15 mmol, 3.0 eq) in ClCH2CH2Cl (50 mL) was stirred at 50° C. overnight. After the reaction was completed, the mixture solution was purified by chromatography on a silica gel column (PE/EA=2/1, v/v) to give tert-butyl (5-((5-((3-chloro-8-iodoquinolin-6-yl)methyl)-1,3,4-oxadiazole-2-carboxamido)methyl)-4,6-dimethylpyridin-2-yl)carbamate (500 mg, 73.5%) as a white solid.

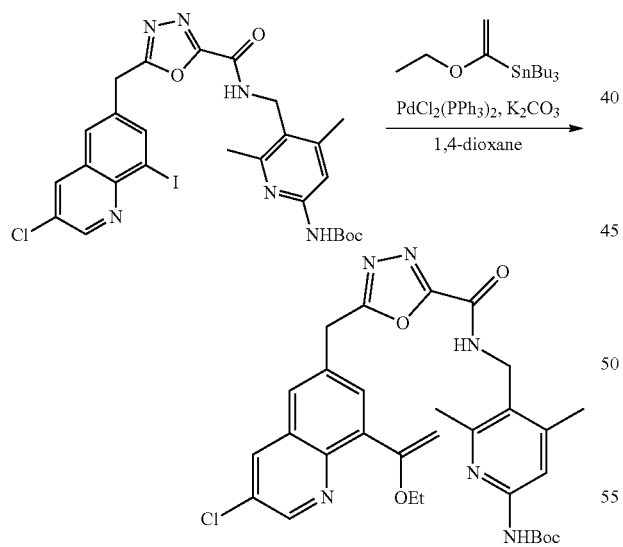

A mixture of tert-butyl (5-((5-((3-chloro-8-iodoquinolin-6-yl)methyl)-1,3,4-oxadiazole-2-carboxamido)methyl)-4,6-dimethylpyridin-2-yl)carbamate (450 mg, 0.69 mmol, 1.0 eq), tributyl-(1-ethoxy-vinyl)-stannane (276 mg, 0.76 mmol, 1.2 eq), PdCl2(PPh3)2 (48 mg, 0.069 mmol, 0.1 eq), K2CO3 (190 mg, 1.38 mmol, 2.0 eq) in 1.4-dioxane (20 mL) was stirred at 90° C. overnight. After the reaction was completed, the mixture solution was diluted with H2O and extracted with DCM (30 mL×3). The combined organic layers were concentrated and purified by chromatography on a silica gel column (PE/DCM/EA=5/1/1, v/v) to give tert-butyl (5-((5-((3-chloro-8-(1-ethoxyvinyl)quinolin-6-yl)methyl)-1,3,4-oxadiazole-2-carboxamido)methyl)-4,6-dimethylpyridin-2-yl)carbamate (200 mg, 49%) as a white solid.

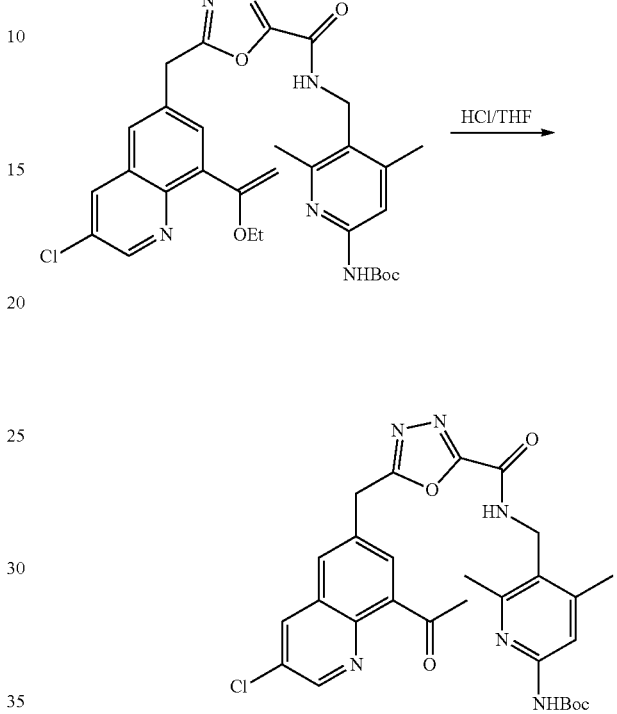

A solution of tert-butyl (5-((5-((3-chloro-8-(1-ethoxyvinyl)quinolin-6-yl)methyl)-1,3,4-oxadiazole-2-carboxamido)methyl)-4,6-dimethylpyridin-2-yl)carbamate (180 mg, 0.3 mmol, 1.0 eq) in HCl (1 M, 6 mL) and THF (6 mL) was stirred at rt for 1 h. After the reaction was completed, the solvents were evaporated. The resulting residue was diluted with EA and washed with saturated NaHCO3 aqueous solution. The organic layer was concentrated and dried in vacuo to give tert-butyl (5-((5-((8-acetyl-3-chloroquinolin-6-yl)methyl)-1,3,4-oxadiazole-2-carboxamido)methyl)-4,6-dimethylpyridin-2-yl)carbamate (200 mg, 1) as a yellow solid.

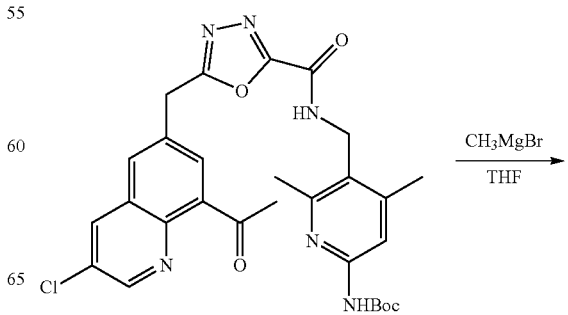

-continued

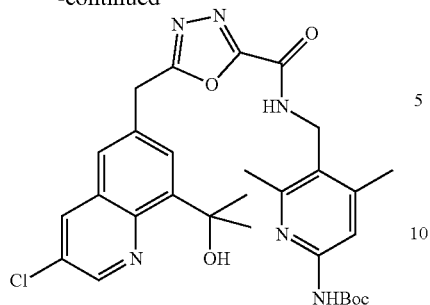

To a stirred solution of tert-butyl (5-((5-((8-acetyl-3-chloroquinolin-6-yl)methyl)-1,3,4-oxadiazole-2-carboxamido)methyl)-4,6-dimethylpyridin-2-yl)carbamate (180 mg, 0.32 mmol) in THF (30 mL) was added CH3MgBr (0.1 mL, 0.32 mmol, 1.0 eq) at −70° C. under N2. The mixture was stirred for 1 h and then quenched with aq NH4Cl and extracted with EA (20 mL×3). The combined organic layers were concentrated and dried in vacuo to give tert-butyl (5-((5-((3-chloro-8-(2-hydroxypropan-2-yl)quinolin-6-yl)methyl)-1,3,4-oxadiazole-2-carboxamido)methyl)-4,6-dimethylpyridin-2-yl)carbamate (200 mg, 1) as a yellow solid.

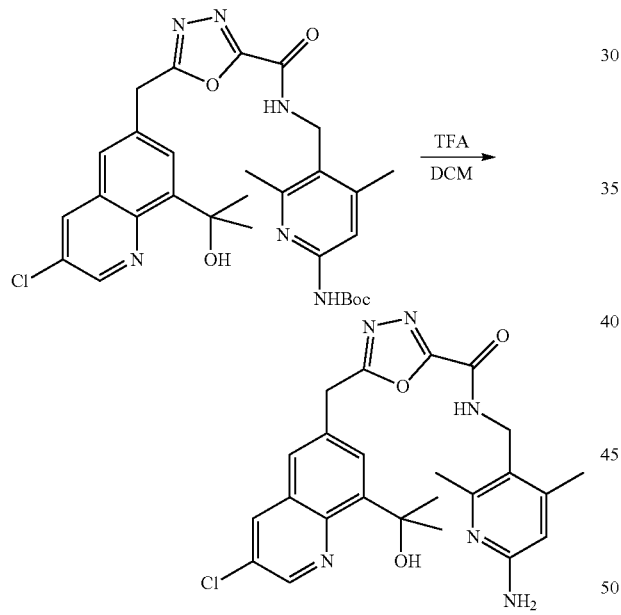

A mixture of tert-butyl (5-((5-((3-chloro-8-(2-hydroxypropan-2-yl)quinolin-6-yl)methyl)-1,3,4-oxadiazole-2-carboxamido)methyl)-4,6-dimethylpyridin-2-yl)carbamate (80 mg, 0.138 mmol, 1.0 eq) in TFA (4 mL) and DCM (4 mL) was stirred at rt for 2 h. The solvents were evaporated and the resulting residue was purified by prep-HPLC to give N-((6-amino-2,4-dimethylpyridin-3-yl)methyl)-5-((3-chloro-8-(2-hydroxypropan-2-yl)quinolin-6-yl)methyl)-1,3,4-oxadiazole-2-carboxamide (2 mg, 3%) as a white solid. LRMS (M+H+) m/z calculated 481.2, found 481.0. 1H NMR (DMSO-d6, 400 MHz) δ 9.33 (t, 1H), 8.90 (s, 1H), 8.57 (s, 1H), 7.95 (t, 1H), 7.79 (s, 1H) 6.10 (s, 1H), 5.81 (s, 1H), 5.72 (s, 2H), 4.56 (s, 2H), 4.34 (d, 2H), 2.29 (s, 3H), 2.16 (s, 3H), 1.72 (s, 6H).

Example 87: Preparation of N-((6-amino-2,4-dimethylpyridin-3-yl)methyl)-2-((3-chloroquinolin-6-yl)methyl)-4-cyanooxazole-5-carboxamide

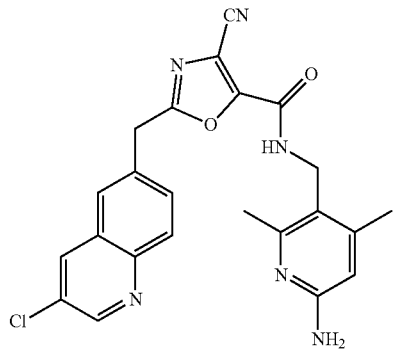

N-((6-amino-2,4-dimethylpyridin-3-yl)methyl)-2-((3-chloroquinolin-6-yl)methyl)-4-cyanooxazole-5-carboxamide

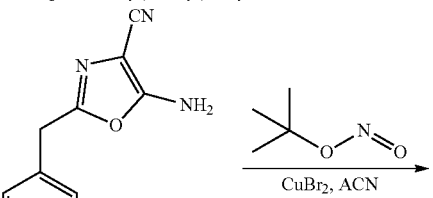

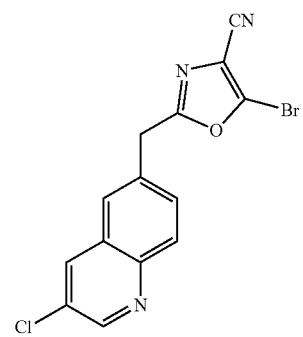

To a stirred mixture of 5-amino-2-((3-chloroquinolin-6-yl)methyl)oxazole-4-carbonitrile (16.1 g, 56.17 mmol, 1 eq) and CuBr2 (25.3 g, 113.4 mmol, 2 eq) in ACN (500 mL) was added tert-butyl nitrite (13.5 mL, 113.4 mmol, 2 eq). The mixture was stirred at rt for 3 h. Then ACN was evaporated, and the resulting residue was diluted with water and NH3.H2O. The mixture was extracted with EA. The combined organic layers were dried and concentrated. The resulting residue was purified by chromatography on a silica gel column (PE/EA=15/1, v/v) to give 5-bromo-2-((3-chloroquinolin-6-yl)methyl)oxazole-4-carbonitrile (8.0 g, 41%) as a white solid.

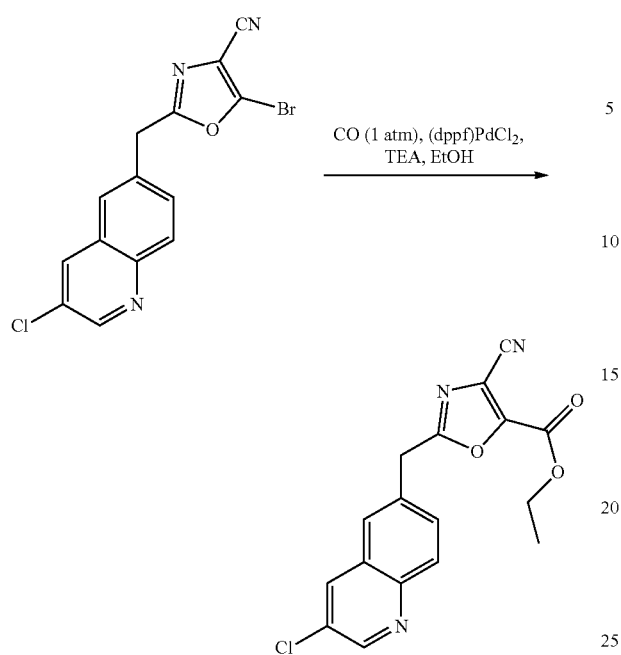

A mixture of 5-bromo-2-((3-chloroquinolin-6-yl)methyl)oxazole-4-carbonitrile (3 g, 8.6 mmol, 1 eq), Pd(dppf)Cl2 (706 mg, 0.86 mmol, 0.1 eq) and TEA (3.6 mL, 25.8 mmol, 3 eq) in EtOH (120 mL) was stirred at 70° C. under carbon monoxide atmosphere (1 atm) overnight. Then the mixture was concentrated and the resulting residue was purified by chromatography on a silica gel column (PE/EA=10/1, v/v) to give ethyl 2-((3-chloroquinolin-6-yl)methyl)-4-cyanooxazole-5-carboxylate (1.64 g, 56%) as a white solid.

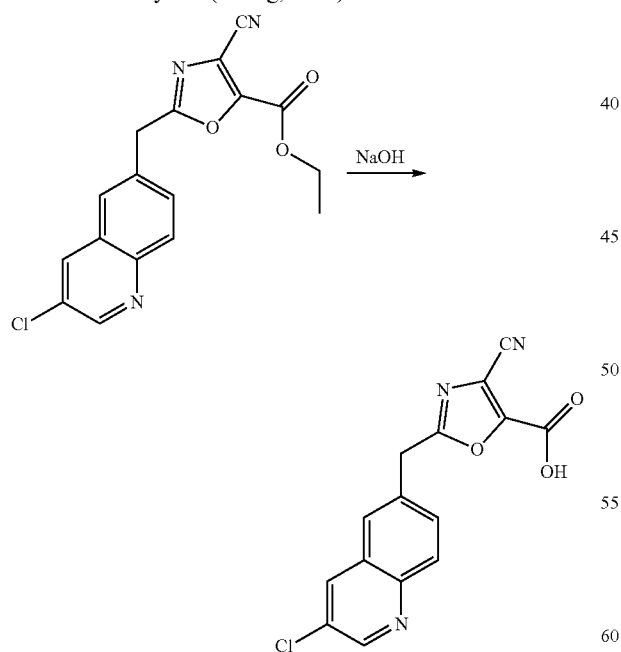

To a solution of 2-(3-chloro-quinolin-6-ylmethyl)-4-cyano-oxazole-5-carboxylic acid ethyl ester (520 mg, 1.52 mmol, 1.0 eq) in THF (20 mL) was added 0.5 M aqueous NaOH solution (122 mg, 3.04 mmol, 2.0 eq) (6 mL). The mixture was stirred at rt for 2 h. THF was removed by evaporation, and the aqueous layer was adjusted to pH 3 with 1 N HCl. Then a white precipitate formed, which was collected by filtration and dried to give 2-(3-chloro-quinolin-6-ylmethyl)-4-cyano-oxazole-5-carboxylic acid (216 mg, 45%).

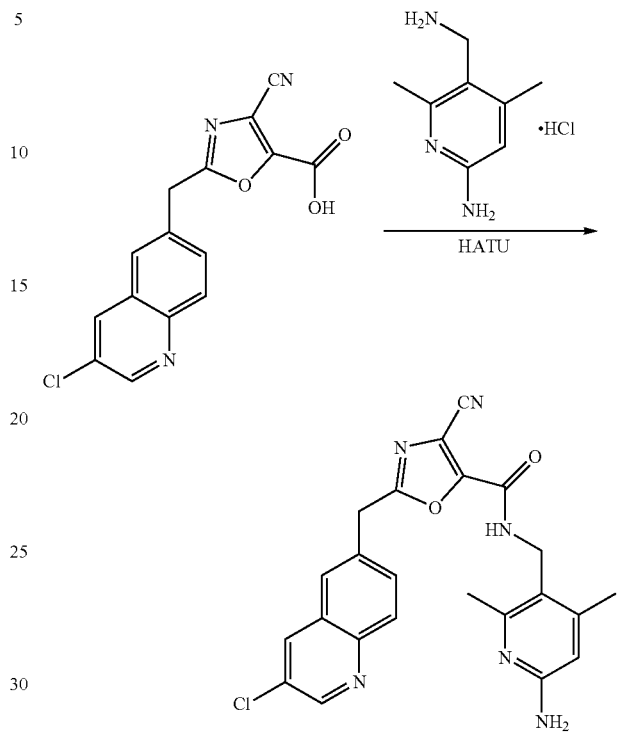

A mixture of 2-(3-chloro-quinolin-6-ylmethyl)-4-cyano-oxazole-5-carboxylic acid (100 mg, 0.29 mmol, 1.0 eq), 5-aminomethyl-4,6-dimethyl-pyridin-2-ylamine hydrochloride (80 mg, 0.43 mmol, 1.5 eq), HATU (163 mg, 0.43 mmol, 1.5 eq) and Et3N (87 mg, 0.86 mmol, 3.0 eq) in DMF (2 mL) was stirred at rt overnight. The mixture was concentrated and the resulting residue was purified by prep-HPLC to afford N-((6-amino-2,4-dimethylpyridin-3-yl)methyl)-2-((3-chloroquinolin-6-yl)methyl)-4-cyanooxazole-5-carboxamide (30 mg, 15%) as a white solid. LRMS (M+H+) m/z calculated 447.1, found 447.0. 1H NMR (DMSO-d6, 400 MHz): δ 9.03 (t, 1 H), 8.88 (d, 1H), 8.54 (d, 1H), 8.03 (d, 1H), 7.89 (s, 1H), 7.77 (dd, 1H), 6.11 (s, 1H), 5.70 (s, 2H), 4.48 (s, 2H), 4.33 (d, 2H), 2.29 (s, 3H), 2.17 (s, 3H).

Example 88: Preparation of N-((6-amino-2-methylpyridin-3-yl)methyl)-2-((3-chloroquinolin-6-yl)methyl)-4-cyanooxazole-5-carboxamide

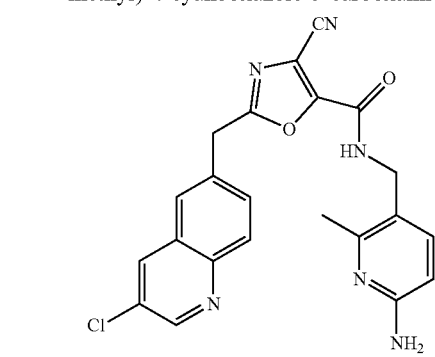

N-((6-amino-2-methylpyridin-3-yl)methyl)-2-((3-chloroquinolin-6-yl)methyl)-4-cyanooxazole-5-carboxamide -continued

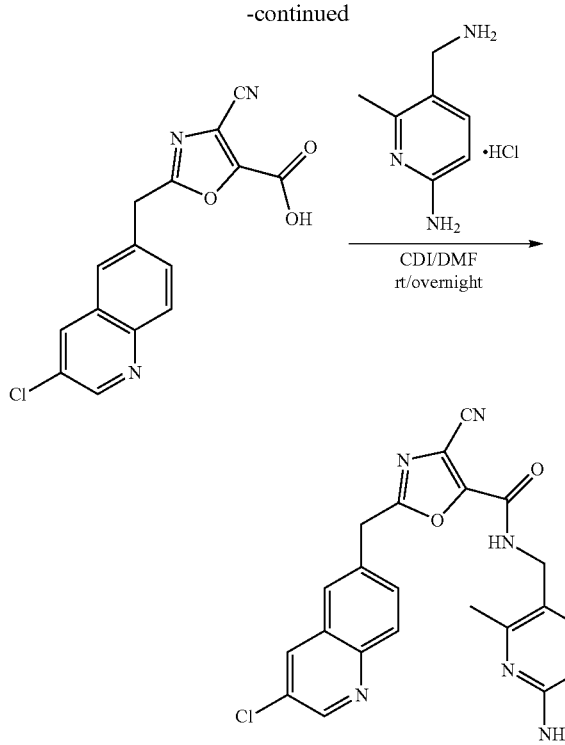

To a suspension of 2-(3-chloro-quinolin-6-ylmethyl)-4-cyano-oxazole-5-carboxylic acid (100 mg, 0.319 mmol, 1.0 eq) in 10 mL of dry DMF was added CDI (67 mg, 0.42 mmol, 1.3 eq) at rt. Then the mixture was stirred at 50° C. for 2 h until the reaction was complete. After cooling to 5° C., 5-aminomethyl-6-methyl-pyridin-2-ylamine hydrochloride (66 mg, 0.38 mmol, 1.2 eq) was added to the mixture. The resulting mixture was stirred at rt overnight and concentrated. The resulting residue was purified by chromatography on a silica gel column (DCM/MeOH=20/1 to 10/1, v/v) to give 130 mg of crude product, which was further purified by pre-HPLC to give N-((6-amino-2-methylpyridin-3-yl)methyl)-2-((3-chloroquinolin-6-yl)methyl)-4-cyanooxazole-5-carboxamide (39 mg, 28%) as a white solid. LRMS (M+H+) m/z calculated 433.1, found 432.9. 1H NMR (DMSO-d6, 300 MHz): δ 9.32 (t, 1H), 8.88 (d, 1H), 8.55 (s, 1H), 8.05 (d, 1H), 7.90 (s, 1H), 7.77 (d, 1H), 7.27 (d, 1H), 6.21 (d, 1H), 5.76 (s, 2H), 4.50 (s, 2H), 4.26 (d, 2H), 2.28 (s, 3H).

Example 89: Preparation of N-((6-amino-2,4-dimethylpyridin-3-yl)methyl)-2-((3-chloroquinolin-6-yl)methyl)oxazole-5-carboxamide

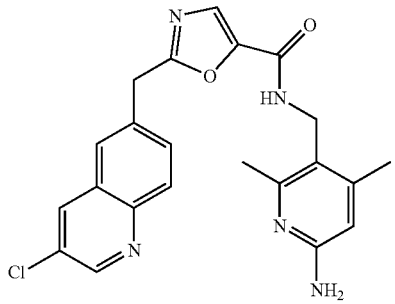

N-((6-amino-2,4-dimethylpyridin-3-yl)methyl)-2-((3-chloroquinolin-6-yl)methyl)oxazole-5-carboxamide -continued

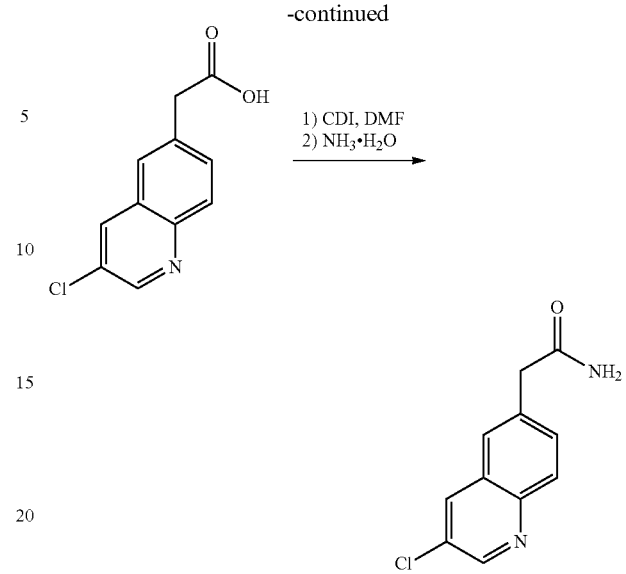

To a solution of (3-chloro-quinolin-6-yl)-acetic acid (4.0 g, 18.1 mmol, 1 eq) in DMF (70 mL) was added CDI (3.5 g, 21.7 mmol, 1.2 eq) at rt. The mixture was stirred at rt for 1.5 h and then to this mixture was added NH3/H2O (10 mL). The resulting mixture was stirred at rt for 0.5 h and concentrated under reduced pressure. To the resulting residue was added 100 mL of H2O and the mixture was stirred at rt overnight. The resulting precipitate was collected by filtration and washed with water and acetone subsequently to give 2-(3-chloro-quinolin-6-yl)-acetamide (3.2 g, 80%).

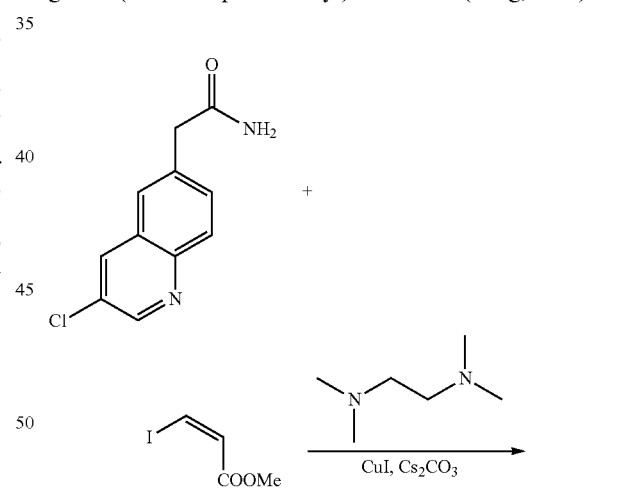

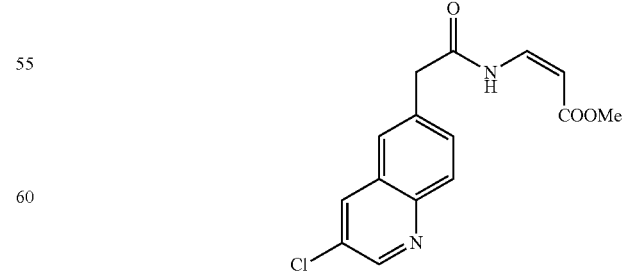

A mixture of 2-(3-chloro-quinolin-6-yl)-acetamide (3.5 g, 15.9 mmol, 1 eq), 3-iodo-acrylic acid methyl ester (4.0 g, 19.1 mmol, 1.2 eq), N,N,N',N'-tetramethyl-ethane-1,2-diamine (280 mg, 3.18 mmol, 0.2 eq), CuI (302 mg, 1.59 mmol, 0.1 eq) and Cs2CO3 (10.4 g, 31.8 mmol, 2 eq) in dry THF (160 mL) was stirred at 70° C. for 6 h under N2. Then the mixture was filtered though a pad of Celite. The filtrate was concentrated and the resulting residue was purified by chromatography on a silica gel column (EA/PE=1/8, v/v) to give 3-[2-(3-chloro-quinolin-6-yl)-acetylamino]-acrylic acid methyl ester (1.2 g, 25%).

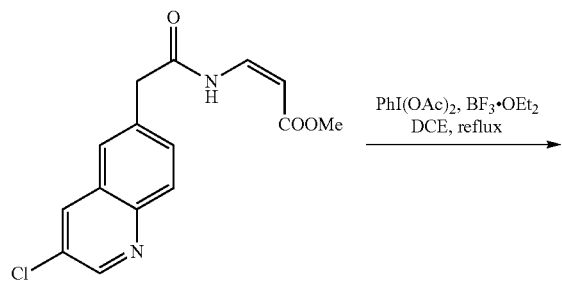

To a solution of 3-[2-(3-chloro-quinolin-6-yl)-acetylamino]-acrylic acid methyl ester (540 mg, 1.78 mmol, 1 eq) in dry DCE (10 mL) was added BF3.OEt2 (0.45 mL, 3.56 mmol, 2 eq). The mixture was heated to reflux, and then iodobenzene diacetate (744 mg, 2.31 mmol, 1.3 eq) was added in one portion rapidly. After stirring under reflux for 40 min, the mixture was cooled to rt, quenched with saturated NaHCO₃ aqueous solution and then extracted with DCM. The combined organic layer were washed with brine, dried and concentrated. The residue was purified by chromatography on a silica column (EA/PE=1/8, v/v) to give 2-(3-chloro-quinolin-6-ylmethyl)-oxazole-5-carboxylic acid methyl ester (223 mg, 42%).

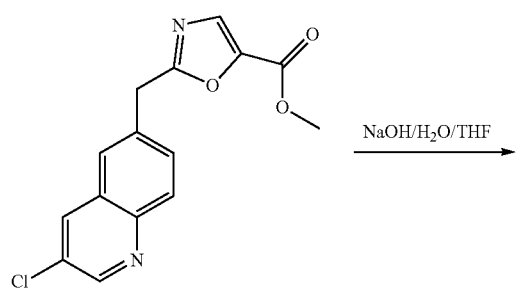

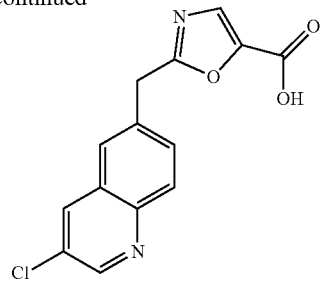

To a solution of 2-(3-chloro-quinolin-6-ylmethyl)-oxazole-5-carboxylic acid methyl ester (335 mg, 1.11 mmol, 1 eq) in THF/H2O (v/v=1/1, 30 mL) was added NaOH (67 mg, 1.66 mmol, 1.5 eq) at rt. The mixture was stirred at rt for 1 h. The volatile was evaporated and the aqueous layer was acidified to pH 3 with 1 N HCl. The resulting precipitate was collected by filtration and dried to give 2-(3-chloro-quinolin-6-ylmethyl)-oxazole-5-carboxylic acid (258 mg, 81%) as a white solid.

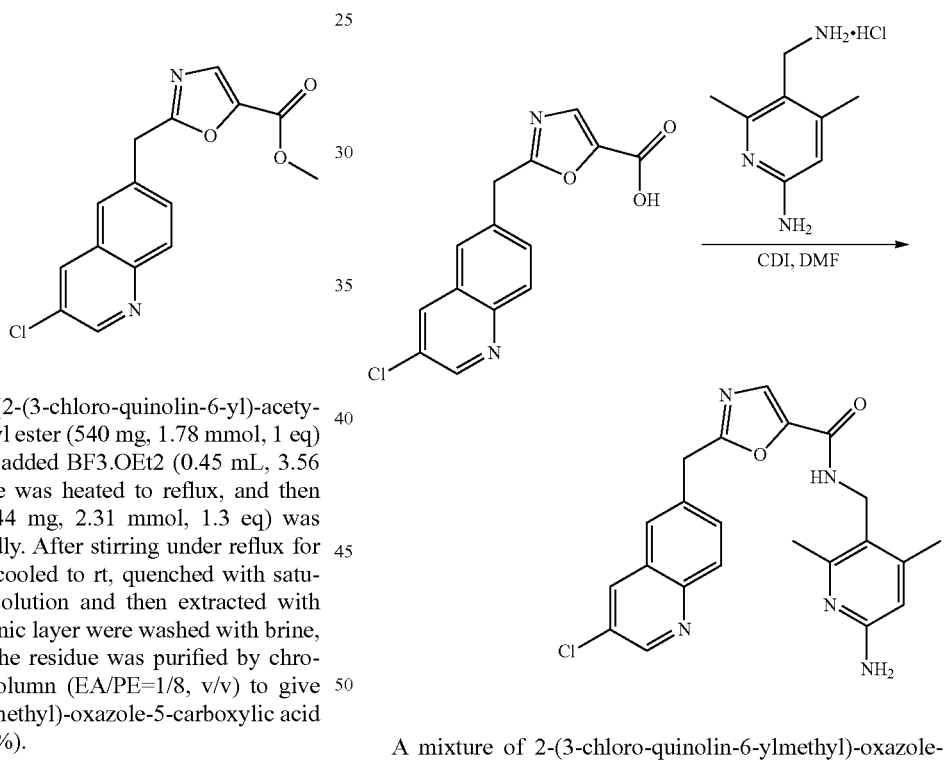

A mixture of 2-(3-chloro-quinolin-6-ylmethyl)-oxazole-5-carboxylic acid (45 mg, 0.156 mmol, 1 eq) and CDI (28 mg, 0.172 mmol, 1.1 eq) in DMF (3 mL) was stirred at rt for 1 h and then to the mixture was added 5-aminomethyl-4,6-dimethyl-pyridin-2-ylamine hydrochloride (32 mg, 0.172 mmol, 1.1 eq). The resulting reaction mixture was stirred at rt for 1 h. The mixture was concentrated and the resulting residue was diluted with water and extracted with DCM. The combined organic layers were dried and concentrated. The residue was purified by chromatography on a silica gel column (DCM/MeOH=20/1, v/v) to give N-((6-amino-2,4-dimethylpyridin-3-yl)methyl)-2-((3-chloroquinolin-6-yl)methyl)oxazole-5-carboxamide (32 mg, 48%) as a white solid. LRMS (M+H+) m/z calculated 422.1, found 422.0. 1H NMR (DMSO-d6, 400 MHz): δ 8.87 (s, 1H), 8.56 (s, 1H), 8.43 (t, 1H), 8.03 (d, 1H), 7.88 (s, 1H), 7.74 (d, 1H), 7.73 (s, 1H), 6.12 (s, 1H), 5.68 (s, 2H), 4.42 (s, 2H), 4.29 (d, 2H), 2.28 (s, 3H), 2.15 (s, 3H).

Example 90: Preparation of N-((6-amino-2-methyl-pyridin-3-yl)methyl)-2-((3-chloroquinolin-6-yl)methyl)oxazole-5-carboxamide

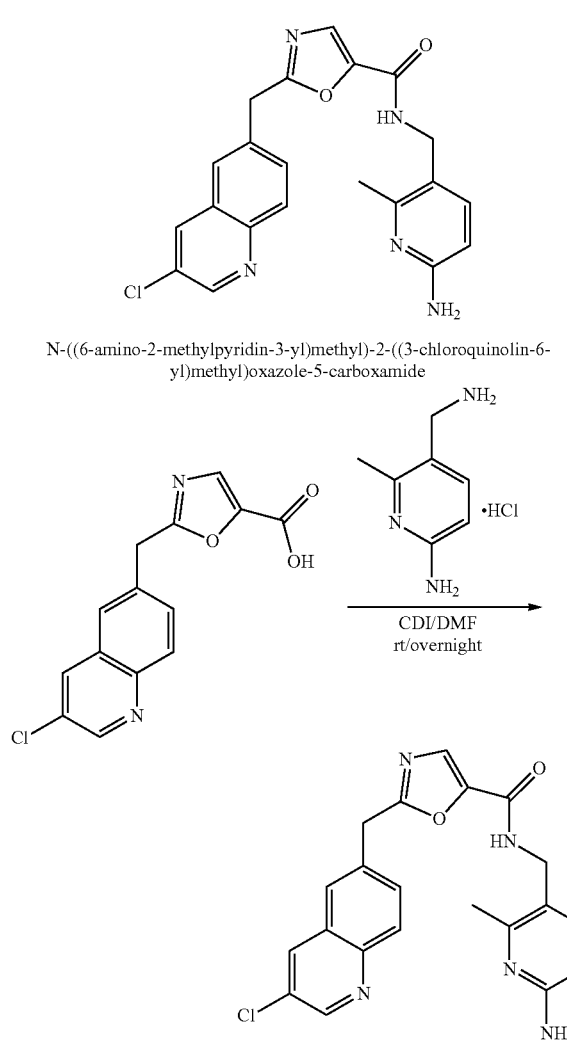

A mixture of 2-(3-chloro-quinolin-6-ylmethyl)-oxazole-5-carboxylic acid (100 mg, 0.346 mmol, 1.0 eq) and CDI (73 mg, 0.45 mmol, 1.3 eq) in DMF (10 mL) was stirred at rt for 1 h and then to the mixture was added 5-aminomethyl-4,6-dimethyl-pyridin-2-ylamine hydrochloride (73 mg, 0.42 mmol, 1.2 eq). The resulting reaction mixture was stirred at rt for 1 h. The mixture was concentrated and the resulting residue was diluted with water and extracted with DCM. The combined organic layers were dried and concentrated. The residue was purified by chromatography on a silica gel column (DCM/MeOH=20/1, v/v) to give 150 mg of crude product, which was further purified by pre-HPLC to give N-((6-amino-2-methylpyridin-3-yl)methyl)-2-((3-chloro-quinolin-6-yl)methyl)oxazole-5-carboxamide (61 mg, 43%). LRMS (M+H+) m/z calculated 408.1, found 407.9. 1H NMR (DMSO-d6, 300 MHz): δ 8.87 (s, 1H), 8.78 (t, 1H), 8.56 (s, 1H), 8.03 (d, 1H), 7.88 (s, 1H), 7.76 (d, 1H), 7.72 (s, 1H), 7.20 (d, 1H), 6.22 (d, 2H), 5.74 (s, 2H), 4.44 (s, 2H), 4.23 (d, 2H), 2.27 (s, 3H).

Example 91: Preparation of N-((6-amino-2,4-dimethylpyridin-3-yl)methyl)-1-((3-chloroquinolin-6-yl)methyl)-3-(difluoromethyl)-1H-pyrazole-4-carboxamide

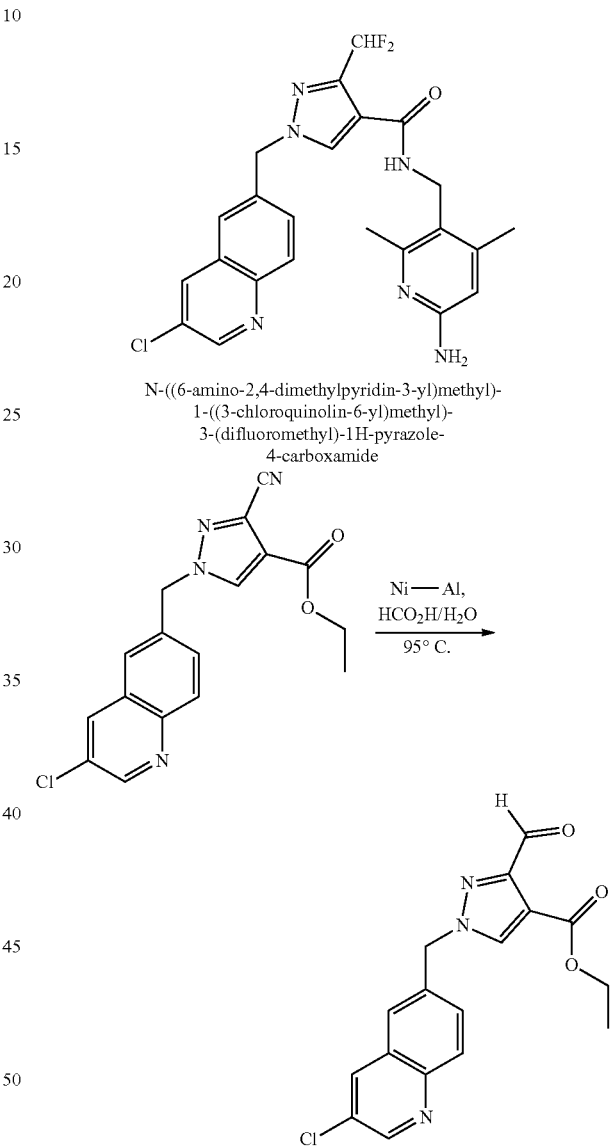

To a mixture of 1-(3-chloro-quinolin-6-ylmethyl)-3-cyano-1H-pyrazole-4-carboxylic acid ethyl ester (2.0 g, 5.88 mmol) was added Ni—Al alloy (2 g) at rt. The mixture was stirred at 95° C. for 4 h under N2. Then 2 g of Ni—Al alloy was added and the mixture was stirred at 95° C. for another 2 h. The mixture was filtered through a bed of celite and the filtrate was concentrated. The resulting residue was diluted with DCM and washed with aqueous NaHCO3 solution. The organic layer was concentrated and the resulting residue was purified by chromatography on a silica gel column (EA/PE=1/3, v/v) to give 1-(3-chloro-quinolin-6-ylmethyl)-3-formyl-1H-pyrazole-4-carboxylic acid ethyl ester (440 mg, 22%) as a white solid.

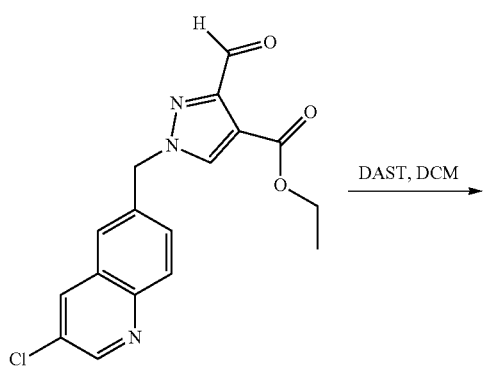

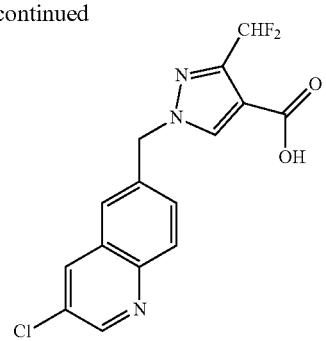

To a stirred mixture of 1-(3-chloro-quinolin-6-ylmethyl)-3-difluoromethyl-1H-pyrazole-4-carboxylic acid ethyl ester (65 mg, 0.178 mmol, 1 eq) in H2O/THF (10 mL, v/v=1/1) was added NaOH (14 mg, 0.356 mmol, 2 eq) at rt. Then the mixture was stirred at 50° C. for 2 h. THF was removed by evaporation, and the aqueous layer was acidified to pH 2 with 1 N HCl. Then a white precipitate formed, which was collected by filtration and dried at 120° C. for 1 h to give 1-(3-chloro-quinolin-6-ylmethyl)-3-difluoromethyl-1H-pyrazole-4-carboxylic acid (53 mg, 88%) as a white solid.

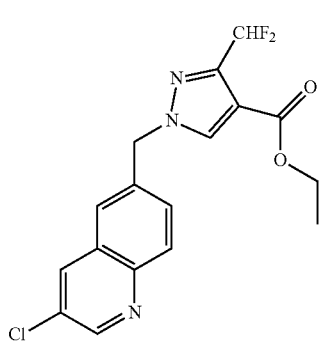

To a suspension of 1-(3-chloro-quinolin-6-ylmethyl)-3-formyl-1H-pyrazole-4-carboxylic acid ethyl ester (130 mg, 0.38 mmol, 1 eq) in dry DCM (0.76 mL) was added DAST (0.86 mL, 0.64 mmol, 1.7 eq) at −20° C. The mixture was stirred at rt overnight. The mixture was quenched with saturated aqueous NaHCO₃ solution and extracted with DCM. The combined organic layers were dried and concentrated. The resulting residue was purified by chromatography on a silica gel column (EA/PE=1/5, v/v) to give 1-(3-chloro-quinolin-6-ylmethyl)-3-difluoromethyl-1H-pyrazole-4-carboxylic acid ethyl ester (70 mg, 50%) as a white solid.

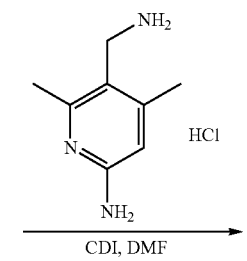

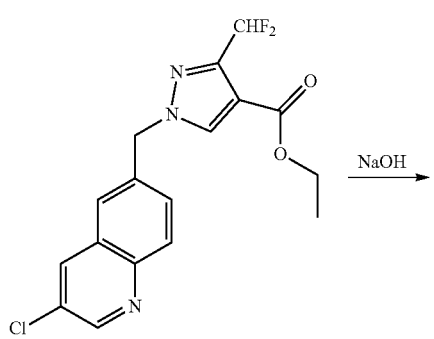

To a mixture of 1-(3-chloro-quinolin-6-ylmethyl)-3-difluoromethyl-1H-pyrazole-4-carboxylic acid (53 mg, 0.157 mmol, 1 eq) in DMF (5 mL) was added CDI (28 mL, 0.173 mmol, 1.1 eq). The mixture was stirred at 50° C. for 2 h. Then 5-(aminomethyl)-4-methylpyridin-2-amine hydrochloride (32 mg, 0.173 mmol, 1.1 eq) was added. The resulting mixture was stirred at 50° C. overnight. Most of the solvent was removed by evaporation and the resulting residue was diluted with 1 NaOH (10 mL). The resulting mixture was stirred at rt for 1 h. The formed precipitate was collected by filtration and dried to give N-(((6-amino-2,4- dimethylpyridin-3-yl)methyl)-1-((3-chloroquinolin-6-yl) methyl)-3-(difluoromethyl)-1H-pyrazole-4-carboxamide (25 mg, 34%) as a white solid. LRMS (M+H+) m/z calculated 471.1, found 471.2. 1H NMR (DMSO-d6, 400 MHz): δ 8.89 (d, 1H), 8.60 (d, 1H), 8.45 (s, 1H), 8.10 (t, 1H), 8.06 (d, 1H), 7.87 (s, 1H), 7.67 (d, 1H), 7.37 (t, 1H), 6.11 (s, 2H), 5.65 (s, 2H), 5.62 (s, 2H), 4.27 (d, 2H), 2.28 (s, 3H), 2.14 (s, 3H).

Example 92: Preparation of N-((6-amino-2,4-dimethylpyridin-3-yl)methyl)-1-((3-chloroquinolin-6-yl) methyl)-3-(hydroxymethyl)-1H-pyrazole-4-carboxamide

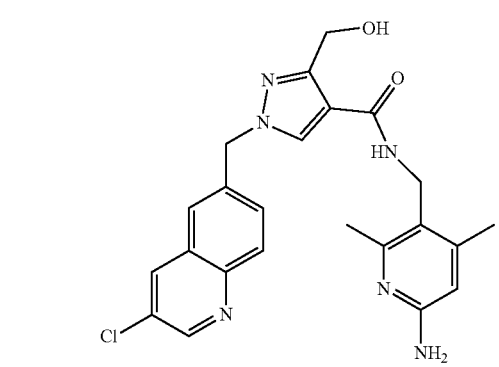

N-((6-amino-2,4-dimethylpyridin-3-yl)methyl)-
1-((3-chloroquinolin-6-yl)methyl)-
3-(hydroxymethyl)-1H-pyrazole-
4-carboxamide

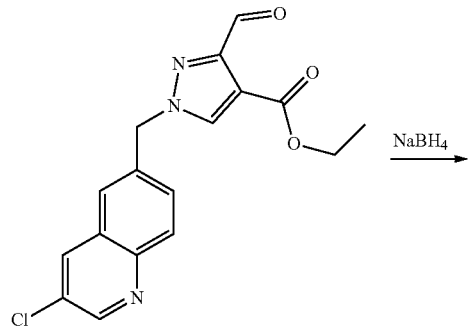

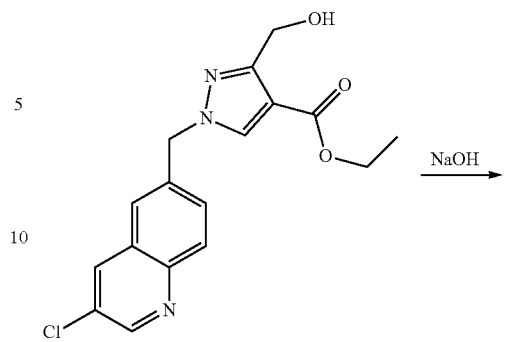

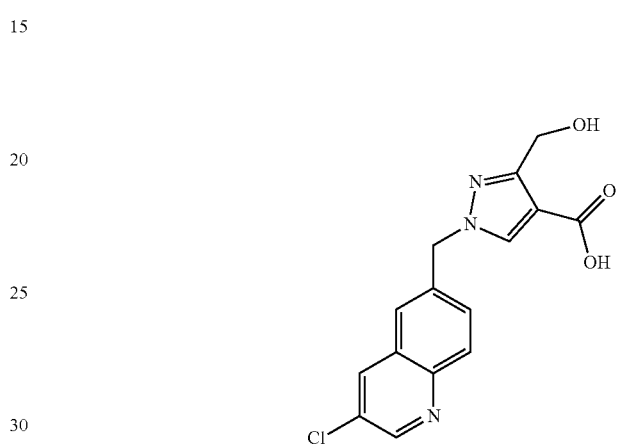

To a solution of 1-(3-chloro-quinolin-6-ylmethyl)-3-hydroxymethyl-1H-pyrazole-4-carboxylic acid ethyl ester (50 mg, 0.14 mmol, 1.0 eq) in THF (2 mL) was added a solution of NaOH (11 mg, 0.29 mmol, 2.0 eq) in H2O (2 mL) at rt. The mixture was stirred at 60° C. for 4 h. The mixture was cooled to rt and neutralized with 1 N HCl to pH 2. The mixture was concentrated and the resulting residue was used to next step directly (60 mg crude).

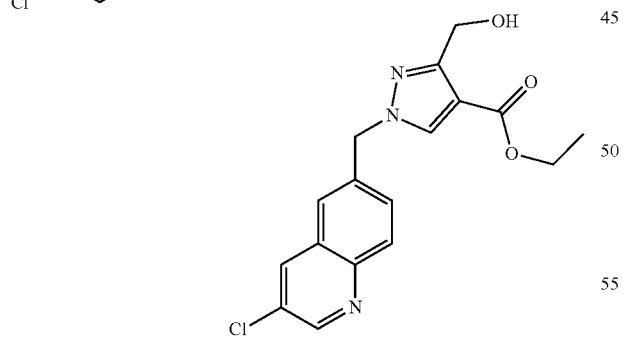

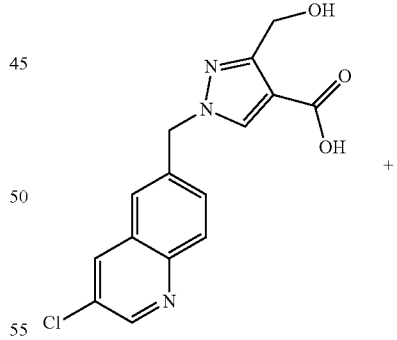

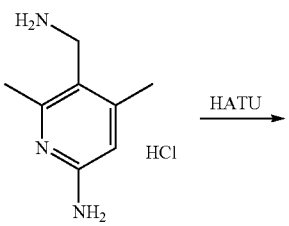

To a solution of 1-(3-chloro-quinolin-6-ylmethyl)-3-formyl-1H-pyrazole-4-carboxylic acid ethyl ester (50 mg, 0.14 mmol, 1.0 eq) in MeOH (10 mL) was added NaBH4 (6.0 mg, 0.14 mmol, 1.0 eq) at 0° C. The mixture was stirred at 0° C. for 30 min. Then DCM (50 mL) and water (30 mL) was added. The organic layer was dried over Na2SO4, filtered and concentrated to afford 1-(3-chloro-quinolin-6-ylmethyl)-3-hydroxymethyl-1H-pyrazole-4-carboxylic acid ethyl ester (50 mg, 98%) as a white solid.

353
-continued

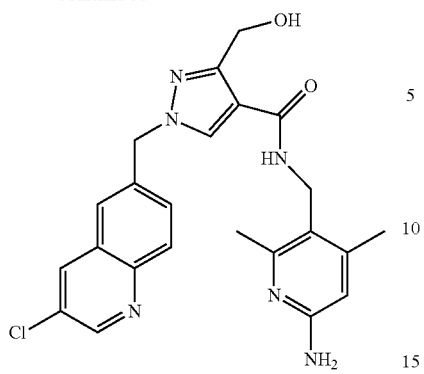

A mixture of 1-(3-chloro-quinolin-6-ylmethyl)-3-hydroxymethyl-1H-pyrazole-4-carboxylic acid (60 mg crude, 0.14 mmol, 1.0 eq), 5-aminomethyl-4,6-dimethyl-pyridin-2-ylamine hydrochloride (39 mg, 0.21 mmol, 1.5 eq), HATU (80 mg, 0.21 mmol, 1.5 eq) and Et3N (42 mg, 0.42 mmol, 3.0 eq) in DMF (3 mL) was stirred at rt overnight. The mixture was concentrated and the resulting residue was purified by prep-HPLC to afford N-((6-amino-2,4-dimethylpyridin-3-yl)methyl)-1-((3-chloroquinolin-6-yl)methyl)-3-(hydroxymethyl)-1H-pyrazole-4-carboxamide (46 mg, 73%) as a white solid. LRMS (M+H+) m/z calculated 451.2, found 451.0. 1H NMR (DMSO-d6, 400 MHz): δ 8.88 (d, 1H), 8.58 (d, 1H), 8.36 (s, 1H), 8.32 (t, 1H), 8.03 (d, 1H), 7.67 (dd, 1H), 6.10 (s, 1H), 5.85 (t, 1H), 5.64 (s, 2H), 5.49 (s, 2H), 4.49 (d, 2H), 4.29 (d, 2H), 2.29 (s, 3H), 2.16 (s, 3H).

Example 93: Preparation of N-((6-amino-2,4-dimethylpyridin-3-yl)methyl)-1-((3-chloroquinolin-6-yl)methyl)-3-(fluoromethyl)-1H-pyrazole-4-carboxamide

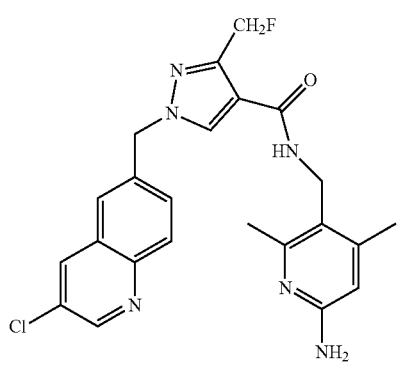

N-((6-amino-2,4-dimethylpyridin-3-yl)methyl)-1-((3-chloroquinolin-6-yl)methyl)-3-(fluoromethyl)-1H-pyrazole-4-carboxamide 354
-continued

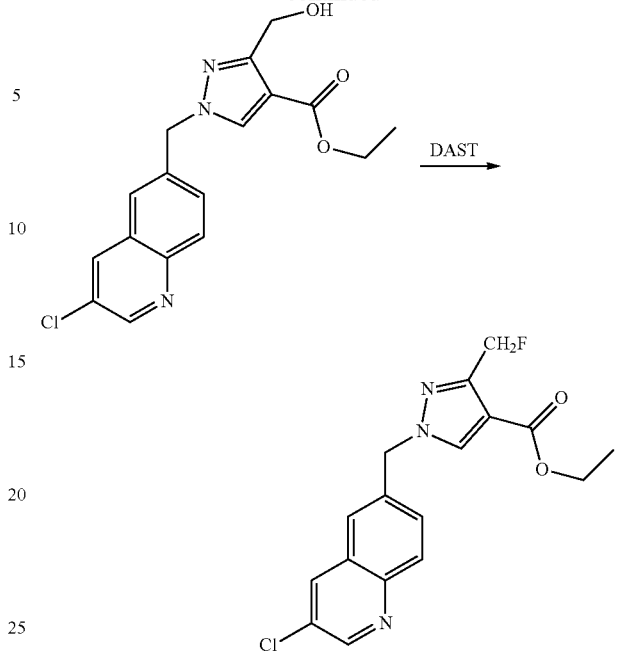

To a solution of 1-(3-chloro-quinolin-6-ylmethyl)-3-hydroxymethyl-1H-pyrazole-4-carboxylic acid ethyl ester (170 mg, 0.49 mmol, 1.0 eq) in DCM (20 mL) was added DAST (79 mg, 0.49 mmol, 1.0 eq) at 0° C. The mixture was stirred at 0° C. for 30 min. The mixture was concentrated and the resulting residue was purified by column chromatography on a silica gel column (PE/EA=3/1, v/v) to afford 1-(3-Chloro-quinolin-6-ylmethyl)-3-fluoromethyl-1H-pyrazole-4-carboxylic acid ethyl ester (150 mg, 78%) as a white solid.

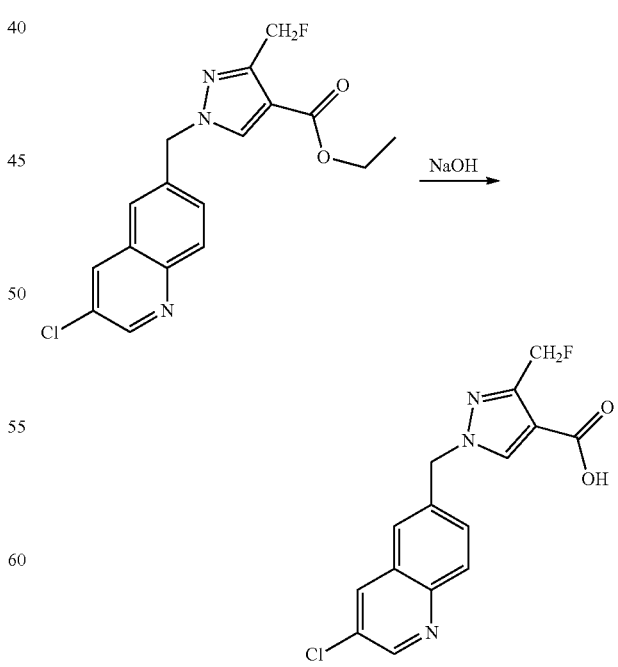

To a solution of 1-(3-chloro-quinolin-6-ylmethyl)-3-fluoromethyl-1H-pyrazole-4-carboxylic acid ethyl ester (70 mg, 0.20 mmol, 1.0 eq) in THF (5 mL) was added a solution of NaOH (8 mg, 0.40 mmol, 2.0 eq) in H2O (5 mL) at rt. The mixture was stirred at 60° C. for 6 h. The mixture was cooled to rt and neutralized with 1N HCl to pH 2. The mixture was concentrated and the resulting residue was used to next step directly (80 mg crude).

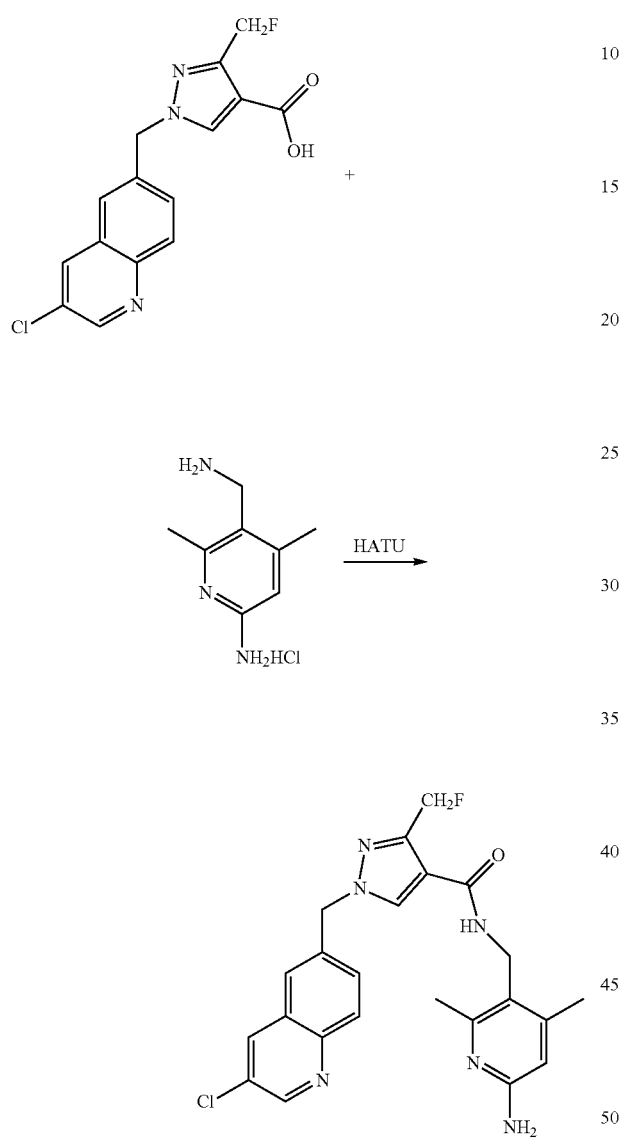

A mixture of 1-(3-chloro-quinolin-6-ylmethyl)-3-fluoromethyl-1H-pyrazole-4-carboxylic acid (80 mg crude, 0.20 mmol, 1.0 eq), 5-aminomethyl-4,6-dimethyl-pyridin-2-ylamine hydrochloride (56 mg, 0.30 mmol, 1.5 eq), HATU (114 mg, 0.30 mmol, 1.5 eq) and Et3N (61 mg, 0.60 mmol, 3.0 eq) in DMF (2 mL) was stirred at rt for 1 h. The mixture was concentrated and the resulting residue was purified by prep-HPLC to afford N-((6-amino-2,4-dimethylpyridin-3-yl)methyl)-1-((3-chloroquinolin-6-yl)methyl)-3-(fluoromethyl)-1H-pyrazole-4-carboxamide (21 mg, 23%) as a white solid. LRMS (M+H+) m/z calculated 453.1, found 452.9. 1H NMR (DMSO-d6, 400 MHz): δ 8.89 (d, 1H), 8.60 (d, 1H), 8.38 (s, 1H), 8.05 (d, 1H), 7.96 (t, 1H), 7.66 (dd, 1H), 6.12 (s, 1H), 5.70 (s, 2H), 5.57 (s, 2H), 5.56 (d, 2H), 4.25 (d, 2H), 2.29 (s, 3H), 2.15 (s, 3H).

Example 94: Preparation of N-((6-amino-2,4-dimethylpyridin-3-yl)methyl)-1-((3-chloroquinolin-6-yl)methyl)-3-(1-hydroxyethyl)-1H-pyrazole-4-carboxamide

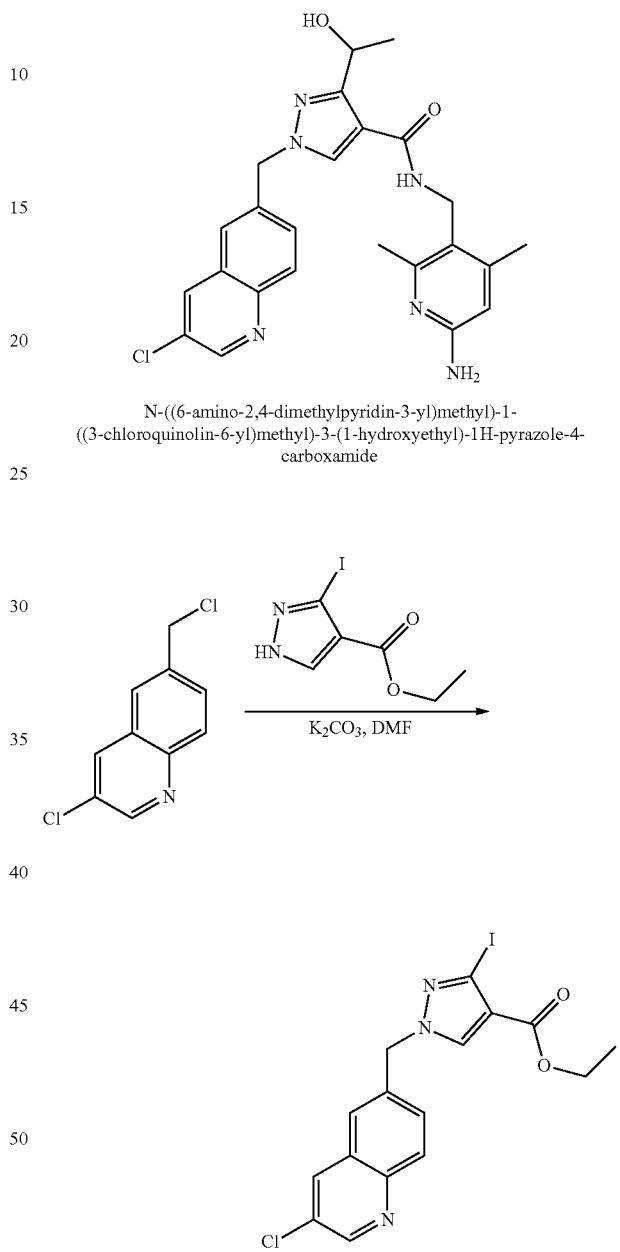

N-((6-amino-2,4-dimethylpyridin-3-yl)methyl)-1-((3-chloroquinolin-6-yl)methyl)-3-(1-hydroxyethyl)-1H-pyrazole-4-carboxamide A mixture of 3-chloro-6-chloromethyl-quinoline (3.0 g, 14.2 mmol, 1 eq) and 3-iodo-1H-pyrazole-4-carboxylic acid ethyl ester (4.2 g, 15.6 mmol, 1.1 eq) and K2CO3 (3.9 g, 28.4 mmol, 2 eq) in DMF (150 mL) was stirred at rt for 3 h. The mixture was then concentrated and the resulting residue was purified by chromatography on a silica gel column (EA/PE=1/4, v/v) to give 1-(3-chloro-quinolin-6-ylmethyl)-3-iodo-1H-pyrazole-4-carboxylic acid ethyl ester (4.1 g, 65%) as an off white solid.

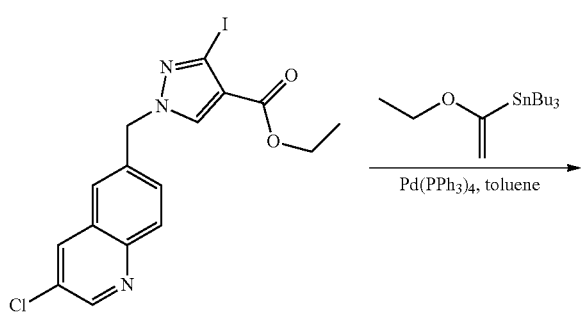

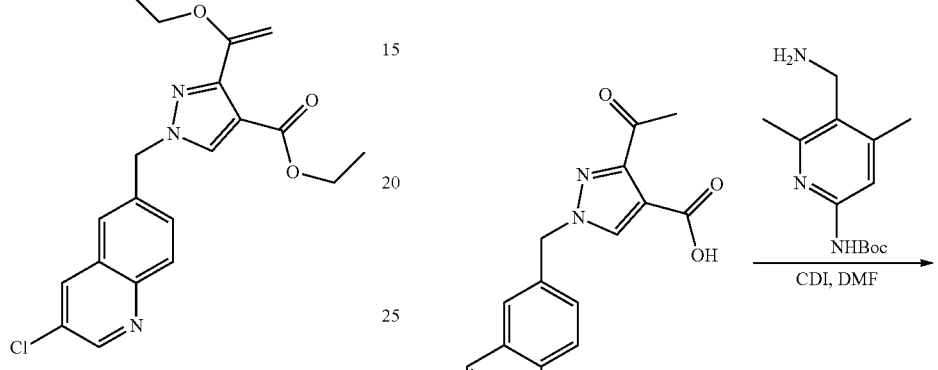

A mixture of 1-(3-chloro-quinolin-6-ylmethyl)-3-iodo-1H-pyrazole-4-carboxylic acid ethyl ester (2.0 g, 4.5 mmol, 1 eq) and tributyl(1-ethoxyvinyl)stannane (1.95 g, 5.4 mmol, 1.2 eq) and Pd(PPh3)4 (416 mg, 0.36 mmol, 0.08 eq) in dry toluene (50 mL) was stirred at 100° C. for 20 h under N2. The mixture was concentrated and the resulting residue was purified by chromatography on a silica gel column (EA/PE=1/4, v/v) to give ethyl 1-((3-chloroquinolin-6-yl)methyl)-3-(1-ethoxyvinyl)-1H-pyrazole-4-carboxylate (1.4 g, 80%) as a yellow oil.

To a stirred mixture of 1-((3-chloroquinolin-6-yl)methyl)-3-(1-ethoxyvinyl)-1H-pyrazole-4-carboxylate (1.4 g, 3.6 mmol, 1 eq) in MeOH/H2O (30 mL, v/v=1/1) was added NaOH (290 mg, 7.3 mmol, 2 eq) at rt. Then the mixture was stirred at 60° C. for 1.5 h. After evaporation to remove MeOH, the aqueous layer was diluted with 5 mL of THF and acidified to pH 1 with 2 N HCl. The resulting mixture was stirred at 50° C. for 1 h. The mixture was evaporation THF and basified to pH 5 with NaHCO3. A white precipitate formed, which was collected by filtration and dried at 110° C. for 1 h to give 3-acetyl-1-((3-chloroquinolin-6-yl)methyl)-1H-pyrazole-4-carboxylic acid (940 mg, 78%).

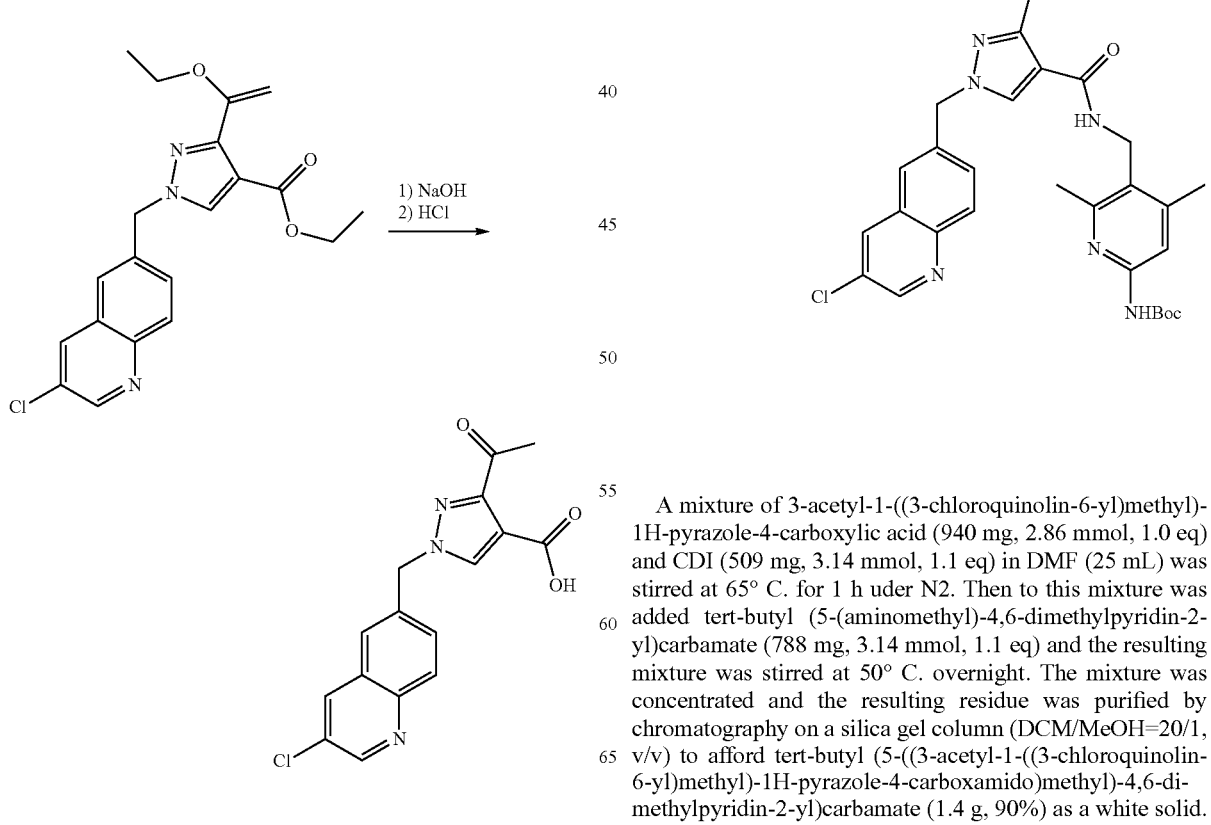

A mixture of 3-acetyl-1-((3-chloroquinolin-6-yl)methyl)-1H-pyrazole-4-carboxylic acid (940 mg, 2.86 mmol, 1.0 eq) and CDI (509 mg, 3.14 mmol, 1.1 eq) in DMF (25 mL) was stirred at 65° C. for 1 h uder N2. Then to this mixture was added tert-butyl (5-(aminomethyl)-4,6-dimethylpyridin-2-yl)carbamate (788 mg, 3.14 mmol, 1.1 eq) and the resulting mixture was stirred at 50° C. overnight. The mixture was concentrated and the resulting residue was purified by chromatography on a silica gel column (DCM/MeOH=20/1, v/v) to afford tert-butyl (5-((3-acetyl-1-((3-chloroquinolin-6-yl)methyl)-1H-pyrazole-4-carboxamido)methyl)-4,6-dimethylpyridin-2-yl)carbamate (1.4 g, 90%) as a white solid.

359

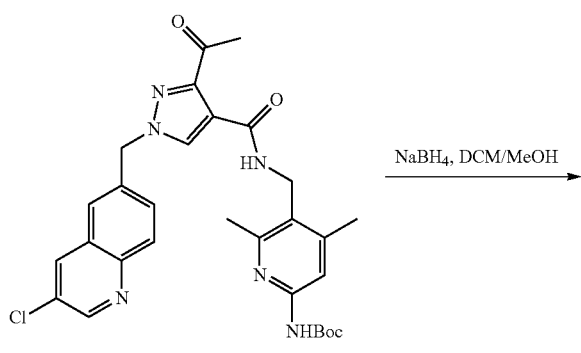

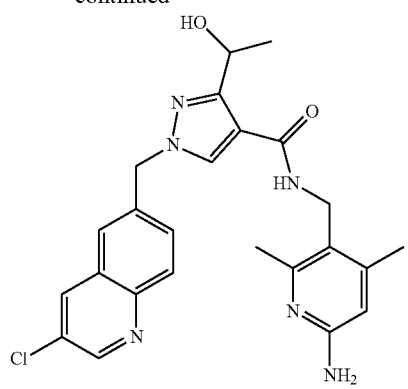

To a solution of tert-butyl (5-((3-acetyl-1-((3-chloroquinolin-6-yl)methyl)-1H-pyrazole-4-carboxamido)methyl)-4,6-dimethylpyridin-2-yl)carbamate (200 mg, 0.356 mmol, 1 eq) in DCM/MeOH (20 mL, v/v=1/1) was added NaBH4 (27 mg, 0.712 mmol, 2 eq) ar rt. The mixture was stirred for 0.5 h and then quenched with NH4Cl aqueous solution. The mixture was extracted with DCM and the combined organic layers were dried and concentrated to give tert-butyl (5-((1-((3-chloroquinolin-6-yl)methyl)-3-(1-hydroxyethyl)-1H-pyrazole-4-carboxamido)methyl)-4,6-dimethylpyridin-2-yl)carbamate (180 mg, 90%) as a yellow solid.

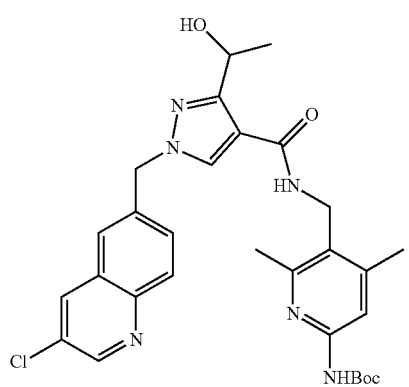

360

-continued

To a solution of tert-butyl (5-((1-((3-chloroquinolin-6-yl)methyl)-3-(1-hydroxyethyl)-1H-pyrazole-4-carboxamido)methyl)-4,6-dimethylpyridin-2-yl)carbamate (180 mg, 0.32 mmol, 1 eq) in DCM (5 mL) was added TFA (5 mL) ar rt. The mixture was stirred at rt for 1 h and then concentrated. The resulting residue was diluted with DCM and washed with NaOH aqueous solution. Then the organic layer was dried and concentrated. The resulting residue was triturated in EA/PE (20 mL, v/v=1/4) to give N-((6-amino-2,4-dimethylpyridin-3-yl)methyl)-1-((3-chloroquinolin-6-yl)methyl)-3-(1-hydroxyethyl)-1H-pyrazole-4-carboxamide (110 mg, 74%) as a white solid. LRMS (M+H+) m/z calculated 465.2, found 465.0. 1H NMR (DMSO-d6, 400 MHz): δ 8.88 (d, 1H), 8.58 (d, 1H), 8.55 (t, 1H), 8.35 (s, 1H), 8.04 (d, 1H), 7.83 (d, 1H), 7.66 (dd, 1H), 6.31 (d, 1H), 6.11 (s, 1H), 5.64 (s, 2H), 5.53 (s, 2H), 4.84-4.78 (m, 1H), 4.30 (d, 2H), 2.32 (s, 3H), 2.17 (s, 3H), 1.36 (d, 3H).

Example 95: Preparation of N-((6-amino-2,4-dimethylpyridin-3-yl)methyl)-2-((3-chloroquinolin-6-yl)methyl)-5-cyano-2H-1,2,3-triazole-4-carboxamide

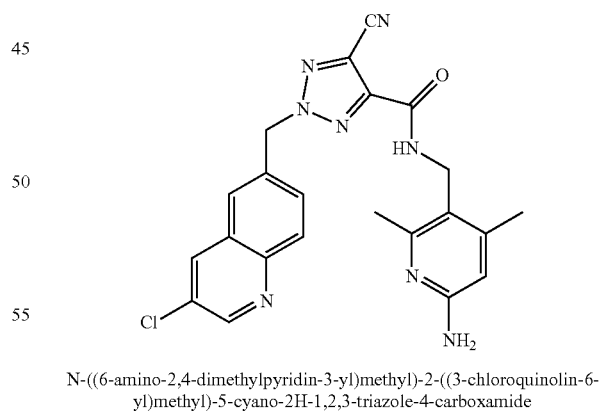

N-((6-amino-2,4-dimethylpyridin-3-yl)methyl)-2-((3-chloroquinolin-6-yl)methyl)-5-cyano-2H-1,2,3-triazole-4-carboxamide

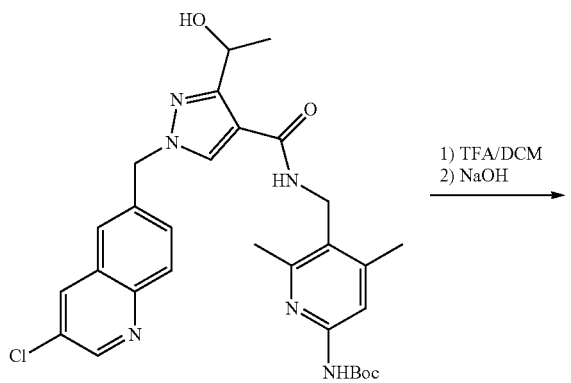

1) TFA/DCM
2) NaOH

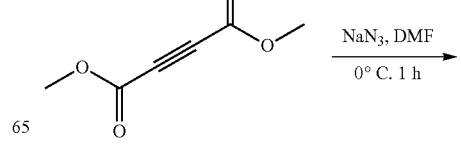

NaN3, DMF
0° C. 1 h

-continued

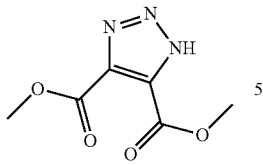

To a stirred suspension of NaN3 (2.503 g, 0.038 mmol, 1.1 eq) in DMF (60.0 mL) was added a solution of dimethyl but-2-ynedioate (5.0 g, 0.035 mmol, 1.0 eq) in DMF (50.0 mL) dropwise at 0° C. over 30.0 min. After 30.0 min the solvent was removed in vacuo to provide a light purple-brown solid. The solid was washed twice with ether and taken up in H2O (100.0 mL). The aqueous solution was acidified with con. HCl to pH2.0. The aqueous layer was first extracted with ether (50.0 mL) then with CHCl3 (20.0 mL×3). The combined organic layers were concentrated to provide dimethyl 1H-1,2,3-triazole-4,5-dicarboxylate as a light red solid (5.53 g, 85%).

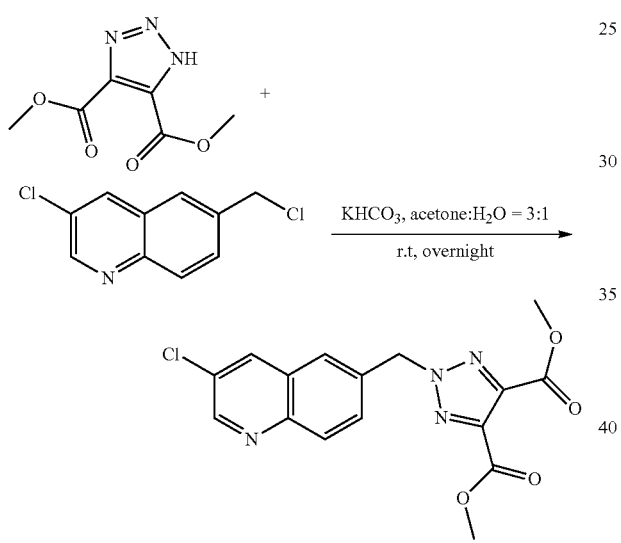

KHCO3 (1.622 g, 16.215 mmol, 3.0 eq) and 3-chloro-6-(chloromethyl)quinoline (1.141 g, 5.405 mmol, 1.0 eq) were added to a solution of dimethyl 1H-1,2,3-triazole-4,5-dicarboxylate (1.0 g, 5.405 mmol, 1.0 eq) in acetone (30.0 mL) and H2O (10.0 mL), the reaction mixture was then stirred at rt overnight. The solvent was then removed under reduced pressure, and the resulting residue was purified by prep-HPLC to provide dimethyl2-((3-chloroquinolin-6-yl)methyl)-2H-1,2,3-triazole-4,5-dicarboxylate as a white solid (524.0 mg, 27%).

-continued

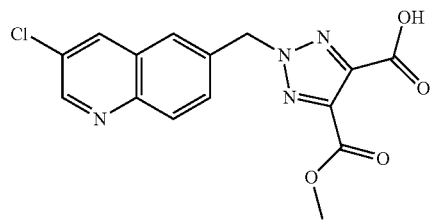

Aqueous NaOH (1N, 1.5 mL, 1.528 mmoL, 1.1 eq) was added to a suspension of dimethyl 2-((3-chloroquinolin-6-yl)methyl)-2H-1,2,3-triazole-4,5-dicarboxylate (524.0 mg, 1.456 mmoL, 1.0 eq) in MeOH (10.0 mL) at rt under N2 atmosphere. The reaction mixture was stirred at rt overnight. 1.65 mL of 1N HCl was added and the methanol was removed under reduced pressure. Then 20.0 mL of H2O was added to the resulting residue, white precipitate was formed and filtered to provide 2-((3-chloroquinolin-6-yl)methyl)-5-(methoxycarbonyl)-2H-1,2,3-triazole-4-carboxylic acid as a white solid (430.0 mg, 85%).

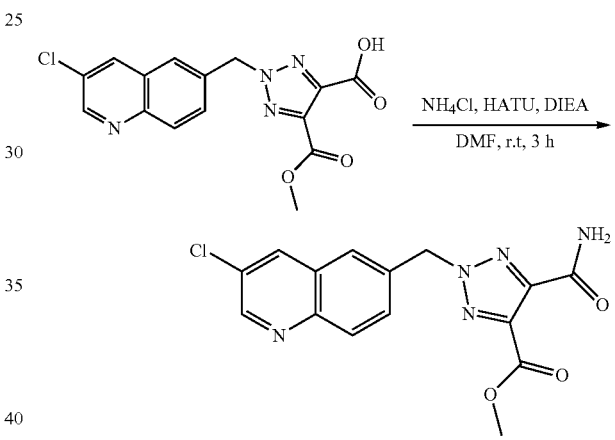

2-((3-Chloroquinolin-6-yl)methyl)-5-(methoxycarbonyl)-2H-1,2,3-triazole-4-carboxylic acid (430.0 mg, 1.243 mmol, 1.0 eq), NH4Cl (100.0 mg, 1.864 mmol, 1.5 eq), HATU (708.0 mg, 1.864 mmol, 1.5 eq) and DIPEA (400.0 mg, 3.108 mmol, 3.0 eq) were dissolved in DMF (10.0 mL), then the reaction mixture was stirred at rt for 3.0 h. EA (15.0 mL) was then added and the organic layer was washed with H2O (10.0 mL×2) and brine (15.0 mL). The organic layers were dried over anhydrous Na2SO4 and concentrated. The resulting residue was purified by column chromatography (hexane/ethyl acetate: 1:1) to provide methyl 5-carbamoyl-2-((3-chloroquinolin-6-yl)methyl)-2H-1,2,3-triazole-4-carboxylate (509.0 mg, ca. 100%).

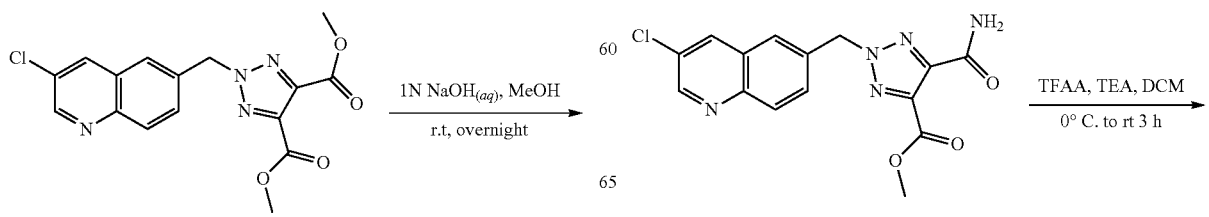

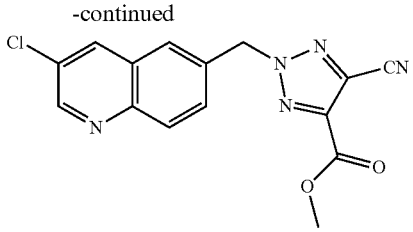

To a mixture of methyl 5-carbamoyl-2-((3-chloroquinolin-6-yl)methyl)-2H-1,2,3-triazole-4-carboxylate (509.0 mg, 1.475 mmol, 1.0 eq) and TEA (671.0 mg, 6.639 mmol, 5.0 eq) in DCM (10.0 mL) was added TFAA (620.0 mg, 2.950 mmol, 2.0 eq) at 0° C. with stirring. The resulting mixture was warmed to rt for 3.0 h. The mixture was washed with H2O (10.0 mL×2) and brine (15.0 mL). The organic layers were dried over anhydrous Na2SO4 and concentrated. The resulting residue was purified by column chromatography (hexane/ethyl acetate 3:1 to 1:1) to provide methyl 2-((3-chloroquinolin-6-yl)methyl)-5-cyano-2H-1,2,3-triazole-4-carboxylate as a yellow solid (215.0 mg, 53%).

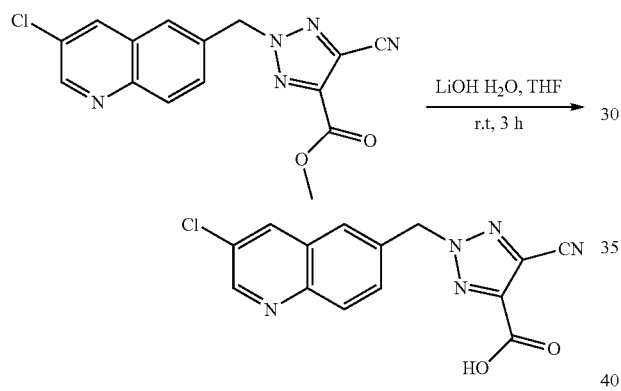

Methyl 2-((3-chloroquinolin-6-yl)methyl)-5-cyano-2H-1,2,3-triazole-4-carboxylate (50 mg, 0.153 mmol) and LiOH.H2O (19 mg, 0.459 mmol) were dissolved in THF (3 mL), and the reaction mixture was stirred at rt for 3 h. The solvent was removed under reduced pressure and 2-((3-chloroquinolin-6-yl)methyl)-5-cyano-2H-1,2,3-triazole-4-carboxylic acid was provided as a white solid which was used in the next step without further purification (48 mg, ca. 100%).

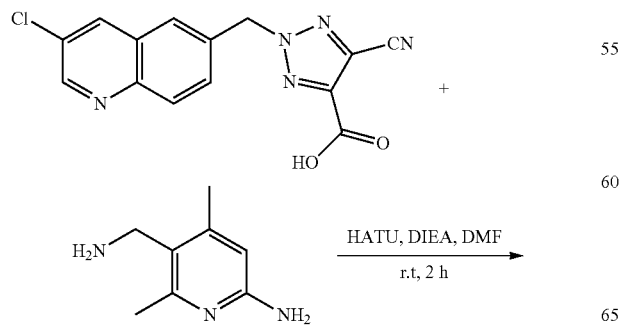

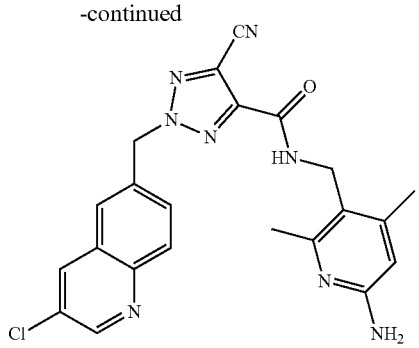

To a solution of 2-((3-chloroquinolin-6-yl) methyl)-5-cyano-2H-1,2,3-triazole-4-carboxylic acid (48.0 mg, 0.153 mmol, 1.0 eq), 5-(aminomethyl)-4,6-dimethylpyridin-2-amine (35.0 mg, 0.23 mmol, 1.5 eq) and HATU (87.0 mg, 0.23 mmol, 1.5 eq) in DMF (2.0 mL) were added DIEA (49.0 mg, 0.383 mmol, 2.5 eq) and the resulting mixture was stirred at rt for 2.0 h. The resulting mixture was purified by prep-HPLC to provide N-((6-amino-2,4-dimethylpyridin-3-yl)methyl)-2-((3-chloroquinolin-6-yl)methyl)-5-cyano-2H-1,2,3-triazole-4-carboxamide as a white solid (19.0 mg, 28%). LCMS (M+H+) m/z calculated 447.1, found 447.2. 1H NMR (DMSO-d6, 400 MHz) δ 8.91 (s, 1H), 7.87 (s, 1H), 8.60 (s, 1H), 8.08 (s, 1H), 7.89 (s, 1H), 7.76 (s, 1H), 6.05 (d, 3H), 5.65 (s, 2H), 4.35 (s, 2H), 2.31 (s, 3H), 2.18 (s, 3H).

Example 96: Preparation of N-((6-amino-2,4-dimethylpyridin-3-yl)methyl)-5-((3-chloroquinolin-6-yl)methyl)-4H-1,2,4-triazole-3-carboxamide

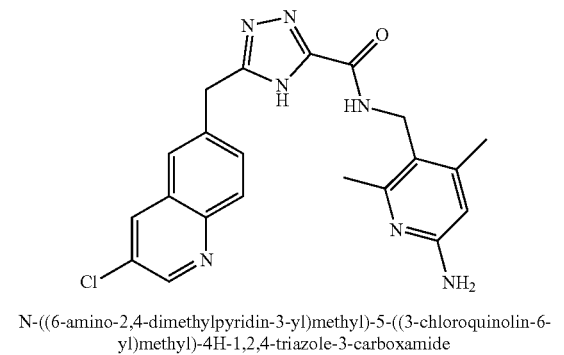

N-((6-amino-2,4-dimethylpyridin-3-yl)methyl)-5-((3-chloroquinolin-6-yl)methyl)-4H-1,2,4-triazole-3-carboxamide LiOH.H2O (3.8 g, 90.50 mmol, 2.0 eq) was added to a solution of methyl 3-chloroquinoline-6-carboxylate (10.0 g, 45.25 mmol, 1.0 eq) in MeOH (40.0 mL), THF (40.0 mL) and H2O (40.0 mL). The reaction mixture was stirred at rt for 1 h. The solvent was removed under reduced pressure. 50 mL of H2O was added and acidified to pH 2.0 with conc. HCl. White precipitate was formed and collected to provide 3-chloroquinoline-6-carboxylic acid as a white solid (9.35 g, ca 100%).

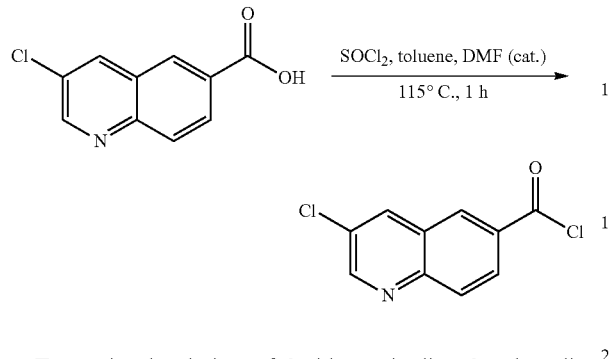

To a stirred solution of 3-chloroquinoline-6-carboxylic acid (3.0 g, 14.493 mmol, 1.0 eq) in toluene (15.0 mL) under inert atmosphere was added SOCl2 (6.84 g, 57.971 mmol, 4.0 eq) and DMF (cat.) at rt, and the reaction was heated under reflux for 1 h. After the reaction was complete, the reaction mixture was cooled to rt and concentrated under reduced pressure to provide 3-chloroquinoline-6-carbonyl chloride (3.275 g, ca. 100%) which was used in the next step directly.

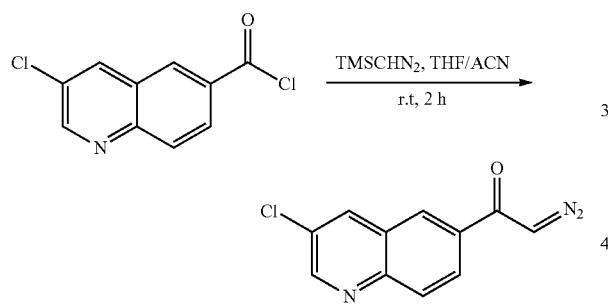

3-Chloroquinoline-6-carbonyl chloride (3.275 g, 15.0 mmol, 1.0 eq) was dissolved in THF (25.0 mL) and ACN (25.0 mL), then a solution of TMSCHN2 (14.5 mL, 28.986 mmol, 2.0 M in hexane, 1.9 eq) in THF (25.0 mL) and ACN (25.0 mL) was added. The resulting mixture was stirred at rt for 2.0 h. AcOH (5.0 mL) and H2O (20.0 mL) were added, then concentrated in vacuo. The resulting residue was diluted with sat. aqueous NaHCO₃ (40.0 mL), extracted with EA (20.0 mL×3). The combined organic layers were washed with brine (15.0 mL×3) and dried over anhydrous Na2SO4. The solvent was removed in vacuo. The resulting residue was purified by column chromatography (hexane/ethyl acetate 10:1) to provide 1-(3-chloroquinolin-6-yl)-2-diazoethanone (2.8 g, 84% over two steps).

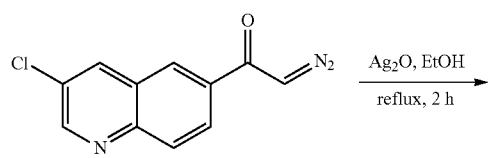

To a stirred solution of 1-(3-chloroquinolin-6-yl)-2-diazoethanone (1.0 g, 4.317 mmol, 1.0 eq) in EtOH (30.0 mL) was added Ag2O (2.0 g, 8.634 mmol, 2.0 eq) at 55° C., then the reaction was heated under reflux for 2.0 h, then cooled to rt and filtered. The resulting filtrate was used in the next step directly.

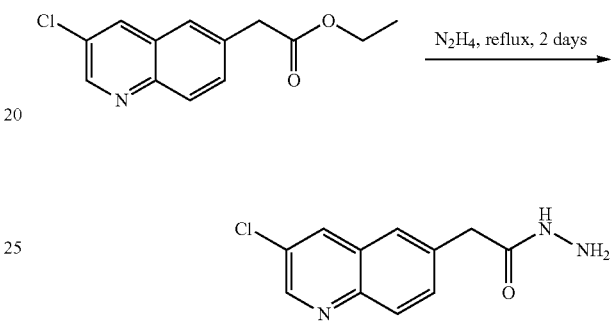

To the above solution of ethyl 2-(3-chloroquinolin-6-yl)acetate was added N2H4 (2.5 mL), then the reaction was heated under reflux for 2 days, then cooled. White precipitate was formed and collected to provide 2-(3-chloroquinolin-6-yl)acetohydrazide (580.0 mg, 57% over two steps).

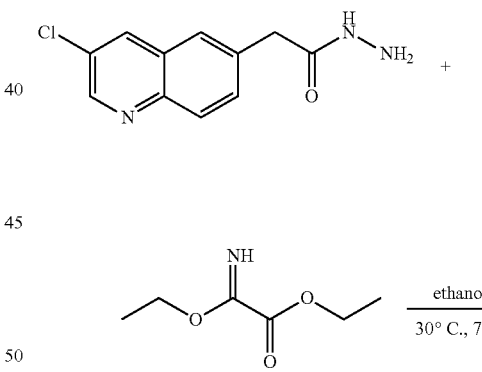

2-(3-Chloroquinolin-6-yl)acetohydrazide (170.0 mg, 0.723 mmol, 1.0 eq) and ethyl 2-ethoxy-2-iminoacetate (231.0 mg, 1.591 mmol, 2.0 eq) in ethanol (20.0 mL) were stirred at 30° C. for 72.0 h. The solvent was removed in vacuo. to provide (Z)-ethyl 2-amino-2-(2-(2-(3-chloroquinolin-6-yl)acetyl)hydrazono)acetate (242.0 mg, ca. 100%).

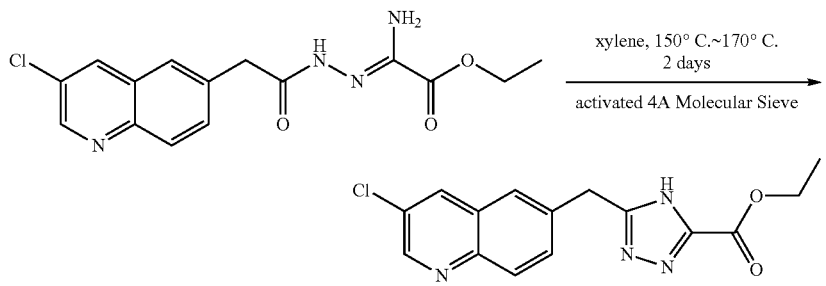

(Z)-ethyl 2-amino-2-(2-(2-(3-chloroquinolin-6-yl)acetyl) hydrazono)acetate (242.0 mg, 0.723 mmol, 1.0 eq) and activated 4 Å molecular sieve were suspended in xylene (30.0 mL) and heated at 150° C. for 2 days. The solvent was removed in vacuo. The resulting residue was purified by column chromatography (DCM/MeOH 10:1) to provide ethyl 5-((3-chloroquinolin-6-yl) methyl)-4H-1,2,4-triazole-3-carboxylate (80.0 mg, 35% over two steps).

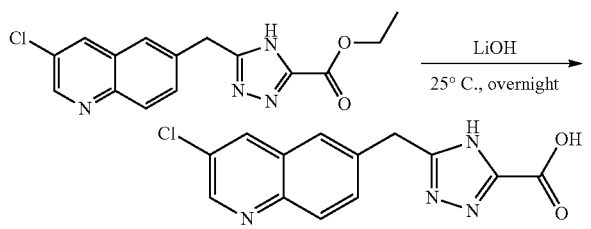

Ethyl 5-((3-chloroquinolin-6-yl)methyl)-4H-1,2,4-triazole-3-carboxylate (80.0 mg, 0.253 mmol, 1.0 eq) and LiOH.H2O (21.0 mg, 0.506 mmol, 2.0 eq) were dissolved in THF (4.0 mL) and H2O (0.4 mL) and the reaction mixture was stirred at rt overnight. Then the solvent was removed in vacuo. 10.0 mL of H2O was added, and the mixture was acidified to pH 2.0 with 2 N aq. HCl, then concentrated in vacuo. to provide 5-((3-chloroquinolin-6-yl)methyl)-4H-1,2,4-triazole-3-carboxylic acid hydrochloride which was used in the next step without further purification (86.0 mg).

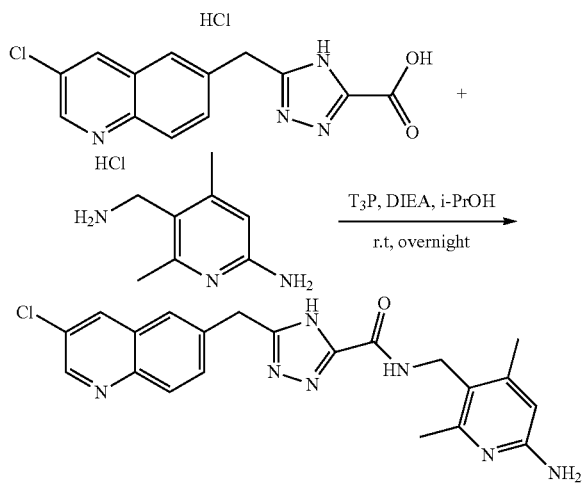

A mixture of 5-((3-chloroquinolin-6-yl)methyl)-4H-1,2,4-triazole-3-carboxylic acid hydrochloride (86.0 mg, 0.265 mmol, 1.0 eq), 5-(aminomethyl)-4,6-dimethylpyridin-2-amine hydrochloride (74.0 mg, 0.398 mmol, 1.5 eq) and DIEA (103.0 mg, 0.795 mmol, 3.0 eq) in 8.0 mL of i-PrOH was stirred vigorously for 10.0 min, then T3P (252.0 mg, 0.398 mmol, 50% by wt. in EtOH) was added. The resulting mixture was stirred at rt overnight, then purified by prep-HPLC to provide N-((6-amino-2,4-dimethylpyridin-3-yl) methyl)-5-((3-chloroquinolin-6-yl)methyl)-4H-1,2,4-triazole-3-carboxamide (33.0 mg, 31% over two steps). LCMS (M+H+) m/z calculated 422.1, found 422.1. 1H NMR (DMSO-d6, 400 MHz) δ 8.90 (s, 1H), 8.86 (s, 1H), 8.55 (s, 1H), 8.01 (d, 1H), 7.79 (d, 3H), 7.70 (d, 1H), 6.61 (s, 1H), 4.32 (m, 4H), 2.37 (m, 6H).

Example 97: Preparation of N-((6-amino-2-methylpyridin-3-yl)methyl)-5-((3-chloroquinolin-6-yl) methyl)-4H-1,2,4-triazole-3-carboxamide

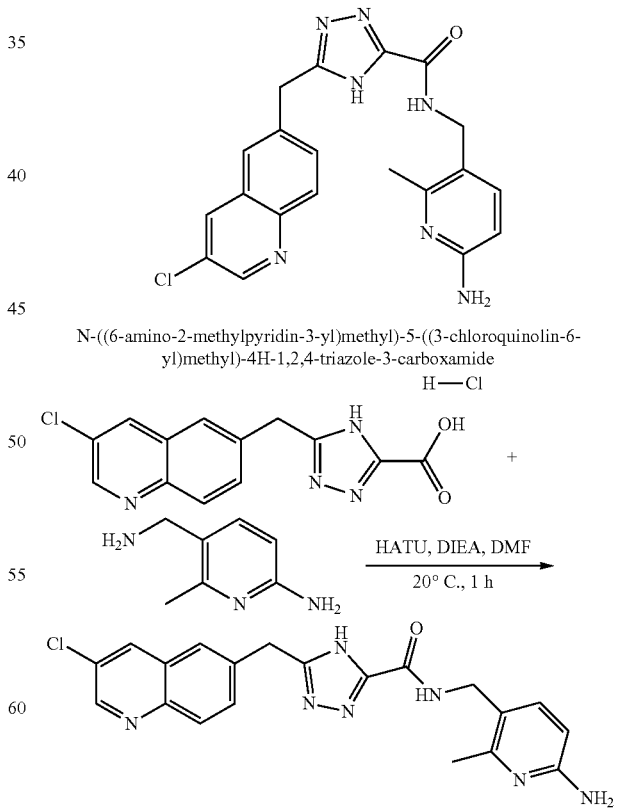

A mixture of 5-((3-chloroquinolin-6-yl)methyl)-4H-1,2,4-triazole-3-carboxylic acid hydrochloride (200.0 mg, 0.617 mmol, 1.0 eq), 5-(aminomethyl)-6-methylpyridin-2-amine (101.0 mg, 0.740 mmol, 1.2 eq), HATU (352.0 mg, 0.926 mmol, 1.5 eq) and DIEA (199.0 mg, 1.543 mmol, 2.5 eq) in 10.0 mL of DMF was stirred at rt for 1.0 h. The mixture was purified by prep-HPLC to provide N-((6-amino-2-methyl-pyridin-3-yl)methyl)-5-((3-chloroquinolin-6-yl)methyl)-4H-1,2,4-triazole-3-carboxamide (68.0 mg, 27%). LCMS (M+H+) m/z calculated 408.1, found 408.2. 1H NMR (DMSO-d6, 400 M Hz) δ 8.84 (d, 1H), 8.72 (m, 1H), 8.53 (d, 1H), 7.99 (d, 1H), 7.80 (s, 1H), 7.72 (dd, 1H), 7.23 (d, 1H), 6.21 (d, 1H), 5.69 (s, 2H), 4.28 (s, 2H), 4.24 (d, 2H), 2.28 (s, 3H).

Example 98: Preparation of N-((6-amino-2,4-dimethylpyridin-3-yl)methyl)-5-((3-chloroquinolin-6-yl)methyl)-4-methyl-4H-1,2,4-triazole-3-carboxamide

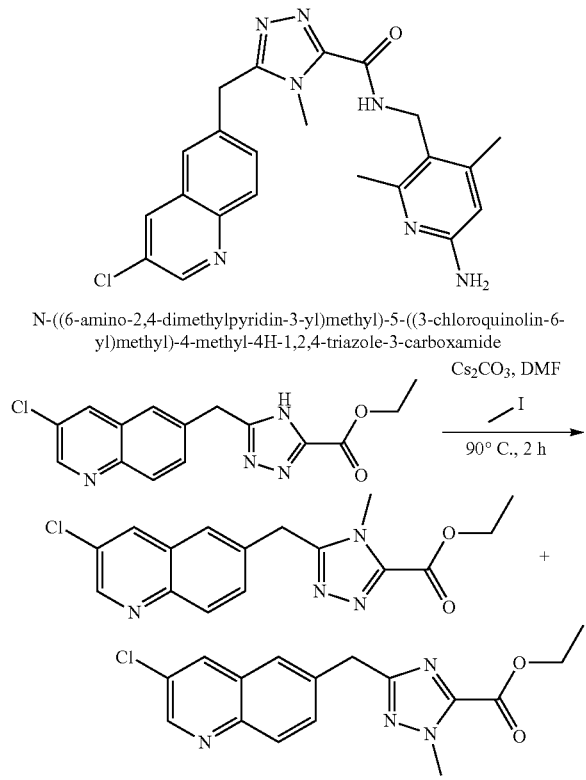

N-((6-amino-2,4-dimethylpyridin-3-yl)methyl)-5-((3-chloroquinolin-6-yl)methyl)-4-methyl-4H-1,2,4-triazole-3-carboxamide MeI (1.022 g, 7.198 mmol, 1.2 eq) was added to a solution of ethyl 5-((3-chloroquinolin-6-yl)methyl)-4H-1,2,4-triazole-3-carboxylate (1.9 g, 5.999 mmol, 1.0 eq) and Cs2CO3 (4.92 g, 14.998 mmol, 2.5 eq) in DMF (100.0 mL) at rt, then the reaction was heated at 90° C. for 2.0 h. The solvent was then removed in vacuo. and The resulting residue was purified by prep-HPLC to provide the mixture of two regio-isomers (ethyl 5-((3-chloroquinolin-6-yl)methyl)-4-methyl-4H-1,2,4-triazole-3-carboxylate (1.4 g, 46%); ethyl 3-((3-chloroquinolin-6-yl)methyl)-1-methyl-1H-1,2,4-triazole-5-carboxylate (700.0 mg, 23%).

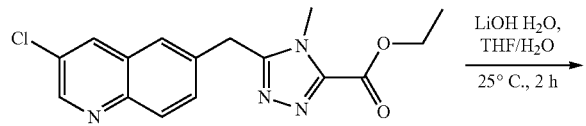

Ethyl 5-((3-chloroquinolin-6-yl)methyl)-4-methyl-4H-1,2,4-triazole-3-carboxylate (10.0 mg, 0.03 mmol, 1.0 eq) and LiOH.H2O (3.0 mg, 0.06 mmol, 2.0 eq) were dissolved in THF (2.0 mL) and H2O (0.2 mL) and the resulting mixture was stirred at rt for 2.0 h, then concentrated in vacuo. 10.0 mL of H2O was added and the mixture was acidified to pH 2.0 with 2 N aq. HCl, then concentrated in vacuo to provide 5-((3-chloroquinolin-6-yl)methyl)-4-methyl-4H-1,2,4-triazole-3-carboxylic acid hydrochloride (9.0 mg), which was used in the next step without further purification.

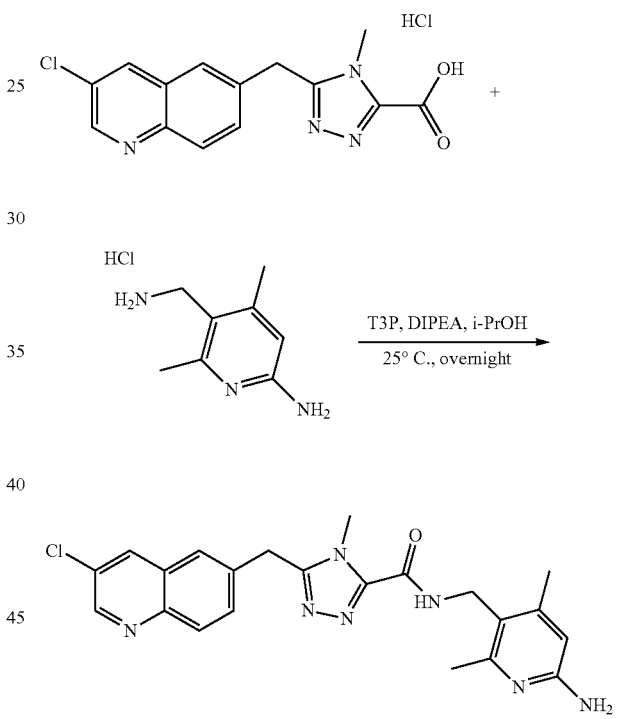

A mixture of 5-((3-chloroquinolin-6-yl)methyl)-4-methyl-4H-1,2,4-triazole-3-carboxylic acid hydrochloride (9.0 mg, 0.027 mmol, 1.0 eq), 5-(aminomethyl)-4,6-dimethylpyridin-2-amine hydrochloride (7.0 mg, 0.040 mmol, 1.5 eq) and DIEA (10.0 mg, 0.081 mmol, 3.0 eq) in 4.0 mL of i-PrOH was stirred vigorously for 10.0 min, then T3P (13.0 mg, 0.04 mmol, 50% by wt. in EtOH) was added. The mixture was stirred at rt overnight, then purified by prep-HPLC to provide N-((6-amino-2,4-dimethylpyridin-3-yl)methyl)-5-((3-chloroquinolin-6-yl)methyl)-4-methyl-4H-1,2,4-triazole-3-carboxamide (3.0 mg, 23% over two steps). LCMS (M+H+) m/z calculated 436.2, found 436.2. 1H NMR (CDCl3, 400 MHz) δ 8.69 (d, 1H), 7.99 (d, 1H), 7.94 (m, 1H), 7.55-7.59 (m, 2H), 7.03 (s, 1H), 6.13 (s, 1H), 4.42 (d, 2H), 4.32 (s, 2H), 4.18 (s, 3H), 4.11 (s, 2H), 2.35 (s, 3H), 2.18 (s, 3H).

Example 99: Preparation of N-((6-amino-2,4-dimethylpyridin-3-yl)methyl)-3-((3-chloroquinolin-6-yl)methyl)-1-methyl-1H-1,2,4-triazole-5-carboxamide

Example 100: Preparation of N-((6-amino-2,4-dimethylpyridin-3-yl)methyl)-5-bromo-1-((3-chloroquinolin-6-yl)methyl)-1H-1,2,4-triazole-3-carboxamide

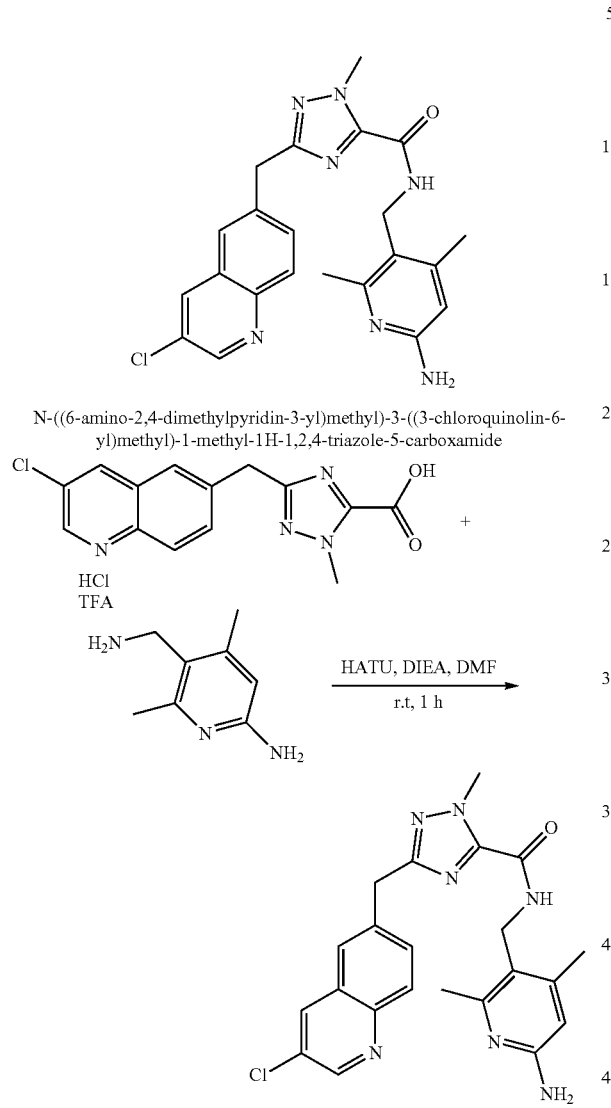

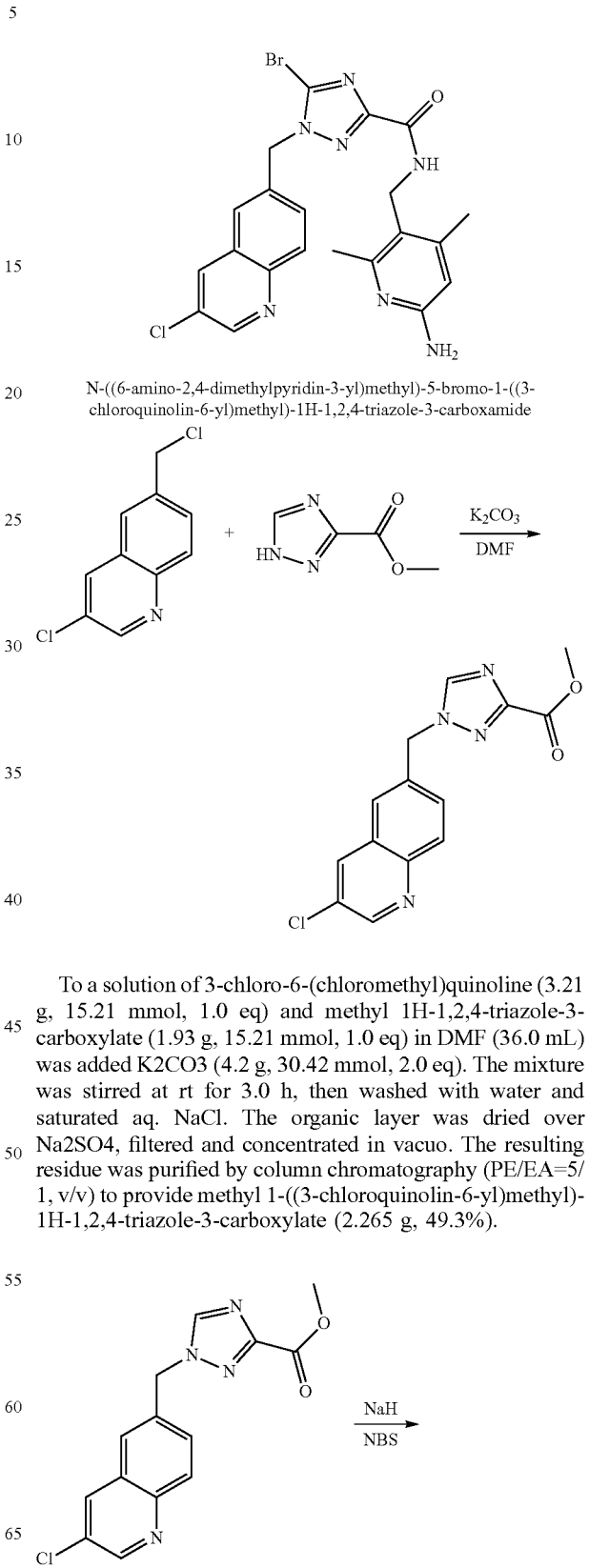

A mixture of 3-((3-chloroquinolin-6-yl)methyl)-1-methyl-1H-1,2,4-triazole-5-carboxylic acid hydrochloride (450.0 mg, 1.487 mmol, 1.0 eq prepared as 5-((3-chloroquinolin-6-yl)methyl)-4-methyl-4H-1,2,4-triazole-3-carboxylic acid hydrochloride), 5-(aminomethyl)-4,6-dimethylpyridin-2-amine (442.0 mg, 1.784 mmol, 1.2 eq), HATU (848.0 mg, 2.231 mmol, 1.5 eq) and DIEA (480.0 mg, 3.718 mmol, 2.5 eq) in 15.0 mL of DMF was stirred at rt for 1.0 h. The solvent was removed in vacuo. The resulting residue was purified by column chromatography to provide N-((6-amino-2,4-dimethylpyridin-3-yl)methyl)-3-((3-chloroquinolin-6-yl)methyl)-1-methyl-1H-1,2,4-triazole-5-carboxamide as a white solid (253.0 mg, 39%). LCMS (M+H+) m/z calculated 436.2, found 436.2. 1H NMR (DMSO-d6, 400 MHz) δ 8.85 (d, 1H), 8.54 (d, 1H), 8.14 (t, 1H), 8.01 (d, 1H), 7.77 (s, 1H), 7.68-7.71 (m, 1H), 6.09 (s, 1H), 5.63 (s, 2H), 4.44 (s, 2H), 4.31 (s, 2H), 3.85 (s, 3H), 2.29 (s, 3H), 2.16 (s, 3H).

To a solution of 3-chloro-6-(chloromethyl)quinoline (3.21 g, 15.21 mmol, 1.0 eq) and methyl 1H-1,2,4-triazole-3-carboxylate (1.93 g, 15.21 mmol, 1.0 eq) in DMF (36.0 mL) was added K2CO3 (4.2 g, 30.42 mmol, 2.0 eq). The mixture was stirred at rt for 3.0 h, then washed with water and saturated aq. NaCl. The organic layer was dried over Na2SO4, filtered and concentrated in vacuo. The resulting residue was purified by column chromatography (PE/EA=5/1, v/v) to provide methyl 1-((3-chloroquinolin-6-yl)methyl)-1H-1,2,4-triazole-3-carboxylate (2.265 g, 49.3%).

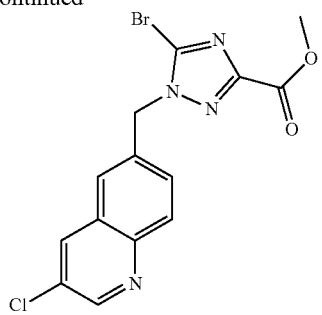

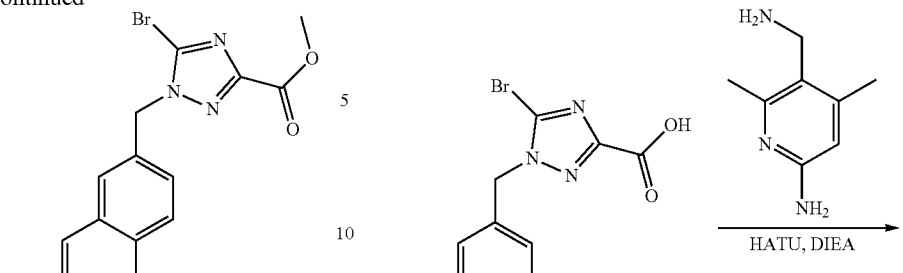

To a solution of methyl 1-((3-chloroquinolin-6-yl)methyl)-1H-1,2,4-triazole-3-carboxylate (2.265 g, 7.5 mmol, 1.0 eq) and NaH (60% in mineral oil, 900.0 mg, 22.5 mmol, 3.0 eq) in THF (30.0 mL) was added NBS (6.675 g, 37.5 mmol, 5.0 eq). The mixture was stirred at rt for 3.0 h under nitrogen atmosphere. After the reaction was complete, the mixture was washed with water and saturated aq. NaCl. The organic layer was dried over Na2SO4, filtered and concentrated in vacuo. The resulting residue was purified by column chromatography (PE/EA=5/1, v/v) to provide methyl 5-bromo-1-((3-chloroquinolin-6-yl) methyl)-1H-1,2,4-triazole-3-carboxylate (1.0 g, 35.1%).

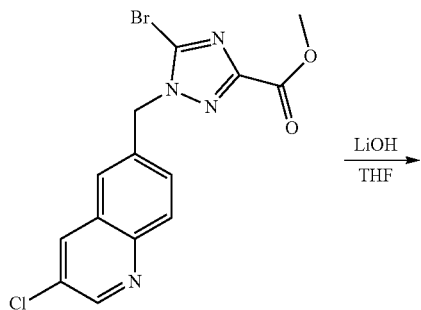

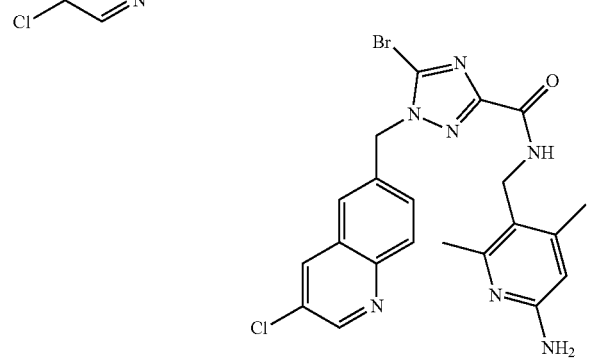

To a solution of 5-bromo-1-((3-chloroquinolin-6-yl)methyl)-1H-1,2,4-triazole-3-carboxylic acid (963.0 mg, 2.63 mmol, 1.0 eq), 5-(aminomethyl)-4,6-dimethylpyridin-2-amine (1.045 g, 3.95 mmol, 1.5 eq) and HATU (1.5 g, 3.95 mmol, 1.5 eq) in DMF (10.0 mL) was added DIEA (1.357 g, 7.9 mmol, 3.0 eq). The reaction mixture was stirred at rt for 1 h. Water was added, and the mixture was extracted with EA. The organic layer was washed with saturated aq. NaCl, dried over Na2SO4, filtered and concentrated. The resulting residue was purified by column chromatography (PE/EA=1/1, v/v) to provide N-((6-amino-2,4-dimethylpyridin-3-yl)methyl)-5-bromo-1-((3-chloroquinolin-6-yl)methyl)-1H-1,2,4-triazole-3-carboxamide (1.0 g, 76.2%). LCMS (M+H+) m/z calculated 500.1, found 500.0. 1H NMR (CD3OD-d4, 400 MHz) δ 8.82 (d, 1H), 8.41 (d, 1H), 8.05 (d, 1H), 7.83 (s, 1H), 7.73-7.76 (m, 1H), 6.30 (s, 1H), 5.70 (s, 2H), 4.51 (s, 2H), 2.41 (s, 3H), 2.29 (s, 3H).

Example 101: Preparation of N-((6-amino-2,4-dimethylpyridin-3-yl)methyl)-1-((3-chloroquinolin-6-yl)methyl)-5-cyano-1H-1,2,4-triazole-3-carboxamide

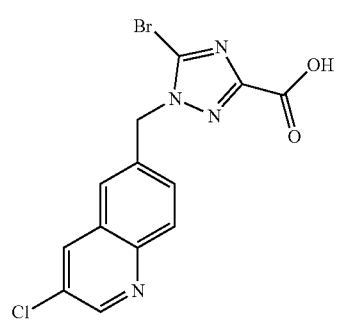

To a solution of methyl 5-bromo-1-((3-chloroquinolin-6-yl)methyl)-1H-1,2,4-triazole-3-carboxylate (1.0 g, 2.63 mmol, 1.0 eq) in THF/H2O (35.0 mL, v:v=1:1) was added LiOH (221.0 mg, 5.26 mmol, 2.0 eq). The mixture was stirred at rt overnight. After the reaction was complete, the mixture was concentrated under vacuum to provide 5-bromo-1-((3-chloroquinolin-6-yl)methyl)-1H-1,2,4-triazole-3-carboxylic acid (963.0 mg, crude) as a white solid which was used in the next step directly.

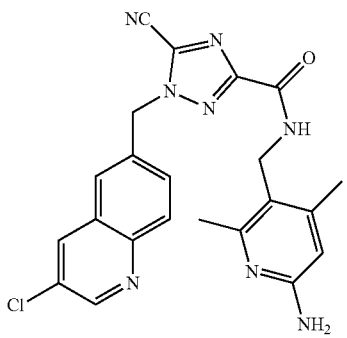

N-((6-amino-2,4-dimethylpyridin-3-yl)methyl)-1-((3-chloroquinolin-6-yl)methyl)-5-cyano-1H-1,2,4-triazole-3-carboxamide

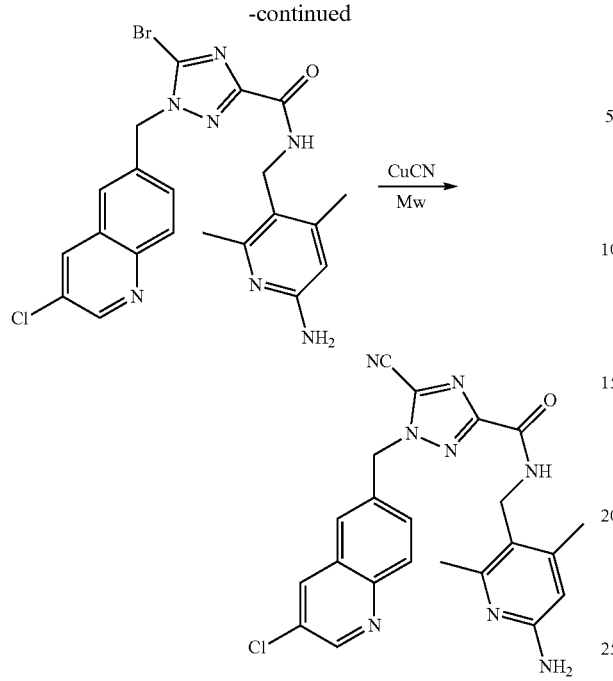

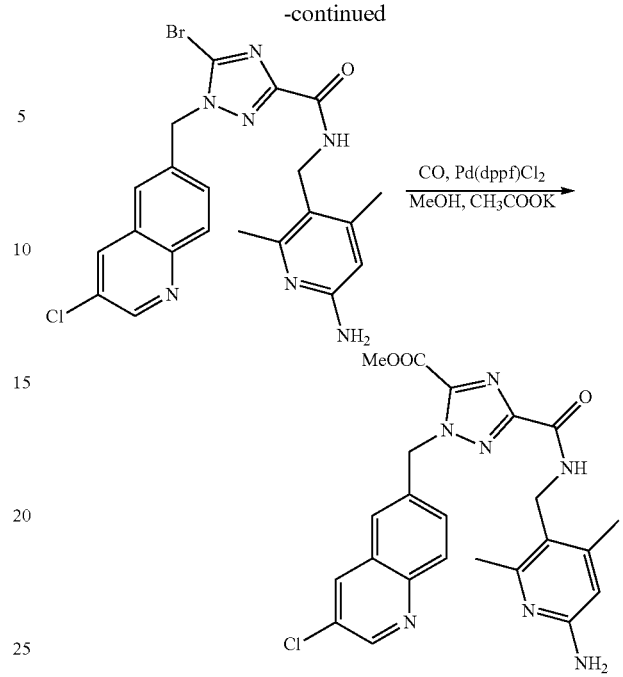

To a solution of N-((6-amino-2,4-dimethylpyridin-3-yl)methyl)-5-bromo-1-((3-chloroquinolin-6-yl)methyl)-1H-1,2,4-triazole-3-carboxamide (300.0 mg, 0.6 mmol, 1.0 eq) in DMF (3.0 mL) was added CuCN (108.0 mg, 1.2 mmol, 2.0 eq). The reaction mixture was stirred at 150° C. for 2.0 h under microwave irradiation. After the reaction was complete, water was added and the mixture was extracted with EA. The organic layer was washed with saturated aq. NaCl, dried over Na2SO4, filtered and concentrated. The resulting residue was purified by prep-HPLC to provide N-((6-amino-2,4-dimethylpyridin-3-yl)methyl)-1-((3-chloroquinolin-6-yl)methyl)-5-cyano-1H-1,2,4-triazole-3-carboxamide (120.0 mg, 44.8%) as a white solid. LCMS (M+H+) m/z calculated 447.1, found 447.2. 1H NMR (CD3OD-d4, 400 MHz) δ 8.85 (d, 1H), 8.44 (d, 1H), 8.08 (d, 1H), 7.97 (s, 1H), 7.77-7.80 (m, 1H), 6.67 (s, 1H), 5.89 (s, 2H), 4.50 (s, 2H), 2.59 (s, 3H), 2.46 (s, 3H).

Example 102: Preparation of methyl 3-(((6-amino-2,4-dimethylpyridin-3-yl)methyl) carbamoyl)-1-((3-chloroquinolin-6-yl)methyl)-1H-1,2,4-triazole-5-carboxylate To a solution of N-((6-amino-2,4-dimethylpyridin-3-yl)methyl)-5-bromo-1-((3-chloroquinolin-6-yl)methyl)-1H-1,2,4-triazole-3-carboxamide (50.0 mg, 0.1 mmol, 1.0 eq) and Pd(dppf)Cl2 (29.0 mg, 0.05 mmol, 0.5 eq) in DMF/MeOH (10.0 mL, v:v=1:1) was added CH3COOK (38.0 mg, 0.3 mmol, 3.0 eq). The reaction mixture was stirred at 90° C. overnight under CO atmosphere. After the reaction was complete, the reaction was cooled to rt and water was added. The mixture was extracted with EA. The organic layer was washed with saturated aq. NaCl, dried over Na2SO4, filtered and concentrated in vacuo. The resulting residue was purified by prep-HPLC to provide methyl 3-(((6-amino-2,4-dimethylpyridin-3-yl)methyl) carbamoyl)-1-((3-chloroquinolin-6-yl)methyl)-1H-1,2,4-triazole-5-carboxylate (7.0 mg, 14.6%) as a white solid. LCMS (M+H+) m/z calculated 480.2, found 480.2. 1H NMR (CD3OD-d4, 400 MHz) δ 8.81 (d, 1H), 8.40 (d, 1H), 8.02 (d, 1H), 7.87 (s, 1H), 7.78-7.80 (m, 1H), 6.67 (s, 1H), 6.05 (s, 2H), 4.51 (s, 2H), 3.98 (s, 3H), 2.60 (s, 3H), 2.47 (s, 3H).

Example 103: Preparation of N-((6-amino-2,4-dimethylpyridin-3-yl)methyl)-2-((3-chloroquinolin-6-yl)methyl)-1H-imidazole-4-carboxamide

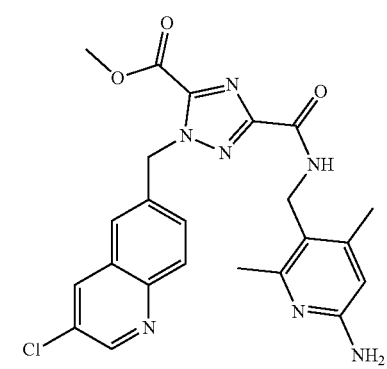

methyl 3-(((6-amino-2,4-dimethylpyridin-3-yl)methyl)carbamoyl)-1-((3-chloroquinolin-6-yl)methyl)-1H-1,2,4-triazole-5-carboxylate

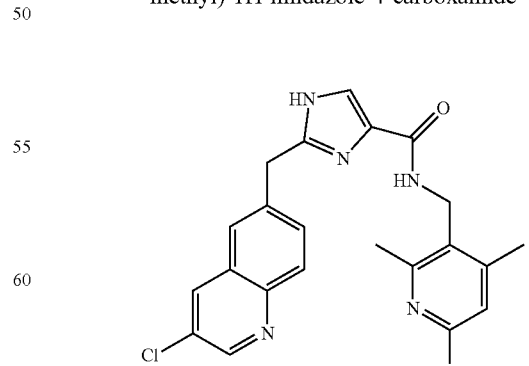

N-((6-amino-2,4-dimethylpyridin-3-yl)methyl)-2-((3-chloroquinolin-6-yl)methyl)-1H-imidazole-4-carboxamide

377

-continued

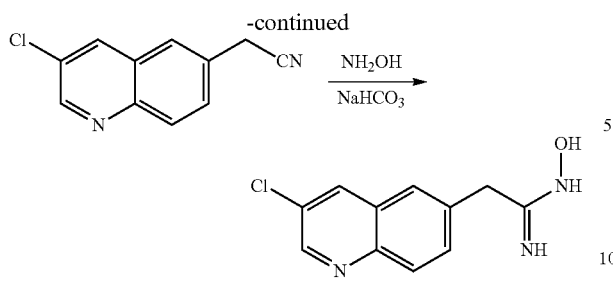

To a solution of 2-(3-chloroquinolin-6-yl)acetonitrile (2.3 g, 11.39 mmol, 1.0 eq) and NaHCO₃ (2.3 g, 27.33 mmol, 2.4 eq) in MeOH/H2O (30.0 mL, v/v=5:1) was added NH2OH.HCl (1.7 g, 25.05 mmol, 2.2 eq). The mixture was stirred at 70° C. overnight. After the reaction was complete, the reaction was cooled to rt. The mixture was washed with water and EA. The organic layer was dried over Na2SO4, filtered and concentrated under vacuum. The resulting residue was purified by column chromatography (PE/EA=20/1, v/v) to provide 2-(3-chloroquinolin-6-yl)-N-hydroxyacetimidamide (2.35 g, 87.8%) as a white solid.

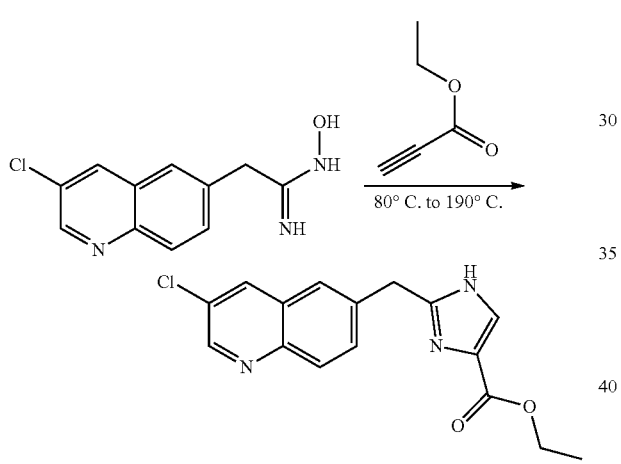

To a solution of 2-(3-chloroquinolin-6-yl)-N-hydroxyacetimidamide (2.35 g, 10 mmol, 1.0 eq) in EtOH (30.0 mL) was added ethyl propiolate (1.08 g, 11 mmol, 1.1 eq). The mixture was stirred at 70° C. overnight. After the reaction was complete, the reaction was cooled to rt and concentrated in vacuo, then diphenyl ether (10.0 mL) was added. The mixture was stirred at 190° C. for 2 h then cooled and washed with PE, filtered and concentrated in vacuo. The resulting residue was purified by column chromatography (PE/EA=5/1, v/v) to provide ethyl 2-((3-chloroquinolin-6-yl) methyl)-1H-imidazole-4-carboxylate (630.0 mg, 20%) as gray solid.

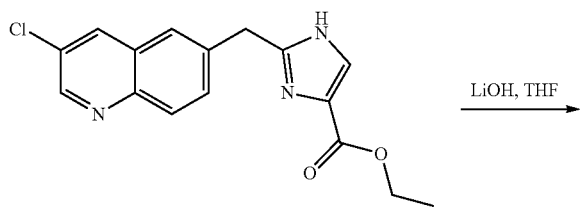

378

-continued

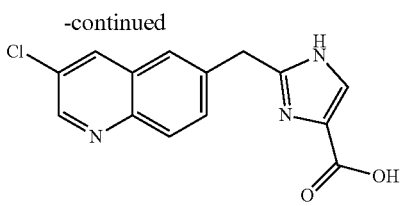

To a solution of ethyl 2-((3-chloroquinolin-6-yl) methyl)-1H-imidazole-4-carboxylate (50.0 mg, 0.159 mmol, 1.0 eq) in THF (5.0 mL) was added LiOH (34.0 mg, 0.795 mmol, 5.0 eq). The mixture was stirred at 50° C. for 2.0 days, then cooled and concentrated in vacuo to provide 2-((3-chloroquinolin-6-yl)methyl)-1H-imidazole-4-carboxylic acid (40.0 mg, 87%) as a white solid which was used in the next step directly.

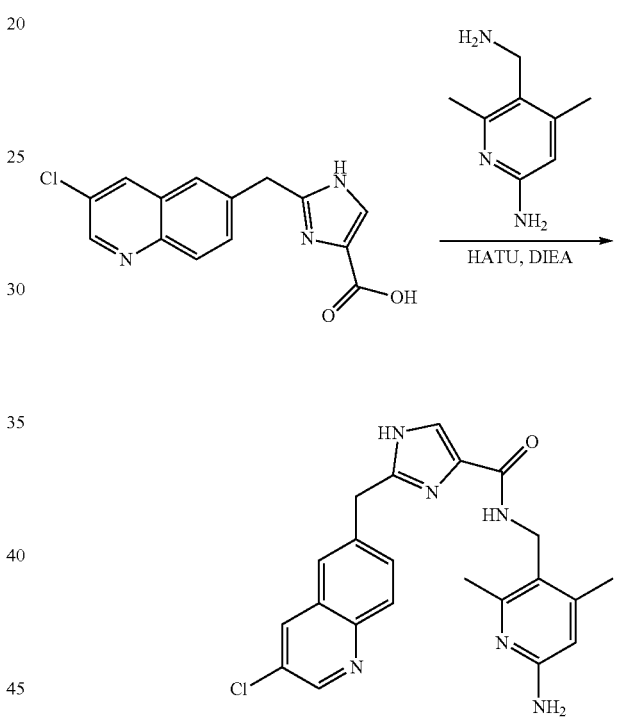

To a solution of 2-((3-chloroquinolin-6-yl)methyl)-1H-imidazole-4-carboxylic acid (40.0 mg, 0.139 mmol, 1.0 eq), 5-(aminomethyl)-4,6-dimethylpyridin-2-amine (25.0 mg, 0.167 mmol, 1.2 eq) and HATU (89.0 mg, 0.209 mmol, 1.5 eq) in DMF (3.0 mL) was added DIEA (61.0 mg, 0.417 mmol, 3.0 eq). The reaction mixture was stirred at rt for 1 h. Water was added and the mixture was extracted with EA. The organic layer was washed with saturated aq. Na2CO3, dried over Na2SO4, filtered and concentrated in vacuo. The resulting residue was purified by prep-HPLC to provide N-((6-amino-2,4-dimethylpyridin-3-yl)methyl)-2-((3-chloroquinolin-6-yl) methyl)-1H-imidazole-4-carboxamide (13.0 mg, 22.4%) as a white solid. LCMS (M+H+) m/z calculated 421.1, found 421.2. 1H NMR (CD3OD-d4, 400 MHz) δ 8.76 (d, 1H), 8.35 (d, 1H), 7.99 (d, 1H), 7.73 (s, 1H), 7.61-7.66 (m, 2H), 6.29 (s, 1H), 4.48 (s, 2H), 4.26 (s, 2H), 2.39 (s, 3H), 2.27 (s, 3H).

Example 104: Preparation of N-((6-amino-2,4-dimethylpyridin-3-yl)methyl)-2-((3-chloroquinolin-6-yl)methyl)-1-methyl-1H-imidazole-4-carboxamide

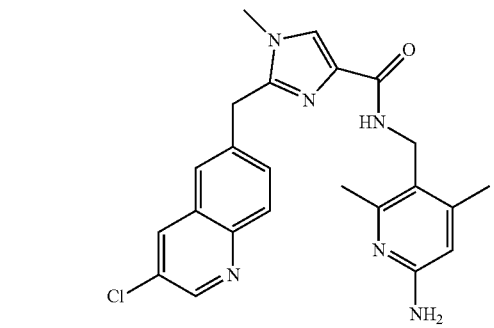

N-((6-amino-2,4-dimethylpyridin-3-yl)methyl)-2-((3-chloroquinolin-6-yl)methyl)-1-methyl-1H-imidazole-4-carboxamide

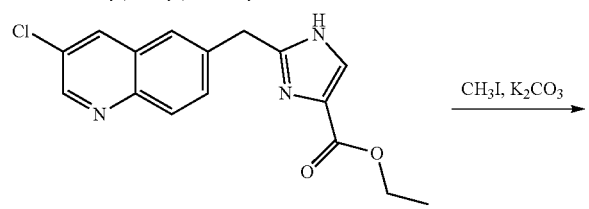

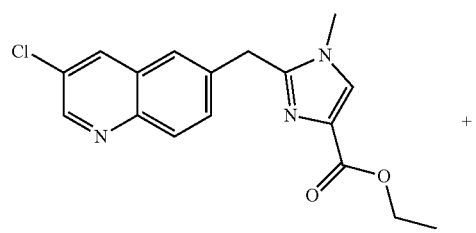

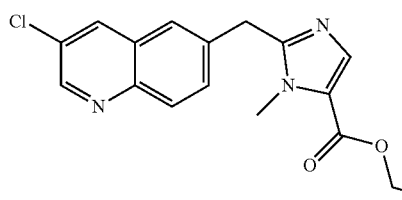

To a solution of ethyl 2-((3-chloroquinolin-6-yl)methyl)-1H-imidazole-4-carboxylate (190.0 mg, 0.603 mmol, 1.0 eq) and K2CO3 (125.0 mg, 0.905 mmol, 1.5 eq) in DMF (10.0 mL) was added CH3I (95.0 mg, 0.663 mmol, 1.1 eq). The reaction mixture was stirred at rt for 3.0 h. After the reaction was complete, water was added and the mixture was extracted with EA. The organic layer was washed with saturated aq. NaCl, dried over Na2SO4, filtered and concentrated in vacuo. The resulting residue was purified by column chromatography (PE/EA=10/1, v/v) to provide ethyl 2-((3-chloroquinolin-6-yl)methyl)-1-methyl-1H-imidazole-4-carboxylate (55.0 mg, 40.9%) and ethyl 2-((3-chloroquinolin-6-yl)methyl)-1-methyl-1H-imidazole-5-carboxylate (26.0 mg, 40.9%) as a white solid.

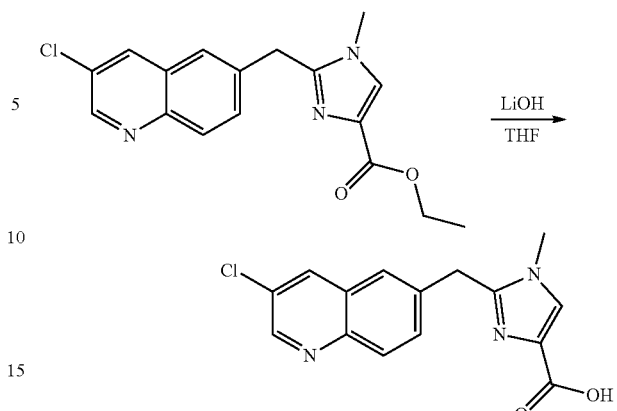

To a solution of ethyl 2-((3-chloroquinolin-6-yl)methyl)-1-methyl-1H-imidazole-4-carboxylate (55.0 mg, 0.167 mmol, 1.0 eq) in THF (10.0 mL) was added LiOH (35.0 mg, 0.836 mmol, 5.0 eq). The mixture was stirred at 50° C. for 2.0 days, then cooled and concentrated in vacuo. to provide 2-((3-chloroquinolin-6-yl)methyl)-1-methyl-1H-imidazole-4-carboxylic acid (50.0 mg, 99%) as a white solid which used in the next step.

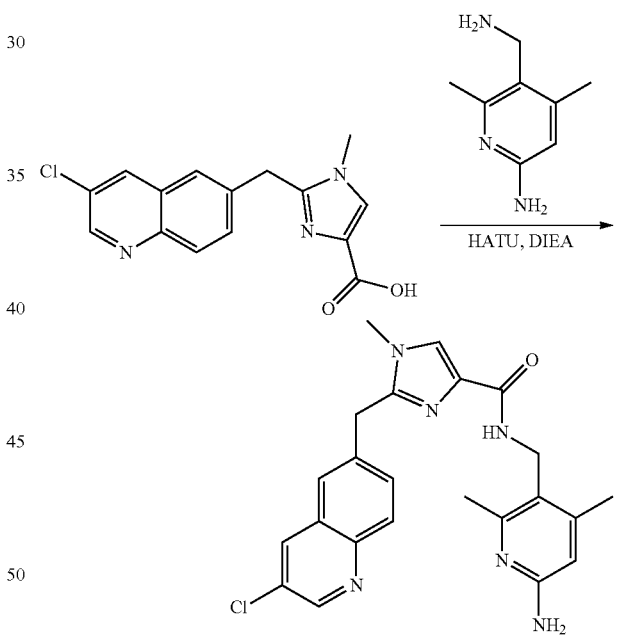

To a solution of 2-((3-chloroquinolin-6-yl)methyl)-1-methyl-1H-imidazole-4-carboxylic acid (50.0 mg, 0.167 mmol, 1.0 eq), 5-(aminomethyl)-4,6-dimethylpyridin-2-amine (38.0 mg, 0.249 mmol, 1.5 eq) and HATU (95.0 mg, 0.249 mmol, 1.5 eq) in DMF (3.0 mL) was added DIEA (64.0 mg, 0.498 mmol, 3.0 eq). The reaction mixture was stirred at rt for 1 h. Water was added, and the mixture was extracted with EA. The organic layer was washed with saturated aq. NaCl, dried over Na2SO4, filtered and concentrated. The resulting residue was purified by prep-HPLC to provide N-((6-amino-2,4-dimethylpyridin-3-yl)methyl)-2-((3-chloroquinolin-6-yl)methyl)-1-methyl-1H-imidazole-4-carboxamide (26.0 mg, 36%) as a white solid. LCMS (M+H+) m/z calculated 435.2, found 435.2. 1H NMR (CD3OD-d4, 400 MHz) δ 8.77 (d, 1H), 8.35 (d, 1H), 7.99 (d, 1H), 7.62-7.67 (m, 2H), 7.50 (s, 1H), 6.31 (s, 1H), 4.44 (s, 2H), 4.38 (s, 2H), 3.81 (s, 3H), 2.39 (s, 3H), 2.27 (s, 3H).

Example 105: Preparation of methyl N-((6-amino-2,4-dimethylpyridin-3-yl)methyl)-2-((3-chloroquinolin-6-yl)methyl)-1-methyl-1H-imidazole-5-carboxamide

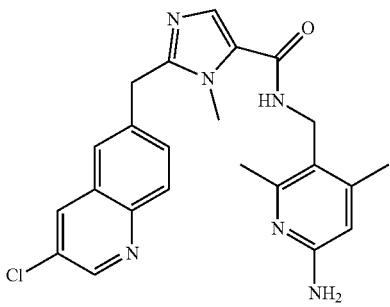

N-((6-amino-2,4-dimethylpyridin-3-yl)methyl)-2-((3-chloroquinolin-6-yl)methyl)-1-methyl-1H-imidazole-5-carboxamide

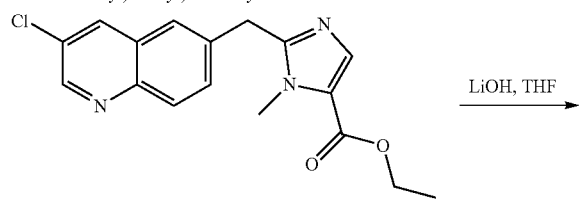

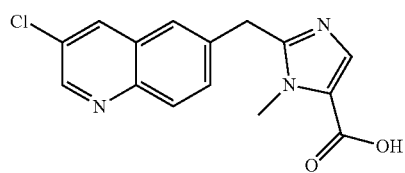

To a solution of ethyl 2-((3-chloroquinolin-6-yl)methyl)-1-methyl-1H-imidazole-5-carboxylate (26.0 mg, 0.079 mmol, 1.0 eq) in THF (10.0 mL) was added LiOH (17.0 mg, 0.395 mmol, 5.0 eq). The mixture was stirred at 50° C. for 2.0 days, then cooled and concentrated in vacuo to provide 2-((3-chloroquinolin-6-yl)methyl)-1-methyl-1H-imidazole-5-carboxylic acid (23.0 mg, 99%) as a white solid.

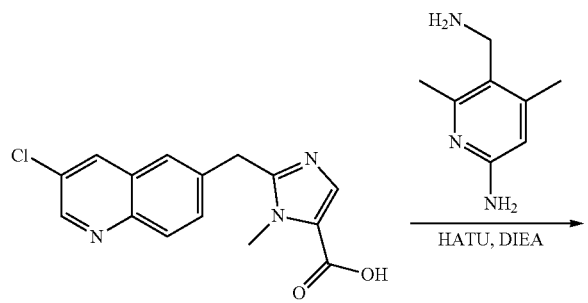

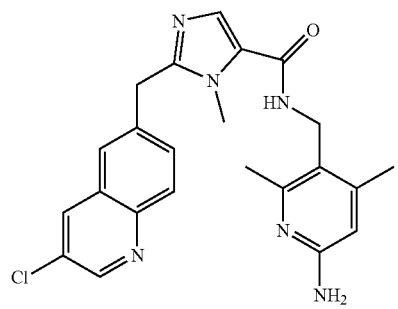

To a solution of 2-((3-chloroquinolin-6-yl)methyl)-1-methyl-1H-imidazole-5-carboxylic acid (23.0 mg, 0.079 mmol, 1.0 eq), 5-(aminomethyl)-4,6-dimethylpyridin-2-amine (18.0 mg, 0.119 mmol, 1.5 eq) and HATU (45.0 mg, 0.119 mmol, 1.5 eq) in DMF (3.0 mL) was added DIEA (31.0 mg, 0.238 mmol, 3.0 eq). The reaction mixture was stirred at rt for 1.0 h. After the reaction was complete, water was added, and the mixture was extracted with EA. The organic layer was washed with saturated aq. NaCl, dried over Na2SO4, filtered and concentrated in vacuo. The resulting residue was purified by prep-HPLC to provide N-((6-amino-2,4-dimethylpyridin-3-yl)methyl)-2-((3-chloroquinolin-6-yl)methyl)-1-methyl-1H-imidazole-5-carboxamide (10.5 mg, 30.9%) as a white solid. LCMS (M+H+) m/z calculated 435.2, found 435.2. 1H NMR (CD3OD-d4, 400 MHz) δ 8.74-8.77 (m, 1H), 8.31-8.34 (m, 1H), 7.99 (d, 1H), 7.62-7.66 (m, 3H), 6.27 (s, 1H), 4.47 (s, 2H), 4.30 (s, 2H), 3.62 (s, 3H), 2.38 (s, 3H), 2.25 (s, 3H).

Example 106: Preparation of N-((6-amino-2,4-dimethylpyridin-3-yl)methyl)-4-bromo-2-((3-chloroquinolin-6-yl)methyl)-1H-imidazole-5-carboxamide

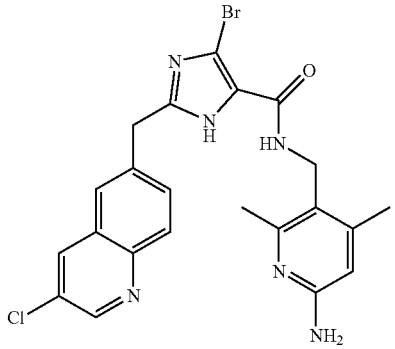

N-((6-amino-2,4-dimethylpyridin-3-yl)methyl)-4-bromo-2-((3-chloroquinolin-6-yl)methyl)-1H-imidazole-5-carboxamide

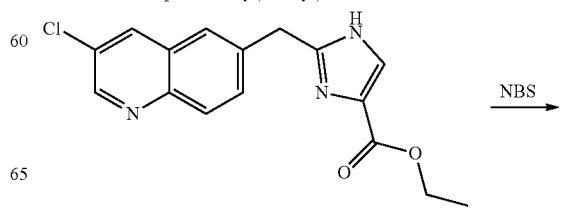

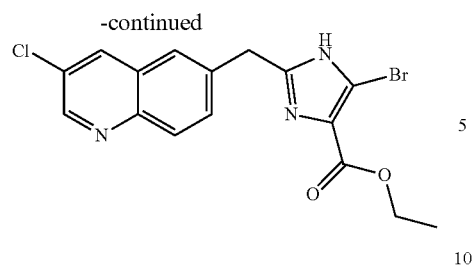

To a solution of ethyl 2-((3-chloroquinolin-6-yl) methyl)-1H-imidazole-4-carboxylate (345.0 mg, 1.1 mmol, 1.0 eq) in CH3CN (3.0 mL) was added NBS (214.0 mg, 1.2 mmol, 1.1 eq). The reaction mixture was stirred at rt overnight. The mixture was added saturated aq. Na2SO3 and extracted with EA. The organic layer was dried over Na2SO4, filtered and concentrated in vacuo. The resulting residue was purified by column chromatography (PE/EA=2/1, v/v) to provide ethyl 5-bromo-2-((3-chloroquinolin-6-yl)methyl)-1H-imidazole-4-carboxylate (325.0 mg, 76.8%).

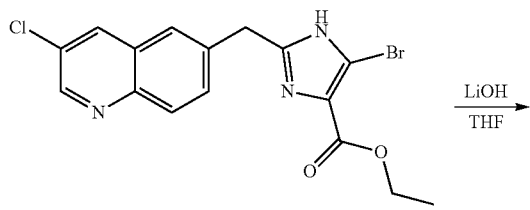

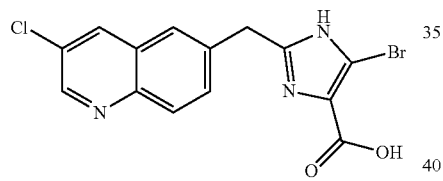

To a solution of ethyl 5-bromo-2-((3-chloroquinolin-6-yl) methyl)-1H-imidazole-4-carboxylate (150.0 mg, 0.382 mmol, 1.0 eq) in THF (10.0 mL) was added LiOH (80.0 mg, 1.908 mmol, 5.0 eq). The mixture was stirred at 50° C. for 2.0 days, then cooled and concentrated in vacuo to provide 5-bromo-2-((3-chloroquinolin-6-yl)methyl)-1H-imidazole-4-carboxylic acid (140.0 mg, 99%) as a white solid.

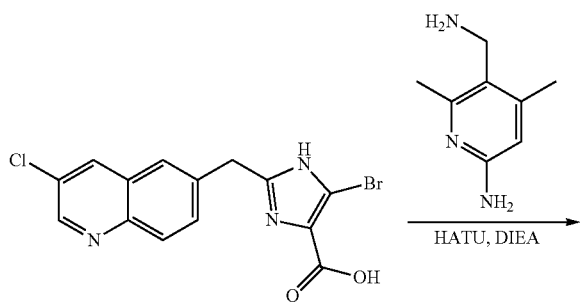

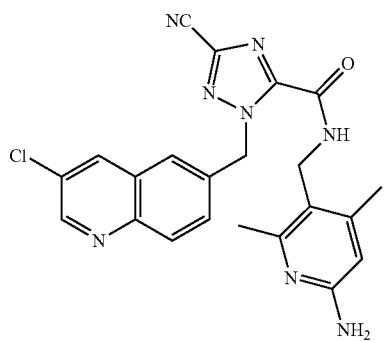

To a solution of 5-bromo-2-((3-chloroquinolin-6-yl) methyl)-1H-imidazole-4-carboxylic acid (140.0 mg, 0.382 mmol, 1.0 eq), 5-(aminomethyl)-4,6-dimethylpyridin-2-amine (87.0 mg, 0.573 mmol, 1.5 eq) and HATU (217.0 mg, 0.573 mmol, 1.5 eq) in DMF (5.0 mL) was added DIEA (148.0 mg, 1.146 mmol, 3.0 eq). The reaction mixture was stirred at rt for 1.0 h. After the reaction was complete, water was added, and the mixture was extracted with EA. The organic layer was washed with saturated aq. Na2CO3, dried over Na2SO4, filtered and concentrated in vacuo. The resulting residue was purified by prep-HPLC to provide N-((6-amino-2,4-dimethylpyridin-3-yl)methyl)-5-bromo-2-((3-chloroquinolin-6-yl)methyl)-1H-imidazole-4-carboxamide (113.0 mg, 59.5%) as a white solid. LCMS (M+H+) m/z calculated 501.0, found 501.0. 1H NMR (CD3OD-d4, 400 MHz) δ 8.77 (d, 1H), 8.36 (d, 1H), 7.99 (d, 1H), 7.75 (s, 1H), 7.66-7.68 (m, 1H), 6.56 (s, 1H), 4.48 (s, 2H), 4.24 (s, 2H), 2.54 (s, 3H), 2.43 (s, 3H).

Example 107: Preparation of N-((6-amino-2,4-dimethylpyridin-3-yl)methyl)-1-((3-chloroquinolin-6-yl)methyl)-3-cyano-1H-1,2,4-triazole-5-carboxamide N-((6-amino-2,4-dimethylpyridin-3-yl)methyl)-1-((3-chloroquinolin-6-yl)methyl)-3-cyano-1H-1,2,4-triazole-5-carboxamide

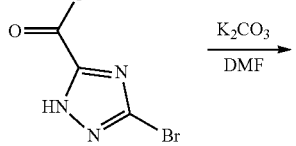

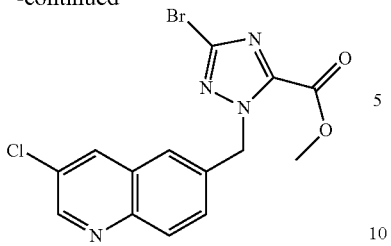

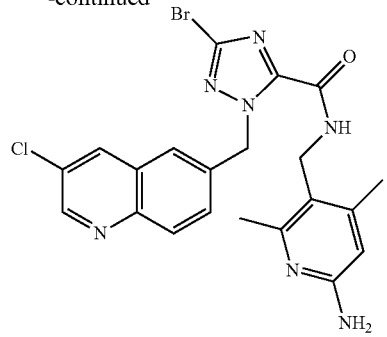

To a solution of 3-chloro-6-(chloromethyl)quinoline (359.0 mg, 1.7 mmol, 1.0 eq) and methyl 3-bromo-1H-1,2,4-triazole-5-carboxylate (350.0 mg, 1.70 mmol, 1.0 eq) in DMF (31.0 mL) was added K2CO3 (469.0 mg, 3.4 mmol, 2.0 eq). The mixture was stirred at rt overnight. The mixture was washed with water and saturated aq. NaCl, the organic layer was dried over Na2SO4, filtered and concentrated in vacuo. The resulting residue was purified by column chromatography (PE/EA=5/1, v/v) to provide methyl 3-bromo-1-((3-chloroquinolin-6-yl)methyl)-1H-1,2,4-triazole-5-carboxylate (286.0 mg, 44.3%) as a white solid.

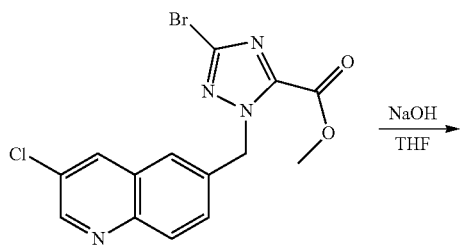

To a solution of methyl 3-bromo-1-((3-chloroquinolin-6-yl)methyl)-1H-1,2,4-triazole-5-carboxylate (286.0 mg, 0.75 mmol, 1.0 eq) in THF/H2O (10.0 mL, v:v=1:1) was added NaOH (60.0 mg, 1.5 mmol, 2.0 eq). The mixture was stirred at rt overnight, then concentrated in vacuo to provide 3-bromo-1-((3-chloroquinolin-6-yl) methyl)-1H-1,2,4-triazole-5-carboxylic acid (293.0 mg, crude) as a white solid.

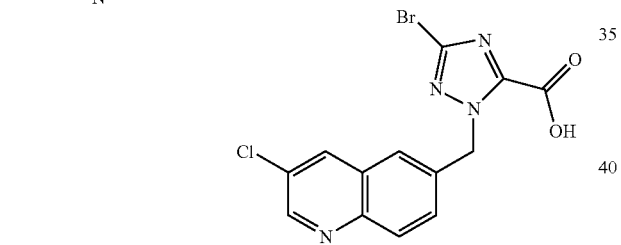

To a solution of 3-bromo-1-((3-chloroquinolin-6-yl)methyl)-1H-1,2,4-triazole-5-carboxylic acid (33.0 mg, 0.09 mmol, 1.0 eq), 5-(aminomethyl)-4,6-dimethylpyridin-2-amine (15.0 mg, 0.099 mmol, 1.1 eq) and HATU (50.0 mg, 0.135 mmol, 1.5 eq) in DMF (3.0 mL) was added DIEA (37.0 mg, 0.27 mmol, 3.0 eq). The reaction mixture was stirred at rt for 1.0 h. Water was added, and the mixture was extracted with EA. The organic layer was washed with saturated aq. NaCl, dried over Na2SO4, filtered and concentrated in vacuo. The resulting residue was purified by prep-HPLC to provide N-((6-amino-2,4-dimethylpyridin-3-yl)methyl)-3-bromo-1-((3-chloroquinolin-6-yl)methyl)-1H-1,2,4-triazole-5-carboxamide (11.1 mg, 24.7%) as a white solid. LCMS (M+H+) m/z calculated 500.1, found 500.0. 1H NMR (CD3OD-d4, 400 MHz) δ 8.81 (s, 1H), 8.40 (s, 1H), 8.02 (d, 1H), 7.86 (s, 1H), 7.76 (d, 1H), 6.40 (s, 1H), 6.01 (s, 2H), 4.47 (s, 2H), 2.43 (s, 3H), 2.30 (s, 3H).

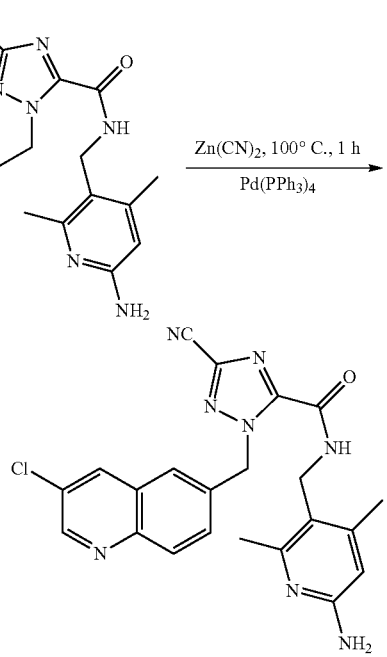

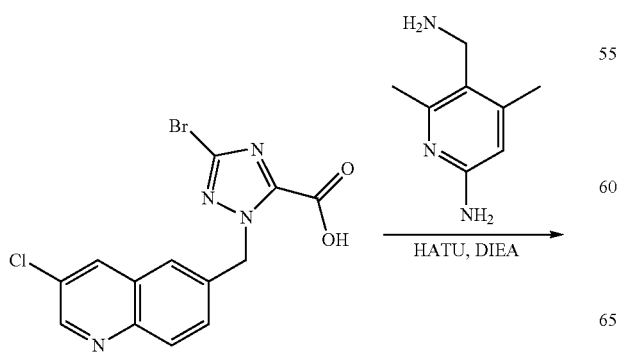

To a solution of N-((6-amino-2,4-dimethylpyridin-3-yl)methyl)-3-bromo-1-((3-chloroquinolin-6-yl)methyl)-1H-1,2,4-triazole-5-carboxamide (50.0 mg, 0.1 mmol, 1.0 eq) and Zn(CN)2 (23.0 mg, 0.2 mmol, 2.0 eq) in DMF (3.0 mL) was added Pd(PPh3)4 (12.0 mg, 0.01 mmol, 0.1 eq). The reaction mixture was stirred at 130° C. for 1 h under microwave irradiation. After the reaction was complete, it was cooled to rt and water was added. The mixture was extracted with EA. The organic layer was washed with saturated aq. NaCl, dried over Na2SO4, filtered and concentrated in vacuo. The resulting residue was purified by prep-HPLC to provide N-((6-amino-2,4-dimethylpyridin-3-yl)methyl)-1-((3-chloroquinolin-6-yl)methyl)-3-cyano-1H-1,2,4-triazole-5-carboxamide (6.0 mg, 13.5%) as a white solid. LCMS (M+H+) m/z calculated 447.1, found 447.2.1H NMR (CD3OD-d4, 400 MHz) δ 8.81 (s, 1H), 8.41 (s, 1H), 8.03 (d, 1H), 7.88 (s, 1H), 7.78 (d, 1H), 6.32 (s, 1H), 6.11 (s, 2H), 4.49 (s, 2H), 2.38 (s, 3H), 2.25 (s, 3H).

Example 108: Preparation of N-((6-amino-2,4-dimethylpyridin-3-yl)methyl)-1-((3-chloroquinolin-6-yl)methyl)-5-cyano-1H-pyrazole-3-carboxamide

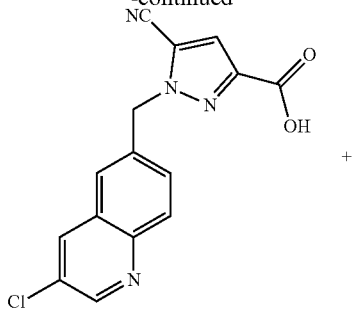

-continued

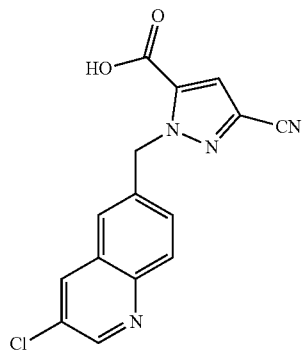

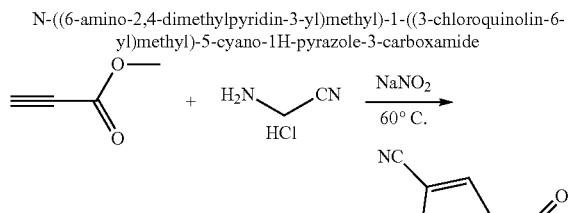

N-((6-amino-2,4-dimethylpyridin-3-yl)methyl)-1-((3-chloroquinolin-6-yl)methyl)-5-cyano-1H-pyrazole-3-carboxamide To a solution of methyl propiolate (300.0 mg, 3.57 mmol, 1.0 eq) and 2-aminoacetonitrile (660.0 mg, 7.14 mmol, 2.0 eq) in CHCl3/H2O (31.0 mL, v:v=1:1) was added NaNO2 (740.0 mg, 10.71 mmol, 3.0 eq). The mixture was stirred at rt for 12.0 h, then stirred at 60° C. for 3.0 h. After being cooled, the mixture was washed with saturated aq. NaHCO3. The organic layer was dried over Na2SO4, filtered and concentrated in vacuo The resulting residue was purified by column chromatography (PE/EA=2/1, v/v) to provide methyl 5-cyano-1H-pyrazole-3-carboxylate (151.0 mg, 28%) as a white solid.

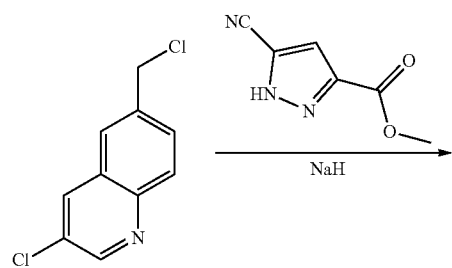

To a solution of methyl 5-cyano-1H-pyrazole-3-carboxylate (151.0 mg, 1.0 mmol, 1.0 eq) and NaH (60% in mineral oil, 120.0 mg, 3.0 mmol, 3.0 eq) in DMF (5.0 mL) was added 3-chloro-6-chloromethyl-quinoline (211.0 mg, 1.0 mmol, 1.0 eq). The mixture was stirred at 0° C. for 2.0 h under nitrogen atmosphere, then quenched by water and extracted by EA. The organic layer was concentrated in vacu. The resulting residue was purified by prep-HPLC to provide 1-((3-chloroquinolin-6-yl)methyl)-5-cyano-1H-pyrazole-3-carboxylic acid (30.0 mg, 22.5%) and 1-((3-chloroquinolin-6-yl)methyl)-3-cyano-1H-pyrazole-5-carboxylic acid (40.0 mg, 22.5%).

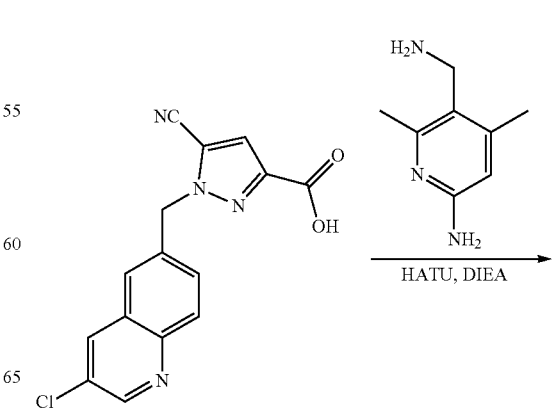

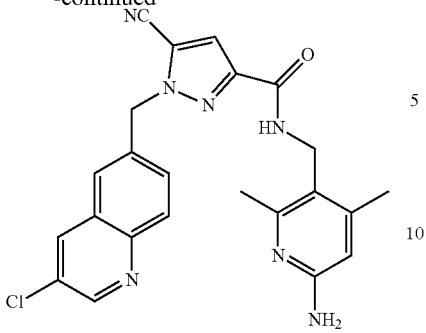

To a solution of 1-((3-chloroquinolin-6-yl) methyl)-5-cyano-1H-pyrazole-3-carboxylic acid (30.0 mg, 0.096 mmol, 1.0 eq), 5-(aminomethyl)-4,6-dimethylpyridin-2-amine (16.0 mg, 0.106 mmol, 1.1 eq) and HATU (55.0 mg, 0.144 mmol, 1.5 eq) in DMF (3.0 mL) was added DIEA (37.0 mg, 0.288 mmol, 3.0 eq). The reaction mixture was stirred at rt for 1.0 h. Water was added. The mixture was extracted with EA. The organic layer was washed with water, dried over Na2SO4, filtered and concentrated in vacuo. The resulting residue was purified by prep-HPLC to provide N-((6-amino-2,4-dimethylpyridin-3-yl)methyl)-1-((3-chloroquinolin-6-yl)methyl)-5-cyano-1H-pyrazole-3-carboxamide (12.0 mg, 29%) as a white solid. LCMS (M+Na+) m/z calculated 446.1, found 446.3. 1H NMR (CD3OD-d4, 400 MHz) δ 8.82 (d, 1H), 8.41 (d, 1H), 8.06 (d, 1H), 7.84 (s, 1H), 7.72 (d, 1H), 7.41 (s, 1H), 6.30 (s, 1H), 5.79 (s, 2H), 4.51 (s, 2H), 2.40 (s, 3H), 2.27 (s, 3H).

Example 109: Preparation of N-((6-amino-2,4-dimethylpyridin-3-yl)methyl)-1-((3-chloroquinolin-6-yl)methyl)-3-cyano-1H-pyrazole-5-carboxamide

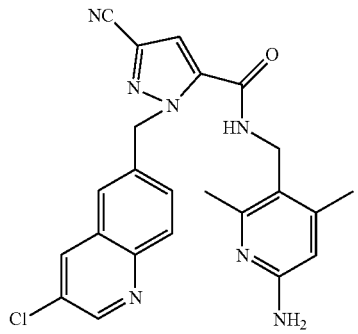

N-((6-amino-2,4-dimethylpyridin-3-yl)methyl)-1-((3-chloroquinolin-6-yl)methyl)-3-cyano-1H-pyrazole-5-carboxamide

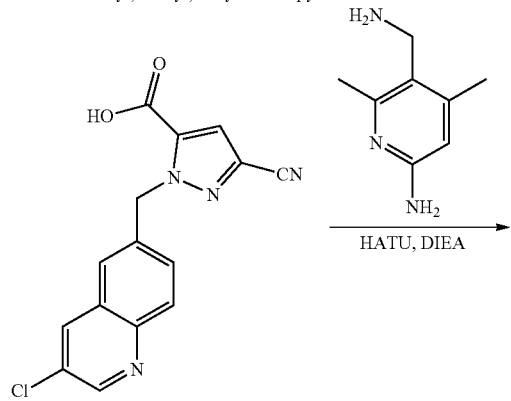

HATU, DIEA

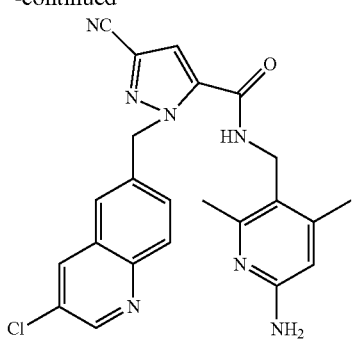

To a solution of 1-((3-chloroquinolin-6-yl)methyl)-3-cyano-1H-pyrazole-5-carboxylic acid (40.0 mg, 0.128 mmol, 1.0 eq), 5-(aminomethyl)-4,6-dimethylpyridin-2-amine (21.0 mg, 0.141 mmol, 1.1 eq) and HATU (73.0 mg, 0.192 mmol, 1.5 eq) in DMF (3.0 mL) was added DIEA (50.0 mg, 0.384 mmol, 3.0 eq). The reaction mixture was stirred at rt for 1.0, water was added. The mixture was extracted with EA. The organic layer was washed with water, dried over Na2SO4, filtered and concentrated in vacuo. The resulting residue was purified by prep-HPLC to provide N-((6-amino-2,4-dimethylpyridin-3-yl)methyl)-1-((3-chloroquinolin-6-yl)methyl)-3-cyano-1H-pyrazole-5-carboxamide (20.0 mg, 35%). LCMS (M+Na+) m/z calculated 446.1, found 446.3. 1H NMR (CD3OD-d4, 400 MHz) δ 8.81 (d, 1H), 8.36 (d, 1H), 7.99 (d, 1H), 7.69 (s, 1H), 7.62 (d, 1H), 7.26 (s, 1H), 6.49 (s, 1H), 6.01 (s, 2H), 4.38 (s, 2H), 2.40 (s, 3H), 2.23 (s, 3H).

Example 110: Preparation of N-((6-amino-2,4-dimethylpyridin-3-yl)methyl)-1-((3-chloroquinolin-6-yl)methyl)-2-(hydroxymethyl)-1H-imidazole-4-carboxamide and N-((6-amino-2,4-dimethylpyridin-3-yl)methyl)-1-((3-chloroquinolin-6-yl)methyl)-2-(hydroxymethyl)-1H-imidazole-5-carboxamide

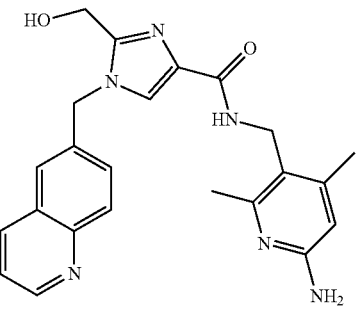

N-((6-amino-2,4-dimethylpyridin-3-yl)methyl)-1-((3-chloroquinolin-6-yl)methyl)-2-(hydroxymethyl)-1H-imidazole-4-carboxamide -continued

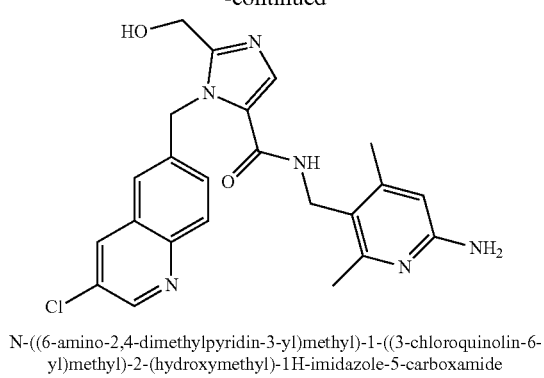

N-((6-amino-2,4-dimethylpyridin-3-yl)methyl)-1-((3-chloroquinolin-6-yl)methyl)-2-(hydroxymethyl)-1H-imidazole-5-carboxamide

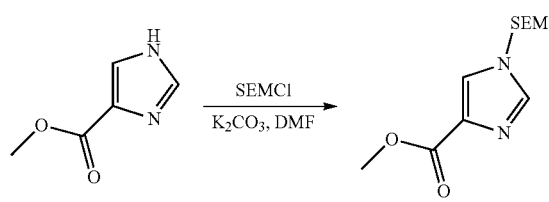

To a solution of methyl 1H-imidazole-4-carboxylate (1.26 g, 10.0 mmol, 1.0 eq) in DMF (18.0 mL) was added K2CO3 (3.5 g, 25.0 mmol, 2.5 eq), followed by 2-(trimethylsilyl)ethoxymethyl chloride (2.3 mL, 13.0 mmol, 1.3 eq). The reaction mixture was stirred at 80° C. for 12.0 h, then cooled and quenched by water (100.0 mL) and extracted with EA (50.0 mL×2). The combined organic layers were dried over Na2SO4, filtered and concentrated in vacuo. The resulting residue was purified by column chromatography (EA/PE=1/30, v/v) to provide methyl 1-((2-(trimethylsilyl)ethoxy)methyl)-1H-imidazole-4-carboxylate (1.08 g, 42.5%).

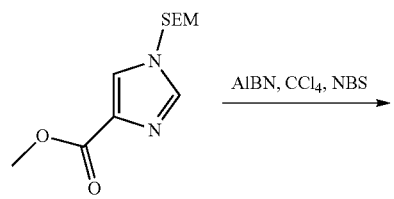

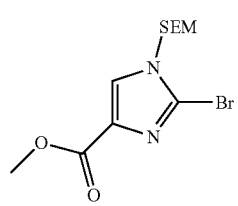

To a solution of methyl 1-((2-(trimethylsilyl)ethoxy)methyl)-1H-imidazole-4-carboxylate (1.08 g, 4.2 mmol, 1.0 eq) in CCl4 (30.0 mL) was added NBS (0.82 g, 4.6 mmol, 1.1 eq) and AIBN (34.0 mg, 0.21 mmol, 0.05 eq). The mixture was stirred at 65° C. for 3.0 h, then cooled and concentrated. The resulting residue was purified by column chromatography (EA/PE=1/30, v/v) to provide methyl 2-bromo-1-((2-(trimethylsilyl)ethoxy)methyl)-1H-imidazole-4-carboxylate (620.0 mg, 44.9%).

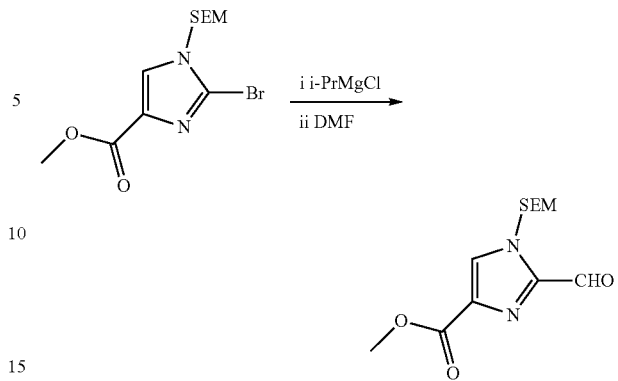

To a solution of methyl 2-bromo-1-((2-(trimethylsilyl)ethoxy)methyl)-1H-imidazole-4-carboxylate (620.0 mg, 1.85 mmol) in dry THF (20.0 mL) was added i-PrMgCl (3.7 mL, 5.6 mmol, 3 eq) at −40° C. under N2 atmosphere. The resulting mixture was allowed to stir for 15 min and cooled to −78° C. The reaction was quenched by DMF (1.0 mL). After the reaction mixture was slowly warmed to rt, it was acidified with 3N HCl to pH 6-7 and concentrated in vacuo. The residual was extracted with EA (30 mL×2) and the combined organic layers were concentrated to provide crude methyl 2-formyl-1-((2-(trimethylsilyl)ethoxy)methyl)-1H-imidazole-4-carboxylate (500.0 mg, 95.1%).

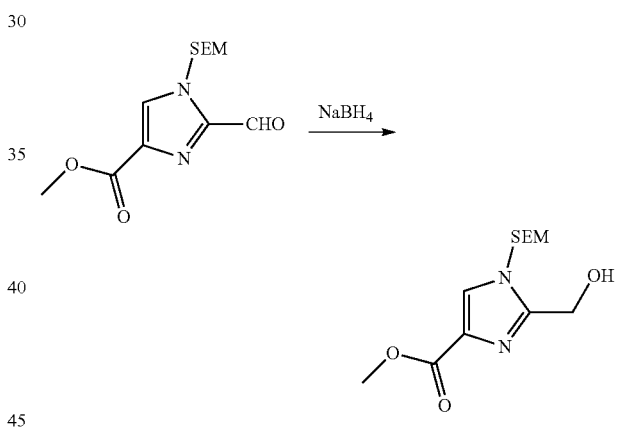

To a solution of methyl 2-formyl-1-((2-(trimethylsilyl)ethoxy)methyl)-1H-imidazole-4-carboxylate (500.0 mg, 1.76 mmol, 1.0 eq) in MeOH (20.0 mL) was added NaBH4 (67.0 mg, 1.76 mmol, 1.0 eq) at 0° C. The reaction mixture was stirred for 1 h. Water (30.0 mL) was added and the mixture was extracted with EA (30.0 mL×2). The combined organic layers were washed with water, dried over Na2SO4, filtered and concentrated. The resulting residue was purified by column chromatography (PE/EA=5/1, v/v) to provide methyl 2-(hydroxymethyl)-1-((2-(trimethylsilyl)ethoxy)methyl)-1H-imidazole-4-carboxylate (200.0 mg, 39.7%).

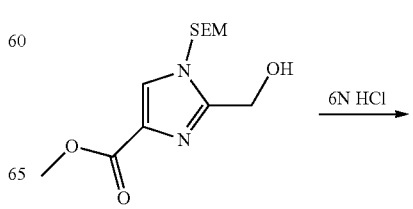

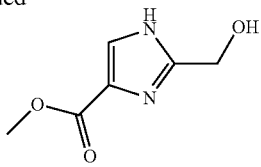

To a solution of methyl 2-(hydroxymethyl)-1-((2-(trimethylsilyl)ethoxy) methyl)-1H-imidazole-4-carboxylate (200.0 mg, 0.7 mmol, 1.0 eq) in THF (5.0 mL) was added 6 N HCl (4.0 mL). The mixture was stirred at 50° C. for 12 h, then cooled and concentrated in vacuo. The resulting residue was purified by column chromatography (PE/EA=2/1, v/v) to provide methyl 2-(hydroxymethyl)-1H-imidazole-4-carboxylate (58.0 mg, 53.1%).

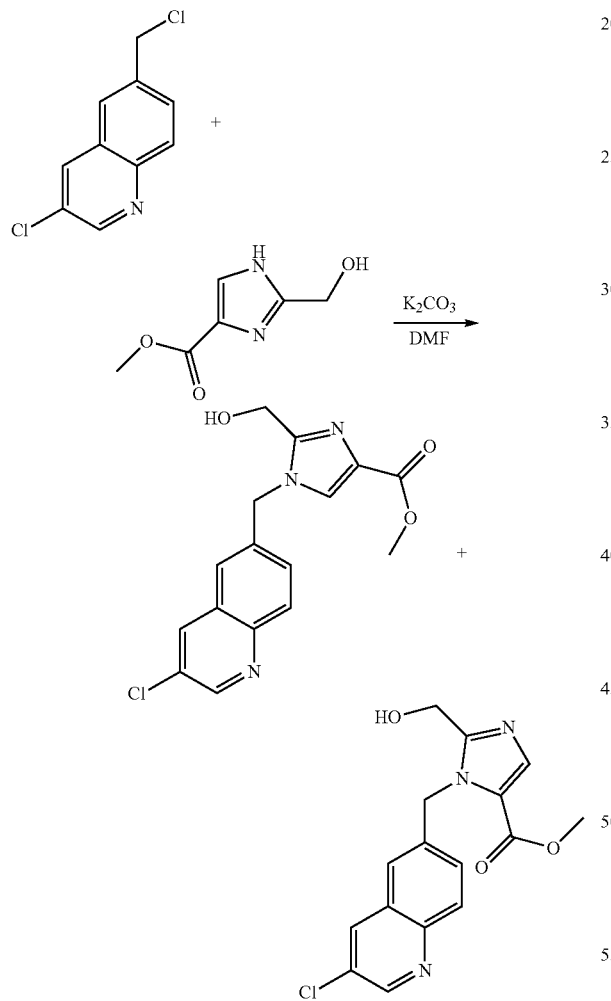

To a solution of methyl 2-(hydroxymethyl)-1H-imidazole-4-carboxylate (58.0 mg, 0.37 mmol, 1.0 eq) and K2CO3 (100.0 mg, 0.74 mmol, 2.0 eq) in DMF (5 mL) was added 3-chloro-6-chloromethyl-quinoline (80.0 mg, 0.4 mmol, 1.1 eq). The mixture was stirred at 85° C. for 2 h under nitrogen atmosphere, then cooled, poured into water (30.0 mL) and extracted with EA (30.0 mL×2). The combined organic layers were washed with brine, dried over Na2SO4, filtered and concentrated in vacuo. The resulting residue was purified by column chromatography (PE/EA=2/1, v/v) to provide the mixture (methyl 1-((3-chloroquinolin-6-yl)methyl)-2-(hydroxymethyl)-1H-imidazole-4-carboxylate and methyl 1-((3-chloroquinolin-6-yl)methyl)-2-(hydroxymethyl)-1H-imidazole-5-carboxylate 99.0 mg, 80.8%).

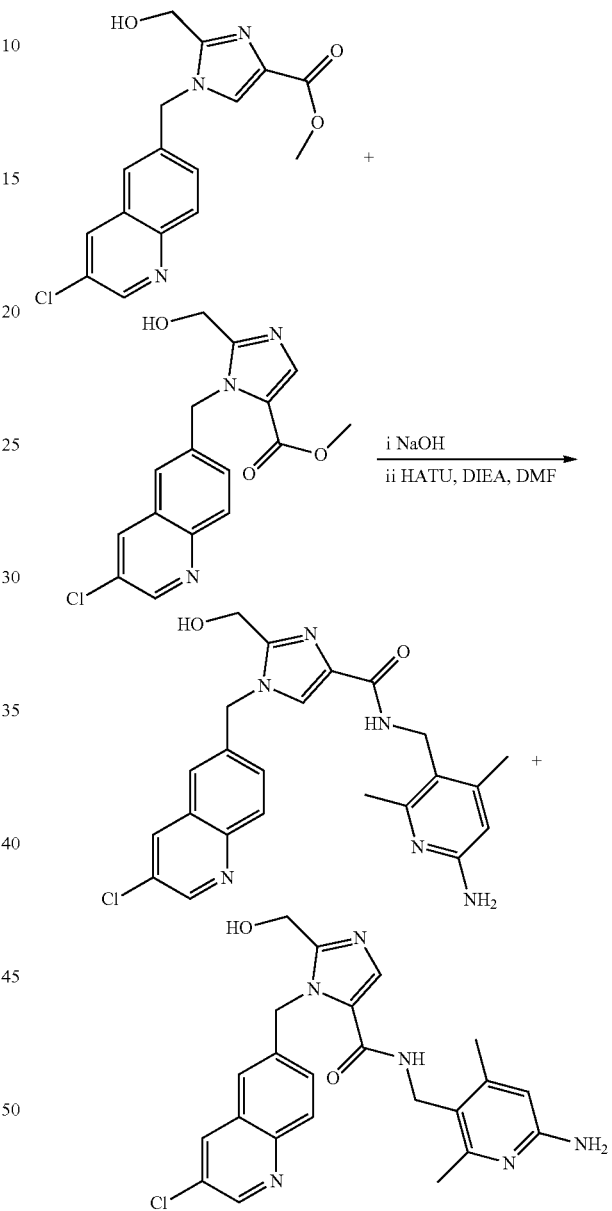

To a mixture of methyl 1-((3-chloroquinolin-6-yl)methyl)-2-(hydroxymethyl)-1H-imidazole-4-carboxylate and methyl 1-((3-chloroquinolin-6-yl)methyl)-2-(hydroxymethyl)-1H-imidazole-5-carboxylate (99.0 mg, mixture) in MeOH (6.0 mL) was added NaOH aqueous solution (1 N, 0.3 mL). The reaction mixture was stirred at 50° C. for 2 h, then cooled and adjusted to pH 5.0. The solvent was removed in vacuo, and the resulting residue was dissolved in DMF (2.0 mL). 5-(Aminomethyl)-4,6-dimethylpyridin-2-amine (45.0 mg, 0.3 mmol, 1.0 eq), HATU (130 mg, 0.33 mmol, 1.1 eq) and DIEA (68.0 mg, 0.6 mmol, 2.0 eq) were added. The mixture was stirred at rt for 2 h under N2 atmosphere, then purified via prep-TLC to provide N-((6-amino-2,4-dimethylpyridin-3-yl)methyl)-1-((3-chloroquinolin-6-yl)methyl)-2-(hydroxymethyl)-1H-imidazole-4-carboxamide (8.4 mg, 6.2%). 1H NMR (CD3OD-d4, 400 MHz) δ 8.81 (d, 1H), 8.39 (d, 1H), 8.63 (d, 1H), 8.04 (d, 1H), 7.74-7.69 (m, 2H), 6.31 (s, 1H), 5.54 (s, 2H), 4.60 (s, 2H), 4.48 (s, 2H), 2.40 (s, 3H), 2.28 (s, 3H). LCMS (M+H+) m/z calculated 451.2, found 451.2. N-((6-amino-2,4-dimethylpyridin-3-yl)methyl)-1-((3-chloroquinolin-6-yl)methyl)-2-(hydroxymethyl)-1H-imidazole-5-carboxamide (1.5 mg, 1.1%). 1H NMR (CD3OD-d4, 400 MHz) δ 8.79 (t, 1H), 8.30 (s, 1H), 8.79 (t, 1H), 7.61-7.48 (m, 3H), 6.16 (s, 1H), 5.93 (s, 2H), 4.69 (s, 2H), 4.28 (s, 2H), 2.14 (s, 3H), 1.99 (s, 3H). LCMS (M+H+) m/z calculated 451.2, found 451.2.

Example 111: Preparation of N4-((6-amino-2,4-dimethylpyridin-3-yl)methyl)-1-((3-chloroquinolin-6-yl)methyl)-1H-imidazole-2,4-dicarboxamide

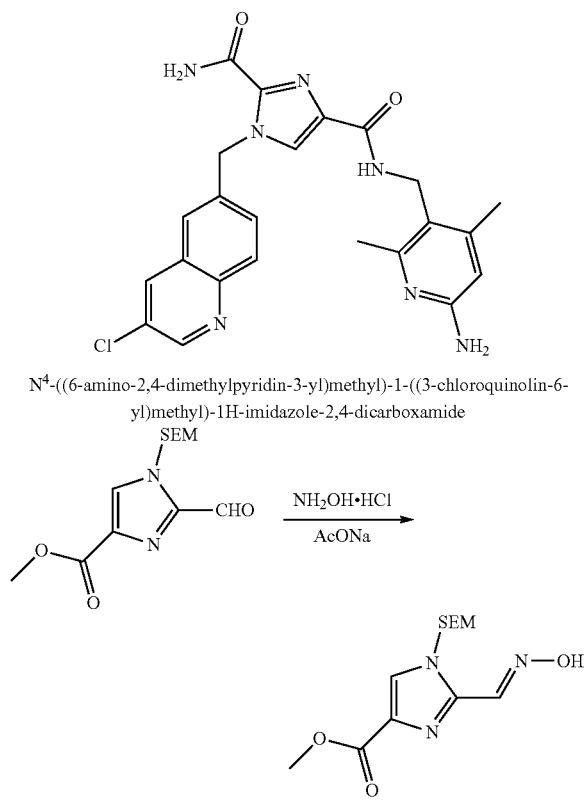

N4-((6-amino-2,4-dimethylpyridin-3-yl)methyl)-1-((3-chloroquinolin-6-yl)methyl)-1H-imidazole-2,4-dicarboxamide

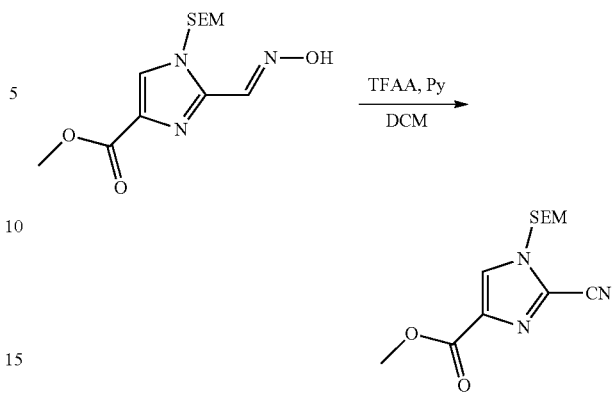

To a solution of methyl 2-((hydroxyimino)methyl)-1-((2-(trimethylsilyl)ethoxy) methyl)-1H-imidazole-4-carboxylate (1.4 g, 4.6 mmol, 1.0 eq) in DCM (20.0 mL) were added pyridine (1.48 g, 18.7 mmol, 4.0 eq) and TFAA (2.0 mL, 13.8 mmol, 3.0 eq). The reaction mixture was stirred at rt for 12 h. The solvent was removed in vacuo, diluted with EA (50 mL), washed with aq. NaHCO₃ solution, dried over Na2SO4, filtered and concentrated in vacuo. The resulting residue was purified by column chromatography (PE/EA=10/1, v/v) to provide methyl 2-cyano-1-((2-(trimethylsilyl)ethoxy)methyl)-1H-imidazole-4-carboxylate (1.18 g, 91.2%).

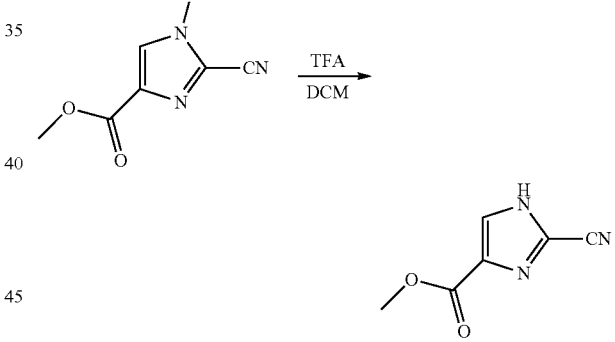

To a solution of methyl 2-formyl-1-((2-(trimethylsilyl)ethoxy)methyl)-1H-imidazole-4-carboxylate (2.0 g, 7.0 mmol, 1.0 eq) in EtOH/H2O (20.0 mL/10.0 mL) were added NH2OH.HCl (0.75 g, 10.5 mmol, 1.5 eq) and NaOAc (1.2 g, 14.0 mmol, 2.0 eq). The reaction mixture was heated at 70° C. for 2 h. Water (30.0 mL) was added and the mixture was extracted with EA (30.0 mL×2). The combined organic layers were washed with water, dried over Na2SO4, filtered and concentrated in vacuo. The resulting residue was purified by column chromatography (PE/EA=10/1, v/v) to provide methyl 2-((hydroxyimino)methyl)-1-((2-(trimethylsilyl)ethoxy)methyl)-1H-imidazole-4-carboxylate (1.4 g, 66.9%).

To a solution of methyl 2-cyano-1-((2-(trimethylsilyl)ethoxy)methyl)-1H-imidazole-4-carboxylate (1.18 g, 4.2 mmol, 1.0 eq) in DCM (5.0 mL) was added TFA (2.0 mL). The reaction mixture was stirred at rt for 12 h. The solvent was removed, diluted with EA (50 mL), washed with aq. NaHCO₃ solution, dried over Na2SO4, filtered and concentrated in vacuo. The resulting residue was purified by column chromatography (PE/EA=5/1, v/v) to provide methyl 2-cyano-1H-imidazole-4-carboxylate (0.48 g, 75.9%).

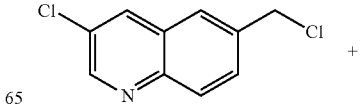

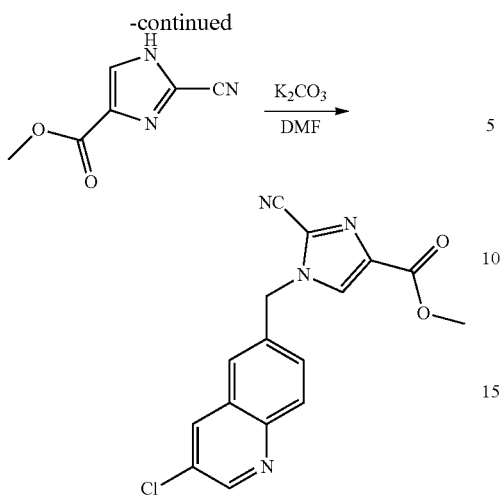

To a solution of methyl 2-cyano-1H-imidazole-4-carboxylate (0.3 g, 2.0 mmol, 1.0 eq) and K2CO3 (0.56 g, 4.0 mmol, 2.0 eq) in DMF (5 mL) was added 3-chloro-6-chloromethyl-quinoline (0.44 g, 2.1 mmol, 1.05 eq). The mixture was stirred at 85° C. for 3 h under nitrogen atmosphere, then cooled, poured into water (30.0 mL) and extracted with EA (30.0 mL×2). The combined organic layers were washed with brine, dried over Na2SO4, filtered and concentrated in vacuo. The resulting residue was purified by column chromatography (PE/EA=2/1, v/v) to provide the product. (0.4 g, 61.3%).

To a mixture of methyl 1-((3-chloroquinolin-6-yl)methyl)-2-cyano-1H-imidazole-4-carboxylate (150.0 mg, 0.46 mmol, 1.0 eq) in THF (10.0 mL) was added LiOH aqueous solution (1 N, 0.7 mL). The reaction mixture was stirred at rt for 12 h, water (10.0 mL) was added and extracted with EA (20.0 mL×2). The combined organic layers were washed with brine, dried over Na2SO4, filtered and concentrated in vacuo. The resulting residue was purified by column chromatography (PE/EA=1/1, v/v) to provide methyl 2-carbamoyl-1-((3-chloroquinolin-6-yl)methyl)-1H-imidazole-4-carboxylate (94.0 mg, 59.3%).

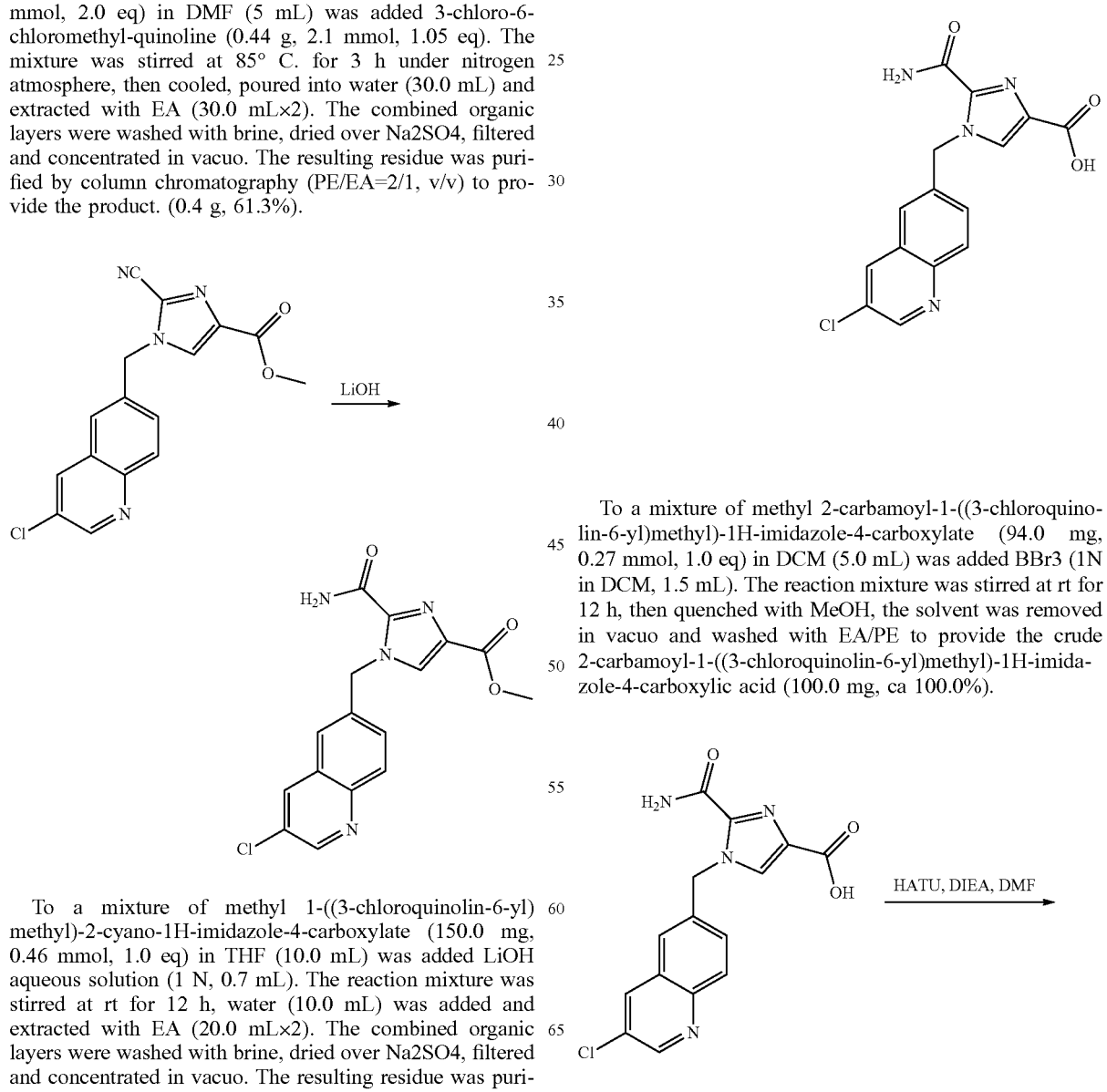

To a mixture of methyl 2-carbamoyl-1-((3-chloroquinolin-6-yl)methyl)-1H-imidazole-4-carboxylate (94.0 mg, 0.27 mmol, 1.0 eq) in DCM (5.0 mL) was added BBr3 (1N in DCM, 1.5 mL). The reaction mixture was stirred at rt for 12 h, then quenched with MeOH, the solvent was removed in vacuo and washed with EA/PE to provide the crude 2-carbamoyl-1-((3-chloroquinolin-6-yl)methyl)-1H-imidazole-4-carboxylic acid (100.0 mg, ca 100.0%).

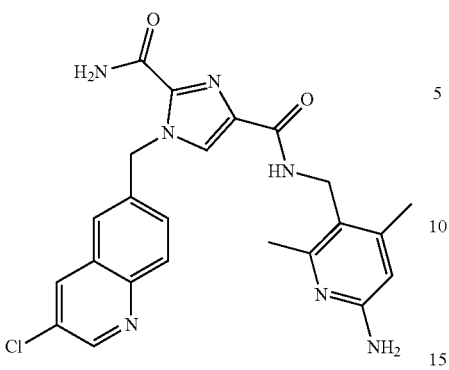

To a solution of 2-carbamoyl-1-((3-chloroquinolin-6-yl)methyl)-1H-imidazole-4-carboxylic acid (100.0 mg, 0.3 mmol, 1.0 eq) in DMF (5.0 mL) were added 5-(aminomethyl)-4,6-dimethylpyridin-2-amine (45.0 mg, 0.3 mmol, 1.0 eq), HATU (130 mg, 0.33 mmol, 1.1 eq) and DIEA (68.0 mg, 0.6 mmol, 2.0 eq). The mixture was stirred at rt for 2 h under N2, then purified by prep-TLC to provide N-((6-amino-2,4-dimethylpyridin-3-yl)methyl)-1-((3-chloroquinolin-6-yl)methyl)-2-(hydroxymethyl)-1H-imidazole-4-carboxamide (55.0 mg, 39.5%). 1H NMR (CD3OD-d4, 400 MHz) δ 8.78 (d, 1H), 8.37 (s, 1H), 8.01 (d, 1H), 7.90 (s, 1H), 7.73-7.67 (m, 2H), 6.31 (s, 1H), 5.93 (s, 2H), 4.50 (s, 2H), 2.41 (s, 3H), 2.28 (s, 3H). LCMS (M+H+) m/z calculated 464.2, found 464.2.

Example 112: Preparation of N-((6-amino-2,4-dimethylpyridin-3-yl)methyl)-2-(aminomethyl)-1-((3-chloroquinolin-6-yl)methyl)-1H-imidazole-4-carboxamide

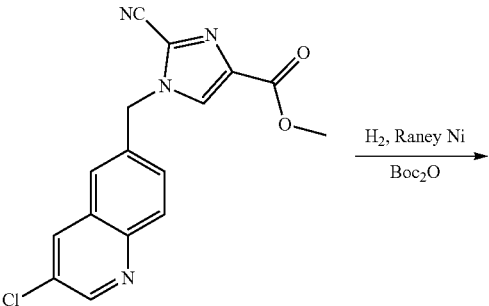

N-((6-amino-2,4-dimethylpyridin-3-yl)methyl)-2-(aminomethyl)-1-((3-chloroquinolin-6-yl)methyl)-1H-imidazole-4-carboxamide

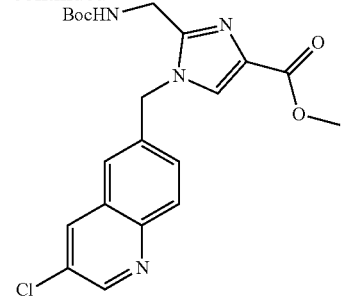

A mixture of methyl 1-((3-chloroquinolin-6-yl)methyl)-2-cyano-1H-imidazole-4-carboxylate (100 mg, 0.3 mmol, 1.0 eq), Raney Ni (50 mg) and Boc2O (100.0 mg, 0.45 mmol, 1.5 eq) in THF (10.0 mL) was stirred at rt for 12 h under hydrogen (1 atm). The Raney Ni was filtered off and washed with MeOH. The solvent was removed in vacuo and the resulting residue was purified by column chromatography (PE/EA=1/1, v/v) to provide methyl 2-(((tert-butoxycarbonyl)amino)methyl)-1-((3-chloroquinolin-6-yl)methyl)-1H-imidazole-4-carboxylate (140 mg, ca 100%).

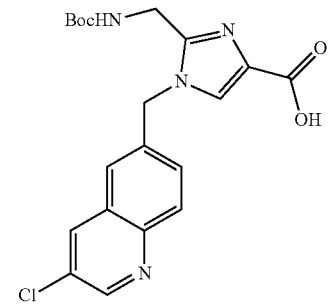

To a mixture of methyl 2-(((tert-butoxycarbonyl)amino)methyl)-1-((3-chloroquinolin-6-yl)methyl)-1H-imidazole-4-carboxylate (140 mg, 0.32 mmol) in MeOH (6.0 mL) was added aqueous LiOH solution (1 N, 0.6 mL). The reaction mixture was stirred at 50° C. for 2 h, then cooled and adjusted to pH 5.0 with HOAc, concentrated in vacuo to provide crude 2-(((tert-butoxycarbonyl)amino)methyl)-1-((3-chloroquinolin-6-yl)methyl)-1H-imidazole-4-carboxylic acid which used in the next step without further purification.

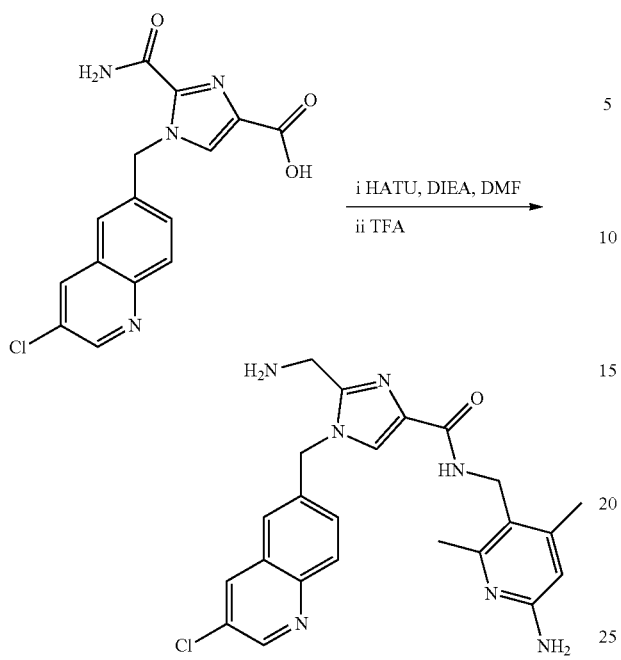

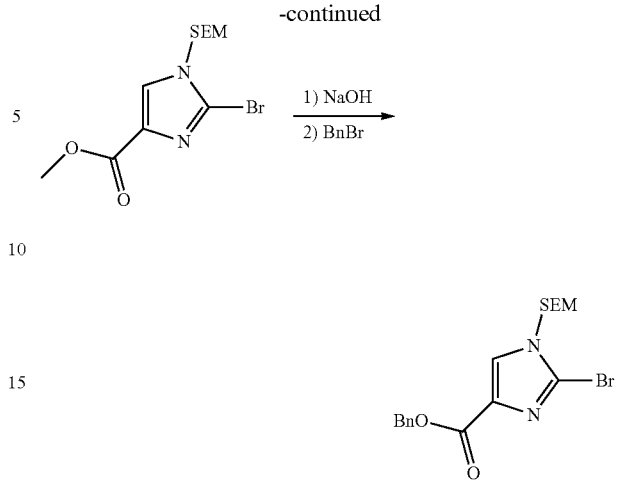

To a mixture of 2-carbamoyl-1-((3-chloroquinolin-6-yl)methyl)-1H-imidazole-4-carboxylic acid (120.0 mg, 0.32 mmol, 1.0 eq) in DMF (5.0 mL) were added 5-(aminomethyl)-4,6-dimethylpyridin-2-amine (55.0 mg, 0.32 mmol, 1.0 eq), HATU (140 mg, 0.35 mmol, 1.2 eq) and DIEA (68.0 mg, 0.6 mmol, 2.0 eq). The mixture was stirred at rt for 2 h under N2. After the reaction was complete, the mixture was poured into water (30.0 mL) and extracted with EA (30.0 mL×2). The combined organic layers were washed with brine, dried over Na2SO4, filtered and concentrated in vacuo. The resulting residue was dissolved in DCM (5.0 mL), then TFA (1.0 mL) was added. The mixture was stirred for 2 h and concentrated in vacuo. The resulting residue was purified by prep-TLC to provide N-((6-amino-2,4-dimethylpyridin-3-yl)methyl)-2-(aminomethyl)-1-((3-chloroquinolin-6-yl)methyl)-1H-imidazole-4-carboxamide (28.7 mg, 19.9%). 1H NMR (CD3OD-d4, 400 MHz) δ 8.81 (d, 1H), 8.39 (d, 1H), 8.05 (d, 1H), 7.73-7.62 (m, 3H), 6.31 (s, 1H), 5.48 (s, 2H), 4.93 (s, 2H), 3.80 (s, 2H), 2.41 (s, 3H), 2.29 (s, 3H). LCMS (M+H+) m/z calculated 450.2, found 450.2.

Example 113: Preparation of N-((6-amino-2,4-dimethylpyridin-3-yl)methyl)-1-((3-chloroquinolin-6-yl)methyl)-2-cyano-1H-imidazole-4-carboxamide

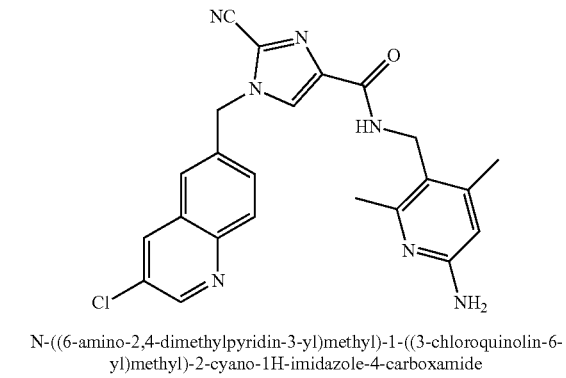

N-((6-amino-2,4-dimethylpyridin-3-yl)methyl)-1-((3-chloroquinolin-6-yl)methyl)-2-cyano-1H-imidazole-4-carboxamide To a mixture of methyl 2-bromo-1-((2-(trimethylsilyl)ethoxy)methyl)-1H-imidazole-4-carboxylate (530.0 mg, 1.6 mmol) in MeOH (10.0 mL) was added aqueous LiOH solution (1 N, 3.2 mL). The reaction mixture was stirred at 50° C. for 2 h, then cooled and concentrated in vacuo. The resulting residue was dissolved in DMF (5.0 mL) and BnBr (0.2 mL, 1.8 mmol) was added. The mixture was stirred for 2 h, then poured into water (30.0 mL), extracted with EA (20.0 mL×3). The combined organic layers were dried and concentrated in vacuo. The resulting residue was purified by silica column chromatography (PE/EA=10:1) to provide benzyl 2-bromo-1-((2-(trimethylsilyl)ethoxy)methyl)-1H-imidazole-4-carboxylate (0.52 g, 79.3%).

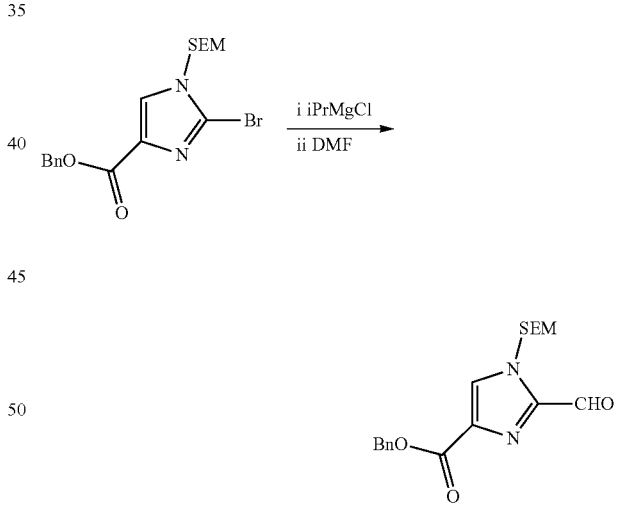

To a solution of benzyl 2-bromo-1-((2-(trimethylsilyl)ethoxy)methyl)-1H-imidazole-4-carboxylate (520.0 mg, 1.26 mmol) in dry THF (20.0 mL) was added i-PrMgCl (1.5 mL, 3.8 mmol, 3.0 eq) at −40° C. under N2 atmosphere. The resulting mixture was allowed to stir for 15 min and cooled to −78° C., then quenched by DMF (1.0 mL). After the reaction mixture was slowly warmed to rt, it was acidified by 3N HCl to pH 6-7, and concentrated in vacuo. The resulting residue was extracted with EA (30 mL×2) and the combined organic layers were concentrated to provide crude benzyl 2-formyl-1-((2-(trimethylsilyl) ethoxy)methyl)-1H-imidazole-4-carboxylate (470.0 mg, ca 100.0%).

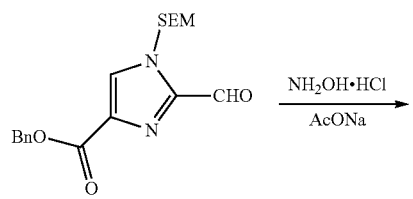

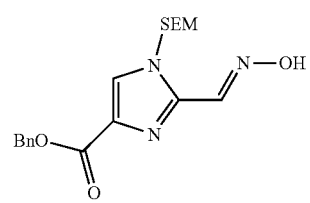

To a solution of benzyl 2-formyl-1-((2-(trimethylsilyl)ethoxy)methyl)-1H-imidazole-4-carboxylate (0.47 g, 1.3 mmol, 1.0 eq) in EtOH/H2O (10.0 mL/2.0 mL) were added NH$_2$OH.HCl (140.0 mg, 1.9 mmol, 1.5 eq) and NaOAc (0.21 g, 2.6 mmol, 2.0 eq). The reaction mixture was heated at 70° C. for 2 h. Water (30.0 mL) was added and the mixture was extracted with EA (30.0 mL×2). The combined organic layers were washed with water, dried over Na2SO4, filtered and concentrated. The resulting residue was purified by column chromatography (PE/EA=10/1, v/v) to provide benzyl 2-((hydroxyimino)methyl)-1-((2-(trimethylsilyl)ethoxy)methyl)-1H-imidazole-4-carboxylate (120.0 mg, 24.6%).

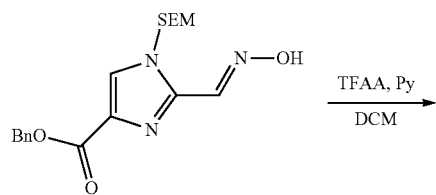

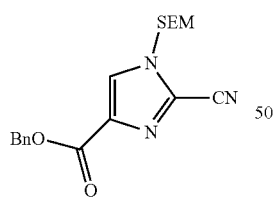

To a solution of benzyl 2-((hydroxyimino)methyl)-1-((2-(trimethylsilyl) ethoxy)methyl)-1H-imidazole-4-carboxylate (120.0 mg, 0.32 mmol, 1.0 eq) in DCM (5.0 mL) were added pyridine (100 mg, 1.3 mmol, 4.0 eq) and TFAA (0.15 mL, 1.0 mmol, 3.0 eq). The reaction mixture was stirred at rt for 12 h. The solvent was removed, diluted with EA (20.0 mL), washed with aq. NaHCO$_3$ solution, dried over Na2SO4, filtered and concentrated in vacuo. The resulting residue was purified by column chromatography (PE/EA=10/1, v/v) to provide benzyl 2-cyano-1-((2-(trimethylsilyl)ethoxy)methyl)-1H-imidazole-4-carboxylate (108.0 mg, 94.5%).

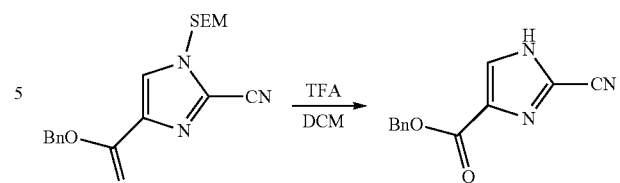

To a solution of benzyl 2-cyano-1-((2-(trimethylsilyl)ethoxy)methyl)-1H-imidazole-4-carboxylate (108 mg, 0.3 mmol, 1.0 eq) in DCM (5.0 mL) was added TFA (2.0 mL). The reaction mixture was stirred at rt for 12 h. The solvent was removed, diluted with EA (20 mL), washed with aq. NaHCO$_3$ solution, dried over Na2SO4, filtered and concentrated in vacuo. The resulting residue was purified by column chromatography (PE/EA=5/1, v/v) to provide benzyl 2-cyano-1H-imidazole-4-carboxylate (45.0 mg, 66.1%).

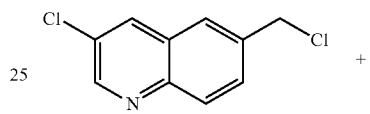

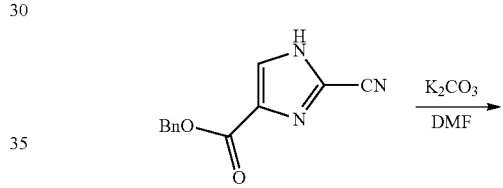

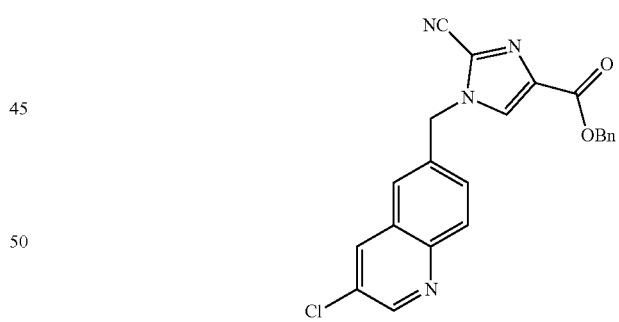

To a solution of benzyl 2-cyano-1H-imidazole-4-carboxylate (45.0 mg, 0.2 mmol, 1.0 eq) and K2CO3 (56.0 mg, 0.4 mmol, 2.0 eq) in DMF (5 mL) was added 3-chloro-6-chloromethyl-quinoline (45.0 mg, 0.21 mmol, 1.05 eq). The mixture was stirred at 85° C. for 3 h under nitrogen atmosphere, then cooled, poured into water (20.0 mL) and extracted with EA (30.0 mL×2). The combined organic layers were washed with brine, dried over Na2SO4, filtered and concentrated. The resulting residue was purified by column chromatography (PE/EA=2/1, v/v) to provide benzyl 1-((3-chloroquinolin-6-yl)methyl)-2-cyano-1H-imidazole-4-carboxylate (43.0 mg, 50.0%).

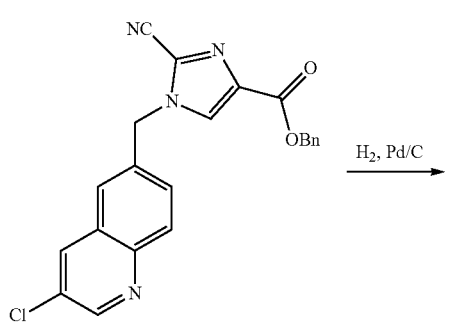

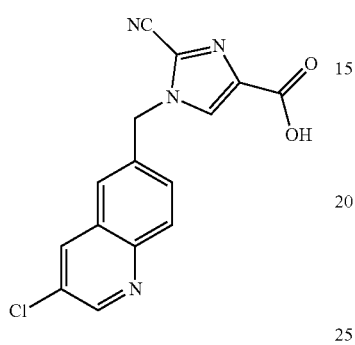

To a mixture of benzyl 1-((3-chloroquinolin-6-yl)methyl)-2-cyano-1H-imidazole-4-carboxylate (43.0 mg, 0.1 mmol, 1.0 eq) in THF (5.0 mL) was added Pd/C (5.0 mg). The reaction mixture was stirred at rt under hydrogen atmosphere for 5 h, filtered, washed with MeOH, concentrated in vacuo to provide 1-((3-chloroquinolin-6-yl)methyl)-2-cyano-1H-imidazole-4-carboxylic acid (31.0 mg, ca 100.0%).

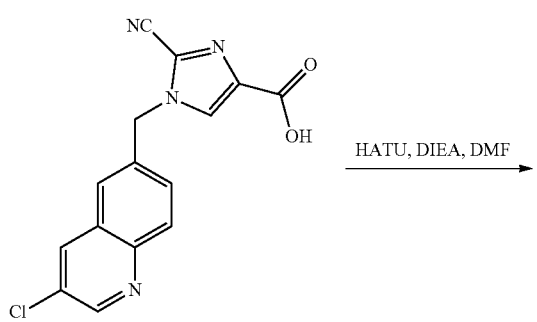

To a mixture of 1-((3-chloroquinolin-6-yl)methyl)-2-cyano-1H-imidazole-4-carboxylic acid (31.0 mg, 0.1 mmol, 1.0 eq) in DMF (5.0 mL) were added 5-(aminomethyl)-4,6-dimethylpyridin-2-amine (18.0 mg, 0.1 mmol, 1.0 eq), HATU (45.0 mg, 0.12 mmol, 1.1 eq) and DIEA (30.0 mg, 0.2 mmol, 2.0 eq). The mixture was stirred at rt for 2 h under N2 atmosphere. The reaction mixture was purified by prep-TLC to provide N-((6-amino-2,4-dimethylpyridin-3-yl)methyl)-1-((3-chloroquinolin-6-yl)methyl)-2-cyano-1H-imidazole-4-carboxamide (5.0 mg, 11.2%). 1H NMR (CD3OD-d4, 400 MHz) δ 8.83 (d, 1H), 8.43 (d, 1H), 8.08 (d, 1H), 8.04 (s, 1H), 7.85 (s, 1H), 7.73-7.70 (m, 1H), 6.30 (s, 1H), 5.65 (s, 2H), 4.48 (s, 2H), 2.40 (s, 3H), 2.28 (s, 3H). LCMS (M+H+) m/z calculated 446.1, found 446.2.

Example 114: Preparation of N-((6-amino-2,4-dimethylpyridin-3-yl)methyl)-2-((3-chloroquinolin-6-yl)methyl)oxazole-5-carboxamide

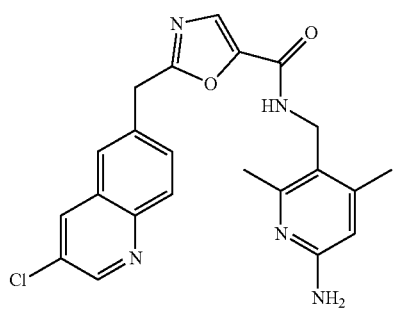

N-((6-amino-2,4-dimethylpyridin-3-yl)methyl)-2-((3-chloroquinolin-6-yl)methyl)oxazole-5-carboxamide

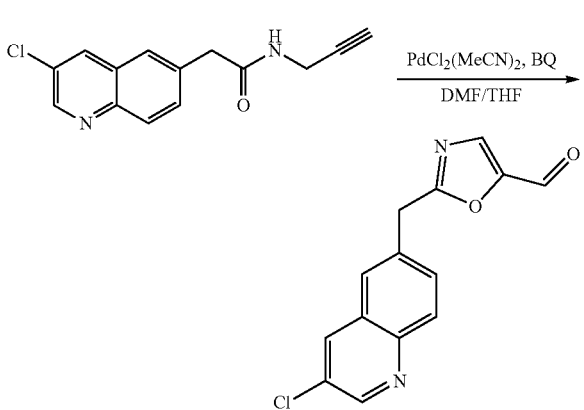

To a mixture of 2-(3-chloroquinolin-6-yl)acetic acid (7.78 g, 35.2 mmol, 1.0 eq) in DMF (100.0 mL) were added prop-2-yn-1-amine (2.3 g, 42.2 mmol, 1.2 eq), HATU (16.0 g, 42.2 mmol, 1.2 eq) and DIEA (20.0 mL, 105.6 mmol, 3.0 eq). The mixture was stirred at rt for 2 h under N2 atmosphere. After the reaction was complete, the reaction mixture was poured into water (200.0 mL), and the solid was collected and dried to provide 2-(3-chloroquinolin-6-yl)-N-(prop-2-yn-1-yl)acetamide (8.27 g, 90.8%).

407

To a mixture of 2-(3-chloroquinolin-6-yl)-N-(prop-2-yn-1-yl)acetamide (200.0 mg, 0.77 mmol, 1.0 eq) in DMF/THF (6.0 mL/10 mL) were added PdCl2(MeCN)2 (26.0 mg, 0.1 mmol, 0.15 eq) and 1,4-Benzoquinone (83.0 mg, 0.77 mmol, 1.0 eq). The mixture was stirred at 60° C. for 16 h under N2. The reaction mixture was poured into water (30.0 mL) and extracted with EA (30.0 mL×2). The combined organic layers were washed with brine, dried over Na2SO4, filtered and concentrated in vacuo. The resulting residue was purified by column chromatography (PE/EA=3/1, v/v) to provide 2-((3-chloroquinolin-6-yl)methyl)oxazole-5-carbaldehyde (40.0 mg, 20.0%).

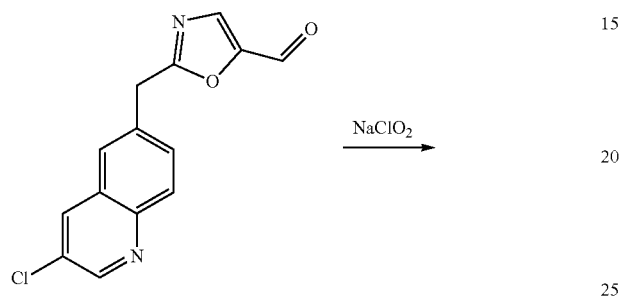

NaClO2 →

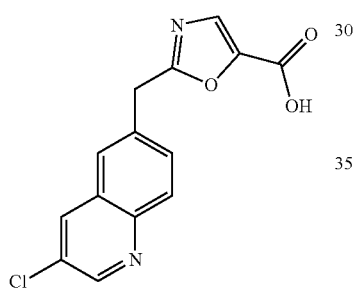

To a mixture of 2-((3-chloroquinolin-6-yl)methyl)oxazole-5-carbaldehyde (200.0 mg, 0.73 mmol, 1.0 eq) in THF (10.0 mL) was added a solution of NaClO2 (130.0 mg, 1.46 mmol, 2.0 eq) and NaH2PO4 (120.0 mg, 1.0 mmol, 1.5 eq) in water (2.0 mL) at 0° C. The mixture was stirred at rt for 1 hr. The solvent was removed in vacuo, and the resulting residue was purified by column chromatography (DCM/MeOH=10/1, v/v) to provide 2-((3-chloroquinolin-6-yl)methyl)oxazole-5-carboxylic acid (89.0 mg, 42.2%).

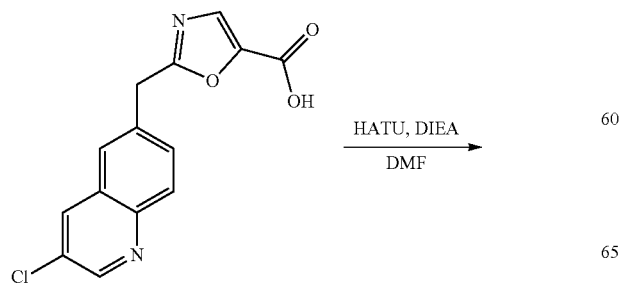

HATU, DIEA
DMF →

408

-continued

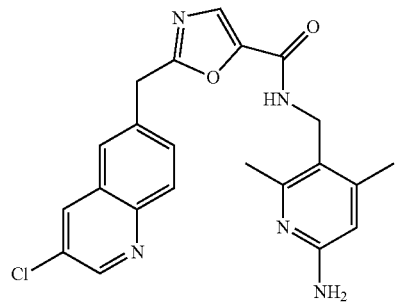

To a mixture of 2-((3-chloroquinolin-6-yl)methyl)oxazole-5-carboxylic acid (89.0 mg, 0.3 mmol, 1.0 eq) in DMF (5.0 mL) were added 5-(aminomethyl)-4,6-dimethylpyridin-2-amine (54.0 mg, 0.3 mmol, 1.0 eq), HATU (140.0 mg, 0.4 mmol, 1.3 eq) and DIEA (80.0 mg, 0.6 mmol, 2.0 eq). The mixture was stirred at rt for 2 h under N2 atmosphere. The reaction mixture was purified on prep-TLC to provide N-((6-amino-2,4-dimethylpyridin-3-yl)methyl)-2-((3-chloroquinolin-6-yl)methyl)oxazole-5-carboxamide (35.0 mg, 27.6%). 1H NMR (CD3OD-d4, 400 MHz) δ 8.80 (t, 1H), 8.38 (t, 1H), 8.03-8.00 (m, 1H), 7.86 (s, 1H), 7.78-7.75 (m, 1H), 7.67 (s, 1H), 6.31 (s, 1H), 4.49 (s, 2H), 4.43 (s, 2H), 2.38 (s, 3H), 2.27 (s, 3H). LCMS (M+H+) m/z calculated 422.1, found 422.1.

Example 115: Preparation of N-((6-amino-2,4-dimethylpyridin-3-yl)methyl)-2-((3-chloroquinolin-6-yl)methyl)-5-(trifluoromethyl)-2H-1,2,3-triazole-4-carboxamide and N-((6-amino-2,4-dimethylpyridin-3-yl)methyl)-1-((3-chloroquinolin-6-yl)methyl)-4-(trifluoromethyl)-1H-1,2,3-triazole-5-carboxamide

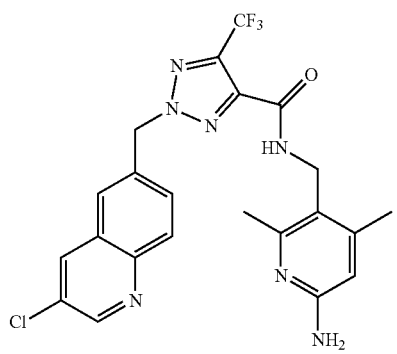

N-((6-amino-2,4-dimethylpyridin-3-yl)methyl)-2-((3-chloroquinolin-6-yl)methyl)-5-(trifluoromethyl)-2H-1,2,3-triazole-4-carboxamide

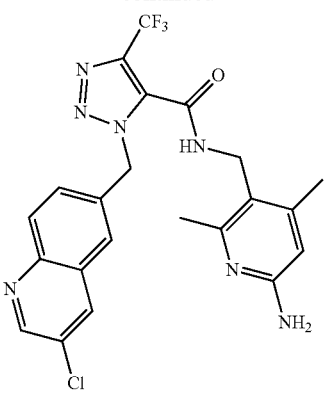

N-((6-amino-2,4-dimethylpyridin-3-yl)methyl)-1-((3-chloroquinolin-6-yl)methyl)-4-(trifluoromethyl)-1H-1,2,3-triazole-5-carboxamide

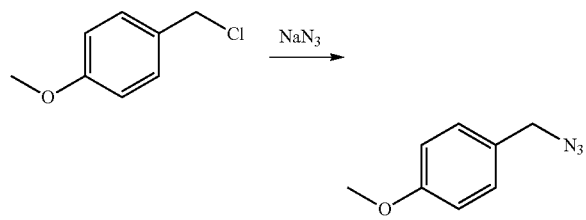

To a solution of 1-(chloromethyl)-4-methoxybenzene (3.0 g, 1.09 mmol, 1.0 eq) in DMF (50 mL), was added NaN3 (1.37 g, 21 mmol, 1.1 eq). The mixture was stirred and heated at 65° C. for 4 h, then cooled. EA (50.0 mL) and water (50.0 mL) were added to the mixture, and the organic layer was washed with water (50 mL), brine (50 mL). Toluene (40 mL) was added to the organic layer, most of the organic solvent was removed in vacuo to provide the product 1-(azidomethyl)-4-methoxybenzene (3.12 g, 100%).

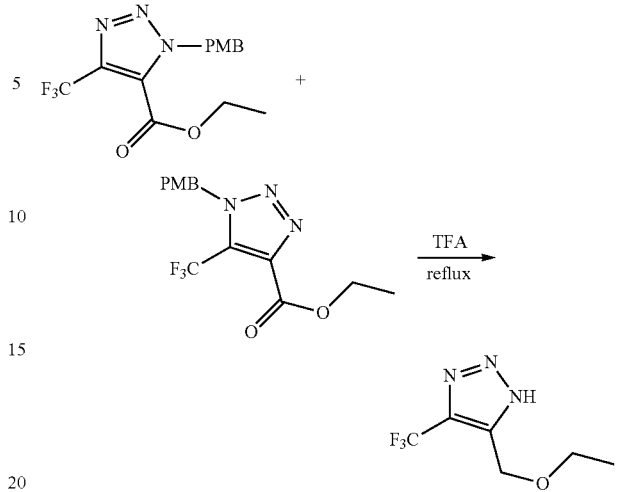

The mixture of ethyl 1-(4-methoxyphenethyl)-4-(trifluoromethyl)-1H-1,2,3-triazole-5-carboxylate and ethyl 1-(4-methoxyphenethyl)-5-(trifluoromethyl)-1H-1,2,3-triazole-4-carboxylate (3.28 g, 9.57 mmol, 1.0 eq) in TFA (50 mL) was stirred at 75° C. for 12 h, then cooled. The solvent was removed under vacuum and The resulting residue was purified by prep-HPLC to provide ethyl 4-(trifluoromethyl)-1H-1,2,3-triazole-5-carboxylate (910 mg, 45.5%) as a white solid.

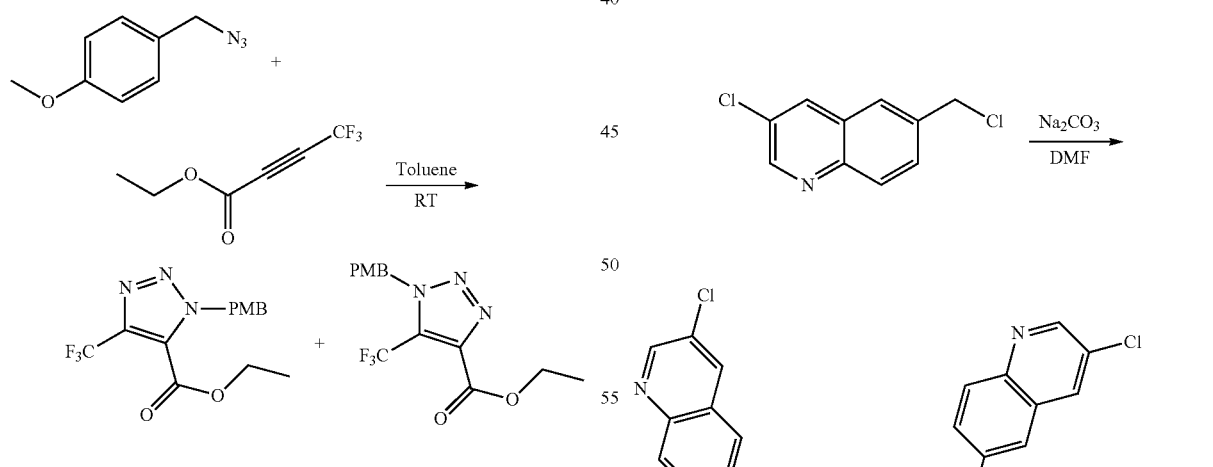

To a solution of 1-(azidomethyl)-4-methoxybenzene (1.56 g, 9.58 mmol, 1.0 eq), ethyl 4,4,4-trifluorobut-2-ynoate (1.6 g, 9.58 mmol, 1.0 eq) in toluene (30.0 mL) was added. The mixture was stirred at rt for 12 h. The solvent was removed in vacuo to provide the mixture of ethyl 1-(4-methoxyphenethyl)-4-(trifluoromethyl)-1H-1,2,3-triazole-5-carboxylate and ethyl 1-(4-methoxyphenethyl)-5-(trifluoromethyl)-1H-1,2,3-triazole-4-carboxylate (3.28 g, 100%).

411
-continued

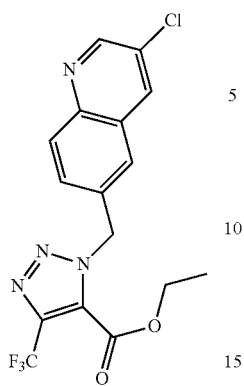

The mixture of 4-(trifluoromethyl)-1H-1,2,3-triazole-5-carboxylate (900 mg, 4.3 mmol, 1.0 eq), 3-chloro-6-(chloromethyl)quinoline (1.07 g, 4.3 mmol, 1.0 eq), Na2CO3 (1.37 g, 12.9 mmol, 3.0 eq) in DMF (20 mL) was stirred at 70° C. for 3 h, then cooled. The solvent was removed in vacuo and the resulting residue was purified by column chromatography (PE/EA=5:1) to provide the mixture of ethyl 2-((3-chloroquinolin-6-yl)methyl)-5-(trifluoromethyl)-2H-1,2,3-triazole-4-carboxylate, ethyl 1-((3-chloroquinolin-6-yl)methyl)-5-(trifluoromethyl)-1H-1,2,3-triazole-4-carboxylate and ethyl 1-((3-chloroquinolin-6-yl)methyl)-4-(trifluoromethyl)-1H-1,2,3-triazole-5-carboxylate (1.27 g, 65.1%).

412
-continued

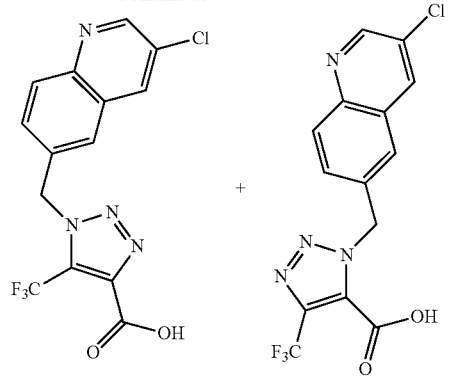

The mixture of 2-((3-chloroquinolin-6-yl)methyl)-5-(trifluoromethyl)-2H-1,2,3-triazole-4-carboxylate, ethyl 1-((3-chloroquinolin-6-yl)methyl)-5-(trifluoromethyl)-1H-1,2,3-triazole-4-carboxylate, ethyl 1-((3-chloroquinolin-6-yl)methyl)-4-(trifluoromethyl)-1H-1,2,3-triazole-5-carboxylate (1.27 g, 3.31 mmol, 1.0 eq) and LiOH.H2O (417 mg, 9.93 mmol, 3.0 eq) in MeOH/H2O (20 mL/5 mL) was stirred at rt for 4 h. After the reaction was complete, the solvent of the mixture was removed in vacuo and the resulting residue was purified by prep-HPLC to provide 2-((3-chloroquinolin-6-yl)methyl)-5-(trifluoromethyl)-2H-1,2,3-triazole-4-carboxylic acid (135 mg, 11.5%, yellow solid), 1-((3-chloroquinolin-6-yl)methyl)-5-(trifluoromethyl)-1H-1,2,3-triazole-4-carboxylic acid (160 mg, 13.7%, yellow solid) and 1-((3-chloroquinolin-6-yl)methyl)-4-(trifluoromethyl)-1H-1,2,3-triazole-5-carboxylic acid (25 mg, 2.14%, yellow solid).

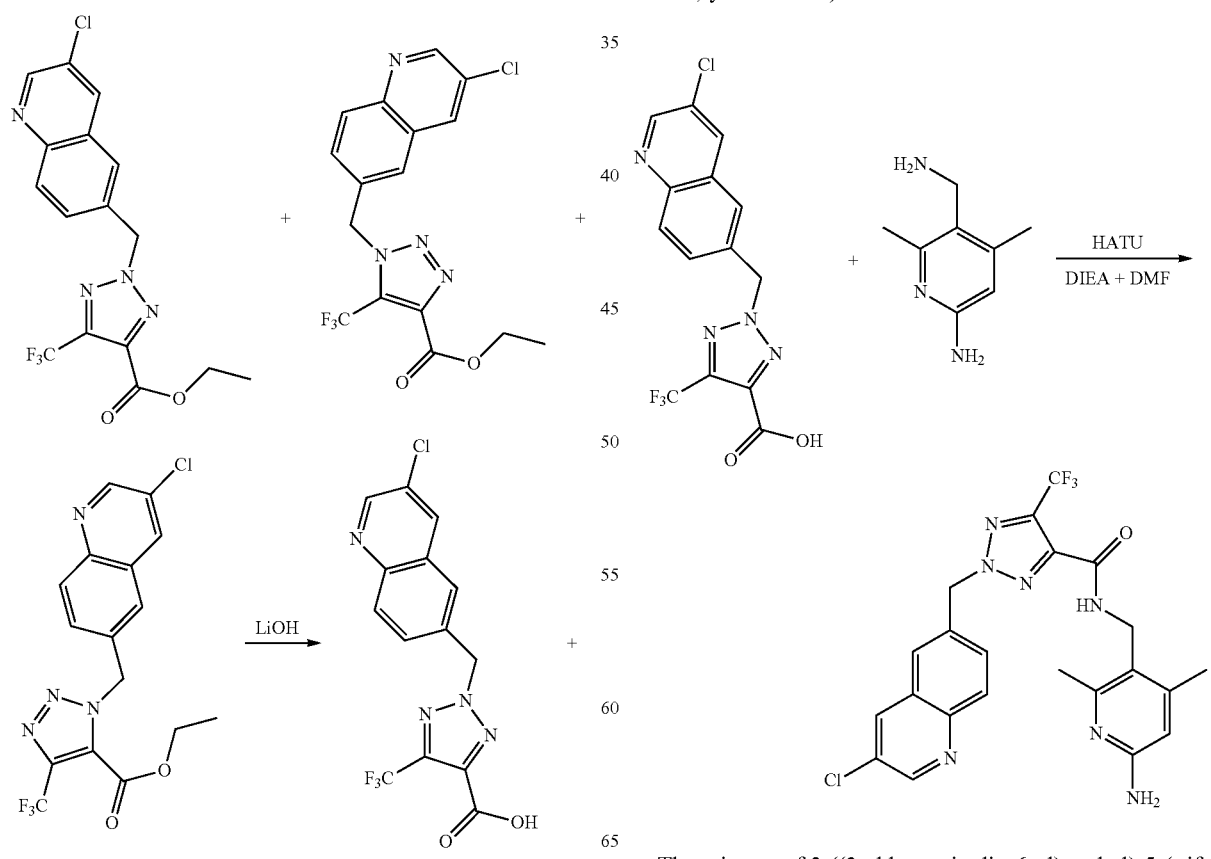

The mixture of 2-((3-chloroquinolin-6-yl)methyl)-5-(trifluoromethyl)-2H-1,2,3-triazole-4-carboxylic acid (135 mg, 0.38 mmol, 1.0 eq), 5-(aminomethyl)-4,6-dimethylpyridin-2-amine (57.3 mg, 0.38 mmol, 1.0 eq), HATU (173.0 mg, 0.46 mmol, 1.2 eq), DIEA (98.0 mg, 0.76 mmol, 2.0 eq) in DMF (2.0 mL) was stirred at rt for 2 h. After the reaction was complete, the solvent was removed in vacuo. The resulting residue was purified by prep-HPLC to provide N-((6-amino-2,4-dimethylpyridin-3-yl)methyl)-2-((3-chloroquinolin-6-yl)methyl)-5-(trifluoromethyl)-2H-1,2,3-triazole-4-carboxamide (32.9 mg, 17.8%) as a white solid. 1H NMR (CD3OD-d4, 400 MHz) δ 8.81 (d, 1H), 8.40 (d, 1H), 8.04 (d, 1H), 7.91 (s, 1H), 7.76 (dd, 1H), 6.28 (s, 1H), 5.91 (s, 2H), 4.48 (s, 2H), 2.37 (s, 3H), 2.25 (s, 3H). LCMS (M+H+) m/z calculated 490.1, found 490.2.

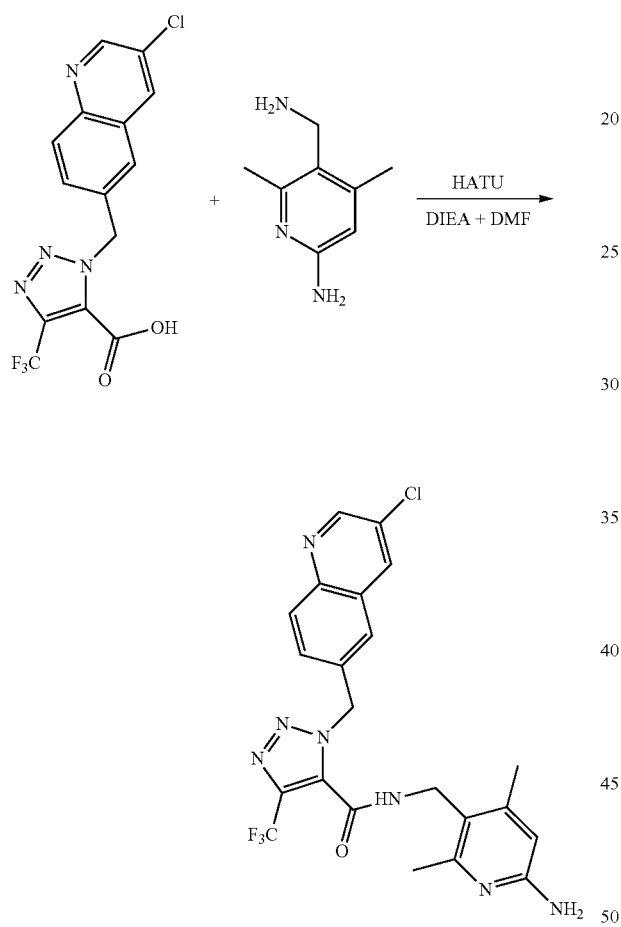

The mixture of 1-((3-chloroquinolin-6-yl)methyl)-4-(trifluoromethyl)-1H-1,2,3-triazole-5-carboxylic acid (25.0 mg, 0.07 mmol, 1.0 eq), 5-(aminomethyl)-4,6-dimethylpyridin-2-amine (11.0 mg, 0.075 mmol, 1.0 eq), HATU (32.0 mg, 0.084 mmol, 1.2 eq), DIEA (18.1 mg, 0.14 mmol, 2.0 eq) in DMF (2.0 mL) was stirred at rt for 2 h. The solvent was removed in vacuo and the resulting residue was purified by prep-HPLC to provide N-((6-amino-2,4-dimethylpyridin-3-yl)methyl)-1-((3-chloroquinolin-6-yl)methyl)-4-(trifluoromethyl)-1H-1,2,3-triazole-5-carboxamide (4.5 mg, 13.1%) as a white solid. 1H NMR (CD3OD-d4, 400 MHz) δ 8.83 (d, 1H), 8.40 (d, 1H), 8.05 (d, 1H), 7.75 (s, 1H), 7.64 (d, 1H), 6.69 (s, 1H), 6.06 (s, 2H), 4.51 (s, 2H), 2.60 (s, 3H), 2.48 (s, 3H). LCMS (M+H+) m/z calculated 490.1, found 490.1.

Example 116: Preparation of N-((6-amino-2,4-dimethylpyridin-3-yl)methyl)-1-((3-chloroquinolin-6-yl)methyl)-5-(trifluoromethyl)-1H-pyrazole-3-carboxamide and N-((6-amino-2,4-dimethylpyridin-3-yl)methyl)-1-((3-chloroquinolin-6-yl)methyl)-3-(trifluoromethyl)-1H-pyrazole-5-carboxamide

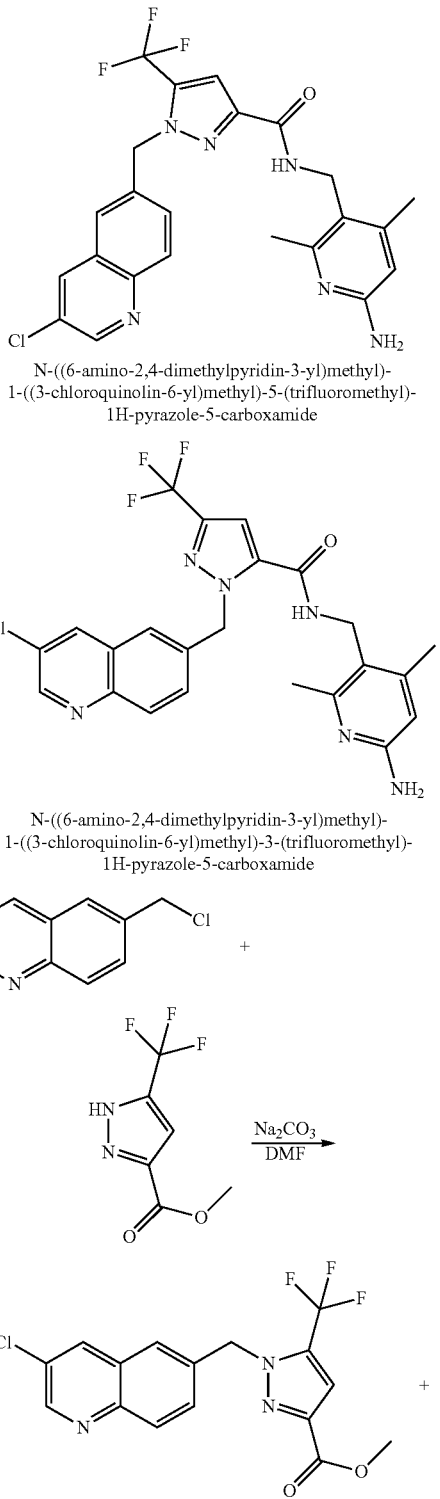

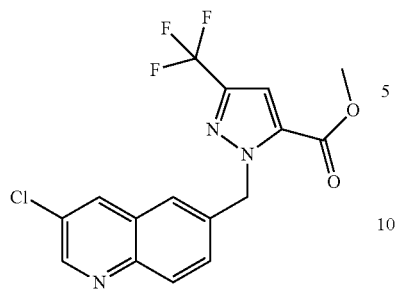

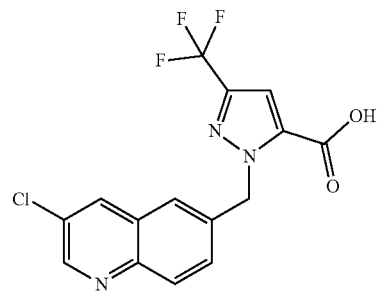

To a solution of 3-chloro-6-(chloromethyl)quinoline hydrochloride (128.0 mg, 0.52 mmoL, 1.0 eq) and methyl 5-(trifluoromethyl)-1H-pyrazole-3-carboxylate (100.0 mg, 0.52 mmol, 1.0 eq) in DMF (5.0 mL) was added Na2CO3 (164.0 mg, 1.56 mmol, 3.0 eq). The reaction mixture was heated at 70° C. for 3 h, then cooled and quenched by H2O and filtered. The solid was washed by water, dried in vacuo to provide a mixture of methyl 1-((3-chloroquinolin-6-yl)methyl)-5-(trifluoromethyl)-1H-pyrazole-3-carboxylate and methyl 1-((3-chloroquinolin-6-yl)methyl)-3-(trifluoromethyl)-1H-pyrazole-5-carboxylate (150 mg, 78.9%) as a white solid. LCMS (M+H+) m/z calculated 370, found 370.

To a solution of a mixture of methyl 1-((3-chloroquinolin-6-yl)methyl)-5-(trifluoromethyl)-1H-pyrazole-3-carboxylate and methyl 1-((3-chloroquinolin-6-yl)methyl)-3-(trifluoromethyl)-1H-pyrazole-5-carboxylate (150.0 mg, 0.41 mmol, 1.0 eq) in THF/MeOH/H2O (v/v/v=4:2:1, 5.0 mL) was added LiOH.H2O (52.0 mg, 1.23 mmol, 3.0 eq). The reaction mixture was stirred at rt overnight, then concentrated in vacuo. The resulting residue was diluted by H2O, adjusted to pH 1~2 by 1N HCl, extracted by EA (50.0 mL×3), washed by brine, dried over Na2SO4 and concentrated in vacuo. The resulting residue was purified by prep-HPLC to provide a mixture of 1-((3-chloroquinolin-6-yl)methyl)-5-(trifluoromethyl)-1H-pyrazole-3-carboxylic acid and 1-((3-chloroquinolin-6-yl)methyl)-3-(trifluoromethyl)-1H-pyrazole-5-carboxylic acid (22 mg, 15%) as a white solid. LCMS (M+H+) m/z calculated 356, found 356.

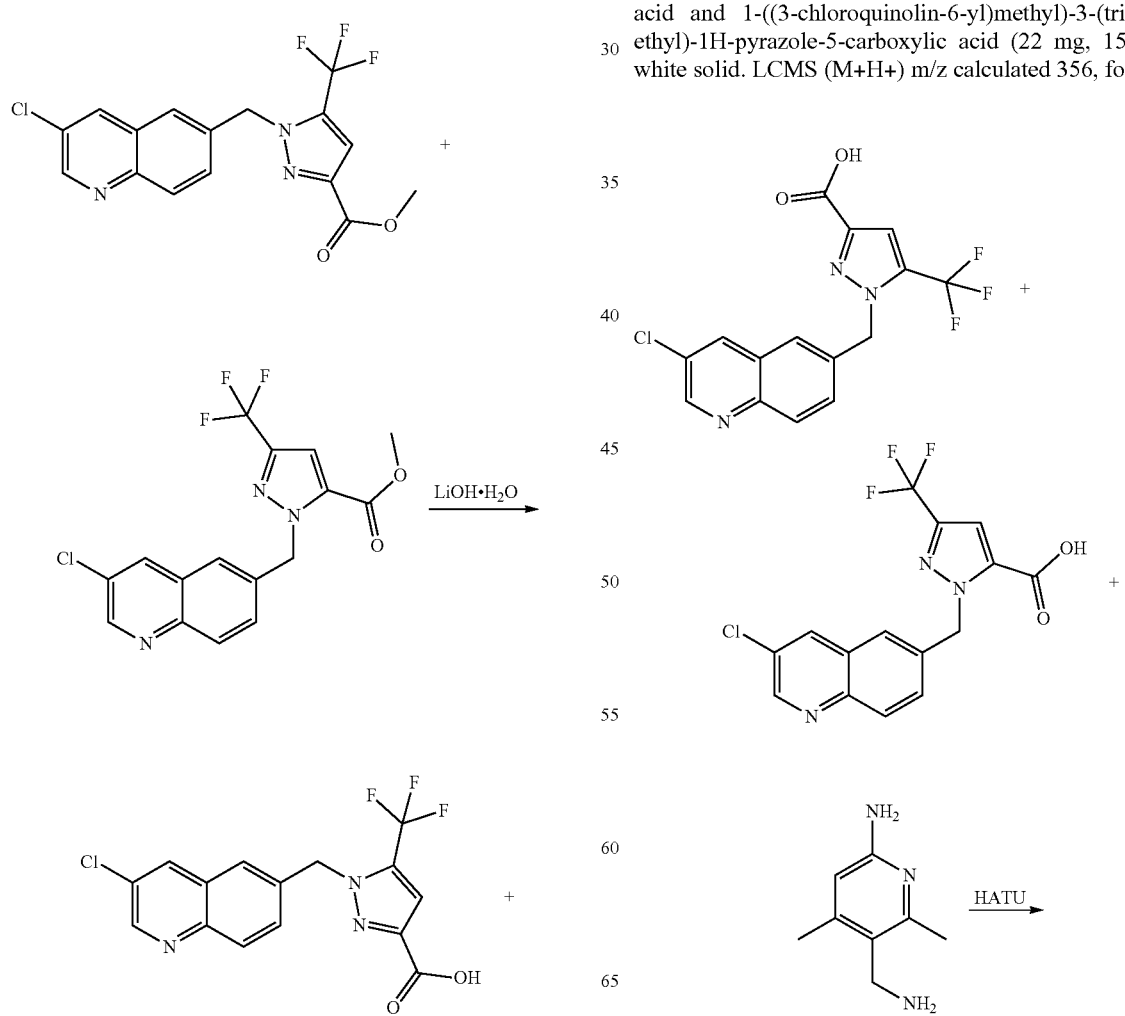

-continued

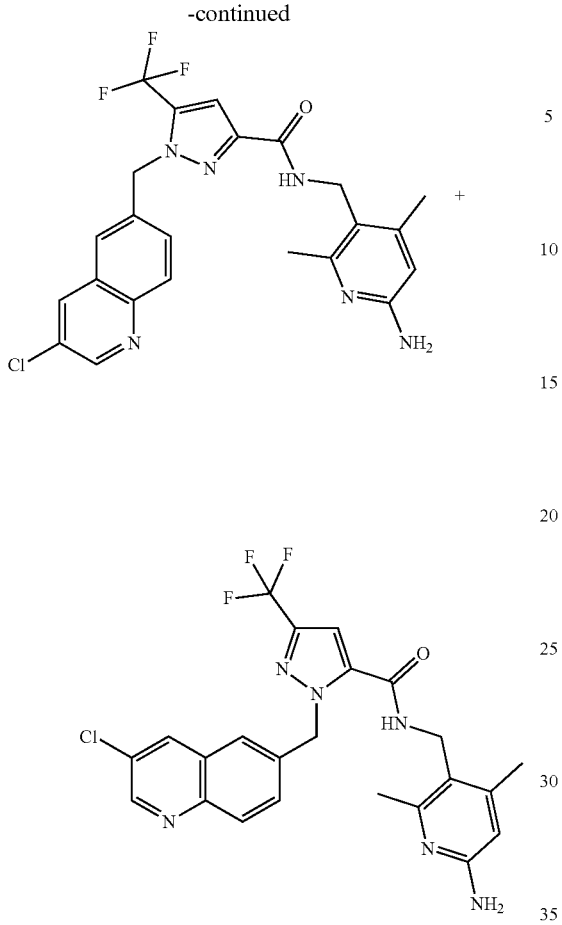

To a solution of the mixture of 1-((3-chloroquinolin-6-yl)methyl)-5-(trifluoromethyl)-1H-pyrazole-3-carboxylic acid and 1-((3-chloroquinolin-6-yl)methyl)-3-(trifluoromethyl)-1H-pyrazole-5-carboxylic acid (22.0 mg, 0.06 mmol, 1.0 eq) and 5-(aminomethyl)-4,6-dimethylpyridin-2-amine (8.0 mg, 0.06 mmol, 1.0 eq) in DMF (3.0 mL) was added HATU (23.0 mg, 0.06 mmol, 1.0 eq) and the mixture was stirred at rt for 10 min. Then DIEA (23 mg, 0.18 mmol, 3.0 eq) was added, and the reaction mixture was stirred at rt overnight. After the reaction was complete, the mixture was purified by prep-HPLC to provide N-((6-amino-2,4-dimethylpyridin-3-yl)methyl)-1-((3-chloroquinolin-6-yl)methyl)-5-cyano-1H-pyrazolo[3,4-c]pyridine-3-carboxamide (3.2 mg, 10.7%) as a white solid. 1H NMR (CD3OD-d4, 400 MHz) δ 8.81 (d, 1H), 8.38 (d, 1H), 8.02 (d, 1H), 7.70 (s, 1H), 7.65 (dd, 1H), 7.26 (s, 1H), 6.31 (s, 1H), 5.75 (s, 2H), 4.51 (s, 2H), 2.41 (s, 3H), 2.29 (s, 3H). LCMS (M+H+) m/z calculated 489.1, found 489.1. N-((6-amino-2,4-dimethylpyridin-3-yl)methyl)-1-((3-chloroquinolin-6-yl)methyl)-3-(trifluoromethyl)-1H-pyrazole-5-carboxamide (4.4 mg, 14.6%) as a white solid. 1H NMR (CD3OD-d4, 400 MHz) δ 8.80 (d, 1H), 8.36 (d, 1H), 7.98 (d, 1H), 7.71 (s, 1H), 7.63 (dd, 1H), 7.13 (s, 1H), 6.23 (s, 1H), 6.01 (s, 2H), 4.39 (s, 2H), 2.24 (s, 3H), 2.10 (s, 3H). LCMS (M+H+) m/z calculated 489.1, found 489.1.

Example 117: Preparation of N-((6-amino-2,4-dimethylpyridin-3-yl)methyl)-5-chloro-1-((3-chloroquinolin-6-yl)methyl)-1H-pyrrolo[2,3-c]pyridine-3-carboxamide

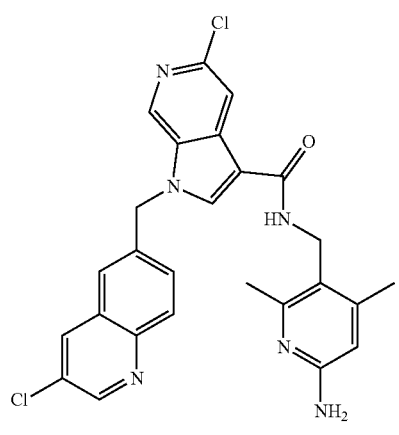

N-((6-amino-2,4-dimethylpyridin-3-yl)methyl)-5-chloro-1-((3-chloroquinolin-6-yl)methyl)-1H-pyrrolol[2,3-c]pyridine-3-carboxamide

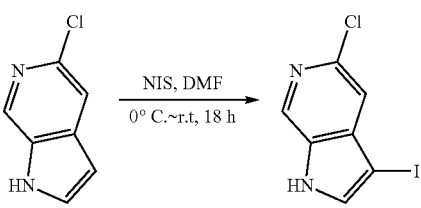

5-Chloro-1H-pyrrolo[2,3-c]pyridine (400.0 mg, 2.614 mmol, 1.0 eq) was dissolved in DMF (20.0 mL). After cooling to 0° C., NIS (882 mg, 3.922 mmol, 1.5 eq) was added and the resulting mixture was stirred at rt for 18 h, then concentrated in vacuo. The resulting residue was purified by column chromatography to provide 5-chloro-3-iodo-1H-pyrrolo[2,3-c]pyridine (725 mg, ca 100%).

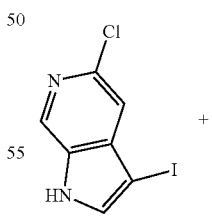

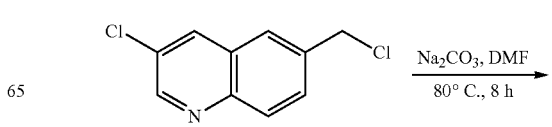

-continued

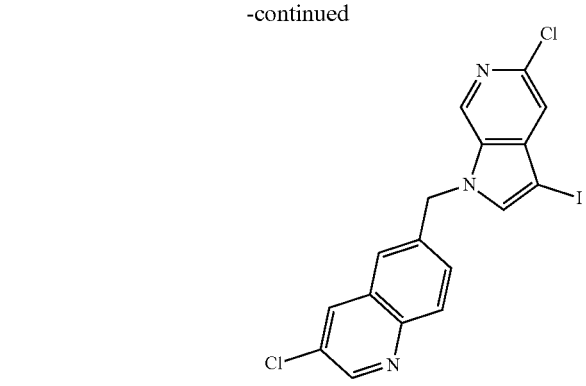

5-Chloro-3-iodo-1H-pyrrolo[2,3-c]pyridine (725.0 mg, 2.608 mmol, 1.0 eq), 3-chloro-6-(chloromethyl)quinoline (663.0 mg, 3.129 mmol, 1.2 eq) and Na2CO3 (691.0 mg, 6.520 mmol, 2.0 eq) were dissolved in DMF (25.0 mL). The resulting mixture was heated at 80° C. for 8 h, then cooled to rt, 12.5 mL of H2O was added and stirred at rt for 30 mins. 3-chloro-6-((5-chloro-3-iodo-1H-pyrrolo[2,3-c]pyridine-1-yl)methyl)quinoline was provided via filtration (685 mg, 58%).

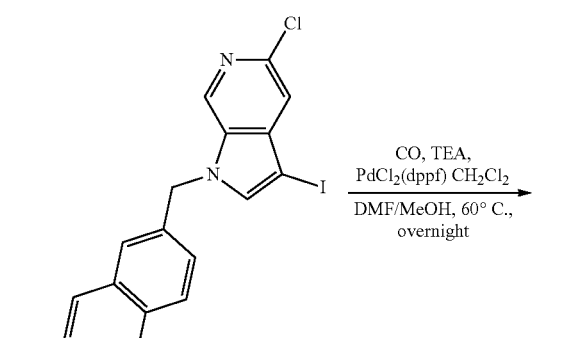

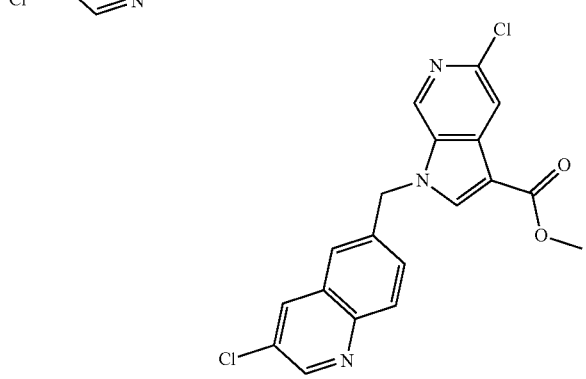

3-Chloro-6-((5-chloro-3-iodo-1H-pyrrolo[2,3-c]pyridin-1-yl)methyl)quinoline (685.0 mg, 1.512 mmoL, 1.0 eq), TEA (458.0 mg, 4.536 mmol, 3.0 eq) and PdCl2(dppf).CH2Cl2 (185.0 mg, 0.227 mmol, 0.15 eq) were dissolved in DMF (10.0 mL) and H2O (10.0 mL). The resulting mixture was degassed and heated at 60° C. overnight under CO atmosphere, the cooled and concentrated in vacuo, then 30.0 mL of H2O was added. The mixture was extracted with EA (15 mL×3). The combined organic layers were washed with brine (15 mL×3), and dried over anhydrous Na2SO4. The solvent was removed in vacuo. The resulting residue was purified by prep-HPLC to provide methyl 5-chloro-1-((3-chloroquinolin-6-yl)methyl)-1H-pyrrolo[2,3-c]pyridine-3-carboxylate as off white solid (311.0 mg, 53%).

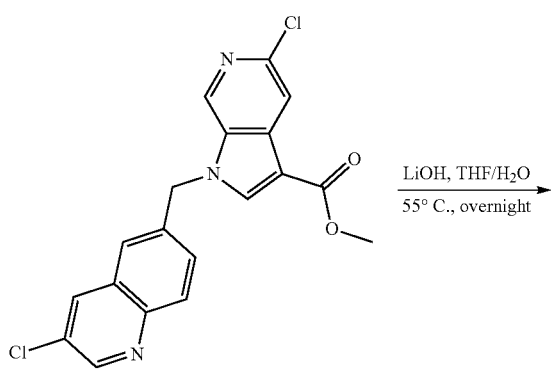

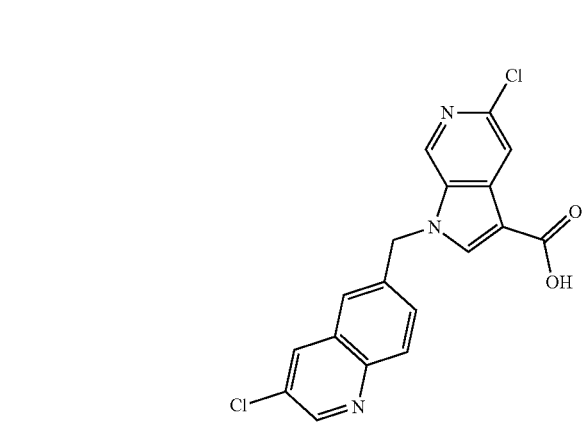

LiOH.H2O (51.0 mg, 1.21 mmol) was added to a solution of methyl 5-chloro-1-((3-chloroquinolin-6-yl)methyl)-1H-pyrrolo[2,3-c]pyridine-3-carboxylate (110.0 mg, 0.242 mmol) in THF (5.0 mL) and H2O (5.0 mL). The reaction mixture was heated at 55° C. overnight, then cooled and concentrated in vacuo, 10 mL of H2O was added, adjusted to pH 2.0 with 1N aq. HCl, extracted with EA (10 mL×3). The combined organic layers were washed with brine (10 mL×3), dried over anhydrous Na2SO4 and concentrated to provide 5-chloro-1-((3-chloroquinolin-6-yl)methyl)-1H-pyrrolo[2,3-c]pyridine-3-carboxylic acid which was used in the next step without further purification (105.0 mg).

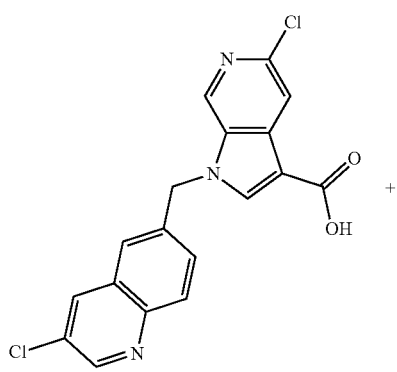

-continued

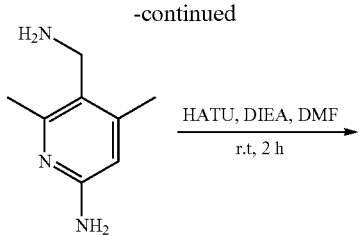

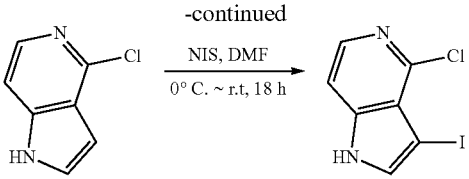

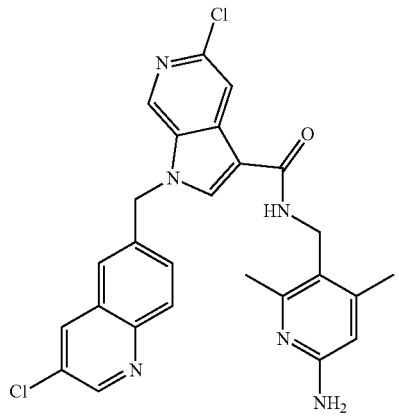

NIS (767.0 mg, 3.441 mmol, 1.5 eq) was added to a solution of 4-chloro-1H-pyrrolo[3,2-c]pyridine (350.0 mg, 2.294 mmol, 1.0 eq) in DMF (15.0 mL) at 0° C. The reaction mixture was stirred at rt for 18 h, then concentrated in vacuo and purified via column chromatography (0~50% ethyl acetate in petroleum ether) to provide 4-chloro-3-iodo-1H-pyrrolo[3,2-c]pyridine (618.0 mg, 97%).

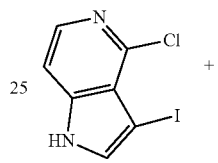

DIEA (91.0 mg, 0.705 mmol, 2.5 eq) was added to a solution of 5-chloro-1-((3-chloroquinolin-6-yl)methyl)-1H-pyrrolo[2,3-c]pyridine-3-carboxylic acid (105.0 mg, 0.282 mmol, 1.0 eq), 5-(aminomethyl)-4,6-dimethylpyridin-2-amine (64.0 mg, 0.423 mmol, 1.5 eq) and HATU (107.0 mg, 0.282 mmol, 1.0 eq) in DMF (2.0 mL). The resulting mixture was stirred at rt for 2 h, then purified by prep-HPLC to provide N-((6-amino-2,4-dimethylpyridin-3-yl)methyl)-5-chloro-1-((3-chloroquinolin-6-yl)methyl)-1H-pyrrolo[2,3-c]pyridine-3-carboxamide as a white solid (78 mg, 64% over two steps). LCMS (M+H+) m/z calculated 504.1, found 505.1. 1H NMR (DMSO-d6, 400 MHz) δ 8.87 (s, 1H), 8.77 (s, 1H), 8.55 (s, 1H), 8.49 (s, 1H), 8.03-8.08 (m, 3H), 7.82 (s, 1H), 7.67 (d, J=8.8 Hz, 1H), 6.14 (s, 1H), 5.78 (s, 2H), 5.64 (s, 2H), 4.34 (d, J=4.0 Hz, 2H), 2.32 (s, 3H), 2.19 (s, 3H).

Example 118: Preparation of N-((6-amino-2,4-dimethylpyridin-3-yl)methyl)-1-((3-chloroquinolin-6-yl)methyl)-4-oxo-4,5-dihydro-1-pyrrolo[3,2-c]pyridine-3-carboxamide

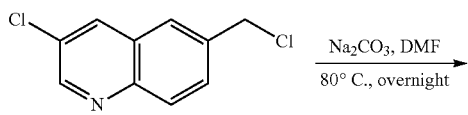

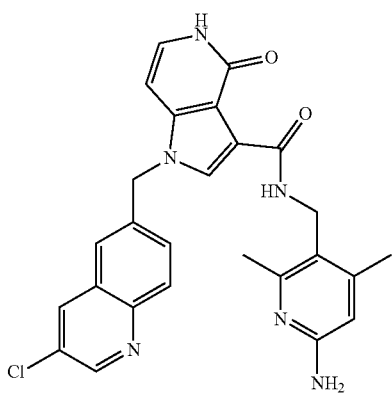

N-((6-amino-2,4-dimethylpyridin-3-yl)methyl)-1-((3-chloroquinolin-6-yl)methyl)-4-oxo-4,5-dihydro-1H-pyrrolo[3,2-c]pyridine-3-carboxamide 4-Chloro-3-iodo-1H-pyrrolo[3,2-c]pyridine (618.0 mg, 2.223 mmol, 1.0 eq), 3-chloro-6-(chloromethyl)quinoline (566.0 mg, 2.668 mmol, 1.2 eq) and Na2CO3 (589.0 mg, 5.558 mmol, 2.5 eq) were dissolved in DMF (20.0 mL). The resulting mixture was heated at 80° C. overnight. 30.0 mL of H2O was added, extracted with EA (15.0 mL×3), the combined organic layers were washed with brine (15.0 mL×3), dried over anhydrous Na2SO4 and concentrated in vacuo. The resulting residue was purified by column chromatography to provide 3-chloro-6-((4-chloro-3-iodo-1H-pyrrolo[3,2-c]pyridin-1-yl)methyl) quinoline (820.0 mg, 81%).

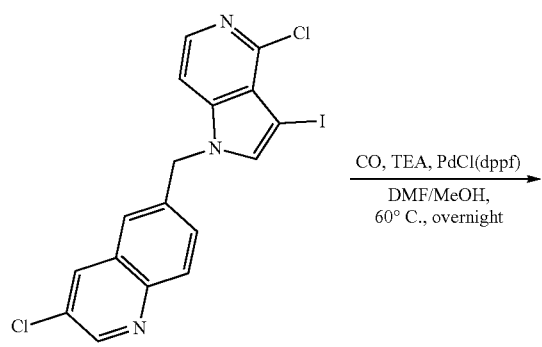

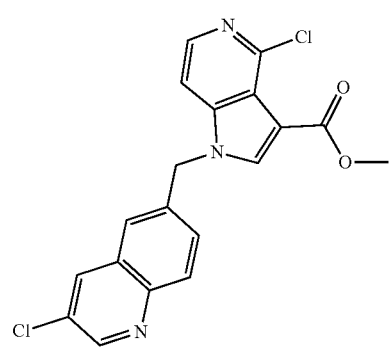

3-Chloro-6-((4-chloro-3-iodo-1H-pyrrolo[3,2-c]pyridin-1-yl)methyl)quinoline (820.0 mg, 1.907 mmol, 1.0 eq), TEA (578.0 mg, 5.721 mmol, 3.0 eq) and PdCl2(dppf)·CH2Cl2 (233.0 mg, 0.286 mmol, 0.15 eq) were dissolved in DMF (10.0 mL) and H2O (10.0 mL). The resulting mixture was degassed and heated at 60° C. overnight under CO atmosphere, then cooled and concentrated in vacuo. 30.0 mL of H2O was added and the mixture was extracted with EA (15.0 mL×3). The combined organic layers were washed with brine (15.0 mL×3), dried over anhydrous Na2SO4 and concentrated in vacuo. The resulting residue was purified by column chromatography to provide methyl 4-chloro-1-((3-chloroquinolin-6-yl)methyl)-1H-pyrrolo[3,2-c]pyridine-3-carboxylate (310.0 mg, 42%).

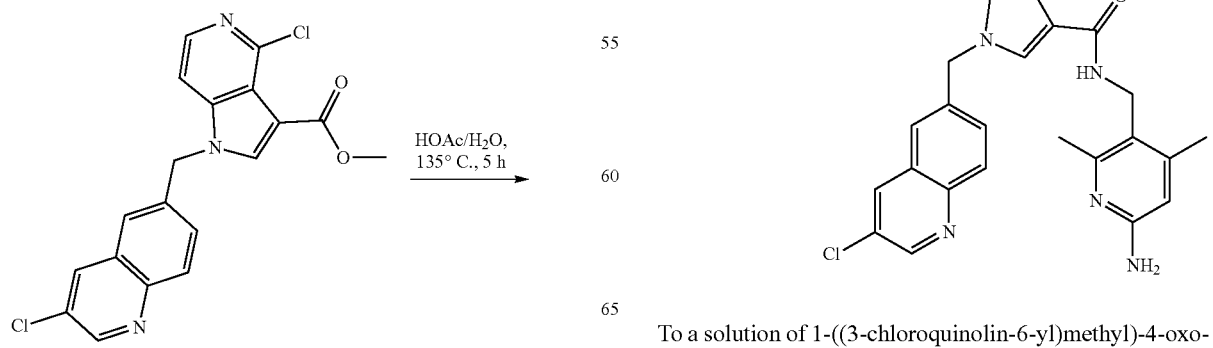

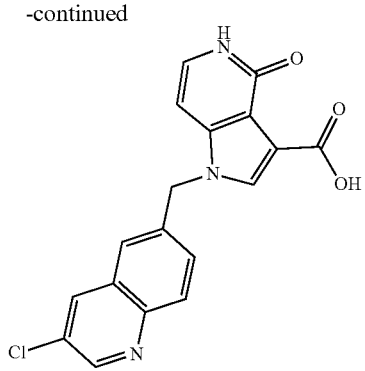

Methyl 4-chloro-1-((3-chloroquinolin-6-yl)methyl)-1H-pyrrolo[3,2-c]pyridine-3-carboxylate (130.0 mg, 0.338 mmol, 1.0 eq) was suspended in 4.0 mL HOAc/H2O (v:v=3:1). The mixture was heated at 130° C. for 5 h, then cooled and concentrated in vacuo. The resulting residue was re-suspended in 2 N aq. Aq. NaOH. The solution was acidified to pH 2~3 with con. HCl The precipitate formed. collected via filtration and dried in vacuo to provide 1-((3-chloroquinolin-6-yl)methyl)-4-oxo-4,5-dihydro-1H-pyrrolo[3,2-c]pyridine-3-carboxylic acid (130 mg).

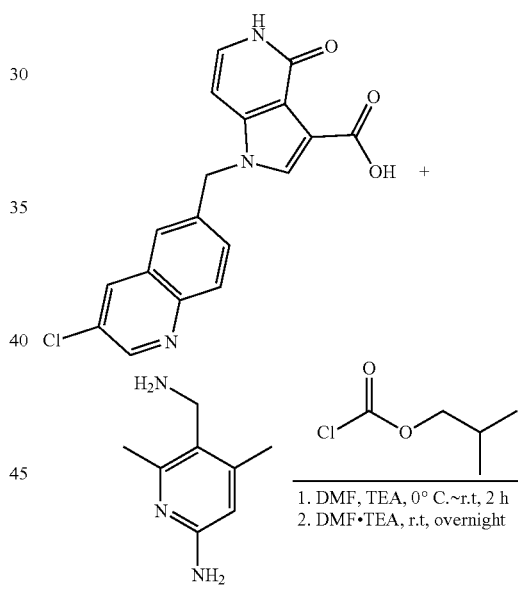

To a solution of 1-((3-chloroquinolin-6-yl)methyl)-4-oxo-4,5-dihydro-1H-pyrrolo [3,2-c]pyridine-3-carboxylic acid (100.0 mg, 0.283 mmol, 1.0 eq) in dry DMF (6.0 mL) were added TEA (34.0 mg, 0.340 mmol, 1.2 eq) and isobutyl carbonochloridate (47.0 mg, 0.340 mmol, 1.2 eq) at 0° C. The white suspension formed was and was stirred at 0° C. for 2 h, 5-(aminomethyl)-4,6-dimethylpyridin-2-amine (51.0 mg, 0.34 mmol, 1.2 eq) and TEA (34.0 mg, 0.34 mmol, 1.2 eq) were added to above solution. The resulting mixture was stirred at rt overnight, then concentrated in vacuo. The resulting residue was purified by prep-HPLC to provide N-((6-amino-2,4-dimethylpyridin-3-yl)methyl)-1-((3-chloroquinolin-6-yl)methyl)-4-oxo-4,5-dihydro-1H-pyrrolo[3,2-c]pyridine-3-carboxamide as a white solid (13.0 mg, 9%). LCMS (M+H+) m/z calculated 487.2, found 487.2. 1H NMR (DMSO-d6, 400 MHz) δ 11.51-11.53 (m, 2H), 8.88 (s, 1H), 8.55 (s, 1H), 8.04 (d, 1H, J=8.4 Hz), 7.96 (s, 1H), 7.74 (s, 1H), 7.54-7.65 (m, 3H), 7.20 (t, 1H), 6.72 (d, 1H, J=6.4 Hz), 6.64 (s, 1H), 5.65 (s, 2H), 4.40 (d, 2H, J=4.4 Hz), 2.60 (m, 6H).

Example 119: Preparation of N-((6-amino-2,4-dimethylpyridin-3-yl)methyl)-4-chloro-1-((3-chloroquinolin-6-yl)methyl)-1H-pyrazolo[4,3-c]pyridine-3-carboxamide

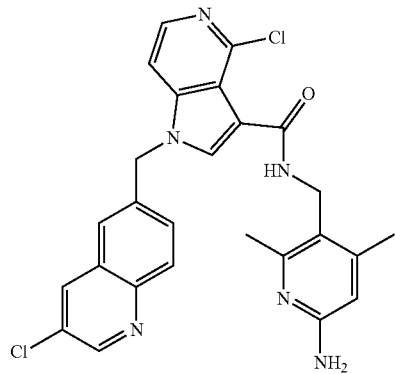

N-((6-amino-2,4-dimethylpyridin-3-yl)methyl)-4-chloro-1-((3-chloroquinolin-6-yl)methyl)-1H-pyrazolo[4,3-c]pyridine-3-carboxamide

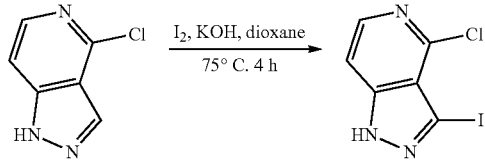

A solution of 4-chloro-1H-pyrazolo[4,3-c]pyridine (750.0 mg, 4.902 mmol, 1.0 eq), KOH (988.0 mg, 17.647 mmol, 4.0 eq) and I2 (2.49 g, 9.804 mmoL, 2.0 eq) in 1,4-dioxane (20.0 mL) was stirred at 75° C. for 4 h, then cooled and quenched by sat. aq. Na2SO3 and the precipitate was collected by filtration to provide 4-chloro-3-iodo-1H-pyrazolo[4,3-c]pyridine (1.57 g).

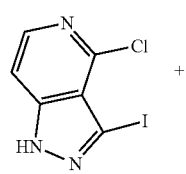

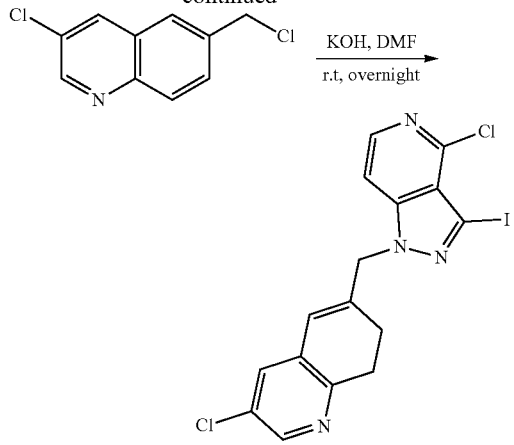

A mixture of 4-Chloro-3-iodo-1H-pyrazolo[4,3-c]pyridine (570.0 mg, 2.05 mmol, 1.0 eq), 3-chloro-6-(chloromethyl)quinoline (522.0 mg, 2.46 mmol, 1.2 eq) and KOH (230.0 mg, 4.1 mmol, 2.0 eq) in DMF (10.0 mL) was stirred at rt overnight. 30.0 mL of H2O was added and the mixture was extracted with EA (15.0 mL×3). The combined organic layers were washed with brine (15.0 mL×3), dried over anhydrous Na2SO4, then concentrated in vacuo. The resulting residue was purified by column chromatography to provide 3-chloro-6-((4-chloro-3-iodo-1H-pyrazolo[4,3-c]pyridin-1-yl)methyl)-7,8-dihydroquinoline (380 mg, 41%).

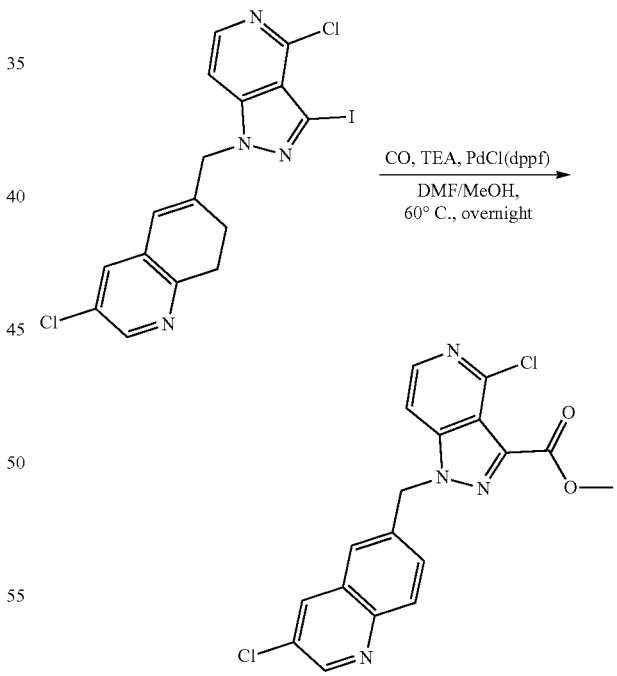

3-Chloro-6-((4-chloro-3-iodo-1H-pyrazolo[4,3-c]pyridin-1-yl)methyl)-7,8-dihydroquinoline (380.0 mg, 0.837 mmol, 1.0 eq), TEA (254.0 mg, 2.511 mmol, 3.0 eq) and PdCl2(dppf).CH2Cl2 (102 mg, 0.126 mmol, 0.15 eq) were dissolved in DMF (5.0 mL) and H2O (5.0 mL). The resulting mixture was degassed and heated at 60° C. overnight under CO atmosphere. The solvent was concentrated in vacuo. 30 mL of H2O was added and the mixture was extracted with EA (15.0 mL×3). The combined organic layers were washed with brine (15.0 mL×3), dried over anhydrous Na2SO4, and concentrated in vacuo. The resulting residue was purified by prep-HPLC to provide methyl4-chloro-1-((3-chloroquinolin-6-yl)methyl)-1H-pyrazolo[4,3-c]pyridine-3-carboxylate as off white solid (181.0 mg, 56%).

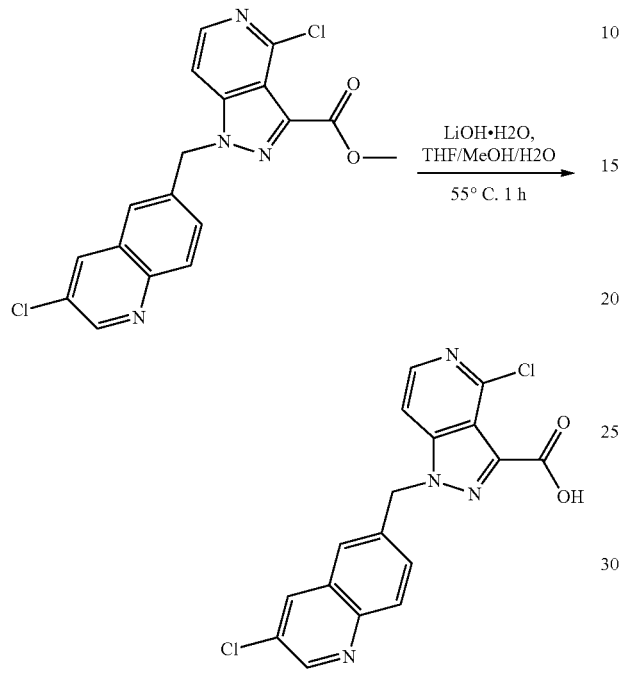

LiOH.H2O (43.0 mg, 1.036 mmol, 10.0 eq) was added to a solution of methyl 4-chloro-1-((3-chloroquinolin-6-yl)methyl)-1H-pyrazolo[4,3-c]pyridine-3-carboxylate (40.0 mg, 0.104 mmol, 1.0 eq) in THF/MeOH/H2O (6.0 mL, v/v/v=1/1/1). The reaction mixture was heated at 55° C. for 1 h, then cooled and concentrated in vacuo. 10.0 mL of H2O was added to the resulting residue and the mixture was adjusted pH=2.0 with 1N aq. HCl, then extracted with EA (10.0 mL×3). The combined organic layers were washed with brine (10.0 mL×3), and dried over anhydrous Na2SO4, and concentrated in vacuo to provide 4-chloro-1-((3-chloroquinolin-6-yl)methyl)-1H-pyrazolo[4,3-c]pyridine-3-carboxylic acid which was used in the next step without further purification (39.0 mg, ca 100%).

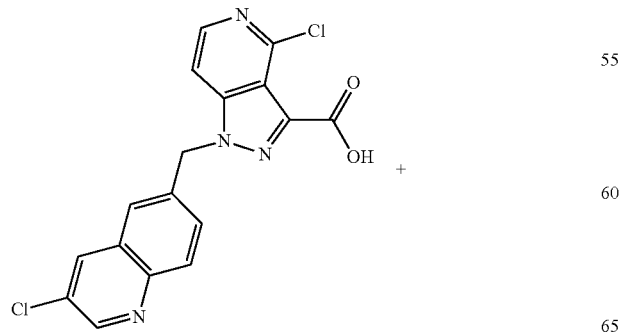

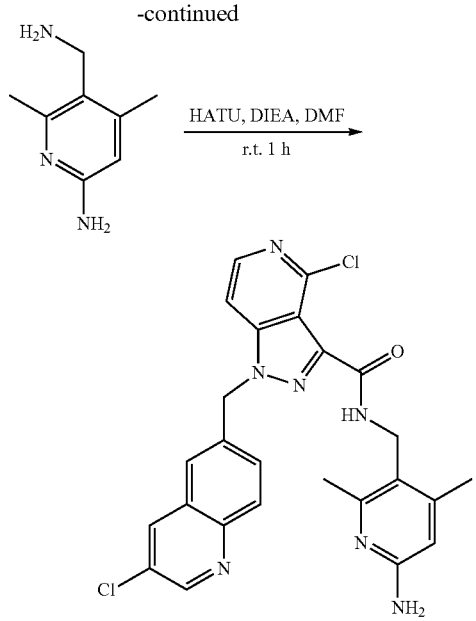

DIEA (34.0 mg, 0.26 mmol, 2.5 eq) was added to a solution of 4-chloro-1-((3-chloroquinolin-6-yl)methyl)-1H-pyrazolo[4,3-c]pyridine-3-carboxylic acid (39.0 mg, 0.104 mmol, 1.0 eq), 5-(aminomethyl)-4,6-dimethylpyridin-2-amine (16.0 mg, 0.104 mmol, 1.0 eq) and HATU (40.0 mg, 0.104 mmol, 1.0 eq) in DMF (1.0 mL). The resulting mixture was stirred at rt for 1 h and purified by prep-HPLC to provide N-((6-amino-2,4-dimethylpyridin-3-yl)methyl)-4-chloro-1-((3-chloroquinolin-6-yl)methyl)-1H-pyrazolo[4,3-c]pyridine-3-carboxamide as a white solid (10 mg, 19%). LCMS (M+H+) m/z calculated 506.1, found 506.2. 1H NMR (DMSO-d6, 400 MHz) δ 14.01 (s, 1H), 8.98 (t, 1H), 8.87 (d, 1H), 8.55 (s, 1H), 8.26 (d, 1H), 8.03 (d, 1H), 7.93-7.95 (m, 2H), 7.85 (s, 1H), 8.66 (s, 1H), 5.97 (s, 2H), 5.52 (bs, 2H), 4.44 (d, 2H), 2.55 (s, 3H), 2.43 (s, 3H).

Example 120: Preparation of N-((6-amino-2,4-dimethylpyridin-3-yl)methyl)-1-((3-chloroquinolin-6-yl)methyl)-4-oxo-4,5-dihydro-1-pyrazolo[4,3-c]pyridine-3-carboxamide

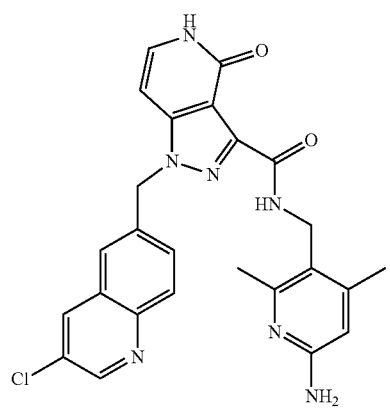

N-((6-amino-2,4-dimethylpyridin-3-yl)methyl)-1-((3-chloroquinolin-6-yl)methyl)-4-oxo-4,5-dihydro-1H-pyrazolo[4,3-c]pyridine-3-carboxamide

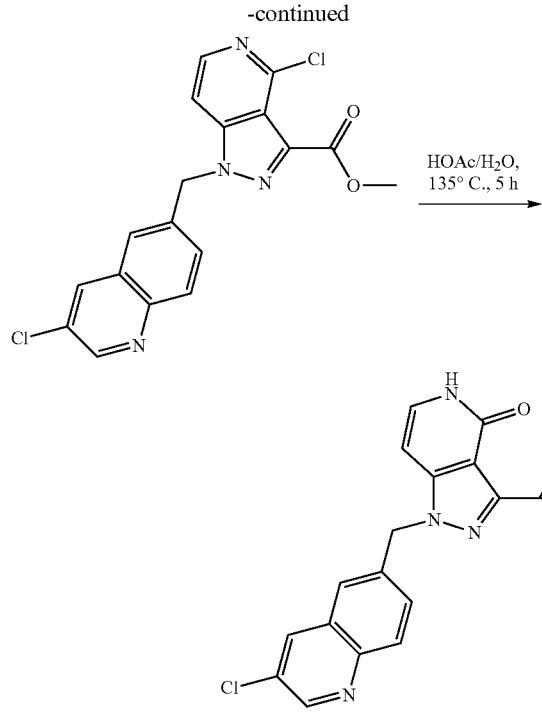

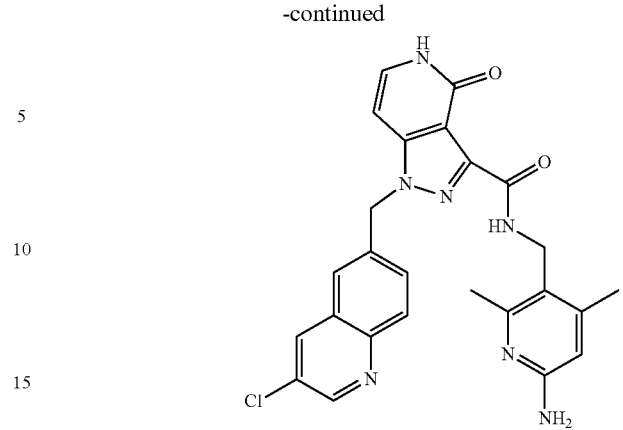

A mixture of methyl4-chloro-1-((3-chloroquinolin-6-yl)methyl)-1H-pyrazolo[4,3-c]pyridine-3-carboxylate (129.0 mg, 0.334 mmol, 1.0 eq) in HOAc (6.0 mL) and H2O (2.0 mL) was heated at 130° C. for 5 h, then cooled and concentrated in vacuo. The resulting residue was re-suspended in 2 N Aq. NaOH. The solution was acidified to pH 2~3 with con. HCl. The precipitate was collected by filtration and dried in vacuo to provide 1-((3-chloroquinolin-6-yl)methyl)-4-oxo-4,5-dihydro-1H-pyrazolo[4,3-c]pyridine-3-carboxylic acid (56 mg, 47%).

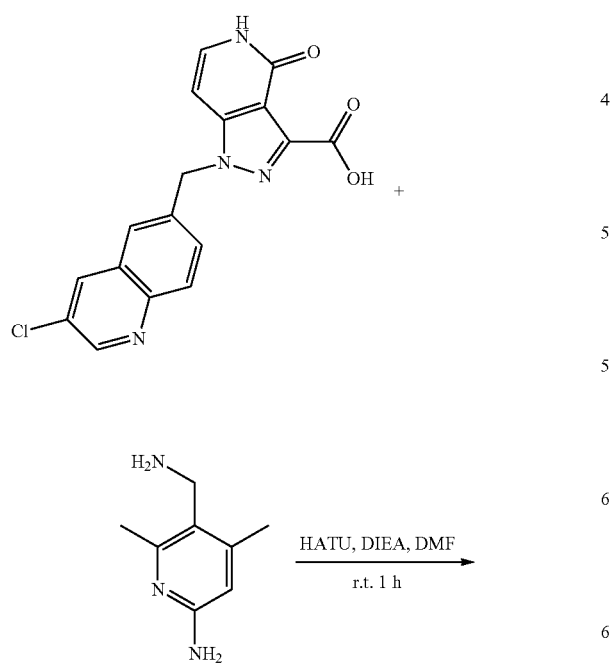

DIEA (51 mg, 0.395 mmol) was added to a solution of 1-((3-chloroquinolin-6-yl)methyl)-4-oxo-4,5-dihydro-1H-pyrazolo[4,3-c]pyridine-3-carboxylic acid (56 mg, 0.158 mmol), 5-(aminomethyl)-4,6-dimethylpyridin-2-amine (29 mg, 0.190 mmol) and HATU (72 mg, 0.190 mmol) in DMF (2 mL). The resulting mixture was stirred at rt for 1 h. This reaction was monitored by LCMS, and the desired compound was formed and purified by prep-HPLC to provide N-((6-amino-2,4-dimethylpyridin-3-yl)methyl)-1-((3-chloroquinolin-6-yl)methyl)-4-oxo-4,5-dihydro-1H-pyrazolo[4,3-c]pyridine-3-carboxamide as a white solid (12.0 mg, 16%). LCMS (M+H+) m/z calculated 488.2, found 488.3. 1H NMR (DMSO-d6, 400 MHz) δ 11.78 (d, 1H, J=5.2 Hz), 11.45 (t, 1H), 8.88 (d, 1H, J=2.0 Hz), 8.57 (d, 1H, J=2.0 Hz), 8.04 (d, 1H, J=8.8 Hz), 7.76 (s, 1H), 7.64 (d, 1H, J=9.2 Hz), 7.53 (s, 2H), 7.43 (t, 1H), 6.96 (d, 1H, J=7.2 Hz), 6.66 (s, 1H), 5.87 (s, 2H), 4.47 (d, 2H, J=4.8 Hz), 2.59 (s, 3H), 2.49 (s, 3H).

Example 121: Preparation of N-((6-amino-2,4-dimethylpyridin-3-yl)methyl)-1-((3-chloroquinolin-6-yl)methyl)-5-methoxy-1H-pyrrolo[2,3-c]pyridine-3-carboxamide

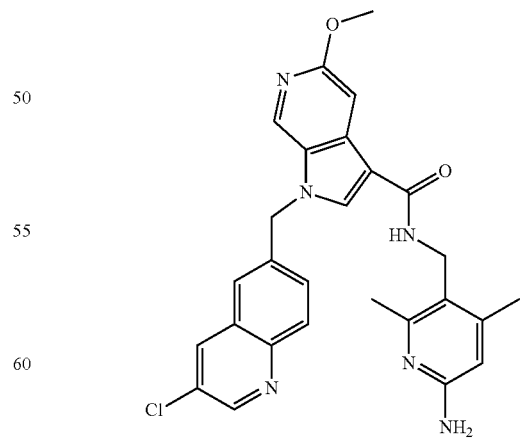

N-((6-amino-2,4-dimethylpyridin-3-yl)methyl)-1-((3-chloroquinolin-6-yl)methyl)-5-methoxy-1H-pyrrolo[2,3-c]pyridine-3-carboxamide -continued

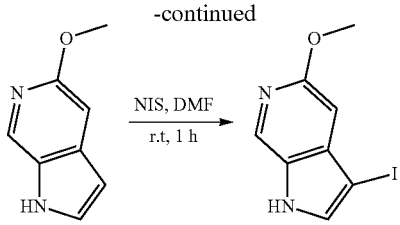

NIS (798.0 mg, 3.547 mmol, 1.05 eq) was added a solution of 5-methoxy-1H-pyrrolo[2,3-c]pyridine (500.0 mg, 3.378 mmol, 1.0 eq) in DMF (15.0 mLat 0° C. The resulting mixture was stirred at rt for 1 h. Then CHCl3 (50.0 mL) and H2O (50.0 mL) were added. The organic layer was dried over anhydrous Na2SO4, concentrated in vacuo. The resulting residue was purified by column chromatography to provide 3-iodo-5-methoxy-1H-pyrrolo[2,3-c]pyridine (926.0 mg, ca 100%).

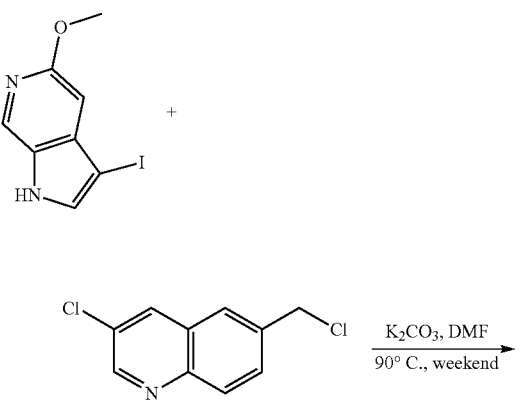

3-Iodo-5-methoxy-1H-pyrrolo[2,3-c]pyridine (926.0 mg, 3.38 mmol, 1.0 eq), 3-chloro-6-(chloromethyl)quinoline (788.0 mg, 3.718 mmol, 1.1 eq) and K2CO3 (1168 mg, 8.450 mmol) were dissolved in DMF (20.0 mL). Then the resulting mixture was heated at 90° C. over weekend. 30 mL of H2O was added and the mixture was extracted with EA (15.0 mL×3). The combined organic layers were washed with brine (15.0 mL×3), dried over anhydrous Na2SO4 and concentrated in vacuo. The resulting residue was purified by column chromatography to provide 3-chloro-6-((3-iodo-5-methoxy-1H-pyrrolo[2,3-c]pyridin-1-yl)methyl)quinoline (1075 mg, 71%).

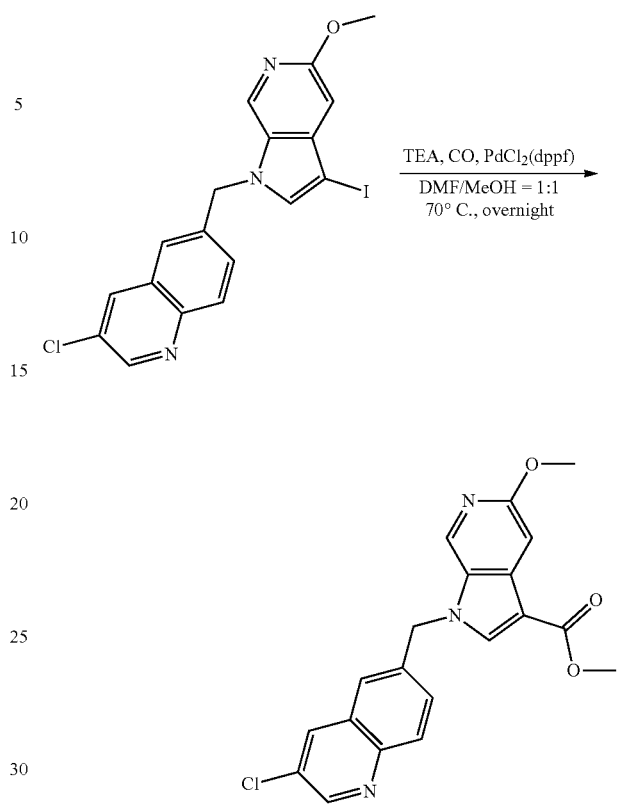

3-Chloro-6-((3-iodo-5-methoxy-1H-pyrrolo[2,3-c]pyridin-1-yl)methyl)quinoline (1.0 g, 2.227 mmol, 1 eq), TEA (675.0 mg, 6.682 mmol, 3.0 eq) and PdCl2(dppf).CH2Cl2 (273.0 mg, 0.334 mmol, 0.15 eq) were dissolved in DMF (10.0 mL) and H2O (10.0 mL). The resulting mixture was degassed and heated at 70° C. overnight under CO atmosphere, then cooled and concentrated in vacuo. 30 mL of H2O was added and the mixture was extracted with EA (15.0 mL×3). The combined organic layers were washed with brine (15.0 mL×3), dried over anhydrous Na2SO4 and concentrated in vacuo. The resulting residue was purified by column chromatography to provide methyl 1-((3-chloroquinolin-6-yl)methyl)-5-methoxy-1H-pyrrolo[2,3-c]pyridine-3-carboxylate (619 mg, 73%).

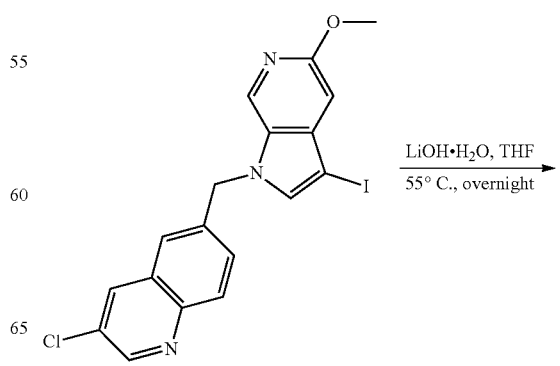

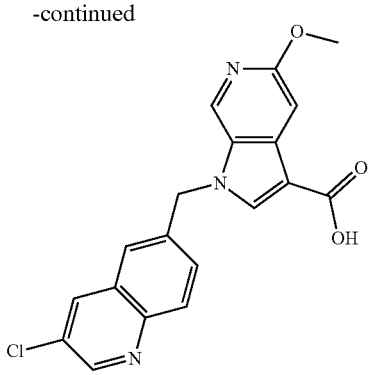

LiOH.H2O (110.0 mg, 2.62 mmoL, 10.0 eq) was added to a solution of methyl1-((3-chloroquinolin-6-yl)methyl)-5-methoxy-1H-pyrrolo[2,3-c]pyridine-3-carboxylate (100.0 mg, 0.262 mmol, 1.0 eq) in THF (5.0 mL). The reaction mixture was heated at 55° C. overnight, then cooled and concentrated in vacuo. 30 mL of H2O was added and the mixture was extracted with EA (15.0 mL×3). The combined organic layers were washed with brine (15.0 mL×3), dried over anhydrous Na2SO4 and concentrated in vacuo to provide 1-((3-chloroquinolin-6-yl)methyl)-5-methoxy-1H-pyrrolo[2,3-c]pyridine-3-carboxylic acid (77.0 mg, 80%) which was used in the next step without further purification.

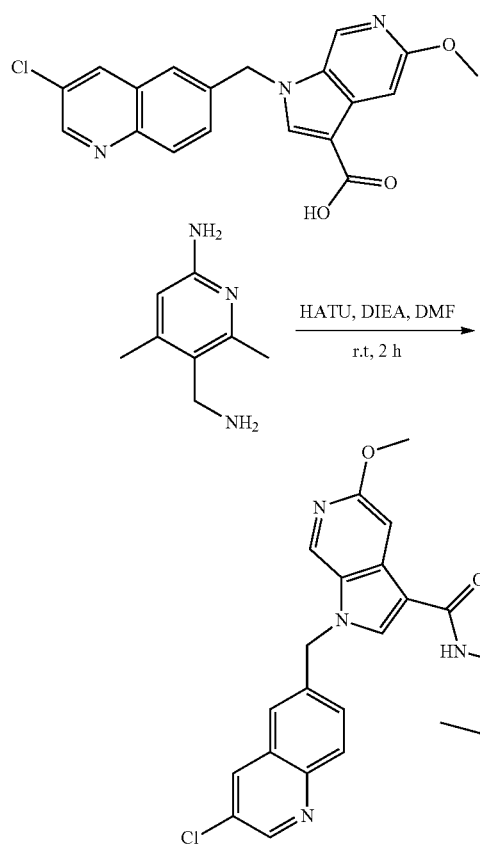

DIEA (68.0 mg, 0.525 mmol, 2.5 eq) was added to a solution of 1-((3-chloroquinolin-6-yl)methyl)-5-methoxy-1H-pyrrolo[2,3-c]pyridine-3-carboxylic acid (77.0 mg, 0.21 mmol, 1.0 eq), 5-(aminomethyl)-4,6-dimethylpyridin-2-amine (32.0 mg, 0.21 mmol, 1.0 eq) and HATU (80.0 mg, 0.21 mmol, 1.0 eq) in DMF (2.0 mL). The resulting mixture was stirred at rt for 2 h and purified by prep-HPLC to provide N-((6-amino-2,4-dimethylpyridin-3-yl)methyl)-1-((3-chloroquinolin-6-yl)methyl)-5-methoxy-1H-pyrrolo[2,3-c]pyridine-3-carboxamide (26 mg, 25%) as a white solid. LCMS (M+H+) m/z calculated 501.2, found 501.2. 1H NMR (DMSO-d6, 400 MHz) δ 8.87 (s, 1H), 8.59 (s, 1H), 8.49 (s, 1H), 8.40 (s, 1H), 8.04 (d, J=9.0 Hz, 1H), 7.85 (s, 2H), 7.66 (d, J=9.0 Hz, 1H), 7.40 (s, 1H), 6.13 (s, 1H), 5.66 (d, 4H), 4.33 (d, J=4.0 Hz, 2H), 3.83 (s, 3H), 2.33 (s, 3H), 2.20 (s, 3H).

Example 122: Preparation of N-((6-amino-2,4-dimethylpyridin-3-yl)methyl)-1-((3-chloroquinolin-6-yl)methyl)-5-methoxy-1H-pyrazolo[3,4-c]pyridine-3-carboxamide

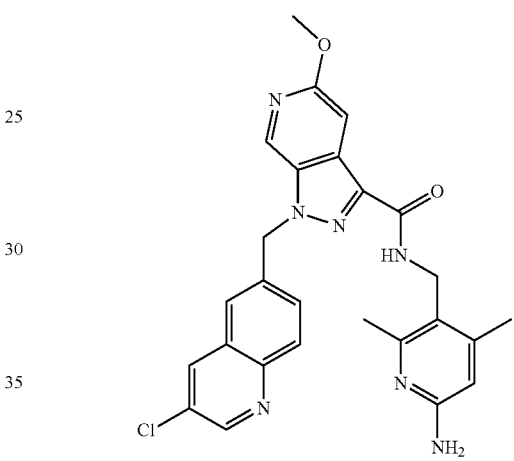

N-((6-amino-2,4-dimethylpyridin-3-yl)methyl)-1-((3-chloroquinolin-6-yl)methyl)-5-methoxy-1H-pyrazolo[3,4-c]pyridine-3-carboxamide

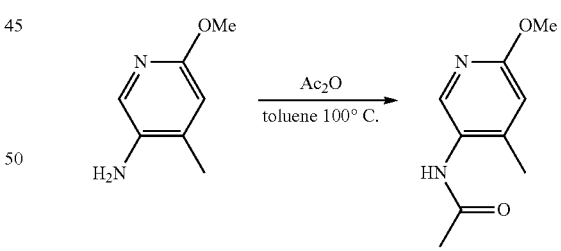

To a solution of 6-methoxy-4-methylpyridin-3-amine (5.0 g, 36.2 mmol, 1.0 eq) in toluene (100.0 mL), was added acetic anhydride (5.2 g, 50.7 mmol, 1.4 eq). The mixture was stirred and heated at 100° C. for 2 h, then cooled. The solvent of the mixture was removed in vacuo to provide N-(6-methoxy-4-methylpyridin-3-yl)acetamide (6.5 g, 100%).

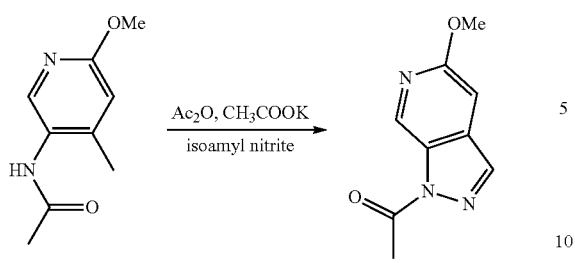

To the mixture of N-(6-methoxy-4-methylpyridin-3-yl)acetamide (6.5 g, 36.2 mmol, 1.0 eq), acetic anhydride (13.3 g, 130.3 mmol, 3.6 eq), CH3COOK (3.6 g, 36.2 mmol, 1.0 eq), was added a solution of isoamyl nitrite (10.7 g, 91.2 mmol, 2.52 eq) in CHCl3 (100.0 mL). The mixture was stirred and heated at 100° C. for 12 h, then cooled and concentrated in vacuo. The resulting residue was purified by column chromatography (PE/EA=20:1) to provide 1-(5-methoxy-1H-pyrazolo[3,4-c]pyridin-1-yl)ethanone (5 g, 72.5%) as a white solid.

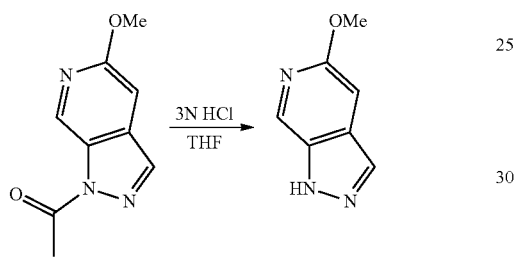

The mixture of 1-(5-methoxy-1H-pyrazolo[3,4-c]pyridin-1-yl)ethanone (5.0 g, 26.2 mmol, 1.0 eq) in 3N HCl (50.0 mL) and THF (50.0 mL) was stirred at rt for 12 h, then concentrated in vacuo to provide 5-methoxy-1H-pyrazolo[3,4-c]pyridine (3.9 g, 100%).

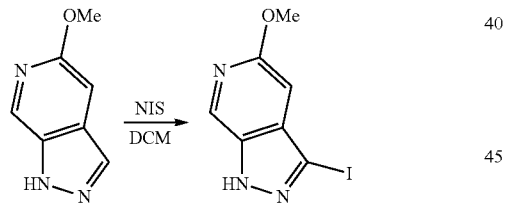

The mixture of 5-methoxy-1H-pyrazolo[3,4-c]pyridine (2.0 g, 13.4 mmol, 1.0 eq) NIS (4.5 g, 20.1 mmol, 1.5 eq) in DCM (40.0 mL) was stirred at rt for 2 h. After the reaction was complete, the solvent of the mixture was concentrated in vacuo. The resulting residue was purified by column chromatography (PE/EA=5:1) to provide 3-iodo-5-methoxy-1H-pyrazolo[3,4-c]pyridine (3.0 g, 81.1%) as a yellow solid.

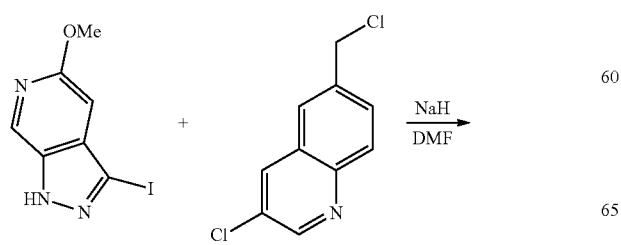

-continued

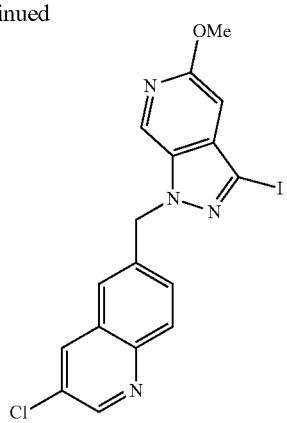

To the solution of 3-iodo-5-methoxy-1H-pyrazolo[3,4-c]pyridine (500.0 mg, 1.82 mmol, 1.0 eq) in dry DMF (10 mL) was added NaH (60% in mineral oil, 146.0 mg, 3.64 mmol, 2.0 eq) at 0° C. in portions. The mixture was stirred at 0° C. for additional 0.5 h. 3-chloro-6-(chloromethyl)quinoline (497.0 mg, 2.0 mmol, 1.1 eq) was added and the mixture was stirred at rt for 12 h. Water (10.0 mL) was added to quench the reaction, and the mixture was filtered to provide 3-chloro-6-((3-iodo-5-methoxy-1H-pyrazolo[3,4-c]pyridin-1-yl)methyl)quinoline (600.0 mg, 73.3%).

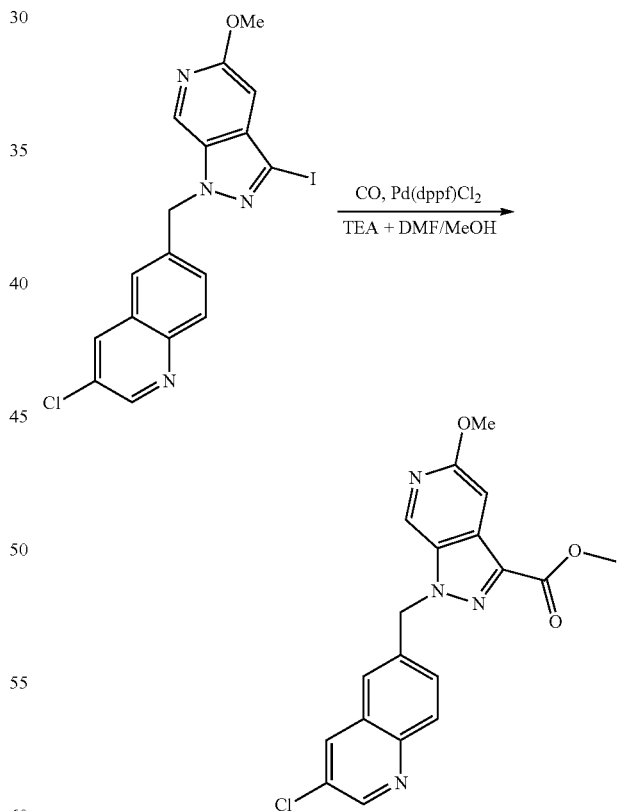

The mixture of 3-chloro-6-((3-iodo-5-methoxy-1H-pyrazolo[3,4-c]pyridin-1-yl) methyl)quinoline (600.0 mg, 1.33 mmol, 1.0 eq), Pd(dppf)Cl2 (163.0 mg, 0.2 mmol, 0.15 eq), TEA (269.0 mmol, 2.67 mmol, 2.0 eq) in DMF/MeOH (15 mL/15 mL) was heated at 70° C. for 12 h under CO atmosphere, cooled, diluted by water (15.0 mL) and EA (30.0 mL). The organic layer was washed with brine (20.0 mL), dried over anhydrous Na2SO4 and concentrated in vacuo. The resulting residue was purified by column chromatography (PE/EA=5:1) to provide methyl 1-((3-chloroquinolin-6-yl)methyl)-5-methoxy-1H-pyrazolo[3,4-c]pyridine-3-carboxylate (250 mg, 49.1%) as a white solid.

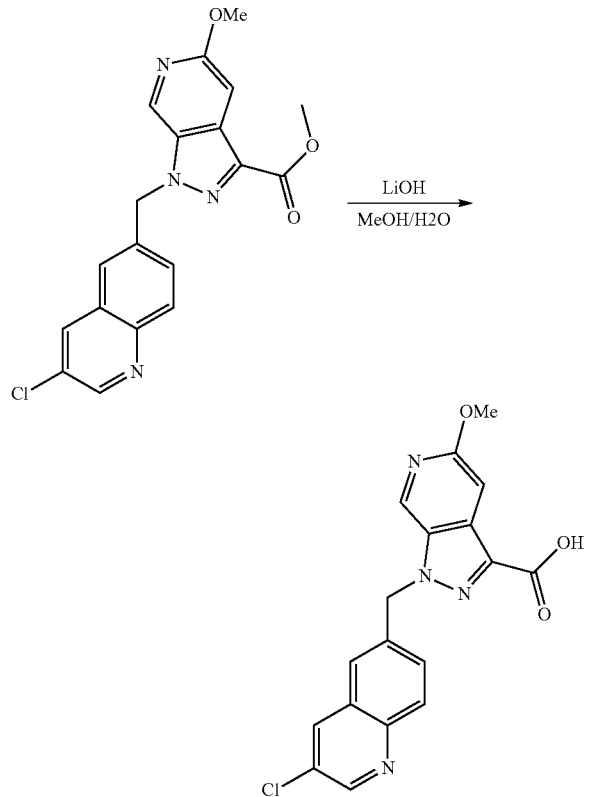

The mixture of 1-((3-chloroquinolin-6-yl)methyl)-5-methoxy-1H-pyrazolo[3,4-c]pyridine-3-carboxylate (250.0 mg, 0.654 mmol, 1.0 eq), LiOH.H2O (54.0 mg, 1.309 mmol, 2.0 eq) in MeOH/H2O (10.0 mL/2.0 mL) was stirred at rt for 12 h, then concentrated in vacuo. The resulting residue was added water (5.0 mL), Adjusted to pH=2-3 with 2N HCl, extracted with EA (30.0 mL). The organic layer was dried over anhydrous Na2SO4 and concentrated in vacuo to provide 1-((3-chloroquinolin-6-yl)methyl)-5-methoxy-1H-pyrazolo[3,4-c]pyridine-3-carboxylic acid (235 mg, 97.5%) as a white solid.

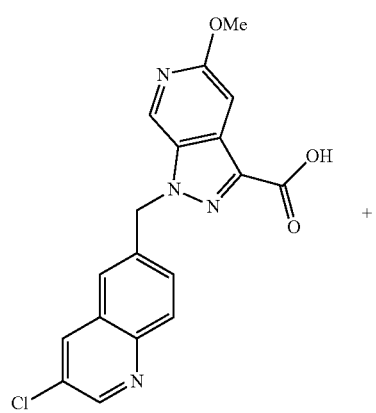

+

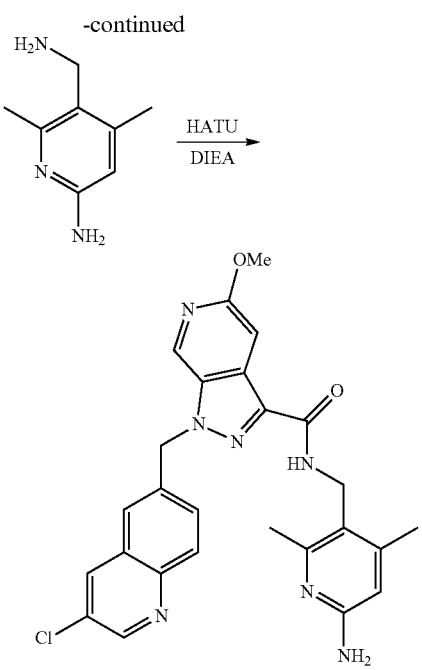

The mixture of 1-((3-chloroquinolin-6-yl)methyl)-5-methoxy-1H-pyrazolo [3,4-c]pyridine-3-carboxylic acid (115.0 mg, 0.313 mmol, 1.0 eq), 5-(aminomethyl)-4,6-dimethylpyridin-2-amine (52.0 mg, 0.344 mmol, 1.1 eq), HATU (143.0 mg, 0.376 mmol, 1.2 eq), DIEA (80.6 mg, 0.625 mmol, 2.0 eq) in DMF (3.0 mL) was stirred at rt for 2 h, then concentrated in vacuo. The resulting residue was purified by prep-HPLC to provide N-((6-amino-2,4-dimethylpyridin-3-yl)methyl)-1-((3-chloroquinolin-6-yl)methyl)-5-methoxy-1H-pyrazolo[3,4-c]pyridine-3-carboxamide (90 mg, 57.5%) as a white solid. 1H NMR (DMSO-d6, 400 MHz) δ 8.93 (s, 1H), 8.86 (d, 1H), 8.3 (d, 1H), 8.27 (t, 1H), 8.01 (d, 1H), 7.83 (s, 1H), 7.69 (d, 1H), 7.34 (s, 1H), 6.11 (s, 1H), 6.00 (s, 2H), 5.62 (s, 2H), 4.41 (d, 2H), 3.89 (s, 3H), 2.34 (s, 3H), 2.21 (s, 3H). LCMS (M+H+) m/z calculated 502.2, found 502.2.

Example 123: Preparation of N-((6-amino-2,4-dimethylpyridin-3-yl)methyl)-1-((3-chloroquinolin-6-yl)methyl)-4-cyano-1H-pyrrolo[2,3-c]pyridine-3-carboxamide

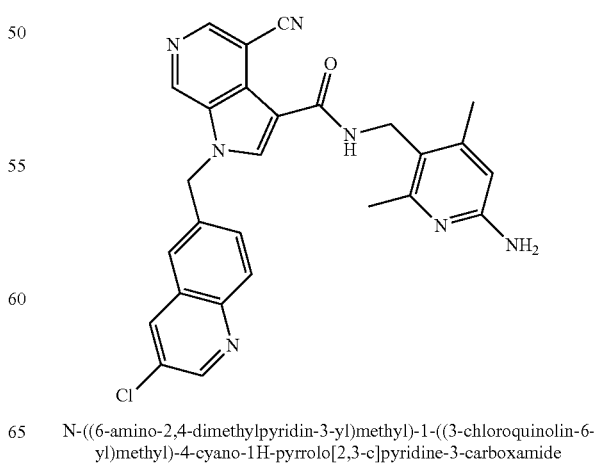

N-((6-amino-2,4-dimethylpyridin-3-yl)methyl)-1-((3-chloroquinolin-6-yl)methyl)-4-cyano-1H-pyrrolo[2,3-c]pyridine-3-carboxamide -continued

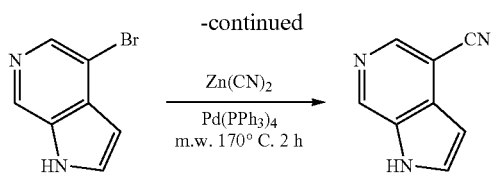

The mixture of 4-bromo-1H-pyrrolo[2,3-c]pyridine (800.0 mg, 4.06 mmol, 1.0 eq), Zn(CN)2 (1.43 g, 12.18 mmol, 3.0 eq), Pd(PPh3)4 (469 mg, 0.406 mmol, 0.1 eq) in DMF (10.0 mL) was stirred and heated to 170° C. under M.W. for 2 h, cooled, concentrated in vacuo. The resulting residue was purified by column chromatography (PE/EA=1:1) to provide 1H-pyrrolo[2,3-c]pyridine-4-carbonitrile (600.0 mg, 91.9%).

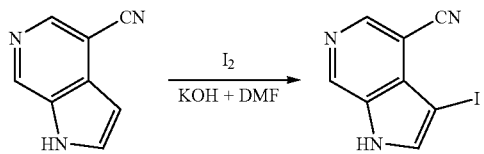 [SMILES: N#Cc1cncc2[nH]ccc12 ; "I2" ; "KOH + DMF" ; N#Cc1cncc2[nH]cc(I)c12]

The mixture of 1H-pyrrolo[2,3-c]pyridine-4-carbonitrile (600.0 mg, 4.2 mmol, 1.0 eq), I2 (1.09 g, 4.3 mmol, 1.02 eq), KOH (5.9 g, 10.5 mmol, 2.5 eq) in DMF (15.0 mL) was stirred at rt for 12 h. Sat. Na2S2O3 solution (15.0 mL) was added to the mixture, and extracted with EA (30 mL×2). The combined organic layers were washed with brine (20.0 mL), dried over anhydrous Na2SO4 and concentrated in vacuo. The resulting residue was purified by column chromatography (PE/EA=1:2) to provide 3-iodo-1H-pyrrolo[2,3-c]pyridine-4-carbonitrile (400.0 mg, 35.7%).

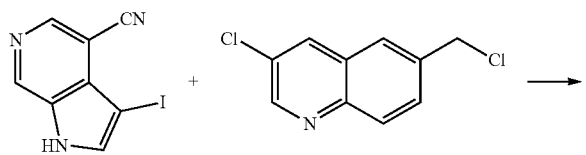

The mixture of 3-iodo-1H-pyrrolo[2,3-c]pyridine-4-carbonitrile (400.0 mg, 1.49 mmol, 1.0 eq), 3-chloro-6-(chloromethyl)quinoline (370.0 mg, 1.49 mmol, 1.0 eq), Na2CO3 (474.0 mg, 4.47 mmol, 3.0 eq) in DMF (5.0 mL) was stirred and heated at 170° C. for 12 h. After the reaction was complete, it was cooled to rt. EA (20.0 mL) and water (20.0 mL) were added and the aqueous layer was extracted with EA (20.0 mL×2). The combined organic layers were washed with brine (30.0 mL), dried over anhydrous Na2SO4 and concentrated in vacuo. The resulting residue was purified by column chromatography (PE/EA=1:2) to provide 1-((3-chloroquinolin-6-yl)methyl)-3-iodo-1H-pyrrolo[2,3-c]pyridine-4-carbonitrile (520 mg, 66.7%).

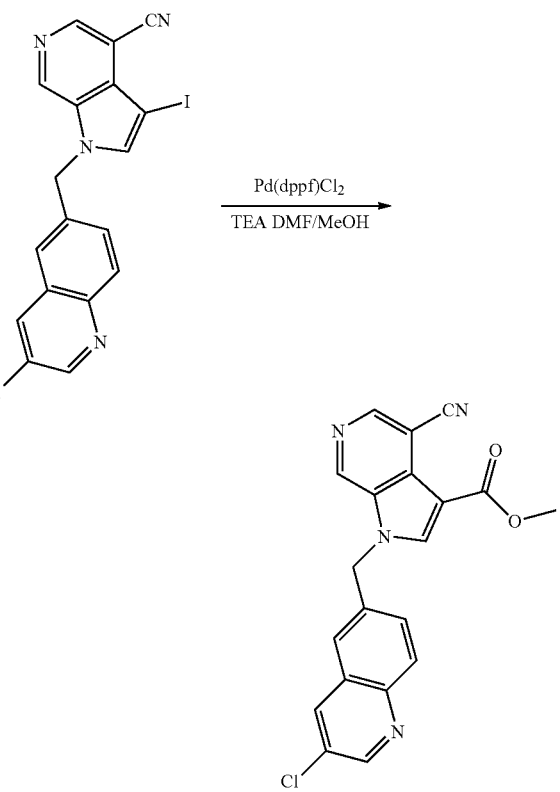

The mixture of 1-((3-chloroquinolin-6-yl)methyl)-3-iodo-1H-pyrrolo [2,3-c]pyridine-4-carbonitrile (520.0 mg, 1.17 mmol, 1.0 eq), Pd(dppf)Cl2 (95.5 mg, 0.117 mmol, 0.10 eq), TEA (236.0 mmol, 2.34 mmol, 2.0 eq) in DMF/MeOH (5.0 mL/5.0 mL) was heated to 60° C. and stirred under CO atmosphere for 12 h. After the reaction was complete, the solvent was concentrated in vacuo. The resulting residue was purified by column chromatography (PE/EA=3:1) to provide methyl 1-((3-chloroquinolin-6-yl)methyl)-4-cyano-1H-pyrrolo [2,3-c]pyridine-3-carboxylate (150.0 mg, 34.1%).

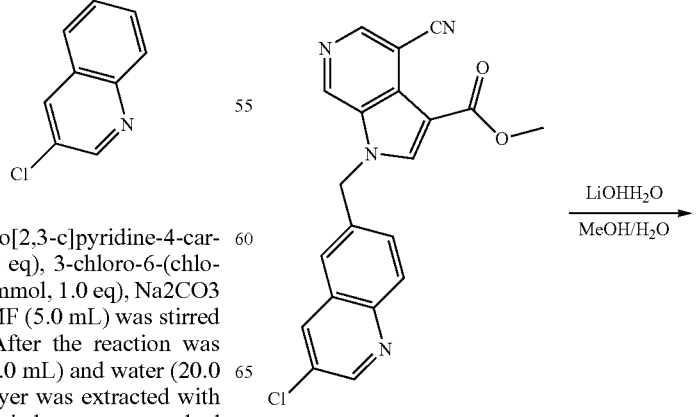

-continued

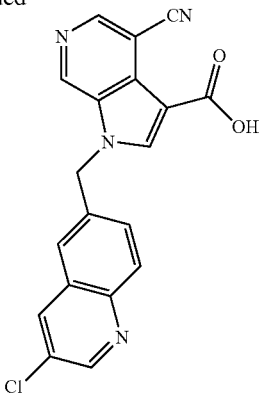

The mixture of 1-((3-chloroquinolin-6-yl)methyl)-4-cyano-1H-pyrrolo [2,3-c]pyridine-3-carboxylate (36.6 mg, 0.097 mmol, 1.0 eq), LiOH.H2O (12.3 mg, 0.292 mmol, 3.0 eq) in MeOH/H2O (2.0 mL/0.5 mL) was stirred at rt for 12 h. After the reaction was complete, most of MeOH was concentrated in vacuo. Water (5.0 mL) was added to the resulting residue. 2N HCl was added to adjust pH=2-3. The mixture was extracted with EA (30.0 mL). The organic layer was, dried over anhydrous Na2SO4, then concentrated in vacuo to provide 1-((3-chloroquinolin-6-yl)methyl)-4-cyano-1H-pyrrolo[2,3-c]pyridine-3-carboxylic acid (30.0 mg, 85.2%).

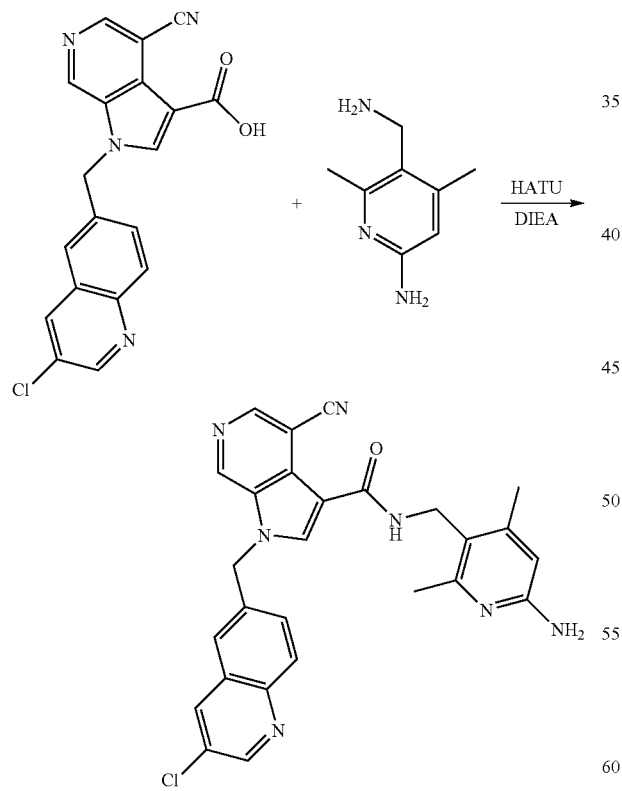

The mixture of 1-((3-chloroquinolin-6-yl)methyl)-4-cyano-1H-pyrrolo [2,3-c]pyridine-3-carboxylic acid (30.0 mg, 0.083 mmol, 1.0 eq), 5-(aminomethyl)-4,6-dimethyl-pyridin-2-amine (14.0 mg, 0.091 mmol, 1.1 eq), HATU (38 mg, 0.099 mmol, 1.2 eq), DIEA (21.4 mg, 0.166 mmol, 2.0 eq) in DMF (3.0 mL) was stirred at rt for 2 h, then concentrated in vacuo. The resulting residue was purified by prep-HPLC to provide N-((6-amino-2,4-dimethylpyridin-3-yl)methyl)-1-((3-chloroquinolin-6-yl)methyl)-4-cyano-1H-pyrrolo[2,3-c]pyridine-3-carboxamide (10.8 mg, 26.3%) as a white solid. 1H NMR (DMSO-d6, 400 MHz) δ 9.20 (s, 1H), 8.86 (d, 1 H), 8.65 (s, 1H), 8.54 (d, 1H), 8.50 (s, 1H), 8.17 (t, 1H), 8.01-8.04 (d, 1H), 7.84 (s, 1H), 7.68 (d, 1H), 6.12 (s, s1H), 5.86 (s, 2H), 5.62 (s, 2H), 4.37 (d, 2H), 2.34 (s, 3H), 2.21 (s, 3H). LCMS (M+H+) m/z calculated 496.2, found 496.2.

Example 124: Preparation of N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide

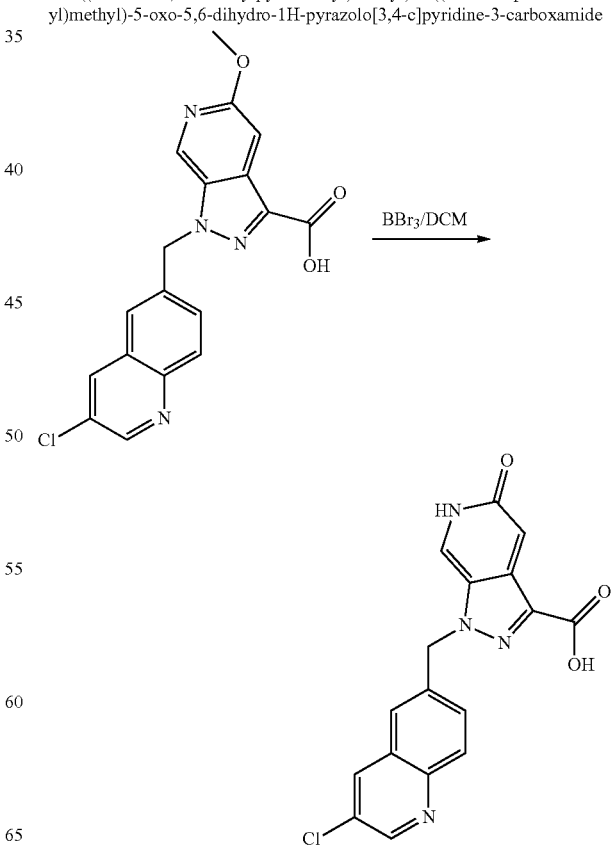

N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide

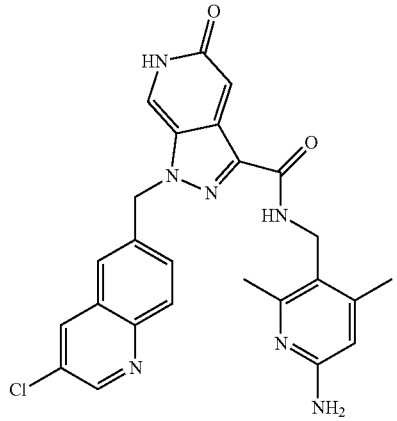

The mixture of 1-((3-chloroquinolin-6-yl)methyl)-5-methoxy-1H-pyrazolo[3,4-c]pyridine-3-carboxylic acid (100 mg, 0.27 mmol, 1.0 eq) in BBr3/DCM (1 N, 10.0 mL) was stirred at rt for 48 h. After the reaction was complete, the mixture was poured into ice-water, and the aqueous layer was separated, then concentrated in vacuo. The resulting residue was purified by prep-HPLC to provide 1-((3-chloroquinolin-6-yl)methyl)-5-oxo-5,6-dihydro-1H-pyrazolo[3,4-c]pyridine-3-carboxylic acid (46.8 mg, 22.1%).

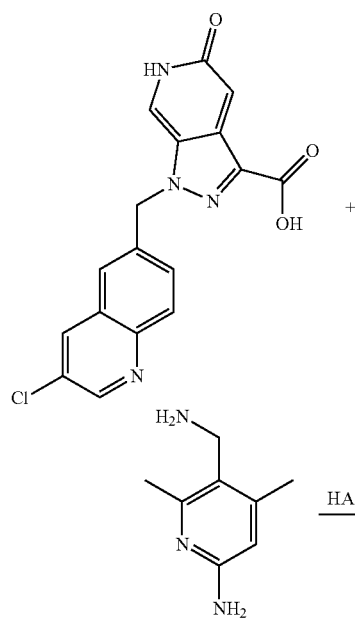

The mixture of 1-((3-chloroquinolin-6-yl)methyl)-5-oxo-5,6-dihydro-1H-pyrazolo[3,4-c]pyridine-3-carboxylic acid (46.8 mg, 0.132 mmol, 1.0 eq), 5-(aminomethyl)-4,6-dimethylpyridin-2-amine (22.0 mg, 0.145 mmol, 1.1 eq), HATU (60.0 mg, 0.158 mmol, 1.2 eq), DIEA (34.0 mg, 0.264 mmol, 2.0 eq) in DMF (2.0 mL) was stirred at rt for 2 h, then concentrated in vacuo. The resulting residue was purified by prep-HPLC to provide N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide (17.3 mg, 26.9%). 1H NMR (DMSO-d6, 400 MHz) δ 13.72 (s, 1H), 8.83-8.87 (m, 2H), 8.74-8.75 (m, 1H), 8.54 (s, 1H), 8.02 (d, 1H), 7.77-7.78 (m, 2H), 7.66 (d, 1H), 7.18 (s, 1H), 6.63 (s, 1H), 5.99 (s, 2H), 4.40 (d, 2H), 2.55 (s, 3H), 2.41 (s, 3H). LCMS (M+H+) m/z calculated 488.2, found 488.2.

Example 125: Preparation of N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide

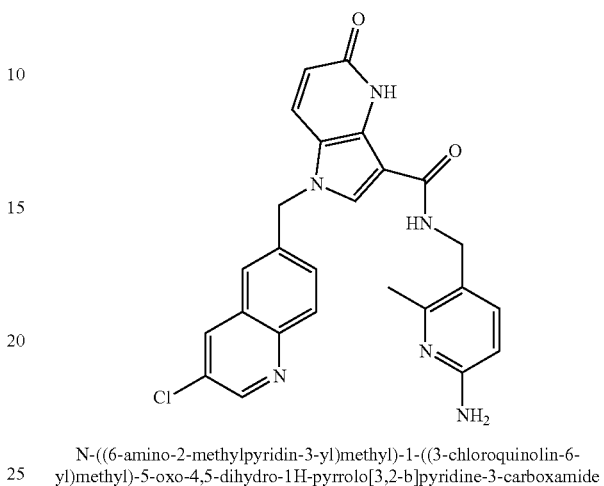

N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide

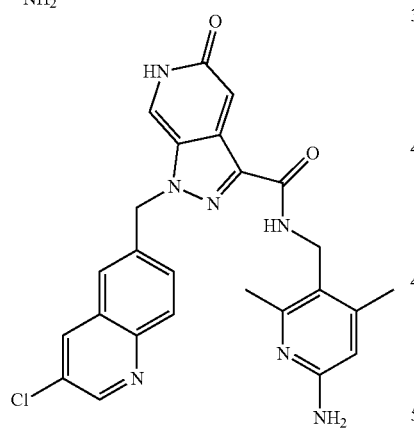

To a solution of 5-methoxy-1H-pyrrolo[3,2-b]pyridine (100.0 mg, 0.675 mmol, 1.0 eq) in CH3CN/DMF=1:1 (5.0 mL) was added NIS (152.0 mg, 0.675 mmol, 1.0 eq), and the reaction mixture was stirred at rt overnight, quenched by H2O (500.0 mL), extracted by EA (50.0 mL×3), washed by brine, dried over Na2SO4, and concentrated. The resulting residue was purified by column chromatography (PE:EA=3:1) to provide 3-iodo-5-methoxy-1H-pyrrolo[3,2-b]pyridine (185 mg, ca 100.0%) as a white solid. LCMS (M+H+) m/z calculated 275, found 275.

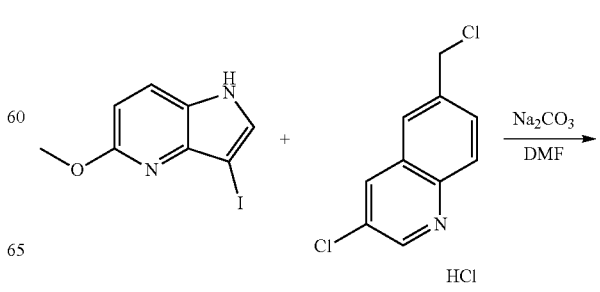

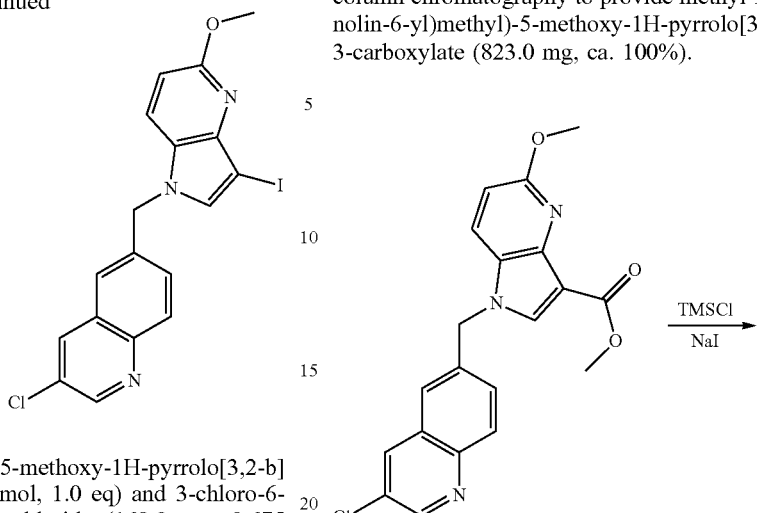

To a solution of 3-iodo-5-methoxy-1H-pyrrolo[3,2-b]pyridine (185.0 mg, 0.675 mmol, 1.0 eq) and 3-chloro-6-(chloromethyl)quinoline hydrochloride (168.0 mg, 0.675 mmol, 1.0 eq) in DMF (5.0 mL) was added Na2CO3 (214.7 mg, 2.025 mmol, 3.0 eq) and the reaction mixture was heated at 70° C. for 3 hs. After the reaction was complete, the reaction mixture was quenched by H2O and filtered. The solid was collected and washed by water, dried in vacuo to provide 3-chloro-6-((3-iodo-5-methoxy-1H-pyrrolo[3,2-b]pyridin-1-yl)methyl)quinoline (215.0 mg, 71.0%) as a white solid. LCMS (M+H+) m/z calculated 450, found 450.

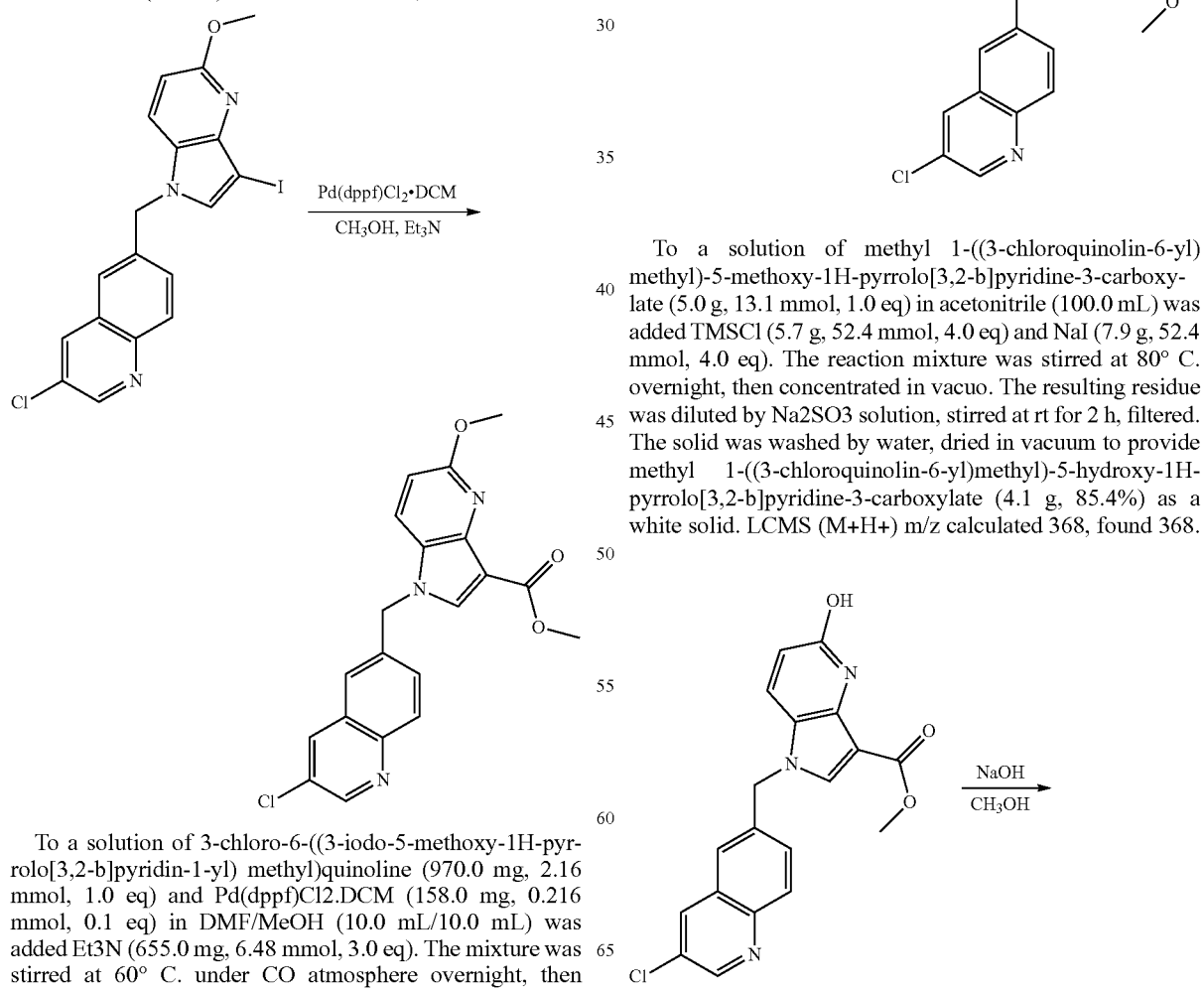

To a solution of 3-chloro-6-((3-iodo-5-methoxy-1H-pyrrolo[3,2-b]pyridin-1-yl) methyl)quinoline (970.0 mg, 2.16 mmol, 1.0 eq) and Pd(dppf)Cl2.DCM (158.0 mg, 0.216 mmol, 0.1 eq) in DMF/MeOH (10.0 mL/10.0 mL) was added Et3N (655.0 mg, 6.48 mmol, 3.0 eq). The mixture was stirred at 60° C. under CO atmosphere overnight, then concentrated in vacuo. The resulting residue was purified by column chromatography to provide methyl 1-((3-chloroquinolin-6-yl)methyl)-5-methoxy-1H-pyrrolo[3,2-b] pyridine-3-carboxylate (823.0 mg, ca. 100%).

To a solution of methyl 1-((3-chloroquinolin-6-yl)methyl)-5-methoxy-1H-pyrrolo[3,2-b]pyridine-3-carboxylate (5.0 g, 13.1 mmol, 1.0 eq) in acetonitrile (100.0 mL) was added TMSCl (5.7 g, 52.4 mmol, 4.0 eq) and NaI (7.9 g, 52.4 mmol, 4.0 eq). The reaction mixture was stirred at 80° C. overnight, then concentrated in vacuo. The resulting residue was diluted by Na2SO3 solution, stirred at rt for 2 h, filtered. The solid was washed by water, dried in vacuum to provide methyl 1-((3-chloroquinolin-6-yl)methyl)-5-hydroxy-1H-pyrrolo[3,2-b]pyridine-3-carboxylate (4.1 g, 85.4%) as a white solid. LCMS (M+H+) m/z calculated 368, found 368.

447

-continued

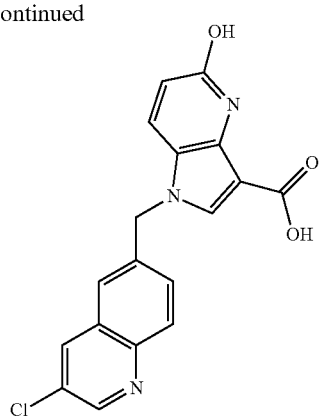

To a solution of methyl 1-((3-chloroquinolin-6-yl)methyl)-5-hydroxy-1H-pyrrolo [3,2-b]pyridine-3-carboxylate (1.6 g, 4.4 mmol, 1.0 eq) in CH3OH/H2O (50.0 mL/20.0 mL) was added NaOH (0.35 g, 8.8 mmol, 2.0 eq). The mixture was stirred at 55° C. for 48 h, adjusted to pH 3 by conc. HCl, then concentrated in vacuo to provide 1-((3-chloroquinolin-6-yl)methyl)-5-hydroxy-1H-pyrrolo[3,2-b]pyridine-3-carboxylic acid (1.9 g, 100.0%) as a white solid. LCMS (M+H+) m/z calculated 354, found 354.

448

To a solution of 1-((3-chloroquinolin-6-yl)methyl)-5-oxo-4,5-dihydro-1H-pyrrolo [3,2-b]pyridine-3-carboxylic acid (200.0 mg, 0.57 mmol, 1.0 eq) and 5-(aminomethyl)-6-methylpyridin-2-amine (78.1 mg, 0.57 mmol, 1.0 eq) in DMF (5.0 mL) was added HATU (216.8 mg, 0.57 mmol, 1.0 eq). The mixture was stirred at rt for 10 min, then DIEA (220.6 mg, 1.71 mmol, 3.0 eq) was added. The reaction mixture was stirred at rt overnight and purified by column chromatography (CH2Cl2:CH3OH=30:1) to provide N-((6-amino-2-methylpyridin-3-yl)methyl)-1-((3-chloroquinolin-6-yl) methyl)-5-oxo-4,5-dihydro-1H-pyrrolo[3,2-b]pyridine-3-carboxamide (150.0 mg, 54.5%) as a white solid. 1H NMR (DMSO-d6, 400 MHz) δ 10.21 (s, 1H), 9.12 (s, 1H), 8.85 (d, 1H), 8.52 (s, 1H), 8.03 (d, 2H), 7.81 (t, 2H), 7.67 (d, 1H), 7.31 (d, 1H), 7.16 (t, 1H), 6.76 (d, 1H), 6.30 (d, 1H), 5.65-5.62 (m, 3H), 4.36 (s, 2H), 2.33 (s, 3H). LCMS (M+H+) m/z calculated 473.1, found 473.2.

Example 126: Preparation of N-((6-amino-2,4-dimethylpyridin-3-yl)methyl)-1-((3-chloroquinolin-6-yl) methyl)-5-oxo-4,5-dihydro-1H-pyrrolo[3,2-b]pyridine-3-carboxamide

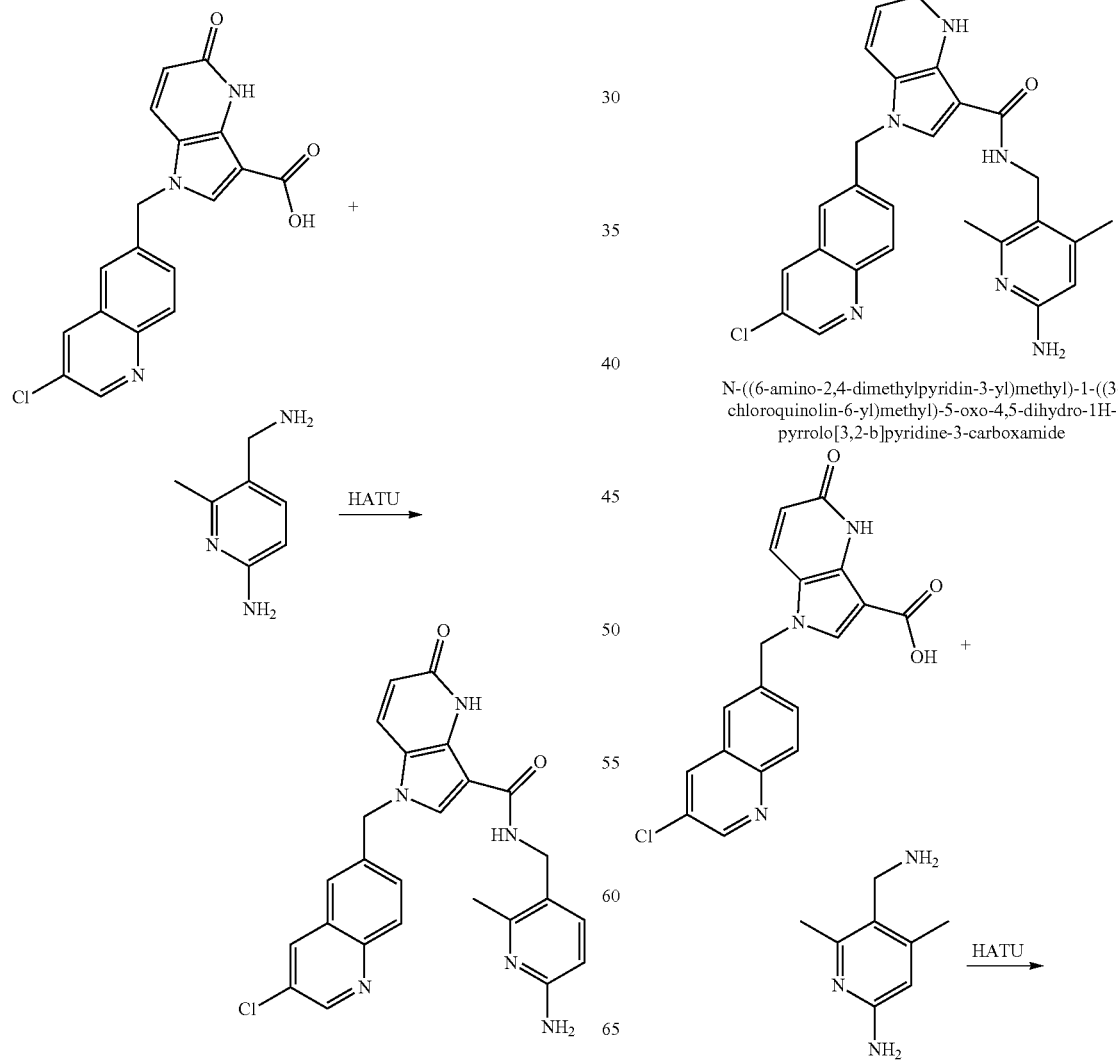

N-((6-amino-2,4-dimethylpyridin-3-yl)methyl)-1-((3-chloroquinolin-6-yl)methyl)-5-oxo-4,5-dihydro-1H-pyrrolo[3,2-b]pyridine-3-carboxamide -continued

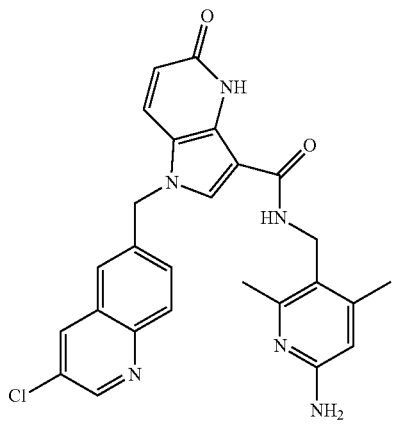

To a solution of 1-((3-chloroquinolin-6-yl)methyl)-5-oxo-4,5-dihydro-1H-pyrrolo[3,2-b]pyridine-3-carboxylic acid (200.0 mg, 0.57 mmol, 1.0 eq) and 5-(aminomethyl)-4,6-dimethylpyridin-2-amine (86.2 mg, 0.57 mmol, 1.0 eq) in DMF (5.0 mL) was added HATU (216.8 mg, 0.57 mmol, 1.0 eq). The mixture was stirred at rt for 10 min, then DIEA (220.6 mg, 1.71 mmol, 3.0 eq) was added. The reaction mixture was stirred at rt overnight. The reaction was complete and purified by column chromatography (CH2Cl2:CH3OH=30:1) to give N-((6-amino-2,4-dimethylpyridin-3-yl)methyl)-1-((3-chloroquinolin-6-yl) methyl)-5-oxo-4,5-dihydro-1H-pyrrolo[3,2-b]pyridine-3-carboxamide (150.0 mg, 54.5%) as a white solid. 1H NMR (DMSO-d6, 400 MHz) δ 10.48-10.16 (m, 1H), 8.86 (s, 1H), 8.56 (s, 1H), 8.25-8.02 (m, 3H), 7.83-7.67 (m, 2H), 7.63 (d, 1H), 6.52 (s, 1H), 6.12 (s, 1H), 5.65-5.59 (m, 4H), 4.37 (s, 2H), 2.40 (s, 3H), 2.30 (s, 3H). LCMS (M+H+) m/z calculated 487.2, found 487.2.

Example 127: Preparation of N-((6-amino-2,4-dimethylpyridin-3-yl)methyl)-1-((3-chloroquinolin-6-yl)methyl)-4-cyano-1H-pyrrolo[2,3-b]pyridine-3-carboxamide

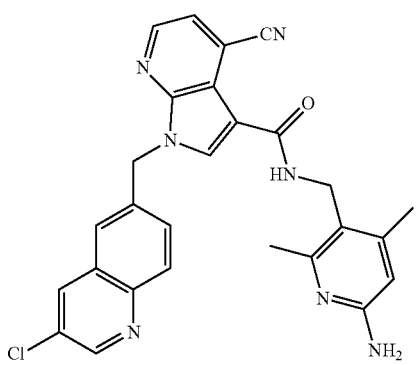

N-((6-amino-2,4-dimethylpyridin-3-yl)methyl)-1-((3-chloroquinolin-6-yl)methyl)-4-cyano-1H-pyrrolo[2,3-b]pyridine-3-carboxamide -continued

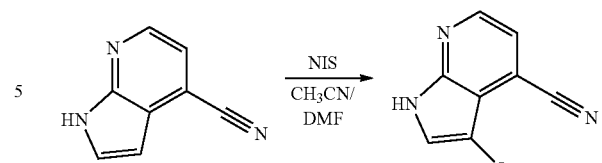

To a solution of 1H-pyrrolo[2,3-b]pyridine-4-carbonitrile (100.0 mg, 0.698 mmol, 1.0 eq) in CH3CN/DMF=1:1 (5.0 mL) was added NIS (157.1 mg, 0.698 mmol, 1.0 eq) and the reaction mixture was stirred at rt overnight, then quenched by H2O (100.0 mL), extracted by EA (100.0 mL×3), washed by brine, dried over Na2SO4, concentrated in vacuo. The residue was purified by column chromatography (PE:EA=3:1) to provide 3-iodo-1H-pyrrolo[2,3-b]pyridine-4-carbonitrile (174 mg, 92.6%) as a white solid.

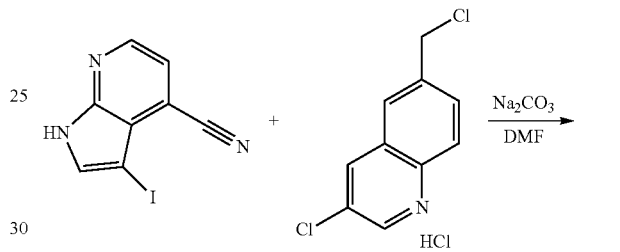

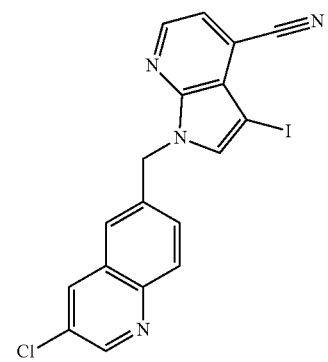

To a solution of 3-iodo-1H-pyrrolo[2,3-b]pyridine-4-carbonitrile (174.0 mg, 0.647 mmol, 1.0 eq) and 3-chloro-6-(chloromethyl)quinoline hydrochloride (161.0 mg, 0.647 mmol, 1.0 eq) in DMF (5.0 mL) was added Na2CO3 (206.0 mg, 1.941 mmol, 3.0 eq) and the reaction mixture was heated at 70° C. for 3 h, then quenched by H2O, filtered. The solid was washed by water, dried in vacuo to provide 1-((3-chloroquinolin-6-yl)methyl)-3-iodo-1H-pyrrolo[2,3-b]pyridine-4-carbonitrile (235.0 mg, 81.9%) as a white solid. LCMS (M+H+) m/z calculated 444.9, found 445.0.

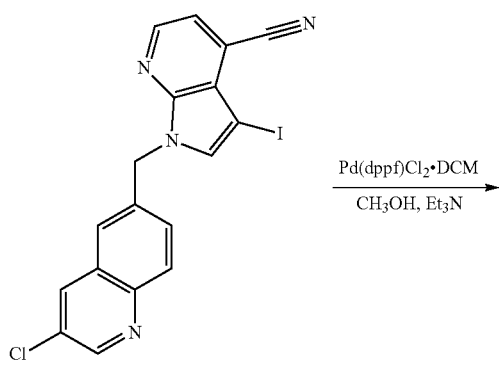

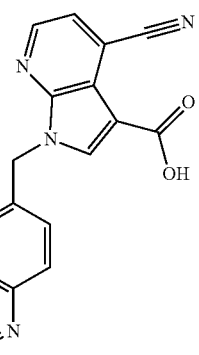

To a solution of 1-((3-chloroquinolin-6-yl)methyl)-3-iodo-1H-pyrrolo[2,3-b] pyridine-4-carbonitrile (235.0 mg, 0.53 mmol, 1.0 eq) and Pd(dppf)Cl2.DCM (39.0 mg, 0.053 mmol, 0.1 eq) in DMF/MeOH (5.0 mL/5.0 mL) was added Et3N (160.0 mg, 1.587 mmol, 3.0 eq). The mixture was stirred at 60° C. under CO atmosphere overnight, then concentrated in vacuo. The resulting residue was purified by column chromatography to provide methyl 1-((3-chloroquinolin-6-yl)methyl)-4-cyano-1H-pyrrolo[2,3-b] pyridine-3-carboxylate (110.0 mg, 55.2%) as brown solid. LCMS (M+H+) m/z calculated 377.1, found 377.1.

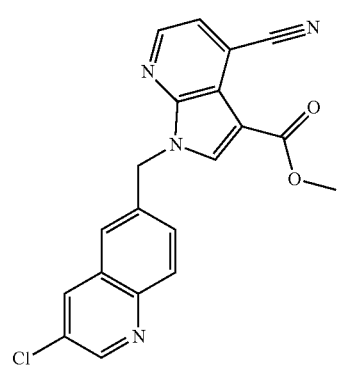

To a solution of methyl 1-((3-chloroquinolin-6-yl)methyl)-4-cyano-1H-pyrrolo [2,3-b]pyridine-3-carboxylate (150.0 mg, 0.4 mmol, 1.0 eq) in THF/MeOH/H2O=4:2:1 (10.0 mL) was added LiOH.H2O (50.0 mg, 1.2 mmol, 3.0 eq). The reaction mixture was stirred at rt overnight, then concentrated in vacuo. The resulting residue was diluted by H2O, adjusted to pH 1~2 with 1N HCl solution, extracted by EA (50.0 mL×3), washed by brine, dried over Na2SO4, and concentrated. The resulting residue was purified by prep-HPLC to provide 1-((3-chloroquinolin-6-yl)methyl)-4-cyano-1H-pyrrolo [2,3-b]pyridine-3-carboxylic acid (33.0 mg, 22.9%) as a white solid. LCMS (M+H+) m/z calculated 363, found 363.

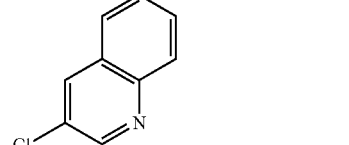

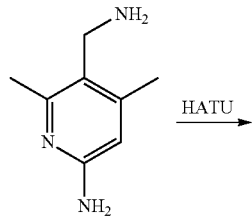

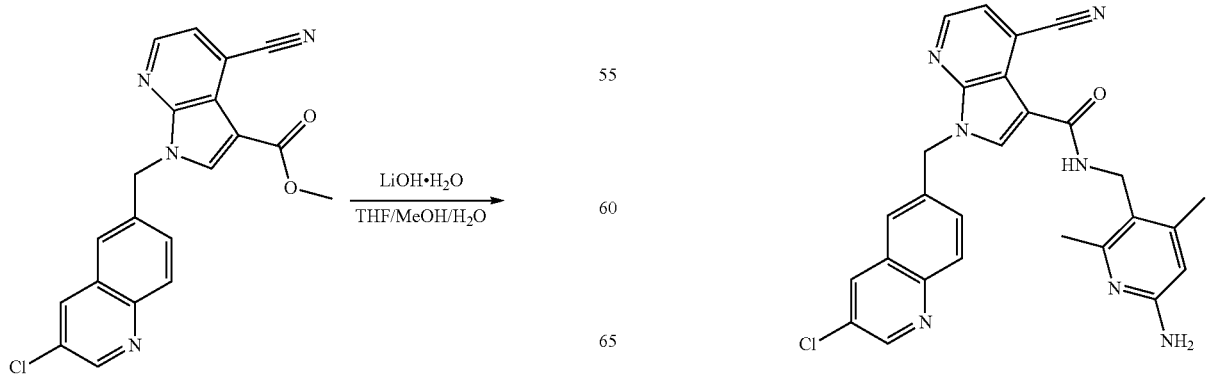

453

To a solution of 1-((3-chloroquinolin-6-yl)methyl)-4-cyano-1H-pyrrolo[2,3-b]pyridine-3-carboxylic acid (33.0 mg, 0.09 mmol, 1.0 eq) and 5-(aminomethyl)-4,6-dimethylpyridin-2-amine (14.0 mg, 0.09 mmol, 1.0 eq) in DMF (2.0 mL) was added HATU (35.0 mg, 0.09 mmol, 1.0 eq) and the mixture was stirred at rt for 10.0 min, then DIEA (35.0 mg, 0.27 mmol, 3.0 eq) was added. The reaction mixture was stirred at rt overnight, then concentrated in vacuo. The residue was purified by prep-HPLC to provide N-((6-amino-2,4-dimethylpyridin-3-yl)methyl)-1-((3-chloroquinolin-6-yl)methyl)-4-cyano-1H-pyrrolo[2,3-b]pyridine-3-carboxamide (7.6 mg, 16.9%) as a white solid. 1H NMR (CD3OD-d4, 400 MHz) δ 8.76 (s, 1H), 8.49 (d, 1H), 8.31 (s, 1H), 8.23 (s, 1H), 7.96 (d, 1H), 7.75-7.69 (m, 2H), 7.59 (d, 1H), 6.29 (s, 1H), 5.76 (s, 2H), 4.54 (s, 2H), 2.41 (s, 3H), 2.29 (s, 3H). LCMS (M+H+) m/z calculated 496.2, found 496.2.

Example 128: Preparation of N-((6-amino-2,4-dimethylpyridin-3-yl)methyl)-1-((3-chloroquinolin-6-yl)methyl)-5-methoxy-1H-pyrrolo[3,2-b]pyridine-3-carboxamide

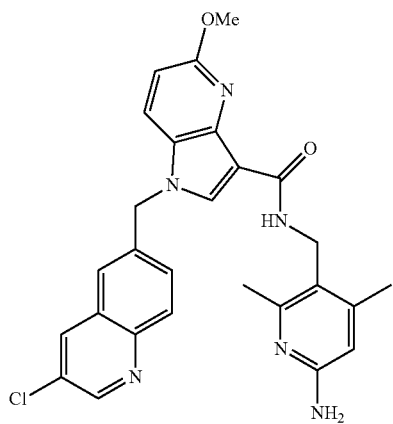

N-((6-amino-2,4-dimethylpyridin-3-yl)methyl)-1-((3-chloroquinolin-6-yl)methyl)-5-methoxy-1H-pyrrolo[3,2-b]pyridine-3-carboxamide

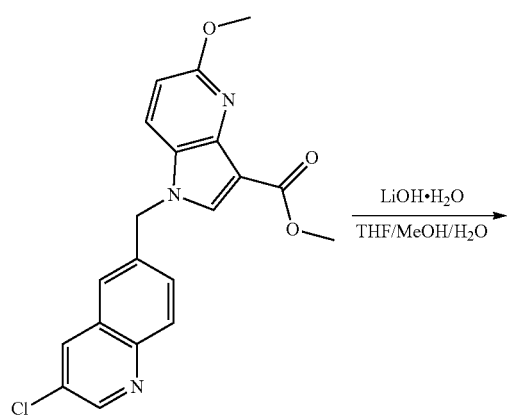

454

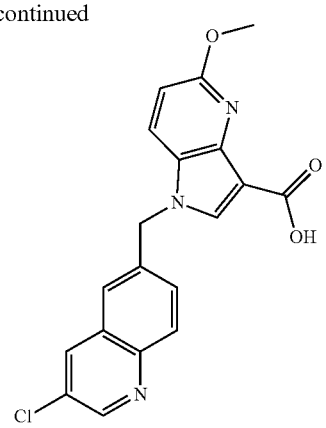

To a solution of methyl 1-((3-chloroquinolin-6-yl)methyl)-5-methoxy-1H-pyrrolo [3,2-b]pyridine-3-carboxylate (1.03 g, 2.7 mmol, 1.0 eq) in THF/MeOH/H2O (10.0 mL, v:v:v=4:2:1) was added LiOH.H2O (568.0 mg, 13.5 mmol, 5.0 eq). The reaction mixture was stirred at rt overnight, then concentrated in vacuo. The resulting residue was diluted by H2O, adjusted to pH 1-2 with 1N HCl solution, extracted by EA (150.0 mL×3), washed by brine, dried over Na2SO4, and concentrated. The resulting residue was purified by column chromatography to provide 1-((3-chloroquinolin-6-yl)methyl)-5-methoxy-1H-pyrrolo[3,2-b]pyridine-3-carboxylic acid (527.0 mg, 53.0%) as a white solid. LCMS (M+H+) m/z calculated 368.1, found 368.1.

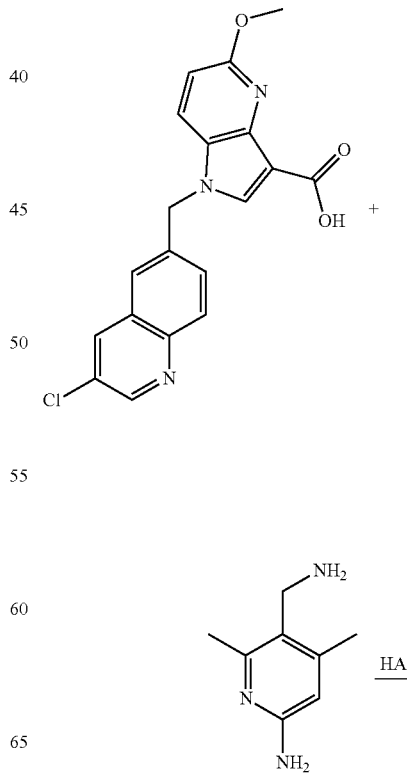

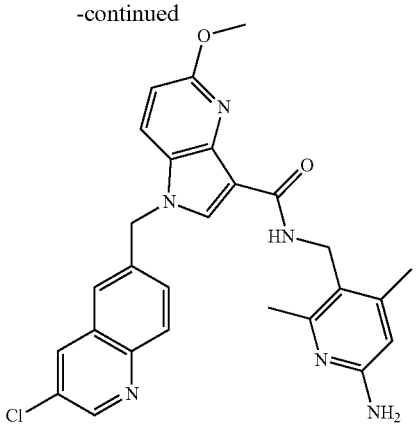

To a solution of 1-((3-chloroquinolin-6-yl)methyl)-5-methoxy-1H-pyrrolo[3,2-b]pyridine-3-carboxylic acid (30.0 mg, 0.08 mmol, 1.0 eq) and 5-(aminomethyl)-4,6-dimethylpyridin-2-amine (12.3 mg, 0.08 mmol, 1.0 eq) in DMF (5.0 mL) was added HATU (31.0 mg, 0.08 mmol, 1.0 eq) and the mixture was stirred at rt for 10 min. Then DIEA (32.0 mg, 0.24 mmol, 3.0 eq) was added and the reaction mixture was stirred at rt overnight, then concentrated in vacuo. The resulting residue was purified by prep-HPLC to provide N-((6-amino-2,4-dimethylpyridin-3-yl)methyl)-1-((3-chloroquinolin-6-yl)methyl)-5-methoxy-1H-pyrrolo[3,2-b]pyridine-3-carboxamide (9.2 mg, 23.0%) as a white solid. 1H NMR (CD3OD-d4, 400 MHz) δ 8.77 (s, 1H), 8.33 (s, 1H), 8.12 (s, 1H), 8.00 (d, 1H), 7.77-7.62 (m, 3H), 6.60 (d, 1H), 6.34 (s, 1H), 5.65 (s, 2H), 4.58 (s, 2H), 3.56 (s, 3H), 2.45 (s, 3H), 2.33 (s, 3H). LCMS (M+H+) m/z calculated 501.2, found 501.2.

Example 129: Preparation of N-((6-amino-2,4-dimethylpyridin-3-yl)methyl)-1-((3-chloroquinolin-6-yl)methyl)-4-cyano-1H-pyrazolo[3,4-c]pyridine-3-carboxamide

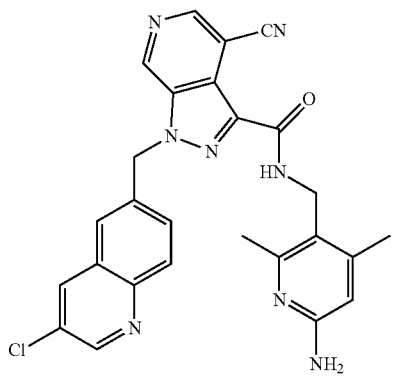

N-((6-amino-2,4-dimethylpyridin-3-yl)methyl)-1-((3-chloroquinolin-6-yl)methyl)-4-cyano-1H-pyrazolo[3,4-c]pyridine-3-carboxamide

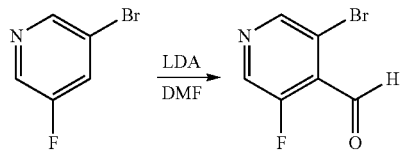

Diisopropylamine (5.7 g, 28.4 mmol, 2.0 eq) was dissolved in anhydrous THF (200.0 mL), and the reaction mixture was cooled to −60° C.~−65° C., then n-BuLi (35.5 mL, 56.8 mmol, 2.0 eq) was added dropwise. The reaction mixture was stirred at the same temperature for 30.0 min, then 3-bromo-5-fluoropyridine (5.0 g, 28.4 mmol, 1.0 eq) in anhydrous THF (50.0 mL) was added to the reaction mixture at −60° C.~−65° C. and stirred at this temperature for 30 min. then DMF (2.5 g, 34.1 mmol, 1.2 eq) was added to the reaction mixture in one portion and stirred at this temperature for 30 min. The reaction was quenched by MeOH, then NH4Cl solution was added, diluted by EA (200.0 mL), extracted by EA (200.0 mL×3), washed by brine, concentrated. The resulting residue was purified by column chromatography (PE:EA=3:1) to provide 3-bromo-5-fluoroisonicotinaldehyde (3.5 g, 60.3%) as brown oil. LCMS (M+H+) m/z calculated 204.1, found 204.2.

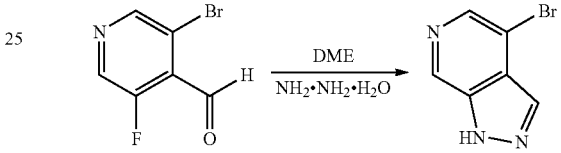

To a solution of 3-bromo-5-fluoroisonicotinaldehyde (5.0 g, 24.5 mmol, 1.0 eq) in DME (25.0 mL) was added NH2NH2-H2O (25.0 mL) and the reaction mixture was heated at 110° C. overnight. After the reaction was complete, the solvent was concentrated. The resulting residue was diluted by water, extracted by EA (100.0 mL×3), washed by brine, dried over Na2SO4, concentrated. The resulting residue was purified by column chromatography (PE:EA=2:1) to provide 4-bromo-1H-pyrazolo[3,4-c]pyridine (1.5 g, 31.3%) as a white solid. LCMS (M+H+) m/z calculated 198.1, found 198.2.

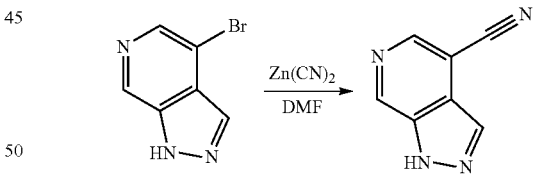

To a solution of 4-bromo-1H-pyrazolo[3,4-c]pyridine (680.0 mg, 3.43 mmol, 1.0 eq) and Pd(PPh3)4 (396.0 mg, 0.343 mmol, 0.1 eq) in DMF (15.0 mL) was added Zn(CN)2 (804.0 mg, 6.87 mmol, 2.0 eq) and the mixture was stirred at 130° C. under microwave irradiation for 2 h. After the reaction was complete, the reaction mixture was diluted by EA (50.0 mL), quenched by H2O (100.0 mL), filtered. The solid was washed by EA (50.0 mL). The filtrate was extracted by EA (50.0 mL×3), washed by brine, dried over Na2SO4, concentrated to get a residue which was purified by column chromatography (PE:EA=2:1) to provide 1H-pyrazolo[3,4-c]pyridine-4-carbonitrile (210 mg, 42.3%) as a white solid. LCMS (M+H+) m/z calculated 145, found 145.

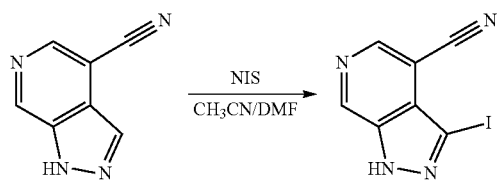

To a solution of 1H-pyrazolo[3,4-c]pyridine-4-carbonitrile (448.0 mg, 3.11 mmol, 1.0 eq) in CH3CN/DMF (20.0 mL/20.0 mL) was added NIS (700.0 mg, 3.11 mmol, 1.0 eq). The reaction mixture was stirred at rt overnight. After the reaction was complete, the reaction mixture was quenched by H2O (200.0 mL), extracted by EA (100.0 mL×3). The combined organic layers were washed by brine, dried over Na2SO4, concentrated to get a residue which purified by column chromatography (PE:EA=3:1) to provide 3-iodo-1H-pyrazolo[3,4-c]pyridine-5-carbonitrile (420.0 mg, 50.0%) as brown solid. LCMS (M+H+) m/z calculated 271.1, found 271.2.

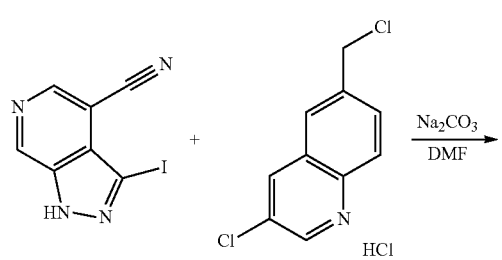

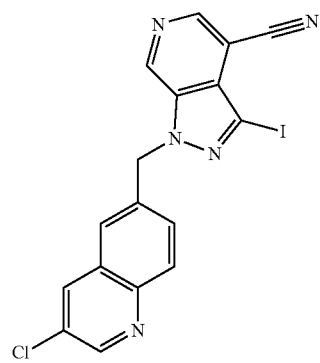

To a solution of 3-iodo-1H-pyrazolo[3,4-c]pyridine-4-carbonitrile (220.0 mg, 0.815 mmoL, 1.0 eq) and 3-chloro-6-(chloromethyl)quinoline hydrochloride (203.0 mg, 0.815 mmol, 1.0 eq) in DMF (10.0 mL) was added Na2CO3 (259.0 mg, 2.445 mmol, 3.0 eq). The reaction mixture was heated at 70° C. for 3 h. After the reaction was complete, the reaction mixture was quenched by H2O, filtered and the solid was washed by water, dried in vacuum to provide 1-((3-chloroquinolin-6-yl)methyl)-3-iodo-1H-pyrazolo[3,4-c]pyridine-4-carbonitrile (274 mg, 75.5%) as a white solid. LCMS (M+H+) m/z calculated 446.1, found 446.2.

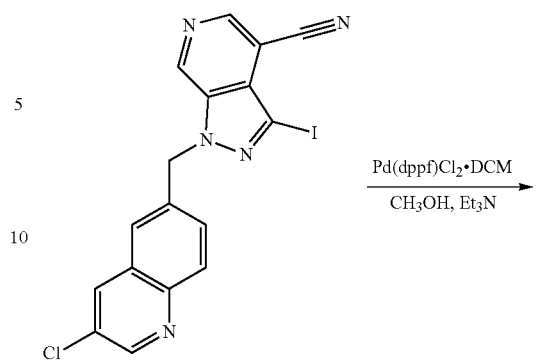

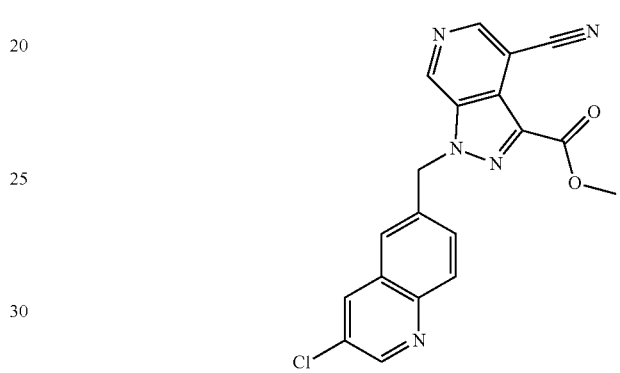

To a solution of 1-((3-chloroquinolin-6-yl)methyl)-3-iodo-1H-pyrazolo [3,4-c]pyridine-4-carbonitrile (235.0 mg, 0.53 mmol, 1.0 eq) and Pd(dppf)Cl2.DCM (39.0 mg, 0.053 mmol, 0.1 eq) in DMF/MeOH (5.0 mL/5.0 mL) was added Et3N (160.0 mg, 1.587 mmol, 3.0 eq). The mixture was stirred at 60° C. under CO atmosphere overnight. After the reaction was complete, the solvent was concentrated to get a residue which was purified by column chromatography to provide methyl 1-((3-chloroquinolin-6-yl)methyl)-4-cyano-1H-pyrazolo [3,4-c]pyridine-3-carboxylate (110 mg, 55.2%) as brown solid. LCMS (M+H+) m/z calculated 378.1, found 378.2.

459
-continued

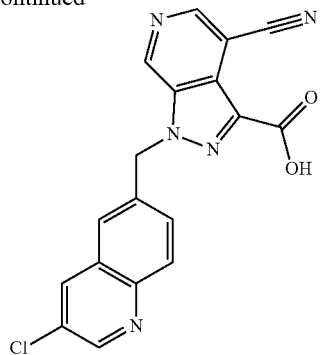

To a solution of methyl 1-((3-chloroquinolin-6-yl)methyl)-4-cyano-1H-pyrazolo [3,4-c]pyridine-3-carboxylate (150 mg, 0.40 mmol, 1.0 eq) in THF/MeOH/H2O (v:v:v=4:2:1.10 mL) was added LiOH.H2O (84.0 mg, 2.0 mmol, 5.0 eq). The reaction mixture was stirred at rt overnight, then concentrated to get a residue which was diluted by H2O, adjusted to pH=1-2 by 1N HCl solution, extracted by EA (50.0 mL×3), washed by brine, dried over Na2SO4 and concentrated. The resulting residue was purified by prep-HPLC to provide 1-((3-chloroquinolin-6-yl)methyl)-4-cyano-1H-pyrazolo[3,4-c]pyridine-3-carboxylic acid (17 mg, 12.0%) as a white solid. LCMS (M+H+) m/z calculated 364, found 364.

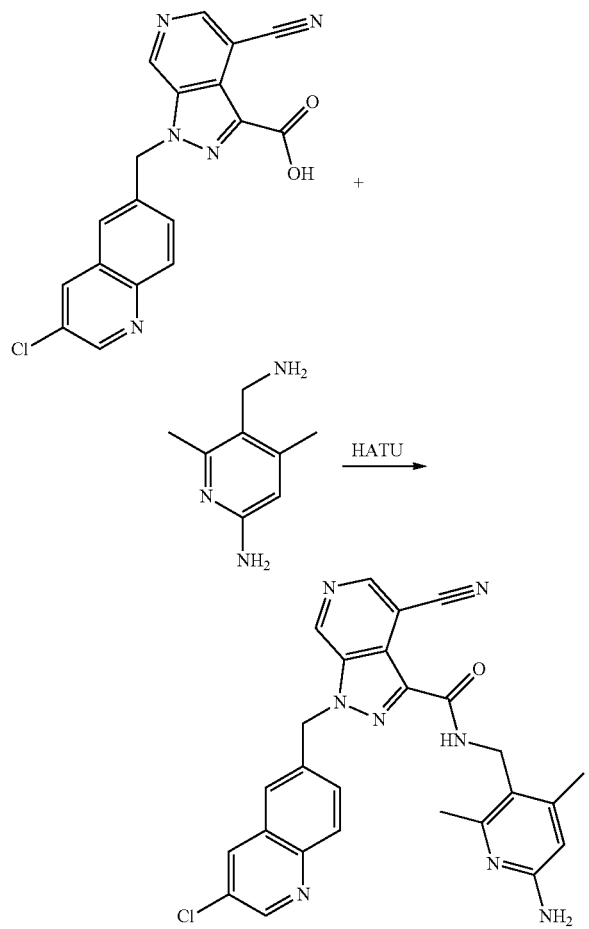

To a solution of 1-((3-chloroquinolin-6-yl)methyl)-4-cyano-1H-pyrazolo [3,4-c]pyridine-3-carboxylic acid (17.0 mg, 0.05 mmol, 1.0 eq) and 5-(aminomethyl)-4,6-dimethylpyridin-2-amine (7.0 mg, 0.05 mmol, 1.0 eq) in DMF (2.0 mL) was added HATU (18.0 mg, 0.05 mmol, 1.0 eq). The mixture was stirred at rt for 10.0 min, then DIEA (18.0 mg, 0.15 mmol, 3.0 eq) was added. The reaction mixture was stirred at rt overnight. After the reaction was complete, the solvent was concentrated. The resulting residue was purified by prep-HPLC to provide N-((6-amino-2,4-dimethylpyridin-3-yl)methyl)-1-((3-chloroquinolin-6-yl)methyl)-4-cyano-1H-pyrazolo[3,4-c]pyridine-3-carboxamide (6.6 mg, 28.4%) as a white solid. 1H NMR (CD3OD-d4, 400 MHz) δ 9.46 (s, 1H), 8.81-8.78 (m, 2H), 8.36 (s, 1H), 8.01 (d, 1H), 7.85 (s, 1H), 7.72 (d, 1H), 6.69 (s, 1H), 6.11 (s, 2H), 4.60 (s, 2H), 2.64 (s, 3H), 2.51 (s, 3H). LCMS (M+H+) m/z calculated 497.2, found 497.2.

Example 130: Preparation of N-((6-amino-2,4-dimethylpyridin-3-yl)methyl)-1-((3-chloroquinolin-6-yl)methyl)-5-cyano-1H-pyrazolo[3,4-c]pyridine-3-carboxamide

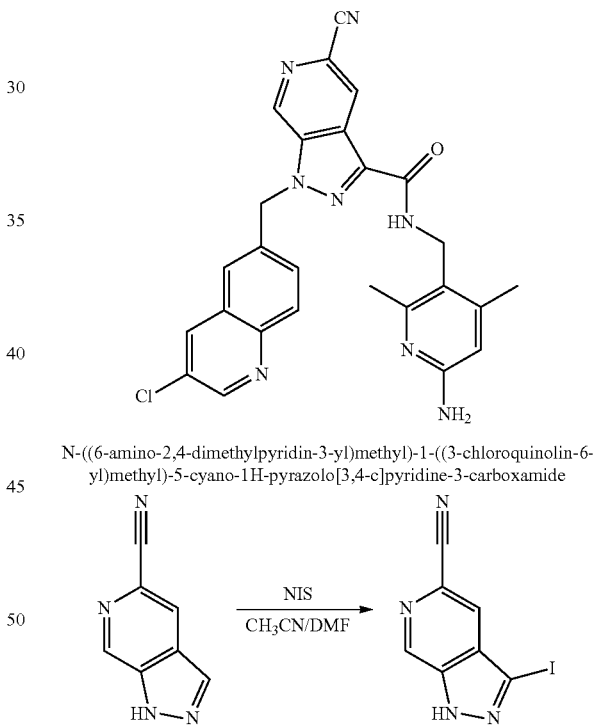

N-((6-amino-2,4-dimethylpyridin-3-yl)methyl)-1-((3-chloroquinolin-6-yl)methyl)-5-cyano-1H-pyrazolo[3,4-c]pyridine-3-carboxamide To a solution of 1H-pyrazolo[3,4-c]pyridine-5-carbonitrile (607.0 mg, 4.21 mmol, 1.0 eq) in CH3CN/DMF (v:v=1:1, 40 mL) was added NIS (947.0 mg, 4.21 mmol, 1.0 eq). The reaction mixture was stirred at rt overnight. After the reaction was complete, it was quenched by H2O (200.0 mL), extracted by EA (100.0 mL×3), washed by brine, dried over Na2SO4, concentrated to get a residue which was purified by column chromatography (PE:EA=3:1) to provide 3-iodo-1H-pyrazolo[3,4-c]pyridine-5-carbonitrile (950 mg, 83.4%) as a white solid. LCMS (M+H+) m/z calculated 271.1, found 271.2.

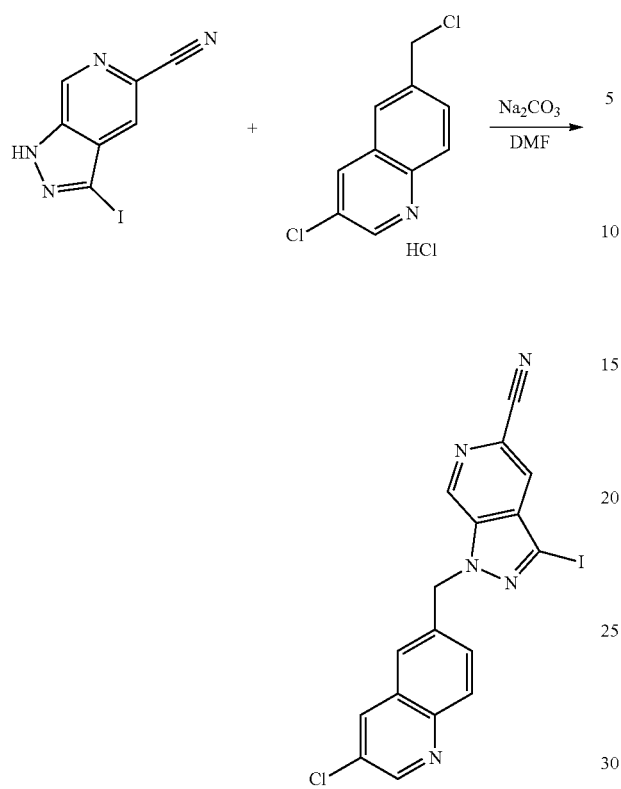

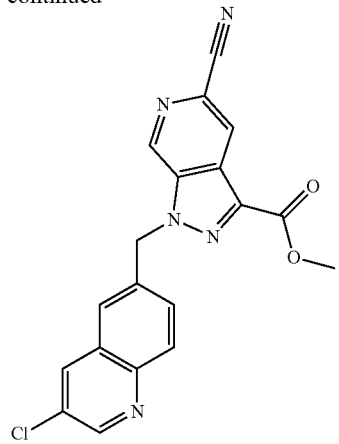

To a solution of 1-((3-chloroquinolin-6-yl)methyl)-3-iodo-1H-pyrazolo[3,4-c] pyridine-5-carbonitrile (62.0 mg, 0.14 mmol, 1.0 eq) and Pd(dppf)Cl2.DCM (10.0 mg, 0.014 mmol, 0.1 eq) in DMF/MeOH (2.0 mL/2.0 mL) was added Et3N (42.0 mg, 0.42 mmol, 3.0 eq) and the mixture was stirred at 60° C. under CO atmosphere (1 atm) overnight. After the reaction was complete, the solvent was concentrated to get a residue which was purified by column chromatography to provide methyl 1-((3-chloroquinolin-6-yl)methyl)-5-cyano-1H-pyrazolo[3,4-c] pyridine-3-carboxylate (34 mg, 64.8%) as a white solid. LCMS (M+H+) m/z calculated 378, found 378.

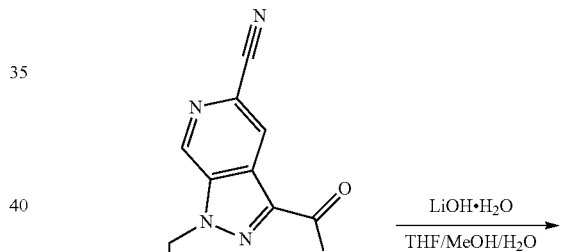

To a solution of 3-iodo-1H-pyrazolo[3,4-c]pyridine-5-carbonitrile (780.0 mg, 2.89 mmoL, 1.0 eq) and 3-chloro-6-(chloromethyl)quinoline hydrochloride (718.0 mg, 2.89 mmol, 1.0 eq) in DMF (20.0 mL) was added Na2CO3 (919.0 mg, 8.67 mmol, 3.0 eq). The reaction mixture was heated at 70° C. for 3 h. After the reaction was complete, it was quenched by H2O, filtered. The solid was washed by water, dried in vacuo to provide 1-((3-chloroquinolin-6-yl)methyl)-3-iodo-1H-pyrazolo[3,4-c]pyridine-5-carbonitrile (820.0 mg, 78.9%) as a white solid. LCMS (M+H+) m/z calculated 446.1, found 446.1.

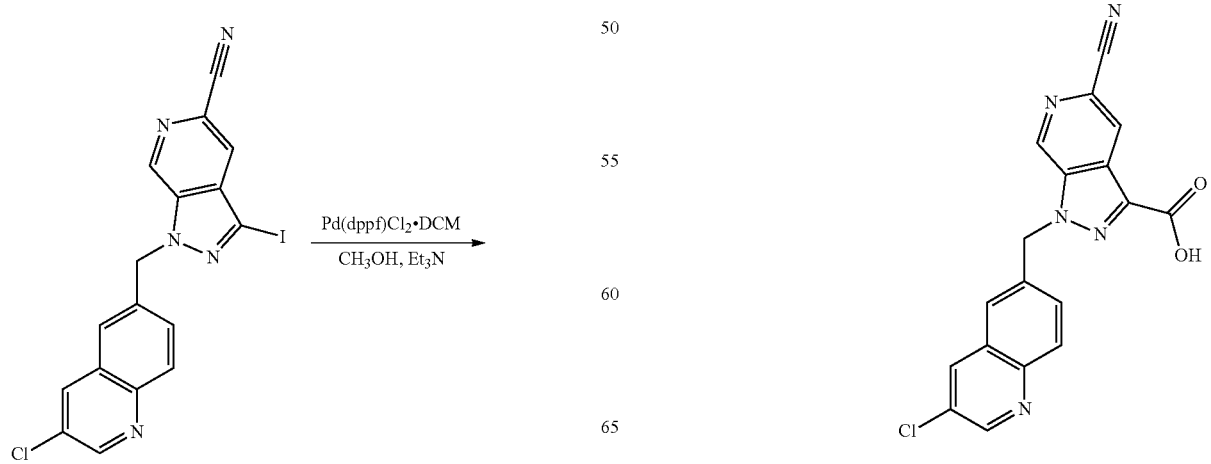

To a solution of methyl 1-((3-chloroquinolin-6-yl)methyl)-5-cyano-1H-pyrazolo[3,4-c]pyridine-3-carboxylate (34.0 mg, 0.09 mmol, 1.0 eq) in THF/MeOH/H2O (v:v:v=4:2:1, 5 mL) was added LiOH.H2O (18.5 mg, 0.44 mmol, 5.0 eq). The reaction mixture was stirred at rt overnight. After the reaction was complete, the solvent was concentrated to get a residue which was diluted by H2O, adjusted to pH=1-2 by 1N HCl solution, extracted by EA (50.0 mL×3), washed by brine, dried over Na2SO4 and concentrated to provide 1-((3-chloroquinolin-6-yl)methyl)-5-cyano-1H-pyrazolo[3,4-c]pyridine-3-carboxylic acid (33 mg, 100%) as a white solid. LCMS (M+H+) m/z calculated 364.1, found 364.2.

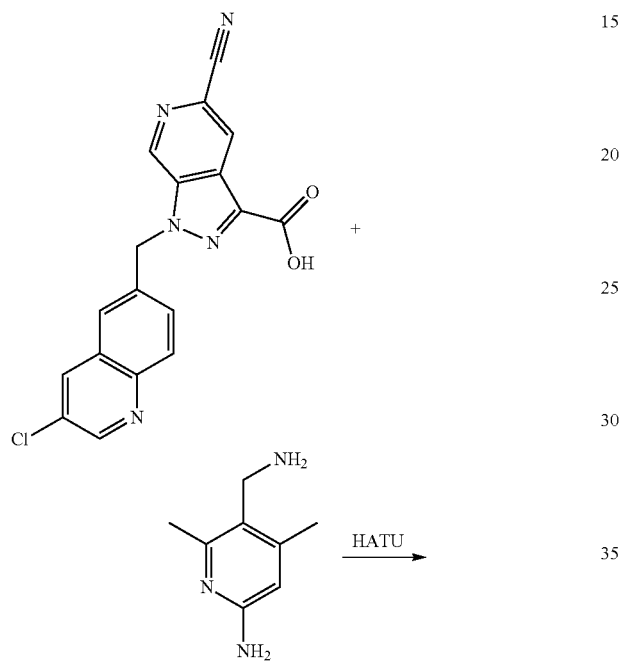

To a solution of 1-((3-chloroquinolin-6-yl)methyl)-5-cyano-1H-pyrazolo[3,4-c]pyridine-3-carboxylic acid (33.0 mg, 0.09 mmol, 1.0 eq) and 5-(aminomethyl)-4,6-dimethylpyridin-2-amine (13.0 mg, 0.09 mmol, 1.0 eq) in DMF (3.0 mL) was added HATU (34.0 mg, 0.09 mmol, 1.0 eq) and the mixture was stirred at rt for 10.0 min, then DIEA (34.0 mg, 0.27 mmol, 3.0 eq) was added. The reaction mixture was stirred at rt overnight. After the reaction was complete, the solvent was concentrated. The resulting residue was purified by prep-HPLC to provide N-(((6-amino-2,4-dimethylpyridin-3-yl)methyl)-1-((3-chloroquinolin-6-yl)methyl)-5-cyano-1H-pyrazolo[3,4-c]pyridine-3-carboxamide (5.4 mg, 12.0%) as a white solid. 1H NMR (CD3OD-d4, 400 MHz) δ 9.29 (s, 1H), 8.81 (s, 1H), 8.66 (s, 1H), 8.37 (s, 1H), 8.02 (d, 1H), 7.85 (s, 1H), 7.72 (t, 1H), 6.69 (s, 1H), 6.10 (s, 2H), 4.56 (s, 2H), 2.64 (s, 3H), 2.51 (s, 3H). LCMS (M+H+) m/z calculated 497.2, found 497.2.

Example 131: Preparation of N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide

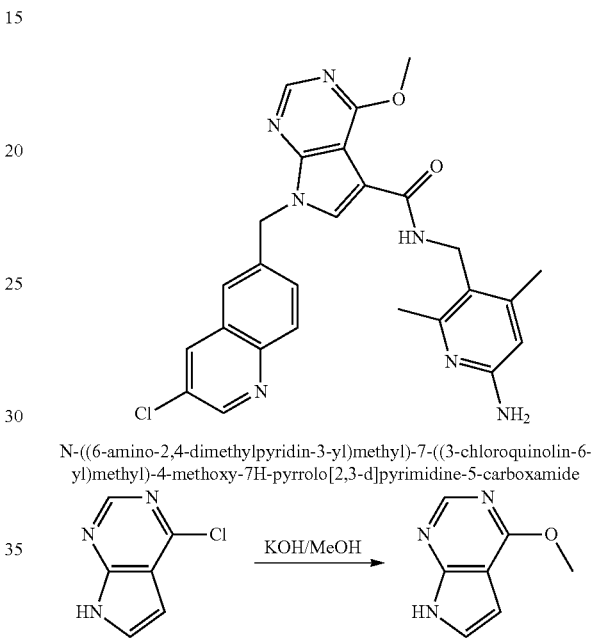

N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide

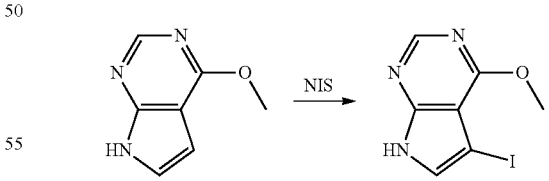

To a solution of 4-chloro-7H-pyrrolo[2,3-d]pyrimidine (1.2 g, 7.84 mmol, 1.0 eq) in MeOH (24.0 mL) was added KOH (0.79 g, 14.12 g, 1.8 eq) at 60° C. for 18 h. After the reaction was complete, the mixture was extracted with EA. The combined organic layers were washed with brine, dried over Na2SO4, filtered and concentrated in vacuo to provide 4-meth-oxy-7H-pyrrolo[2,3-d]pyrimidine (1.2 g, crude) as a white solid.

To a solution of 4-methoxy-7H-pyrrolo[2,3-d]pyrimidine (1.0 g, 6.71 mmol, 1.0 eq), NIS (1.81 g, 8.05 mmol, 1.0 eq) in DCM (20.0 mL) was stirred at rt for 1.5 h. After the reaction was complete, water was added and the mixture was extracted with EA. The organic layer was washed with water, dried over Na2SO4, filtered and concentrated. The resulting residue was purified by column chromatography (EA/PE=1/1, v/v) to provide 5-iodo-4-methoxy-7H-pyrrolo[2,3-d]pyrimidine (1.92 g, 74.3%) as a white solid.

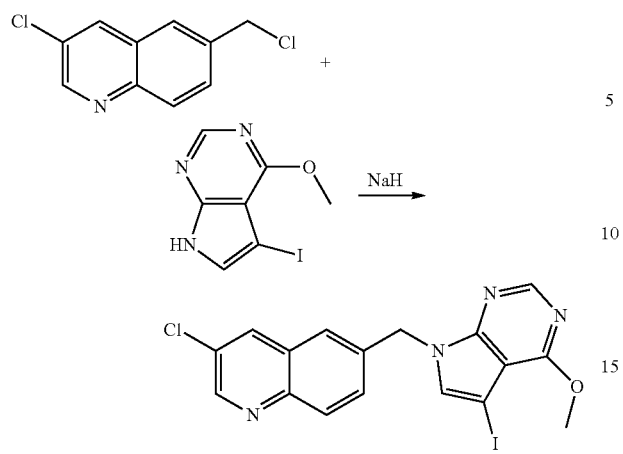

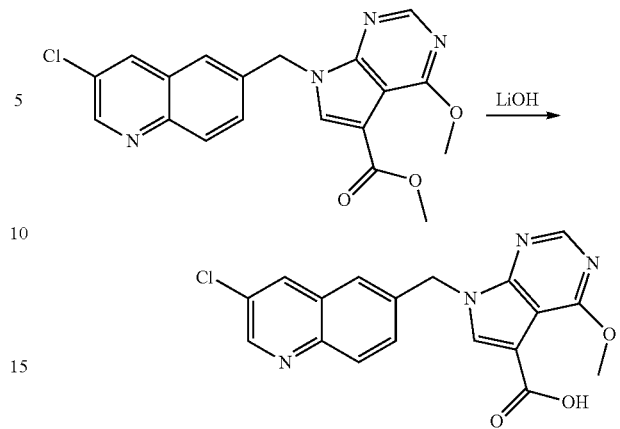

A solution of 5-iodo-4-methoxy-7H-pyrrolo[2,3-d]pyrimidine (1.75 g, 6.36 mmol, 1.0 eq) in DMF (20.0 ml) was stirred at rt for 0.5 h under Ar. NaH (60% in mineral oil, 0.509 g, 12.73 mmol, 2.0 eq) was slowly added and stirred for 0.5 h. Then 3-chloro-6-(chloromethyl)quinoline (1.74 g, 7.0 mmol, 1.1 eq) was added and stirred at rt for 2.0 h under Ar. After the reaction was complete, water was added, and the mixture was extracted with EA. The organic layer was washed with water, dried over Na2SO4, filtered and concentrated. The resulting residue was purified by column chromatography (EA/PE=1/1, v/v) to provide 3-chloro-6-((5-iodo-4-methoxy-7H-pyrrolo[2,3-d]pyrimidin-7-yl)methyl)quinoline (1.5 g, 52%) as a white solid.

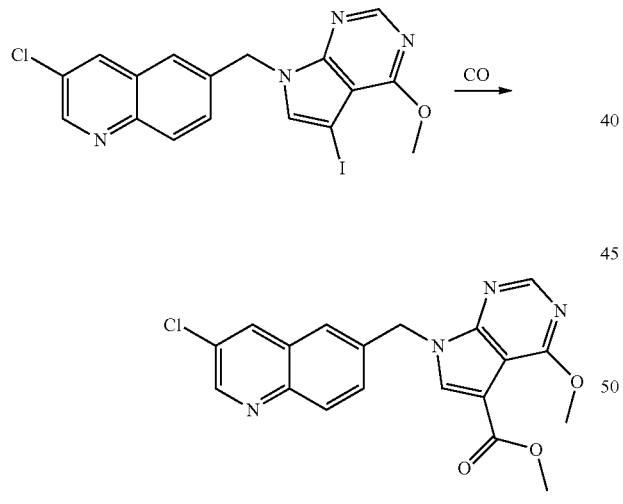

The mixture of 3-chloro-6-((5-iodo-4-methoxy-7H-pyrrolo[2,3-d]pyrimidin-7-yl)methyl)quinoline (1.4 g, 3.11 mmol, 1.0 eq), Pd(dppf)Cl2 (0.381 g, 0.467 mmol, 0.15 eq), TEA (0.943 g, 9.33 mmol, 3 eq) in DMF/MeOH (18.0 mL/18.0 mL) was stirred at 65° C. for 18.0 h under CO atmosphere. After the reaction was complete, the solvent was concentrated to get a residue which was purified by silica gel chromatography (EA/PE=2/1, v/v) to provide methyl 7-((3-chloroquinolin-6-yl)methyl)-4-methoxy-7H-pyrrolo[2,3-d]pyrimidine-5-carboxylate (1.2 g, 98%) as brown solid.

To a solution of methyl methyl 7-((3-chloroquinolin-6-yl)methyl)-4-methoxy-7H-pyrrolo[2,3-d]pyrimidine-5-carboxylate (1.1 g, 2.87 mmol, 1.0 eq), LiOH (1.2 g, 28.72 mmol, 10.0 eq) in MeOH/H2O (10.0 mL/10.0 mL) was stirred at 55° C. for 3 h. After the reaction was complete, water was added, and the mixture was extracted with EA. The water layer was adjusted to pH 3 and extracted with EA. The combined organic layers were washed with water, dried over Na2SO4, filtered and concentrated to provide 7-((3-chloroquinolin-6-yl)methyl)-4-methoxy-7H-pyrrolo[2,3-d]pyrimidine-5-carboxylic acid (0.76 g, 72%).

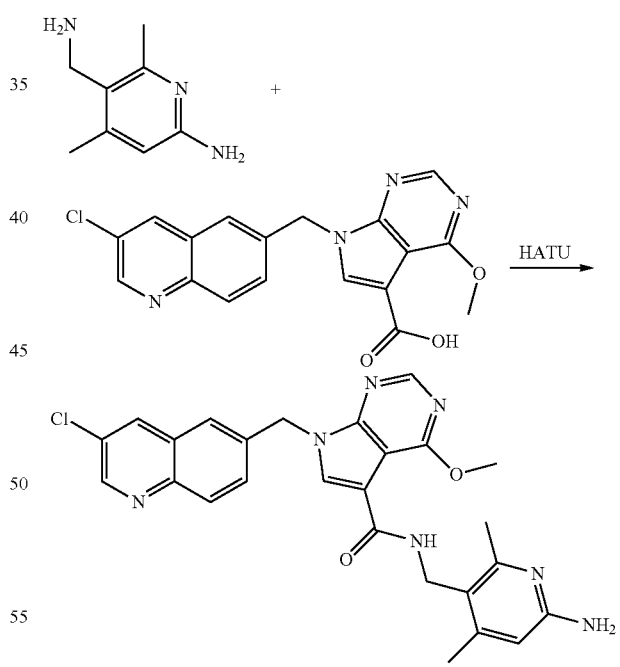

To a solution of 7-((3-chloroquinolin-6-yl)methyl)-4-methoxy-7H-pyrrolo[2,3-d]pyrimidine-5-carboxylic acid (100.0 mg, 0.271 mmol, 1.0 eq) in DMF (3.0 mL) was added 5-(aminomethyl)-4,6-dimethylpyridin-2-amine (49.2 mg, 0.33 mmol, 1.2 eq) followed by HATU (113.0 mg, 0.2981 mmol, 1.1 eq) and DIEA (105.0 mg, 0.813 mmol, 3.0 eq). The reaction mixture was stirred at 25° C. for 2 h. After the reaction was complete, water was added, and the mixture was extracted with EA. The organic layer was washed with water, dried over Na2SO4, filtered and concentrated. The resulting residue was purified by prep-HPLC to provide N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide (35 mg, 26%) as a white solid. 1H NMR (DMSO-d6, 400 MHz) δ 8.55-8.56 (d, 1H), 8.53-8.54 (d, 1H), 8.50 (s, 1H), 8.25 (s, 1H), 8.00-8.03 (m, 2H), 7.72-7.75 (m, 2H), 6.16 (s, 1H), 5.69-5.71 (m, 4H), 4.38-4.39 (d, 2H), 3.88 (s, 3H), 2.35 (s, 3H), 2.23 (s, 3H). LCMS (M+H+) m/z calculated 502.2, found 502.6.

Example 132: Preparation of N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide

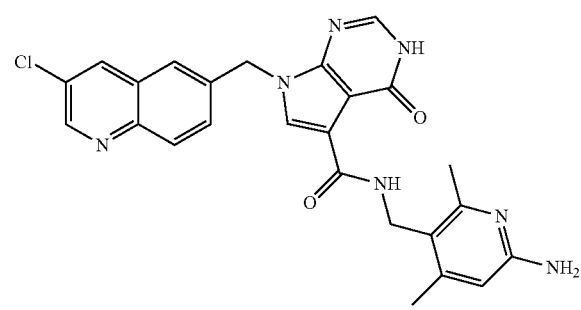

N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide

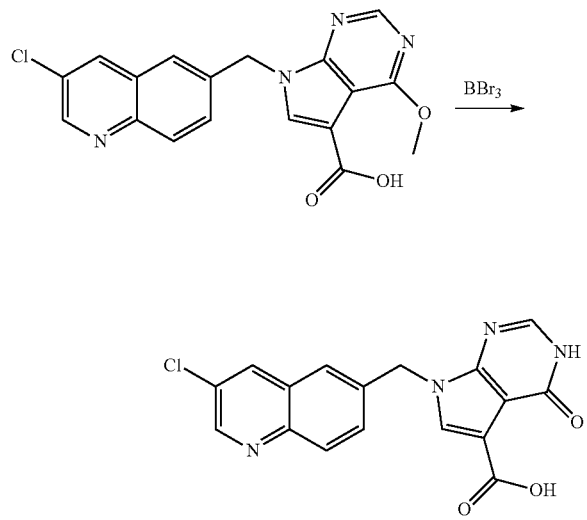

To a solution of 7-((3-chloroquinolin-6-yl)methyl)-4-methoxy-7H-pyrrolo[2,3-d]pyrimidine-5-carboxylic acid (260.0 mg, 0.705 mmol, 1.0 eq) in DCM (13.0 mL) was added BBr3 (1M in DCM, 13.0 mL) slowly at 0° C. under Ar. The reaction mixture was stirred at 25° C. overnight. After the reaction was complete, water was added, and the mixture was extracted with EA. The organic layer was washed with water, dried over Na2SO4, filtered and concentrated. The resulting residue was purified by prep-HPLC to provide 7-((3-chloroquinolin-6-yl)methyl)-4-oxo-4,7-dihydro-3H-pyrrolo[2,3-d]pyrimidine-5-carboxylic acid (45.0 mg, 13%).

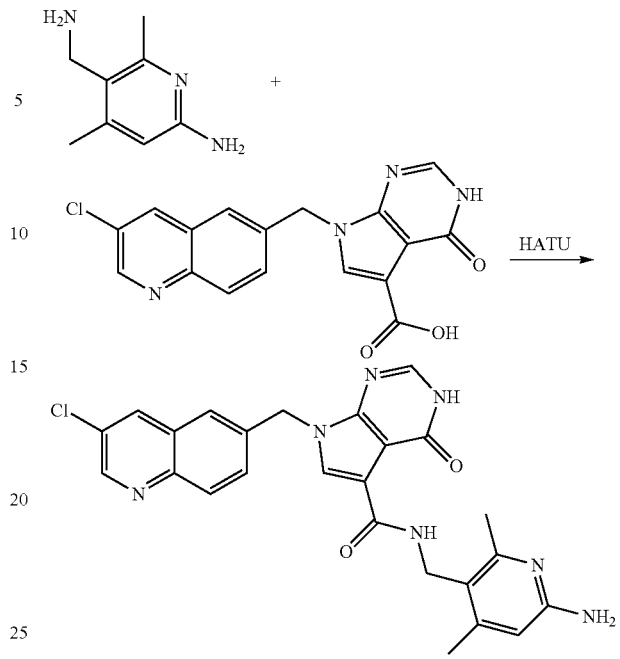

To a solution of 7-((3-chloroquinolin-6-yl)methyl)-4-oxo-4,7-dihydro-3H-pyrrolo [2,3-d]pyrimidine-5-carboxylic acid (45.0 mg, 0.127 mmol, 1.0 eq) in DMF (1.0 mL) was added 5-(aminomethyl)-4,6-dimethylpyridin-2-amine (23.0 mg, 0.152 mmol, 1.2 eq) followed by HATU (53.0 mg, 0.139 mmol, 1.1 eq) and DIEA (49.0 mg, 0.380 mmol, 3.0 eq). The reaction mixture was stirred at 25° C. for 2 h. After the reaction was complete, water was added, and the mixture was extracted with EA. The organic layer was washed with water, dried over Na2SO4, filtered and concentrated. The resulting residue was purified by prep-HPLC to provide N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide (3.7 mg, 5.9%) as a white solid. 1H NMR (DMSO-d6, 400 MHz) δ12.49 (s, 1H), 8.53-8.56 (d, 1H), 8.54-8.55 (d, 1H), 8.06 (s, 1H), 8.00-8.03 (m, 2H), 7.93 (s, 1H), 7.69-7.71 (m, 2H), 6.10 (s, 1H), 5.62 (m, 4H), 4.37 (s, 2H), 3.88 (s, 3H), 2.32 (s, 3H), 2.23 (s, 3H). LCMS (M+H+) m/z calculated 488.2, found 488.5.

Example 133: Preparation of N-((6-amino-2,4-dimethylpyridin-3-yl)methyl)-1-((3-chloroquinolin-6-yl)methyl)-4-cyano-1H-pyrrolo[3,2-c]pyridine-3-carboxamide

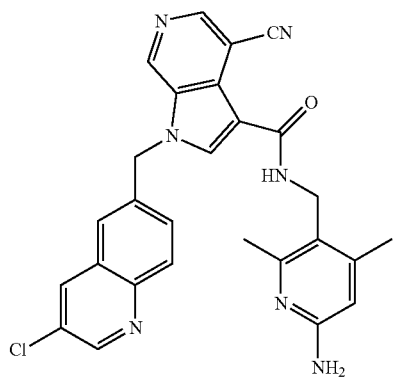

N-((6-amino-2,4-dimethylpyridin-3-yl)methyl)-1-((3-chloroquinolin-6-yl)methyl)-4-cyano-1H-pyrrolo[3,2-c]pyridine-3-carboxamide

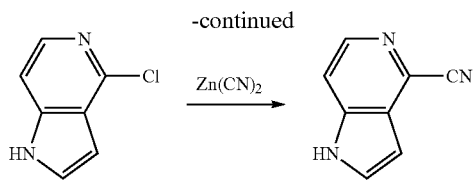

A mixture of 4-chloro-1H-pyrrolo[3,2-c]pyridine (0.5 g, 3.28 mmol, 1.0 eq), Zn(CN)2 (422 mg, 3.61 mmol, 1.1 eq), Pd2(dba)3 (600.0 mg, 0.656 mmol, 0.2 eq), dppf (729.0 mg, 1.312 mmol, 0.4 eq), Zn (21.0 mg, 0.328 mmol, 0.1 eq) in NMP (30.0 mL) was stirred at 120° C. for 18 h under Ar. After the reaction was complete, the mixture was extracted with EA. The organic layer was washed with brine, dried over Na2SO4, filtered and concentrated in vacuo. The resulting residue was purified by column chromatography (EA/PE=1/1, v/v) to provide 1H-pyrrolo[3,2-c] pyridine-4-carbonitrile (68.0 mg, 11%).

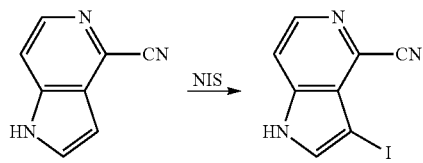

To a solution of 1H-pyrrolo[3,2-c]pyridine-4-carbonitrile (60.0 mg, 0.42 mmol, 1.0 eq), NIS (52.0 mg, 0.46 mmol, 1.1 eq) in DCM (4.0 mL) was stirred at rt for 2 h. After the reaction was complete, water was added, and the mixture was extracted with EA. The organic layer was washed with water, dried over Na2SO4, filtered and concentrated. The resulting residue was purified by column chromatography (EA/PE=1/1, v/v) to provide 3-iodo-1H-pyrrolo[3,2-c]pyridine-4-carbonitrile (160 mg, 97%).

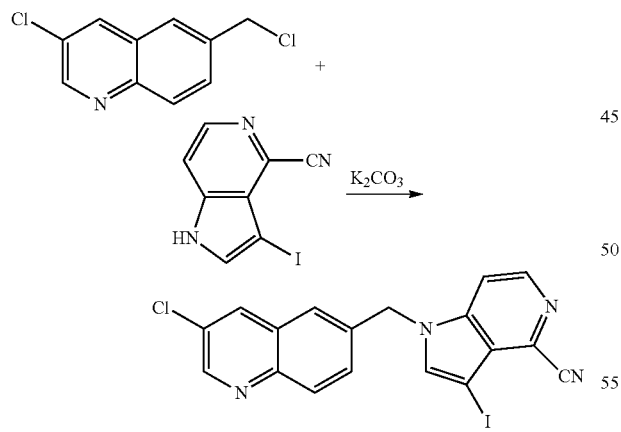

To a solution of 3-iodo-1H-pyrrolo[3,2-c]pyridine-4-carbonitrile (45.0 mg, 0.167 mmol, 1.0 eq), 3-chloro-6-(chloromethyl)quinoline (50.0 mg, 0.12 mmol, 1.2 eq), K2CO3 (69.0 mg, 0.5 mmol, 3.0 eq) in DMF (2.0 mL) was stirred at 85° C. for 3.5 h under Ar. After the reaction was complete, water was added, and the mixture was extracted with EA. The organic layer was washed with water, dried over Na2SO4, filtered and concentrated. The resulting residue was purified by column chromatography (EA/PE=2/1, v/v) to provide 1-((3-chloroquinolin-6-yl)methyl)-3-iodo-1H-pyrrolo[3,2-c] pyridine-4-carbonitrile (100 mg, 100%) as a white solid.

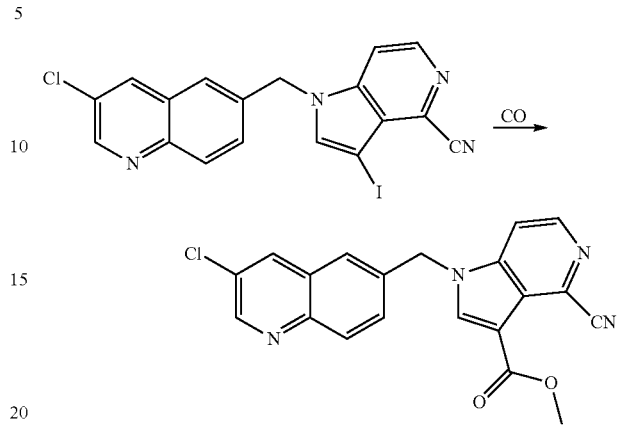

To a solution of 1-((3-chloroquinolin-6-yl)methyl)-3-iodo-1H-pyrrolo[3,2-c] pyridine-4-carbonitrile (0.1 g, 0.224 mmol, 1.0 eq), Pd(dppf)Cl2 (27.5 mg, 0.0337 mmol, 0.15 eq), TEA (68.1 mg, 0.674 mmol, 3 eq) in DMF (2.0 mL) and MeOH (2.0 mL) was stirred at 65° C. for 18 h under CO atmosphere. After the reaction was complete, the solvent was concentrated. The resulting residue was purified by prep-HPLC to provide methyl 1-((3-chloroquinolin-6-yl)methyl)-4-cyano-1H-pyrrolo[3,2-c]pyridine-3-carboxylate (50 mg, 59%) as a white solid.

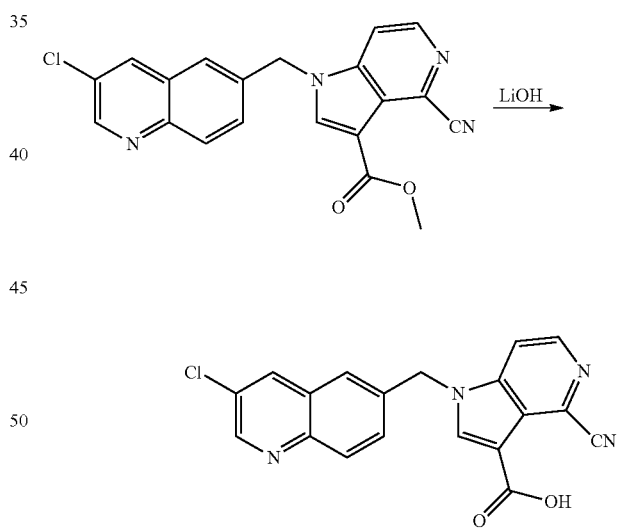

To a solution of methyl 1-((3-chloroquinolin-6-yl)methyl)-4-cyano-1H-pyrrolo [3,2-c]pyridine-3-carboxylate (45.0 mg, 0.12 mmol, 1.0 eq), LiOH (15.1 mg, 0.359 mmol, 3.0 eq) in THF/H2O (6.0 mL/2.0 mL) was stirred at 55° C. for 8.0 h. After the reaction was complete, water was added, and the mixture was extracted with EA. The water layer was adjusted to pH=3 and extracted with EA. The organic layer was washed with water, dried over Na2SO4, filtered and concentrated to provide 1-((3-chloroquinolin-6-yl)methyl)-4-cyano-1H-pyrrolo[3,2-c]pyridine-3-carboxylic acid (18 mg, 42%) as a white solid.

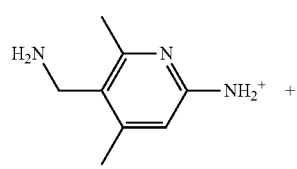 +

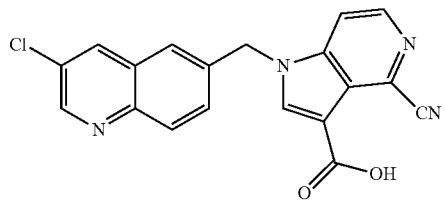 HATU⟶

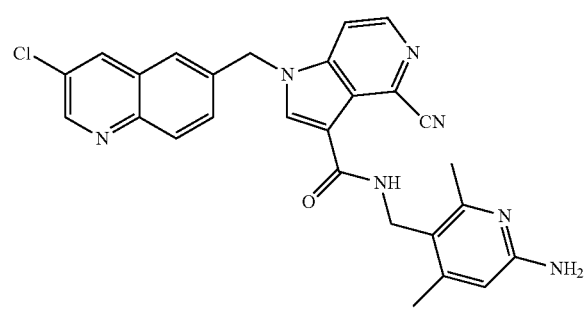

To a solution of 1-((3-chloroquinolin-6-yl)methyl)-4-cyano-1H-pyrrolo[3,2-c] pyridine-3-carboxylic acid (16.5 mg, 0.046 mmol, 1.0 eq) in DMF (2.0 mL) was added 5-(aminomethyl)-4,6-dimethylpyridin-2-amine (8.3 mg, 0.055 mmol, 1.2 eq) followed by HATU (19.1 mg, 0.05 mmol, 1.1 eq) and DIEA (17.6 mg, 0.137 mmol, 3.0 eq). The reaction mixture was stirred at 25° C. for 2.0 h. After the reaction was complete, water was added and the mixture was extracted with EA. The organic layer was washed with water, dried over Na2SO4, filtered and concentrated. The resulting residue was purified by prep-HPLC to provide N-((6-amino-2,4-dimethylpyridin-3-yl)methyl)-1-((3-chloroquinolin-6-yl)methyl)-4-cyano-1H-pyrrolo[3,2-c]pyridine-3-carboxamide (9 mg, 39%) as a white solid. 1H NMR (DMSO-d6, 400 MHz) δ 8.86-8.87 (d, 1H), 8.52-8.53 (d, 1H), 8.41-8.42 (d, 1H), 8.23 (m, 1H), 8.01-8.03 (d, 1H), 7.95-7.96 (d, 1H), 7.67-7.69 (d, 1H), 7.66 (s, 1H), 7.63-7.64 (d, 1H), 6.12 (s, 1H), 5.78 (s, 2H), 5.63 (s, 2H), 4.38-4.39 (d, 2H), 2.30 (s, 3H), 2.19 (s, 3H). LCMS (M+H+) m/z calculated 496.2, found 496.2.

Example 134: Preparation of N-((6-amino-2,4-dimethylpyridin-3-yl)methyl)-1-((3-chloroquinolin-6-yl)methyl)-5-cyano-1H-pyrrolo[2,3-c]pyridine-3-carboxamide

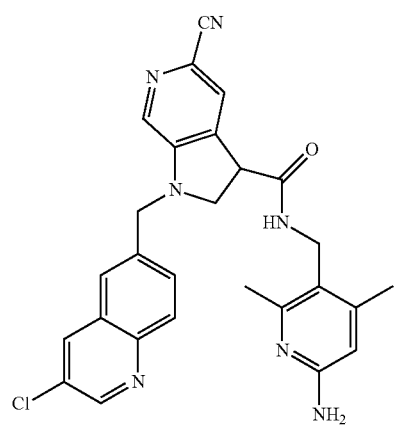

N-((6-amino-2,4-dimethylpyridin-3-yl)methyl)-1-((3-chloroquinolin-6-yl)methyl)-5-cyano-1H-pyrrolo[2,3-c]pyridine-3-carboxamide

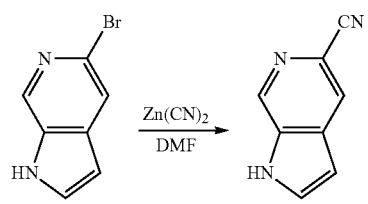

To a solution of 5-bromo-1H-pyrrolo[2,3-c]pyridine (0.9 g, 4.57 mmol, 1.0 eq), Zn(CN)2 (0.32 g, 2.74 mmol, 0.6 eq), Pd(PPh3)4 (234.5 mg, 0.457 mmol, 0.1 eq) in DMF (11.0 mL) at 147° C. for 3.5 h under microwave irradiation. After the reaction was complete, it was extracted with EA. The organic layer was washed with brine, dried over Na2SO4, filtered and concentrated in vacuo. The resulting residue was purified by column chromatography (EA/PE=1/1, v/v) to provide 1H-pyrrolo[2,3-c]pyridine-5-carbonitrile (0.567 g, 78%).

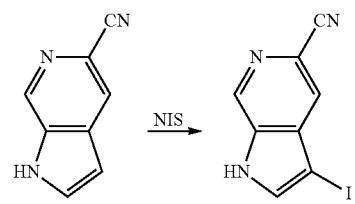

To a solution of 4-meth-oxy-7H-pyrrolo[2,3-d]pyrimidine (0.453 g, 3.168 mmol, 1.0 eq), NIS (780.0 g, 3.48 mmol, 1.1 eq) in DCM (20.0 mL) was stirred at rt for 2 h. After the reaction was complete, water was added, and the mixture was extracted with EA. The organic layer was washed with water, dried over Na2SO4, filtered and concentrated. The resulting residue was purified by column chromatography (EA/PE=1/1, v/v) to provide 3-iodo-1H-pyrrolo[2,3-c]pyridine-5-carbonitrile (850.0 mg, 99.3%) as a yellow solid.

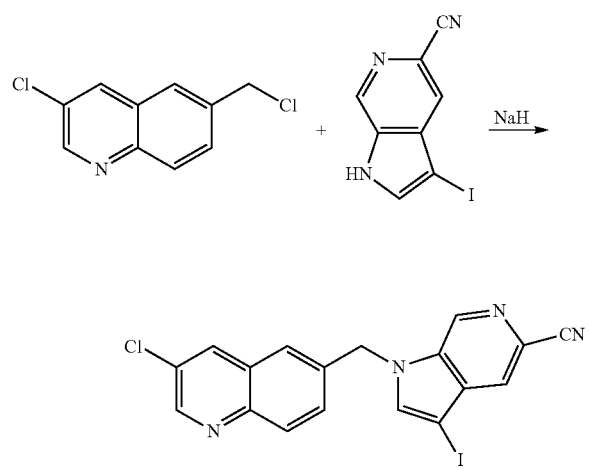

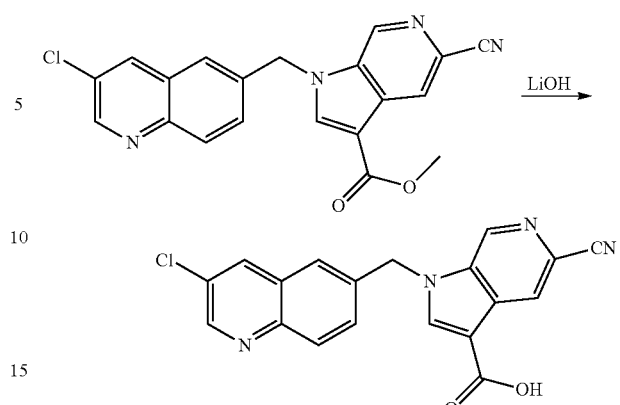

3-iodo-1H-pyrrolo[2,3-c]pyridine-5-carbonitrile (0.738 g, 2.73 mmol, 1.0 eq) in DMF (15.0 mL) was stirred at rt for 0.5 h under Ar. Then NaH (60% in mineral oil, 0.218 g, 5.46 mmol, 2.0 eq) was slowly added and stirred for 0.5 h. 3-Chloro-6-(chloromethyl)quinoline (0.815 g, 3.28 mmol, 1.2 eq) was added and stirred at rt for 2 h under Ar. After the reaction was complete, water was added, and the mixture was extracted with EA. The organic layer was washed with water, dried over Na2SO4, filtered and concentrated. The resulting residue was purified by column chromatography (EA/PE=2/1, v/v) to provide 1-((3-chloroquinolin-6-yl)methyl)-3-iodo-1H-pyrrolo[2,3-c]pyridine-5-carbonitrile (1.1 g, 92%) as a white solid.

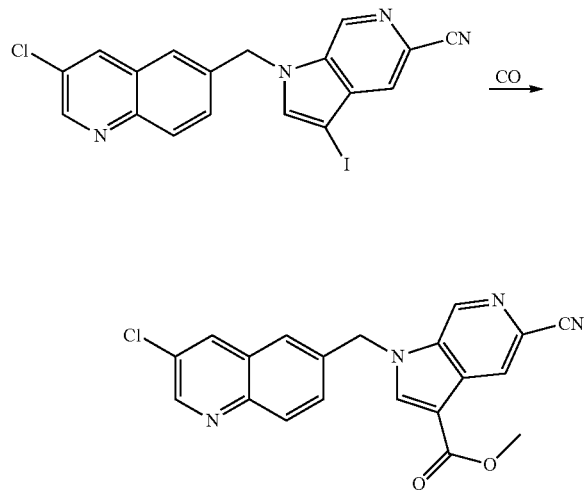

To a solution of 1-((3-chloroquinolin-6-yl)methyl)-3-iodo-1H-pyrrolo[2,3-c] pyridine-5-carbonitrile (0.6 g, 1.35 mmol, 1.0 eq), Pd(dppf)Cl2 (0.165 g, 0.202 mmol, 0.15 eq), TEA (0.408 g, 4.04 mmol, 3.0 eq) in DMF (9.0 mL) and MeOH (9.0 mL) was stirred at 65° C. for 18 h under CO atmosphere. After the reaction was complete, the solvent was concentrated to get a residue which was purified by column chromatography (EA/PE=3/1, v/v) to provide methyl 1-((3-chloroquinolin-6-yl)methyl)-5-cyano-1H-pyrrolo[2,3-c]pyridine-3-carboxylate (0.5 g, 98%) as brown solid.

To a solution of methyl 1-((3-chloroquinolin-6-yl)methyl)-5-cyano-1H-pyrrolo [2,3-c]pyridine-3-carboxylate (0.1 g, 2.66 mmol, 1.0 eq), LiOH (0.035 g, 0.80 mmol, 2.5 eq) in THF/H2O (10.0 mL/3.0 mL) was stirred at 55° C. for 1.5 h. After the reaction was complete, water was added, and the mixture was extracted with EA. The water layer was adjusted to pH=3 and extracted with EA. The organic layer was washed with water, dried over Na2SO4, filtered and concentrated to provide 1-((3-chloroquinolin-6-yl)methyl)-5-cyano-1H-pyrrolo[2,3-c]pyridine-3-carboxylic acid (86.6 mg, 89%) as brown solid.

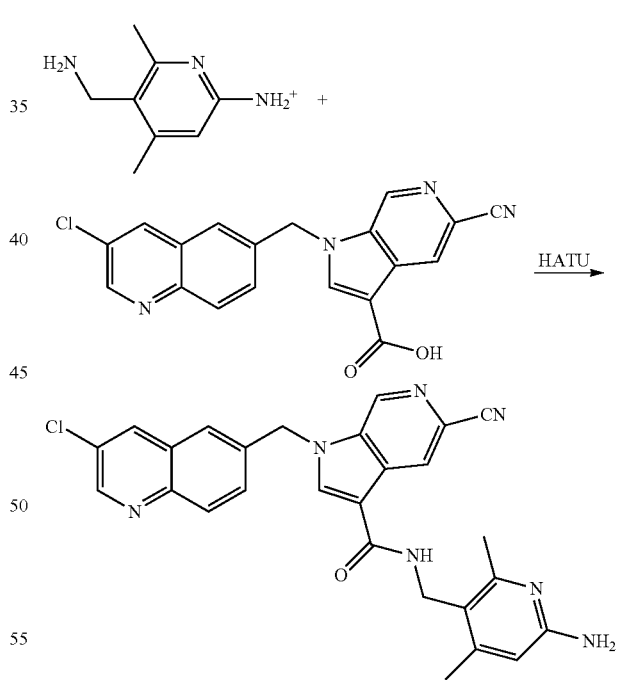

To a solution of 1-((3-chloroquinolin-6-yl)methyl)-5-cyano-1H-pyrrolo[2,3-c] pyridine-3-carboxylic acid (86.6 mg, 0.239 mmol, 1.0 eq) in DMF (3.0 mL) was added 5-(aminomethyl)-4,6-dimethylpyridin-2-amine (43.4 mg, 0.287 mmol, 1.2 eq) followed by HATU (100.0 mg, 0.263 mmol, 1.1 eq) and DIEA (92.6 mg, 0.718 mmol, 3.0 eq). The reaction mixture was stirred at 25° C. for 2.0 h. After the reaction was complete, water was added, and the mixture was extracted with EA. The organic layer was washed with water, dried over Na2SO4, filtered and concentrated. The resulting residue was purified by prep-HPLC to provide N-((6-amino-2,4-dimethylpyridin-3-yl)methyl)-1-((3-chloroquinolin-6-yl)methyl)-5-cyano-1H-pyrrolo[2,3-c]pyridine-3-carboxamide (30.0 mg, 25%) as a white solid. 1H NMR (DMSO-d6, 400 MHz) δ 9.14 (s, 1H), 8.86-8.87 (d, 1H), 8.61 (s, 1H), 8.55-8.57 (d, 2H), 8.12-8.15 (m, 1H), 8.03-8.05 (d, 1H), 7.82 (s, 1H), 7.67-7.69 (d, 1H), 6.12 (s, 1H), 5.87 (s, 2H), 5.64 (s, 2H), 4.35-4.36 (d, 2H), 2.32 (s, 3H), 2.18 (s, 3H). LCMS (M+H+) m/z calculated 496.2, found 496.2.

Example 135: Preparation of N-((6-amino-2,4-dimethylpyridin-3-yl) methyl)-1-((3-chloroquinolin-6-yl)methyl)-5-cyano-1H-pyrrolo[2,3-b]pyridine-3-carboxamide

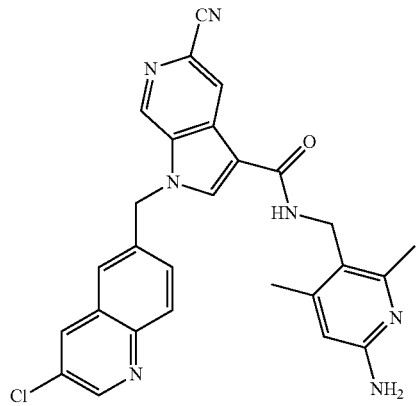

N-((6-amino-2,4-dimethylpyridin-3-yl)methyl)-1-((3-chloroquinolin-6-yl)methyl)-5-cyano-1H-pyrrolo[2,3-c]pyridine-3-carboxamide

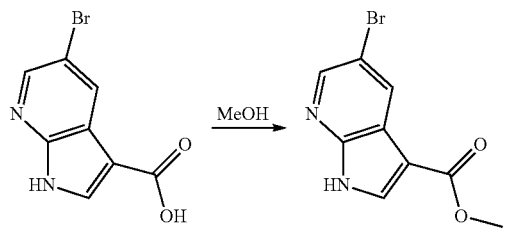

A mixture of 5-bromo-1H-pyrrolo[2,3-b]pyridine-3-carboxylic acid (480 mg, 2 mmol, 1.0 eq) and conc. H2SO4 (0.5 mL, cat.) in methanol was refluxed for 24 h. After the reaction was complete, the solvent was concentrated. The resulting residue was dissolved with EA, washed with aq. NaHCO3, dried over Na2SO4, filtered and concentrated to provide methyl 5-bromo-1H-pyrrolo[2,3-b]pyridine-3-carboxylate (450 mg, 85%) as a white solid. LCMS (M+H+) m/z calculated 256.1 found 256.1.

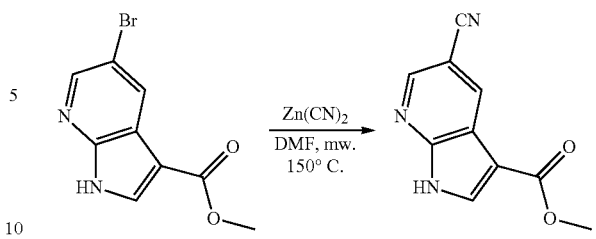

A mixture of methyl 5-bromo-1H-pyrrolo[2,3-b]pyridine-3-carboxylate (450.0 mg, 1.77 mmol, 1.0 eq), Zn(CN)2 (621.0 mg, 5.31 mmol, 3.0 eq) and Pd(PPh3)4 (307.0 mg, 0.26 mmol, 0.15 eq) in DMF (10.0 mL) was stirred under N2 at 150° C. for 16 h. After the reaction was complete, the mixture was cooled and extracted by EA and water. The combined organic layers were washed with brine, dried over Na2SO4 and filtered. The filtrate was concentrated in vacuo and The resulting residue was purified by column chromatography on silica gel (PE:EA=3:1) to provide methyl 5-cyano-1H-pyrrolo[2,3-b]pyridine-3-carboxylate (200.0 mg, 56%) as a white solid.

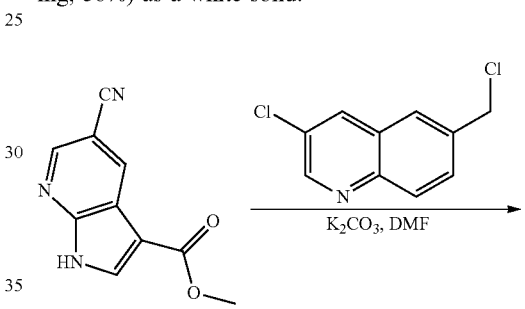

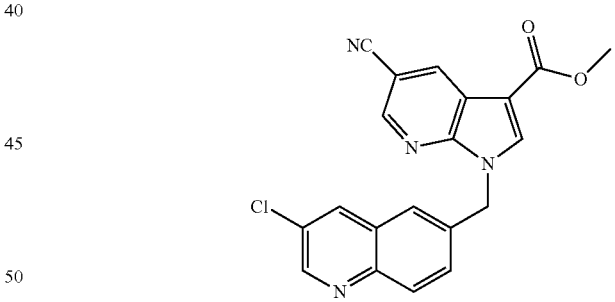

A mixture of methyl 5-cyano-1H-pyrrolo[2,3-b]pyridine-3-carboxylate (120.0 mg, 0.6 mmol, 1.0 eq), 3-chloro-6-(chloromethyl)quinoline (178.0 mg, 0.72 mmol, 1.2 eq) and K2CO3 (205.0 mg, 1.5 mmol, 2.5 eq) in DMF (10.0 mL) was stirred under N2 at 80° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=1:1) to provide methyl 1-((3-chloroquinolin-6-yl)methyl)-5-cyano-1H-pyrrolo[2,3-b] pyridine-3-carboxylate (80.0 mg, 35%) as a white solid. LCMS (M+H+) m/z calculated 377.1 found 377.1.

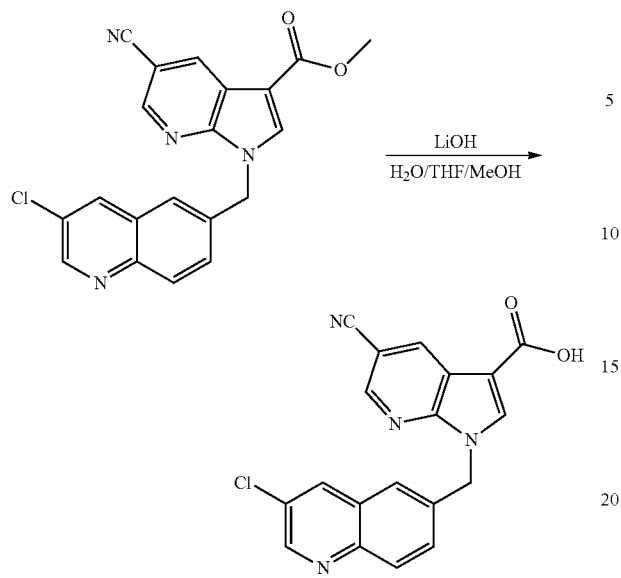

To a solution of methyl 1-((3-chloroquinolin-6-yl)methyl)-5-cyano-1H-pyrrolo[2,3-b]pyridine-3-carboxylate (80.0 mg, 0.21 mmol, 1.0 eq) in THF/MeOH (1.0 mL/1.0 mL) was added LiOH.H2O (41.0 mg, 1 mmol, 5.0 eq). The mixture was stirred at rt for 16 h. After the reaction was complete, the mixture was cooled to rt and extracted by EA and water. The combined organic layers were washed with brine, dried over Na2SO4 and filtered. The filtrate was concentrated in vacuo to provide 1-((3-chloroquinolin-6-yl)methyl)-5-cyano-1H-pyrrolo[2,3-b] pyridine-3-carboxylic acid (18 mg, 40%) as a white solid.

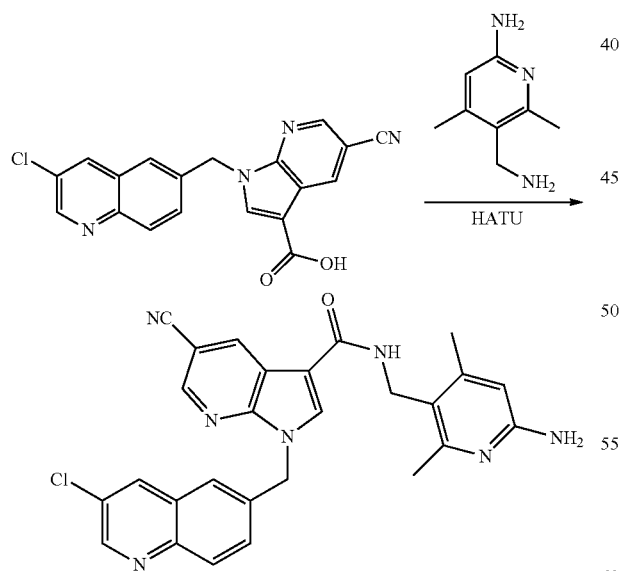

A mixture of 1-((3-chloroquinolin-6-yl)methyl)-5-cyano-1H-pyrrolo[2,3-b]pyridine-3-carboxylic acid (18.0 mg, 0.05 mmol, 1.0 eq), 5-(aminomethyl)-4,6-dimethylpyridin-2-amine (15.0 mg, 0.1 mmol, 2.0 eq), HATU (38.0 mg, 0.1 mmol, 2.0 eq) and DIEA (65.0 mg, 0.5 mmol, 5.0 eq) in DMF (5.0 mL) was stirred at rt for 16 h. After the reaction was complete, the mixture was filtered. The filtrate was purified by prep-HPLC to provide N-((6-amino-2,4-dimethylpyridin-3-yl)methyl)-1-((3-chloroquinolin-6-yl)methyl)-5-cyano-1H-pyrrolo[2,3-b]pyridine-3-carboxamide (12.0 mg, 50%) as a white solid. 1H NMR (DMSO-d6, 400 MHz) δ 8.87 (s, 1H), 8.85 (s, 1H), 8.76 (s, 1H), 8.54 (s, 1H), 8.53 (s, 1H), 8.11 (s, 1H), 8.02 (d, 1H), 7.77 (s, 1H), 7.67 (d, 1H), 6.11 (s, 1H), 5.76 (s, 2H), 5.62 (s, 2H), 4.34 (s, 2H), 2.30 (s, 3H), 2.17 (s, 3H). LCMS (M+H+) m/z calculated 496.7, found 496.7.

Example 136: Preparation of N-((6-amino-2,4-dimethylpyridin-3-yl)methyl)-7-((3-chloroquinolin-6-yl)methyl)-4-cyano-7H-pyrrolo[2,3-d]pyrimidine-5-carboxamide

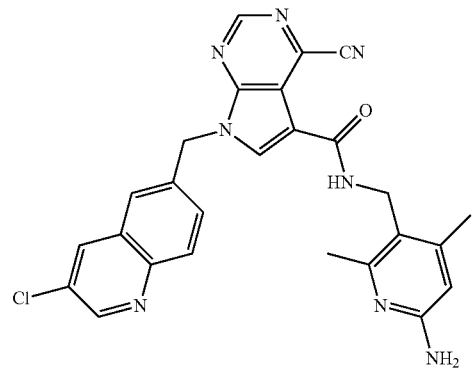

N-((6-amino-2,4-dimethylpyridin-3-yl)methyl)-7-((3-chloroquinolin-6-yl)methyl)-4-cyano-7H-pyrrolo[2,3-d]pyrimidine-5-carboxamide To a solution of 7H-pyrrolo[2,3-d]pyrimidine-4-carbonitrile (288.0 mg, 2.0 mmol, 1.0 eq) in DMF (5.0 mL) at 0° C. was added NIS (450.0 mg, 2.0 mmol, 1.0 eq). The mixture was stirred at 5-10° C. for 2 h. After the reaction was complete, it was quenched with water, extracted with EA. The organic layer was washed with brine, dried over Na2SO4 and filtered. The filtrate was concentrated in vacuo to provide 5-iodo-7H-pyrrolo[2,3-d]pyrimidine-4-carbonitrile (350.0 mg) as a yellow oil which used in the next step directly. LCMS (M+H+) m/z calculated 271.2 found 271.2.

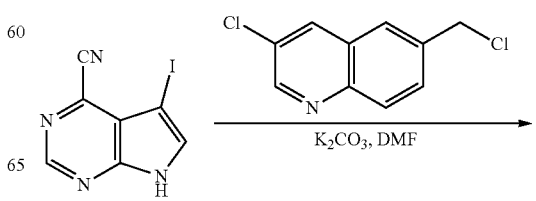

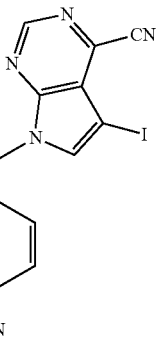

A mixture of 5-iodo-7H-pyrrolo[2,3-d]pyrimidine-4-carbonitrile (340.0 mg, 1.26 mmol, 1.0 eq), 3-chloro-6-(chloromethyl)quinoline (360.0 mg, 1.44 mmol, 1.1 eq) and K2CO3 (520.0 mg, 3.72 mmol, 3.0 eq) in DMF (10.0 mL) was stirred under N2 at 80° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=3:1) to provide 7-((3-chloroquinolin-6-yl)methyl)-5-iodo-7H-pyrrolo[2,3-d]pyrimidine-4-carbonitrile (540.0 mg, 96%). LCMS (M+H+) m/z calculated 446.1 found 446.1.

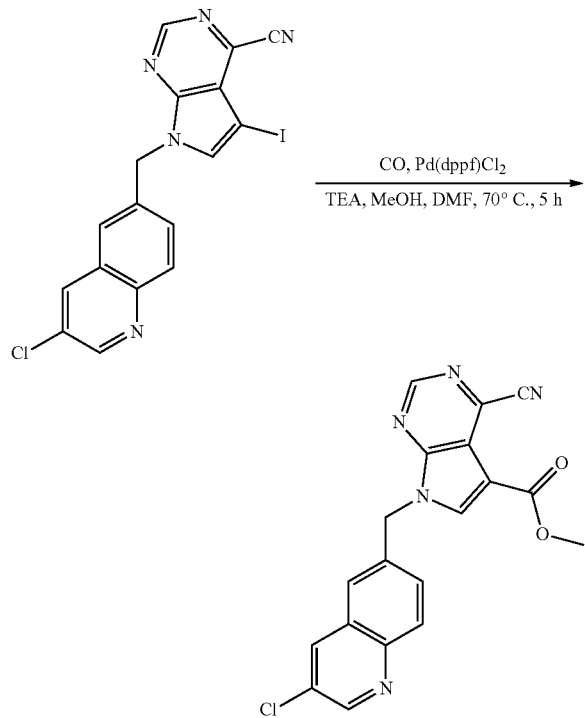

A mixture of 7-((3-chloroquinolin-6-yl)methyl)-5-iodo-7H-pyrrolo[2,3-d] pyrimidine-4-carbonitrile (540.0 mg, 1.21 mmol, 1.0 eq), Et3N (0.5 mL, 3.6 mmol, 3.0 eq) in MeOH (6.0 mL) and DMF (6.0 mL) was degassed with CO. Then PdCl2(dppf).CH2Cl2 (132 mg, 0.18 mmol, 0.15 eq) was added. The mixture was stirred at 70° C. at CO atmosphere for 3 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=1:1) to provide methyl 7-((3-chloroquinolin-6-yl)methyl)-4-cyano-7H-pyrrolo[2,3-d]pyrimidine-5-carboxylate (450.0 mg, 98%) as gray solid. LCMS (M+H+) m/z calculated 378.2 found 378.2.

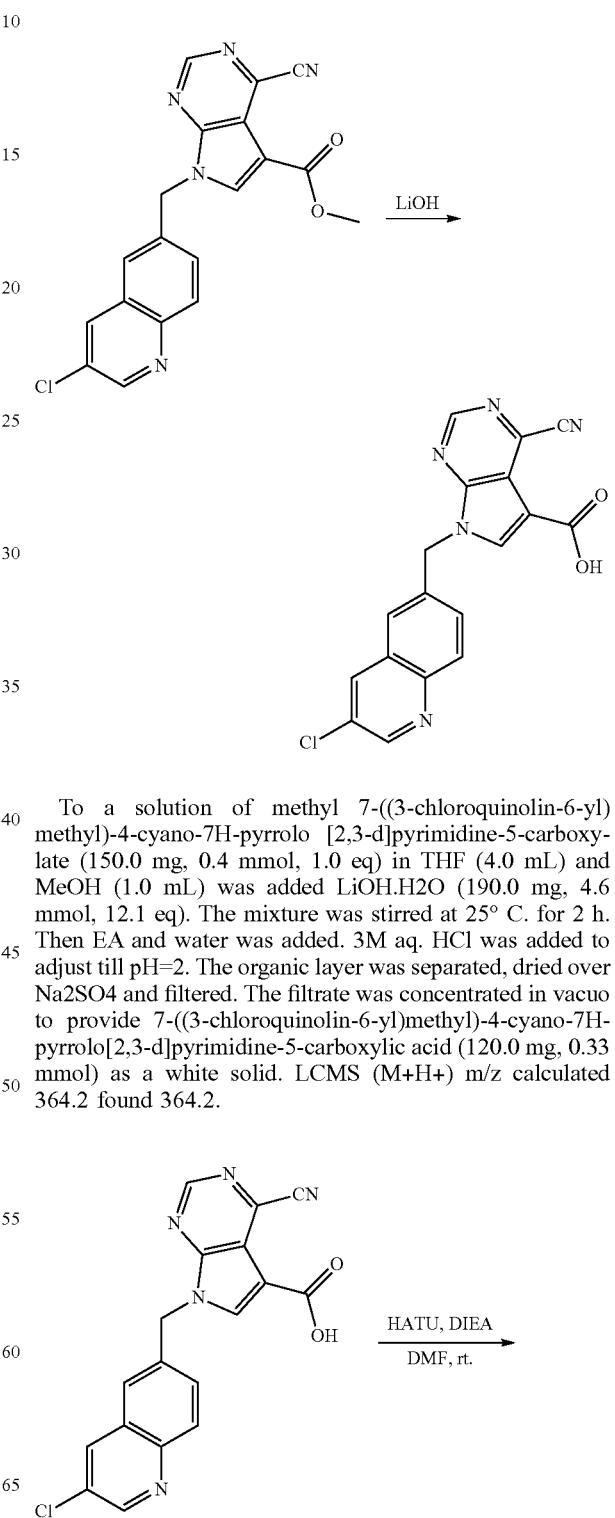

To a solution of methyl 7-((3-chloroquinolin-6-yl)methyl)-4-cyano-7H-pyrrolo [2,3-d]pyrimidine-5-carboxylate (150.0 mg, 0.4 mmol, 1.0 eq) in THF (4.0 mL) and MeOH (1.0 mL) was added LiOH.H2O (190.0 mg, 4.6 mmol, 12.1 eq). The mixture was stirred at 25° C. for 2 h. Then EA and water was added. 3M aq. HCl was added to adjust till pH=2. The organic layer was separated, dried over Na2SO4 and filtered. The filtrate was concentrated in vacuo to provide 7-((3-chloroquinolin-6-yl)methyl)-4-cyano-7H-pyrrolo[2,3-d]pyrimidine-5-carboxylic acid (120.0 mg, 0.33 mmol) as a white solid. LCMS (M+H+) m/z calculated 364.2 found 364.2.

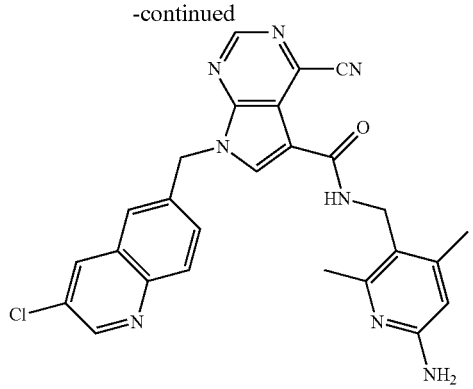

To a solution of 7-((3-chloroquinolin-6-yl)methyl)-4-cyano-7H-pyrrolo[2,3-d]pyrimidine-5-carboxylic acid (120.0 mg, 0.33 mmol, 1.0 eq), 5-(aminomethyl)-4,6-dimethylpyridin-2-amine (75.0 mg, 0.5 mmol, 1.5 eq) and HATU (190.0 mg, 0.5 mmol, 1.5 eq) in DMF (5.0 mL) at rt was added DIEA (215.0 mg, 1.65 mmol, 5.0 eq). The mixture was stirred at 25° C. for 16.0 h. After the reaction was complete, the mixture was cooled to rt and extracted by EA and water. The combined organic layers were washed with brine, dried over Na2SO4 and filtered. The filtrate was concentrated in vacuo. The resulting residue was purified by prep-HPLC to provide N-((6-amino-2,4-dimethylpyridin-3-yl)methyl)-7-((3-chloro-quinolin-6-yl)methyl)-4-cyano-7H-pyrrolo[2,3-d]pyrimidine-5-carboxamide (8 mg, 5%) as a white solid. 1H NMR (CDCl3, 400 MHz) δ 9.00 (s, 1H), 8.78 (s, 1H), 8.53 (s, 1H), 8.72 (s, 1H), 8.00 (d, 1H), 7.81 (s, 1H), 7.73 (d, 1H), 6.31 (s, 1H), 5.78 (s, 2H), 2.42 (s, 3H), 2.30 (s, 3H). LCMS (M+H+) m/z calculated 497.6, found 497.7.

Example 137: Preparation of N-((6-amino-2,4-dimethylpyridin-3-yl)methyl)-1-((3-chloroquinolin-6-yl)methyl)-5-methoxy-1H-pyrazolo[4,3-b]pyridine-3-carboxamide

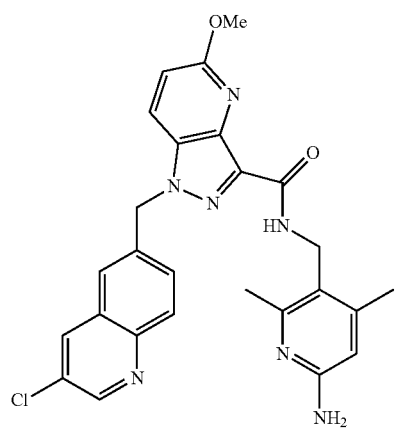

N-((6-amino-2,4-dimethylpyridin-3-yl)methyl)-1-((3-chloroquinolin-6-yl)methyl)-5-methoxy-1H-pyrazolo[4,3-b]pyridine-3-carboxamide

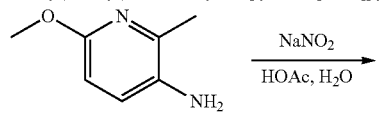

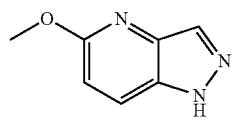

To a solution of 6-methoxy-2-methylpyridin-3-amine (200.0 mg, 1.45 mmol, 1.0 eq) in HOAc (2.0 mL) was added a solution of NaNO2 (150.0 mg, 2.17 mmol, in 0.5 mL of water). The mixture was stirred at rt. for 3 h. Aq. NaHCO3 was added to adjust till pH=7. The mixture was extracted with EA. The organic layer was washed with brine, dried over Na2SO4 and filtered. The filtrate was concentrated in vacuo and The resulting residue was purified by column chromatography on silica gel (PE:EA=3:1) to provide 5-methoxy-1H-pyrazolo[4,3-b] pyridine (300.0 mg, 40%) as red solid. LCMS (M+H+) m/z calculated 150.1 found 150.1.

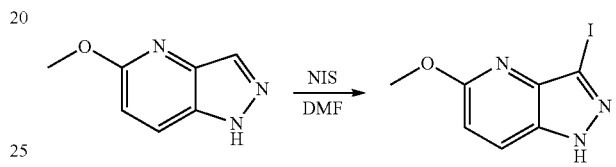

To a solution of 5-methoxy-1H-pyrazolo[4,3-b]pyridine (300.0 mg, 2.0 mmol, 1.0 eq) in DMF (10.0 mL) at 0° C. was added NIS (524.0 mg, 2.3 mmol, 1.15 eq). The mixture was stirred at 0° C. for 2.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=2:1) to provide 3-iodo-5-methoxy-1H-pyrazolo[4,3-b]pyridine (300.0 mg, ca. 100%) as a brown solid. LCMS (M+H+) m/z calculated 276.2 found 276.2.

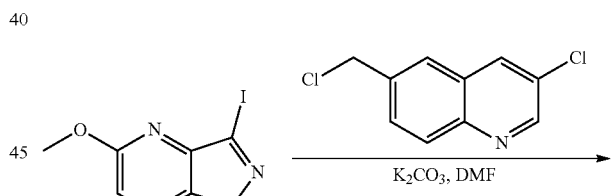

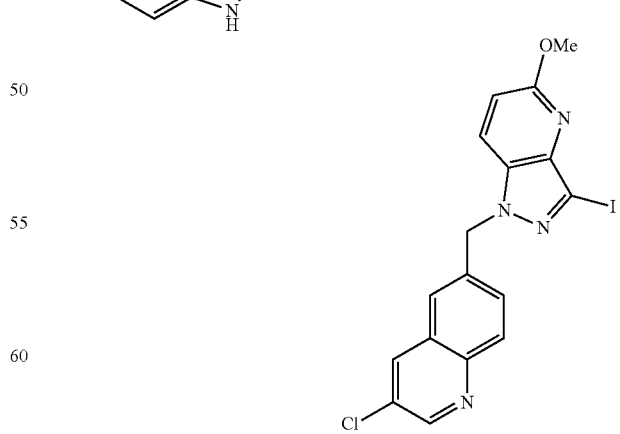

A mixture of 3-iodo-5-methoxy-1H-pyrazolo[4,3-b]pyridine (120.0 mg, 0.44 mmol, 1.0 eq), 3-chloro-6-(chloromethyl)quinoline (120.0 mg, 0.48 mmol, 1.1 eq) and Na2CO3

(120.0 mg, 1.1 mmol, 2.5 eq) in DMF (5.0 mL) was stirred under N2 at 75° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=3:1) to provide 3-chloro-6-((3-iodo-5-methoxy-1H-pyrazolo[4,3-b]pyridin-1-yl)methyl)quinoline (200.0 mg, 99%). LCMS (M+H+) m/z calculated 451.2 found 451.2.

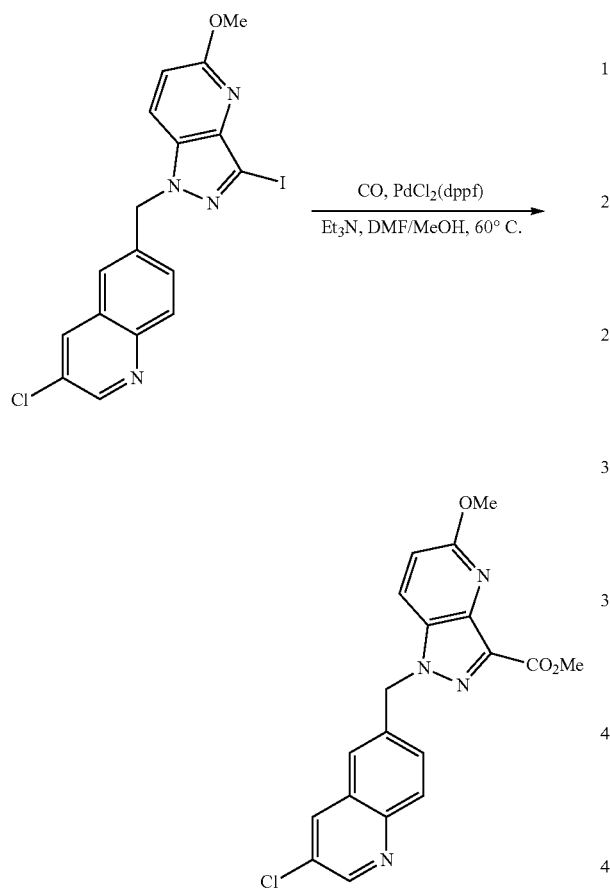

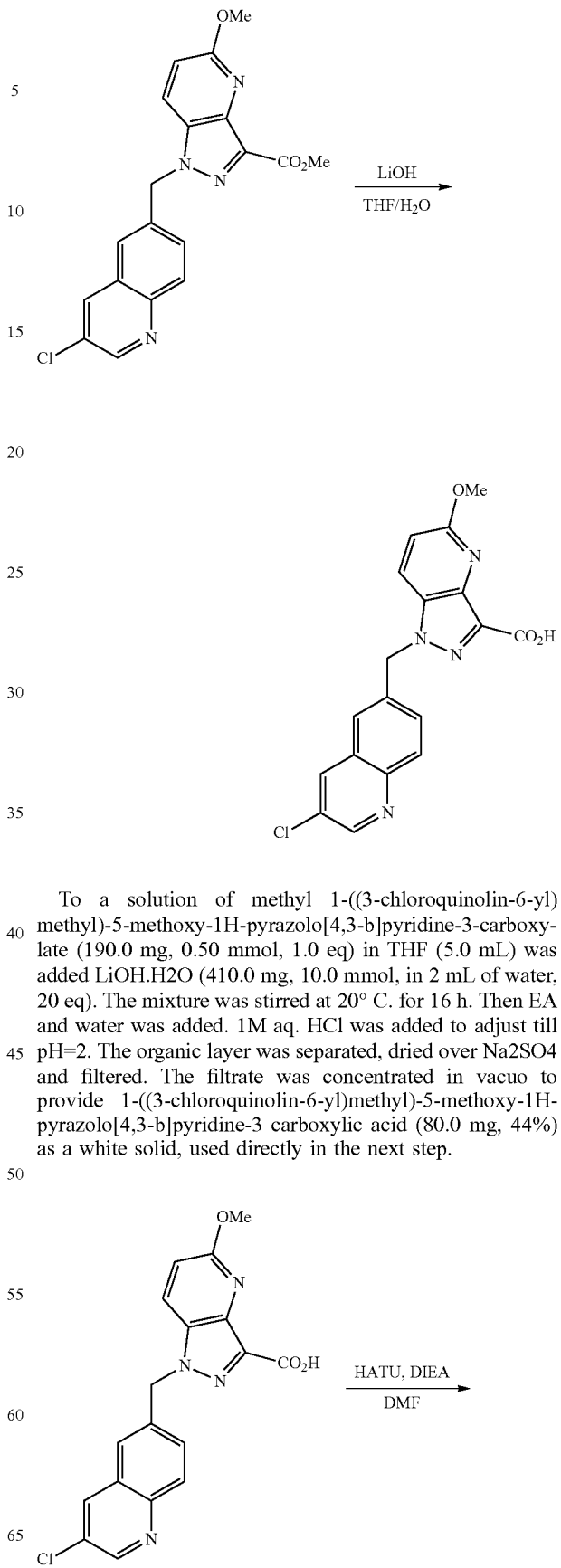

A mixture of 3-chloro-6-((3-iodo-5-methoxy-1H-pyrazolo[4,3-b]pyridin-1-yl) methyl)quinoline (275.0 mg, 0.61 mmol, 1.0 eq), Et3N (250 mg, 2.5 mmol, 4.0 eq) in MeOH/DMF (6.0 mL/6.0 mL) was degassed with CO atmosphere. Then PdCl2(dppf).CH2Cl2 (132.0 mg, 0.18 mmol, 0.15 eq) was added. The mixture was stirred at 60° C. at CO atmosphere for 16 h. After the reaction was complete, the mixture was cooled to rt and extracted by EA and water. The combined organic layers were washed with brine, dried over Na2SO4 and filtered. The filtrate was concentrated in vacuo and The resulting residue was purified by column chromatography on silica gel (PE:EA=1:1) to provide methyl 1-((3-chloroquinolin-6-yl)methyl)-5-methoxy-1H-pyrazolo[4,3-b]pyridine-3-carboxylate (190.0 mg, 82%) as gray solid. LCMS (M+H+) m/z calculated 383.2 found 383.2.

To a solution of methyl 1-((3-chloroquinolin-6-yl)methyl)-5-methoxy-1H-pyrazolo[4,3-b]pyridine-3-carboxylate (190.0 mg, 0.50 mmol, 1.0 eq) in THF (5.0 mL) was added LiOH.H2O (410.0 mg, 10.0 mmol, in 2 mL of water, 20 eq). The mixture was stirred at 20° C. for 16 h. Then EA and water was added. 1M aq. HCl was added to adjust till pH=2. The organic layer was separated, dried over Na2SO4 and filtered. The filtrate was concentrated in vacuo to provide 1-((3-chloroquinolin-6-yl)methyl)-5-methoxy-1H-pyrazolo[4,3-b]pyridine-3 carboxylic acid (80.0 mg, 44%) as a white solid, used directly in the next step.

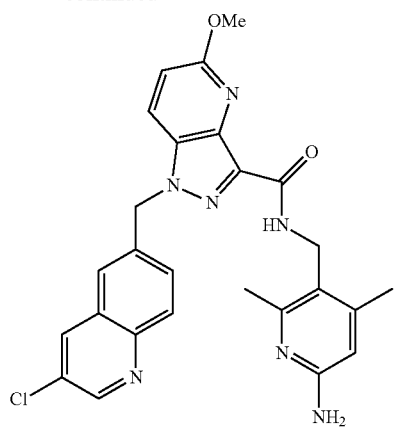

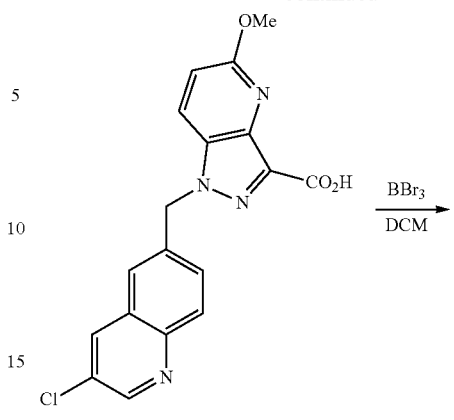

To a solution of 1-((3-chloroquinolin-6-yl)methyl)-5-methoxy-1H-pyrazolo[4,3-b]pyridine-3-carboxylic acid (80.0 mg, 0.22 mmol, 1.0 eq), 5-(aminomethyl)-4,6-dimethylpyridin-2-amine (50.0 mg, 0.33 mmol, 1.5 eq) and HATU (125.0 mg, 0.33 mmol, 1.5 eq) in DMF (5.0 mL) at rt was added DIEA (145.0 mg, 1.1 mmol, 5.0 eq). The mixture was stirred at 23° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by prep-HPLC to provide N-((6-amino-2,4-dimethylpyridin-3-yl)methyl)-1-((3-chloroquinolin-6-yl)methyl)-5-methoxy-1H-pyrazolo[4,3-b]pyridine-3-carboxamide (35.0 mg, 33%) as a white solid. LCMS (M+H+) m/z calculated 502.2 found 502.2. 1H NMR (DMSO-d6, 400 MHz) δ 10.5 (brs, 1H), 8.85 (d, 1H), 8.55 (s, 1H), 8.27 (t, 1H), 8.02 (d, 1H), 7.74 (s, 1H), 7.65 (d, 1H), 6.48 (q, 1H), 6.10 (s, 1H), 5.83 (s, 2H), 5.63 (s, 2H), 4.38 (s, 2H), 2.38 (s, 3H), 2.25 (s, 3H).

Example 138: Preparation of N-((6-amino-2,4-dimethylpyridin-3-yl)methyl)-1-((3-chloroquinolin-6-yl)methyl)-5-hydroxy-1H-pyrazolo[4,3-b]pyridine-3-carboxamide A mixture of 1-((3-chloroquinolin-6-yl)methyl)-5-methoxy-1H-pyrazolo[4,3-b]pyridine-3-carboxylic acid (100.0 mg, 0.28 mmol, 1.0 eq) in BBr3 (1 M in DCM, 10 mL, 10 mmol, 35.7 eq) was stirred at rt for 48.0 h. After the reaction was complete, the mixture was quenched by water, then concentrated in vacuo. The resulting residue was purified by prep-HPLC to provide 1-((3-chloroquinolin-6-yl)methyl)-5-hydroxy-1H-pyrazolo[4,3-b]pyridine-3-carboxylic acid (25.0 mg, 26%) as a white solid. LCMS (M+H+) m/z calculated 341.2 found 341.2.

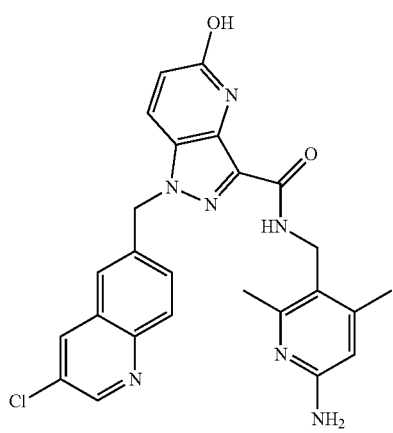

N-((6-amino-2,4-dimethylpyridin-3-yl)methyl)-1-((3-chloroquinolin-6-yl)methyl)-5-hydroxy-1H-pyrazolo[4,3-b]pyridine-3-carboxamide

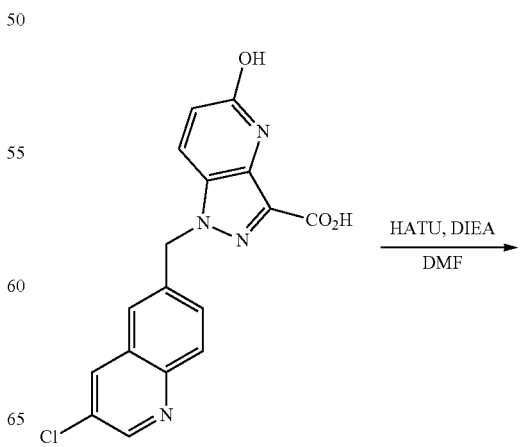

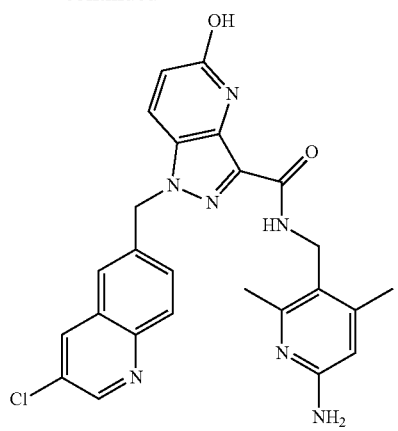

To a solution of 1-((3-chloroquinolin-6-yl)methyl)-5-hydroxy-1H-pyrazolo[4,3-b]pyridine-3-carboxylic acid (25.0 mg, 0.074 mmol, 1.0 eq), 5-(aminomethyl)-4,6-dimethylpyridin-2-amine (16.6 mg, 0.11 mmol, 1.5 eq) and HATU (42.0 mg, 0.11 mmol, 1.5 eq) in DMF (5.0 mL) at rt was added DIEA (48.0 mg, 0.37 mmol, 5.0 eq). The mixture was stirred at 23° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by prep-HPLC to provide N-((6-amino-2,4-dimethylpyridin-3-yl)methyl)-1-((3-chloroquinolin-6-yl)methyl)-5-hydroxy-1H-pyrazolo[4,3-b]pyridine-3-carboxamide (5.0 mg, 13%) as a white solid. 1H NMR (DMSO-d6, 400 MHz) δ 10.5 (brs, 1H), 8.85 (d, 1H), 8.55 (s, 1H), 8.27 (t, 1H), 8.02 (d, 1H), 7.74 (s, 1H), 7.65 (d, 1H), 6.48 (q, 1H), 6.10 (s, 1H), 5.83 (s, 2H), 5.63 (s, 2H), 4.38 (s, 2H), 2.38 (s, 3H), 2.25 (s, 3H). LCMS (M+H+) m/z calculated 488.2, found 488.2.

Example 139: Preparation of N-((6-amino-2-methylpyridin-3-yl)methyl)-1-((3-chloroquinolin-6-yl)methyl)-5-hydroxy-1H-pyrazolo[4,3-b]pyridine-3-carboxamide

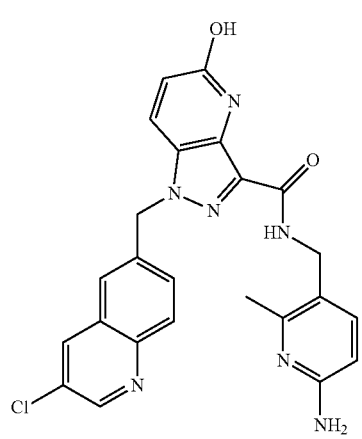

N-((6-amino-2-methylpyridin-3-yl)methyl)-1-((3-chloroquinolin-6-yl)methyl)-5-hydroxy-1H-pyrazolo[4,3-b]pyridine-3-carboxamide

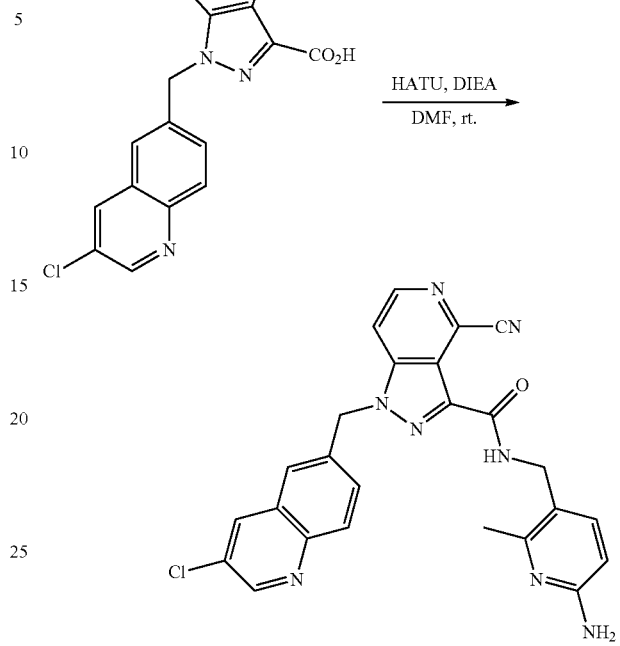

To a solution of 1-((3-chloroquinolin-6-yl)methyl)-5-hydroxy-1H-pyrazolo[4,3-b]pyridine-3-carboxylic acid (270.0 mg, 0.73 mmol, 1.0 eq), 5-(aminomethyl)-6-methylpyridin-2-amine (250.0 mg, 1.4 mmol, 2.0 eq) and HATU (330.0 mg, 0.88 mmol, 1.1 eq) in DMF (10.0 mL) at rt was added DIEA (280.0 mg, 2.2 mmol, 3.0 eq). The mixture was stirred at 23° C. for 16.0 h. After the reaction was complete, the mixture was cooled to rt and extracted by EA and water. The combined organic layers were washed with brine, dried over Na2SO4 and filtered. The filtrate was concentrated in vacuo and The resulting residue was purified by prep-HPLC to provide N-((6-amino-2-methylpyridin-3-yl)methyl)-1-((3-chloroquinolin-6-yl)methyl)-4-hydroxy-1H-pyrazolo[4,3-c]pyridine-3-carboxamide (261.6 mg, 75.4%) as a white solid. 1H NMR. (DMSO-d6, 400 MHz) δ 10.47 (s, 1H), 8.87 (d, 1H), 8.69 (t, 1H), 8.57 (d, 1H), 8.04 (d, 2H), 7.75 (s, 1H), 7.67-7.65 (m, 1H), 7.27 (d, 1H), 6.54-6.44 (m, 1H), 6.21 (d, 1H), 5.86 (s, 2H), 5.70 (s, 2H), 4.29 (d, 2H), 2.30 (s, 3H). LRMS (M+H+) m/z calculated 474.1, found 474.2.

II. Biological Evaluation

Example 1: In Vitro Enzyme Inhibition

The ability of the compounds disclosed herein to inhibit human plasma kallikrein activity was quantified according to the procedures below.

A 10 mM solution of the test compound was made in DMSO. This solution was serially diluted 1:5 in DMSO to yield 2000, 400, 80, 16, 3.2, 0.64, 0.128, 0.0256 and 0.00512 μM compound test solutions. A control tube containing only DMSO is included. 16 μL of each compound test solution was combined with 384 μL of assay buffer (50 mM Tris-HCl pH 7.5, 150 mM NaCl, 0.01% Triton X-100) to yield a "4× test compound buffer stock".

Separately, a 40 nM solution of human Plasma Kallikrein (Abcam) and a 93.6 μM solution Pro-Phe-Arg-AMC (Bachem) were made using assay buffer. These solutions are hereby referred to as 4×hPK and 2×PFR-AMC, respectively.

60 μL of each 4× test compound buffer stock was combined with 60 μL of 4×hPK to yield 120 μL of "2× test compound buffer stock/2×hPK". 50 μL was removed from this mixture and placed into duplicate wells on a Microfluor 1Black U-bottom microtiter plate (Thermo Scientific). This plate was incubated for 5 minutes at 37° C. To each well, 50 μL of pre-warmed 2×PFR-AMC was added to start the enzymatic reaction. Cleavage of PFR-AMC was monitored in a Biotek Synergy H4 reader set at 37° C. Readings are taken every 43 seconds for 1 hour. The highest mean velocity over 20 reads (~15 minutes) is used to calculate the $IC_{50}$. The $IC_{50}$ is calculated using the Gen5 (Biotek Instruments).

The ability of the compounds listed in Table 2 to inhibit human plasma kallikrein activity was determined.

TABLE 2

| Chemical Synthesis Example | Name | hPK $IC_{50}$ | HWB $EC_{50}$ |
|---|---|---|---|
| 1 | N-((6-amino-2,4-dimethylpyridin-3-yl)methyl)-1-((3-chloroquinolin-6-yl)methyl)-1H-pyrazole-3-carboxamide | A | A |
| 2 | N-((6-amino-2,4-dimethylpyridin-3-yl)methyl)-1-((3-chloroquinolin-6-yl)methyl)-1H-pyrazole-4-carboxamide | A | A |
| 3 | N-((6-amino-2,4-dimethylpyridin-3-yl)methyl)-1-((3-chloroquinolin-6-yl)methyl)-1H-imidazole-4-carboxamide | A | A |
| 4 | N-((6-amino-2,4-dimethylpyridin-3-yl)methyl)-1-((3-chloroquinolin-6-yl)methyl)-1H-1,2,4-triazole-3-carboxamide | A | A |
| 5 | N-((6-amino-2,4-dimethylpyridin-3-yl)methyl)-2-((3-chloroquinolin-6-yl)methyl)-1H-imidazole-5-carboxamide | A | A |
| 6 | N-((6-amino-2,4-dimethylpyridin-3-yl)methyl)-3-((3-chloroquinolin-6-yl)methyl)-1,2,4-oxadiazole-5-carboxamide | A | A |
| 7 | N-((6-amino-2,4-dimethylpyridin-3-yl)methyl)-5-((3-chloroquinolin-6-yl)methyl)-1,2,4-oxadiazole-3-carboxamide | A | A |
| 8 | N-((6-amino-2,4-dimethylpyridin-3-yl)methyl)-1-((3-chloroquinolin-6-yl)methyl)-1H-pyrrolo[3,2-b]pyridine-3-carboxamide | A | |
| 9 | N-((6-amino-2,4-dimethylpyridin-3-yl)methyl)-3-((3-chloroquinolin-6-yl)methyl)imidazo[1,5-a]pyridine-1-carboxamide | A | A |
| 10 | N-((6-amino-2,4-dimethylpyridin-3-yl)methyl)-1-((3-chloroquinolin-6-yl)methyl)-1H-1,2,3-triazole-4-carboxamide | A | A |
| 11 | N-((6-amino-2,4-dimethylpyridin-3-yl)methyl)-1-((3-chloroquinolin-6-yl)methyl)-1H-indole-3-carboxamide | A | |
| 12 | N-((6-amino-2,4-dimethylpyridin-3-yl)methyl)-1-((3-chloroquinolin-6-yl)methyl)-1H-pyrrolo[2,3-b]pyridine-3-carboxamide | A | A |
| 13 | N-((6-amino-2,4-dimethylpyridin-3-yl)methyl)-1-((3-chloroquinolin-6-yl)methyl)-1H-indazole-3-carboxamide | A | A |
| 14 | N-((6-amino-2,4-dimethylpyridin-3-yl)methyl)-2-((3-chloroquinolin-6-yl)methyl)-2H-indazole-3-carboxamide | D | |
| 15 | N-((6-amino-2,4-dimethylpyridin-3-yl)methyl)-1-((3-chloroquinolin-6-yl)methyl)-3-(trifluoromethyl)-1H-pyrazole-4-carboxamide | A | A |
| 16 | N-((6-amino-2,4-dimethylpyridin-3-yl)methyl)-1-((3-chloroquinolin-6-yl)methyl)-1H-pyrrolo[2,3-c]pyridine-3-carboxamide | A | A |
| 17 | 3-amino-N-((6-amino-2,4-dimethylpyridin-3-yl)methyl)-1-((3-chloroquinolin-6-yl)methyl)-1H-pyrazole-4-carboxamide | A | A |
| 18 | N-((6-amino-2,4-dimethylpyridin-3-yl)methyl)-1-((3-chloroquinolin-6-yl)methyl)-4-nitro-1H-pyrazole-3-carboxamide | A | |
| 19 | 4-acetamido-N-((6-amino-2,4-dimethylpyridin-3-yl)methyl)-1-((3-chloroquinolin-6-yl)methyl)-1H-pyrazole-3-carboxamide | A | A |
| 20 | 5-amino-N-((6-amino-2,4-dimethylpyridin-3-yl)methyl)-1-((3-chloroquinolin-6-yl)methyl)-1H-1,2,4-triazole-3-carboxamide | A | A |
| 21 | N-((6-amino-2,4-dimethylpyridin-3-yl)methyl)-2-((3-chloroquinolin-6-yl)methyl)-2H-1,2,3-triazole-4-carboxamide | A | A |

TABLE 2-continued

| Chemical Synthesis Example | Name | hPK IC$_{50}$ | HWB EC$_{50}$ |
|---|---|---|---|
| 22 | N-((6-amino-2,4-dimethylpyridin-3-yl)methyl)-1-((3-chloroquinolin-6-yl)methyl)-4-(trifluoromethyl)-1H-pyrazole-3-carboxamide | A | A |
| 23 | N-((6-amino-2,4-dimethylpyridin-3-yl)methyl)-1-((3-chloroquinolin-6-yl)methyl)imidazo[1,5-a]pyridine-3-carboxamide | A | |
| 24 | 2-amino-N-((6-amino-2,4-dimethylpyridin-3-yl)methyl)-1-((3-chloroquinolin-6-yl)methyl)-1H-imidazole-4-carboxamide | A | A |
| 25 | 4-amino-N-((6-amino-2,4-dimethylpyridin-3-yl)methyl)-1-((3-chloroquinolin-6-yl)methyl)-1H-pyrazole-3-carboxamide | A | A |
| 26 | N-((6-amino-2,4-dimethylpyridin-3-yl)methyl)-1-((3-chloroquinolin-6-yl)methyl)-3-cyano-1H-pyrazole-4-carboxamide | A | B |
| 27 | N-((6-amino-2,4-dimethylpyridin-3-yl)methyl)-3-(aminomethyl)-1-((3-chloroquinolin-6-yl)methyl)-1H-pyrazole-4-carboxamide | A | A |
| 28 | 2-amino-N-((6-amino-2,4-dimethylpyridin-3-yl)methyl)-1-((3-chloroquinolin-6-yl)methyl)-1H-imidazole-4-carboxamide | A | A |
| 29 | N-((6-amino-2,4-dimethylpyridin-3-yl)methyl)-2-((3-chloroquinolin-6-yl)methyl)oxazole-4-carboxamide | A | A |
| 30 | N-((6-amino-2,4-dimethylpyridin-3-yl)methyl)-5-((3-chloroquinolin-6-yl)methyl)-1,3,4-oxadiazole-2-carboxamide | A | A |
| 31 | N-((6-amino-2,4-dimethylpyridin-3-yl)methyl)-5-((3-chloroquinolin-6-yl)methyl)oxazole-2-carboxamide | A | A |
| 32 | N-((6-amino-2,4-dimethylpyridin-3-yl)methyl)-7-((3-chloroquinolin-6-yl)methyl)-7H-pyrrolo[2,3-d]pyrimidine-5-carboxamide | A | A |
| 33 | 4-amino-N-((6-amino-2,4-dimethylpyridin-3-yl)methyl)-1-((3-chloroquinolin-6-yl)methyl)-1H-indazole-3-carboxamide | B | |
| 34 | 4-amino-N-((6-amino-2,4-dimethylpyridin-3-yl)methyl)-7-((3-chloroquinolin-6-yl)methyl)-7H-pyrrolo[2,3-d]pyrimidine-5-carboxamide | A | |
| 35 | N-((6-amino-2,4-dimethylpyridin-3-yl)methyl)-1-((3-chloroquinolin-6-yl)methyl)-1H-pyrrolo[3,2-c]pyridine-3-carboxamide | A | A |
| 36 | N-((6-amino-2,4-dimethylpyridin-3-yl)methyl)-1-((3-chloroquinolin-6-yl)methyl)-4-cyano-1H-pyrazole-3-carboxamide | A | A |
| 37 | N-((6-amino-2,4-dimethylpyridin-3-yl)methyl)-2-((3-chloroquinolin-6-yl)methyl)-4-(trifluoromethyl)oxazole-5-carboxamide | A | A |
| 38 | N-((6-amino-2,4-dimethylpyridin-3-yl)methyl)-1-((3-chloroquinolin-6-yl)methyl)-3-methyl-1H-pyrazole-4-carboxamide | A | A |
| 39 | N-((6-amino-2,4-dimethylpyridin-3-yl)methyl)-1-((3-chloroquinolin-6-yl)methyl)-3-methoxy-1H-pyrazole-4-carboxamide | A | A |
| 40 | N-((6-amino-2,4-dimethylpyridin-3-yl)methyl)-1-((3-chloroquinolin-6-yl)methyl)-5-cyano-1H-pyrazole-4-carboxamide | C | |
| 41 | N-((6-amino-2,4-dimethylpyridin-3-yl)methyl)-5-((3-chloroquinolin-6-yl)methyl)-1H-imidazole-2-carboxamide | B | |
| 42 | N-((5-chloro-1H-indazol-3-yl)methyl)-5-((3-chloroquinolin-6-yl)methyl)-1,3,4-oxadiazole-2-carboxamide | B | |
| 43 | N-((3-chloro-4-fluoro-1H-indol-5-yl)methyl)-5-((3-chloroquinolin-6-yl)methyl)-1,3,4-oxadiazole-2-carboxamide | B | |
| 44 | N-((3-chloro-6-fluoro-1H-indol-5-yl)methyl)-5-((3-chloroquinolin-6-yl)methyl)-1,3,4-oxadiazole-2-carboxamide | B | |
| 45 | N-((3-chloro-1H-pyrrolo[2,3-b]pyridin-5-yl)methyl)-5-((3-chloroquinolin-6-yl)methyl)-1,3,4-oxadiazole-2-carboxamide | B | |
| 46 | N-((1-aminoisoquinolin-6-yl)methyl)-5-((3-chloroquinolin-6-yl)methyl)-1,3,4-oxadiazole-2-carboxamide | B | |

TABLE 2-continued

| Chemical Synthesis Example | Name | hPK IC$_{50}$ | HWB EC$_{50}$ |
|---|---|---|---|
| 47 | N-((3-chloro-4-fluoro-1H-indol-5-yl)methyl)-1-((3-chloroquinolin-6-yl)methyl)-3-cyano-1H-pyrazole-4-carboxamide | B | |
| 48 | N-((5-chloro-1H-indazol-3-yl)methyl)-1-((3-chloroquinolin-6-yl)methyl)-3-cyano-1H-pyrazole-4-carboxamide | B | |
| 49 | N-((1-aminoisoquinolin-6-yl)methyl)-1-((3-chloroquinolin-6-yl)methyl)-3-cyano-1H-pyrazole-4-carboxamide | A | |
| 50 | N-((3-chloro-1H-pyrrolo[2,3-b]pyridin-5-yl)methyl)-1-((3-chloroquinolin-6-yl)methyl)-3-cyano-1H-pyrazole-4-carboxamide | B | |
| 51 | N-((3-chloro-6-fluoro-1H-indol-5-yl)methyl)-1-((3-chloroquinolin-6-yl)methyl)-3-cyano-1H-pyrazole-4-carboxamide | B | |
| 52 | N-((6-amino-2,4-dimethylpyridin-3-yl)methyl)-1-((3-chloro-8-fluoroquinolin-6-yl)methyl)-3-cyano-1H-pyrazole-4-carboxamide | A | A |
| 53 | N-((3-chloro-6-fluoro-1H-indol-5-yl)methyl)-1-((3-chloro-8-fluoroquinolin-6-yl)methyl)-3-cyano-1H-pyrazole-4-carboxamide | A | |
| 54 | N-((1-aminoisoquinolin-6-yl)methyl)-1-((3-chloro-8-fluoroquinolin-6-yl)methyl)-3-cyano-1H-pyrazole-4-carboxamide | A | A |
| 55 | N-((5-chloro-1H-indazol-3-yl)methyl)-1-((3-chloro-8-fluoroquinolin-6-yl)methyl)-3-cyano-1H-pyrazole-4-carboxamide | B | |
| 56 | N-((3-chloro-1H-pyrrolo[2,3-b]pyridin-5-yl)methyl)-1-((3-chloro-8-fluoroquinolin-6-yl)methyl)-3-cyano-1H-pyrazole-4-carboxamide | A | |
| 57 | N-((3-chloro-4-fluoro-1H-indol-5-yl)methyl)-1-((3-chloro-8-fluoroquinolin-6-yl)methyl)-3-cyano-1H-pyrazole-4-carboxamide | B | |
| 58 | N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide | A | A |
| 59 | N-((1-aminoisoquinolin-6-yl)methyl)-1-((3-chloro-8-(2-hydroxypropan-2-yl)quinolin-6-yl)methyl)-3-cyano-1H-pyrazole-4-carboxamide | A | A |
| 60 | N-((6-amino-2,4-dimethylpyridin-3-yl)methyl)-1-((3-chloro-8-sulfamoylquinolin-6-yl)methyl)-3-cyano-1H-pyrazole-4-carboxamide | A | |
| 61 | N-((6-amino-2,4-dimethylpyridin-3-yl)methyl)-3-cyano-1-((3-methyl-8-(methylsulfonyl)quinolin-6-yl)methyl)-1H-pyrazole-4-carboxamide | A | A |
| 62 | N-((6-amino-2,4-dimethylpyridin-3-yl)methyl)-3-cyano-1-((8-cyano-3-methylquinolin-6-yl)methyl)-1H-pyrazole-4-carboxamide | A | A |
| 63 | N4-((6-amino-2,4-dimethylpyridin-3-yl)methyl)-1-((8-cyano-3-methylquinolin-6-yl)methyl)-1H-pyrazole-3,4-dicarboxamide | B | |
| 64 | N-((6-amino-2,4-dimethylpyridin-3-yl)methyl)-1-((3-chloroquinolin-6-yl)methyl)-4-cyano-1H-pyrazole-5-carboxamide | — | |
| 65 | N-((6-amino-2,4-dimethylpyridin-3-yl)methyl)-3-cyano-1-((3-cyclopropylquinolin-6-yl)methyl)-1H-pyrazole-4-carboxamide | A | A |
| 66 | N-((6-amino-2-methylpyridin-3-yl)methyl)-3-cyano-1-((3-cyclopropylquinolin-6-yl)methyl)-1H-pyrazole-4-carboxamide | A | A |
| 67 | N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide | C | A |
| 68 | N-((6-amino-2,4-dimethylpyridin-3-yl)methyl)-1-((3-chloro-8-(methylsulfonyl)quinolin-6-yl)methyl)-3-cyano-1H-pyrazole-4-carboxamide | A | |
| 69 | N-((6-amino-2,4-dimethylpyridin-3-yl)methyl)-1-((3-chloro-8-cyanoquinolin-6-yl)methyl)-3-cyano-1H-pyrazole-4-carboxamide | A | A |
| 70 | N-((6-amino-2,4-dimethylpyridin-3-yl)methyl)-1-((3-chloro-8-fluoroquinolin-6-yl)methyl)-5-cyano-1H-pyrazole-4-carboxamide | D | |

TABLE 2-continued

| Chemical Synthesis Example | Name | hPK IC$_{50}$ | HWB EC$_{50}$ |
|---|---|---|---|
| 71 | N4-((6-amino-2,4-dimethylpyridin-3-yl)methyl)-1-((3-chloro-8-fluoroquinolin-6-yl)methyl)-1H-pyrazole-4,5-dicarboxamide | D | |
| 72 | 6-((4-(((6-amino-2,4-dimethylpyridin-3-yl)methyl)carbamoyl)-3-cyano-1H-pyrazol-1-yl)methyl)-3-chloroquinoline-8-carboxamide | A | |
| 73 | N-((6-amino-2,4-dimethylpyridin-3-yl)methyl)-3-cyano-1-((3-(trifluoromethyl)quinolin-6-yl)methyl)-1H-pyrazole-4-carboxamide | A | A |
| 74 | N-((6-amino-2-methylpyridin-3-yl)methyl)-3-cyano-1-((3-(trifluoromethyl)quinolin-6-yl)methyl)-1H-pyrazole-4-carboxamide | A | A |
| 75 | N-((6-amino-2,4-dimethylpyridin-3-yl)methyl)-5-((3-chloro-8-fluoroquinolin-6-yl)methyl)-1,3,4-oxadiazole-2-carboxamide | A | A |
| 76 | N-((6-amino-2,4-dimethylpyridin-3-yl)methyl)-1-((3-chloroquinolin-6-yl)methyl)-4-cyano-1H-pyrazolo[4,3-c]pyridine-3-carboxamide | A | |
| 77 | N-((6-amino-2-methylpyridin-3-yl)methyl)-1-((3-chloroquinolin-6-yl)methyl)-3-cyano-1H-pyrazole-4-carboxamide | A | |
| 78 | 6-((4-(((6-amino-2,4-dimethylpyridin-3-yl)methyl)carbamoyl)-3-cyano-1H-pyrazol-1-yl)methyl)-3-methylquinoline-8-carboxamide | A | A |
| 79 | N-((6-amino-2-methylpyridin-3-yl)methyl)-5-((3-chloroquinolin-6-yl)methyl)-1,3,4-oxadiazole-2-carboxamide | B | |
| 80 | N-((6-amino-2,4-dimethylpyridin-3-yl)methyl)-2-(3-chloroquinoline-6-carbonyl)oxazole-5-carboxamide | D | |
| 81 | N-((6-amino-2,4-dimethylpyridin-3-yl)methyl)-3-cyano-1-((3-methylquinolin-6-yl)methyl)-1H-pyrazole-4-carboxamide | A | A |
| 82 | N-((6-amino-2-methylpyridin-3-yl)methyl)-3-cyano-1-((3-methylquinolin-6-yl)methyl)-1H-pyrazole-4-carboxamide | A | A |
| 83 | N-((6-amino-2-methylpyridin-3-yl)methyl)-2-((3-chloroquinolin-6-yl)methyl)oxazole-4-carboxamide | B | |
| 84 | N-((6-amino-2-methylpyridin-3-yl)methyl)-5-((3-chloroquinolin-6-yl)methyl)oxazole-2-carboxamide | A | |
| 85 | N-((6-amino-2-methylpyridin-3-yl)methyl)-1-((3-chloroquinolin-6-yl)methyl)-3-methyl-1H-pyrazole-4-carboxamide | A | |
| 86 | N-((6-amino-2,4-dimethylpyridin-3-yl)methyl)-5-((3-chloro-8-(2-hydroxypropan-2-yl)quinolin-6-yl)methyl)-1,3,4-oxadiazole-2-carboxamide | A | |
| 87 | N-((6-amino-2,4-dimethylpyridin-3-yl)methyl)-2-((3-chloroquinolin-6-yl)methyl)-4-cyanooxazole-5-carboxamide | A | |
| 88 | N-((6-amino-2-methylpyridin-3-yl)methyl)-2-((3-chloroquinolin-6-yl)methyl)-4-cyanooxazole-5-carboxamide | B | |
| 89 | N-((6-amino-2,4-dimethylpyridin-3-yl)methyl)-2-((3-chloroquinolin-6-yl)methyl)oxazole-5-carboxamide | A | |
| 90 | N-((6-amino-2-methylpyridin-3-yl)methyl)-2-((3-chloroquinolin-6-yl)methyl)oxazole-5-carboxamide | A | |
| 91 | N-((6-amino-2,4-dimethylpyridin-3-yl)methyl)-1-((3-chloroquinolin-6-yl)methyl)-3-(difluoromethyl)-1H-pyrazole-4-carboxamide | A | |
| 92 | N-((6-amino-2,4-dimethylpyridin-3-yl)methyl)-1-((3-chloroquinolin-6-yl)methyl)-3-(hydroxymethyl)-1H-pyrazole-4-carboxamide | A | |
| 93 | N-((6-amino-2,4-dimethylpyridin-3-yl)methyl)-1-((3-chloroquinolin-6-yl)methyl)-3-(fluoromethyl)-1H-pyrazole-4-carboxamide | A | |
| 94 | N-((6-amino-2,4-dimethylpyridin-3-yl)methyl)-1-((3-chloroquinolin-6-yl)methyl)-3-(1-hydroxyethyl)-1H-pyrazole-4-carboxamide | A | |
| 95 | N-((6-amino-2,4-dimethylpyridin-3-yl)methyl)-2-((3-chloroquinolin-6-yl)methyl)-5-cyano-2H-1,2,3-triazole-4-carboxamide | A | A |

TABLE 2-continued

| Chemical Synthesis Example | Name | hPK IC$_{50}$ | HWB EC$_{50}$ |
|---|---|---|---|
| 96 | N-((6-amino-2,4-dimethylpyridin-3-yl)methyl)-5-((3-chloroquinolin-6-yl)methyl)-4H-1,2,4-triazole-3-carboxamide | A | A |
| 97 | N-((6-amino-2-methylpyridin-3-yl)methyl)-5-((3-chloroquinolin-6-yl)methyl)-4H-1,2,4-triazole-3-carboxamide | A | |
| 98 | N-((6-amino-2,4-dimethylpyridin-3-yl)methyl)-5-((3-chloroquinolin-6-yl)methyl)-4-methyl-4H-1,2,4-triazole-3-carboxamide | A | A |
| 99 | N-((6-amino-2,4-dimethylpyridin-3-yl)methyl)-3-((3-chloroquinolin-6-yl)methyl)-1-methyl-1H-1,2,4-triazole-5-carboxamide | A | |
| 100 | N-((6-amino-2,4-dimethylpyridin-3-yl)methyl)-5-bromo-1-((3-chloroquinolin-6-yl)methyl)-1H-1,2,4-triazole-3-carboxamide | A | |
| 101 | N-((6-amino-2,4-dimethylpyridin-3-yl)methyl)-1-((3-chloroquinolin-6-yl)methyl)-5-cyano-1H-1,2,4-triazole-3-carboxamide | D | |
| 102 | methyl 3-(((6-amino-2,4-dimethylpyridin-3-yl)methyl)carbamoyl)-1-((3-chloroquinolin-6-yl)methyl)-1H-1,2,4-triazole-5-carboxylate | D | |
| 103 | N-((6-amino-2,4-dimethylpyridin-3-yl)methyl)-2-((3-chloroquinolin-6-yl)methyl)-1H-imidazole-4-carboxamide | A | |
| 104 | N-((6-amino-2,4-dimethylpyridin-3-yl)methyl)-2-((3-chloroquinolin-6-yl)methyl)-1-methyl-1H-imidazole-4-carboxamide | D | |
| 105 | N-((6-amino-2,4-dimethylpyridin-3-yl)methyl)-2-((3-chloroquinolin-6-yl)methyl)-1-methyl-1H-imidazole-5-carboxamide | C | |
| 106 | N-((6-amino-2,4-dimethylpyridin-3-yl)methyl)-4-bromo-2-((3-chloroquinolin-6-yl)methyl)-1H-imidazole-5-carboxamide | A | |
| 107 | N-((6-amino-2,4-dimethylpyridin-3-yl)methyl)-1-((3-chloroquinolin-6-yl)methyl)-5-cyano-1H-1,2,4-triazole-3-carboxamide | B | |
| 108 | N-((6-amino-2,4-dimethylpyridin-3-yl)methyl)-1-((3-chloroquinolin-6-yl)methyl)-5-cyano-1H-pyrazole-3-carboxamide | B | |
| 109 | N-((6-amino-2,4-dimethylpyridin-3-yl)methyl)-1-((3-chloroquinolin-6-yl)methyl)-3-cyano-1H-pyrazole-5-carboxamide | D | |
| 110 | N-((6-amino-2,4-dimethylpyridin-3-yl)methyl)-1-((3-chloroquinolin-6-yl)methyl)-2-(hydroxymethyl)-1H-imidazole-4-carboxamide | A | |
| 111 | N4-((6-amino-2,4-dimethylpyridin-3-yl)methyl)-1-((3-chloroquinolin-6-yl)methyl)-1H-imidazole-2,4-dicarboxamide | B | |
| 112 | N-((6-amino-2,4-dimethylpyridin-3-yl)methyl)-2-(aminomethyl)-1-((3-chloroquinolin-6-yl)methyl)-1H-imidazole-4-carboxamide | B | |
| 113 | N-((6-amino-2,4-dimethylpyridin-3-yl)methyl)-1-((3-chloroquinolin-6-yl)methyl)-2-cyano-1H-imidazole-4-carboxamide | B | |
| 114 | N-((6-amino-2,4-dimethylpyridin-3-yl)methyl)-2-((3-chloroquinolin-6-yl)methyl)oxazole-5-carboxamide | A | A |
| 115 | N-((6-amino-2,4-dimethylpyridin-3-yl)methyl)-2-((3-chloroquinolin-6-yl)methyl)-5-(trifluoromethyl)-2H-1,2,3-triazole-4-carboxamide | A | A |
| 116 | N-((6-amino-2,4-dimethylpyridin-3-yl)methyl)-1-((3-chloroquinolin-6-yl)methyl)-5-(trifluoromethyl)-1H-pyrazole-3-carboxamide | C | |
| 117 | N-((6-amino-2,4-dimethylpyridin-3-yl)methyl)-5-chloro-1-((3-chloroquinolin-6-yl)methyl)-1H-pyrrolo[2,3-c]pyridine-3-carboxamide | A | |
| 118 | N-((6-amino-2,4-dimethylpyridin-3-yl)methyl)-1-((3-chloroquinolin-6-yl)methyl)-4-oxo-4,5-dihydro-1H-pyrrolo[3,2-c]pyridine-3-carboxamide | D | |
| 119 | N-((6-amino-2,4-dimethylpyridin-3-yl)methyl)-4-chloro-1-((3-chloroquinolin-6-yl)methyl)-1H-pyrazolo[4,3-c]pyridine-3-carboxamide | B | |

TABLE 2-continued

| Chemical Synthesis Example | Name | hPK IC$_{50}$ | HWB EC$_{50}$ |
|---|---|---|---|
| 120 | N-((6-amino-2,4-dimethylpyridin-3-yl)methyl)-1-((3-chloroquinolin-6-yl)methyl)-4-oxo-4,5-dihydro-1H-pyrazolo[4,3-c]pyridine-3-carboxamide | C | |
| 121 | N-((6-amino-2,4-dimethylpyridin-3-yl)methyl)-1-((3-chloroquinolin-6-yl)methyl)-5-methoxy-1H-pyrrolo[2,3-c]pyridine-3-carboxamide | A | |
| 122 | N-((6-amino-2,4-dimethylpyridin-3-yl)methyl)-1-((3-chloroquinolin-6-yl)methyl)-5-methoxy-1H-pyrazolo[3,4-c]pyridine-3-carboxamide | A | A |
| 123 | N-((6-amino-2,4-dimethylpyridin-3-yl)methyl)-1-((3-chloroquinolin-6-yl)methyl)-4-cyano-1H-pyrrolo[2,3-c]pyridine-3-carboxamide | A | A |
| 124 | N-((6-amino-2,4-dimethylpyridin-3-yl)methyl)-1-((3-chloroquinolin-6-yl)methyl)-5-oxo-5,6-dihydro-1H-pyrazolo[3,4-c]pyridine-3-carboxamide | B | |
| 125 | N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide | A | A |
| 126 | N-((6-amino-2,4-dimethylpyridin-3-yl)methyl)-1-((3-chloroquinolin-6-yl)methyl)-5-oxo-4,5-dihydro-1H-pyrrolo[3,2-b]pyridine-3-carboxamide | A | A |
| 127 | N-((6-amino-2,4-dimethylpyridin-3-yl)methyl)-1-((3-chloroquinolin-6-yl)methyl)-4-cyano-1H-pyrrolo[2,3-b]pyridine-3-carboxamide | A | A |
| 128 | N-((6-amino-2,4-dimethylpyridin-3-yl)methyl)-1-((3-chloroquinolin-6-yl)methyl)-5-methoxy-1H-pyrrolo[3,2-b]pyridine-3-carboxamide | C | |
| 129 | N-((6-amino-2,4-dimethylpyridin-3-yl)methyl)-1-((3-chloroquinolin-6-yl)methyl)-4-cyano-1H-pyrazolo[3,4-c]pyridine-3-carboxamide | A | A |
| 130 | N-((6-amino-2,4-dimethylpyridin-3-yl)methyl)-1-((3-chloroquinolin-6-yl)methyl)-5-cyano-1H-pyrazolo[3,4-c]pyridine-3-carboxamide | A | |
| 131 | N-((6-amino-2,4-dimethylpyridin-3-yl)methyl)-7-((3-chloroquinolin-6-yl)methyl)-4-methoxy-7H-pyrrolo[2,3-d]pyrimidine-5-carboxamide | B | |
| 132 | N-((6-amino-2,4-dimethylpyridin-3-yl)methyl)-7-((3-chloroquinolin-6-yl)methyl)-4-oxo-4,7-dihydro-3H-pyrrolo[2,3-d]pyrimidine-5-carboxamide | D | |
| 133 | N-((6-amino-2,4-dimethylpyridin-3-yl)methyl)-1-((3-chloroquinolin-6-yl)methyl)-4-cyano-1H-pyrrolo[3,2-c]pyridine-3-carboxamide | A | |
| 134 | N-((6-amino-2,4-dimethylpyridin-3-yl)methyl)-1-((3-chloroquinolin-6-yl)methyl)-5-cyano-1H-pyrrolo[2,3-c]pyridine-3-carboxamide | A | A |
| 135 | N-((6-amino-2,4-dimethylpyridin-3-yl)methyl)-1-((3-chloroquinolin-6-yl)methyl)-5-cyano-1H-pyrrolo[2,3-b]pyridine-3-carboxamide | B | |
| 136 | N-((6-amino-2,4-dimethylpyridin-3-yl)methyl)-7-((3-chloroquinolin-6-yl)methyl)-4-cyano-7H-pyrrolo[2,3-d]pyrimidine-5-carboxamide | B | |
| 137 | N-((6-amino-2,4-dimethylpyridin-3-yl)methyl)-1-((3-chloroquinolin-6-yl)methyl)-5-methoxy-1H-pyrazolo[4,3-b]pyridine-3-carboxamide | B | |
| 138 | N-((6-amino-2,4-dimethylpyridin-3-yl)methyl)-1-((3-chloroquinolin-6-yl)methyl)-5-oxo-4,5-dihydro-1H-pyrazolo[4,3-b]pyridine-3-carboxamide | A | A |
| 139 | N-((6-amino-2-methylpyridin-3-yl)methyl)-1-((3-chloroquinolin-6-yl)methyl)-5-oxo-4,5-dihydro-1H-pyrazolo[4,3-b]pyridine-3-carboxamide | A | A |
| 140 | 4-amino-N-((6-amino-2,4-dimethylpyridin-3-yl)methyl)-2-((3-chloroquinolin-6-yl)methyl)-2H-indazole-3-carboxamide | D | |

TABLE 2-continued

| Chemical Synthesis Example | Name | hPK IC$_{50}$ | HWB EC$_{50}$ |
|---|---|---|---|
| 141 | N-((6-amino-2,4-dimethylpyridin-3-yl)methyl)-1-((3-chloroquinolin-6-yl)methyl)-4-(trifluoromethyl)-1H-1,2,3-triazole-5-carboxamide | D | |
| 142 | ethyl 3-(((6-amino-2,4-dimethylpyridin-3-yl)methyl)carbamoyl)-1-((3-chloroquinolin-6-yl)methyl)-1H-1,2,4-triazole-5-carboxylate | D | |

Note:
Biochemical assay IC$_{50}$ and HWB EC$_{50}$ data are designated within the following ranges:
A: ≤0.10 μM
B: >0.10 μM to ≤1.0 μM
C: >1.0 μM to ≤10 μM
D: >10 μM Example 2: Human Whole Blood Kallikrein Inhibition The ability of the compounds disclosed herein to inhibit human plasma kallikrein activity was quantified according to the procedures below.

All dilutions were prepared in an assay buffer comprising 50 mM Tris-HCl pH 7.2, 150 mM NaCl, and 0.01% Triton X-100.

Human plasma was thawed on ice and centrifuged for 15 min at 4° C. to remove platelets. A 1 mM stock solution of ellagic acid was diluted to 8 μM and mixed with human plasma, after removing platelets, at a ratio of 1:0.8. The mixture of human plasma and ellagic acid was further diluted 32-fold in the assay buffer, to yield the final mixture for use in the inhibition assay.

A 22.5 μL volume of the final mixture of human plasma and ellagic acid was added to a 96-well microwell plate and the plate was incubated for 15 min at 37° C.

The test compound solution was prepared to provide final concentrations of 20 μM, 5 μM, 1.25 μM, 312.5 nM, 78.125 nM, 19.531 nM, 4.883 nM, 1.221 nM, 0.305 nM, and 0.076 nM. Each test compound concentration was tested in duplicates.

In addition to the inhibitor control and test wells, the 96 well assay plate included positive control wells which contain the mixture of human plasma and ellagic acid without test compounds, and background wells which contain neither the mixture of human plasma and ellagic acid nor the test compounds. The total volume of liquid in positive control and background wells was brought up to 35 μL using the assay buffer.

The assay plate containing test compounds mixed with human plasma and ellagic acid and appropriate controls was incubated at 37° C. for 5 min. A 10 mM stock solution of substrate Z-FR-2-AMC was diluted to 133.2 μM in the assay buffer, and 15 μL of the diluted substrate was added to each well, to yield a final substrate concentration of 40 μM in each well. The reagents were mixed by shaking the plate gently for 30 sec.

The enzyme reaction was quantified by immediate kinetic reading of the assay plate using excitation/emission wavelengths of 330 nm/440 nm respectively. Fluorescence intensity was recorded for 60 min, using a time interval of 43 sec.

The inhibition activity of the test compounds were evaluated using the IC$_{50}$ values, calculated according to the dose-response curve of the test compounds, fitted using the "log(inhibitor)–response(variable slope)" equation in GraphPadPrism software (GraphPad Software, Inc.).

The percentage inhibition (EC$_{50}$) was calculated using the following equation:

$$\text{Inhibition \%} = 100 - \frac{\text{Sample value} - \text{Mean } (BG)}{\text{Mean } (PC) - \text{Mean } (BG)} \times 100$$

where, Mean(BG) is the average value of the fluorescence intensity of the background wells and Mean(PC) is the average value of the fluorescence intensity of the positive control wells. Human whole blood kallikrein inhibition EC$_{50}$ results for select compounds is provided in Table 2.

III. Pharmacokinetic Evaluation

Pharmacokinetic studies of select compounds were performed to assess the pharmacokinetic properties. Male Sprague-Dawley rats were administered a single oral dose of the test compound at 10 mg/kg (dose concentration: 2 mg/mL, dose volume: 5 ml/kg) via oral gavage. Blood samples were collected via jugular vein at pre-dose, post-dose 5 min, 15 min, 30 min, 1 h, 2 h, 4 h, 6 h, 8 h, 10 h and 24 h, and centrifuged (8000 rpm for 6 minutes at 2-8° C.). The resulting plasma fractions were analyzed by LC/MS/MS to determine the concentration of the test compound. Oral exposure data for select compounds are shown in Table 3.

TABLE 3

| Chemical Synthesis Example | Name | AUC |
|---|---|---|
| 1 | N-((6-amino-2,4-dimethylpyridin-3-yl)methyl)-1-((3-chloroquinolin-6-yl)methyl)-1H-pyrazole-3-carboxamide | B |
| 2 | N-((6-amino-2,4-dimethylpyridin-3-yl)methyl)-1-((3-chloroquinolin-6-yl)methyl)-1H-pyrazole-4-carboxamide | B |
| 3 | N-((6-amino-2,4-dimethylpyridin-3-yl)methyl)-1-((3-chloroquinolin-6-yl)methyl)-1H-imidazole-4-carboxamide | B |
| 4 | N-((6-amino-2,4-dimethylpyridin-3-yl)methyl)-1-((3-chloroquinolin-6-yl)methyl)-1H-1,2,4-triazole-3-carboxamide | A |
| 5 | N-((6-amino-2,4-dimethylpyridin-3-yl)methyl)-2-((3-chloroquinolin-6-yl)methyl)-1H-imidazole-5-carboxamide | BLQ |
| 6 | N-((6-amino-2,4-dimethylpyridin-3-yl)methyl)-3-((3-chloroquinolin-6-yl)methyl)-1,2,4-oxadiazole-5-carboxamide | B |

TABLE 3-continued

| Chemical Synthesis Example | Name | AUC |
|---|---|---|
| 7 | N-((6-amino-2,4-dimethylpyridin-3-yl)methyl)-5-((3-chloroquinolin-6-yl)methyl)-1,2,4-oxadiazole-3-carboxamide | C |
| 9 | N-((6-amino-2,4-dimethylpyridin-3-yl)methyl)-3-((3-chloroquinolin-6-yl)methyl)imidazo[1,5-a]pyridine-1-carboxamide | B |
| 10 | N-((6-amino-2,4-dimethylpyridin-3-yl)methyl)-1-((3-chloroquinolin-6-yl)methyl)-1H-1,2,3-triazole-4-carboxamide | C |
| 12 | N-((6-amino-2,4-dimethylpyridin-3-yl)methyl)-1-((3-chloroquinolin-6-yl)methyl)-1H-pyrrolo[2,3-b]pyridine-3-carboxamide | B |
| 13 | N-((6-amino-2,4-dimethylpyridin-3-yl)methyl)-1-((3-chloroquinolin-6-yl)methyl)-1H-indazole-3-carboxamide | B |
| 15 | N-((6-amino-2,4-dimethylpyridin-3-yl)methyl)-1-((3-chloroquinolin-6-yl)methyl)-3-(trifluoromethyl)-1H-pyrazole-4-carboxamide | C |
| 16 | N-((6-amino-2,4-dimethylpyridin-3-yl)methyl)-1-((3-chloroquinolin-6-yl)methyl)-1H-pyrrolo[2,3-c]pyridine-3-carboxamide | B |
| 17 | 3-amino-N-((6-amino-2,4-dimethylpyridin-3-yl)methyl)-1-((3-chloroquinolin-6-yl)methyl)-1H-pyrazole-4-carboxamide | B |
| 19 | 4-acetamido-N-((6-amino-2,4-dimethylpyridin-3-yl)methyl)-1-((3-chloroquinolin-6-yl)methyl)-1H-pyrazole-3-carboxamide | B |
| 20 | 5-amino-N-((6-amino-2,4-dimethylpyridin-3-yl)methyl)-1-((3-chloroquinolin-6-yl)methyl)-1H-1,2,4-triazole-3-carboxamide | A |
| 21 | N-((6-amino-2,4-dimethylpyridin-3-yl)methyl)-2-((3-chloroquinolin-6-yl)methyl)-2H-1,2,3-triazole-4-carboxamide | C |
| 22 | N-((6-amino-2,4-dimethylpyridin-3-yl)methyl)-1-((3-chloroquinolin-6-yl)methyl)-4-(trifluoromethyl)-1H-pyrazole-3-carboxamide | B |
| 24 | 2-amino-N-((6-amino-2,4-dimethylpyridin-3-yl)methyl)-1-((3-chloroquinolin-6-yl)methyl)-1H-imidazole-4-carboxamide | B |
| 25 | 4-amino-N-((6-amino-2,4-dimethylpyridin-3-yl)methyl)-1-((3-chloroquinolin-6-yl)methyl)-1H-pyrazole-3-carboxamide | C |
| 26 | N-((6-amino-2,4-dimethylpyridin-3-yl)methyl)-1-((3-chloroquinolin-6-yl)methyl)-3-cyano-1H-pyrazole-4-carboxamide | B |
| 27 | N-((6-amino-2,4-dimethylpyridin-3-yl)methyl)-3-(aminomethyl)-1-((3-chloroquinolin-6-yl)methyl)-1H-pyrazole-4-carboxamide | A |
| 28 | 2-amino-N-((6-amino-2,4-dimethylpyridin-3-yl)methyl)-1-((3-chloroquinolin-6-yl)methyl)-1H-imidazole-4-carboxamide | A |
| 29 | N-((6-amino-2,4-dimethylpyridin-3-yl)methyl)-2-((3-chloroquinolin-6-yl)methyl)oxazole-4-carboxamide | C |
| 30 | N-((6-amino-2,4-dimethylpyridin-3-yl)methyl)-5-((3-chloroquinolin-6-yl)methyl)-1,3,4-oxadiazole-2-carboxamide | C |
| 31 | N-((6-amino-2,4-dimethylpyridin-3-yl)methyl)-5-((3-chloroquinolin-6-yl)methyl)oxazole-2-carboxamide | C |
| 32 | N-((6-amino-2,4-dimethylpyridin-3-yl)methyl)-7-((3-chloroquinolin-6-yl)methyl)-7H-pyrrolo[2,3-d]pyrimidine-5-carboxamide | A |
| 35 | N-((6-amino-2,4-dimethylpyridin-3-yl)methyl)-1-((3-chloroquinolin-6-yl)methyl)-1H-pyrrolo[3,2-c]pyridine-3-carboxamide | BLQ |
| 36 | N-((6-amino-2,4-dimethylpyridin-3-yl)methyl)-1-((3-chloroquinolin-6-yl)methyl)-4-cyano-1H-pyrazole-3-carboxamide | B |
| 37 | N-((6-amino-2,4-dimethylpyridin-3-yl)methyl)-2-((3-chloroquinolin-6-yl)methyl)-4-(trifluoromethyl)oxazole-5-carboxamide | B |
| 38 | N-((6-amino-2,4-dimethylpyridin-3-yl)methyl)-1-((3-chloroquinolin-6-yl)methyl)-3-methyl-1H-pyrazole-4-carboxamide | C |
| 39 | N-((6-amino-2,4-dimethylpyridin-3-yl)methyl)-1-((3-chloroquinolin-6-yl)methyl)-3-methoxy-1H-pyrazole-4-carboxamide | C |
| 52 | N-((6-amino-2,4-dimethylpyridin-3-yl)methyl)-1-((3-chloro-8-fluoroquinolin-6-yl)methyl)-3-cyano-1H-pyrazole-4-carboxamide | B |
| 54 | N-((1-aminoisoquinolin-6-yl)methyl)-1-((3-chloro-8-fluoroquinolin-6-yl)methyl)-3-cyano-1H-pyrazole-4-carboxamide | A |
| 58 | N-((6-amino-2,4-dimethylpyridin-3-yl)methyl)-1-((3-chloro-8-(2-hydroxypropan-2-yl)quinolin-6-yl)methyl)-3-cyano-1H-pyrazole-4-carboxamide | A |
| 59 | N-((1-aminoisoquinolin-6-yl)methyl)-1-((3-chloro-8-(2-hydroxypropan-2-yl)quinolin-6-yl)methyl)-3-cyano-1H-pyrazole-4-carboxamide | A |
| 61 | N-((6-amino-2,4-dimethylpyridin-3-yl)methyl)-3-cyano-1-((3-methyl-8-(methylsulfonyl)quinolin-6-yl)methyl)-1H-pyrazole-4-carboxamide | A |
| 62 | N-((6-amino-2,4-dimethylpyridin-3-yl)methyl)-3-cyano-1-((8-cyano-3-methylquinolin-6-yl)methyl)-1H-pyrazole-4-carboxamide | A |
| 65 | N-((6-amino-2,4-dimethylpyridin-3-yl)methyl)-3-cyano-1-((3-cyclopropylquinolin-6-yl)methyl)-1H-pyrazole-4-carboxamide | B |
| 66 | N-((6-amino-2-methylpyridin-3-yl)methyl)-3-cyano-1-((3-cyclopropylquinolin-6-yl)methyl)-1H-pyrazole-4-carboxamide | B |
| 67 | N-((6-amino-2,4-dimethylpyridin-3-yl)methyl)-5-cyano-1-((8-(2-hydroxypropan-2-yl)-3-methylquinolin-6-yl)methyl)-1H-pyrazole-4-carboxamide | A |
| 69 | N-((6-amino-2,4-dimethylpyridin-3-yl)methyl)-1-((3-chloro-8-cyanoquinolin-6-yl)methyl)-3-cyano-1H-pyrazole-4-carboxamide | A |
| 73 | N-((6-amino-2,4-dimethylpyridin-3-yl)methyl)-3-cyano-1-((3-(trifluoromethyl)quinolin-6-yl)methyl)-1H-pyrazole-4-carboxamide | B |
| 74 | N-((6-amino-2-methylpyridin-3-yl)methyl)-3-cyano-1-((3-(trifluoromethyl)quinolin-6-yl)methyl)-1H-pyrazole-4-carboxamide | C |
| 75 | N-((6-amino-2,4-dimethylpyridin-3-yl)methyl)-5-((3-chloro-8-fluoroquinolin-6-yl)methyl)-1,3,4-oxadiazole-2-carboxamide | C |
| 78 | 6-((4-(((6-amino-2,4-dimethylpyridin-3-yl)methyl)carbamoyl)-3-cyano-1H-pyrazol-1-yl)methyl)-3-methylquinoline-8-carboxamide | A |
| 81 | N-((6-amino-2,4-dimethylpyridin-3-yl)methyl)-3-cyano-1-((3-methyl quinolin-6-yl)methyl)-1H-pyrazole-4-carboxamide | B |
| 82 | N-((6-amino-2-methylpyridin-3-yl)methyl)-3-cyano-1-((3-methyl quinolin-6-yl)methyl)-1H-pyrazole-4-carboxamide | B |
| 95 | N-((6-amino-2,4-dimethylpyridin-3-yl)methyl)-2-((3-chloroquinolin-6-yl)methyl)-5-cyano-2H-1,2,3-triazole-4-carboxamide | B |
| 96 | N-((6-amino-2,4-dimethylpyridin-3-yl)methyl)-5-((3-chloroquinolin-6-yl)methyl)-4H-1,2,4-triazole-3-carboxamide | D |
| 98 | N-((6-amino-2,4-dimethylpyridin-3-yl)methyl)-5-((3-chloroquinolin-6-yl)methyl)-4-methyl-4H-1,2,4-triazole-3-carboxamide | C |
| 114 | N-((6-amino-2,4-dimethylpyridin-3-yl)methyl)-2-((3-chloroquinolin-6-yl)methyl)oxazole-5-carboxamide | C |
| 115 | N-((6-amino-2,4-dimethylpyridin-3-yl)methyl)-2-((3-chloroquinolin-6-yl)methyl)-5-(trifluoromethyl)-2H-1,2,3-triazole-4-carboxamide | B |
| 122 | N-((6-amino-2,4-dimethylpyridin-3-yl)methyl)-1-((3-chloroquinolin-6-yl)methyl)-5-methoxy-1H-pyrazolo[3,4-c]pyridine-3-carboxamide | B |
| 123 | N-((6-amino-2,4-dimethylpyridin-3-yl)methyl)-1-((3-chloroquinolin-6-yl)methyl)-4-cyano-1H-pyrrolo[2,3-c]pyridine-3-carboxamide | A |
| 125 | N-((6-amino-2-methylpyridin-3-yl)methyl)-1-((3-chloroquinolin-6-yl)methyl)-5-oxo-4,5-dihydro-1H-pyrrolo[3,2-b]pyridine-3-carboxamide | A |
| 126 | N-((6-amino-2,4-dimethylpyridin-3-yl)methyl)-1-((3-chloroquinolin-6-yl)methyl)-5-oxo-4,5-dihydro-1H-pyrrolo[3,2-b]pyridine-3-carboxamide | A |

TABLE 3-continued

| Chemical Synthesis Example | Name | AUC |
|---|---|---|
| 127 | N-((6-amino-2,4-dimethylpyridin-3-yl)methyl)-1-((3-chloroquinolin-6-yl)methyl)-4-cyano-1H-pyrrolo[2,3-b]pyridine-3-carboxamide | B |
| 129 | N-((6-amino-2,4-dimethylpyridin-3-yl)methyl)-1-((3-chloroquinolin-6-yl)methyl)-4-cyano-1H-pyrazolo[3,4-c]pyridine-3-carboxamide | A |
| 134 | N-((6-amino-2,4-dimethylpyridin-3-yl)methyl)-1-((3-chloroquinolin-6-yl)methyl)-5-cyano-1H-pyrrolo[2,3-c]pyridine-3-carboxamide | BLQ |
| 138 | N-((6-amino-2,4-dimethylpyridin-3-yl)methyl)-1-((3-chloroquinolin-6-yl)methyl)-5-oxo-4,5-dihydro-1H-pyrazolo[4,3-b]pyridine-3-carboxamide | A |
| 139 | N-((6-amino-2-methylpyridin-3-yl)methyl)-1-((3-chloroquinolin-6-yl)methyl)-5-oxo-4,5-dihydro-1H-pyrazolo[4,3-b]pyridine-3-carboxamide | B |

Note:
Pharmacokinetic data are designated within the following ranges:
A: ≤100 ng · h/mL
B: >100 ng · h/mL to ≤1000 ng · h/mL
C: >1000 ng · h/mL to ≤10,000 ng · h/mL
D: >10,000 ng · h/mL
BLQ means below level of quantitation

III. Preparation of Pharmaceutical Dosage Forms

Example 1: Oral Tablet

A tablet is prepared by mixing 48% by weigh of a compound of Formula (I), (Ia), (II), (III), (IV), (V), (VI), (VII), (VIII), (IX), (X), (XI) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, having the structure of Formula (I):

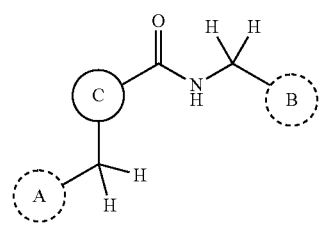

(I)

wherein,
Ring A is an optionally substituted quinolin-6-yl or an optionally substituted quinolin-3-yl;
Ring B is an 6 amino-2,4-dimethylpyridin-3-yl;
and
Ring C is chosen from:

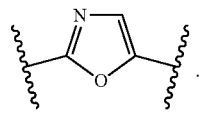 [SMILES: *c1cnc(*)o1]

2. The compound of claim 1, or a pharmaceutically acceptable salt thereof, wherein the optionally substituted quinolin-6-yl or optionally substituted quinolin-3-yl is substituted with at least one substituent selected from optionally substituted C1-C3 alkyl, C3-C7 cycloalkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or —OMe.

3. The compound of claim 2, or a pharmaceutically acceptable salt thereof, wherein the optionally substituted quinolin-6-yl is substituted at least at the 3-position.

4. The compound of claim 3, or a pharmaceutically acceptable salt thereof, wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

5. The compound of claim 2, or a pharmaceutically acceptable salt thereof, wherein the optionally substituted quinolin-3-yl is substituted at least at the 6-position or the 7-position.

6. The compound of claim 2, or a pharmaceutically acceptable salt thereof, wherein Ring A is an optionally substituted quinolin-6-yl.

7. A pharmaceutical composition comprising a compound of Formula (I) as described in claim 1, or a pharmaceutically acceptable salt thereof, and a pharmaceutically acceptable excipient.

8. A method of treating angioedema in a patient in need thereof comprising administering a composition comprising a compound of Formula (I) as described in claim 1, or a pharmaceutically acceptable salt thereof.

9. The method of claim 8, wherein the angioedema is hereditary angioedema.

10. A method of inhibiting kallikrein enzyme comprising contacting the enzyme with a compound of Formula (I) as described in claim 1.

11. A method of inhibiting plasma kallikrein in a subject comprising administering to the subject a composition comprising a compound of Formula (I) as described in claim 1, or a pharmaceutically acceptable salt thereof.

* * * * *